(12) United States Patent
Alves-Junior et al.

(10) Patent No.: US 12,145,967 B2
(45) Date of Patent: Nov. 19, 2024

(54) COMPOSITIONS AND METHODS FOR IMPROVING CROP YIELDS THROUGH TRAIT STACKING

(71) Applicants: Monsanto Technology LLC, St. Louis, MO (US); BASF Plant Science LP, Research Triangle Park, NC (US); BASF Plant Science Company GmbH, Ludwigshafen am Rhein (DE)

(72) Inventors: Leonardo Alves-Junior, Limburgerhof (DE); Wesley B. Bruce, Raleigh, NC (US); Charles R. Dietrich, Chesterfield, MO (US); Natalia Ivleva, Webster Groves, MO (US); Kian Kiani, Cary, NC (US); Ryan Rapp, Hillsborough, NC (US); Thomas L. Slewinski, Chesterfield, MO (US)

(73) Assignees: Monsanto Technology LLC, St. Louis, MO (US); BASF Plant Science LP, Research Triangle Park, NC (US); BASF Plant Science Company GmbH, Ludwigshafen am Rhein (DE)

( * ) Notice: Subject to any disclaimer, the term of this patent is extended or adjusted under 35 U.S.C. 154(b) by 0 days.

(21) Appl. No.: 17/822,380

(22) Filed: Aug. 25, 2022

(65) Prior Publication Data

US 2023/0265132 A1    Aug. 24, 2023

Related U.S. Application Data

(62) Division of application No. 16/276,616, filed on Feb. 15, 2019, now Pat. No. 11,472,852.

(60) Provisional application No. 62/631,344, filed on Feb. 15, 2018.

(51) Int. Cl.
| | |
|---|---|
| *C12N 15/82* | (2006.01) |
| *C07K 14/415* | (2006.01) |
| *C12N 9/02* | (2006.01) |
| *C12N 15/52* | (2006.01) |

(52) U.S. Cl.
CPC .......... *C07K 14/415* (2013.01); *C12N 9/0004* (2013.01); *C12N 15/52* (2013.01); *C12N 15/8223* (2013.01); *C12N 15/8265* (2013.01)

(58) Field of Classification Search
None
See application file for complete search history.

(56) References Cited

U.S. PATENT DOCUMENTS

| | | | |
|---|---|---|---|
| 5,159,135 A | 10/1992 | Umbeck et al. | |
| 5,188,958 A | 2/1993 | Moloney et al. | |
| 5,322,938 A | 6/1994 | Mcpherson et al. | |
| 5,352,605 A | 10/1994 | Fraley et al. | |
| 5,463,174 A | 10/1995 | Moloney et al. | |
| 5,510,474 A | 4/1996 | Quail et al. | |
| 5,538,880 A | 7/1996 | Lundquist et al. | |
| 5,550,318 A | 8/1996 | Adams et al. | |
| 5,591,616 A | 1/1997 | Hiei et al. | |
| 5,641,876 A | 6/1997 | Mcelroy et al. | |
| 5,750,871 A | 5/1998 | Moloney et al. | |
| 5,824,877 A | 10/1998 | Hinchee et al. | |
| 5,939,539 A | 8/1999 | Lange et al. | |
| 6,153,812 A | 11/2000 | Fry et al. | |
| 6,160,208 A | 12/2000 | Lundquist et al. | |
| 6,194,636 B1 | 2/2001 | Mcelroy et al. | |
| 6,232,526 B1 | 5/2001 | Mcelroy et al. | |
| 6,372,211 B1 | 4/2002 | Isaac et al. | |
| 6,384,301 B1 | 5/2002 | Martinell et al. | |
| 6,399,861 B1 | 6/2002 | Anderson et al. | |
| 6,420,547 B1 | 7/2002 | Maiti et al. | |
| 6,429,357 B1 | 8/2002 | McElroy et al. | |
| 7,439,417 B2 | 10/2008 | Da Costa E Silva et al. | |
| 9,309,512 B2 | 4/2016 | Allen et al. | |
| 2004/0111768 A1 | 6/2004 | e Silva et al. | |
| 2004/0216189 A1 | 10/2004 | Houmard et al. | |
| 2005/0160500 A1 | 7/2005 | Castigioni et al. | |
| 2005/0283856 A1 | 12/2005 | Conner et al. | |
| 2006/0200878 A1 | 9/2006 | Lutfiyya et al. | |
| 2008/0052792 A1* | 2/2008 | da Costa e Silva | C07K 14/415 536/23.6 |

(Continued)

FOREIGN PATENT DOCUMENTS

| | | |
|---|---|---|
| CN | 101978061 A | 2/2011 |
| CN | 103451200 A | 12/2013 |

(Continued)

OTHER PUBLICATIONS

Doerks et al., (TIG, 14:248-250, 1998).*

(Continued)

*Primary Examiner* — Vinod Kumar

(74) *Attorney, Agent, or Firm* — MORRISON & FOERSTER LLP

(57) ABSTRACT

The present disclosure provides modified, transgenic, or genome edited/mutated corn plants that are semi-dwarf and have one or more improved ear traits relative to a control plant, such as increase in ear area, increased single kernel weight, increased ear fresh weight, increased number of florets, and mitigated flowering delay. The modified, transgenic, or genome edited/mutated corn plants comprise a transgene encoding one or more CONSTANS (CO) or CONSTANS-like (COL) polypeptide and have a reduced expression of one or more GA20 or GA3 oxidase genes. Also provided are methods for producing the modified, transgenic, or genome edited/mutated corn plants.

6 Claims, 16 Drawing Sheets

Specification includes a Sequence Listing.

(56) References Cited

U.S. PATENT DOCUMENTS

| | | | |
|---|---|---|---|
| 2009/0070898 | A1 | 3/2009 | Allen et al. |
| 2011/0035839 | A1 | 2/2011 | Utfiyya et al. |
| 2011/0296555 | A1 | 12/2011 | Ivashuta et al. |
| 2017/0114356 | A1 | 4/2017 | Li et al. |
| 2018/0051295 | A1* | 2/2018 | Allen .................. C12N 15/8261 |

FOREIGN PATENT DOCUMENTS

| | | |
|---|---|---|
| EP | 1881074 A2 | 1/2008 |
| WO | 0009722 A2 | 2/2000 |
| WO | 2009092009 A2 | 7/2009 |
| WO | 2011140329 A1 | 11/2011 |

OTHER PUBLICATIONS

Smith et al. (Nature Biotechnology, 15:1222-1223, 1997).*
Bork et al. (TIG, 12:425-427, 1996).*
Petti et al. (Plant Physiol., 169:705-716; Sep. 2015).*
Wenkel et al. (The Plant Cell, 18:2971-2984, 2006).*
Gutterson (HortScience 30:964-966, 1995).*
Bruening (Proc. Natl. Acad. Sci., 95:13349-13351, 1998).*
Elomaa et al. (Molecular Breeding, 2:41-50, 1996).*
Colliver et al. (Plant molecular Biology, 35:509-522, 1997).*
Emery et al. (Current Biology 13:1768-1774, 2003).*
Nunes et al. (Planta 224: 125-132; 2006).*
Arziman et al. (Nucleic Acids Research, 33:582-588, 2005).*
Bonawitz et al.,(Annu. Rev. Genet. 44: 337-363, 2010).*
Paul et al., (Plant Cell Reports; 35:1417-1427; 2016).*
Wells (Biochemistry 29:8509-8517, 1990).*
Guo et al. (PNAS, 101: 9205-9210, 2004 ).*
Ngo et al., (The Protein Folding Problem and Tertiary Structure Prediction, K. Merz, and S. Le Grand (eds.) pp. 492-495, 1994).*
Thornton et al. (Nature structural Biology, structural genomics supplement, Nov. 2000).*
Keskin et al. (Protein Science, 13:1043-1055, 2004).*
Nishimura et al. (Plant Cell Physiol., 41(5):583-590, 2000).*
Yang et al. (PNAS, 98:11438-11443, 2001).*
McConnell et al. (Nature, 411:709-713, 2001).*
Song et al. (Gene, 482:34-42, Published Aug. 2011; online version pp. 1-21 at the end of the article)).*
Qiao et al. (Plant Mol Biol Reporter, 29:952-960, 2011.*
GenBank Accession No. AQK99102.1, last updated Feb. 7, 2017, located at https://www.ncbi.nlm.nih.gov/protein/AQK99102.1/, last visited on Aug. 17, 2023, 1 page.
GenBank Accession No. JX307638.1, last updated Apr. 7, 2015, located at https://www.ncbi.nlm.nih.gov/nuccore/JX307638.1/, last visited on Aug. 17, 2023, 2 pages.
GenBank Accession No. NM_001153053.1, last updated Dec. 29, 2017, located at https://www.ncbi.nlm.nih.gov/nuccore/NM_001153053.1/, last visited on Aug. 17, 2023, 2 pages.
GenBank Accession No. NM_001321686.1, last updated Sep. 7, 2017, located at https://www.ncbi.nlm.nih.gov/nuccore/NM_001321686.1/, last visited on Aug. 17, 2023, 2 pages.
Wu, J.-M. et al. (2016). "Studies on the Gene of Key Component GA20-oxidase for Gibberellin Biosynthesis in Plant," Biotechnology Bulletin 32(7):1-12, 12 pages. English Abstract only.
Allen, E. et al. (Apr. 22, 2005). "MicroRNA-directed Phasing During Trans-Acting SiRNA Biogenesis in Plants," Cell 121(2):207-221.
Allen, E. et al. (Dec. 2004). "Evolution of MicroRNA Genes by Inverted Duplication of Target Gene Sequences In *Arabidopsis thaliana*," Nat. Genet. 36(12):1282-1290.
Altschul, S. F. et al. (Oct. 1990). "Basic Local Alignment Search Tool," J. Mol. Biol. 215(3):403-410.
Altschul, S. F. et al. (Sep. 1, 1997). "Gapped BLAST and PSI-BLAST: A New Generation of Protein Database Search Programs," Nucleic Acids Res. 25(17):3389-3402.
Arziman, Z. et al. (Jul. 1, 2005). "E-RNAi: A Web Application to Design Optimized RNAi Constructs," Nucleic Acids Research 33:582-588.
Axtell, M. J. et al. (Nov. 3, 2006). "A Two-Hit Trigger for SiRNA Biogenesis in Plants," Cell 127(3):565-577.
Beurdeley, M. et al. (Apr. 23, 2013). "Compact Designer TALENs for Efficient Genome Engineering," Nature Communications 4:1762, 8 pages.
Bonawitz, N. D. et al. (2010). "The Genetics of Lignin Biosynthesis: Connecting Genotype to Phenotype," Annu. Rev. Genet. 44:337-363.
Bork, P. et al. (Oct. 1996). "Go Hunting in Sequence Databases but Watch Out for the Traps," Trends Genet. 12(10):425-427.
Bruening, G. (Nov. 10, 1998). "Plant Gene Silencing Regularized," Proc. Natl. Acad. Sci. 95(23):13349-13351.
Cai, D. et al. (2017). "Identification and Characterization of Constans-like (COL) Gene Family in Upload Cotton (*Gossypium hirsutum*)," PLOS ONE 12(6): e0179038, 13 pages.
Cermak, T. et al. (Jul. 2011). "Efficient Design and Assembly of Custom TALEN and Other TAL Effector-Based Constructs for DNA Targeting," Nucleic Acids Research 39:e82, 11 pages.
Chenna, R. et al. (Jul. 1, 2003). "Multiple Sequence Alignment with the Clustal Series of Programs," Nucleic Acids Research 31(13):3497-3500.
Colbert, T. et al. (Jun. 2001). "High-throughput Screening for Induced Point Mutations," Plant Physiol 126(2):480-484.
Coles, J. P. et al. (Mar. 1999). "Modification of Gibberellin Production and Plant Development in *Arabidopsis* by Sense and Antisense Expression of Gibberellin 20-oxidase Genes," Plant J. 17(5):547-556.
Colliver, S. P. et al. (Nov. 1997). "Differential Modification of Flavonoid and Isoflavonoid Biosynthesis with an Antisense Chalcone Synthase Construct in Transgenic Lotus Corniculatus," Plant Molecular Biology 35:509-522.
Datta, S. et al. (Jan. 2006). "*Arabidopsis* Constans-LIKE3 is a Positive Regulator of Red Light Signaling and Root Growth," Plant Cell 18(1):70-84.
Doerks, T. et al. (Jun. 1998). "Protein Annotation: Detective Work for Function Prediction," Trends Genet. 14(6):248-250.
Doyle, E. L. et al. (Jul. 2012). "Nucleic Acids TAL Effector-Nucleotide Targeter (TALE-NT) 2.0: Tools for TAL Effector Design and Target Prediction," Research 40:W117-122.
Elomaa, P. et al. (1996). "Transformation of Antisense Constructs of the Chalcone Synthase Gene Superfamily into *Gerbera hybrida*: Differential Effect on the Expression of Family Members," Molecular Breeding 2(1):41-50.
Emery, J. F. et al. (Oct. 14, 2003). "Radial Patterning of *Arabidopsis* Shoots by Class III HD-Zip and Kanadi Genes," Current Biology 13(20):1768-1774.
Fernandez-Suarez, X. M. et al. (Jan. 1, 2013). "The 2013 Nucleic Acids Research Database Issue and the online Molecular Biology Database Collection," Nucleic Acids Research 41:DI-D7.
Franco-Zorrilla, J. M. et al. (Aug. 2007). "Target Mimicry Provides a New Mechanism for Regulation of MicroRNA Activity," Nature Genetics 39(8):1033-1037.
Griffiths-Jones, S. et al. (Jan. 1, 2003). "Rfam: an RNA Family Database," Nucleic Acids Res. 31(1):439-441.
Guo, H. H. et al. (Jun. 14, 2004). "Protein Tolerance to Random Amino Acid Change," PNAS 101(25):9205-9210.
Gutterson, N (Aug. 1995). "Anthocyanin Biosynthetic Genes and Their Application to Flower Color Modification through Sense Suppression," HortScience 30(5):964-966.
Hedden, P. et al. (May 15, 2012). "Gibberellin Biosynthesis and its Regulation," Biochem. J. 444(1):11-25.
International Search Report and Written Opinion, mailed Jun. 24, 2019, for PCT Application No. PCT/US2010/018130, filed Feb. 15, 2019, 14 pages.
Jones-Rhoades, M. W. et al. (Jun. 18, 2004). "Computational Identification of Plant MicroRNAs and Their Targets, Including a Stress-Induced miRNA," Mal. Cell 14(6):787-799.
Katoh, T. et al. (2007). "Specific Residues at Every Third Position of siRNA Shape its Efficient RNAi Activity," Nucleic Acids Res. 35(4):e27, 14 pages.

(56) References Cited

OTHER PUBLICATIONS

Keskin, O. et al. (Jan. 1, 2009). "A New, Structurally Nonredundant, Diverse Data Set of Protein-Protein Interfaces and its Implications," Protein Science 13(4):1043-1055.
Khanna, R. et al. (Nov. 2009). "The *Arabidopsis* B-Box Zinc Finger Family," Plant Cell 21(11):3416-3420.
Khvorova, A. et al. (Oct. 17, 2003). "Functional siRNAs and miRNAs Exhibit Strand Bias," Cell 115(2):209-216.
Kim, V. N. (May 1, 2005). "MicroRNA Biogenesis: Coordinated Cropping and Dicing," Nature Rev. Mal. Cell. Biol. 6:376-385.
Larkin, M. A. et al. (Nov. 1, 2001). "Clustal Wand Clustal Version 2.0," Bioinformatics 23(21):2947-2948.
Last, D. I. et al. (May 1991). "PEmu: An Improved Promoter for Gene Expression in Cereal Cells," Theor. Appl. Genet. 81:581-588.
McCallum, C. M. et al. (Apr. 2000). "Targeted Screening for Induced Mutations," Nat. Biotechnol. 18(4):455-457.
McConnell, J. R. et al. (Jun. 7, 2001). "Role of Phabulosa and Phavoluta in Determining Radial Patterning in Shoots," Nature 411(6838):709-713.
McCormick, S. et al. (Apr. 1986). "Leaf Disc Transformation of Cultivated Tomato (*L. Esculentum*) Using Agrobacterium Tumefaciens," Plant Cell Reports 5:81-84.
McElroy, D. et al. (Dec. 1991). "Construction of Expression Vectors Based on the Rice Actin 1 (Act1) 5' Region for Use in Monocot Transformation," Mal. Gen. Genet. 231(1):150-160.
Ngo, J. T. et al. (1994). "Computational Complexity, Protein Structure Prediction, and the Levinthal Paradox" Chapter 14 in The Protein Folding Problem and Tertiary Structure Prediction, Merz, K. et al eds., Springer Science Business Media pp. 492-495.
Nishimura, A. et al. (May 2000). "Over-expression of Tobacco Knotted1-Type Class1 Homeobox Genes Alters Various Leaf Morphology," Plant Cell Physiol. 41(5):583-590.
Nunes, A. C. S. et al. (Jun. 2006). "RNAi-mediated Silencing of the Myo-Inositol-1-Phosphate Synthase Gene (GmMIPS1) in Transgenic Soybean Inhibited Seed Development and Reduced Phytate Content," Planta 224:125-132.
Parizotto, E. A. et al. (Sep. 15, 2004). "In Vivo Investigation of the Transcription, Processing, Endonucleolytic Activity, and Functional Relevance of the Spatial Distribution of a Plant MiRNA," Genes Dev. 18(18):2237-2242.
Pater, B. S. D. et al. (Nov. 1992). "The Promoter of the Rice Gene GOS2 is Active in Various Different Monocol Tissues and Binds Rice Nuclear Factor ASF-1," The Plant Journal 2(6):837-844.
Paul, J. W. et al. (Jul. 2016). "CRISPR/Cas9 for Plant Genome Editing: Accomplishments, Problems and Prospects," Plant Cell Reports 35(7):1417-1427.
Petti, C. et al. (Sep. 2015). "Mapping of a Cellulose-Deficient Mutant Named dwarf1-1 in Sorghum Bicolor to the Green Revolution Gene Gibberellin20-oxidase Reveals a Positive Regulatory Association between Gibberellin and Cellulose Biosynthesis, " Plant Physiology 169(1):705-716.
Putterill, J. et al. (Mar. 24, 1995). "The Constans Gene of *Arabidopsis* Promotes Flowering and Encodes a Protein Showing Similarities to Zinc Finger Transcription Factors," Cell 80(6):847-857.
Qiao, F. et al. (2011). "The Influence of RNAi Targeting of OsGA20ox2 Gene on Plant Height in Rice," Plant Molecular Biology Reporter 29(4):952-960.
Qiao, F. et al. (2013). "Alteration of Rice Growth and Development via Antisense Expression of OsGA20ox2 Gene," African Journal of Biotechnology 12(5):3898-3904.
Reynolds, A. et al. (Feb. 1, 2004). "Rational SiRNA Design for RNA Interference," Nature Biotechnol. 22:326-330.
Rhoades, M. W. et al. (Aug. 23, 2002). "Prediction of Plant MicroRNA Targets," Cell 110(4):513-520.
Robson, F. et al. (Dec. 2001). "Functional Importance of conserved domains in the Flowering-Time Gene Constans Demonstrated by Analysis of Mutant Alleles and Transgenic Plants, " The Plant Journal 28(6):619-631.
Russnogle, J. (Feb. 1, 1998). "Dwarf Com Earns Tall Praise," located at a href="https://www.farmprogress.com/dwarf-corn-earns-tall-praise" target="_blank"https://www.farmprogress.com/dwarf-com-earns-tall-praise/a last visited on Sep. 21, 2021, 4 pages.
Scofield, G. N. et al. (2007). "The Role of the Sucrose Transporter, OsSUT1, in Germination and Early Seedling Growth and Development of Rice Plants," Journal of Experimental Botany 58(3):483-495.
Shimizu, M. et al. (Nov. 26, 2004). "Photoperiod-regulated Expression of the PpCOLI gene encoding a homolog of CO/COL protein in the Moss Physcomitrella Patens," Biochem Biophys. Res. Commun. 324(4):1296-1301.
Smith, T. F. et al. (Nov. 1, 1997). "The Challenges of Genome Sequence Annotation or 'The Devil is in the Details'," Nature Biotechnology 15:1222-1223.
Song, J. et al. (2011) "Genome-Wide Identification of Gibberellins Metabolic Enzyme Genes and Expression Profiling Analysis During Seed Germination in Maize" Gene, 482:34-42.
Suarez-Lopez, P. et al. (Apr. 26, 2001). "Constans Mediates between the Circadian Clock and the Control of Flowering in *Arabidopsis*," Nature 410(6832):1116-1120.
Sunkar, R. et al. (Aug. 2004). "Novel and Stress-Regulated MicroRNAs and Other Small RNAs from *Arabidopsis*," Plant Cell 16(8):2001-2019.
Thompson, J. D. et al. (Nov. 11, 1994). "Clustal W: Improving the Sensitivity of Progressive Multiple Sequence Alignment through Sequence Weighting, Position-Specific Gap Penalties and Weight Matrix Choice," Nucleic Acids Research 22(22):4673-4680.
Thornton, J. M. et al. (Nov. 2000). "From Structure to Function: Approaches and Limitations," Nature structural Biology 7:991-994.
Vaucheret, H. (Sep. 6, 2005). "MicroRNA-Dependent Trans-Acting siRNA Production," Science STKE 2005(300):pe43.
Wells, J. A. (Sep. 18, 1990). "Additivity of Mutational Effects in Proteins," Biochemistry 29(37):8509-8517.
Wenkel, S. et al. (Nov. 2006). "Constans and the CCAAT Box Binding Complex Share a Functionally Important Domain and Interact to Regulate Flowering of *Arabidopsis*," The Plant Cell 18(11):2971-2984.
Yang, D. et al. (Sep. 25, 2001). "Expression of the REB Transcriptional Activator in Rice Grains Improves the Yield of Recombinant Proteins Whose Genes are Controlled by a Reb-Responsive Promoter," PNAS 98(20):11438-11443.
Yanik, M. et al. (Dec. 5, 2013). "TALE-PvuII Fusion Proteins—Novel Tools for Gene Targeting, " PLoS One 8(12):e82539:13 pages.
Yoshikawa, M. et al. (Sep. 15, 2005). "A Pathway for the Biogenesis of Trans-Acting siRNAs in *Arabidopsis*," Genes Dev. 19(18):2164-2175.
Zeng, Y. et al. (Jun. 2002). "Both Natural and Designed Micro RNAs Can Inhibit the Expression of Cognate mRNAs When Expressed in Human Cells," Mal. Cell 9(6):1327-1333.

\* cited by examiner

SEQUENCE LISTING

```
Sequence total quantity: 452
SEQ ID NO: 1            moltype = DNA  length = 1741
FEATURE                 Location/Qualifiers
source                  1..1741
                        mol_type = unassigned DNA
                        organism = Zea mays
SEQUENCE: 1
gacggtagtt ttcatctaaa gtttattctt cgtcacatgg gatggccgtt tgcttgtttg   60
ttgcttccgg gaggcggtgg tgaattgaag cagatcgaca agcatggctg cccactggtc  120
tcgatcgatc ggcctgccat gccatgccat gccactagag tccgtcctga ctggccgccc  180
gttcccccgt ataaaaaggc aggcaggcag gcagagcggg gacgagcaag caagcagttg  240
```

```
cagttgcagc ggcctcctcc tctgcttcct ccctcctcct cctcaccatg gtgctggctg    300
cgcacgatcc ccctcccctt gtgttcgacg ctgcccgcct gagcggcctc tccgacatcc    360
cgcagcagtt catctggccg gcggacgaga gccccacccc ggactccgcc gaggagctgg    420
ccgtgccgct catcgacctc tccggggacg ccgccgaggt ggtccggcag gtccggcgcg    480
cctgcgacct gcacggcttc ttccaggtgg tggggcagg catcgacgcg gcgctgacgg    540
cggaggccca ccgctgcatg gacgccttct tcacgctgcc gctcccggac aagcagcgcg    600
cgcagcgccg ccaggggac agctgcggct acgccagcag cttcacgggc cggttcgcgt    660
ccaagctgcc ctgaaggag acgctgtcgt tccgctacac cgacgacgac gacggcgaca    720
agtccaagga cgtcgtggcg tcctacttcg tggacaagct gggcgagggg taccggcacc    780
acggggaggt gtacgggcgc tactgctctg agatgagccg tctgtcgctg gagctcatgg    840
aggtgctagg cgagagcctg ggcgtggggc ggcgccactt ccggcgcttc ttccagggga    900
acgactccat catgcgcctc aactactacc cgccgtgcca gcggcctac gacacgctgg    960
gcacggggcc gcattgcgac cccacgtcgc tcaccatcct gcaccaggac gacgtgggcg   1020
gactcaggt gttcgacgcc gccacgctcg cgtggcgctc catcaggccc cgcccgggcg   1080
ccttcgtcgt caacatcggc gacaccttca tggcgctctc caacgggcgc tacaggagct   1140
gcctccaccg cgccgtcgtc aacagccggg tggcacgccg ctcgctcgcc ttcttcctgt   1200
gcccggagat ggacaaggtg gtcaggccgc caaggagct ggtggacgac gccaacccga   1260
gggcgtaccc ggacttcacg tggaggacgc tgctggactt caccacaggt cactacaggt   1320
cggacatgag gacgctcgag gccttctcca actggctcag caccagtagc aatggcggac   1380
agcacctgct ggagaagaag taggcatgct atttgggtat ggaagatggt ggatgtaagc   1440
aaacaaagcc aaattaagca gagtaggtta ttaaggttg gctgatgatc catttaggga    1500
aggagctgat ctccctgact ccctcctcca attttctcaa ccaaatttat atagtataat   1560
aataataata aaatagcaag taatagttgt atcgtattat tattaattaa tttattagct   1620
ggtaggcaag tagtattaaa taccattgt agtacgatgg gcgtatttct attttggcgt   1680
tttgctctgt gttttttgac gtttcctttg gatttggggg gacctcagat cagctcggcc   1740
t                                                                  1741

SEQ ID NO: 2           moltype = DNA  length = 1116
FEATURE                Location/Qualifiers
source                 1..1116
                       mol_type = unassigned DNA
                       organism = Zea mays
SEQUENCE: 2
atggtgctgg ctgcgcacga tcccctccc cttgtgttcg acgctgcccg cctgagcggc    60
ctctccgaca tcccgcagca gttcatctgg ccggcggacg agagccccac cccggactcc   120
gccgaggagc tggccgtgcc gctcatcgac ctctccgggg acgccgccga ggtggtccgg   180
caggtccggc gcgcctgcga cctgcacggc ttcttccagg tggtggggca cggcatcgac   240
gcggcgctga cggcggaggc ccaccgctgc atggacgcct tcttcacgct gccgctcccg   300
gacaagcagc gcgcgcagcg ccgccagggg gacagctgcg gctacgccag cagcttcacg   360
ggccggttcg cgtccaagct gccctggaag gagacgctgt cgttccgcta caccgacgac   420
gacgacggca caagtccaa ggacgtcgtg gcgtcctact tcgtggacaa gctgggcgag   480
gggtaccggc accacgggga ggtgtacggg cgctactgct ctgagatgag ccgtctgtcg   540
ctggagctca tggaggtgct aggcgagagc ctgggcgtgg ggcggcgcca cttccggcgc   600
ttcttccagg ggaacgactc catcatgcgc ctcaactact accggccgtg ccagcggccc   660
tacgacacgc tgggcacggg gccgcattgc gaccccacgt cgctcaccat cctgcaccag   720
gacgacgtgg cggactcca ggtgttcgac gccgccacgc tcgcgtggcg ctccatcagg   780
ccccgcccgg gcgccttcgt cgtcaacatc ggcgacacct tcatggcgct ctccaacggg   840
cgctacagga gctgcctcca ccgcgccgtc gtcaacagcc gggtggcacg ccgctcgctc   900
gccttcttcc tgtgcccgga gatggacaag gtggtcaggc cgcccaagga gctggtggac   960
gacgccaacc cgagggcgta cccggacttc acgtggagga cgctgctgga cttcaccatg  1020
aggcactaca ggtcggacat gaggacgctc gaggccttct ccaactggct cagcaccagt  1080
agcaatggcg gacagcacct gctggagaag aagtag                            1116

SEQ ID NO: 3           moltype = AA   length = 371
FEATURE                Location/Qualifiers
source                 1..371
                       mol_type = protein
                       organism = Zea mays
SEQUENCE: 3
MVLAAHDPPP LVFDAARLSG LSDIPQQFIW PADESPTPDS AEELAVPLID LSGDAAEVVR    60
QVRRACDLHG FFQVVGHGID AALTAEAHRC MDAFFTLPLP DKQRAQRRQG DSCGYASSFT   120
GRFASKLPWK ETLSFRYTDD DDGDKSKDVV ASYFVDKLGE GYRHHGEVYG RYCSEMSRLS   180
LELMEVLGES LGVGRRHFRR FFQGNDSIMR LNYYPPCQRP YDTLGTGPHC DPTSLTILHQ   240
DDVGGLQVFD AATLAWRSIR PRPGAFVVNI GDTFMALSNG RYRSCLHRAV VNSRVARRSL   300
AFFLCPEMDK VVRPPKELVD DANPRAYPDF TWRTLLDFTM RHYRSDMRTL EAFSNWLSTS   360
SNGGQHLLEK K                                                       371

SEQ ID NO: 4           moltype = DNA  length = 1517
FEATURE                Location/Qualifiers
source                 1..1517
                       mol_type = unassigned DNA
                       organism = Zea mays
SEQUENCE: 4
caggaataaa ataagcctcc gcccggcttc gttgcatcca cgcacgcagc aagcgatcgg    60
atttcgccag catggcggcg gcggccgtgg tgttcgacgc cgaggcgctg agccgggagg   120
agcacatccc ggcgcagttc gtgtggccca ccgaggagcg ggccggcgcg ggcggcgtgg   180
aggaggtcgc catcccgtg gtcgacctcg gcgagttcct ccgccgcggg gtgctcccgc   240
gcggcgtggc ggaggcgtgc gagcgccacg gcgtcttcca ggtggtgaac cacggcgtgg   300
gcgccgcgct gctcgccgag gcctaccgct gttgcgacgc cttttacgcg ctcccgctcg   360
```

```
cggacaagca gcgcgcgcag cgccggcacg gggagaacca cggctacgcc agcagcttca  420
cgggccgctt ccactgctgc ctgccgtgga aggagacgct gtccttcaac tgccccgccg  480
gtgccgggac tgcgcgcgcc gtcgtcggct acttcgtcga cgtcctcggc gaggactacc  540
gccacatggg ggaggtgtac caggagtact gcgacgcgat gacgcgtctg cgctggacg   600
tgacggaggt gctggcggca gcgctggggc tggaccgcgg cgcactgcgg ggcttcttcg  660
agggcggcga ctccgtcatg cggctgaacc actaccggc gtgccggcag ccgcacctga   720
cgctggggac gggcccgcac cgggacccga cgtcgctgac gctgctgcac caggacgacg  780
tgggcgggct gcaggtgcgc gccggcgcg ggccgtggcg cgcggtgcgg ccccgcgcgg   840
acgcgttcgt ggtcaacatt ggcgacacct tcgccgcgct caccgacggg cgtcacacca  900
gctgcctgca ccgcgccgtg gtgaccggcg gcggctcccg ccgtcgctc gccttcttcc   960
tcaacccgcc gctggaccgc gtcgtccgcc cgccgggcgc gctcctccag gagaacaagc  1020
aggcgggccg cccgcgcgcg ttcccggact tcacgtggcg cgagttcctc gagttcacgc  1080
agaagcacta ccggtcggac gcgggcacca tggacgcctt cgtgtcgtgg atcgcggag   1140
gccgccgcca ccatggcgga caggaggagg gcaactgaa tcgatgcatc tctagctca    1200
ggcagcagcg cagcagctac caagaataat ggccggcgac ggagatgcag ctacgacga   1260
caaataaatt gagtgtttgt ggtacaataa ggacgaggac gatcaatggc gacctgtaac  1320
cggtgcagtt ttagttaatc tttcatggcg atatggcatt aaccaatcgt tggtgtaaaa  1380
tgcgtgcatg ctttgcatgc caatgttggc catgtgatgg cacagcgtga gtgtagctca  1440
cccaccgtga caacgtgcta atttcgtgtg gtcctagata ccaaggtcgt ctaatgaact  1500
tgatggattg atgattt                                                 1517

SEQ ID NO: 5           moltype = DNA  length = 1107
FEATURE                Location/Qualifiers
source                 1..1107
                       mol_type = unassigned DNA
                       organism = Zea mays
SEQUENCE: 5
atggcggcgg cggccgtggt gttcgacgcc gaggcgctga gccggagga gcacatcccg    60
gcgcagttcg tgtggcccac cgaggagcgg gcgccggcgg gcggcgtgga ggaggtcgcc  120
atcccggtgg tcgacctcgg cgagttcctc cgccgcgggg tgctcccgcg cggcgtggga  180
gaggcgtgcg agcgccacgg cgtcttccag gtggtgaacc acggcgtggg cgccgcgctg  240
ctcgccgagg cctaccgctg ttgcgacgcc ttttacgcgc tcccgctcgc ggacaagcag  300
cgcgcgcagc gccggcacgg ggagaaccac ggctacgcca gcagcttcac gggccgcttc  360
cactgctgcc tgccgtggaa ggagacgctg tccttcaac gccccgcgg tgccgggact   420
gcgcgcgccg tcgtcggcta cttcgtcgac gtcctcggcg aggactaccg ccacatgggg  480
gaggtgtacc aggagtactg cgacgcgatg acgcgtctgg cgctggacgt gacggaggtg  540
ctggcggcag cgctggggct ggaccgcggc gcactgcgcg gcttcttcga gggcggcgac  600
tccgtcatgc ggctgaacca ctaccggcg tgccggcagc cgcacctgac gctggggacg   660
ggcccgcacc gggacccgac gtcgctgacg ctgctgcacc aggacgacgt gggcgggctg  720
caggtgcgcg ccggcggcgg gccgtggcgc gcggtgcggc cccgcgcgga cgcgttcgtg  780
gtcaacattg gcgacacctt cgccgcgctc accgacgggc gtcaccag ctgcctgcac    840
cgcgccgtgt gaccggcgg cggctcccgc cgtcgctcg ccttcttcct caacccgccg    900
ctggaccgcg tcgtccgccc gccgggcgcg ctcctccagg agaacaagc cgggccgc     960
ccgcgcgcgt tcccggactt cacgtggcgc gagttcctcg agttcacgca gaagcactac  1020
cggtcggacg cgggcaccat ggacgccttc gtgtcgtgga tcgcggagg ccgccgcac    1080
catggcggac aggaggaggg caactga                                       1107

SEQ ID NO: 6           moltype = AA  length = 368
FEATURE                Location/Qualifiers
source                 1..368
                       mol_type = protein
                       organism = Zea mays
SEQUENCE: 6
MAAAAVVFDA EALSREEHIP AQFVWPTEER APAGGVEEVA IPVVDLGEFL RRGVLPRGVA    60
EACERHGVFQ VVNHGVGAAL LAEAYRCCDA FYALPLADKQ RAQRRHGENH GYASSFTGRF   120
HCCLPWKETL SFNCPAGAGT ARAVVGYFVD VLGEDYRHMG EVYQEYCDAM TRLALDVTEV   180
LAAALGLDRG ALRGFFEGGD SVMRLNHYPA CRQPHLTLGT GPHRDPTSLT LLHQDDVGGL   240
QVRAGGGPWR AVRPRADAFV VNIGDTFAAL TDGRHTSCLH RAVVTGGGSR RSLAFFLNPP   300
LDRVVRPPGA LLQENKQAGR PRAFPDFTWR EFLEFTQKHY RSDAGTMDAF VSWIAGGRRH   360
HGGQEEGN                                                            368

SEQ ID NO: 7           moltype = DNA  length = 1522
FEATURE                Location/Qualifiers
source                 1..1522
                       mol_type = unassigned DNA
                       organism = Zea mays
SEQUENCE: 7
gcacactcgc agctcgcaca tctcatggtg tcctaagaac ggcaagagcc agctctgcct    60
agcagcagcg cacagccaca tcctatggacg ccagcccgac cccaccgctc ccctccgcg   120
ccccaactcc cagcattgac ctccccgctg caaggacag ggccgacgcg gcggctaaca    180
aggccgcggc tgtgttcgac ctgcgccggg agcccaagat cccggagcca ttcctgtggc  240
cgcacgaaga ggcgcggccg acctcggccg cggagctgga ggtgccggtg gtggacgtgg  300
gcgtgctgcg caatggcgac ggcgcggggc tccgccgcgc cgcggcgcaa gtggcggcgg  360
ccgccgcgac gcacggggttc ttccaggtgt gcgggcacgg ggtgcccggc gcgctggggc  420
gcgccgcgct ggacggcgcc agcgacttct tccggcgtgcc gctggctgag aagcagcggg   480
cccggcgcgt cccggcacc gtgtccggggt acacgagcgc gcacgccgac cggttcgcgt   540
ccaagctccc ctgaaggag accctgtcct tcggcttca cgacgcgcc gcggcgccc     600
tcgtcgtgga ctacttcacc ggcaccctcg gccaagattt cgagccagtg gggcgggtgt   660
accagaggta ctgcgaggag atgaaggagc tgtcgctgac gatcatggag ctgctggagc   720
```

| | | | | |
|---|---|---|---|---|
| tgagcctggg | cgtggagcgc | ggctactacc | gggagttctt | cgaggacagc cgctccatca | 780 |
| tgcggtgcaa | ctactacccg | ccgtgcccgg | tgcggagcg | cacgctgggc acgggcccgc | 840 |
| actgcgaccc | cacggcgctg | accatcctcc | tgcaggacga | cgtcggcggg ctggaggtcc | 900 |
| tggtggacgg | cgagtggcgc | cccgtccggc | cgtcccagg | cgccatggtc atcaacatcg | 960 |
| gcgacacctt | catgggcctg | tccaacgggc | ggtacaagag | ctgcctgcac cgcgcggtg | 1020 |
| tgaaccggcg | gcaggagcgg | caatcgctgg | ccttcttcct | gtgcccgcgc gaggaccggg | 1080 |
| tggtgcgccc | gccggccagc | gccgcgcgc | ggcagtaccc | ggacttcacc tgggccgacc | 1140 |
| tcatgcgctt | cacgcagcgc | cactaccgcg | ccgacacccg | cacgctggac gccttcaccc | 1200 |
| gctggctctc | ccacggcccg | gcggcggcgg | ctccctgcac ctaacgagcc ggccgtctct | 1260 |
| ttcgccgggg | cccgcgcggg | gttcgcccac | gtggtgatca | ggtggcagac atgtggccca | 1320 |
| cgggcccgc | gccgccttcc | ccattttggg | acgaccctac | tgctactact actagtgtac | 1380 |
| atatgcaaaa | aaatacatat | atatataggt | actttctcta | atattttat atataagcaa | 1440 |
| ggcggcctgg | tgttcttttc | tttgttttgt | cgacaactgt | tgatcccat cctatggacg | 1500 |
| atggatagtt | caatgtttgt | ac | | | 1522 |

```
SEQ ID NO: 8              moltype = DNA  length = 1161
FEATURE                   Location/Qualifiers
source                    1..1161
                          mol_type = unassigned DNA
                          organism = Zea mays
SEQUENCE: 8
```

| | | | | | |
|---|---|---|---|---|---|
| atggacgcca | gcccgacccc | accgctcccc | ctccgcgccc | caactcccag cattgacctc | 60 |
| cccgctggca | aggacagggc | cgacgcggcg | gctaacaagg | ccgcggctgt gttcgacctg | 120 |
| cgccgggagc | ccaagatccc | ggagccattc | ctgtggccgc | acgaagaggc gcggccgacc | 180 |
| tcggccgcg | agctggaggt | gccggtggtg | gacgtgggcg | tgctgcgcaa tggcgacggc | 240 |
| gcggggctcc | gccgcgccgc | ggccgaagtg | gcggccgcgc | ggcgacgca cgggttcttc | 300 |
| caggtgtgcg | gcacgcgcgt | ggacgcggcg | ctggggcgcg | ccgcgctgga cggcgccagc | 360 |
| gacttcttcc | ggctgccgct | ggctgagaag | cagcgggccc | ggcgcgtccc cggcaccgtg | 420 |
| tccgggtaca | cgagcgcgca | cgccgaccgg | ttcgcgtcca | agctcccctg gaaggagacc | 480 |
| ctgtccttcg | gcttccacga | ggccgccgcg | cccgtcgtg | gactcttcaccggc | 540 |
| accctcggcc | aagatttcga | gccagtgggg | cgggtgtacc | agaggtactg cgaggagatg | 600 |
| aaggagctgt | cgctgacgat | catgagctg | ctggagctga | gcctggggcgt ggagcgcggc | 660 |
| tactaccggg | agttcttcga | ggacagccgc | tccatcatgc | ggtgcaacta ctacccgccg | 720 |
| tgcccggtgc | cggagcgcac | gctgggcacg | ggcccgcact | gcgacccac ggcgctgacc | 780 |
| atcctcctgc | aggacgacgt | cggcgggctg | gaggtcctgg | tggacggcga gtggcgcccc | 840 |
| gtccggcccg | tcccaggcgc | catggtcatc | aacatcggcg | acaccttcat ggcgctgtcc | 900 |
| aacgggcggt | acaagagctg | cctgcaccgc | gcggtggtga | accggcggca ggagcggcaa | 960 |
| tcgctggcct | tcttcctgtg | cccgcgcgag | gaccgggtg | tgcgcccgcc ggccagcgcc | 1020 |
| gcgccggcc | agtacccgga | cttcacctgg | gccgacctca | tgcgcttcac gcagcgccac | 1080 |
| taccgcgcc | acacccgcac | gctggacgcc | ttcacccgct | ggctctccca cggccggcg | 1140 |
| gcggcggctc | cctgcaccta | a | | | 1161 |

```
SEQ ID NO: 9              moltype = AA  length = 386
FEATURE                   Location/Qualifiers
source                    1..386
                          mol_type = protein
                          organism = Zea mays
SEQUENCE: 9
```

| | | | | | |
|---|---|---|---|---|---|
| MDASPTPPLP | LRAPTPSIDL | PAGKDRADAA | ANKAAAVFDL | RREPKIPEPF LWPHEEARPT | 60 |
| SAAELEVPVV | DVGVLRNGDG | AGLRRAAAQV | AAACATHGFF | QVCGHGVDAA LGRAALDGAS | 120 |
| DFFRLPLAEK | QRARRVPGTV | SGYTSAHADR | FASKLPWKET | LSFGFHDGAA APVVVDYFTG | 180 |
| TLGQDFEPVG | RVYQRYCEEM | KELSLTIMEL | LELSLGVERG | YYREFFEDSR SIMRCNYYPP | 240 |
| CPVPERTLGT | GPHCDPTALT | ILLQDDVGGL | EVLVDGEWRP | VRPVPGAMVI NIGDTFMALS | 300 |
| NGRYKSCLHR | AVVNRRQERQ | SLAFFLCPRE | DRVVRPPASA | APRQYPDFTW ADLMRFTQRH | 360 |
| YRADTRTLDA | FTRWLSHGPA | AAAPCT | | | 386 |

```
SEQ ID NO: 10             moltype = DNA  length = 1457
FEATURE                   Location/Qualifiers
source                    1..1457
                          mol_type = unassigned DNA
                          organism = Zea mays
SEQUENCE: 10
```

| | | | | | |
|---|---|---|---|---|---|
| taatcacctc | atcacaggtc | ccccagcct | cactctcgcg | ccggctcaag gtacattgcg | 60 |
| tgtcctagcc | aagacacgca | gctcatctca | gcctcacaag | ccacagcaaga gcgaggcgtg | 120 |
| attcgccatg | gcggcctca | ctatggacca | ggccttcgtg | caggccccg agcaccgccc | 180 |
| caagcccatc | gtcaccgagg | ccaccggcat | ccctctcatc | gacctctcgc ctctggccgc | 240 |
| cagcggcggc | gccgtggacg | cgctggccgc | cgaggtgggc | gcggcgagcc gggactgggg | 300 |
| cttcttcgtg | gtcgtgggcc | acggcgtgcc | cgcagagcc | gtggcgcgcg cgacggaggc | 360 |
| gcagcgagcg | ttcttcgcg | tgccggcaga | gcggaaggcc | gccgtgcgga ggaacgaggc | 420 |
| ggagccgctc | gggtactacg | agtcggagca | caccaagaac | gtgagggact ggaaggaggt | 480 |
| gtacgacctc | gtgccgcgcg | agcgccgcc | gccggcagcc | gtggccgacg gcgagcttgt | 540 |
| gttcgataac | aagtggcccc | aggatctacc | gggcttcaga | gaggcgctgg aggagtacgc | 600 |
| gaaagcgatg | gaagagctgg | cgttcaagct | gctggagctg | atcgcccgga gcctgaagct | 660 |
| gaggccgacc | cggctgcacg | gcttcttcaa | ggaccaagaa | accttcatcc ggctgaacca | 720 |
| ctaccctcct | tgcccgagcc | ccgacctggc | cctcggcgtg | gggcggcaca aggacgccgg | 780 |
| cgccctgacc | atcctgtacc | aggacgacgt | cggggggctc | gacgtccggc ggcgctccga | 840 |
| cggcgagtgg | gtccgcgtca | ggcccgtgcc | cgactcgttc | atcatcaacg tcggcgacct | 900 |
| catccaggta | cgagagcgcg | gagcaccggg | tgtcggtgaa | ctcggcgagg agaggttct | 960 |
| ccatgcccta | cttcttcaac | ccggcgacct | acaccatggt | ggagccggtg gagagctgg | 1020 |

```
tgagcaagga cgatccgccc aggtacgacg cctacaactg gggcgacttc ttcagcacca    1080
ggaagaacag caacttcaag aagctcaacg tggagaacat tcagatcgcg catttcaaga    1140
agagcctcgt cctcgcctaa ctactgctac tgctaggatc catgccattg ccatgtcgtc    1200
ttcagattca gagcacgcca tgtcgtcgct agcttcgtgg tagaacaaat aatgatgtgc    1260
gtgctgtgtg taagcatgga tatggatgtg aatatgtaat atgatgagca ctcctacttt    1320
ggtatgtttg ggaataacag acttgtgttg gtctggttca ttatttgtaa gaaaatcaaa    1380
aagagttagt agggcaggag gctaaccaca gtcatgctgc accacatccc tggtggaaag    1440
ctggccgggt tacgcta                                                   1457

SEQ ID NO: 11           moltype = DNA   length = 1116
FEATURE                 Location/Qualifiers
source                  1..1116
                        mol_type = unassigned DNA
                        organism = Zea mays
SEQUENCE: 11
atgggcggcc tcactatgga ccaggccttc gtgcaggccc ccgagcaccg ccccaagccc      60
atcgtcaccg aggccaccgg catccctctc atcgacctct cgcctctggc cgccagcggc    120
ggcgccgtgg acgcgctggc cgccgaggtg gcgcgcgaga gccggactg ggcgcttctc      180
gtggtcgtgg gccacggcgt gcccgcagag accgtggcgc gcgcgacgga ggcgcagcga    240
gcgttcttcg cgctgccggc agagcggaag gccgccgtgc ggaggaacga ggcggagccg    300
ctcgggtact acgagtcgga gcacaccaag aacgtgaggg actggaagga ggtgtacgac    360
ctcgtgccgc gcgagccgcc ccgccggca gcctgcgc tgtgttcgat    420
aacaagtggc cccaggatct accgggcttc agagaggcgc tggaggagta cgcgaaagcc    480
atggaagagc tggcgttcaa gctgctggag ctgatcgccc ggagcctgaa gctgaggccc    540
gaccggctgc acggcttctt caaggaccag acgaccttca tccggctgaa ccactaccct    600
ccttgcccga gccccgacct ggcctcggc gtggggcggc acaaggacgc cggcgccctc    660
accatcctgt accaggacga cgtcggggg ctcgacgtcc ggcggcgctc cgacggcgag    720
tgggtccgcg tcaggcccgt gcccgactcg ttcatcatca acgtcggcga cctcatccag    780
gtacgagagc gcggagcacc gggtgtcggt gaactcggcg agggagaggt tctccatgcc    840
ctacttcttc aaccggcga cctaccacat ggtggagcgg gtggaggagc tggtgagcaa    900
ggacgatccg cccaggtacg acgcctacaa ctgggggcga ttcttcagca ccaggaagaa    960
cagcaacttc aagaagctca acgtggagaa cattcagatc gcgcatttca gaagagcct    1020
cgtcctcgcc taactactgc tactgctagg atccatgcca ttgccatgtc gtcttcagat    1080
tcagagcacg ccatgtcgtc gctagcttcg tggtag                              1116

SEQ ID NO: 12           moltype = AA    length = 371
FEATURE                 Location/Qualifiers
source                  1..371
                        mol_type = protein
                        organism = Zea mays
SEQUENCE: 12
MGGLTMDQAF VQAPEHRPKP IVTEATGIPL IDLSPLAASG GAVDALAAEV GAASRDWGFF     60
VVVGHGVPAE TVARATEAQR AFFALPAERK AAVRRNEAEP LGYYESEHTK NVRDWKEVYD    120
LVPREPPPPA AVADGELVFD NKWPQDLPGF REALEEYAKA MEELAFKLLE LIARSLKLRP    180
DRLHGFFKDQ TTFIRLNHYP PCPSPDLALG VGRHKDAGAL TILYQDDVGG LDVRRRSDGE    240
WVRVRPVPDS FIINVGDLIQ VRERGAPGVG ELGEGEVLHA LLLQPGDLHH GGAGGGAGEQ    300
GRSAQVRRLQ LGRLLQHEEQ QLQEAQRGEH SDRAFQEEPR PRLTTATAR IHAIAMSSSD    360
SEHAMSSLAS W                                                         371

SEQ ID NO: 13           moltype = DNA    length = 1733
FEATURE                 Location/Qualifiers
source                  1..1733
                        mol_type = unassigned DNA
                        organism = Zea mays
SEQUENCE: 13
atgaggccgc gcctccctcc aaatgttccc tccctgcctt cgtctttgtc gttgctcgca     60
aactccctgt cctcccctgt tacaaatacc ccaccgcc cggacagctt ccctgcatac    120
ttgcagctcg cacatctcat ggtgtcgcag gaacgacaag agccagctgt gcctagcagc    180
agcagcagca gcgccaagcg cgcagcacg tccatgaacg ccagcccgc cccgccgctc    240
ctcctccgcg cccccactcc cagcccccagc attgacctcc ccgctggcaa ggacaaggcc    300
gacgcggcgg ccagcaaggc cggcgcggcc gtgttcgacc tgcgccggga gcccaagatc    360
cccgcgccat tcctgtggcc gcaggaagag gcgcggccgt cctcggccgc ggagctggag    420
gtgccgatgg tggacgtggg cgtgctgcgc aatggcgacc gcgcggggct gcggcgcgcc    480
ggggcgcagg tggccggcgc gtgcgcgacg cacgggttct tccaggtgtg cgggcacggc    540
gtggacgcgg cgctggggcg cgccgcgctg gacggcgcca gcgacttctt ccggctgccg    600
ctcgccgaga gcagcgcgc cggcgcgtc ccggcaccg tgtccgggta cacgagcgcg    660
cacgccgacc ggttcgcggc caagctcccc tggaaggaga cctgtcgtt cggctaccac    720
gacggcgccg cgtcgcctgt cgtcgtggac tacttcgtcg gcaccctcgg ccaggatttc    780
gagccaatgg ggtgggtgta ccagaggtac tgcgaggaga tgcgggagct gtcgctgacg    840
atcatggagc tgctggagct gagcctgggc gtggagctgc gcggctacta ccgggagttc    900
ttcgaggaca gccggtccat catgcggtgc aactactacc cgccgtgccc ggagccggag    960
cgcacgctgg gcacgggccc gcactgcgac cccacgcgc tcaccatcct cctgcaggac    1020
gacgtgggcg ggctggaggt gctggtgac ggtgagtggc ccccgtccg gccgtcccg    1080
ggcgccatgg tcatcaacat cggcgacacc ttcctgcgg tgtcgaacgg gaggtacaag    1140
agctgcctgc accgcgcggt ggtgaaccag cggcgggcgc ggcggtcgct ggccttcttc    1200
ctgtgcccgc gcgaggaccg ggtggtgcgc ccgcggcca gtgctgcgcc gcggcgctac    1260
ccggacttca cctgggccga cctcatgcgc ttcacgcagc gccactaccg cgccgacacc    1320
cgcacgctgg acgccttcac ccgctggctc tcccacggcc cggcccaggc ggcggcgcct    1380
ccctgcacct agcgagccgg gccaaggccg tctctttcgc cccacgtgcg cgcccagctg    1440
```

```
ggcaggtggc cagacacgcg ccccgcgggc cccgcgccgc cttgccattt tttgacgctg    1500
gccctactgc tgtgctacta gtgtacatat gcaagagtac atatatatat atatatatac    1560
gtattttcta tatattatat ataaaagcaa ggcggcccgg tgcccttctc ttgttttgtc    1620
cacaactgtt tgatcccatt attctatgga ccatggatac ttcaatgttt gtactaagac    1680
cgtgaacgtg ggattctttt ccttcctctg tgttttttct gagaaaaatt aaa           1733

SEQ ID NO: 14          moltype = DNA  length = 1392
FEATURE                Location/Qualifiers
source                 1..1392
                       mol_type = unassigned DNA
                       organism = Zea mays
SEQUENCE: 14
atgaggccgc gcctccctcc aaatgttccc tccctgcctt cgtctttgtc gttgctcgca    60
aactccctgt cctccctgt tacaaatacc cccacccgcc cggacagctt ccctgcatac    120
ttgcagctcg cacatctcat ggtgtcgcag aacgacaag agccagctgt gcctagcagc     180
agcagcagca cgccaagcg cgcagccacg tccatgacg ccagcccggc cccgccgctc      240
ctcctccgcg cccccactcc cagccccagc attgacctcc ccgctggcaa ggacaaggcc    300
gacgcgccgg ccagcaaggc cggcgcggcc gtgttcgacc tgcgccggga gccaagatc     360
cccgcgccat tcctgtggcc gcaggaagag gcgcggccgt cctcggccgc ggagctggaa    420
gtgccgatgg tggacgtggg cgtgctgcgc aatggcgacc gcgcggggct gcggcgcgcc    480
gcggcgcagg tggccgcggc gtgcgcgacg cacgggttct ccaggtgtg cgggcacggc     540
gtggacgcgg cgctggggcg cgccgcgctg gacggccgca gcgactctt ccggctgccg     600
ctcgccgaga gcagcgcgc cggcgcgtc cccggcaccg tgtccgggta cacgagcgcg      660
cacgccgacc ggttcgcggc caagctcccc tggaaggaga ccctgtcgtt cggctaccac    720
gacggcgccg cgtcgcctgt cgtcgtggac tacttcgtcg caccctcgg ccaggatttc     780
gagccaatgg ggtgggtgta ccagaggtac tgcgaggagc tgaagagct gtcgctgacg     840
atcatggagc tgctggagct gagcctgggc gtggagctgc gcggctacta ccgggagttc    900
ttcgaggaca gccggtccat catgcggtgc aactactacc gccgtgccc ggagccggag     960
cgcacgctgg gcacgggccc gcactgcgac cccacgcgc tcaccatcct cctgcaggac    1020
gacgtgggcg ggctggaggt gctggtggac ggtgagtggc gcccgtccg gcccgtcccg   1080
ggcgccatgg tcatcaacat cggcgacacc ttcatggcc tgtcgaacgg gaggtacaag    1140
agctgcctgc accgcgcggt ggtgaaccag cggcgggcc ggcggtcgct ggccttcttc    1200
ctgtgccccg cgaggaccg ggtggtgcgc ccgccggca gtgctgcgcc gcggcgctac    1260
ccggacttca cctgggccga cctcatgcgc ttcacgcagc gccactaccg cgccgacacc    1320
cgcacgctgg acgccttcac ccgctggctc tcccacggcc cggcccaggc ggcggcgcct    1380
ccctgcacct ag                                                       1392

SEQ ID NO: 15          moltype = AA  length = 463
FEATURE                Location/Qualifiers
source                 1..463
                       mol_type = protein
                       organism = Zea mays
SEQUENCE: 15
MRPRLPPNVP  SLPSSLSLLA  NSLSSPVTNT  PTRPDSFPAY  LQLAHLMVSQ  ERQEPAVPSS    60
SSSSAKRAAT  SMDASPAPPL  LLRAPTPSPS  IDLPAGKDKA  DAAASKAGAA  VFDLRREPKI   120
PAPFLWPQEE  ARPSSAAELE  VPMVDVGVLR  NGDRAGLRRA  AAQVAAACAT  HGFFQVCGHG   180
VDAALGRAAL  DGASDFFRLP  LAEKQRARRV  PGTVSGYTSA  HADRFAAKLP  WKETLSFGYH   240
DGAASPVVVD  YFVGTLGQDF  EPMGWVYQRY  CEEMKELSLT  IMELLELSLG  VELRGYYREF   300
FEDSRSIMRC  NYYPPCPEPE  RTLGTGPHCD  PTALTILLQD  DVGGLEVLVD  GEWRPVRPVP   360
GAMVINIGDT  FMALSNGRYK  SCLHRAVVNQ  RRARRSLAFF  LCPREDRVVR  PPASAAPRRY   420
PDFTWADLMR  FTQRHYRADT  RTLDAFTRWL  SHGPAQAAAP  PCT                      463

SEQ ID NO: 16          moltype = DNA  length = 1510
FEATURE                Location/Qualifiers
source                 1..1510
                       mol_type = unassigned DNA
                       organism = Zea mays
SEQUENCE: 16
aaagagcgcg cgacggcggc ccctgggaga gccatgcgag actgaggcg gaaccgcgca      60
cgacaccaag ctgccgcgcc ggactgctgc acgcaagcgc agcgaggac cgaccgacct     120
ccgtaggcac gcacgcgcc ggcggcatgg cggagcacct cctgtcgacg gccgtgcacg      180
acacgctgcc ggggagctac gtgcggccgg agcggagcg cccgcgcctc gcggaggtcg     240
tgaccggcgc gcgcatcccc gtcgtggacc tgggcagccc cgaccgcggc gcggtcgtgg     300
ccgccgtcgg cgacgcctgc cgctcgcacg gcttcttcca ggtcgtcaac cacgggatac     360
acgccgccct ggtcgcggcg gtgatggccg cggggcgcgg cttcttccgg ctgcccccgg     420
aggagggc caagctctac tccgacacc ccgccaggaa gatccggctg tccaccagct        480
tcaacgtgcg caaggagacg gtgcacaact ggcgcgacta cctccgcctg cactgccatc     540
ccctcgacga gttcctgccc gattggccgt ccaacccgcc cgatttcaag gagaccatgg     600
gcacctactg caaggagtc cgggagctcg gttcaggct gtaccgcgg atctcggaga         660
gcctggcct agaggcgagc tacatgaagg aagcgctggg ggagcaggag cagcacatgg       720
cggtcaactt ctaccgccg tgccggagc cggagctcac ctacgcctc ccggcgcaca        780
ccgaccccaa cgcgctcacc atcctgctca tggacccgga cgtcgccggc ctgcaggtgc     840
tccacgccgg ccagtgggtc gccgtcaacc cgcagcccgg cgcgctcatc atcaacatcg     900
gcgaccggcg ccaggagctg agcaacgggc agtaccggag cgtgtggcc gcggcgggtc       960
tgaactcgga ccgggagcgc atgtccgtgg cgtcgttcct gtgccgtgc aaccacgtcg     1020
tgctcggccc cgcgcggaag ctcgtcaccg gaacaccc ggccgtgtac aggaactaca      1080
cgtacgacaa gtactacgcc aagttctgga gcaggaacct ggaccaggag cactgcctcg    1140
agctcttcag aacctagcga atcggatacg gatggatgga tacattacat acgcgccctc    1200
tgttttttct catgacgtta gaagaacacg ttctgcaatg tttgtccatt caaggtggta    1260
```

```
tcaatcaagg ctgtggtcgt tgcaattctt ccgctccata tacatgatta aatgctttga   1320
aagaaaaaga aaaaaaagaa acacaagtat tatggcacta ctagtgtttt taggaacaag   1380
gaaagagggg ttgcccctgc tggctatata tattaaatat aaataaaggt aaggctgtag   1440
acattggtga ataagagaaa gtatttgagt ttctctattg tcactccaga acagactcct   1500
ttgcctcgat                                                           1510

SEQ ID NO: 17          moltype = DNA   length = 1011
FEATURE                Location/Qualifiers
source                 1..1011
                       mol_type = unassigned DNA
                       organism = Zea mays
SEQUENCE: 17
atggcggagc acctcctgtc gacggccgtg cacgacacgc tgccggggag ctacgtgcgg     60
ccggagcggg agcgcccgcg cctcgcggag gtcgtgaccg gcgcgcgcat ccccgtcgtg   120
gacctgggca gccccgaccg cggcgcggtc gtggccgccg tcggcgacgc ctgccgctcg   180
cacggcttct tccaggtcgt caaccacggg atacacgccg ccctggtcgc ggcggtgatg   240
gccgcggggc gcggcttctt ccggctgccc ccgaggaga aggccaagct ctactccgac    300
gaccccgcca ggaagatccg gctgtccacc agcttcaacg tgcgcaagga cacggtgcac   360
aactggcgcg actacctccg cctgcactgc catcccctcg acgagttcct gcccgattgg   420
ccgtccaacc cgcccgattt caaggagacc atgggcacct actgcaagga ggtccgggag   480
ctcgggttca ggctgtacgc cgcgatcctg gagagcctgg gcctagaggc gagctacatg   540
aaggaagcgc tgggggagca ggagcagcac atggcggtca acttctaccc gccgtgcccg   600
gagccggagc tcacctacgg cctccccggc cacaccgacc ccaacgctcc caccatcctg   660
ctcatggacc cggacgtcgc cggcctgcag gtgctccacg ccggccagtg ggtcgccgtc   720
aacccgcagc ccggcgcgct catcatcaac atcggcgacc agctgcaggc gctgagcaac   780
gggcagtacc ggagcgtgtg gcaccgcgcg gtggtgaatc ggacgcatgtcc            840
gtggcgtcgt tcctgtgccc gtgcaaccac gtcgtgctcg gccccgcgcg gaagctcgtc   900
accgaggaca ccccggccgt gtacaggaac tacacgtacg acaagtacta cgccaagttc   960
tggagcagga acctggacca ggagcactgc ctcgagctct cagaaccta g             1011

SEQ ID NO: 18          moltype = AA    length = 336
FEATURE                Location/Qualifiers
source                 1..336
                       mol_type = protein
                       organism = Zea mays
SEQUENCE: 18
MAEHLLSTAV HDTLPGSYVR PEPERPRLAE VVTGARIPVV DLGSPDRGAV VAAVGDACRS    60
HGFFQVVNHG IHAALVAAVM AAGRGFFRLP PEEKAKLYSD DPARKIRLST SFNVRKETVH   120
NWRDYLRLHC HPLDEFLPDW PSNPPDFKET MGTYCKEVRE LGFRLYAAIS ESLGLEASYM   180
KEALGEQEQH MAVNFYPPCP EPELTYGLPA HTDPNALTIL LMDPDVAGLQ VLHAGQWVAV   240
NPQPGALIIN IGDQLQALSN GQYRSVWHRA VVNSDRERMS VASFLCPCNH VVLGPARKLV   300
TEDTPAVYRN YTYDKYYAKF WSRNLDQEHC LELFRT                             336

SEQ ID NO: 19          moltype = DNA   length = 1387
FEATURE                Location/Qualifiers
source                 1..1387
                       mol_type = unassigned DNA
                       organism = Zea mays
SEQUENCE: 19
gttttctttt tgaacgtaac tgacagaagc tatctgccta gctacggcgt gtcggttgct     60
tgtctcacca aagcagcgac atggaagcct gacagctcgt cgcgtcgcgc catttccacc   120
caacaaagcg gcggcgccag cacgcactgc ttctgcttgt gcgtgctcct ccgttccggg   180
cacgcctcta aagtctatac agcctcgaat ccatcccggc cgccgctcct ggggatact    240
acagcgagcc gaagcgggga tggcggagat ccctgtgatc gacctgcgcg tcgcggctc    300
ggccgccgag gagtccgcgc ggctgcgggc cgcgtccgag gcctcgggct gcttccggat   360
gaccggccac ggcgtgccct cggtgctcct ggcagagatg aaggccgccg tgcgcgcgct   420
cttcgacctc cccgacgacg ccaagcgccg caacgccgac gtcatcaccg gcagcggcta   480
cgtcgccccc agcccgacca accgctcta cgaggcttc gggctcctcg acgccgccgt     540
gcccaccgac gtcgacgcct tttgcgcgct cctcgacgcg ccgccaaca tcagggagac   600
cgtcaaggcc tacgcggaga agatgcacga tgtgatcgtt ggcgtcgccc gcgagctggc   660
gtctagcctg gggctagtcg aggagcactc gttccaggac tggccgtgcc agttccgcat   720
caacaggtac aactacacgc gggagacggt gggctcctcc ggcgtgcaga cccacacgga   780
ctcgggcttc ctcaccgtgc tccatgagga cgagtgtgtc ggcggcctcg aggtcctgga   840
cccgggcacc ggcgagttcg tgcccgtgga cccgtccgga ggctcctttc tcgtaaacat   900
cggcgacgtc ggcacggcgt ggagcaacgg gaggctgcac aacgtgaagc accgggtgcg   960
gtgcgtcgca cccgtgccgc gcatctccat cgccatgttc ctgctcgcac ccaaggacga  1020
cagcgtgagc gcaccggcgg cgttcgtgga cgcggaccac ccgcgcaggt acaaggtgtt  1080
caactacaac gactatcgga ggctcagact gtccaccggc gagcacgcag gcgaggcgct  1140
cgcacggatg gcgcgcgtgac gtggctggag ctgcaaattg gattggaagc cgagacaagg  1200
cgttagttat ttaccatgcc cgtgcgttca ccgcacacaa tcatattcaa agccataaa   1260
ataaaaaata attttaatat cagtcaacat atggtttaaa tatcatatgg agtacaaat   1320
tccgaattttt tttttgtaat ttagtctgtc ttttgaaaaa aatgcacatc tagacctccg  1380
gatgact                                                             1387

SEQ ID NO: 20          moltype = DNA   length = 900
FEATURE                Location/Qualifiers
source                 1..900
                       mol_type = unassigned DNA
                       organism = Zea mays
```

```
SEQUENCE: 20
atggcggaga tccctgtgat cgacctgcgc gtcgccggct cggcggccga ggagtccgcg   60
cggctgcggg ccgcgtgcga gcgcctgggc tgcttccggg tgaccggcca cggcgtgccc  120
tcggtgctcc tggcagagat gaaggccgcc gtgcgcgcgc tcttcgacct ccccgacgac  180
gccaagcgcc gcaacgccga cgtcatcacc ggcagcggtc acgtcgcccc cagcccgacc  240
aacccgctct acgaggcctt cgggctcctc gacgccgccg tgcccaccgt cgtcgacgcc  300
ttttgcgcgc tcctcgacgc gccgcccaac atcagggaga ccgtcaaggc ctacgcggag  360
aagatgcacg atgtgatcgt tggcgtcgcc cgcgagctgg cgtctagcct ggggctagtc  420
gaggagcact cgttccagga ctggccgtgc cagttccgca tcaacaggta caactacacg  480
cgggagacgg tgggctcctc cggcgtgcag acccacacgg actcgggctt cctcaccgtg  540
ctccatgagg acgagtgtgt cggcggcctc gaggtcctgg acccgggcac cggcgagttc  600
gtgcccgtgg accccgtcgc gggctccttt ctcgtaaaca tcggcgacgt cggcacggcc  660
tggagcaacg ggaggctgca caacgtgaag caccgggtgc ggtgcgtcgc acccgtgccg  720
cgcatctcca tcgccatgtt cctgctcgca cccaaggacg acagcgtgag cgcaccggcg  780
gcgttcgtgg acgcggacca cccgcgcagg tacaaggtgt tcaactacaa cgactatcgg  840
aggctcagac tgtccaccgg cgagcacgca ggcgaggcgc tcgcacggat ggcggcgtga  900

SEQ ID NO: 21             moltype = AA   length = 299
FEATURE                   Location/Qualifiers
source                    1..299
                          mol_type = protein
                          organism = Zea mays
SEQUENCE: 21
MAEIPVIDLR  VAGSAAEESA  RLRAACERLG  CFRVTGHGVP  SVLLAEMKAA  VRALFDLPDD   60
AKRRNADVIT  GSGYVAPSPT  NPLYEAFGLL  DAAVPTDVDA  FCALLDAPPN  IRETVKAYE   120
KMHDVIVGVA  RELASSLGLV  EEHSFQDWPC  QFRINRYNYT  RETVGSSGVQ  THTDSGFLTV  180
LHEDECVGGL  EVLDPGTGEF  VPVDPVAGSF  LVNIGDVGTA  WSNGRLHNVK  HRVRCVAPVP  240
RISIAMFLLA  PKDDSVSAPA  AFVDADHPRR  YKVFNYNDYR  RLRLSTGEHA  GEALARMAA   299

SEQ ID NO: 22             moltype = DNA   length = 1496
FEATURE                   Location/Qualifiers
source                    1..1496
                          mol_type = unassigned DNA
                          organism = Zea mays
SEQUENCE: 22
gtcggtctct tgtctcacca aaccggcgac atggtacatg gaggccagcc cgtcgcttgg   60
cgccacaagt ctcggtgccg tccgtccgac aagcggcgcc agcgcacgct ggctgctcgt  120
gcacgcctct aaatacggcc ccggaccgcc caccaagcga aggccaatcc cgtccgcgc   180
ccccaccaa ccacgaacca cgcaagcgaa cccggccagc ggcggggcag gcgatggcg   240
gagatcccgg tgatcgacct gcgcctcgcc ggctcgtcgc ccgacgagtc ggcgcggctg  300
cgcgacgcgt gcgagcgcct gggctgcttt cgggtgaccg gccacggcgc gcccgcgggg  360
ctcctggccg acatgaaggc cgccgtgcgc gcgctcttcg acctcccga cgacgccaag   420
cgccgcaacg ccgacgtcat ccccggcagc ggctacgtcg cgccctgccc cgccaaccg  480
ctctacgagg ccttcgggct cctcgacgcc gccgcgcccg ccgacgtcga cgccttctgc  540
gcgcgcctcg acgcgccgcc caaagtcagg gagaccgtca agacctacgc ggagaagatg  600
cacgacgtga tcgtcggcgt cgccggcgag ctggccacca gcctggggct gggcctggag  660
gagcactcgt tccaggactg gccgtgccag ttccgcatca acaggtacaa ctacacgcag  720
gagacggtgg gctcctccgg cgtgcagacc cacacggact cgggcttcct caccgtgctc  780
caggaggacg agtgcgtcgg cggcctcgag gtgctggacc ccgccgccgg tgagttcgtg  840
cccgtggacc ccgtcgccgg ctccttcctc gtcaacatcg gcgacgtcgg cacggcgtgg  900
agcaacggga ggctccacaa cgtgaagcac cgggtgcggt gcgtcgccc cgtgccgcgc   960
atctccatcg ccatgttcct gctgcgcgcc aaggacgacc gcgtgagcgc ccgggaggcg  1020
ttggtcgacg cggaccaccc gcgtcggtac aagccgttca actacgacga ctaccggagg  1080
ctccggctgt ccaccggcga gcgcgcaggc gaggcgctcg cgcggatggc ggcgtgatgt  1140
cgtcacgcac gtgcaagccg ttaattatag gctcgcgcat gcatacgcct acacgagagg  1200
ttgtctcgtt aagccgttct attaaaatgt gtgggggaga aagatgacta ccgtggtgcc  1260
atgtggattg ctatcgggtc tgatcaataa aatcttgcaa cacttgcacg tgcgattcca  1320
tatcctagca cgggtgggcg ccacgctagt aggtagagac cggagcggcc aaaaaatggc  1380
tacagcacca gtaggtgaac tctcaagcaa cactggctat cccacttctg acgttgtctc  1440
tctcatcact atgtatgacc agcgaatgaa gtgtttaaaa atctgacgcc gtgaaa       1496

SEQ ID NO: 23             moltype = DNA   length = 903
FEATURE                   Location/Qualifiers
source                    1..903
                          mol_type = unassigned DNA
                          organism = Zea mays
SEQUENCE: 23
atggcggaga tcccggtgat cgacctgcgc ctcgccggct cgtcgcccga cgagtcggcg   60
cggctgcgcg acgcgtgcga gcgcctgggc tgctttcggg tgaccggcca cggcgcgccc  120
gcggggctcc tggccgacat gaaggccgcc gtgcgcgcgc tcttcgacct ccccgacgac  180
gccaagcgcc gcaacgccga cgtcatcccc ggcagcggct acgtcgcgcc ctgccccgcc  240
aacccgctct acgaggcctt cgggctcctc gacgccgccg cgcccgccga cgtcgacgcc  300
ttctgcgcgc gcctcgacgc gccgcccaaa gtcagggaga ccgtcaagac ctacgcggag  360
aagatgcacg acgtgatcgt cggcgtcgcc ggcgagctgg ccaccagcct ggggctggag  420
ctggaggagc actcgttcca ggactggccg tgccagttcc gcatcaacag gtacaactac  480
acgcaggaga cggtgggctc ctccggcgtg cagacccaca cggactcggg cttcctcacc  540
gtgctccagg aggacgagtg cgtcggcggc ctcgaggtgc tggaccccgc cgccggtgag  600
ttcgtgcccg tggaccccgt cgccggctcc ttcctcgtca acatcggcga cgtcggcacg  660
gcgtggagca acgggaggct ccacaacgtg aagcaccggg tgcggtgcgt cgcgcccgtg  720
```

```
ccgcgcatct ccatcgccat gttcctgctg gcgcccaagg acgaccgcgt gagcgcccg    780
gaggcgttgg tcgacgcggg ccacccgcgt cggtacaagc cgttcaacta cgacgactac    840
cggaggctcc ggctgtccac cggcgagcgc gcaggcgagg cgctcgcgcg gatggcggcg    900
tga                                                                   903

SEQ ID NO: 24           moltype = AA   length = 300
FEATURE                 Location/Qualifiers
source                  1..300
                        mol_type = protein
                        organism = Zea mays
SEQUENCE: 24
MAEIPVIDLR LAGSSPDESA RLRDACERLG CFRVTGHGAP AGLLADMKAA VRALFDLPDD    60
AKRRNADVIP GSGYVAPCPA NPLYEAFGLL DAAAPADVDA FCARLDAPPK VRETVKTYAE    120
KMHDVIVGVA GELATSLGLG LEEHSFQDWP CQFRINRYNY TQETVGSSGV QTHTDSGFLT    180
VLQEDECVGG LEVLDPAAGE FVPVDPVAGS FLVNIGDVGT AWSNGRLHNV KHRVRCVAPV    240
PRISIAMFLL APKDDRVSAP EALVDAGHPR RYKPFNYDDY RRLRLSTGER AGEALARMAA    300

SEQ ID NO: 25           moltype = DNA   length = 1614
FEATURE                 Location/Qualifiers
source                  1..1614
                        mol_type = unassigned DNA
                        organism = Zea mays
SEQUENCE: 25
accacacgaa ttgcacatct ccacagctca cgattccaac actagctaca tatatatgta    60
gctttctagg ctactatata cactcaccac caagtgtgaa gtgtgtatat atagtgacag    120
ctactgcaat atatacatac gcgtcaccta tatattagcc aagctagcta tatgagcttg    180
gttgcggcgc caatggcgat cgtcgacgtg gccaacgccc agctgcagca agcagcagca    240
gcagctgcca agaaagacga ggacggccat gagcagcagg agtcgtccta cgactacggc    300
gcgctgatga aaggcgtgag gcacctgtcg gacagcggga ttaccaggct gcccgacagg    360
tacgtcctgc ccgcgtccga ccgccccggc gtccttgccg tctcgtcgtc cgtggcgggc    420
agcggcaggg tcaagctccc tgtcgtcaac ctcgccggcc tccgcgaccc ctgccagcgg    480
gccgccgtgc tggccacgct cgacgccgcg tgccgggagt acggcttctt tcaggtggta    540
aaccacgggt tcgggagcga cgtgagcggc gggatgctgg acgtggcgca gcgcttcttc    600
gagctgccgc tggccgagcg agcgcggcac atgtcggcgg acgtgcgggc gccggtcgc    660
tacggcacca gcttcaacca ggccaaggac gacgtgctct gctgcgcga cttcctcaag    720
ctcgtctgcc agccgctgca ggcggtgctc ccgtactggc cccagcagcc ggcggacctc    780
agggacgtgg ccaccaggta cgccacggcg agccaccggc tgttcatgga ggtcatggag    840
gcggcgctgg aggcctgggg catccccacg gccggcggcc tgctcgggga gctggcagcg    900
tcgtcctcgc acatgatgac ggtgaactgc taccggccg gccgcagcc tgagctcacg    960
ctggggatgc cctcgcactc ggactacggc ctcttcacgt tcgtcctgca ggaccacgtc    1020
gagggcctcc aggtcatgca cgacggccgc tggctcacca tcgacccat cccgggatcg    1080
ttcgtcgtca acgtcggcga ccacctagag atctacagca cgggcggta caagagcgcg    1140
ctgcaccggg tgcacgtgaa ctccacgcgg ccgcgcatct cggtggcgtc gttccacagc    1200
ctgccggcgg agcgagtgat cgggccggcg ccggagctgg tggacgacga ggccggcaac    1260
ccgcggcggt acatggacac cgactcgct accttcctcg cctacctcgc atccgcggac    1320
ggcaagaaca agaccttcct ccagtcaagg aagctgcctg ctgctgctcc tccatgcctc    1380
tagctaacta gatagctgct tattaatctg acagaataaa attaatcgat tcagcgcaca    1440
attccacaag cgaaaacaaa cctggatttg ttttaattag ctctgcccttt cattattaca    1500
ttcaagctag ctcttggtca acgcatgcac acaagcttga gcattgactg gtcccttttc    1560
aatcggttgc attgtactcc ctccgtacca aaattggttg tcgctatagt attt          1614

SEQ ID NO: 26           moltype = DNA   length = 1212
FEATURE                 Location/Qualifiers
source                  1..1212
                        mol_type = unassigned DNA
                        organism = Zea mays
SEQUENCE: 26
atgagcttgg ttgcggcgcc aatggcgatc gtcgacgtgg ccaacgccca gctgcagcaa    60
gcagcagcag cagctgccaa gaaagacgag gacggccatg agcagcagga gtcgtcctac    120
gactacggcg cgctgatgaa aggcgtgagg cacctgtcgg acagcgggat taccaggctg    180
cccgacaggt acgtcctgcc cgcgtccgac cgccccggcg tccttgccgt ctcgtcgtcc    240
gtggcgggca gcggcagggt caagctccct gtcgtcaacc tcgccggcct ccgcgacccc    300
tgccagcgcg ccgccgtgct ggccacgctc gacgccgcgt gccgggagta cggcttcttt    360
caggtggtaa accacgggtt cgggagcgac gtgagcggcg gatgctgga cgtggcgcag    420
cgcttcttcg agctgccgct ggccgagcga gcgcggcaca tgtcggcgga cgtgcgggcg    480
ccggtcgcgct acggcaccag cttcaaccag gccaaggacg acgtgctctg ctggcgcgac    540
ttcctcaagc tcgtctgcca gccgctgcag gcggtgctcc cgtactggcc ccagcagccg    600
gcggacctca gggacgtggc caccaggtac gccacggcga gccaccggct gttcatggag    660
gtcatggagg cggcgctgga ggcctggggc atccccacgg ccggcggcct gctcggggag    720
ctggcagcgt cgtcgtcgca catgatgacg gtgaactgct accggccgtg cccgcagcct    780
gagctcacgc tggggatgcc ctcgcactcg gactacggcc tcttcacgtt cgtcctgcag    840
gaccacgtcg agggcctcca ggtcatgcac gacggccgct ggctcaccat cgaccccatc    900
ccgggatcgt tcgtcgtcaa cgtcggcgac cacctagaga tctacagcaa cgggcggtac    960
aagagcgcgc tgcaccgggt gcacgtgaac tccacgcggc cgcgcatctc ggtggcgtcg    1020
ttccacagcc tgccggcgga gcgagtgatc gggccggcgc cggagctggt ggacgacgag    1080
gccggcaacc cgcggcggta catggacacc gactcgcta ccttcctcgc ctacctcgca    1140
tccgcggacg gcaagaacaa gaccttcctc cagtcaagga agctgcctgc tgctgctcct    1200
ccatgcctct ag                                                         1212
```

```
SEQ ID NO: 27           moltype = AA   length = 403
FEATURE                 Location/Qualifiers
source                  1..403
                        mol_type = protein
                        organism = Zea mays
SEQUENCE: 27
MSLVAAPMAI VDVANAQLQQ AAAAAAKKDE DGHEQQESSY DYGALMKGVR HLSDSGITRL    60
PDRYVLPASD RPGVLAVSSS VAGSGRVKLP VVNLAGLRDP CQRAAVLATL DAACREYGFF   120
QVVNHGFGSD VSGGMLDVAQ RFFELPLAER ARHMSADVRA PVRYGTSFNQ AKDDVLCWRD   180
FLKLVCQPLQ AVLPYWPQQP ADLRDVATRY ATASHRLFME VMEAALEALG IPTAGGVLGE   240
LAASSSHMMT VNCYPACPQP ELTLGMPSHS DYGLFTFVLQ DHVEGLQVMH DGRWLTIDPI   300
PGSFVVNVGD HLEIYSNGRY KSALHRVHVN STRPRISVAS FHSLPAERVI GPAPELVDDE   360
AGNPRRYMDT DFATFLAYLA SADGKNKTFL QSRKLPAAAP PCL                     403

SEQ ID NO: 28           moltype = DNA   length = 1863
FEATURE                 Location/Qualifiers
source                  1..1863
                        mol_type = unassigned DNA
                        organism = Zea mays
SEQUENCE: 28
tgccaccata ccactagtgc aaggtcctag atttacactt ggtgctacac cttgcttcgc    60
cccttcctt  ccttccttcc ttccttccct ccttccttgg tctctaggca gctagcagtg   120
tggtgctgct gccggccgcc tattggccgc ctgggactgg gatccattaa ttactgcgcg   180
cgcgcggcta accaaccaat cccagcgtgc gtaatctatt gcccacatgc cgacgccgtc   240
gcacctcaac aagaacccgc gctacctgga cttccgggcg gcgcggcggg tgccggagtc   300
gcacgcctgg ccgggcctgc acgaccaccc cgtcgtggca ggcggcgcgc cgggcccgga   360
cgccgtgccg gtggtggacc tgggcgccgc ggacccggcg ccgcgccgg  cggcggcggt   420
ggcccgcgcc gccgagcaat ggggcgcgtt cctgctcacg ggccacgcg  tccccgcgga   480
cctgctggcg cgcgtggagg accggatcgc caccatgttc gcgctgccgg ccgacgacaa   540
gatgcgccgc gtgcgcgggc ccggcgacgc ctgcgggtac ggctccccgc ccatctcctc   600
cttcttctcc aagtgcatgt ggtccgaggg ctacaccttc tcgccggcct ccctccgcgc   660
cgacctccgc aagctctggc caaggccgg  cgacgactac accagcttct gtgatgtgat   720
ggaggagttc cacaagcaca tgcgcgccct cgcggacaag ctgctggagc tgttcctcat   780
ggcgctgggg ctcaccacga gcaggccag  cgccgtcgag gccgagcgga ggatcgccga   840
gacgatgacc gccaccatgc atctcaactg gtaccggacc cgcggcgcg  gctggggctg   900
atcgcgcaca ccgactcggg cttcttcacc ttcgtgatgc agagcctcgt   960
gcccgggctg cagctcttcc gccacgcccc ggaccggtgg gtggcggtgc cggccgtgcc  1020
gggcgccttc gtcgtcaacg tgggcgacct cttccacatc ctcaccaacg gccggttcca  1080
cagcgtgtac caccgcgccg tcgtgaaccg ggacctcgac aggatctcgc tcggctactt  1140
cctcggcccg ccgccgcacg ccaaggtggc ggcgctgcgc gaggccgtgc gcccggccg   1200
ggcccccgcg taccgcgccg tcacgtggcc cgagtacatg ggcgtccgca agaaggcctt  1260
caccaccggc ggctccgcgc tcaagatggt cgccctcgcc ccgccgccg  acctcgacga  1320
cgacggcgac gccgccgtcg tccatcagca gcagcagcta gtcgtctcgt cgtagccgag  1380
accgatcgcc ggagactgat gctgatgatg atgcatatat acatgagaga aatcgtcgag  1440
tagactagcc gattgcaaaa gcaacccccag ctgccgaaac ctggcatatc gatcccattc  1500
tctgctgcgc acatgtatgc atgcatgcgc ttcgtccgtt cgactcgtgt gtgcttgctt  1560
gcttcgcgt  gcagcagaac taattccgtt ccgcagctga ctgctctgct ctgctctgct  1620
ggaatgtaat taagtagtag tatatggtag tagagaaaag attagctagg cgatcgatat  1680
agatgacggg ccggggaaga agacgaatta attaagatcg atcgacgacg acgagctgtg  1740
cgtgcctggc tgtgttcttc tctagcctag ttacagaggc cggctgctgc tgcttccaat  1800
cgggctgctt gtcgctactg acgatcgtta gtggatccat taactaatct ggaattctgg  1860
att                                                               1863

SEQ ID NO: 29           moltype = DNA   length = 1149
FEATURE                 Location/Qualifiers
source                  1..1149
                        mol_type = unassigned DNA
                        organism = Zea mays
SEQUENCE: 29
atgccgacgc cgtcgcacct caacaagaac ccgcgctacc tggacttccg ggcggcgcgg    60
cgggtgccgg agtcgcacgc ctggccgggc ctgcacgacc accccgtcgt ggacggcggc   120
gcgccgggcc ccgacgccgt gccggtggtg gacctgggcg ccgcggaccc ggcgccggcg   180
ccggcggcgg cggtggcccg cgccgccgag caatggggcg cgttcctgct cacgggccac   240
ggcgtccccg cggacctgct ggcgcgcgtg gaggaccgga tcgccaccat gttcgccacc   300
ccggccgacg acaagatgcg cgccgtcgcc gggcccggcg acgcctgcgg ctacggctcc   360
ccgcccatct cctccttctt ctccaagtgc atgtggtccg agggctacac cttctcgccg   420
gcctccctcc gcgccgacct ccgcaagctc tggcccaagg ccggcgacga ctacaccagc   480
ttctgtgatg tgatggagga gttccacaag cacatgcgcg ccctcgcgga caagctgctg   540
gagctgttcc tcatggcgct ggggctcacc acgagcaggc cagcgccgtc gaggccgcgt   600
cggaggatcg ccgagacgat gaccgccacc atgcatctca actggtaccc gaggtgcccg   660
gacccgcggc gcgcgctggg gctgatcgcg cacaccgact cgggcttctt caccttcgtg   720
atgcagagcc tcgtgcccgg gctgcagctc ttccgccacg ccccggaccg gtgggtggcg   780
gtgccggccg tgccgggcgc cttcgtcgtc aacgtgggcg acctcttcca catcctcacc   840
aacggccggt tccacagcgt gtaccaccgc gccgtcgtga accgggacct cgacaggatc   900
tcgctcggct acttcctcgg cccgccgccg cacgccaagg tggcggcgct gcgcgaggcc   960
gtgcgcccgc cgggccccgc cgtaccgcgc cgtcacgt ggcccgagta catgggcgtc  1020
cgcaagaagg ccttcaccac cggcggcctc cgcgctcaag atggtcgccct cgccgccgcc  1080
gccgacctcg acgacgacgg cgacgccgcc gtcgtccatc agcagcagca gctagtcgtc  1140
tcgtcgtag                                                         1149
```

```
SEQ ID NO: 30           moltype = AA   length = 382
FEATURE                 Location/Qualifiers
source                  1..382
                        mol_type = protein
                        organism = Zea mays
SEQUENCE: 30
MPTPSHLNKN PRYLDFRAAR RVPESHAWPG LHDHPVVDGG APGPDAVPVV DLGAADPAPA    60
PAAAVARAAE QWGAFLLTGH GVPADLLARV EDRIATMFAL PADDKMRAVR GPGDACGYGS   120
PPISSFFSKC MWSEGYTFSP ASLRADLRKL WPKAGDDYTS FCDVMEEFHK HMRALADKLL   180
ELFLMALGLT DEQASAVEAE RRIAETMTAT MHLNWYPRCP DPRRALGLIA HTDSGFFTFV   240
MQSLVPGLQL FRHAPDRWVA VPAVPGAFVV NVGDLFHILT NGRFHSVYHR AVVNRDLDRI   300
SLGYFLGPPP HAKVAPLREA VPPGRAPAYR AVTWPEYMGV RKKAFTTGAS ALKMVALAAA   360
ADLDDDGDAA VVHQQQQLVV SS                                           382

SEQ ID NO: 31           moltype = DNA   length = 1439
FEATURE                 Location/Qualifiers
source                  1..1439
                        mol_type = unassigned DNA
                        organism = Zea mays
SEQUENCE: 31
gacctccatt ttgattatct ctatcctgta cgtgccgaga gtccttcaaa gccgacgacg    60
agacgacgat gcagtcgtcg tcgtcatcag cctcgacgcc ggctgccgct tccggcctcg   120
tcttcgatct cgggtctgcg gcgggcgtgc cggagacaca cgcgtggccg ggggtgaacg   180
agtacccgtc ggtggagtcc gctggccgcg acgtggtccc ggtggtggac atgggggtgg   240
cctgccgga cgcgacgcgg gcgttggcgc gcgccgcaga cgagtgtggg gcgtgtttctgc   300
tcgtcggcca cggcgtgccc cgggaagtgg cggcgcgtgc cgaggagcag gtcgcgcgcc   360
tgttcgtgct cccggctcct gacaaggccc gcgcggggcg ccgccccggg agcccacgg   420
ccaccggcta cggcaggccg cccctggcac tccgcttctc caagtcatg tggtccgagg   480
ggtacacgtt ccgcgccgcc accgtccgcg aagagttcca ccgacgtcgg   540
gcgacgacta cctccgcttc tgcgacgtga tggaggagta cgacagagag atgagggctc   600
tcggtgcag gctgctcgac ctcttcttca tggcgctcgg cctcaccgac gtccagttcg   660
ccaccggcga gacggagcgg aggatccgcg agacctggac ggcgacgatg cacccaatcc   720
tgtgtccgga accggagcgc gccatccgcg tgaccggccca acggcctc ggcttcatca   780
cgctcatcat gcagagcccc gtgcccgggc tgcactgtct cccgccgcgg ccggaccggt   840
gggtgacggt gccggcgccg ccgggccgcc cgtcatcgt gctcggcgac ctgttccagg   900
tgctcacgaa cggccgcttc cggagcccta tccaccgcgc cgtcgtaagc cgagagcgcg   960
agcggatctc cgtgccctac ttcctctgcc cgccggagga catgacggtg cgccgctcg  1020
cgtccgctct gctgccgggg aggaaggccg tgttccggcc cgtgacgtgg ccagagtaca  1080
tggaggtcaa gcacaaggtg ttcggcacgg atgcgccggc cctggagatg ctgcagctgc  1140
aggtggatga ggaagaacaa ggtgaaaggg ccgccaccac ctaagcccta aggaactact  1200
agctgaatcc ataaactaat aaagaattcg tgaataaggg cgttggaaga ctggacacaa  1260
cacaagagag ttgctatata tcgtatttct gaaatttaag gcaaatatct tagttaaaaa  1320
actggtatat ttaaatagac aatatatatc taaatataag atagttcacc attttttacgg  1380
tcgaacaatg ataaagttat atattgtctg aatagtaaca aattaaagat ttccaggag  1439

SEQ ID NO: 32           moltype = DNA   length = 1116
FEATURE                 Location/Qualifiers
source                  1..1116
                        mol_type = unassigned DNA
                        organism = Zea mays
SEQUENCE: 32
atgcagtcgt cgtcgtcatc agcctcgacg ccggctgccg cttccggcct cgtcttcgat    60
ctcgggtctg cggcgggcgt gccggagaca cacgcgtggc cggggtgaa cgagtacccg   120
tcggtggagt ccgctggccg cgacgtggtc ccggtggtc acatgggggt ggcctgcccg   180
gacgcgacgc gggcgttggc gcgcgccgca gacgagtggg gcgtgtttct gctcgtcggc   240
cacggcgtgc cccgggaagt ggcggcgcgt gccgaggagc aggtcgcgcg cctgttcgtg   300
ctcccggctc ctgacaaggc ccgcgcgggg cgccgccccg gggagcccac ggccaccggc   360
tacggcaggc cgccctggc actccgcttc tccaagctca tgtggtccga ggggtacacg   420
ttccgcgccg ccaccgtccg cgaagagttc cgccgcgtct ggccgcgtgg cggcgacgac   480
tacctccgct tctgcgacgt gatggaggag tacgacagag atgagggc tctcggtggc   540
aggctgctcg acctcttctt catggcgctc ggcctcaccg acgtccagtt cgccaccggc   600
gagacggagc ggaggatccg cgagacctgg acggcgacga tgcacccaat cctgtgtccg   660
gaaccggagc gcgccatccg gctgacggcc cacacgact cggccttcat cacgctcatc   720
atgcagagcc ccgtgcccgg gctgcagctg ctccgccgcg gccggaccgg tgggtgacgg   780
tgccggcgcg cgccgggcgc gctcatcgt catgctcggcg acctgttcca ggtgctcacg   840
aacgccgct ccggagccc tatccaccgc gccgtcgtaa gccgagagcg cgagcggatc   900
tccgtgccct acttcctctg cccgccggag gacatgacgt ggcgccgct cgcgtccgct   960
ctgctgccgg ggaggaaggc cgtgttccgg cccgtgacgt ggccagagta catggaggtc  1020
aagcacaagg tgttcggcac ggatgcgccg gccctggaga tgctgcagct gcaggtggat  1080
gaggaagaac aaggtgaaag gccgccacc acctaa                             1116

SEQ ID NO: 33           moltype = AA   length = 371
FEATURE                 Location/Qualifiers
source                  1..371
                        mol_type = protein
                        organism = Zea mays
SEQUENCE: 33
MQSSSSSAST PAAASGLVFD LGSAAGVPET HAWPGVNEYP SVESAGRDVV PVVDMGVACP    60
```

```
DATRALARAA DEWGVFLLVG HGVPREVAAR AEEQVARLFV LPAPDKARAG RRPGEPTATG  120
YGRPPLALRF SKLMWSEGYT FRAATVREEF RRVWPDGGDD YLRFCDVMEE YDREMRALGG  180
RLLDLFFMAL GLTDVQFATG ETERRIRETW TATMHPILCP EPERAIGLTA HTDSGFITLI  240
MQSPVPGLQL LRRGPDRWVT VPAPPGALIV MLGDLFQVLT NGRFRSPIHR AVVSRERERI  300
SVPYFLCPPE DMTVAPLASA LLPGRKAVFR AVTWPEYMEV KHKVFGTDAP ALEMLQLQVD  360
EEEQGERAAT T                                                      371

SEQ ID NO: 34          moltype = DNA   length = 4095
FEATURE                Location/Qualifiers
source                 1..4095
                       mol_type = unassigned DNA
                       organism = Zea mays
SEQUENCE: 34
taaatttgtg atccttgtga agttgttata tcatgaattg tgaacttgtt gcatttgtga   60
tcttttgtca actttgttgt attgtgaagt ttgatatgtt taccgatcgt attttagatt  120
tcgatcgtta ccggtgtatt ttccgcacca aactttttgtt tccgatgttt tcgaaatacc  180
gatatcgttt ccgtttctat agttacccct ttcaatttta tttccgatta aaaatatgaa  240
aacggtaatg gttttagtgt ttatcgaccg ttttcatctc taatcatccc tgccggtgaa  300
gtttaatttt tcccttggct aaagagatgc aagctgctgt aaaatacgtt aaaacaggca  360
aggcagcccc agcagccagc atcgcgtgcc cgtctatgta catcagtgga tacgtagcat  420
ctctagtgag taatataacg attgcatttg gctggaggac gtatgttata taagtatgtc  480
atttaccagt tgcattagta tcttcccataa ctccatataa aactctcttc gtggaatgga  540
cgtagacgta tgctatataa gtattaaaaa atagtttttt aagctggtgt cctcaatttt  600
gctattgttc tcgttttat ctttagttgt gtcacaaatt taatccgtac aacaaatcaa  660
aaaataccata cccttcttat attaatttc taacataaca tttgtttaga tattttcagt  720
cgtgaaaata caattctaat tctaacgtcg tagtatcaaa tcaaaccatc cagaatttga  780
ccaagcttaa ttataaaaaa tataaaattt atgatactga atagatagca ttagatttgt  840
tatataaatat attttttataa aatacccattt ttatggtata aatattggta ctcctttact  900
ttaaactata gatagttttg actaaggatg caactagaat tgcatcctct tttcactgca  960
ccttcattag tttttaatatt tatttagatg ggcccttgca aactgctagat atcatctctt 1020
gcaacattct ttctatagca ccacgaaaat gtattgcggc tttgaaatta taattgaatt 1080
agttgtatca tttctcttcac cgatgcgtta aattcaaaat taagtgttat atttcttcat 1140
aatttgttaa atatatatagac cctataatcc accattattt actataatag catacattaa 1200
cattggttt agcctacact acgacactcg aggcattgaa ttttcctcta tcaaagaatt 1260
atatgtgtag tagtattgtt cttgacaaaa aggggatta aaattaaact accaatattg 1320
atacttatct tatcacatcc atgaatacaa tcaacactct tacaaaagat aagatacaag 1380
attaaaaagt accatgataa tacattaaga ttattagcaa tgcattaaat taaataaatg 1440
tgcaagtgaa tcatgatttt agttttatct attttacttt taaaaatatga tattctctga 1500
ctacttctaa gcataaatgt gattctaagt catgaccgat cgtgcttatt cagaaaaatg 1560
aaggagacac agatttctat aaaaaaaggt tgtcatggga ctattgggtc aaccatctta 1620
ttcatttggg aaaataagtt tagaacacat caacccattt tagatgttga gtttggccct 1680
aatggtccat tgaccttact tttgtgggtt gacatagacc atctatccca agttattgtt 1740
gtgtcacatt ccctgatatc atgaatctat attttagct tccgttttca tattttttagt 1800
cgttacatat ttttttatccg cgtactagat taaaactcta gttgttgcaa tacatttttgt 1860
tcattttttt ctatttcttc tttactaaca acatattcta gttcctagct acattcttaa 1920
gtaccatagt gctataaaca tttttttatcc tacattattc cacttaagaa attgaatttt 1980
ctgcataaaa aaattttata tccagtagtg ttgtcttata aaagcataaa gtgattaaaa 2040
ttaaaaccat tattgatatc ttatttttca aaaaaaaata taagcttata gaaagtgaat 2100
taatttcatg gtaaattaat atagtttaaa ttgaattatt agtgttatta ctatgtttat 2160
tatcaatgaa acatttttca tggttgatat aacttagtgt tacttatttt agtatttttt 2220
atataattct agttaacttt tagttttgga tttaaaaaaa cgagaattgt gtccttttgt 2280
ggagtgagta taaagaaagt aatatctcgtt catcataatt tggttttta aggtacgtga 2340
aacttgcttt atatttggac tcaagctatg tctaaataca tagtaaaaaa gcaatattc 2400
tagaaaagac aaaacatctt ataattaga atcaaggaaa tatatagatt ttatgtgcag 2460
tgagaagcca tttacaatgg aacgttcaac gttgggccaa tagatatttt gcgatatgat 2520
gatgggcata tttttgcatg gttgtccctc cactagctat agtttgatga tacgatacgc 2580
tgcacacacc attgggttgt accatgttag tgtagcaaca gtagaaaccc aattgtggcc 2640
gtgaaccatg ataatactag gtagagtgct agctagaggt ttcaggctat tgatgcgtga 2700
attaaactttt ctgttgtgtt gcgaggaaac gagtattgtg aaatattttga aacggttttt 2760
tttgtgaaag attttgaaacg gtatttttgt tgtgaaataa agatcaaggc taaataaatt 2820
caaactaata aaacatatta attgacggcc tgaagccccc gccccatgg ccccatgcca 2880
tagcatcagg tccacatgga catgaggccg cgcctccctc tatgttggct ccctgccttc 2940
gccgttgtcg tcgctcccga actccctctc ctcccctgtt acaaatacccc ccacccgccc 3000
ggacagcttc cctgcacact cgcagctcgc acatctgcag gtgtcctaag aacggcaaga 3060
gccagctctg cctagcagca gcgcacagcc acatccatgg acgccagccc gacccccaccg 3120
ctcccccctcc gcgcccccaac tcccagcatt gacctcccccg ctgcaaggaa cagggccgac 3180
gcggcggcta acaaggccgc ggctgtgttc gacctgcgcc gggagcccaa gatcccggag 3240
ccattcctgt ggccgcacga agaggccggg gccgacctcgg ccgcggagct ggaggtgccg 3300
gtggtggacg tggggcgtgct gcgcaatggc gacggcgcgg ggctccgccg cgcgcggcgg 3360
caagtggcgg cggcgtgcgc gacgcacggg ttcttccagg tgtgcgggca cggcgtggac 3420
gcggcgctgg ggcgcgccgc gctggacggc gccagcgact tcttccggct gccgctggct 3480
gagaagcagc ggcccggcgg cgtccccgcc acggtgccgg gtacacgag cgcgcacgcc 3540
gaccggttcg cgtccaagct ccctggaag gagacccctgt ccttcggctt ccacgacggc 3600
gccgcgcctc gtcgtcgt ggactacttc accggcaccg tcggccaaga tttcgagcca 3660
gtgggggtgag taaagaagaa gatgcgccgc aatttacatt tataagtagg accagcagaa 3720
gcccctgccc ctgggggcct tagcattgca ttcgactgat gaatacgcat ggcaggcggg 3780
tgtaccagag gtactgcgag gagatgaagg agctgtcgct gacgatcatg gagctgctgg 3840
agctgagcct gggcgtggag cgcggctact accgggagtt cttcgaggac agccgctcca 3900
tcatgcggtg caactactac ccgccgtgcc cggtgccgga gcgcacgctg gcacgggcc 3960
```

```
cgcactgcga ccccacggcg ctgaccatcc tcctgcagga cgacgtcggc gggctggagg 4020
tcctggtgga cggcgagtgg cgccccgtcc ggcccgtccc aggcgccatg gtcatcaaca 4080
tcggcgacac cttca                                                 4095

SEQ ID NO: 35         moltype = DNA  length = 7404
FEATURE               Location/Qualifiers
source                1..7404
                      mol_type = unassigned DNA
                      organism = Zea mays
SEQUENCE: 35
cctattttgt gtctaatact cttcttatat taattgtttg gtcaaacttt agataaattt   60
gactaatgat gcaattaaaa ctgcatcacc tttactaagg tactgcttta tatgtttcga  120
caaaattttc aattattctc tatgtgtttt aatctttgcg ctacacctcc attgatttaa  180
atactcattt attttaaacc ataacttaaa ttatatcgga tctttgcatc ctttctatgg  240
caccatacat gaatcgatat tttggctgca aattttttaat catgttagtt ttagcatttt  300
ttcatatcca tgtgttaagt ttgaatcatg tgttgttttt atataattta ttgaaaatat  360
agatcctaaa cttcactaat acttacaaca atagcatcat catgtgtttt aatccacgcc  420
acaacactca aggcattgaa ttttcttcta ccaaagagtt gtatgtgtgt attgttcttt  480
aaaaaataga gtgattataa ttaaactacc agtattcata tgtaaaatgt atagacatct  540
aaaataaaat ttgcaaaaaa cattgttgca gactttcaat ataattaaga atgggtttta  600
gggtcatgat atatggtttg ttaaagaaac ttgtttttttt ttgcaattga taaactataa  660
aatacatttt cactattgtg tgcatatgta cttggtatac atagtggcat atatcatttt  720
tgtttacttt gaggtttgaa ttatctatgt taaaatttgga taacatagat acattggtgt  780
gcgtcctttg gcccatttac ttgactgagg agcaatacta taaagtaaaa catatttgga  840
tattttatct taaactccta gcataatatt gatttaatta tgaacaaata tatgtttagg  900
tgatagtttc atgggtggta aactatataa gaaggcttac catgatcttt gcaaactcta  960
ggctatgaaa gagttccatg atttgtctta gaagcataga caaaacagtg ataatgatct 1020
aaatcacact tatggcactg atgaccatat atgcaaagct aaatgcatgt taagttgtat 1080
tatatcatat gtttacaatg actatcgcat ataacgagga atacattgtc tatatagata 1140
gctattactg tagtagtgcc aaatgttgga caacatgaat cataatcttc aaacctagag 1200
aaattgtagt cagtcgtaca catatcgtct agtaagttgt ctatactttt tatttattgt 1260
atcaaatttt attgttatct tgcttgcttg tttgtttgta ccatagacac aatatggtca 1320
aaaagtggtc aatcgattcg aagaagattg caattgacga gtgctaacag ttgatccttt 1380
tgttgtgcac gctagcggag tagcatgaaa agagtaaaat atgaaattag cgttctaaac 1440
tgtttgtgct ataggtactt cgtatttaat ggagtgacta actataggaa ggtgagagct 1500
cagaagtcag cacctcaca cagagttcta gagttagtgg tcatcgaacc acgacaaact 1560
acatgatgag cagaagaggc aacatcaaga ctatgatcaa tagtttcggg tcaatgaatg 1620
acatcgtgat gagtatttat ctaactatat agaacaacaa cacatgatgt tttaagtaag 1680
ttcaactgac cttctattgc tatctttaag tatttaacgt agcgaataat gttttatcta 1740
tttcattcat aaataatgtt gtgacaaaag gggataacca tcacttttac catgttctag 1800
ataccacaac catctccacc atcataatgg gttcttcatt ggtgcttgga cctcaaataa 1860
tcatatctat agccaactta gctcaattct aataaaatta ggcaacttgg cttcattgta 1920
gcaaaaatag ccaacttagc tcaattttat ctaaacttag ctaatctagc acaacttaga 1980
tcaatattag gaaaaactaa tcaatcataat ctagctcaac tatagcgaaa gatagatatt 2040
gtagcataac ttagtagatc tatctcaaat tttagcaaaa actaatcaat ttagataaac 2100
tctataaaat tttaatcatt atgacttatt ccaactaat tgtaacttgc atgatttta   2160
tgttccttct ttataattag caacacctaa agacacgaat gatgagggt ctaacgcatt  2220
cattaaccag ttgttaaata atactctagg tagatgataa gaactctaat tattctatga  2280
atctaagcta aaagatgttt aatatttaag tattggtgtt tattatgtta tttagaacga  2340
ttcatgttac ttaaagattt gttatgattt taaaatgat ttatgataat ttatgtggtg   2400
tggattaact tgtgaacata tgtgatgtag atgaaatgt atgttgtgga tggaaccata   2460
tgaatatata tacacactca tatactattc gttggtgtag gtaaagcttc atccatcggt  2520
aattactaaa tggtcttcag tcattaccac taggtgaagc ttcacacgac cgataattat  2580
tgaagaacgc tcattaattt ccggtaatgg cttattggcc ttcactagtc ggtgaaaatt  2640
agctattttt ataccaataa aaattagcta atatatgtaa accaggtcta attttttatgg 2700
gcctcttacc gaccaaaatt gattagatta ttgttacaat agttttagtc aaaagctagc  2760
tatgctataa aaattttgaa ttaaagtgag tttcgtaata aaaattgcat acttttaaaa  2820
taaaataatt aaaaaacagt ttttagaaat acaatcaaac accttatgct ataaaaaaat  2880
tgtaatgtac ctacaaatat ataatactt actttaaat aggcctgtgc cttctcggct   2940
ctatatgggc tgcctccaac gaagcgccat ggccatgggc tccactgtgt cgggtcccac 3000
atgaggccgc gcctccctcc aaatgttccc tccctgcctt cgtctttgtc gttgctcgca 3060
aactccctgt cctccctgt tacaaatacc cccaccgcc cggacagctt ccctgcatac   3120
ttgcagctcg cacatctcat ggtgtcgcag gaacgacaag agccagctgt gcctagcagc 3180
agcagcagca gcgccaagcg cgcagccacg tccatgacg cgcagccggc ccgctggtc   3240
ctcctccgcg cccccactcc cagccccagc attgacctcc ccgctggcaa ggacaaggcc 3300
gacgcggcgg ccagcaaggc cggcgcggcc gtgttcgacc tgcgccggga gcccaagatc 3360
cccgcgccat tcctgtggcc gcaggaagag gcgcggccgt cctcggccgc ggagctggag 3420
gtgccgatgg tggacgtggg cgtgctgcgc aatggcgagc gcgcggggct gcggcgcgcc 3480
ggggcgcagg tggcggcgc gtgcgcgacg caccggttct tccaggtgtg cgggcacggc 3540
gtggacgcgg cgctggggcg cgccgcgctg gacgcggcca gcgacttctt ccggctgccg 3600
ctcgccgaga gcagcggcgc ccggcgcgtc ccggcacccg tgtccgggta cacgagcgcg 3660
cacgccgacc ggttcgcggc caagctcccc tggaaggaga ccctgtcgtt cggctaccac 3720
gacggcgccg cgtcgcctgt cgtcgtggac tacttcgtcg gcaccctcgg ccaggatttc 3780
gagccatgg ggtaagtaag gtagtaagaa ggagcgccgg tttacattta cgcacgtcg   3840
gcgtgcggtc gagtcgggac tcggagacg tatgaacccc cgtcccgtcc catgcatgtg  3900
tgcaggtgg gtgtaccaga ggtactgcga ggagatgaag gagctgtcgc tgacgatcat  3960
ggagctgctg gagctgagcc tgggcgtgga gctgcgcggc tactaccggg agttcttcga 4020
ggacagccgg tccatcatgc ggtgcaacta ctacccgccg tgcccggagc ggagcgcac   4080
gctgggcacg ggcccgcact gcgaccccac ggcgctcacc atcctcctgc aggacgacgt 4140
```

```
gggcgggctg gaggtgctgg tggacggtga gtggcgcccc gtccggcccg tcccgggcgc    4200
catggtcatc aacatcggcg acaccttcat ggtaacgaaa cgaaagcgct cgctcctctg    4260
ttttccttgg ccgctcttgt cctgtgtgta tattcagttg agctctctct gtgctgttat    4320
ttcccgaatc ctagtggacc taaacgggca ggttattaca gcacgcacac gtaggcatgt    4380
catgtagcta gtacatacat agcgatgccg atgcaaatgc aatagagaca tgcgttcgag    4440
ttggttccta tctcggcggg ctacggcagg tacacgcggc cgcggcgcgc tctctctagt    4500
ctatccgcgg ccgcgcccag gccgatcgag gcttccgggg gagagttgcg acaagagaac    4560
ggaccgaggg ggtcggctag cggtagcaag ttccctgttg gtttgtggcg ttggagcgtt    4620
gcggagaggc ttgcgcggcg gcggggacgt cgacggggac gtggcgggga gacgatacga    4680
tgggtgccgg gcaggtttcc gaattccaaa cgtttttgtg gcgtgcgtcc atggggcgcc    4740
cccaaacttc ggacgtttcc ggcgctccaa caaatcttct cgcttcacac gtcaccgtcg    4800
tcccggattc atttgcctcg tcgctccacc attcgctgct ctcctctcca cgtactctta    4860
ccctgacctt tgggaaagaa ctgaacattc gagatgcaca acagttcaaa tataacatat    4920
gcagcacaag atcgttcgac tgctatccga caagccaaca acgtgcccag tagaactgaa    4980
tgtacctgtg atttccagca ctaacttaca gcaacgttgt gaaaaaacaa aaacgaaaac    5040
aaacggcaga aaaaacagat gtattgttct acagttacac caaatatttt ctggtccttt    5100
cagcaccaac aagagccata cgcatatcta gaagacaaaa ttcctctaat ttcaccccta    5160
cgtggtagca gttcctcctc aacacagttc acgtgctagc gtcgagttct ttgggccgcc    5220
acatcgactt ctcgacgcag agcaggcccc cgctgccctt ggtgtaggtc atccgcacct    5280
cccactgcac ggacttggcc atgctctcca gctcatttat cgtgtccgcg gtgtccctca    5340
cgatcagctt gccctgtggc ctcagtacac ggtcgacctc ggcgaaaact gcagccagtt    5400
tgcatctgta aacaggcaac acagatttt agtatctaaa acactgcagg caaacgccac    5460
aggttttagt cgcaagaagc aataaaagca tgcaaacaat gctacgtgta cgtatcaaag    5520
gaacatgtca aaactcgttg catgaacgat cattgatgtt tccttgctga actagtcaca    5580
tcagtctgct tcaacttctg ggtttcacta gtagatatac cagaagggta gaataatgtg    5640
aagagcaaga aatacagacc tcttctgag ctttgagaac agatggtccg cgtgcagaag    5700
gtcatacgtt cttgggtaag tgctgaaaga ctcgcaccag tcatggtaca tgccaaacaa    5760
accgcgctcg tagatgatgg gcagcgtgtc tggtgaatcg atcggcacga tattcatgac    5820
ccagaccttt tggtccctca gagctgcagc aaaactgcca tgcaacaatg taaagcatta    5880
gtcaagaaga aggtgtacag tgcatttctc ctttgtcaaca gcttcagta acaaaaaaaa    5940
agtgttatgc ttgactgaat cttcaaaga aatatgcttg atgacttatg gtggacaagt    6000
tgcctgttat agtgttatgt tttaattaac tatgtgccag cttgggtaac tagtagttat    6060
gtagtgtgat ctgaattacc aaaatataaa taaataaata aacatgccca agaaactacg    6120
aaaaccattt acttaccctc catagacagc tctcatgtcc atgacatttc tcactttgga    6180
ccagtcaatt cccatgccat tcacatacga tttacttaca acccgtttcc agtgggcatt    6240
atctgcctca aaatcttcat ttgcaggctt ccatagaca ccaaccttgg aaccatcaat    6300
ccagaaaggg gtcttctcaa gcctttgcgg ccataactct ggccattttg atcctcggac    6360
ttttgagcca ccaggcagtt tgtgcatgca tgcttccaac ggtacattcc tgcaaatcaa    6420
aaggctgtgt aagcaaagca gagaagcact ttttctccatt gaaaatatac tcttctcaaa    6480
gaaccgaaac cataccaagc agcatctgca tcatcagatt ccttgcacaa tggcgggctg    6540
ttttcagatc tttttctcata gcaaatattg tccattggtt tctgatatat gaccatacca    6600
acttggttta acttatcctt agtcttgttg accatcttcc agcacatgga ctttgtcaaa    6660
gtagacatgg ctgaaaaggg tatgtggcca catgttaagt tagaaataaa attcaatttt    6720
gaacagttgg tccatagcat gtattttgaa caaatgcaat ccttctccat ccatgaaaga    6780
agttgaccct tcatacttag gattattcag tactttcact catgtctgct gaatttgttc    6840
tcttggtagt tgctatacaa gaaaggggga agtacagagt agctaaactt atacaagcta    6900
tagtctgata tttgtatgaa acataaattt tggtatgat gtcttattaa aatgggaggt    6960
tgtataatat ttttctagcc tacctcaact tgcttgagac taaaaggctt tgttgttgtt    7020
gttgaggctg tatggtgctt tgactttaca aatcaagtta tcagctaccc tacttatgga    7080
tatacacctc tcataaaatg atggtaagaa gtttcgatat gtcacattaa cataagaact    7140
tcattcagtt agggtacaac gaagttaagt agttacggaa ataccattcc aaatctcaaa    7200
atcctctggg agcttttggt aaacaggagt ggcagaccag acaaagtaac caccagggcg    7260
taacaagcgg ttcaattcca gcaaaagcat gccacctaaa agtagcgagc cagcaataag    7320
attcagttct atagcaaatc aataaatgaa aggaggacat gtcaatatgt aaccagcagg    7380
acaaaccttc gatgtgccaa ggga                                           7404

SEQ ID NO: 36           moltype = DNA   length = 1788
FEATURE                 Location/Qualifiers
source                  1..1788
                        mol_type = unassigned DNA
                        organism = Zea mays
SEQUENCE: 36
aatcccagcg tgcgtaatct attgcccaca tgccgacgcc gtcgcacctc aacaagaacc      60
cgcgctacct ggacttccgg gcggcgcggc gggtgccgga tgcgcacgcc tggccgggcc     120
tgcacgacca ccccgtcgtg gacggcggcg cgccggggcc cgacgccgtg ccggtggtgg     180
acctgggcgc gcggaccccg gcggcggcgc cggcggcggc ggtggcccgc gccgccgagc     240
aatgggggcgc gttcctgctc acgggccacg gcgtccccgc ggacctgctg gcgcgcgtgg     300
aggaccggat cgccaccatg ttcgcgctgc cggccgacag caagatgcgc gccgtgcgcg     360
ggcccggcga cgcctgcgcc tacggctccc cgccatcctc ctccttcttc tccaagtgca     420
tgtggtccga gggctacacc ttctcgccgg cctccctccg cgccgacctc cgcaagctct     480
ggcccaaggc cggcgacgac tacaccagct tctggtacgt tgcgttgcgt gcttgtgtgc     540
gcgcacacct gccgaccgcg gccacaccgt acgcaaccca cgcgtacgta cgtgcgctag     600
ctacctgctt cgctcgcttc gctcctctcg cctcgccatg catatgcacg tacggccgta     660
caggtacagc agcaggtcac agcacgaac gcacgcacgca accagcacg atatgataca     720
tcatcgacgt gtcgtccccc cgtctaaggc catgcatgca tgcaagcacg cctagctagc     780
ccttttggct tgctagctga cgaggggagc taggacgagc atacttactg tgcgcgtcat     840
gctcaattgc tcacactata ctactacttg ttactacagt gatgtgatgg aggagttcca     900
caagcacatg cgcgcccctcg cggacaagct gctggagctg ttcctcatgg cgctggggct     960
caccgacgag caggccagcg ccgtcgaggc cgagcggagg atcgccgaga cgatgaccgc    1020
```

```
caccatgcat ctcaactggt gggtatatat tattgtctgt catgttgtcg tcgtcgtacg   1080
cgttgcggtt gggtgtacat gtatataaca caaacaacaa aaaactaacg ccgtgccgac   1140
gacgacgacg atcatcaggt acccgaggtg cccggacccg cggcgcgcgc tggggctgat   1200
cgcgcacacc gactcgggct tcttcacctt cgtgatgcag agcctcgtgc ccgggctgca   1260
gctcttccgc cacgcccggg accggtgggt ggcggtgccg gccgtgccgg gcgccttcgt   1320
cgtcaacgtg ggcgacctct tccacatcct caccaacggc cggttccaca gcgtgtacca   1380
ccgcgccgtc gtgaaccggg acctcgacag gatctcgctc ggctacttcc tcggcccgcc   1440
gccgcacgcc aaggtggcgc cgctgcgcga ggccgtgccg cccggccggg cccccgcgta   1500
ccgcgccgtc acgtggcccg agtacatggg cgtccgcaag aaggccttca ccaccggcgc   1560
ctccgcgctc aagatggtcg ccctcgccgc cgccgccaac ctcgacgacg acggcgacga   1620
cgccgtcgtc catcagcagc agcagctagt cgtctcgtcg tagccgagac cgatcgccgg   1680
agactgatgc tgatgatgat gcatatatac atgagagaaa tcgtcgagta gactagccga   1740
ttgcaaaagc aaccccagct gccgaaacct ggcatatcga tcccattc              1788

SEQ ID NO: 37          moltype = DNA  length = 1698
FEATURE                Location/Qualifiers
source                 1..1698
                       mol_type = unassigned DNA
                       organism = Zea mays
SEQUENCE: 37
cgtgccgaga gtccttcaaa gccgacgacg agacgacgat gcagtcgtcg tcgtcatcag    60
cctcgacgcc ggctgccgct tccggcctcg tcttcgatct gggtctgcg gcgggcgtgc    120
cggagacaca cgcgtggccg ggggtgaacg agtaccgtc ggtggagtcc gctggccgca    180
acgtggtccc ggtggtggac atgggggtgg cctgccccgga cgcgacgcgg gcgttggcgc   240
gcgccgcaga cgagtgggc gtgtttctgc tcgtcggcca cggcgtgccc cgggaagtgg    300
cggcgcgtgc cgaggagcag gtcgcgcgcc tgttcgtgcc cccggctcct gacaaggccc   360
gcgcggggcg ccgccccggg gagcccacgg ccaccggcta cggcaggccg cccctggcac   420
tccgcttctc caagctcatg tggtccgagg ggtacacgtt ccgcgccgcc accgtccgcg   480
aagagttccg ccgcgtctgg cccgacgcg gcgacgacta cctccgcttc tggtacgtac    540
gagcgccatg tcacgtgctt gtgctttcat gcctcgtacc gtcgtcgtgc tgtacgtgtt   600
atgtttatcg gccggtacgt cacgcgtgct acactggtta acgacgtgag cgtgcccacg   660
ttgactgcat gcatgtgcat gcgcgcgccc agcgacgtga tgaggagta cgacagagag    720
atgagggctc tcggtggcag gctgctcgac ctcttcttca tggcgctcgg cctcaccgac   780
gtccagttcg ccaccggcga gacggagcgg aggatccgcg agacctggac ggcgacgatg   840
cacccaatcc tgtacgtacg tcaaaaacga atatctgcat aatgcaaacg tttttctgca   900
atgccagtca tccactcatc ctgtacgtac ctctggactc tgcttgtcca tctactgatg   960
acacgtatgt taggtacccc aggtgtccgg aacggagcg cgccatcggg ctgacggcgc   1020
acacggactc gggcttcatc acgctcatca tgcagagccc cgtgcccggg ctgcagctgc   1080
tccgccgcgg gccggaccgg tgggtgacgg tgccggcgcc gccgggcgcg ctcatcgtca   1140
tgctcggcga cctgttccag gtgctcacga acggccgctt ccggagccct atccaccgcg   1200
ccgtcgtaag ccgagagcgc gagcggatct ccgtgcccta cttcctctgc ccgccggagg   1260
acatgacggt ggcgccgctc gcgtccgctc tgctgccggg gaggaaggcc gtgttccggg   1320
ccgtgacgtg gccagagtac atggaggtca agcacaaggt gttcggcacg gatgcgcgg   1380
ccctggagat gctgcagctg caggtggatg aggaagaaca aggtgaaagg ccgccacca   1440
cctaagccct aaggaactac tagctgaatc cataaactaa taagaattc gtgaataagg    1500
gcgttggaag actggacaca acacaagaga gttgctatat atcgtatttc tgaaatttaa   1560
ggcaaatatc ttagttaaaa aactggtata tttaaataga caatatatat ctaaaataaa   1620
gatagttcac cattttttacg gtcgaacaat gataaagtta tatattgtct gaatagtaac   1680
aaattaaaga tttccagg                                               1698

SEQ ID NO: 38          moltype = DNA  length = 4095
FEATURE                Location/Qualifiers
source                 1..4095
                       mol_type = unassigned DNA
                       organism = Zea mays
SEQUENCE: 38
cggtctaagt gaccgtttga gagaggaaaa gggttgaaag agaccccggtc tttgtgacca    60
cctcaacggg gagtaggttt ataagaaccg aacctcggta aaacgaatca ccgtgtcatc    120
cgccttattt gctgtgatt tgttttcgcc ctctcttcg gactcgttta tatttctaac    180
gctaacccg acttgtagtt gtgcttaaag tttgtaaatt tcagattcgc cctattcacc    240
ccctctaggc gactttcata taaatattgg gagaaatatg aaaaacaaat gaaggtcgaa    300
cgagtcagag acaccataaa aaagaggtcg tcttaactag ggtgctaaac ctcaacattg    360
tagtagatct tagtactgag tttgacatct ttgacaccaa caagatggtg atacgttact    420
ttctacgtta acttgggtag gtatatcgac tatagtggcc tataacacta ggctatgtaa    480
tatgatattg tgttgagtct ttataaacat gattttttt aaaaaaaaga gctaaaataa    540
aaaatagaaa tcgacggtac gatgcaagtt cttctcaaga caaccaaacg cacccttgcc    600
cctttattga aattgaagta tgtgctttat caaatgttta aatactaatt ataagtatta    660
aatataattt aattataata ctaattatat agataaagac taaataacaa gacaaattta    720
ttaaatataa ttaattcatt attaacaaat acttaatgta gcacgatcga atcatggact    780
aattagtctt gatagactcg tcttaccatt taatcataat tagttttgta tactgtttat    840
aatatttcta actagctagt attaaacttt tgatgtaacc taactaaagt ttagtcacgc    900
caatacataa ggactcggat cgttcgatca cccatgacat cacgtatact aagagcatct    960
ccaaaagctc tccagaagtc tcccctaaat ctatttttt gggaaaaaca caaaacatg   1020
tctccaacag aaattcacaa gcgccccaa cttttttcata gccctaaaa ctccctcatt   1080
tgtagctaca aatgaggggt tttttgggct cccagaaac aaactgttga tttaaggagat   1140
ctgttggaga aaggattaaa atttaccctc acttattatt tagatgtccc ttaaactga   1200
ttttgaggag tcgtttatg tagagctctt ggagatgctc taacacaccg agcacaaccg   1260
catcatcaat caaaacaacc caagttgt tcggtacaag tcatcagcct gtgtacacac   1320
atcagcctcg gccccgggag aagcgctagc aaacaaggtt cacctaaaa tccatccaga   1380
```

```
ttcattgaat ccaaccagca caaacgtccc atttattaat cacctcatca caggtccccc   1440
cagcctcact ctcgcgccgg ctcaaggtac attgcgtgtc ctagccaaga cacgcagctc   1500
atctcagcct cacacgcaca gcaagagcga ggcgtgattc gccatgggcg gcctcactat   1560
ggaccaggcc ttcgtgcagg cccccgagca ccgccccaag cccatcgtca ccgaggccac   1620
cggcatccct ctcatcgacc tctcgcctct ggccggccgg gcgggcgtg tggacgcgct   1680
ggccgcgag gtgggcgcgg cgagccggga ctggggcttc ttcgtggtcg tgggccacgg   1740
cgtgcccgca gagaccgtgg cgcgcgcgac ggaggcgcag cgagcgttct tcgcgctgcc   1800
ggcagagcgg aaggccgccg tgcggaggaa cgaggcggag ccgctcgggt actacgagtc   1860
ggagcacacc aagaacgtga gggactggaa ggaggtgtac gacctcgtgc cgcgcgagcc   1920
gccgccgccg gcagccgtgg ccgacggcga gcttgtgttc gataacaagt ggccccagga   1980
tctaccgggc ttcaggtgac gaaattaact atatatccct ttcgatcata gttgcgttaa   2040
taaattaagg gaatcgtgag cgtacgtacg taagtttccg cagagaggcg ctggaggagt   2100
acgcgaaagc gatggaagag ctggcgttca agctgctgga gctgatcgcc cggagcctga   2160
agctgaggcc cgaccggctg cacggcttct tcaaggacca gacgaccttc atccggctga   2220
accactaccc tccttgcccg agccccgacc tggcccctcgg cgtggggcgg cacaaggacg   2280
ccggcgccct gaccatcctg taccaggacg acgtcgggg gctcgacgtc cggcggcgct   2340
ccgacggcga gtgggtccgc gtcaggcccg tgcccgactc gttcatcatc aacgtcggcg   2400
acctcatcca ggtacgtgcc cacctgatga actgagctga actgaggtta catgcactgc   2460
atgtgtatag gcttctcaga tcgcttcgtg tggcgtaagg tgtggagcaa cgacaggtac   2520
gagagcgcgg agcaccgggt gtcggtgaac tcgcgaggg agaggttctc catgccctac   2580
ttcttcaacc cggcgaccta caccatggtg agccggtgg aggagctggt gagcaaggac   2640
gatccgccca ggtacgacgc ctacaactgg ggcgacttct tcagcaccag gaagaacagc   2700
aacttcaaga agctcaacgt ggagaacatt cagatcgcgc atttcaagaa gagcctcgtc   2760
ctcgcctaac tactgctact gctaggatcc atgccattgc catgtcgtct tcagattcag   2820
agcacgccat gtcgtcgcta gcttcgtggt agaacaaata atgatgtgcg tgctgtgtgt   2880
aagcatggat atggatgtga atatgtaata tgatgagcat tcctactttg gtatgttttgg   2940
gaataacaga cttgtgttgg tctggtcat tatttgtaag aaaatcaaaa agagttagta   3000
gggcaggagg ctaaccacag tcatgctgca ccacatccct ggtggaaagc tggccgggtt   3060
acgctacgct cgtgcagcca gattactgca gggccgggat atgcttccgg tggaaggaag   3120
gggacggtgg ctgaggacca tggggctgga gcctgggaga gaggtcgagc tagaagaaag   3180
ggggagagag aagacgcaca acgaagatgg gtcagccagg gatttcgacc caaggggag   3240
ctagtggatt ttgggagaaa acagaaaaga gaaaagagaa aagaagaaaa atttgttggt   3300
gtgaacacaa ggttgattg tcttttctta tttggattga tgatgagtcg tggactaacc   3360
gacccgtgag ctattgtgtc gtataatcat gtctctcggt ttctggtgtg caggtttgaa   3420
gcacagagac ggtggtcgac gcaaaggtga acgtcatgca ggttcgtgcc gatggaccgg   3480
gagcagtgaa agacgagcgt tgggacttga caaagggacc agagtcgccg gatgactagc   3540
cgcagtggct gacgcctgga acacgcatag acgtgaggac gtggtagagc aggtgaaaat   3600
cgcctagagg ggggggggt gaatagacaa aacctaaaaa ttataaactt tgaacacaaa   3660
ctttacctga ggttaccgtt agaacgagta ttaatgaaat cggagtgcgg aaggcaagtt   3720
cttcttgcta cgagttgctt aatcaatatt gataactttg ggagtcaact caaaatgatc   3780
acaagcaaaa gaactagaga gagaggagag aagaatcaa ctcgcaaagt aatgatcaac   3840
acaaatgaac acaatgattt atttctcgag gtttggttcc gaagaaccta ctccccgttc   3900
aggagtccac ataggacatg tctctcttcaa ccctttctct ctctcaaatg gtcacataga   3960
ctggttcagt tgagagcacc tagagggggg tgaataggtg atcttgtaaa atcaaacact   4020
aatagccaca aaacttagtt taaagtgtta gtacggctaa gtagctttga agcgagttat   4080
tgtgaacaca acaat                                                    4095

SEQ ID NO: 39         moltype = DNA  length = 21
FEATURE               Location/Qualifiers
misc_feature          1..21
                      note = suppression oligo
source                1..21
                      mol_type = other DNA
                      organism = synthetic construct
SEQUENCE: 39
ctccatcatg cggtgcaact a                                              21

SEQ ID NO: 40         moltype = RNA  length = 21
FEATURE               Location/Qualifiers
misc_feature          1..21
                      note = suppression oligo
source                1..21
                      mol_type = other RNA
                      organism = synthetic construct
SEQUENCE: 40
tagttgcacc gcatgatgga g                                              21

SEQ ID NO: 41         moltype = DNA  length = 19
FEATURE               Location/Qualifiers
misc_feature          1..19
                      note = suppression oligo
source                1..19
                      mol_type = other DNA
                      organism = synthetic construct
SEQUENCE: 41
ggtactgcga ggagatgaa                                                 19

SEQ ID NO: 42         moltype = RNA  length = 21
FEATURE               Location/Qualifiers
```

```
misc_feature          1..21
                      note = suppression oligo
source                1..21
                      mol_type = other RNA
                      organism = synthetic construct
SEQUENCE: 42
ttcatctcct cgcagtacct a                                              21

SEQ ID NO: 43         moltype = DNA  length = 19
FEATURE               Location/Qualifiers
misc_feature          1..19
                      note = suppression oligo
source                1..19
                      mol_type = other DNA
                      organism = synthetic construct
SEQUENCE: 43
caggcgccat ggtcatcaa                                                 19

SEQ ID NO: 44         moltype = RNA  length = 21
FEATURE               Location/Qualifiers
misc_feature          1..21
                      note = suppression oligo
source                1..21
                      mol_type = other RNA
                      organism = synthetic construct
SEQUENCE: 44
ttgatgacca tggcgcctgg a                                              21

SEQ ID NO: 45         moltype = DNA  length = 19
FEATURE               Location/Qualifiers
misc_feature          1..19
                      note = suppression oligo
source                1..19
                      mol_type = other DNA
                      organism = synthetic construct
SEQUENCE: 45
tcatgcggtg caactacta                                                 19

SEQ ID NO: 46         moltype = RNA  length = 21
FEATURE               Location/Qualifiers
misc_feature          1..21
                      note = suppression oligo
source                1..21
                      mol_type = other RNA
                      organism = synthetic construct
SEQUENCE: 46
tagtagttgc accgcatgat a                                              21

SEQ ID NO: 47         moltype = DNA  length = 19
FEATURE               Location/Qualifiers
misc_feature          1..19
                      note = suppression oligo
source                1..19
                      mol_type = other DNA
                      organism = synthetic construct
SEQUENCE: 47
tcgctcgcct tcttcctca                                                 19

SEQ ID NO: 48         moltype = RNA  length = 21
FEATURE               Location/Qualifiers
misc_feature          1..21
                      note = suppression oligo
source                1..21
                      mol_type = other RNA
                      organism = synthetic construct
SEQUENCE: 48
tgaggaagaa ggcgagcgac a                                              21

SEQ ID NO: 49         moltype = DNA  length = 19
FEATURE               Location/Qualifiers
misc_feature          1..19
                      note = suppression oligo
source                1..19
                      mol_type = other DNA
                      organism = synthetic construct
SEQUENCE: 49
tccaacgggc ggtacaaga                                                 19

SEQ ID NO: 50         moltype = RNA  length = 21
```

-continued

```
FEATURE                 Location/Qualifiers
misc_feature            1..21
                        note = suppression oligo
source                  1..21
                        mol_type = other RNA
                        organism = synthetic construct
SEQUENCE: 50
tcttgtaccg cccgttggac c                                                      21

SEQ ID NO: 51           moltype = DNA  length = 19
FEATURE                 Location/Qualifiers
misc_feature            1..19
                        note = suppression oligo
source                  1..19
                        mol_type = other DNA
                        organism = synthetic construct
SEQUENCE: 51
gcatcaacag gtacaacta                                                         19

SEQ ID NO: 52           moltype = RNA  length = 21
FEATURE                 Location/Qualifiers
misc_feature            1..21
                        note = suppression oligo
source                  1..21
                        mol_type = other RNA
                        organism = synthetic construct
SEQUENCE: 52
tagttgtacc tgttgatgcg a                                                      21

SEQ ID NO: 53           moltype = DNA  length = 19
FEATURE                 Location/Qualifiers
misc_feature            1..19
                        note = suppression oligo
source                  1..19
                        mol_type = other DNA
                        organism = synthetic construct
SEQUENCE: 53
tggacgatgg atagttcaa                                                         19

SEQ ID NO: 54           moltype = RNA  length = 21
FEATURE                 Location/Qualifiers
misc_feature            1..21
                        note = suppression oligo
source                  1..21
                        mol_type = other RNA
                        organism = synthetic construct
SEQUENCE: 54
ttgaactatc catcgtccat c                                                      21

SEQ ID NO: 55           moltype = DNA  length = 19
FEATURE                 Location/Qualifiers
misc_feature            1..19
                        note = suppression oligo
source                  1..19
                        mol_type = other DNA
                        organism = synthetic construct
SEQUENCE: 55
tggaccatgg atacttcaa                                                         19

SEQ ID NO: 56           moltype = RNA  length = 21
FEATURE                 Location/Qualifiers
misc_feature            1..21
                        note = suppression oligo
source                  1..21
                        mol_type = other RNA
                        organism = synthetic construct
SEQUENCE: 56
ttgaagtatc catggtccat c                                                      21

SEQ ID NO: 57           moltype = DNA  length = 19
FEATURE                 Location/Qualifiers
misc_feature            1..19
                        note = suppression oligo
source                  1..19
                        mol_type = other DNA
                        organism = synthetic construct
SEQUENCE: 57
gcaaggtcct agatttaca                                                         19
```

```
SEQ ID NO: 58         moltype = RNA   length = 21
FEATURE               Location/Qualifiers
misc_feature          1..21
                      note = suppression oligo
source                1..21
                      mol_type = other RNA
                      organism = synthetic construct
SEQUENCE: 58
tgtaaatcta ggaccttgca a                                           21

SEQ ID NO: 59         moltype = DNA   length = 19
FEATURE               Location/Qualifiers
misc_feature          1..19
                      note = suppression oligo
source                1..19
                      mol_type = other DNA
                      organism = synthetic construct
SEQUENCE: 59
cagagtacat ggaggtcaa                                              19

SEQ ID NO: 60         moltype = RNA   length = 21
FEATURE               Location/Qualifiers
misc_feature          1..21
                      note = suppression oligo
source                1..21
                      mol_type = other RNA
                      organism = synthetic construct
SEQUENCE: 60
ttgacctcca tgtactctgg a                                           21

SEQ ID NO: 61         moltype = DNA   length = 19
FEATURE               Location/Qualifiers
misc_feature          1..19
                      note = suppression oligo
source                1..19
                      mol_type = other DNA
                      organism = synthetic construct
SEQUENCE: 61
ccatgcccta cttcttcaa                                              19

SEQ ID NO: 62         moltype = RNA   length = 21
FEATURE               Location/Qualifiers
misc_feature          1..21
                      note = suppression oligo
source                1..21
                      mol_type = other RNA
                      organism = synthetic construct
SEQUENCE: 62
ttgaagaagt agggcatgga a                                           21

SEQ ID NO: 63         moltype = DNA   length = 19
FEATURE               Location/Qualifiers
misc_feature          1..19
                      note = suppression oligo
source                1..19
                      mol_type = other DNA
                      organism = synthetic construct
SEQUENCE: 63
acatggcggt caacttcta                                              19

SEQ ID NO: 64         moltype = RNA   length = 21
FEATURE               Location/Qualifiers
misc_feature          1..21
                      note = suppression oligo
source                1..21
                      mol_type = other RNA
                      organism = synthetic construct
SEQUENCE: 64
tagaagttga ccgccatgtg a                                           21

SEQ ID NO: 65         moltype = DNA   length = 726
FEATURE               Location/Qualifiers
source                1..726
                      mol_type = unassigned DNA
                      organism = Rice tungro bacilliform virus
SEQUENCE: 65
tcctacaaaa gggagtagta atatttaatg agcttgaagg aggatatcaa ctctctccaa  60
ggtttattgg agacctttat gctcatggtt ttattaaaca aataaacttc acaaccaagg 120
ttcctgaagg gctaccgcca atcatagcgg aaaaacttca agactataag ttccctgat  180
```

```
caaataccgt cttaatagaa cgagagattc ctcgctggaa cttcaatgaa atgaaaagag  240
aaacacagat gaggaccaac ttatatatct tcaagaatta tcgctgtttc tatggctatt  300
caccattaag gccatacgaa cctataactc ctgaagaatt tgggtttgat tactacagtt  360
gggaaaatat ggttgatgaa gacgaaggag aagttgtata catctccaag tatactaaga  420
ttatcaaagt cactaaagag catgcatggg cttggccaga acatgatgga gacacaatgt  480
cctgcaccac atcaatagaa gatgaatgga tccatcgtat ggacaatgct taaagaagct  540
ttatcaaaag caactttaag tacgaatcaa taaagaagga ccagaagata taaagcggga  600
acatcttcac atgctaccac atggctagca tctttacttt agcatctcta ttattgtaag  660
agtgtataat gaccagtgtg cccctggact ccagtatata aggagcacca gagtagtgta  720
atagat                                                              726

SEQ ID NO: 66           moltype = DNA  length = 165
FEATURE                 Location/Qualifiers
source                  1..165
                        mol_type = unassigned DNA
                        organism = Rice tungro bacilliform virus
SEQUENCE: 66
acgaatcaat aaagaaggac cagaagatat aaagctggaa catcttcaca tgctaccaca  60
tggctagcat ctttacttta gcatctctat tattgtaaga gtgtataatg accagtgtgc  120
ccctggactc cagtatataa ggagcaccag agtagtgtaa tagat                  165

SEQ ID NO: 67           moltype = DNA  length = 2000
FEATURE                 Location/Qualifiers
source                  1..2000
                        mol_type = unassigned DNA
                        organism = Zea mays
SEQUENCE: 67
ctgcaatata tacaccaaaa gtattataaa ctgtcatata tatgaccaaa acctttttat  60
tttagaaaag tatattaatc atggtatatt aatcaaagtt gttgttgggg ctgcaaaaat  120
cataccctte ttccacaagc tgttccttga actgcaggta ctcaggaact ctcagctcct  180
caacagcgag ctcactgacg ttgaccctca catactccca gacaccaggc ctagggcgga  240
tggcaagtgc aacccatggg gggatgacaa tcgcctcctg taagataata gagctagaat  300
gattaaagaa ggtgcacact acaaaaggaa cagtgctgtc cagcgagatc tgaatctgat  360
gcaaacctga gctgccctca ggacatcctc aaaagcacta tccttgagct tctcgcgctc  420
agcctcaggg atcgcattgt tgtactcggc aatgatctgg tggggctgca gcatacccctt  480
tccaaggttt ttcagcctgc gcaaaacgat gtgccaaata acatcagact atgccagatc  540
tataaactca tcaaacatat acaatttcaa gaaatagttt agacgtatga tcagcagtca  600
gtagcgtggg aacatatgca acatagcgaa gaggcacaac agcaaattca ttcgaaaaaa  660
tgaaaacaaa gattcctctc ttttaactga acttctcgaa accccttca tgcctacaca  720
tccgatctag tcagatgcct atgcgttcat gctgaacaga acgtgtcaga actaagcata  780
aactggttag caagcattat cgtattcgat agaccctttta gtaacaagct atacattggg  840
taagttcaga ctccaatcat tctgttcaga aacatcgtat tgaatataaa actaagaac  900
acacatgcag gtgcagccag atctaacagc agtttacagt cggtactaaa aaaagcatgg  960
tgtatgtatg tatcatcagt atccagtact aggtttcgac aaaatcctgg atgctaatta  1020
aatactcatc ttattaggga acacaggaac attatgtcta cagcattgaa tgatggccac  1080
atcatgctag atctaacaat acataatatg atggaactgg tcttaaaaag tcgcattcgc  1140
tcaaataata cccgtagcaa aataaatgta aacttgcaga cgaagcgggg gaaatgaggg  1200
cagacctggt gaagacggcg acaagctcat tggggtgggc agagagtgag tcgccaatgc  1260
gctccctgac gctgtggagg cggctcagga cacggtcacc tgcaccttcc cccattgctg  1320
tcctcttcct ggatcctcag gcctgcacag cgaaaccgaa acggaagcgg aagcttcagt  1380
cagcagagaa aactgaaacc gaaaaacggt tcagatccgt tgacataaaa gctgcgatga  1440
catcctaaaa ctaaaacccc tccagcaaga cataaaccca actgccaaca accagtcttt  1500
taagtctcga cacaccttg acgctgcgcc acgaaactat attgcaggca agaaaccaac  1560
agaacctaac tctggaaggg gggaaagaaa cggcagacag gagcaagacc caaaaaaaaa  1620
cgactcagat cctggtacta tagtcctagt acctagacca gaaagaagaa acaaccaata  1680
caacaagagg catacaagaa ctgaatcgat gaactgaaac gcttcagagg accgaggaat  1740
ggcgagaag ggaggcgcct atttatacag atctgacgag agaaccgaac aaaaacacat  1800
cgatgggaac catggagaag aaaagggctg ccgcatggc accaatggcc tcggcctcca  1860
aaaagccgtt gaatccaaag caggcgagga cgaagcgtga cgcggcaggg tacttctcta  1920
gaaaagcacg gcatcagcaa ggtgggggg ctggggttcc ttattgcagg caatcacgag  1980
gtgattagca caaacggaag                                              2000

SEQ ID NO: 68           moltype = DNA  length = 2000
FEATURE                 Location/Qualifiers
source                  1..2000
                        mol_type = unassigned DNA
                        organism = Oryza sativa
SEQUENCE: 68
ctgaaatata catcagagat attacaatga catatatatc gataaaagaa aaataataaa  60
attaagttttt aaattttaag aatatatgtt tttagtatcc caattatgca gatttcatac  120
ccttcttcca aagctgttc cttgaactgc aagtactcgg ggactgtcag caactcaaca  180
gcgagctcgc tcacattgac cctcacatac tcccagacac cgggcctcgg gcggatggca  240
agggcaaccc atggggagat aacaatcccc tcctgcatga taaaaacaa ttacaagtta  300
agaca agttagagca agcggtagag taaagatgga tctctgtgat gcaatgaaat ctgaatctga  360
ttcaaacctg tgcactcctc aggacatcct caaaagcacc gtccttcagc ttctcacgat  420
cagcctcaga gattgcgttg ttgtactcag caatgatctg gtgggcctga agcattccct  480
ttccgaggtt aaccagcctg cgcaaataac agtgtcaaca aaaatatcag gccagatcta  540
tcaactcagc ctataaatat tcaataaga taattttagc acttgagcat ttgcgcataa  600
taagaaaatt tgctattagc cacttaaaaa gaccatatat gatctgtttg cattgagatg  660
```

```
aattaaaaat ttcattgtag atatgaaatg attagttttg accatttaat tggacttaat    720
gaaatatgcg cgataatcag atctacgcgc tcgcgccaat agatctagta agatgtaggt    780
tttttatttt ttttgtgaaa ctttgctacc acaacaagca tctgtaccag tgcagaattc    840
attacttgta ttcagtttgt aaaccgtata tataatataa ataacatgca catgcagtca    900
gatctagcac taccagtcca cagtaatcca aaactactt tgtatatttc atcattattc    960
agtagtacta ggtttgtaca aaatcttggc tgcagaaggc cgcacttaaa tattcattct   1020
aatcagaaac ttaaaaaaaa agtgactaca aaatgattgc atccaattca gtaaatatga   1080
gccattcctg gccagatcta acaatctcaa caacaaagat cctatatgaa catctccttc   1140
taaaagaaaa tacagtaaca tctgaaggca gtagactaga aaccaacaaa atctaatgct   1200
gggaaatcac taaatcagca cgaacctggt gaagacgcg acgagctcat tggggtgggc    1260
ggagagggag tcgccgatgc gctccctgac gctgtggagg cggctcagga cgcggtcgcc   1320
ggcagcttcc cccattgctc tcctcttcct cttggctcct caagcctgcg tgcacaacca   1380
accaccatca tcagatacat ccagacccag tcaacacaat cactccagga aaaaaaaaag   1440
tcaagccata aaccccaacc aaaaaccacg cctttgacaa acactggaag aaaaagaaaa   1500
tcgcagcttt ttcacaagca atctagaaga aaagaaaaag aaaagactac atagcagcta   1560
taattgactg agaagcatac aggaatcaaa caatggagaa ggggagggag gaagaacaat   1620
gatgctccag gctgaggacc gaggaactgg gtgaagcggg gtaggcgcgt atttatgcag   1680
atctgaggag agaaaccacc aaaacaatcc gatggtttca acgaaaaaga tcgtcgcttc   1740
ttgctgcacc agctcaccca tagccgttga gatcgaagct aagctagcag cagcaaagct   1800
ggaacgaaga gtgacgcatt caagctcctc tcctctcctc tcctctcctc cggagcacga   1860
ggccagcatg ggatggattg gggtttcttg ttggccatgg caaaggagga ggtcattaac   1920
gttgacacgg cgtaatttaa ttaaatctta tcttaaaata tgatttaagt ggtagtaaca   1980
aggaagatta atactatgaa                                              2000

SEQ ID NO: 69         moltype = DNA   length = 2000
FEATURE               Location/Qualifiers
source                1..2000
                      mol_type = unassigned DNA
                      organism = Oryza sativa
SEQUENCE: 69
gctgtttaag aaaaacagaa gtaaaattca gtcactgtta ttttgcttca gttataatct     60
gcaaatcgtc gttctggtac ttactgtcca tcaacaagct gttccttgaa tgccaagtac    120
tcagaaacac tcagctcttc cactgccaac tcacttacat tcacccgaat gtagtcccag    180
acaccaggcc ttggcctgat ggccagtgca acccagggcg gcacacaat ggcttcctac     240
atacagtcaa ggaagtaagt tagaaagact ggtatttgac tttgagttga ctatcataac    300
catcctggct cattgccaaa tttacctgag cagcccggag aatgtcttca aagggagcat    360
atttctcttt gtcagcttcg atcaaggcat cgaactccgc aagcagctgg tgacgctgga    420
gcattccctt tccctggtta acatacctgc atagagtgat atttaagaaa tagaaccaat    480
gcttagatct cacatccttt ctgcggctga actatgttaa tggcactacc acataaacct    540
gattttact tcttatttt aagaccacat gatctgtact taatctagct atgaacaaac      600
aatatttcaa catcatctaa gattcatgac tcaagacaaa aatgttagag ctcatcacag    660
attattatag ataccatcat taaaactaaa gagatgcata accttgtcag ctaagaattt    720
gtaacatact aacatgttat cgtttcacat ctggggttgac taagaactaa ccaactgtat   780
ggataaaatc attgaaaact caaaacaatt agtagcaggt tccaagaaga cacaagatat    840
tatattgaga tcttcaccta gagaagagtg caatcaactc attgggatga gacgagaagg    900
tggcaccgag gcgttcgcgg agactgtgga ggcgagctag cttggcagcc atgactcaat    960
ttcaggaact gcaaagaaag gttacacttta gcaacacgta ccaaaaccac tcacttgcac   1020
aagaataatt agtcaacagc catcactaag cattgcaaga ctatctctga acaggaaagc    1080
catgctaaat caacactaat aacatcacac aaaagcattg gaagatcaaa acataactaa    1140
aaacagctgt ttcatctaca caactgaaag catctatggt ttacgaagca gagtgcgagt    1200
actgattcaa aataaatcaa cctgaaccaa tatactctga caatgttttc aaagggataa    1260
aagaaccagc tttatcaaat ggatttgttg ggttttagta agtatcattg agataccgat    1320
ggcatatctc aaactttgca aaattataat ggcatggttc caaattaccc tttagtatta    1380
gcaccagtta gatcctaatt cctaaatccg ataggacaga gcgaaagatc cctggagata    1440
tgaagatttg gctacagatt aagcagagcc aacatgaagt tccgaatatt atgaatccgc    1500
aagcggggag atcaaagaga agaatacgga aggtcgcgac tccatgaaag aatccaacca    1560
aaaacccaaa gattttctc agttcaaaaa aaaaaaaccc ttcattttg gttcgccatc      1620
caccgacagg caccaagaca ttcctcagga agcaaaaaag attaagcaga acaagtgata    1680
agcaagacac agtatcaacg gactacgagt cgagaaaatc actgaggcgc gattcttact    1740
gcaccaagta aaaaaaaatt tgggggcaaa ggaactctg caatggggcg gagcaacgtg     1800
gcagcaaaac taaaggtcga ggatttgagg ttttttgccg gttttcctcg aaaccccgaa    1860
tccgctcata gtaaacccac taaactgcag cagaaacccc cctcttggtt cagatttacc    1920
gaaagcagta aacccaagaa catgtcagca aaaactcctg caagattcag ctgacgaccc    1980
accaaagaat cgcaagaaat                                              2000

SEQ ID NO: 70         moltype = DNA   length = 2000
FEATURE               Location/Qualifiers
source                1..2000
                      mol_type = unassigned DNA
                      organism = Oryza sativa
SEQUENCE: 70
tggcggacgc gccacgcaca aacacaaacc tgcacacccc tgtgtcagag gaggagaggc      60
caagaaagga aatcgagtgg aggaagtgag gagcggcgga gacgtaggag gagagggggg    120
agatggaaat ggaaagccgc gcgagagagg aggcgcgtgg tggatggaga ggagagggag    180
aggtggtggg tttgtgtttg gagagacgag cgagcgaggc gaagcattta agggaggaa     240
gagggggaga gagagagaga gagagagaga gagagagaga gagagagaaa ggaggaatat    300
aataaagggt ggtgcacctg ccaactgcta tgctcaccaa cactttgtac acacccagtt    360
acacccccct gcctttatta tttccagtgc agtaataact tcaacaatta ttgaaatgaa    420
aatggaatta atggagttag tatcggatta gcgacacgct gccgagcttc ctagacggtg    480
```

```
cgattattc  agcgggaacg  actttctgta  ggtgaattta  atagaggagt  gttttaaatc   540
cactcgacgt  tgtaatagct  ggtttaattc  gtttgtactg  tcgagtagtt  atccaaaatc   600
aattttggat  atttaaaaga  aaaaaaaaca  gatccgaagt  attggaccta  ctggcaaata   660
ggaattttgc  tatatatagg  tgtgcgttca  tttataatgg  agtagcatgg  agtttattta   720
atccagtaaa  tgttttcatt  gatttaatta  ataataacgaa  tttcgcttga  ggccatattt   780
gttaaacgct  tttatctcta  tcatcattca  tcctaccagt  aaagagcacc  ggagatcgca   840
cttcatttaa  atatatgtcc  atgttggata  aaccatagtt  tattatagtg  ttctttttata   900
tgttttgtgg  ggaatttaga  ttgtttaata  tggcatacat  atccatccat  cattattata   960
ttctaacaca  actggataag  tgttctaaac  tattgtagaa  taactttgta  gtatgatcga   1020
tcttgtggaa  taaaaaaagt  ctgacaataa  cctttcataa  aggaatatga  atacccgtaa   1080
tcaacgcatc  aaatcattca  cggtgtacgc  ctagcgaatt  cgttggcgag  tgctcgtgcg   1140
gccgtgggct  cgctgtgatg  catgcatggc  tctctggcta  cgtcgagata  gcgattagta   1200
gcaaaattaa  gcaagccact  tattaattaa  tctttggaga  tatcatatga  ttaaggcatt   1260
aattcgtacg  tactcgtcgt  cagcgttttc  tgcaaagtcc  actacagttt  tttctttctt   1320
tgctgaaaat  gctgatgtgt  tggagatgga  gtgacgtgca  caacctgccg  ccacgtggat   1380
ggttgctgga  gcctacgtgt  catcttaatt  tgaacaaaaa  aaaaagagga  ataatacatc   1440
aatacatttt  cgaatttcag  ttctgccatt  gaccagtaat  acacatgtcg  gcctcacatt   1500
ttaccctgat  cttagtaacg  ggtggtcgcc  tggtcggtca  ctgaaaaaag  ttcaggaaat   1560
tatagtcaaa  ctgaaacgaa  catattcact  ccttaaaaaa  actaaatctt  tttatatatt   1620
tgtgatattg  taaaatagct  acgggataat  gatatagata  tatatagtga  taagggatag   1680
atggatcgag  atatggagtt  gtgctttctt  taatttccac  tacttgggct  accatattat   1740
ggtagttggt  atgaaaagat  acacagcagt  atagtgatgt  gatcaatgac  atgtatatct   1800
cacatgctcc  catgttggag  tcaaattttg  ctagactaaa  atccaattcc  aagcagtccc   1860
tagccaagaa  caaacaaaat  tcagtgaggt  cactgctgca  ccaaggactg  catgcatgca   1920
ggagaagggc  attttctctt  tttctttg  gagactcgat  tcaattcggt  cggtcggtcg   1980
caatggtcag  cttaattaaa                                                    2000

SEQ ID NO: 71          moltype = DNA  length = 2000
FEATURE                Location/Qualifiers
source                 1..2000
                       mol_type = unassigned DNA
                       organism = Oryza sativa
SEQUENCE: 71
tgtgaaaggt  ggcggcacca  gcttagccgc  agcttctctc  gtcgtctccc  tgaaacgaga    60
gggaggaagt  tggtagcgtg  atatatttag  gcatgtcatc  tcttgtataa  gaagtcttat   120
ctgtgctaat  tcacacggtt  ctctaatctc  tctccattct  gttttttgtaa  attggttcag   180
tagatagcgt  agggttatgc  ttatatatac  tccgtgaagt  atatatttaa  aaattagtca   240
cacgtaaagt  actacatatg  ttttatcgtc  taataacaat  aaaaaacacta  atcataaaat   300
ttttttaaat  aatacgaatg  gttaaacgtt  gaatatgaat  cgtgcaaaac  tatatttatt   360
ttgtaacaga  gaaaatattt  cacattaatt  agattgttgt  tttatggaag  gttggagagc   420
tgcgccgccg  ttgcgcagac  ctaggaggct  gcttataagt  tataatcaat  caattcacgg   480
atgccggctg  ggacgcggcc  catcgtccgg  gaagacgaca  actcaacgca  aaaagccgat   540
atgcctccaa  attgccattg  ccacctctac  ggctgtttat  actgctccaa  atcaaaagcg   600
tccatggaag  aatctagtat  ttcccgcaaa  gacgatgatg  atatgcagga  ttggatatat   660
aggggggttgt  tgcatgattg  ctagaactcc  cgtttccgaa  gttgttcgtc  catttttaaa   720
gctgccaaat  aggaatttat  tttgttttca  agtgtaatag  agttctgtcc  agatgagtga   780
attataattt  ggttcacatt  ttatttgcta  agtttcagtt  tgaacattct  caaataactt   840
ttttcttcac  ttttaaccg   agtaacttag  ttatttttc   cgtttggacc  acccaacaat   900
ttgttgctaa  gtgcatctca  cccgtcaaat  aattcctttg  aatccaaatt  caattatatc   960
ccaaaaataa  aaaacttctg  aattccacat  caattcaaac  cccaaccatt  ttaatttctc  1020
tccatattt   tccatttctct  attttttaccct  tttctttttt  tccatctatt  tatttttttc  1080
cttttctatt  tctttcttttc  tccttcctttt  tctctgtttcc  ttcttcttct  cctcggctag  1140
gcccgagcca  gcccgtgccg  cctcgcgcca  acctgtgcc   gccttacgcc  gcgcttgcgt  1200
gcgctcgcgc  ccacctcgtg  cccaacccgc  gcacgccaca  cgcacacacg  aggacgatcg  1260
acggacgaat  gcaatcatat  cccttcctt   actcagctag  aaggctcaag  aaccgcaact  1320
ttgatctctt  ccaccctctc  aaatccgccc  caacccctgc  tgactcaatc  gccattaccg  1380
gaggaaaaat  ccccgaaacc  ctattaccgg  cgccactaac  agagctccaa  aattcgtcgc  1440
ataattcgaa  atattctga   aattgaaggt  aaaaatggaa  tctacatgcg  aagtactccc  1500
tttccctcc   aatccgtcac  tggaacgccg  ccggcgccgc  ctcccgctgc  cactgccctg  1560
tttggccgcc  gacagccgca  cggcgcgccg  ctgctccagg  ccgccctagc  ttcaaccacc  1620
gccaccttg   gctccgcctc  cctcctctta  tgctcaccaa  gcccgcctcc  ctcgccggag  1680
atcgccggaa  ccaccgccgc  catggccgcc  accgcctcct  gcttctggcc  gccgcgcca   1740
gcctcgccac  cggcgcctat  gccaccgccg  accacgaaa   cggagtccct  acaccttggg  1800
gaccacaaaa  ccggcgggcat  ccctcccaaa  accggcctcc  tcccaccgcg  gcgttcgttgg  1860
gattccggcc  agttcgtgc   agagcgagag  aagaagagga  aaaatagatt  ttcctattga  1920
aagataaatc  agaaaattcc  ttttttcttt  cctatcaagt  tgaccatccg  tttgacctca  1980
aaatcaaaat  ctgagaccta                                                   2000

SEQ ID NO: 72          moltype = DNA  length = 786
FEATURE                Location/Qualifiers
source                 1..786
                       mol_type = unassigned DNA
                       organism = Zea mays
SEQUENCE: 72
gacatggagg  tggaaggcct  gacgtagata  gagaagatgc  tcttagcttt  cattgtcttt    60
cttttgtagt  catctgattt  acctctctcg  tttatacaac  tggttttta   aacactcctt   120
aacttttcaa  attgtctctt  tctttaccct  agactagata  attttaatgg  tgattttgct   180
aatgtggcgc  catgttagat  agaggtaaaa  tgaactagtt  aaaagctcag  agtgataaat   240
caggctctca  aaaattcata  aactgttttt  taaatatcca  aatattttta  catggaaaat   300
```

```
aataaaattt agtttagtat taaaaaattc agttgaatat agttttgtct tcaaaaatta   360
tgaaactgat cttaattatt tttccttaaa accgtgctct atctttgatg tctagtttga   420
gacgattata taatttttt tgtgcttaac tacgacgagc tgaagtacgt agaaatacta    480
gtggagtcgt gccgcgtgtg cctgtagcca ctcgtacgct acagcccaag cgctagagcc   540
caagagcg gaggtggaag gcgtcgcggc actatagcca ctcgccgcaa gagcccaaga    600
gaccggagct ggaaggatga gggtctgggt gttcacgaat tgcctggagg caggaggctc   660
gtcgtccgga gccacaggcg tggagacgtc cgggataagg tgagcagccg ctgcgatagg   720
ggcgcgtgtg aaccccgtcg cgccccacgg atggtataag aataaaggca ttccgcgtgc   780
aggatt                                                              786

SEQ ID NO: 73              moltype = DNA  length = 1160
FEATURE                    Location/Qualifiers
source                     1..1160
                           mol_type = unassigned DNA
                           organism = Zea mays
SEQUENCE: 73
atgtgctggt gccccataag gtaggcacct aggtctgtgt ttgaagcatc gacagatttg    60
taaacatgtt cctatgaacc tatttctgat tgataatttg tcaaaactca tcatttgtct   120
tcatccttgc ctgcttgcgt tcacgtgaca aagtacgtat atgtcttcgg cctttgctgt   180
gtatgtttcg cattgcttag atgtggtgaa agaacatcag aagatgcatt gatggcgtgc   240
ttaaaccagt gatgtgctcc aggtgttcct gcagtctgca gagatattta ctcttgtagt   300
cttgttgaca gcacagttgt atgtgattc ttggatgtaa tgtaaaccaa atgaaagata    360
ggaacagttc gtcctcttcc gtatacgaag gtcactgtat catttgtcgt ggcacaagat   420
gatctgcagg caggactgca acatggtttc ttggactgtc ctgaatgccc gttcttgttc   480
tttagttgag ccagagcagc agcctggtgt cggtgcctga gacctgacga agcacacggc   540
aaacaaacaa gtcgcagcag ctagcagggg cgttgccatc ggccacaagcc cccaagagac   600
ccgccgagga aaagaaaaaa aaactacggc cgccgttgcc aagccgagcg tgcgaaccga   660
tccacggat ggagatcaga gatcacccac cgcaggcggg cggcagtggc tggcgaggtg    720
cgtccacaga acctgctgca ggtccctgtc cgtcccggcg accccttttc taggcgagca   780
actcccatg gcagagctgc acgcagcagg gcccgtcgtt ggttgcagct ttaaccctt    840
ttgttttaac catacaatgc agagtcgcag aggtgaaaca ggacggaaat tacagaaaag   900
atggtggtgt gccagcagcc ccagcatgaa gaagatcagg acaaaagaaa agcttgtgat   960
tggtgacagc aacaggattg gattggagcc aagctaggca gtgagaggca ggcagcaaga  1020
cgcgtcagcc actgaaatcc agagggcaac ctcggcctca caactcatat ccccttgtgc  1080
tgttgcgcgc cgtggttagc caggtgtgct gcaggcctcc tccttgttta tatatgggag  1140
atgctctcac cctctaaggt                                              1160

SEQ ID NO: 74              moltype = DNA  length = 1532
FEATURE                    Location/Qualifiers
source                     1..1532
                           mol_type = unassigned DNA
                           organism = Oryza sativa
SEQUENCE: 74
tagtcctcta atatatgaaa ttttgatata ggtaaagaag ggtattgcaa ggataagaat    60
gtaaaagaa ataagagtaa tccttaccga taatagtatt cctctctac cgttaaaagt    120
taaacctgtg cgtgtagcat tttaatccag gatctatcga atccgtccct cgttggcgtg   180
ggcgacgaac acgtgcagaa gaagctttcc ccagaaagca cctcaccgcc tcgccgtctg   240
gcagactggc acgcggggcc ctaccctcgc tgccgcctggg cccgtccgcc ttctgcacac   300
tgtcacgccc ccaccgctc gccgcctcgc gcctctctct ccgcctccgc cgcggccgcc   360
cgacgtgata gcgacacgta ggactcgcca aacacaaaaa atccatgcg attttttggaa   420
ttttgttaca aaccaaatcc cgcattagag atttaattta attacgtagg                480
agtaccagat aaggagatcg agttaaaaaa gctaacggcg cggcgtggtt atctccgaat    540
cggctgtgg tcccgcgtc ggcgtcgcg cggcggcggc gcgccggccg aaccctggcc      600
gtcggatcgg gcgtcgtcct gggccccacg cgccacgggc ggctgtcgtt tgctcctcgg   660
agcggggtgg gcccaccatg gccaccacca caggtcggtc tcgcggctga cctggcggta   720
gtcccgtgct cgcggtgttt tttttttttc actctctttc tctcggtgga cagtagcggg   780
ggccgcggcc cgcgggggca gagattcaa aaacagcgga aacggaagat tgcaaaattg    840
caactgcttt cctgtttta attcgggatc aaaaagattc tttcgtcggg gtccccgtgc    900
cattgttgta ttgcgcgtag gtccttgctt gtaaaagata atctccttaa ttttttcttt   960
gtactactag tgtatatgca gtaagaatat accatgagta aaatgaacca caaaactaat  1020
tacgatatac cattctcatg tagacgttct ctttttcttt gctagtcata cgtgcatata  1080
taaccaaaca aaaaaatgtt tgaagtactc ctatccaatt tattactcca gtagacaaca  1140
aaagaaaatg tttgaagtaa taactgatcc atggtacagt aggggttgtcg tcaatcttgt  1200
gtttctttca ttcccattgta cttacaatcg tactccagtc agcacagcac aatgggctta 1260
agctttggac cccaaattct gatcttgtcg gggaccccgtc cgaaaatact cccgtagaga  1320
tgcagatacc gtcacaacct acaaccaacg aatgttaaga aaacaaaggg aaaaaaaaag  1380
aggcgaattc ggaggagaaa aaacggtggc taaaatatag tgcgggtgtg gggacgcgac  1440
gcgagcgacg aaagaggaga gaggatgggt tggcctgccc ccccctcccc tgtctataaa  1500
tgcagaggcg ccgagtgccc tagtcgccgc tc                                1532

SEQ ID NO: 75              moltype = DNA  length = 841
FEATURE                    Location/Qualifiers
source                     1..841
                           mol_type = unassigned DNA
                           organism = Oryza sativa
SEQUENCE: 75
tcgaggtcat tcatatgctt gagaagagag tcgggatagt ccaaaataaa acaaaggtaa    60
gattacctgc tcaaagtga aaacatcagt taaaggtgg tataaagtaa aatatcggta    120
ataaaggtg gcccaaagtg aaattactc ttttctacta ttataaaaat tgaggatgtt   180
```

```
tttgtcggta ctttgatacg tcattttgt atgaattggt ttttaagttt attcgctttt      240
ggaaatgcat atctgtattt gagtcgggtt ttaagttcgt ttgcttttgt aaatacagag      300
ggatttgtat aagaaatatc tttagaaaaa cccatatgct aatttgacat aattttgag       360
aaaaatatat attcaggcga attctcacaa tgaacaataa taagattaaa atagctttcc      420
cccgttgcag cgcatgggta ttttttctag taaaaataaa agataaactt agactcaaaa     480
catttacaaa aacaacccct aaagttccta aagcccaaag tgctatccac gatccatagc      540
aagcccagcc caacccaacc caacccaacc caccccagtc cagccaactg gacaatagtc      600
tccacacccc cccactatca ccgtgagttg tccgcacgca ccgcacgtct cgcagccaaa      660
aaaaaaaaga aagaaaaaaa agaaaaagaa aaaacagcag gtgggtccgg gtcgtggggg      720
ccggaaacgc gaggaggatc gcgagccagc gacgaggccg gccctccctc cgcttccaaa      780
gaaacgcccc ccatcgccac tatatacata ccccccctc tcctcccatc cccccaaccc       840
t                                                                      841

SEQ ID NO: 76           moltype = DNA  length = 1392
FEATURE                 Location/Qualifiers
source                  1..1392
                        mol_type = unassigned DNA
                        organism = Oryza sativa
SEQUENCE: 76
ctcgaggtca ttcatatgct tgagaagaga gtcgggatag tccaaaataa aacaaaggta      60
agattacctg tcaaaagtg aaaacatcag ttaaaaggtg gtataagtaa aatatcggta       120
ataaaaggtg gcccaaagtg aaatttactc ttttctacta ttataaaaat tgaggatgtt      180
ttgtcggtac tttgatacgt cattttgta tgaattggtt tttaagttta ttcgcgattt       240
tggaaatgca tatctgtatt tgagtcgggt tttaagttcg tttgcttttg taaatacaga      300
gggatttgta taagaaatat ctttaaaaaa acccatatgc taatttgaca taattttga      360
gaaaaatata tattcaggcg aattctcaca atgaacaata ataagattaa aatagcttgc     420
ccccgttgca gcgatgggta ttttttctag taaaataaaa gataaactta gactcaaaac     480
atttacaaaa acaaccccta aagtcctaaa gcccaaagtg ctatgcacga tccatagcaa     540
gcccagccca acccaaccca acccaaccca cccagtgca gccaactggc aaatagtctc      600
cacaccccgg cactatcacc gtgagttgtc cgcaccaccg cacgtctcgc agccaaaaaa     660
aaaaaaagaa agaaaaaaa gaaaaagaaa aaacagcagg tgggtccggg tcgtgggggc     720
cggaaaagcg aggaggatcg cgagcagcga cgaggccggc cctccctccg cttccaaaga     780
aacgccccc atcgccacta tatacatacc ccccctctc ctcccatccc ccaaccccta      840
ccaccaccac caccaccacc tcctccccc tcgctgccgg acgacgagct cctcccccct     900
ccccctccgc cgccgccggt aaccaccccg cgtccctctc ctcttttct ctccgttttt    960
ttttccgtc tcgtctcgat ctttggcctt ggtagtttgg gggcgagagg cggcttcgtc    1020
gcccagatcg gtgcgcggga ggggcgggat ctcgcggctg gtctcggcg tgcggccgga    1080
tcctcgcggg gaatgggggct ctcggatgta gatctgatcc gccgttgttg ggggagatga    1140
tgggggcgttt aaaatttcgc catgctaaac aagatcagga agagggggaaa agggcactat    1200
ggtttatatt tttatatatt tctgctgctg ctcgtcaggc ttagatgtgc tagatctttc     1260
tttcttcttt ttgtgggtag aatttgaatc cctcagcatt gttcatcggt agttttttctt    1320
ttcatgattt gtgacaaatg cagcctcgtg cggagctttt ttgtaggtag aagatggctg    1380
acgccgagga ta                                                         1392

SEQ ID NO: 77           moltype = DNA  length = 743
FEATURE                 Location/Qualifiers
source                  1..743
                        mol_type = unassigned DNA
                        organism = Oryza sativa
SEQUENCE: 77
gaattcccgg acctccatgc ctacatcaac taatttgatt ccttgagttt acgtttagtg     60
atatgtctat ttttagagct tgttggggct tcggcctcag ctctagccag ccaaacatgt     120
tctaccaagt accctatgtt ggcatgatat agtgatgcat tataacaata aatgagcgag     180
ggattgctgc tgaaaaagc tatactagct gcatttggtt atagttaacc gaactattaa     240
ttgcgtgtac aacaaaataa aaaaaatgca tgttgcacat tctttcatta acattatgtt     300
ttggtagtgt gaattagaaa tttgattgac agtagatcga caaacatagt ttcaatatgc     360
ttaagttagt tatgactta acatatcagt ctccttgata ttttcgtttt agattcgtct      420
ctctactagt gtgtatgtcc accttccata gcagtgaagg gttccattcc atccctggta    480
aaaaaaatc aaccactact attttatttcc taaaagcaa aatgataaaa tatcatttt      540
ttaataaaaa taaaaaaatt ttgggtaca taattgatgt tgccccttgg gattaaccttt    600
aaaaaagggc gaattttcta gggtttggcc aagtttgca atgcaccaaa ttattccct     660
tgggccggcc gccacccaa aaaaaacccc aaccccaac tttccattga aggccgggcc    720
cccttaaatc ctcatccccc caa                                              743

SEQ ID NO: 78           moltype = DNA  length = 144
FEATURE                 Location/Qualifiers
source                  1..144
                        mol_type = unassigned DNA
                        organism = Oryza sativa
SEQUENCE: 78
taaaaagggg cgaatttct agggtttggc caagttttgc aatgcaccaa attattcccc      60
ttgggccggc cgccacccca aaaaaaaccc caaccccaa ctttccattg aaggccgggc     120
cccttaaat cctcatcccc ccaa                                              144

SEQ ID NO: 79           moltype = DNA  length = 612
FEATURE                 Location/Qualifiers
source                  1..612
                        mol_type = unassigned DNA
                        organism = Cauliflower mosaic virus
```

```
SEQUENCE: 79
ggtccgattg agactttca acaaagggta atatccggaa acctcctcgg attccattgc    60
ccagctatct gtcactttat tgtgaagata gtggaaaagg aaggtggctc ctacaaatgc   120
catcattgcg ataaaggaaa ggccatcgtt gaagatgcct ctgccgacag tggtcccaaa   180
gatggacccc cacccacgag gagcatcgtg gaaaaagaag acgttccaac cacgtcttca   240
aagcaagtgg attgatgtga tggtccgatt gagacttttc aacaaagggt aatatccgga   300
aacctcctcg gattccattg cccagctatc tgtcacttta ttgtgaagat agtggaaaag   360
gaaggtggct cctacaaatg ccatcattgc gataaaggaa aggccatcgt tgaagatgcc   420
tctgccgaca gtggtcccaa agatggaccc cacccacgag ggagcatcgt ggaaaaagaa   480
gacgttccaa ccacgtcttc aaagcaagtg gattgatgtg atatctccac tgacgtaagg   540
gatgacgcac aatcccacta tccttcgcaa gacccttcct ctatataagg aagttcattt   600
catttggaga gg                                                      612

SEQ ID NO: 80           moltype = DNA   length = 837
FEATURE                 Location/Qualifiers
source                  1..837
                        mol_type = unassigned DNA
                        organism = Coix lacryma-jobi
SEQUENCE: 80
agcagactcg cattatcgat ggagctctac caaactggcc ctaggcatta acctaccatg    60
gatcacatcg taaaaaaaaa accctaccat ggatcctatc tgttttcttt ttgcccctgaa  120
agagtgaagt catcatcata tttaccatgg cgcgcgtagg agcgcttcgt cgaagacca   180
tagggggggcg gtactcgcac cgtggttgtt tcctgttatg taatatcgga tggggagca   240
gtcggctagg ttggtcccat cggtactggt cgtcccctag tgcgctagat gcgcgatgtt   300
tgtcctcaaa aactctttc ttcttaataa caatcatacg caaattttt gcgtattcga    360
gaaaaaaaga agattctatc tgtttttttt ttgaaatggc tccaatttat aggaggagcc   420
cgtttaacgg cgtcgacaaa tctaacggac accaaccagc gaatgagcga acccaccagc   480
gccaagctag ccaagcgaag cagacggccg agacgctgac acccttgcct tggcgcggca   540
tctccgtcgc tggctcgctg gctctggccc cttcgcgaga gttccggtcc acctccacct   600
gtgtcggttt ccaactccgt tccgccttcg cgtgggactt gttccgttca tccgttggcg   660
gcatccggaa attgcgtggc gtagagcacg gggccctcct ctcacacggc acggaaccgt   720
cacgagctca cggcaccggc agcacggcgg ggattcctc cccaccaccg ctccttccct    780
ttcccttcct cgcccgccat cataaatagc caccctccc agcttccttc gccacat       837

SEQ ID NO: 81           moltype = DNA   length = 947
FEATURE                 Location/Qualifiers
source                  1..947
                        mol_type = unassigned DNA
                        organism = Oryza sativa
SEQUENCE: 81
aatccgaaaa gtttctgcac cgttttcacg tcctaactaa caatataggg aacgtgtgct    60
aaatataaaa tgagacctta tatatgtagc gctgataact agaactatgt aagaaaaact   120
catccaccta ctttagtggc aatcgggcta aataaaaaag atcgctaca ctagtttcgt   180
tttccttagt aattaagtgg gaaaatgaaa tcattattgc ttagaatata cgttcacatc   240
tctgtcatga agttaaatta ttcgaggtag ccataattgt catcaaactc ttcttgaata   300
aaaaaatctt tctagctgaa ctcaatgggt aaagagagat attttttttt aaaaaaaaat   360
agaatgaaga tattctgaac gtatcggcaa agattttaaac atataattat ataattttat   420
agtttgtgca ttcgttatat cgcacgtcat taaggacatg tcttactcca tctcaatttt   480
tatttagtaa ttaaagacaa ttgacttatt tttattattt atcttttttc gattagatgc   540
aaggtactta cgcacacact ttgtgctcat gtgcatgtgt gagtgcacct cctcaataca   600
cgttcaacta gcgacacatc tccaatatca ctcgcctatt taatacattt aggtagcaat   660
atctgaattc aagcactcca ccatcaccag accacttta ataatatcta aaatacaaaa   720
aataatttta cagaatagca tgaaaagtat gaaacgaact atttaggttt ttcacataca   780
aaaaaaaaa gaattttgct cgtgcgcgag cgccaatctc ccatattggg cacacaggca   840
acaacagagt ggctgcccac agaacaaccc acaaaaaacg atgatctaac ggaggacagc   900
aagtccgcaa caacctttta acagcaggct ttgcggccag gagagag                 947

SEQ ID NO: 82           moltype = DNA   length = 721
FEATURE                 Location/Qualifiers
source                  1..721
                        mol_type = unassigned DNA
                        organism = Mirabilis mosaic caulimovirus
SEQUENCE: 82
tggagattca gaaaaatctc catcaacaaa taatccaagt aaggattaat ggattgatca    60
acatccttac cgctatgggt aagattgatg aaaagtcaaa aacaaaaatc aattatgcac   120
accagcatgt gttgatcacc agctattgtg ggacaccaat ttcgtccaca gacatcaaca   180
tcttatcgtc ctttgaagat aagataataa tgttgaagat aagagtggga gccaccacta   240
aaacattgct ttgtcaaaag ctaaaaaaga tgatgcccga cagccacttg tgtgaagcat   300
gtgaagccgg tccctccact aagaaaatta gtgaagcatc ttccagtggt ccctccactc   360
acagctcaat cagtgagcaa caggacgaag gaaatgacgt aagccatgac gtctaatccc   420
acaagaattt cctatataa ggaacacaaa tcagaaggaa gagatcaatc gaaatcaaaa    480
tcggaatcga aatcaaaatc ggaatcgaaa tctctcatct ctctctacct tctctctaaa   540
aaacacttag atgtgtgagt aatcacccac tgggggttgt aatatgtagt agtaaataag   600
ggaaccttag ggtataccat tgttgtaata ttattttcag tatcaataaa ataatctttc   660
agtttatctt atattcattt gtgtgacacc gtattcccat aaaaccgatc ctaatctctc   720
c                                                                   721

SEQ ID NO: 83           moltype = DNA   length = 352
FEATURE                 Location/Qualifiers
```

```
source                     1..352
                           mol_type = unassigned DNA
                           organism = Peanut chlorotic streak caulimovirus
SEQUENCE: 83
acagagggat ttctctgaag atcatgtttg ccagctatgc gaacaatcat cgggagatct   60
tgagccaatc aaagaggagt gatgtagacc taaagcaata atggagccat gacgtaaggg  120
cttacgccat tacgaaataa ttaaaggctg atgtgacctg tcggtctctc agaacctta   180
ctttttatat ttggcgtgta tttttaaatt tccacggcaa tgacgatgtg acctgtgcat  240
ccgctttgcc tataaataag ttttagtttg tattgatcga cacgatcgag aagacacggc  300
catttggacg atcatttgag agtctaaaag aacgagtctt gtaatatgtt tt          352

SEQ ID NO: 84              moltype = DNA  length = 1648
FEATURE                    Location/Qualifiers
source                     1..1648
                           mol_type = unassigned DNA
                           organism = Sorghum bicolor
SEQUENCE: 84
cactcgcaca tctcatggtg tcccaagaac ggcaagagcc agcactgcct ctgcctagca   60
acagcagcag cgccaagcga gcagccgcgc ccatggacgc cagcagcccg gccccgccgc  120
tcctcctccg cgcccccact cccagtccca gcattgacct ccccgctgcc gctggcaagg  180
ccgcggccgt gttcgacctg cggcgggagc ccaagatccc ggcgccattc ctgtggccgc  240
acgaggaggc gcgcccgacc tcggccgcgg agctggaggt tccggtggtg gacgtgggcg  300
tgctgcgcaa tggcgaccgc gcggggctgc ggcgcgccgc ggcgcaggtg gcctcggcgt  360
gcgcgacgca cggttcttc caggtgtgcg ggcacggcgt ggacgcggcc ctggggcgcg  420
ccgcgctgga cggcgccagc gacttcttcc ggctgccgct ggccgacaag cagcgcgccc  480
ggcgcgtccc cggcaccgtg tccgggtaca cgagcgcgca cgaccggttc gcgctgtcca  540
agctcccctg gaaggagacc ctgtccttcg gcttccacga cggcgccgcg tcgcccgtcg  600
tcgtggacta cttcaccggc accctcggcc aagatttcga gccaatgggg cgggtgtacc  660
agaggtactg cgagaagatg aaggagctgt cgctgacgat catggagctg ctggagctga  720
gcctgggcgt ggagcgcggc tactaccggg agttcttcga ggacagccgc tccatcatgc  780
ggtgcaacta ctaccgcgcc tgcccggagc cggagcgcac gctgggcacg ggcccgcact  840
gcgaccctac ggcgctgacc atcctcctgc aggacgacgt cggcgggctg gaggtgctgg  900
tggacgcga gtggcgcccc gtccggcccg tcccaggcgc catggtcatc aacatcggcg  960
acaccttcat ggcgctgtcg aacgggcggt acaagagctg cctgcaccgc gcggtggtga 1020
accagcggca ggagcggcgg tcgctggcct tcttcctgtg cccgcgcgag gaccgggtg  1080
tgcggccgcc ggccagcagc gccacgccgc ggcagtaccc ggacttcacc tgggccgacc 1140
tcatgcgctt cacgcagcgc cactaccgcg ccgacacccg cacgctggac gccttcaccc 1200
gctggctctc ccacggccca gtcccagccc aggaggcggc ggctccctgc acctagcgag 1260
cgagcgagcc gggccaaaca aacaagggc aaaggccatc tctttcgccg ggggcccgcc 1320
gcggggttcg cccacgtgcg cgcccaggtg ggcgctggcc gcgggcaggt ggcggacatg 1380
tggcctgcgg gccccgcgcc gccttccatt ttttggacgc tgccgcgcat gccgcatgcg 1440
tgcgtcgacg gccctactac ttctactact gctactgcga ctactagtgt acatacgcaa 1500
aaatacatat atacgtattt tctatatata tatatataag caaggcggcc ccccggtgac 1560
cttttctttg tttttgtcga caactgtgtt ttgatcccat tctagctgtt ctatggacca 1620
tggatggttc gttcaatgtt tgtacgta                                    1648

SEQ ID NO: 85              moltype = DNA  length = 1242
FEATURE                    Location/Qualifiers
source                     1..1242
                           mol_type = unassigned DNA
                           organism = Sorghum bicolor
SEQUENCE: 85
atggtgtccc aagaacggca agagccagca ctgcctctgc ctagcaacag cagcagcgcc   60
aagcgagcag ccgcgtccat ggacgccagc agccgggccc gccgctcct cctccgcgcc  120
cccactccca gtcccagcat tgacctcccc gctgccgctg gcaaggccgc ggccgtgttc  180
gacctgcggc gggagcccaa gatcccggcc ccattcctgt ggccgcacga ggaggcgcgc  240
ccgacctcgg ccgcggagct ggaggttccg gtggtgacg tgggcgtgct gcgcaatggc  300
gaccgcgcgg ggctgcggcg cgccgcggcg caggtggcct cggcgtgcgc gacgcacggg  360
ttcttccagg tgtgcgggca cggcgtggac gcggccctgg ggcgcgccgc gctggacggc  420
gccagcgact tcttccggct gccgctggcc gacaagcagc gcgcccggcg cgtccccggc  480
accgtgtccg ggtacacgag cgcgcacgcc gaccggttcg cgtccaagct cccctggaag  540
gagaccctgt ccttcggctt ccacgacggc cgcgtcgc cgtcgtcgt ggactacttc  600
accggcaccc tcggccaaga tttcgagcca atggggcggg tgtaccagag gtactgcgag  660
aagatgaagg agctgtcgct gacgatcatg gagctgctgg agctgagcct gggcgtggag  720
cgcggctact accgggagtt cttcgaggac agccgctcca tcatgcgtg caactactac  780
cgccgtgcc ggagccgga gcgcacgctg gcacgggcc gcactgcga ccctacggcg  840
ctgaccatcc tcctgcagga cgacgtcggc gggctggagg tgctggtgga cgcgagtgg  900
cgccccgtcc ggcccgtccc aggcgccatg gtcatcaaca tcggcgacac cttcatggcg  960
ctgtcgaacg ggcggtacaa gagctgcctg caccgcgcgg tgaacca gcggcaggag 1020
cggcggtcgc tggccttctt cctgtgcccg cgcgaggacc gggtggtgcg gccgccggcc 1080
agcagcgcca cgccgcggca gtacccggac ttcacctggg ccgaccctcat gcgcttcacg 1140
cagcgccact accgcgccga cacccgcacg ctggacgcct tcacccgctg gctctcccac 1200
ggcccagtcc cagcccagga ggcggcggct ccctgcacct ag                   1242

SEQ ID NO: 86              moltype = AA  length = 413
FEATURE                    Location/Qualifiers
source                     1..413
                           mol_type = protein
                           organism = Sorghum bicolor
```

```
SEQUENCE: 86
MVSQERQEPA LPLPSNSSSA KRAAASMDAS SPAPPLLLRA PTPSPSIDLP AAAGKAAAVF   60
DLRREPKIPA PFLWPHEEAR PTSAAELEVP VVDVGVLRNG DRAGLRRAAA QVASACATHG  120
FFQVCGHGVD AALGRAALDG ASDFFRLPLA DKQRARRVPG TVSGYTSAHA DRFASKLPWK  180
ETLSFGPHDG AASPVVVDYF TGTLGQDFEP MGRVYQRYCE KMKELSLTIM ELLELSLGVE  240
RGYYREFFED SRSIMRCNYY PPCPEPERTL GTGPHCDPTA LTILLQDDVG GLEVLVDGEW  300
RPVRPVPGAM VINIGDTFMA LSNGRYKSCL HRAVVNQRQE RRSLAFFLCP REDRVVRPPA  360
SSATPRQYPD FTWADLMRFT QRHYRADTRT LDAFTRWLSH GPVPAQEAAA PCT         413

SEQ ID NO: 87           moltype = DNA  length = 12906
FEATURE                 Location/Qualifiers
source                  1..12906
                        mol_type = unassigned DNA
                        organism = Sorghum bicolor
SEQUENCE: 87
cactcgcaca tctcatggtg tcccaagaac ggcaagagcc agcactgcct ctgcctagca    60
acagcagcag cgccaagcga gcagccgcgt ccatggacgc cagcagcccg gccccgccgc   120
tcctcctccg cgcccccact cccagtccca gcattgacct ccccgctgcc gctggcaagg   180
ccgcggccgt gttcgacctg cggcgggagc ccaagatccc ggccgccatt ctgtggccgc   240
acgaggaggc gcgcccgacc tcggccgcgg agctggaggt tccggtggtg gacgtgggcg   300
tgctgcgcaa tggcgaccgc gcggggctgc ggcgcgccgc ggcgcaggtg gcctcggcgt   360
gcgcgacgca cgggttcttc caggtgtgcg ggcacggcgt ggacgcggcc ctggggcgcg   420
ccgcgctgga cggcgccagc gacttcttcc ggctgccgct ggccgacaag cagcgcgccc   480
ggcgcgtccc cggcaccgtg tccgggtaca cgagcgcgca cgccgaccgg ttcgcgtcca   540
agctcccctg gaaggagacc ctgtccttcg gcttccacga cggcgccgcg tcgcccgtcg   600
tcgtggacta cttcaccggc accctcggcc aagatttcga gccaatgggt taagcgaagc   660
accgatttac atttaccgcg cgtcggcccc tgaggcctgg gtcttagtct tagcactgca   720
tatacggtcg gtagctctgg atatgatacg tatatatgaa accccgttcc aatcccatgc   780
acggtgtaca caggcgggtg taccagaggt actgcgagaa gatgaaggag ctgtcgctga   840
cgatcatgga gctgctggag ctgagcctgg gcgtggagcg cggctactac cgggagttcc   900
tcgaggacag ccgctccatc atgcggtgca actactaccc gccgtgcccg gagccggagc   960
gcacgctggg cacgggcccg cactgcgacc ctacggcgct gaccatcctc ctgcaggacg  1020
acgtcggcgg gctggaggtg ctggtggacg gcgagtggcg cccccgtccg gcccgtcccag  1080
gcgccatggt catcaacatc ggcgacacct tcatggtaac ccctgctctg tttttttcttg  1140
tcctcctctt gtcctgtgtg tgtgtatatt cacttctctc tgttttttttg ccccgaatcc  1200
tagtggacct aactgacgg attacagcac gcacacgtag gcatgtcatg tagcagcagt  1260
ctgcagcact gtagtactta gcgatgcaat agagacatgc gttccagtcg gttccatctc  1320
ggtgggctac agctacagtc ctacacggac gcggctcgta gtcgtaggga cgggcgcgtt  1380
ctctgtatcc acacacggct gcgcccaggc cgaggcttcc gccgcgggaa agttgcgaca  1440
acagaacggg gtttgtgccg ttggagcgtt gcggagaggc agaggcttgg ggggacgggg  1500
gcgcgatacg ctgcgatggg tgggtgaccg aggcgacgct ttcggcgggg gcccgggcct  1560
gcccaggtgc gcgcggcctc gtcgccttcc cctgttttt tgatgccgcc gctcggtcct  1620
cggtgttctg gctccgcccg cccgctgct gggtgcccat cccatctgat ccgatccgct  1680
ccgctccgcg gtggcggtcc tatgcgatgc cgccgcacga gcgcgggggg ccgcccgtgg  1740
aggagtagaa agtggtacaa ggttggttgg aacttggaat tgtgggggggt tactgctgct  1800
ggtggctgct gctttgcaac ttgccaggct gctgcctgtt gccccccgcg ttttctagcc  1860
gtttccgctc gcgatccggc acgcgcgcc cacaccgggg ctccagctcg gccccttggc  1920
cgtgtaggta gcaggcactt gcatctgtcc gttcgacacg atgattcttg tgcactgtgt  1980
acgtatgtac taaccctttc tggtatgatg tacgcatggc atgcaggcgc tgtcgaacgg  2040
gcggtacaag agctgcctgc accgcgcggt ggtgaaccag cggcaggagc ggcggtcgct  2100
ggcttcttc ctgtgcccgc gcgaggaccg ggtggtgcgg ccgccggcca gcagcgccac  2160
gccgcggcag tacccggact tcacctgggc cgacctcatg cgcttcacgc agcgccacta  2220
ccgcgccgac acccgcacgc tggacgcct cacccgctgg ctctcccacg gcccagtccc  2280
agcccaggag gcggcggctc cctgcaccta gcgagcgagc gagccgggcc aaacaaacaa  2340
ggggcaaagg ccatctcttt cgccggggcc cgcgcgcggg gttcgcccac gtgcgcgccc  2400
aggtgggcgc tggccgcggg caggtggcgg acatgtgggc tgcgggcccc gcgccgcctt  2460
cccatttttg gacgctgccg cgcatgccgc atgcgtgcgt cgacggccct actacttcta  2520
ctactgctac tgcgactact agtgtacata cgcaaaaata catatatacg tattttctat  2580
atatatatat ataagcaagg cggcccccg tgaccttttc cttttgttttt gtcgacaact  2640
gtgttttgat cccattctag ctgttctatg gaccatggat ggttcgttca atgtttgtac  2700
gtactccacg taaccaaact actctcagtgg actagtagat cgggctcatg tgatgaaact  2760
ggaccgacgc ggacgtcacg tcgtcaccc gcgtctggta gcgtagcgc acgagcgccg  2820
aatgtttcct gggcccgcaa gagaatcgct tctcatctcc tctcaccatg aatggggaaa  2880
aatgctgcgt cgaaagttcc agacgtttcc aaattccaaa cggttttgtg gcgtccgatc  2940
catgggcgc cccaaacttc caagacgttt tcaggttcca aatcttcgtg ctccacatca  3000
ccttcttccc agattcattt gcctcgtcgc ttgctctcct gtgttattca cgggtccac  3060
tgttgccccg tctgcgagaa agaaatttat tagagttgaa gcattcgaca tttcgactga  3120
ctgattgtta gtatcactaa attttgtgca catgttttt tggtcattca tctctggata  3180
ttttttttag ataatggata taaatatcgg gcctctacat ctgaggaagt acacagccaa  3240
ttattttcat ctctggacat gggacgatgg aagaggcaga tagatttagg agaccctttca 3300
attcagaatt tcaggtgcac aaggcctgcc tggcttgccc ggattcttgt ttcggacatg  3360
accaactagg ccgcactact tgcactgata gctggagaaa aaacaaaact ttgcaaacag  3420
caggattatc tacaagggaa actccatcca cgtgaaccag cattcaggg agagatgcga  3480
caaaaaaaaa gaggcggcaa caaaaaaatc ttactgcaat tttatctctg cattgaacct  3540
cttccaacca tgccgcatcc tgtactgttt tgtatctttc ccgtctggtcc gttgcgttct  3600
cacgcagttg ataacatgca gtcacgcacc accgaatcca gtgtactagg ggtagtgact  3660
tgtcacgcgc aacaacaggt cggtagcacc aagcaagtcg ctgtagactt gggcgtttaa  3720
caacgacttg cacaacagtt caaatatagc atatgcaatt atgcacaaga ttgttcgact  3780
gctatccgac aaactgaaga agctgcccaa ttgaacagaa tgtaccagtg atttccagca  3840
```

```
cactatctta cagcagcgtt gagaatgaaa caacaaatgg gggaaaacag atgtgtatta  3900
ttctacagtt acaccaaaga gtttgtcctt tcagcatcaa caagaatcat atgcatatct  3960
agtgacaaaa attcctctaa ttttacccta cttggtaaca gttctcttca acacatatat  4020
ttcacgtgct tgcatcgagt tccttgggcc gccacatcga cttctcgacg caaagcaagc  4080
cctcgttgcc cttggtgtag gtcattcgca cctcccactg caggggacttg gccatgcttt  4140
ccagttcgtt tattgtgtcc gcagtgtccc tcacaatcag tttgccttgg ggcctcagta  4200
cacgatcaac ctcggcaaaa actgccatca atttgcatct gtaaacaagc aacacagatt  4260
tagcatctgt aaacaccaca ggtttcattg caagaagcat aaagcatgca aacatgctac  4320
ttgtacatgt caaagaaaca tgtcaaactc aaacacatga aaatcattat tattgttttc  4380
ttgctgaact gatcacatta gttggtttca atttctgagt tccactagta atctatacca  4440
gaaggataga ataatgtcaa gaacaagaga tacaaacctc tttgtgagct ttgagaatag  4500
atggtccgcg tgcagaaggt cataagttct tgggtaagtg ctcaaagact cgcaccagtc  4560
atggtacata ccaaacaaac cacgctcgta aatgatgggc agtgtgtctg gtgaatcaat  4620
cggcacaata ttcatgaccc agaccttttg gtccctcaga gctgcagcaa aactgccatg  4680
caacgatgta aagcattagt aaaaatattg ggttttttaa accaaaacca agaaagataa  4740
ttcctccagc ttaactgaaa gaaagaaaga aaaaaactgc ttaatgactt atggtggaca  4800
agttgcctgt tatgttttat gatagctatg tgccagcttg gctaactggt agttatgtag  4860
tgtgatctga attaccaaaa aagagaagaa aaaaaaatca tgcccaagaa actgagaaag  4920
acacccattt acttaccctc catacacagc tctcatgtcc attacatttc tcactttgga  4980
ccagtcaatt cccatgccat tcacatacga tttacttaca acccttttcc agtgagcatt  5040
atctgcctcg aaatcttcat ttgcaggctt tccatagacc ccaaccttgg aaccatcaat  5100
ccagaaagga gtcttctcaa gccttttgtg ccaaaactct ggccattttg accctcgaac  5160
tttcgagcca acaggcagtt tgtgcatgca tgcttccaaa ggtacattcc tgcaaatcaa  5220
aagattgtgt aagcaaagca gaggaagcac ttcgccgcat tgaaaatacg ttcttctcaa  5280
agaaacaaaa ccataccaag ctgcatctgc atcatcagat tccttgcaca atggtgggtt  5340
gttttcggat cttttctcat agcaaatgtt gtccattggt ttctgaaata tgaccataccc 5400
aacttgattt aacttatcct tagtcttgtt gaccatcttc cagcacatgg acttttgtcaa 5460
agttggacatc gctgaaaaga ttaaggggtc atatgttatg atagaaataa aattcaattt  5520
tgcactgttg gtacatagca tctgtttttga acaaatgcaa tccttcctta tccatgaaag  5580
aagttaaccc ctgatactta ggattattca gtactttcac tcatgaactg ctgaatttgt  5640
tctgccagta gttgctatac tagaaatgtt cagtgtacca aacataaatt tggtacgggt  5700
tccttattaa agatgggagg ctgtatggta tttcgacgta acaaatcaag ttagcagcta  5760
ccctacttat ggatatacac ttctcaaaat gaatatacat agttttgata ggtgacatta  5820
attaatataa gaacttcatg cagttagggt gaaactaaac taagcagtta cggaaatacc  5880
attccaaatc tcaacatcct ctgggagctt ttggtaaaca gggagtggcag accagacaaa  5940
gtaaccacca gggcgtaaca agcggttcaa ttccagcaaa agcatgccac ctaaaaggag  6000
tcagtaataa gattcagttc tatagcaaat caataaatga aaggaagaca tgtcaccaac  6060
aagacaaacc ttcaatgtgc caagggaccc tgcagcgagc gcaatgaatg acatcaaaga  6120
ctctgctggg gtatgcgaagt ctcttggtgc ccatcacagc tgatattgct ggaattccnc  6180
tttctaatgc aaattgtact tgagcttcat gctcatcttt cggagcaaaa gacatggtaa  6240
gcacatctct atcaaacatg tagcctccaa agctggcaac tccacaaccg acatctagaa  6300
tgacgcggct tcgtttgccc catgcaatat caggcagtgc ctgtgaatga cagtttaatc  6360
agcatatgat gaaagcaagt gtgataatat caagttcaat gaaactttca  6420
taatcatgga cagtactaag cttgcttgat agattaatgt atggatgaga ctaaaaaaaa  6480
ggaaagttgt atccatcaga acgagaggct gaaaacacat ggctggctgt gaaagcctga  6540
tgtcgtttag tctagcataa acaaactgtc ctcagcatgt agatttccat agggtggcat  6600
ttgacaaatt atgattgtgg actagcgaat caatcactga ttctcaaaag tgtgagacag  6660
atgagttcaa gtctaagggg tgactaatat gggatgctgg gatgatgatg atgatatata  6720
cctgctgaat agtatcaata tagtggaggg caccattctt gaactgagtc ccacccccag  6780
ggaacaggag gtagtcacct gatacttaa cccaattttg atgtcccttg tactctgcga  6840
gcctagtgtg aggaacattg ctgtaccata cctgcaaaaa gcagcacaag atggtaataa  6900
gtaaacagag atcttggtca gctaaagatg attcagtgtc gtacaattta gaatagacag  6960
aatcaccttg tccctgctcc ttggccactc aattgggcgt ttatatcctt ctgggagtgg  7020
aacaaggcag gtaggaggct cctcagggca atgcctctca cgatgttcat aatgtttagt  7080
agttcgaagc ttcttgatag ccttctcgtt gtcaaggcaa ggtatgtaat ctgtcgaggc  7140
actgctatta catagtttcc aggaatagct agtcgcatca cctgaagact ttgatgacgc  7200
ttggacttcc ttttcattct tggactctgc agcctgtgtg gggaatgaac cattctgggt  7260
atttgactcc ttcagaagct ctgattgggc cccatcagga aatacctcgt ggagtttga   7320
gctctgatcc ttctctccat ttttcttccac ctttctcttct atctgaggtt gctcctcctg  7380
agtggcatca ccttcaggct tctcttcttg atcatccttg ctctctccat caggttttc   7440
atcaccactc tcatttgtga tttcatcatc tttcttctcc ccactcttct cccgtcacc   7500
atcgttcttc atgtcatctg accgcccttc tgatttccca tttgcatcat caaacatatc  7560
cttggtctca gctttctctg tcggcacttc cggctccttc tcttcaggct tctccctctgg 7620
cttctcagtg aacttctctt ccatcgtggc atcctcgtta ttccggctcct ccggcatcgt 7680
ggcatcattg ttgtcggtgt cctcaaattt ctcagaacct tcaccagcat tgtcctgtga  7740
ggcccccaaa ttgacaggcg caggctgctg cttcaccacc ggcttcttat tcgaggagat  7800
ctccagcggg aagacagtgg acgaggtcat catccacgcg ccgaccaggc agagcgccac  7860
aaagacgacg accgtggtgg tcgtgcagaa cgacgacgag gtcgaggacg gccggcggcc  7920
gtccatcttc ccacctcggc caaatgccat tagtcgctgg cgaacatgta ccagagcacc  7980
gaccttcacg cgatttatct ccaccaacta ctgctggacc aagaaccccc aaaaaaatcg  8040
cacctttgtc tgctttgtgc tgctacagcc gcgcggcacc tgaagcaaac cacaaaaaaa  8100
acttaaatcg ccgcggacat aaatcaaggt gctggatcta aagaacaaac gctggatcta  8160
ctcaagcaac aacggaagga agatccgcta ttggtgctag tattagcttc ttgtttccta  8220
gtactacagc ggctctttcc cagtataaga acacgggaaa atccccccttc  8280
gtggccaaac atgaaagaa aattagtaaa gcgtgtgctt taaaaccccc tcgttctgtt  8340
ccttccgcgg agagctaccg catcttccaa ttgagctggt tctcagctgg gcgcaaaacg  8400
cgcactaatc aatgtccgat tccatccaca aagaaaaaaa agacgggaac agctaatcca  8460
gcagctcgct cgctagctag ctagctcatc ggcggaagga cggaaccagc tttgctggat  8520
ccaggacagc aagagtgtgc aaggagaaag aacggagcag caatgcggat tgcggaggcg  8580
```

```
gtggattggt acctcgccgg aaccgaccgg agtggtcgcg gtggccctcc gcgcggatct    8640
cgaagaggag cgaggaaggg gaaggcggat gcgcgtcctt gggttctctg ccaccgcact    8700
gggcctcgcc gcgttataaa ggcgggcggg cgggcgggca gcgcagtgtg agtggagtgc    8760
aatctgttgt gtagtgtgtg aagaggcgga agcggaagcg gaggagatgg gttcgcatta    8820
gacgaccgta cgtaattata cgctatacta gtacttggt tagattactc gggagatctt     8880
ggccaaaatg tccggtctga gtgtttggta gttttatgga tttgcccttt taagatgttg    8940
gtatttctcc gggagcttag aaagaagaaa tggcgatgct ttaggccttg tttagatgcg    9000
aaaaaaattt ggatttcgct actgtggcat ttttatttgt ttgtagcaaa tattgtccaa    9060
acacggacta actaagattc atctcgcgat ttacagttaa actgtacaat tagtttttat    9120
tttcatttat atttaatgtt tcatgatgt gtcgaaagat acgatatgat agaaaatttt      9180
gaaaacttt tagttattga ggttaactaa acaatgcctt aattgagaat ttactcgagc     9240
aaaaagagtt aggtcagtct cagtggagag tttcatggtg ttgtttccaa gactgccata    9300
tcatgtgaaa tgaaatgaaa cttggttgaa acactcactc tcaatggaga gtttcatttt    9360
atagtttcat gggcatttaa tttcaatact catagagagt tgatatcgtg ccaactcatt    9420
tcttctctct cttcttaaat acacagtcat atcatcaaaa aaaatcctat gtagcaacat    9480
atttaatgca aataaaactc atatggtgga ctgtaggagt agcattaggc caagggcaca    9540
cacacgtca cggtgtgagt gcgacggtgc gagtgggccc gcggcggtag taagtgcgtg     9600
cgcgcccggc gccccctcc gcggcgacga cgcagcggca gcgcgtcgtc cagtgcaccg      9660
tctgctgttc ggcgctgcgg gtcctccgcg ccacgcgca gtgaaccggg cgcgtgcatc     9720
ccgggagcgg cggcttggca ctcccctgct tgtcggtggc ggccgtcggc atcgctcggc    9780
cccggagcgt cacgaggctg ctgattggga gcgagagcga gtagtggggc tggttgggga   9840
caatcccatt cccaccggc caccaggct gggactggtc cactagtcac tagtgggtgg     9900
ctcatgggtg tgggtgggct ggctaatgcc gcctgcccaa caaccaaccc aacccctgtg    9960
gacgctggta ccggtagttg ccgcgccatg gtggactgct gccgcctgat gccttttgcct   10020
gccacgctcc acgagttgag gcgcaccaaa ctgtgctgtg ctcctgattt gtgctaatcg    10080
gccgacgcgt accattcttt cttttctttcg tctacgacga gagaggccgg ttgactgttt    10140
cttcgttgga gggccatgtt gactcgtact aataataaaa ataataatac taggttgact   10200
ttttcaattc caacgcagca gtgcaaagct gcccaccat gagcacaggt ccttttttaa     10260
ctccgttttt gtacgtacac acgtactgtc cagcctgtgt ctaataatct taccaaaaac    10320
ctgtcatctc actatcaacc aatcaggctc tccgcctgtt cgtcgaggaa cagcagttgt    10380
tttccctact ccaacataga gtacactatg gacgcacatt accatgccag cttgagctta    10440
gcattgccca ccgttggata actgccatgc cattctcagg ccctgtttag ttcccatcta    10500
aaaatttttc atccattcca tcgaatcttt ggacacatgc atggaacatt aaatgtagat    10560
aaaaaaataa actaattaca cagtttagtt gagaatcgcg agacgaatct tttaagtcta    10620
gttactccat aattagcctt aagtgctaca gtaatccaca tatactaatg acagattaat   10680
tatgcttaat aaatttgtct tacagtttcc tgacgagcta tgtaatttgt ttttttatta    10740
gtttctaaaa acccctcccg acatccttcc gacatatccg atgtgacaac caaaaaattt   10800
tcatcttcaa tctaaacagg ccctcactct catcatctca tgccggggca gcaggtccgt    10860
cgtcaggtct gtcgtcccgt cccgtgccgt ctgaagcaac aggcagagag aacgccgttc   10920
catcggtttg ccgagccgtc agaggataga gctatactcg atccggagag gattgtgaaa    10980
cgaagcacgt ttaagcagtg ccgcgcacgt gctgctctgc tcctgatcc gatccagatc     11040
gactcggggc gtctcggcct cagcggcgat ggcaatcatc gcgcgcgctg ctggagctgg   11100
acgttttcgt cttgcattgc aggaggcgga acagaacgga gaaagccacg gcgcgcttg    11160
ccgacgccac gcgctgacac gagggacccg ttcagcggcc agcacgcagc ctaatcatgc    11220
ctgtcggggg gagctcatcc gttcctgaat ttgggtcatg ctccagtatc aggtattcag   11280
gtactagtac tcctgagcca tgtgctgcga caaaaaagcg aggctcctgt agtagagcct    11340
tgtttactta caaaattttt tacattctca gttatattaa atcttgtgac acatgcataa    11400
agcattaaat atacataaaa gaaataatta tttacacagt tacttataat ttgcgaaacg    11460
aatcttttaa gactggttag tttatgatta gataatattt attaaataca aatgaaagta    11520
atattattta tattttgcaa aaagtaaata agacctaggt agctaggcca acgtgagcat    11580
gtcggacccg gaccggttcg ttctacggcg cgtcccgcaa acctgcagcc aggtagtagt    11640
agtacaccgt gcacgggaga ggtgcgccat gcatgctcgg gcaaaagatc atagagaaag    11700
gtgcagcgtt tcagttgcac acctgaccga gtgacgcctc gccttgtttg gctttgttcc    11760
caaaatttt taaaattcct catcacatta aatctttgaa cgaatatatg gagcattaaa    11820
tataaataaa agaaataatt aatcatacaa tttgtctgta atttgcgaga cgaatctttt   11880
gagcctagtt agtttataat taaataatat ttgttaaata caaacgaaaa tgctacgtta    11940
gccaaaacta aaattttttct ccaaacgtga cccagcacct tccgatcaat catcactcag   12000
cgggtcacgt cagaagatca gatggaccttt gccgtccggg cctgtctctc ggcctcctcc    12060
ccatctggaa cgaacagagg tccagtcctg tttcgagtcg agctgagtcg atcagatggg   12120
cctaaatagg ccgaagacgt aggcaaaggg cccgctgatt tatctgattc ttctaggacc    12180
gtgcatgcgc ggatgggcct aggtggaaac ccaacagatg tgaggcttca aagaggaaga   12240
agtccgttac acatggagag ttagtctata atggataat atttaccaca aacaaataaa     12300
aatactacag tagcgaaatc caaaattttt cacatctaaa caaggcccta gatgtttgt     12360
cagtgccaga ccagagaaaa tctcgtcttc tgctgtcaaa gctttgatg attcctgacg    12420
gcagaggtaa agcttgcctg ggccttgttt agttccgaaa agtgaaagt tttcggtact      12480
gtagcacttt tgtttgttcg tgacaaatat catccaatta tggactaact agaattaaa     12540
gattcgtctc gtgatctaca gctaaactgt gtaattagtt tttgtttcg tctatattta      12600
atgtttcatg catgtgccac aagattcgat gtgacggaga attttgaaaa ttttttggtt    12660
ttcagagtga actaaacaag gcccagatgt aattgaccat gccatcgagc gcgagttgac    12720
tagagtgagt cggccctgat ggttaagtag tgcagactgc caagtggaca accgtctatc   12780
aactttgcag agtgggcgaa atgcactgag gatgttggag aggggcaagc caaggtaaac    12840
ttgaggaaag atgcttgttg acactgtagt atgtgaacaa tcctgtttaa ttttgtgtcc   12900
tcgacg                                                              12906

SEQ ID NO: 88          moltype = DNA   length = 1790
FEATURE                Location/Qualifiers
source                 1..1790
                       mol_type = unassigned DNA
                       organism = Setaria italica
```

```
SEQUENCE: 88
tctcatggtg tcccaagcac agcaagagcc agctctgcct cacagcagca gcaccgccaa    60
gcgcgcagcc gcgtcactca tggacgcccg cccggcccag cctctcctcc tccgcgcccc   120
gactccagc attgacctcc ccgcgtccaa gccggacagg gccgccgcgg cggcggcaa    180
ggccgccgcc gcctccgtgt tcgacctgcg gcgggagccc aagatcccgg cgccattcgt   240
gtggccgcac gacgacgcgc ggccggcgtc ggcggcggag ctggacgtgc cgttggtgga   300
cgtgggcgtg ctgcgcaatg gcgaccgcgc ggggctgcgg cgcgctgcgg cgcaggtggc   360
cgcggcgtgc gcgacgcacg ggttcttcca ggtgtgcggg cacggcgtgg gcgcggacct   420
ggcgcgcgcg gcgctggacg gcgccagtga ctttcttccg ctgccgctgg cggagaagca   480
gcgcgcccgg cgcgtcccgg ggaccgtgtc cggtacacg agcgcgcacg ccgaccggtt   540
cgcgtccaag ctcccctgga aggagaccct ctccttcggg ttccacgacg gcgccgcgtc   600
gcccgtcgtc gtcgactact cgccggcac cctcggcag gacttcgagg cagtggggcg   660
ggtgtaccag aggtactgcg aggagatgaa ggctctgtcg ctgacgatca tggagctcct   720
ggagctgagc ctgggcgtgg agcgcggcta ctaccgcgac ttcttcgagg acagccgctc   780
catcatgcgg tgcaactact acccgccgtg cccggagccg gagcgcacgc tgggcacggg   840
cccgcactgc gaccccaccg cgctgaccat cctcctccag gacgacgtcg gcgggctcga   900
ggtcctcgtc gacggcgact ggcgccccgt ccgcccgtc ccggcgcca tggtcatcaa   960
catcggcgac accttcatgg ctctgtccaa cgggcgggtac aagagctgcc tgcaccgggc  1020
ggtggtgaac cagcggcagg agcggcggtc gctggccttc ttcctgtgcc cgcgcgagga  1080
ccgggtggtg cgcccgccgg ccagcggcgc cgtcggcgag gcgccccgcc gctaccggag  1140
cttcacctgg gccgacctca tgcgcttcac gcagcgccat accgcgccg acacccgcac  1200
gctgacgcc ttcacgcgct ggctctccca cggcccggcc caggacgcc cagtggcggc  1260
ggcggcttcc acctagctag cggcgcggat ccgaccgagc ccattgacga cgccgtccct  1320
ttccgccgcc gccgggggccc gcgcgggggt tcacccacg tgcgcgccca ggtgggcgag  1380
gtggcggcct cgtggcccgc gggccccgcg ccgccttccc attttgggc gctgccgccc  1440
cgcgcgcatg ccggatcgt gcgtccacgg cctactgctg ctactagtgt acatatacaa  1500
acatacatat atacgtagta taaatatata agcaagcggc ccggtgcccc ttttcgtttt  1560
cttgttttgt cgatcacaat ctctggattc gatggatgga taaatgtttg tacgcatgca  1620
tgtagatggg ctcatgaaat ttcagaatct ggaacgacg aggagctcac gtgcctcttc  1680
cgtgtctggt agcggtagct gcgtgccaaa tgtctggtgg gccaaagaa attctagtgc  1740
caccgtccg gatccggcat ccgaaagttc ccgacggttc gacacccgaa             1790

SEQ ID NO: 89        moltype = DNA  length = 1272
FEATURE              Location/Qualifiers
source               1..1272
                     mol_type = unassigned DNA
                     organism = Setaria italica
SEQUENCE: 89
atggtgtccc aagcacagca agagccagct ctgcctcaca gcagcagcac cgccaagcgc    60
gcagccgcgt cactcatgga cgcccgcccg gccagcctc tcctcctccg cccccgact   120
cccagcattg acctcccgc gtccaagccg gacagggccg ccgcggcgg cggcaaggcc   180
gccgccgcct ccgtgttcga cctgcggcgg gagcccaaga tccggcgcc attcgtgtgg   240
ccgcacgacg acgcgcggcc ggcgtcggcg gcggagcccg cgccgttg ggtggacgtg    300
ggcgtgctgc gcaatggcga ccgcgcgggg ctgcggcgcg ctgcggcgca ggtggccgcg   360
gcgtgcgcga cgcacgggtt cttccaggtg tgcgggcacg gcgtgggcgc ggacctggcg   420
cgcggcgcg tggacggcgc cagtgacttc ttccggctgc cgctggcgga agagcagcgc   480
gcccgccgcg tcccggggac cgtgtccggg tacacgagcg cgcacgccga ccggttcgcg   540
tccaagctcc cctggaagga gaccctctcc ttcgggttcc acgacggcgc cgcgtcgccc   600
gtcgtcgtcg actacttcgc cggcaccctc gggcaggact cgaggcagt ggggcggtg    660
taccagaggt actgcgagga gatgaaggct ctgtcgctga cgatcatgga gctcctggag   720
ctgagcctgg gcgtggagcg cggctactac cgcgacttct cgaggacag ccgctccatc    780
atgcggtgca actactaccc gccgtgcccg gagccggagc gcacgctggg cacgggcccg   840
cactgcgacc ccaccgcgct gaccatcctc tccaggacg acgtcggcgg gctcgaggtc   900
ctcgtcgacg gcgactggcg ccccgtccgc ccgtccccg cgccatggt catcaacatc    960
ggcgacacct tcatggctct gtccaacggg cggtacaaga gctgcctgca ccggggggtg  1020
gtgaaccagc ggcaggagcg gcggtcgctg gccttcttcc tgtgcccgcg cgaggaccgg  1080
gtggtgcgcc cgccggccag cggcgccgtc ggcgaggcgc cccgcgcta ccggacttc   1140
acctgggccg acctcatgcg cttcacgcag cgccactacc gcgccgacac ccgcacgctg  1200
gacgccttca cgctggctc tccacggc ccggcccagg acgcgccagt ggcggcggcg  1260
gcttccacct ag                                                       1272

SEQ ID NO: 90        moltype = AA   length = 423
FEATURE              Location/Qualifiers
source               1..423
                     mol_type = protein
                     organism = Setaria italica
SEQUENCE: 90
MVSQAQQEPA LPHSSSTAKR AAASLMDARP AQPLLLRAPT PSIDLPASKP DRAAAAAGKA    60
AAASVFDLRR EPKIPAPFVW PHDDARPASA AELDVPLVDV GVLRNGDRAG LRRAAAQVAA   120
ACATHGFFQV CGHGVGADLA RAALDGASDF FRLPLAEKQR ARRVPGTVSG YTSAHADRFA   180
SKLPWKETLS FGFHDGAASP VVVDYFAGTL GQDFEAVGRV YQRYCEEMKA LSLTIMELLE   240
LSLGVERGYY RDFFEDSRSI MRCNYYPPCP EPERTLGTGP HCDPTALTIL LQDDVGGLEV   300
LVDGDWRPVR PVPGAMVINI GDTFMALSNG RYKSCLHRAV VNQRQERRSL AFFLCPREDR   360
VVRPPASGAV GEAPRRYPDF TWADLMRFTQ RHYRADTRTL DAFTRWLSHG PAQDAPVAAA   420
AST                                                                423

SEQ ID NO: 91        moltype = DNA   length = 2888
FEATURE              Location/Qualifiers
source               1..2888
```

```
                    mol_type = unassigned DNA
                    organism = Setaria italica
SEQUENCE: 91
tctcatggtg tcccaagcac agcaagagcc agctctgcct cacagcagca gcaccgccaa    60
gcgcgcagcc gcgtcactca tggacgcccg cccggcccag cctctcctcc tccgcgcccc   120
gactcccagc attgacctcc ccgcgtccaa gccggacagg gccgccgcgg cggccggcaa   180
ggccgccgcc gcctccgtgt tcgacctgcg cggggagccc aagatcccgg cgccattcgt   240
gtggccgcac gacgacgcgc ggccggcgtc ggcggcggag ctggacgtgc cgttggtgga   300
cgtgggcgtg ctgcgcaatg cgaccgcgc  ggggctgcgg cgcgctgcgg cgcaggtggc   360
cgcggcgtgc gcgacgcacg ggttcttcca ggtgtgcggg cacggcgtgg gcgcggacct   420
ggcgcgcgcg gcgctggacg gcgccagtga cttcttccgg ctgccgctgg cggagaagca   480
gcgcgcccgc cgcgtcccgg ggaccgtgtc cgggtacacg agcgcgcacg ccgaccggtt   540
cgcgtccaag ctcccctgga aggagaccct ctccttcggg ttccacgacg gcgccgcgtc   600
gcccgtcgtc gtcgactact tcgccggcac cctcggggcag gacttcgagg cagtggggta   660
agtatgtagg aatgaacttg gcacgcattg catccacatg gcgtgctgat cgaacgagct   720
gagccaaccg gcatgcacac atggcgtggc aggcgggtgt accagaggta ctgcgaggag   780
atgaaggctc tgtcgctgac gatcatggag ctcctggagc tgagcctggg cgtggagcgc   840
ggctactacc gcgacttctt cgaggacagc cgctccatca tgcggtgcaa ctactacccg   900
ccgtgcccgg agccggagcg cacgctgggc acgggcccgc actgcgaccc caccgcgctg   960
accatcctcc tccaggacga cgtcggcggg ctcgaggtcc tcgtcgacgg cgactggcgc  1020
cccgtccgcc ccgtccccgg cgccatggtc atcaacatcg gcgacacctt catggtacgg  1080
ccgccgctaa tccatccttt tgttgctctt atctcctctg gcgagtgcga gtaacgaaag  1140
cgctagctcc cctgctcctt gtcctgctct gtttcccaag tcctaatgga gctaaccggg  1200
cagactgcaa cacgcacgcg taggcatgtc acgtagccac cacttgcact gtgctgcgca  1260
gcgacgacgc aacgcggacg tgcgttcgag tcggttccat ctcggcgccg ctacacgcgg  1320
ccgcggctcc tagcctccta gggtccctg  atccctatcc ccgagccctt ccgcgggaaa  1380
agttcgttgg cgacggcaga ggagagccga ccgggtccgtg ccgttggagc gtggcggcag  1440
gagaggccgg gagggtgttt tgttgcgttg cgcggcggcg cggaggatgc gatggcgcgg  1500
gcgggcggcg ctttcggcgg tggccccgc  gacccacgtg cgcgcgcggt ctcgtcgcct  1560
tccctgtttt ggtgccacct ctctgtgtcc gggaatgggt tggcttagcg gcgaccgaga  1620
ccgggcggtg gtctgccctg ctccggcgc  ccatccgcc  tggtctctca tcctgctcct  1680
cctatgcgcg agggggcctg tagcggctgg agtacaagca gattggttgg gttgggttgc  1740
tgctgcttgg ctgttgcccg cccgctttct agccgttttcc gctcgccatc cggcacgcgg  1800
cgcccacgcc ggggctccag ctcggcccct ttggccgtgt gggtggcagg caccccctga  1860
tcgtctcgtg cgtccggttt ccgcgcctgg ccccccgcct tgaggtttcc ctgtgctcttt  1920
gacaagactt tcgtagatat atgtgtgtgt atgtgtgtgt gtgcgtgcgc gcgtgtgtgt  1980
atatatatat ataaataaat aacatctgtg aatgatggat tacacgtgta gctgaccggc  2040
tgattgtgtt cgcgtgtgtg tcttcgatgc attgcaggct ctgtccaacg ggcggtacaa  2100
gagctgcctg caccgggcgg tggtgaacca gcggcaggag cggcggtcgc tggccttctt  2160
cctgtgcccg cgcgaggacc gggtggtgcg cccgccggcc agccggcgcc tcggcgaggc  2220
gccccgccgc tacccggact tcacctgggc cgacctcatg cgcttcacgc agcgccacta  2280
ccgcgccgac acccgcacgc tggacgcctt cacacgctgg ctctcccacg gcccggccca  2340
ggacgcgcca gtggcggcgg cggcttccac ctagctaccg gcgcgaatcc gaccgagccc  2400
attgacgacg ccgtcccttt ccgccgccgc cggggcccgc gcgggggttc acccacgtg   2460
cgcgcccagg tgggcgaggt ggcggcctcg tggcccgcgg gccccgcgcc gcttcccat   2520
ttttgggcgc tgccgccccg cgcgcatgcc ggatgcgtgc gtccacggcc tactgctgct  2580
actagtgtac atatacaaac atacatatat acgtagtata aatatataag caagcggccg  2640
ggtgccccctt ttcgttttct tgttttgtcg atcacaatct ctggattcga tggatggata  2700
aatgtttgta cgcatgcatg tagatgggct catgaaatt  cagaatctgg aacgacgag   2760
gagctcacgt gcctcttccg tgtctggtag cggtagctgc gtgccaaatg tctggtgggc  2820
ccaaagaaat tctagtgcca cccgtccgga tccggcatcc gaaagttccc gacggttcga  2880
cacccgaa                                                            2888

SEQ ID NO: 92        moltype = DNA   length = 1567
FEATURE              Location/Qualifiers
source               1..1567
                     mol_type = unassigned DNA
                     organism = Oryza sativa
SEQUENCE: 92
tgcccagaca gctcgccctg cacacacaca cacactcaca ctcacacacg ctctcaactc    60
actcccgctc aacacagcgc tcacttctca tctccaatct catggtggcc gagcacccca   120
cgccaccaca gccgcaccaa ccaccgccca tggactccac cgccggctct ggcattgccg   180
ccccggcggc ggcggcggtg tcgacctga  ggatggagcc caagatcccg gagccattcg   240
tgtggccgaa cggcgacgcg aggccgcgt  cggcggcgga gctggacatg ccgttgtcg   300
acgtgggcgt gctccgcgac ggcgacgccg aggggctgcg ccgccgcgcg cgcaggtgg   360
ccgccgcgtg cgccacgcac gggttcttcc aggtgtccga gcacggcgtc gacgccgctc   420
tggcgcgcgc gcgcgctcga cggcgccagcg acttcttccg cctcccgctc gccgagaagc   480
gccgcgcgcg ccgcgtcccg gcaccgtgt  ccggctacac cagcgcccac gccgaccgct   540
tcgcctccaa gctccccatgg aaggagaccc tctccttcgg cttccacgac ggcgccgccg   600
cccccgtcgt cgccgactac ttctccagca ccctcggccc cgacttcgcg ccaatgggga   660
gggtgtacca gaagtactgc gaggagatga aggagctgtc gctgacgatc atggaactcc   720
tggagctgag cctgggcgtg gagcgaggct actacaggga gttcttcgcg gacagcagct   780
caatcatgcg gtgcaactac tacccgcca  gcccggagcc ggagcggacg ctcggcacgg   840
gcccgcactg cgacccccacc gcctccacca tcctcctcca ggacggcctc  ggaggtcctcgt   900
cgacggcgaa tggcccccgt tcagcccgt  ccccggcgcc atggtcatca                960
acatcggcga caccttcatg gcgctgtcga acgggaggta taagagctgc ctgcacaggg  1020
cggtggtgaa ccagcggcgg gagcggcggt cgctggcgtt cttcctgtgc ccgcgggagg  1080
acagggtggt gcggccgccg ccgagcgccg ccacgccgca gcactacccg gacttcacct  1140
gggccgacct catgcgcttc acgcagcgcc actaccgcgc cgacacccgc acgctcgacg  1200
```

```
                                  -continued
ccttcacgcg ctggctcgcg ccgccggccg ccgacgccgc cgcgacggcg caggtcgagg   1260
cggccagctg atcgccgaac ggaacgaaac ggaacgaaca gaagccgatt tttggcgggg   1320
cccacgccca cgtgaggccc cacgtggaca gtgggcccgg gcggaggtgg cacccacgtg   1380
gaccgcgggc cccgcgccgc cttccaattt tggaccctac cgctgtacat attcatatat   1440
tgcaagaaga agcaaaacgt acgtgtgggt tgggttgggc ttctctctat tactaaaaaa   1500
aatataatgg aacgacggat gaatggatgc ttatttattt atctaaattg aattcgaatt   1560
cggctca                                                              1567

SEQ ID NO: 93           moltype = DNA  length = 1170
FEATURE                 Location/Qualifiers
source                  1..1170
                        mol_type = unassigned DNA
                        organism = Oryza sativa
SEQUENCE: 93
atggtggccg agcaccccac gccaccacag ccgcaccaac caccgcccat ggactccacc    60
gccggctctg gcattgccgc cccggcggcg gcggcggtgt gcgacctgag gatggagccc   120
aagatcccgg agccattcgt gtggccgaac ggcgacgcga ggccggcgtc ggcggcggag   180
ctggacatgc ccgtggtcga cgtgggcgtg ctccgcgacg gcgacgccga ggggctgcgc   240
cgcgccgcgc gcaggtggc cgccgcgtgc gccacgcacg ggttcttcca ggtgtccgag    300
cacggcgtcg acgccgctct ggcgcgcgcc cgctcgacg gcgccagcga cttcttccgc    360
ctcccgctcc ccgagaagcg ccgcgcgcgc gcgtcccgg caccgtgtc cggctacacc    420
agcgccacg ccgaccgctt cgcctccaag ctcccatgga aggagaccct ctccttcggc    480
ttccacgacc gcgccgccgc ccccgtcgtc gccgactact tctccagcac cctcggcccc   540
gacttcgcgc caatggggag ggtgtaccag aagtactgcg aggagatgaa ggagctgtcg   600
ctgacgatca tggaactcct ggagctgagc ctgggcgtgg agcgaggcta ctacaggag   660
ttcttcgcgg acagcagctc aatcatgcgg tgcaactact accgccatg cccgagccg    720
gagcggacgc tcggcacggg cccgcactgc gaccccaccg ccctcaccat cctcctccag   780
gacgacgtcg gcggcctcga ggtcctcgtc gacggcgaat ggcgcccgt cagccccgtc    840
cccgcgcca tggtcatcaa catcggcgac accttcatgg cgctgtcgaa cgggaggtat    900
aagagctgcc tgcacagggc ggtggtgaac cagcggcggg aggcgcgtc gctggcgttc    960
ttcctgtgcc cgcgggagga caggtggtg cggccgccgc cgagcgccgc cacgccgcag   1020
cactaccgg acttcacctg gccgacctc atgcgcttca cgcagcgcca ctaccgcgcc    1080
gacacccgca cgctcgacgc cttcacgcgc tggctcgcgc cgccggccgc cgacgccgcc   1140
gcgacggcgc aggtcgaggc ggccagctga                                     1170

SEQ ID NO: 94           moltype = AA   length = 389
FEATURE                 Location/Qualifiers
source                  1..389
                        mol_type = protein
                        organism = Oryza sativa
SEQUENCE: 94
MVAEHPTPPQ PHQPPPMDST AGSGIAAPAA AAVCDLRMEP KIPEPFVWPN GDARPASAAE    60
LDMPVVDVGV LRDGDAEGLR RAAAQVAAAC ATHGFFQVSE HGVDAALARA ALDGASDFFR   120
LPLAEKRRAR RVPGTVSGYT SAHADRFASK LPWKETLSFG FHDRAAAPVV ADYFSSTLGP   180
DFAPMGRVYQ KYCEEMKELS LTIMELLELS LGVERGYYRE FFADSSSIMR CNYYPPCPEP   240
ERTLGTGPHC DPTALTILLQ DDVGGLEVLV DGEWRPVSPV PGAMVINIGD TFMALSNGRY   300
KSCLHRAVVN QRRERRSLAF FLCPREDRVV RPPPSAATPQ HYPDFTWADL MRFTQRHYRA   360
DTRTLDAFTR WLAPPAADAA ATAQVEAAS                                     389

SEQ ID NO: 95           moltype = DNA  length = 3140
FEATURE                 Location/Qualifiers
source                  1..3140
                        mol_type = unassigned DNA
                        organism = Oryza sativa
SEQUENCE: 95
tgcccagaca gctcgccctg cacacacaca cacactcaca ctcacacacg ctctcaactc    60
actcccgctc aacacagcgc tcacttctca tctccaatct catggtggcc gagcacccca   120
cgccaccaca gccgcaccaa ccaccgccca tggactccac cgccggctct ggcattgccg   180
ccccggcggc ggcggcggtg tgcgacctga ggatggagcc caagatcccg gagccattcg   240
tgtggccgaa cggcgacgcg aggccggcgt cggcggcgga gctggacatg cccgtggtcg   300
acgtgggcgt gctccgcgac ggcgacgccg aggggctgcg ccgcgccgcg cgcaggtgg    360
ccgccgcgtg cgccacgcac gggttcttcc aggtgtccga gcacggcgtc gacgccgctc   420
tggcgcgcgc ccgcgctcgac ggcgcagcg acttcttccg cctcccgctc gccgagaagc   480
gccgcgcgcg ccgcgtcccg gcaccgtgt ccggctacac cagcgcccac gccgaccgct    540
tcgcctccaa gctcccatgg aaggagaccc tctccttcgg cttccacgac cgcgccgccg   600
cccccgtcgt cgccgactac ttctccagca ccctcggccc cgacttcgcg ccaatggggt   660
aattaaaacg atggtggacg acattgcatt tcaaattcaa aacaaattca aaacacaccg   720
accgagatta tgctgaattc aaacgcgttt gtgcgcgcag gagggtgtac cagaagtact   780
gcgaggagat gaaggagctg tcgctgacga tcatggaact cctggagctg agctgggctg   840
tggagcgagg ctactacagg gagttcttcg cggacagcag ctcaatcatg cggtgcaact   900
actaccgcc atgcccggag ccgagcgga gctcggcac gggcccgcac tgcgaccca    960
ccgccctcac catcctcctc caggacgacg tcggcggcct cgaggtcctc gtcgacggcg   1020
aatggcgccc cgtcagcccc gtccccgcg ccatggtcat caacatcggc gacaccttca   1080
tggctaaacca tctcctattc tcctctcctc tgttctctcc tgcttcgaag caacagaaca   1140
agtaattcaa gctttttttt ctctctcgcg cgaaattgac gagaaaaata agatcgtggt   1200
aggggcgggg ctttcagctg aaagcgggaa gaaaccgacc tgacgtgatt tctctgttcc   1260
aatcacaaac aatggaatgc cccactcctc catgtgttat gatttatctc acatcttata   1320
gttaatagga gtaagtaaca agctactttt ttcatattat agttcgtttg atttttttt    1380
tttaaagttt tttagttttt atccaaattt attgaaaaac ttagcaacgt ttataatacc   1440
```

```
aaattagtct catttagttt aatattgtat atattttgat aatatatttta tgttatatta  1500
aaaatattac tatattttc tataaacatt attaaaagcc atttataata taaaatggaa   1560
ggagtaatta atatggatct cccccgacat gagaatattt tccgatggtg tgacgacgcc   1620
atgtaagctt cggtgggcct ggacggcag  aggtgccaac agccacgtcc aacaacccc    1680
gggtccccc  ctaacactcc aaacagtagt gagtagtgtc tcgtcgcgtt ttagtatttg   1740
atgacaaaca aagtgtgagt tgagttagcc accaccaact tgcacacgag cacatacatt   1800
tgtgtccatt ctcgccagtc acttccatct ctagtcctaa ctcctatcta gcgatgtaag   1860
cggataattt catcatccgt atataaacct gtttgttata gttaatttcc tatataaatac  1920
tataacagta tacattttaa aagaaaacaa aattaggata aacaggccct gctcctatcc   1980
atccatggca cttggaagga ccagactcgg tcatgccatg ccaagccaag atatgggtta   2040
tggaagagta gagaagagga gagatgagag ataagcatgc gttctcctcc tcgttggatg   2100
tgtattttgg agggatttgt gtagtagtag cagcggcgcc gcggggacgg atgcggatgg   2160
tggcgctttc ggtggcgttt tcccgggggg gttttggttt ggcgcttggg ggggatggca   2220
tggcgcgcg  tgcggctgca cgccacacac acgcgcggac acgcacgtac gtcgtcgtcg   2280
ccgcgggcgg acggtagctt aggggtggtgt gttccgcgcg cgggcgcgga ttgttccatg   2340
ccgatcgatt tggcgccacc ctcgccgcgg ctcttgtcgc gtcgtgcgcc tctctcgcgc   2400
ggtttgtcct tgtcgcgttg ctcagccggc gacggggca  cggacattgg cgatgtagcc   2460
ctgcacgtgt cggcctctcc gttgatgaat gatgatgtat gtatgtattt ttttttgtct   2520
gaaggaattt gtggggaatt gttgtgtgtg caggcgctgt cgaacgggag gtataagagc   2580
tgcctgcaca gggcggtggt gaaccagcgg cgggagcggc ggtcgctggc gttcttcctg   2640
tgcccgcggg aggacagggt ggtgcggccg ccgccgagcg ccgccacgcc gcagcactac   2700
ccggacttca cctgggccga cctcatgcgc ttcacgcagg cgcactaccg cgccgacacc   2760
cgcacgctcg acgccttcac gcgctggctc gcgccgccgg ccgccgacgc cgccgcgacg   2820
gcgcaggtcg aggcggccag ctgatcgccg aacggaacga aacggaacga acagaagccg   2880
attttggcg  gggcccacgc ccacgtgagg ccccacgtgg acagtgggcc cgggcggagg   2940
tggcacccac gtggaccgcg ggcccccgcg ccgccttccaa ttttggatcc taccgctgta   3000
catattcata tattgcaaga agaagcaaaa cgtacgtgtg ggttgggttg ggcttctctc   3060
tattactaaa aaaaatataa tggaacgacg gatgaatgga tgcttattta tttatctaaa   3120
ttgaattcga attcggctca                                                3140

SEQ ID NO: 96           moltype = DNA  length = 1170
FEATURE                 Location/Qualifiers
source                  1..1170
                        mol_type = unassigned DNA
                        organism = Triticum aestivum
SEQUENCE: 96
atggacacca gccctgcaac tcccctgctc ctccagcctc ctgctcccag cattgacccg    60
ttcgccgcca aggcggccgt caacaagggc ggcggcgcgg caaccgcggt gtacgacctc   120
cggagggagc cgaagatccc cgccccgttc gtgtggccga acgccgaggt gcgccccacc   180
acggcccagg agctggccgt gccggtggtg gacgtggggcg tgctgcgcaa tggcgacgcc   240
gcggggctcc gccgcgccgt ggcgcaggtg gccgcgcgt  gcgccacgca cgggttcttc   300
caggtgtccg gcacggcgt  ggacgaggcc ctggcgcgcg cggcgctgga cggcgcgagc   360
ggcttcttcc ggctgccgct ggccgagaag cagcgccgcg tgcccggcac cgtgggggac   420
tccgggtaca cgagcgcgca cgccgaccgg ttcgcctcca agctccctg  gaaggagacc   480
ctctccttcg gcttccacga ccgcgccggc gccgcgcccg tcgtggtgga ctacttcacc   540
agcacctcg  ggcggacta cgagccaatg ggagggtgt  accaggagta ctgcgggaag   600
atgaaggagc tgtcgctgag gatcatgag  ctgctggagc tgagccaggg cgtggagaag   660
cgcgggtact accggagtt  cttcgcggac agcagctcca tcatgcgcg  caactactac   720
ccgccgtgcc cggagccgga gcgcacgctg gcacgggcc cgcactgcga ccccacggcg   780
ctcaccatcc tactgcagga cgacgtggc  gggctggagg tcctcgtcga cggcgactgg   840
cgcccgtcc  gcccgtccc  cggcgcatg gtcatcaaca tcggcgacac cttcatggcg   900
ctgtcgaacg gcggtacaa  gagctgcctg caccgcgcgg tggtgaaccg cggcaggag    960
cggcggtcgc tggccttctt cctgtgcccg cgcgaggacc gcgtggtgcg gccgccgccg  1020
ggcctgagga gcccgcggcg gtaccccgac ttcacctggg ctgacctcat gcgcttcacg  1080
cagcgccact accgcgccga cacgcgcacc ctcgacgcct tcacccagtg gttctcctcc  1140
tcctcctcct cggcccagga ggcggcctga                                    1170

SEQ ID NO: 97           moltype = AA  length = 389
FEATURE                 Location/Qualifiers
source                  1..389
                        mol_type = protein
                        organism = Triticum aestivum
SEQUENCE: 97
MDTSPATPLL LQPPAPSIDP FAAKAAVNKG GGAATAVYDL RREPKIPAPF VWPHAEVRPT    60
TAQELAVPVV DVGVLRNGDA AGLRRAVAQV AAACATHGFF QVSGHGVDEA LARAALDGAS   120
GFFRLPLAEK QRARRVPGTV SGYTSAHADR FASKLPWKET LSFGFHDRAG AAPVVVDYFT   180
STLGPDYEPM GRVYQEYCGK MKELSLRIME LLELSQGVEK RGYYREFFAD SSSIMRCNYY   240
PPCPEPERTL GTGPHCDPTA LTILLQDDVG GLEVLVDGDW RPVRPVPGAM VINIGDTFMA   300
LSNGRYKSCL HRAVVNRRQE RRSLAFFLCP REDRVVRPPP GLRSPRRYPD FTWADLMRFT   360
QRHYRADTRT LDAFTQWFSS SSSSAQEAA                                     389

SEQ ID NO: 98           moltype = DNA  length = 3050
FEATURE                 Location/Qualifiers
source                  1..3050
                        mol_type = unassigned DNA
                        organism = Triticum aestivum
SEQUENCE: 98
ctcatggtgc tccagaccgc tcagcaagaa ccatccctga cgcgtccgcc tcactgcagc    60
gtcgccagcg cgcgctcgcc ggcggccatg gacaccagcc ctgcaactcc cctgctcctc   120
```

```
cagcctcctg ctcccagcat tgacccgttc gccgccaagg cggccgtcaa caagggcggc    180
ggcgcggcaa ccgcggtgta cgacctccgg agggagccga agatcccgc cccgttcgtg    240
tggccgcacg ccgaggtgcg ccccaccacg gcccaggagc tggccgtgcc ggtggtggac    300
gtgggcgtgc tgcgcaatgg cgacgccgcg gggctccgcc gcgccgtggc gcaggtggcc    360
gcggcgtgcg ccacgcacgg gttcttccag gtgtccggca gcggcgttga cgaggccctg    420
gcgcgcgcgg cgctggacgg gcgcgagcgg ttcttccggc tgccgctggc cgagaagcag    480
cgcgcgcggc gcgtcccggg gaccgtgtcc gggtacacga gcgcgcacgc cgaccggttc    540
gcctccaagc tcccctggaa ggagaccctc tccttcggct tccacgaccg cgccggcgcc    600
gcgcccgtcg tggtggacta cttcaccagc accctcgggc cggactacga gccaatgggg    660
taatatatcc acccgcccac acccctatcc ggccagcaga aatccatccc cgccactgca    720
tttttttcct tttgtttccg cgcgaccgta cgttcgatcg gcgcccacgt acgtacgtgc    780
gtacgcagta gcagtacttg aagccgccgt actacgtgct gagtagtgac aactgaacac    840
gtgcaggagg gtgtaccagg agtactgcgg gaagatgaag gagctgtcgc tgaggatcat    900
ggagctgctg gagctgagcc aggggcgtgga gaagcgcgga tactaccggg agttcttcgc    960
ggacagcagc tccatcatgc ggtgcaacta ctacccgccg tgcccggagc cggagcgcac   1020
gctgggcacg ggcccgcact gcgacccccac ggcgctcacc atcctactgc aggacgacgt   1080
gggcgggctg gaggtcctcg tcgacggcga ctggcgcccc gtccgccccg tccccggcgc   1140
catggtcatc aacatcggcg acaccttcat ggtaattact cctctctcag cgttgctttc   1200
gctgattaat tgcagaaaca gtagtcaact acccatgctc tgttccgctg tgctctgctt   1260
cccaacgagc gaaccggccc ataaaaactg ccttgctgtc ttggaaccaa gaggaaaggg   1320
accgtgggag cctaccgaca cgacgtgatt gcactctgct tcctaacaag cgagccgccg   1380
gtagggctat caccgtaagg ctccctttga ttcaaaggaa tttcttagga tttctgaagg   1440
attgaaatcc ttaggatttt ttcctatgtt ggtacttcga ttcataggat tgaatcccat   1500
aggatttttt tcctatgaaa tcttctgtac tacatttcat aggaaatcta acatccactc   1560
caaccttttt ttatatttcc tttgtttttc atgtgccatc aaacactcct tgttaatcct   1620
ataggattca agtgggcatg ccactccaat cctatacttt tcccattcct acgttttcaa   1680
aatcctacga atcaaagagg ccctaaagct gctgacatga cgtgattttt ttttttcttttt   1740
ctttctttct ttctcagctc caatcaacgc tggttattag atcattagag tggacaggtt   1800
gaattaacat gcagtagtta gtagttagca gccacaaacg ggtcccgttc tctgaagtct   1860
gaactgacat aagtcctgat catcgaccat tctttgcttc ctaggacgat gcctgttgga   1920
acttgcgtcc aatgcccgtt agggagtggt aattgtcatc acttttagac tcgtcgattc   1980
cactgatgaa gacgtagcac atggatgagc caacgtatcc gtttctagtg gtctcgaaaa   2040
gtagggtttc attcattcta tctatctatc cgtccgtcca aaagggctgc gatgcgagca   2100
cttgagtcgg agcaatcag agcgcgagaa aagatagggg gggtagcaag ccatgtcgga   2160
ggggctttg cttccggcag gtttggattc ttgtggtagg cgggcggctc tgtacagtag   2220
cggcggtgac ggtgaggtgg cggcgctttc ggtggcgggc caacccaggt gcatgcacgc   2280
gcgctcgtcg ttttccgcc tgaatctgcc gctgcgccca tggcaagggg gtgggtgctg   2340
ccgccggcg atggagtaga tcacggtcgc cgtcgggctc ggccagttga tcacggttcg   2400
ttcgtgcggt actaggttcc cccacggcac tgtgactgca tcgttccggc cctcgccatt   2460
ggcgatcggg caatcctctg ttcatccgtc gctgttgatt cctcggccac gatagaccat   2520
gcgcgtgccg gtcgtcgccc cgtcgcgctc gcttcacgtg ctcgtcgcgt ggctcccgtc   2580
ccacacgagg ccgccgcttt ctgacccagt ggagcgcgtg atttacagtt tatatatgtc   2640
gctgcatttt tcttttttgtg tgctgctcat tttgcttgga cggagaccgg gaacgattag   2700
ccacggatct aacgcgttgt tgcttgtttt caatgcatgc atgcaggcgc tgtcgaacgg   2760
gcggtacaag agctgcctgc accgcgcggt ggtgaaccgg cggcaggagc ggcggtcgct   2820
ggccttcttc ctgtgcccgc gcgaggaccg cgtggtgcgg ccgccgccgg gcctgaggag   2880
cccgcggcgg tacccggact tcacctgggc tgacctcatg gcttcacgc agcgccacta   2940
ccgcgccgac acgcgcaccc tcgacgcctt cacccagtgg ttctcctcct cctcctcctc   3000
ggcccaggag gcggcctgat tctgctctgc cacgaaacga tcggtccaca              3050
```

SEQ ID NO: 99        moltype = DNA   length = 1486
FEATURE                Location/Qualifiers
source                 1..1486
                       mol_type = unassigned DNA
                       organism = Hordeum vulgare
SEQUENCE: 99

```
gaccagtagc atatagtttt tcttgtgttt gccatggtgg acgtgtcgaa ctttgtagaa      60
gccaatggca atgcagcagt atcgattcct gccatggaag ttgctgggag tcctcacgtc     120
ccgttcgttc ctcgggacgc gaacgcgaca gacagcaaga atgccaagga cgtcctcgac     180
ctctcgcggc agcagaaaca aatcccggct cccttcatct ggcccacgc cgacgcgcgg     240
ccgtcgtcga tcttggagct ggacgtgccc gtggtcgaca tcggcgcggc cctgcacagc     300
gccgccggga tggcccgcgc gcggcgcag gtggccgagg catgcgcgag ccacggcttc     360
ttccaggtga ccgggcacgg cgtcgacccc gcgctggccc aagcagcgct cgacggcgca     420
gcggacttct tccgcctgcc gctcgcacc aagcagcgcc cccgatc cccgggcag       480
gtcaaagggt acgcctccgc ccacgccgac cgcttcgccg ccaagcttcc ctggaaggag     540
actctctcct tcatccacaa ccacgtccac gaggacgtcg gcgcccgcgc aagcagtcac     600
gtcgtcgact acttcacctc cgcccttggc gacgacttca tgcacctagg ggaggtgtac     660
caggagtact gtgaggcgat ggaggacgcg tcgctggcga taatggaggt gctggggtg     720
agcctggggc tggggagagg gtactacagg gacttcttcg ccgacgcaga ctccatcatg     780
aggtgcaact actacccgcg gtgcccggag ccggaccaga cgctgggac ggggccgcac     840
tgcgaccgt cggcgctgac catcctgctg caggacggca aggtgacgg gctccaggtg     900
ctcgtcgacg gcgcatggcg ctccgtgcgg cccaagcccg cgagctcgt cgtaaacatc     960
ggcgacacct tcatggcgct gtcgaacggc cggtacaaga gctgcctcca ccgcgcggtg   1020
gtgcaccgcg agaaggagcg ccggtccgctg gcctacttcc tcgccccgcg gaggaccgg   1080
gtggttcgcc gccgccttc gccggcgccg gcgccgcggc tctacccgga cttcacctgg   1140
gcggagctca tgcgattcac gcagcgccac taccgcgccg acgcccgcac gctcgacgcc   1200
ttcgcgtgct ggctcgacct gcccagctgc cccaccacgc cccaggccca agggactgtc   1260
tagtgtctgt gatgtatcat ctgtctcagc tgttgtatac gaccacttgt gtctgctagc   1320
tctgcgcttg tgttttctta tgtgagctaac taactaaata gtgtgtatat tcttgccgc    1380
```

```
gccttatgca agcccctagtc tagaacatgt aataattaac ttaagcatat acgttgatct  1440
ttggtgtatt tttcatattt ccttcataat gaataatcta ttatgc                 1486

SEQ ID NO: 100         moltype = DNA   length = 1230
FEATURE                Location/Qualifiers
source                 1..1230
                       mol_type = unassigned DNA
                       organism = Hordeum vulgare
SEQUENCE: 100
atggtggacg tgtcgaactt tgtagaagcc aatggcaatg cagcagtatc gattcctgcc   60
atggaagttg ctgggagtcc tcacgtcccg ttcgttcctc gggacgcgaa cgcgacagac  120
agcaagaatg ccaaggacgt cctcgacctc tggcggcagc agaaacaaat cccggctccc  180
ttcatctggc cccacgccga cgcgcggccg tcgtcgatct tggagctgga cgtgcccgtg  240
gtcgacatcg gcgcggccct gcacagcgcc gccgggatgg ccgcgagggc ggcgcaggtg  300
gccgaggcat gcgcgagcca cggcttcttc caggtgaccg ggcacggcgt cgaccccgcg  360
ctggcccaag cagcgctcga cggcgcagcg gacttcttcc gcctgccgct cgccaccaag  420
cagcgcgccc gccgatcccc ggggaccgtc aaagggtacg cctccgccca cgccgaccgc  480
ttcgccgcca agcttccctg gaaggagact ctctccttca tccacaacca cgtccacgag  540
gacgtcggcg cccgcgcaag cagtcacgtc gtcgactact tcacctccgc ccttggcgac  600
gacttcatgc acctagggga ggtgtaccag gagtactgtg aggcgatgga ggacgcgtcg  660
ctggcgataa tggaggtgct gggggtgagc ctggggctgg ggagaggta ctacagggac   720
ttcttcgccg acggcagctc catcatgagg tgcaactact acccgcggtg cccggagccg  780
gaccggacgc tggggacggg gccgcactgc gacccgtcgg cgctgaccat cctgctgcag  840
gacggcgagg tggacgggct ccaggtgctc gtcgacggcg catggcgctc cgtgcggccc  900
aagcccggcg agctcgtcgt aaacatcggc gacaccttca tggcgctgtc gaacggccgg  960
tacaagagct gcctccaccg cgcggtggtg caccggagga aggagcgccg gtcgctggcc 1020
tacttcctcg ccccgcggga ggaccgggtg gttcgcccgc cgccttcgcc ggcgccggcc 1080
ccgcggctct accggacttt cacctgggcg gagctcatgc gattcacgca gcgccactac 1140
cgcgccgacg cccgcacgct cgacgccttc gcgtgctggc tcgacctgcc cagctgcccc 1200
accacgcccc aggcccaagg gactgtctag                                  1230

SEQ ID NO: 101         moltype = AA   length = 409
FEATURE                Location/Qualifiers
source                 1..409
                       mol_type = protein
                       organism = Hordeum vulgare
SEQUENCE: 101
MVDVSNFVEA NGNAAVSIPA MEVAGSPHVP FVPRDANATD SKNAKDVLDL WRQQKQIPAP   60
FIWPHADARP SSILELDVPV VDIGAALHSA AGMARAAAQV AEACASHGFF QVTGHGVDPA  120
LAQAALDGAA DFFRLPLATK QRARRSPGTV KGYASAHADR FAAKLPWKET LSFIHNHVHE  180
DVGARASSHV VDYFTSALGD DFMHLGEVYQ EYCEAMEDAS LAIMEVLGVS LGLGRGYYRD  240
FFADGSSIMR CNYYPRCPEP DRTLGTGPHC DPSALTILLQ DGEVDGLQVL VDGAWRSVRP  300
KPGELVVNIG DTFMALSNGR YKSCLHRAVV HREKERRSLA YFLAPREDRV VRPPPSPAPA  360
PRLYPDFTWA ELMRFTQRHY RADARTLDAF ACWLDLPSCP TTPQAQGTV              409

SEQ ID NO: 102         moltype = DNA   length = 1423
FEATURE                Location/Qualifiers
source                 1..1423
                       mol_type = unassigned DNA
                       organism = Sorghum bicolor
SEQUENCE: 102
cctctcatca caggccccag cctcactctt ctcacagcaa gacatcgcag cctcacaacc   60
acacagcaac gtgatcgcca tgggcgggct caccatggag caggccttcg tgcaggcccc  120
cgagcaccgc cccaagccca ccgtcaccga ggccaccggc atcctggtca tcgacctctc  180
gcctctcacc gccagcgaca ccgacgcggc cggcgtggac gcgctggccg ccgaggtggg  240
cgcggcgagc cgggactggg gcttcttcgt ggtggttggc cacggcgtgc ccgcggagac  300
cgtggcgcgc gcgacggcgg cgcagcgcgc gttcttcgcg ctgccggcgg agcggaaggc  360
cgccgtgcgg aggagcgagg cggagccgct cgggtactac gagtcggagc acaccaagaa  420
cgtcagggac tggaaggagg tgttcgacct cgtcccgcgc gatccgcgcc cgccagcagc  480
cgtggccgac ggcgagctcg tcttcaagaa caagtggccc caggatctgc cgggcttcag  540
agaggcgctg gaggagtacg cggcagcgat ggaggagctg tcgttcaagc tgctggagct  600
gatcgcccgg agcttgaagc tgaggcccga ccggctgcac ggcttcttca aggaccagac  660
gacgttcatc cggctgaacc actaccctcc atgcccgagc ccggacctgg cgctgggagt  720
ggggcggcac aaggacgcgg ggcgctgac catcctgtac cagcagaaag tgggcgggct  780
ggacgtccgg cggcgctcct ccgacgcgcg cggcggcgag tgggtgcggg tgaggccgt  840
gccggagtcg ttcgtcatca acgtcggcga cctcgtccag gtgtgagca acgacaggta  900
cgagagcgcg gagcaccggg tgtcggtgaa ctcggcgagg gagaggttct ccatgcccta  960
cttctttcaac ccggcgagct acaccatggt ggagccggtg gaggagctgg tgagcgacga 1020
cgacccgccc aggtacgacg cctacagctg gggcgagttc ttcagcacca ggaagaacag 1080
caacttcaag aagctcagcg tggagaacat tcagatcgcg catttcaaga gaccctcgt  1140
cctcgcctag ataagcagca ggatactaca ggtctacagg actaggacaa gccgatcgag 1200
gtgaccggcc gtcgtcttca gattcagtat atgcgtgtcg ccgttcgtgt tagaacaaat 1260
taataatgtg cgcgctgtgt gctgtgtgtg tggagtaaaa aaaaactaaa catggatgtg 1320
catgttcaaa aaaaaaaaca tggatgcgag tatgtttggg aataataaca ggcttgtgac 1380
ggtctggttt atttgcaaat tcaaaccgaa ttggttgatc ttc                   1423

SEQ ID NO: 103         moltype = DNA   length = 1071
FEATURE                Location/Qualifiers
source                 1..1071
```

```
                        mol_type = unassigned DNA
                        organism = Sorghum bicolor
SEQUENCE: 103
atgggcgggc tcaccatgga gcaggccttc gtgcaggccc ccgagcaccg ccccaagccc    60
accgtcaccg aggccaccgg catcctggtc atcgacctct cgcctctcac cgccagcgac   120
accgacgcgg ccgcggtgga cgcgctggcc gccgaggtgg gcgcggcgag ccgggactgg   180
ggcttcttcg tggtggttgg ccacggcgtg cccgcggaga ccgtggcgcg cgcgacggcg   240
gcgcagcgcg cgttcttcgc gctgccggcg gagcggaagg ccgccgtgcg gaggagcgag   300
gcggagccgc tcgggtacta cgagtcggag cacaccaaga acgtcaggga ctgaaggag   360
gtgttcgacc tcgtcccgcg cgatccgccg ccgccagcag ccgtggccga cggcgagctc   420
gtcttcaaga acaagtggcc caggatctg ccgggcttca gagaggcgct ggaggagtac   480
gcggcagcga tggaggagct gtcgttcaag ctgctggagc tgatcgcccg gagcttgaag   540
ctgaggcccg accggctgca cggcttcttc aaggaccaga cgacgttcat ccggctgaac   600
cactaccctc catgcccgag cccggacctg cgctggagg tggggcggca caaggacgcg   660
ggggcgctga ccatcctgta ccaggacgaa gtgggcgggc tggacgtccg cgggcgctcc   720
tccgacggcg gcggcggcga gtgggtgcgg gtgaggcccg tgccgagtc gttcgtcatc   780
aacgtcggcg acctcgtcca ggtgtggagc aacgacaggt acgagagcgc ggagcaccgg   840
gtgtcggtga actcggcgag ggagaggttc tccatgccct acttcttcaa cccggcgag   900
tacaccatgg tggagccggt ggaggagctg tgagcgacg acgacccgcc caggtacgac   960
gcctacagct ggggcgagtt cttcagcacc aggaagaaca gcaacttcaa gaagctcagc  1020
gtggagaaca ttcagatcgc gcatttcaag aagaccctcg tcctcgccta g           1071

SEQ ID NO: 104         moltype = AA  length = 356
FEATURE                Location/Qualifiers
source                 1..356
                        mol_type = protein
                        organism = Sorghum bicolor
SEQUENCE: 104
MGGLTMEQAF VQAPEHRPKP TVTEATGILV IDLSPLTASD TDAAAVDALA AEVGAASRDW    60
GFFVVVGHGV PAETVARATA AQRAFFALPA ERKAAVRRSE AEPLGYYESE HTKNVRDWKE   120
VFDLVPRDPP PPAAVADGEL VFKNKWPQDL PGFREALEEY AAAMEELSFK LLELIARSLK   180
LRPDRLHGFF KDQTTFIRLN HYPPCPSPDL ALGVGRHKDA GALTILYQDE VGGLDVRRRS   240
SDGGGGEWVR VRPVPESFVI NVGDLVQVWS NDRYESAEHR VSVNSARERF SMPYFFNPAS   300
YTMVEPVEEL VSDDDPPRYD AYSWGEFFST RKNSNFKKLS VENIQIAHFK KTLVLA       356

SEQ ID NO: 105         moltype = DNA  length = 1499
FEATURE                Location/Qualifiers
source                 1..1499
                        mol_type = unassigned DNA
                        organism = Sorghum bicolor
SEQUENCE: 105
cctctcatca caggccccag cctcactctt ctcacagcaa gacatcgcag cctcacaacc    60
acacgcaaac gtgatcgcca tgggcgggct caccatggag caggccttcg tgcaggcccc   120
cgagcaccgc cccaagccca ccgtcaccga ggccaccggc atcctggtca tcgacctctc   180
gcctctcacc gccagcgaca ccgacgcggc cgcggtggac gcgctggccg ccgaggtggg   240
cgcggcgagc cgggactggg gcttcttcgt ggtggttggc cacggcgtgc ccgcggagac   300
cgtggcgcgc gcgacggcgg cgcagcgcgc gttcttcgcg ctgccggcga gcggaaggc   360
cgccgtgcgg aggagcgagg cggagccgct cgggtactac gagtcggagc acaccaagaa   420
cgtcagggac tggaaggagg tgttcgacct cgtcccgcgc gatccgccgc cgccagcagc   480
cgtggccgac ggcgagctcg tcttcaagaa caagtggccc aggatctgc gggcttcag    540
gtgacgaaat caacttatct tttcgatcat attttaccat ttaatagttt aacaataatt   600
gaacttttttt ttgcagagag gcgctggagg agtacgcggc agcgatggag gagctgtcgt   660
tcaagctgct ggagctgatc gcccggagct tgaagctgag gcccgaccgg ctgcacggct   720
tcttcaagga ccagacgacg ttcatccggc tgaaccacta ccctccatgc ccgagcccgg   780
acctgcgct gggagtgggg cggcacaagg acgcggggc gctgaccatc ctgtaccagg   840
acgaagtggg cgggctggac gtccggcgg gctcctccga cggcggcggc ggcgagtggg   900
tgcgggtgag gcccgtgccg gagtcgttcg tcatcaacgt cggcgacctc gtccaggtgt   960
ggagcaacga caggtacgag agcgcggagc accgggtgtc ggtgaactcg gcgagggaga  1020
ggttctccat gccctacttc ttcaacccgg cgagctacac catggtggag ccggtggag   1080
agctgtcgg cgacgacgac ccgcccaggt acgacgccta cagctggggc gagttcttca  1140
gcaccaggaa gaacagcaac ttcaagaagc tcagcgtgga gaacattcag atcgcgcatt  1200
tcaagaagac cctcgtcctc gcctagataa gcagcaggat actacaggtc tacaggacta  1260
ggacaagccg atcgaggtga ccggccgtcg tcttcagatt cagtatatgc gtgtcgccgt  1320
tcgtgttaga acaaattaat aatgtgcgcg tgtgtgcg tgtgtgtga gtaaaaaaa    1380
actaaacatg gatgtgcatg ttcaaaaaaa aaaacatgga tgcgagtatg tttgggaata  1440
ataacaggct tgtgacggtc tggtttattt gcaaattcaa accgaattgg ttgatcttc   1499

SEQ ID NO: 106         moltype = DNA  length = 1490
FEATURE                Location/Qualifiers
source                 1..1490
                        mol_type = unassigned DNA
                        organism = Setaria italica
SEQUENCE: 106
accccacaca cacacccgca ctgcatgcgg cgtcctagct aatcagtcgc tgctggcagc    60
ctcacaagtc acacaactcc gacgcaggaa agctcgatcc atcgccatgg gcggcttctc   120
catggatcag tccttcgtgc aggccccga gcaccgcccc aagccaccg tcaccgaggc   180
cacgggcatc ccgctcatcg acctctcgcc actcaccggc ggtggcggcg gcgacgcggc   240
cgccgtggac gcgctggccg ccgaggtggg cgcggcgagc gggactggg gcttcttcgt   300
ggtggtgggg cacggtgtgc cggcggagac cgtggcgcgc gccacggagg cgcagcgcgc   360
```

```
gttcttcgcc ctgccggcgg agcggaaagc cgccgtgcgg aggagcgagg cggagccgct   420
cgggtactac gagtcggagc acaccaagaa cgtcagggac tggaaggagg tgtacgacct   480
cgtcccgggc gggcttcagc cgccgatagc cgtggccgac ggcgaggtcg tgttcgaaaa   540
caagtggccc gaagacctgc cgggattcag agaggcgttg gaggagtaca tgcaagcgat   600
ggaagagctg gcattcaaga tactggagct gatcgcccgg agcctgaacc tgaggcctga   660
cagactgcac ggcttcttca aggaccagac caccttcatc cggctcaacc actaccctcc   720
ctgcccgagc cccgacctcg ccctcggcgt cggccggcac aaggacgccg gagcactgac   780
catcctctac caggacgacg tcggcgggct cgacgtccgg cgccgttccg acggcgattg   840
ggtccgcgtc aagcctgtcc ccgactcctt catcatcaac gtcggcgcaa tcatccaggt   900
ttggagcaac gacaggtacg agagcgcgga gcaccgggtt acggtgaact cggccaagga   960
gaggttctcc aggccctact tcttcaaccc ggcgggctac accatggtgg agccggtgga  1020
ggagctggtg agcgaggagg acccgccccg gtacgacgcc tacaactggg gcaacttctt  1080
cagcaccagg aagaacagca acttcaagaa gctgagcgtg gagaacatcc agatcgcgca  1140
tttcaagagg agcgtccgcg cctaggatac gcacagaaag atcccatatg ctgacttgct  1200
gatgaggcga caggcggccg tgtcgtcttc agattcagag actgggagta aacatttgtg  1260
cggtgttctg taatcgtgat gtgacgagaa ctttagatat atgtttggaa ataacagcct  1320
tgtgttggtc tggcttatcc gcaaagtcaa gattttcttc tacattttgg gattattgtt  1380
ggtaagcatt aagcaacgtc cagttcttac ttcttagctc gatcagtgga cgtaggaccg  1440
gcctctgatg acaagggtga tttatgagaa atgtcatgta tatatgttcc               1490

SEQ ID NO: 107        moltype = DNA    length = 1059
FEATURE               Location/Qualifiers
source                1..1059
                      mol_type = unassigned DNA
                      organism = Setaria italica
SEQUENCE: 107
atgggcggct tctccatgga tcagtccttc gtgcaggccc ccgagcaccg ccccaagccc    60
accgtcaccg aggccacggg catcccgctc atcgacctct cgccactcac cggcggtggc   120
ggcggcgacg cggccgccgt ggacgcgctg gccgccgagg tgggcgcggc gagccgggac   180
tggggcttct tcgtggtggt ggggcacggt gtgccggccg agaccgtggc gcgcgccacg   240
gaggcgcagc gcgcgttctt cgccctgccg gcggagcgga agccgccgt gcggaggagc   300
gaggcggagc cgctcgggta ctacgagtcg gagcacacca agaacgtcag ggactggaag   360
gaggtgtacg acctcgtccc gggcgggctt cagccgccga tagccgtggc cgacggcgag   420
gtcgtgttcg aaaacaagtg gcccgaagac ctgccgggat tcagagaggc gttggaggag   480
tacatgcaag cgatggaaga gctggcattc aagatactgg agctgatcgc ccggagcctg   540
aacctgaggc ctgacagact gcacggcttc ttcaaggacc agaccacctt catccggctc   600
aaccactacc ctccctgccc gagccccgac ctcgccctcg cgtcggccg gcacaaggac   660
gccggagcac tgaccatcct ctaccaggac gacgtcggcg ggctcgacgt ccggcgccgt   720
tccgacggcg attgggtccg cgtcaagcct gtccccgact ccttcatcat caacgtcggc   780
gcaatccatcc aggtttggag caacgacagg tacgagagcg cggagcaccg ggttacggtg   840
aactcggcca aggagaggtt ctccaggccc tacttcttca acccggcggg ctacaccatg   900
gtggagccgg tggaggagct ggtgagcgag gagacccgc cccggtacga cgcctacaac   960
tggggcaact tcttcagcac caggaagaac agcaacttca agaagctgag cgtggagaac  1020
atccagatcg cgcatttcaa gaggagcgtc cgcgcctag                        1059

SEQ ID NO: 108        moltype = AA    length = 352
FEATURE               Location/Qualifiers
source                1..352
                      mol_type = protein
                      organism = Setaria italica
SEQUENCE: 108
MGGFSMDQSF VQAPEHRPKP TVTEATGIPL IDLSPLTGGG GGDAAAVDAL AAEVGAASRD    60
WGFFVVVGHG VPAETVARAT EAQRAFFALP AERKAAVRRS EAEPLGYYES EHTKNVRDWK   120
EVYDLVPGGL QPPIAVADGE VVFENKWPED LPGFREALEE YMQAMEELAF KILELIARSL   180
NLRPDRLHGF FKDQTTFIRL NHYPPCPSPD LALGVGRHKD AGALTILYQD DVGGLDVRR   240
SDGDWVRVKP VPDSFIINVG DLIQVWSNDR YESAEHRVTV NSAKERFSRP YFFNPAGYTM   300
VEPVEELVSE EDPPRYDAYN WGNFFSTRKN SNFKKLSVEN IQIAHFKRSV AA          352

SEQ ID NO: 109        moltype = DNA    length = 1886
FEATURE               Location/Qualifiers
source                1..1886
                      mol_type = unassigned DNA
                      organism = Setaria italica
SEQUENCE: 109
accccacaca cacacccgca ctgcatgcgg cgtcctagct aatcagtcgc tgctggcagc    60
ctcacaagtc acacaactcc gacgcaggaa agctcgatcc atcgccatgg gcggcttctc   120
catggatcag tccttcgtgc aggccccga gcaccgcccc aagcccaccg tcaccgaggc   180
cacgggcatc ccgctcatcg acctctcgcc actcaccggc ggtggcggcg gcgacgcggc   240
cgccgtggac gcgctggccg ccgaggtggg cgcggcgagc cggactgggg cttcttcgtg   300
gtggtggggc acggtgtgc cggccgagac cgtggcgcgc gccacggagg cgcagcgcgc   360
gttcttcgcc ctgccggcgg agcggaaagc cgccgtgcgg aggagcgagg cggagccgct   420
cgggtactac gagtcggagc acaccaagaa cgtcagggac tggaaggagg tgtacgacct   480
cgtcccgggc gggcttcagc cgccgatagc cgtggccgac ggcgaggtcg tgttcgaaaa   540
caagtggccc gaagacctgc cgggattcag gtaatccttg cgcatatgtt gcttttgtta   600
ggcattgcat atgatcgtcg tgccagtatg ttttgacaat attttgtttt tcatatttttt   660
ggtgaagatg ggaaaatctt tgttgaaata atcaggaatt tttcacatct ttttttaatc   720
aaagatagaa taggttcggt tactgaattt tgatgatgga cagaaaaagc tgtgtttttca   780
cttttccatct cagcgatgtt ttttttgtgga tgaattctcc taaatttttg tctttttcatg   840
ttaaaaacttg aacgggaatt ctcgcagaga ggcgttggag gagtacatgc aagcgatgga   900
```

-continued

```
agagctggca ttcaagatac tggagctgat cgcccggagc ctgaacctga ggcctgacag    960
actgcacggc ttcttcaagg accagaccac cttcatccgg ctcaaccact accctccctg   1020
cccgagcccc gacctcgccc tcggcgtcgg ccgccacaag gacgccggag cactgaccat   1080
cctctaccag gacgacgtcg gcgggctcga cgtccgcgc cgttccgacg gcgattgggt   1140
ccgcgtcaag cctgtcccg actccttcat catcaacgtc ggcgacctca tccaggtaca   1200
acaaacaaaa acacacgtca ttctcaaatc ttttcgtgct gttaatgctc attcacgaat   1260
tgatatctta catgaacgac tgagactttt tcaggttttgg agcaacgaca ggtacgagag   1320
cgcggagcac cggggttacgg tgaactcggc caaggagagg ttctccaggc cctacttctt   1380
caaccggcg ggctacacca tggtggagcc ggtggaggag ctggtgagcg aggaggaccc   1440
gccccggtac gacgcctaca actggggcaa cttcttcagc accaggaaga acagcaactt   1500
caagaagctg agcgtggaga acatccagat cgcgcatttc aagaggagcg tcgccgccta   1560
ggatacgcac agaaagatcc catatgctga cttgctgatg aggcgacagg cggccgtgtc   1620
gtcttcagat tcagagactg ggagtaaaca ttttgtgcggt gttctgtaat cgtcgatgtga   1680
cgagaacttt agatatatgt ttggaaataa cagccttgtg ttggttctggc ttatccgcaa   1740
agtcaagatt ttcttctaca ttttgggatt attgttggta agcattaagc aacgtccagt   1800
tcttacttct tagctcgatc agtggacgta ggaccggcct ctgatgacaa gggtgattta   1860
tgagaaatgt catgtatata tgttcc                                         1886

SEQ ID NO: 110        moltype = DNA  length = 1379
FEATURE               Location/Qualifiers
source                1..1379
                      mol_type = unassigned DNA
                      organism = Oryza sativa
SEQUENCE: 110
aagccacacg cacacacaca cacacgctga cacacgagac gaacacttgt gctacagctt     60
ctcgccacca gctactgatc gaccatgggc ggcctctcca tggaccaggc gttcgtgcag    120
gcccccgagc accgcccaa ggcgtccgtc gccgaggccg acggcatccc ggtcatcgac    180
ctctcccctc tcctcgccgc cggcgatggc gacgccgacg gggtggacgc gctcgcggcg    240
gaggtcggga gggcgagccg ggactgggc ttcttcgtgg tggtgcgcca cggtgtgccc    300
gcggaggccg tggcgcgcgc ggccggaggcg cagaggacgg tcttcgcgct gccgcccggag   360
cggagggcgg ccgtggcgcg gagcgaggcg gcgccgatgg ggtactacgc gtccgagcac    420
accaagaacg tcagggactg gaaggaggtg ttcgacctcg tcccgcgcca gacgccgccg    480
ccgccgacga ccgccgtggc cgacggcgac ctggtgttcg acaacaagtg gcccgacgac    540
ctgccgggat tcagggaggc aatggaggag tacgcgaag cggtggagga gctggcgttc    600
aagctgctgg agctgatcgc caggagcctc ggcctgagac ccgaccgcct ccatggcttc    660
ttcaaggacg accagaccac cttcatccgg ctcaaccact accctccctg cccgagcccc    720
gacctcgccc tcggcgtcgg ccgccacaag gacgccggcg cgctcaccgt gctctaccag    780
gacgatgtcg gcggcctcga cgtccgcgc cgatccgacg gcgagtgggt gcgcgtcagg    840
cccgtcccctc actccttcat catcaacgtc ggcgacatca tccaggtgtg gagcaatgac    900
aggtacgaga gcgcggagca ccgggtggcg gtgaacgtgg agaaggagag gttctccatc    960
cctttcttct tcaacccggc gggccacacc atggtggagc cactggagga ggtcgtgagc   1020
gacgagagcc cggccaggta caaccctac aactggggca aattcttcag caccaggaag   1080
aacagcaact tcaagaagct ggacgtggag aacgtccaga tcacgcattt caggaagaat   1140
taacgcgccg gctagatcat gttcagtaaa ttttcagatg atgatgcgtg gacaaccata   1200
tagcctttgc gtcataagtt aataatgtct gtgacagtat atcatgtaaa caatcgtatg   1260
atgtggcttc tctatctgcc ggtgatggta atgtgacatt gtagaagagg gtttgtgaga   1320
tacttccttc acttaacttt tacgaatgaa tatagacaac cacaacatcc ttgtcgtga   1379

SEQ ID NO: 111        moltype = DNA  length = 1059
FEATURE               Location/Qualifiers
source                1..1059
                      mol_type = unassigned DNA
                      organism = Oryza sativa
SEQUENCE: 111
atgggcggcc tctccatgga ccaggcgttc gtgcaggccc ccgagcaccg ccccaaggcg     60
tccgtcgccg aggccgacgg catcccggtc atcgacctct cccctctcct cgccgccggc    120
gatggcgacg ccgacggggt ggacgcgctc gcggcggagg tcgggagggc gagccggac    180
tggggcttct tcgtggtggt gcgccacggt gtgcccgcgg aggcggtggc gcgcgcggcg    240
gaggcgcaga ggacgttctt cgcgctgccg ccggagcgga gggcggccgt ggcgcggagc    300
gaggcggccg cgatggggta ctacgcgtcc gagcacacca agaacgtcag ggactgggaa    360
gaggtgttcg acctcgtccc gcgccagacg ccgccgccgc cgacgaccgc cgtggccgac    420
ggcgacctgg tgttcgacaa caagtggccc gacgacctgc cgggattcag ggaggcaatg    480
gaggagtacg gcgaagcggt ggaggagctg gcgttcaagc tgctggagct gatcgccagg    540
agcctcggcc tgagacccga ccgcctccat ggcttcttca aggacgacca gaccaccttc    600
atccggctca accactaccc tccctgcccg agccccgacc tcgccctcgg cgtcggccgc    660
cacaaggacg ccggcgcgct caccgtgctc taccaggacg atgtcggcgg cctcgacgtc    720
cgccgccgat ccgacggcga gtgggtgcgc gtcaggcccg tccctcactc cttcatcatc    780
aacgtcggcg acatcatcca ggtgtggagc aatgacaggt acgagagcgc ggagcaccgg    840
gtggcggtga acgtggagaa ggagaggttc tccatccctt tcttcttcaa cccggcgggc    900
cacaccatgg tggagccact ggaggaggtc gtgagcgacg agagcccggc caggtacaac    960
ccctacaact ggggcgaatt cttcagcacc aggaagaaca gcaacttcaa gaagctggac   1020
gtggagaacg tccagatcac gcatttcagg aagaattaa                           1059

SEQ ID NO: 112        moltype = AA  length = 352
FEATURE               Location/Qualifiers
source                1..352
                      mol_type = protein
                      organism = Oryza sativa
SEQUENCE: 112
```

```
MGGLSMDQAF VQAPEHRPKA SVAEADGIPV IDLSPLLAAG DGDADGVDAL AAEVGRASRD    60
WGFFVVVRHG VPAEAVARAA EAQRTFFALP PERRAAVARS EAAPMGYYAS EHTKNVRDWK   120
EVFDLVPRQT PPPPTTAVAD GDLVFDNKWP DDLPGFREAM EEYGEAVEEL AFKLLELIAR   180
SLGLRPDRLH GFFKDDQTTF IRLNHYPPCP SPDLALGVGR HKDAGALTVL YQDDVGGLDV   240
RRRSDGEWVR VRPVPHSFII NVGDIIQVWS NDRYESAEHR VAVNVEKERF SIPFFFNPAG   300
HTMVEPLEEV VSDESPARYN PYNWGEFFST RKNSNFKKLD VENVQITHFR KN           352

SEQ ID NO: 113            moltype = DNA   length = 2027
FEATURE                   Location/Qualifiers
source                    1..2027
                          mol_type = unassigned DNA
                          organism = Oryza sativa
SEQUENCE: 113
aagccacacg cacacacaca cacacgctga cacacgagac gaacacttgt gctacagctt    60
ctcgccacca gctactgatc gaccatgggc ggcctctcca tggaccaggc gttcgtgcag   120
gcccccgagc accgcccaa ggcgtccgtc gccgaggccg acggcatccc ggtcatcgac   180
ctctcccctc tcctcgccgc cggcgatggc gacgccgacg gggtggacgc gctcgcggcg   240
gaggtgggga gggcgagccg ggactggggc ttcttcgtgg tggtgcgcca cggtgtgccc   300
gcggaggcgg tggcgcgcgc ggcggaggcg cagaggacgt tcttcgcgct gccgccggag   360
cggagggcgg ccgtggcgcg gagcgaggcg gcgccgatgg ggtactacgc gtccgagcac   420
accaagaacg tcagggactg gaaggaggtg ttcgacctcg tcccgcgcca gacgccgccg   480
ccgccgacga ccgccgtggc cgacggcgac ctggtgttcg acaacaagtg gcccgacgac   540
ctgccgggat tcagggtcagg tcaccacatc gatcgatcgt cttcttcatc ctcgcatcaa   600
ttcagttcaa cctcatcgaa ttcttgagca gggaggcaat ggaggagtac ggcgaagcgg   660
tggaggagct ggcgttcaag ctgctggagc tgatcgccag gagcctcggc ctgagacccg   720
accgcctcca tggcttcttc aaggacgacc agaccacctt catccgcctc aaccactacc   780
ctccctgccc gagccccgac ctcgccctcg gcgtcggccg ccacaaggac gccggcgcgc   840
tcaccgtgct ctaccaggac gatgtcggcg gcctcgacgt ccgccgccga tcgacggcg    900
agtgggtgcg cgtcaggccc gtccctcact ccttcatcat caacgtcggc gacatcatcc   960
aggtactttt ttttttgagc agctacatat ttatcaacaa attttcttct aacaatttat  1020
cggacataaa tatattacaa tgaaagaata attgtatcat aacttgtgtg tccttatatg  1080
taagttttag aaatcctata gtaacatggt attttcgcga aagcggagat tgtgagaccg  1140
tatcttttca cccatgcgcg tcatatgatt tttttttctt gccaacttaa ataaatttca  1200
aagtaaatct aatagattaa aattatgtga aacttacata taagttttct acggtaaaac  1260
gctattttca cgaaacggag gtcgttccaa gttgaatgaa tcttgaagta aatctaacga  1320
tttaaaatta tgtgcataca cgttatatta cagttatata caagttataa tataattaca  1380
ctacaattat aacggtattc atagttgaca aacttttaaa agagaattag ttaataaata  1440
tataacaaca ttgtagttta attgttacta tttgacatca tttttatttg cattttgaat  1500
ttgactgaaa aaattgagag tgcgcttgtc caggtgtgga gcaatgacag gtacgagagc  1560
gcggagcacc gggtggcggt gaacgtggag aaggagaggt tctccatccc tttcttcttc  1620
aacccggcgg gccacaccat ggtggagcca ctggaggagg tcgtgagcga cgagagcccg  1680
gccaggtaca acccctacaa ctggggcgaa ttcttcagca ccaggaagaa cagcaacttc  1740
aagaagctgg acgtggagaa cgtccagatc acgcatttca ggaagaatta acgcgccgac  1800
tagatcatgt tcagtaaatt ttcagatgat gatgcgtgga caaccatata gcctttgcgt  1860
cataagttaa taatgtctgt gacagtatat catgtaaaca atcgtatgat gtggcttctc  1920
tatctgccgg tgatggtaat gtgacattgt agaagagggt ttgtgagata cttccttcac  1980
ttaacttttta cgaatgaata tagacaacca caacatcctt gtcgtga              2027

SEQ ID NO: 114            moltype = DNA   length = 1747
FEATURE                   Location/Qualifiers
source                    1..1747
                          mol_type = unassigned DNA
                          organism = Triticum aestivum
SEQUENCE: 114
tcactcaagg ccacaacaca ctcgccagtc catcgccacc atacgtgaca acttgagtta    60
cttgatctgt tgctcatcga tctcgacatc gccatgggcg gcctctccat ggaccaggcc   120
ttcgtgcagg cccccgagca tcgcaccaag gcgaacctcg ccgacgcggc cggcatcccg   180
gtcatcgacc tctcccctct cgccgccggc gacaaggccg gctgacgc cctcgcggcc   240
gaggtgggca gggcgagccg tgactggggg ttcttcgtgg tggtgcgcca cggcgtgccg   300
gcggagacgg tggcgggcc ggcggaggcg cagagggcct tcttcgcgct gccgcgcgac   360
cggaaggcgg ccgtgcggag ggacgaggcg gcgccgatgg ggtactacga gtcggagcac   420
accaagaacg tcagggactg gaaggaggtg ttcgacctcg tccccgcgca gccgccgccg   480
cctgccgcgg ttgccgacgg cgagctcatg ttcgagaaca agtgggccga ggacctgccg   540
gggttcagag aggctctcga agagtacgag aaagcgatgg aggagctggc gttcaagctg   600
ctggagctga tcgcccggag cctgggactg agaccggacc ggctgcacgg cttcttcaag   660
gaccagacca cctttcatccg gctgaaccac taccgccct gccccagccc cgacctcgcc   720
ctcggcgtcg gtcgccacaa ggacgccggc gcgctcacca tcctctacca ggacgacgtc   780
ggcgggctcg acgtccggcg ccgctccgac ggcgagtggg tgcgcgtcag gctcgtcccg   840
gactcctacg tcatcaacgt cggcgacatc atccggtgg gagcaacga caggtacgag   900
agcgcggagc acagggtgtc ggtgaactcg cacaaggaga ggttctccat gcctacttc   960
ttcgaccccg ggagcgacgc catgatcgag ccgttggagg agatggtgag cgacgaaagg  1020
ccggccaggt acgacgccta caactggggc aacttcttca gcaccaggaa gaacagcaac  1080
ttcaggaagc tcgccgtcga aaacgtccag atcgcacact tcagaaagga ccgacccttaa  1140
atgaaggatc cctcatgaat tcatgatcct tccgctcctc tcagtgatca tcgtcaaga  1200
actacaagca tctcccgtt tgtagtaatc atatatataaat aagtattccc tccgtaaact  1260
aatataagag catttaaaac actactctag tgatctaaat gctcttatat tagttttacag  1320
agagagtatt gtgtattaat aatgactttc tctgtttcaa aataagtgat gacgtggttt  1380
tagttcaatt tttttagag agaggcatc tgacggggcct taaactgagg accttagagt  1440
acaaacaagg ttcgacgaaa gtaagtttaa gggatacaag gccgtagcca acaaaacgcg  1500
```

```
acgcagcgcg caatctaaaa tcagcgtgct gtcaaggtag ctggagacgt ccatgccgtt 1560
aatctctctc aagaagctcg ccgaagctca gtgcaccttg cgtgcactct tgtgaagagc 1620
accttcacgt gtcctttgtc ctgagatttt gtcaacagtt tccatgactg caagaaaaac 1680
actagtttgt ataatagctc agcgggatgt cgaatgaatt gccccctcaat caaagcttta 1740
tttctag                                                          1747
```

```
SEQ ID NO: 115          moltype = DNA   length = 1047
FEATURE                 Location/Qualifiers
source                  1..1047
                        mol_type = unassigned DNA
                        organism = Triticum aestivum
SEQUENCE: 115
atgggcggcc tctccatgga ccaggccttc gtgcaggccc ccgagcatcg caccaaggcg   60
aacctcgccg acgcggccgg catcccggtc atcgacctct ccccctctcgc cgccggcgac  120
aaggccggcc tggacgccct cgcggccgag gtgggcaggg cgagccgtga ctgggggttc  180
ttcgtggtgg tgcgccacgg cgtgccggcg gagacggtgg cgcgggcgct ggaggcgcag  240
agggccttct tcgcgctgcc cgcggaccgg aaggcggccg tgcggaggga cgaggcggcg  300
ccgctggggt actacgagtc ggagcacacc aagaacgtca gggactggaa gaggtgttc   360
gacctcgtcc cccgcgagcc gccgccgcct gccgcggttg ccgacggcga gctcatgttc  420
gagaacaagt ggcccgagga cctgccgggg ttcagagagg ctctcgaaga gtacgagaaa  480
gcgatggagg agctggcgtt caagctgctg agctgatcg cccggagcct gggactgaga  540
ccggaccggc tgcacggctt cttcaaggac cagaaccact tcatccgcct gaaccactac  600
ccgcccctgcc ccagcccga cctcgccctc ggcgtcggtc gccacaagga cgccggcgcg  660
ctcaccatcc tctaccagga cgacgtcggg gggctcgacg tccggcgccg ctccgacggc  720
gagtgggtgc gcgtcaggcc tgtcccggac tcctacgtca tcaacgtcgg cgacatcatc  780
caggtgtgga gcaacgacag gtacgagagc gcggagcaca gcgtgtcgat gaactgcac  840
aaggagaggt tctccatgcc ctacttcttc gaccccggga gcgacgccat gatcgagccg  900
ttggaggaga tggtgagcga cgaaaggccg gccaggtacg acgcctacaa ctgggggcaac  960
ttcttcagca ccaggaagaa cagcaacttc aggaagctcg ccgtcgaaaa cgtccagatc 1020
gcacacttca gaaaggaccg accttaa                                    1047
```

```
SEQ ID NO: 116          moltype = AA   length = 348
FEATURE                 Location/Qualifiers
source                  1..348
                        mol_type = protein
                        organism = Triticum aestivum
SEQUENCE: 116
MGGLSMDQAF VQAPEHRTKA NLADAAGIPV IDLSPLAAGD KAGLDALAAE VGRASRDWGF   60
FVVVRHGVPA ETVARALEAQ RAFFALPADR KAAVRRDEAA PLGYYESEHT KNVRDWKEVF  120
DLVPREPPPP AAVADGELMF ENKWPEDLPG FREALEEYEK AMEELAFKLL ELIARSLGLR  180
PDRLHGFFKD QTTFIRLNHY PPCPSPDLAL GVGRHKDAGA LTILYQDDVG GLDVRRRSDG  240
EWVRVRPVPD SYVINVGDII QVWSNDRYES AEHRVSVNSH KERFSMPYFF DPGSDAMIEP  300
LEEMVSDERP ARYDAYNWGN FFSTRKNSNF RKLAVENVQI AHFRKDRP              348
```

```
SEQ ID NO: 117          moltype = DNA   length = 1863
FEATURE                 Location/Qualifiers
source                  1..1863
                        mol_type = unassigned DNA
                        organism = Triticum aestivum
SEQUENCE: 117
tcactcaagg ccacaacaca ctcgccagtc catcgccacc atacgtgaca acttgagtta   60
cttgatctgt tgctcatcga tctcgacatc gccatgggcg gcctctccat ggaccaggcc  120
ttcgtgcagg ccccgagca tcgcaccaag gcgaacctcg ccgacgcggc cggcatcccg  180
gtcatcgacc tctcccctct cgccgccggc gacaaggccg gcctggacgc cctcgcggcc  240
gaggtgggca gggcgagccg tgactgggg ttcttcgtg tggtgcgca cggcgtgccg  300
gcggagacgg tggcgcgggg gctggggcct tcttcgcgct gcccgcggac  360
cggaaggcgg ccgtgcggag gacgaggcg gcgccgctgg gtactacga gtcggagcac  420
accaagaacg tcagggactg gaaggaggtg ttcgacctcg tccccgcga gccgccgccg  480
cctgccgcgg ttgccgacgg cgagctcatg ttcgagaaca agtggcccga ggacctgccg  540
gggttcaggt acgtcatca actcaatcaa ttctgcgacc ccgagagaaa tggttcacta  600
ttattcgtgg ttcatacgta tgattcgac gttaatctcg atgcaaattg atttgtcat  660
gcagagaggc tctcgaagag tacgagaaag cgatggagga gctggcgttc aagctgctgg  720
agctgatcgc ccggagcctg gactgagac cggaccggct gcacggcttc ttcaaggacc  780
agaccacctt catccggctg aaccactacc cgcccctgcc ctcgccctca ctcggcttc  840
gcgtcggtcg ccacaaggac gccggcgcgc tcaccatcct ctaccaggac gacgtcgggc  900
ggctcgacgt ccggcgccgc tccgacggcg agtgggtgcg cgtcaggcct gtcccggact  960
cctacgtcat caacgtcggc gacatcatcc aggtgtggag caacgacagg tacgagagc  1020
cggagcacag ggtgtcggtg aactcgcaca aggagaggt ctccatgcc tacttcttcg  1080
accccggag cgacgccatg atcgagcgt tggaggagat ggtgagcgac gaaaggccgg  1140
ccaggtacga cgcctacaac tggggcaact tcttcagcac caggaagaac agcaacttca  1200
ggaagctcgc cgtcgaaaac gtccagatcg cacacttcag aaaggaccga ccttaaatga  1260
aggatccctc atgaattcat gatccttccg ctctcctcag tgatcctagt gctacaacta  1320
caagcatctc ccgtttgta gtaatcatat ataaataagt attcccctccg taaactaata  1380
taagagcatt taaaacacta ctctagtgat ctaaatgctc ttatattagt ttacagagag  1440
agtattgtgt attaataatg acttttctctg tttcaaaata agtgatgacg tggttttagt  1500
tcaattttttt ttagagagga ggcatctgac gggccttaaa ctgaggacct tagagtacaa  1560
acaaggttcg acgaaagtaa gtttaaggga tacaaggccg tagccaacaa aacgcgacgc  1620
agcgcgcaat ctaaaatcag cgtgctgtca aggtagctgg agacgtccat gccgttaatc  1680
tctctcaaga agctcgccga agctcagtgc acccttgcgt gcactcttgtg aagagcacct  1740
```

```
tcacgtgtcc tttgtcctga gattttgtca acagtttcca tgactgcaag aaaaacacta 1800
gtttgtataa tagctcagcg ggatgtcgaa tgaattgccc ctcaatcaaa gctttatttc 1860
tag                                                                1863

SEQ ID NO: 118          moltype = AA  length = 349
FEATURE                 Location/Qualifiers
source                  1..349
                        mol_type = protein
                        organism = Hordeum vulgare
SEQUENCE: 118
MGGLSMGQAF VQAPEHRTKP TLADADGIPV IDLSPLAAGD EAGVDALAAE VGRASRDWGF   60
FVVVRHGVPA ETVARALEAQ RAFFALPAER KAAVRRDEAA PLGYYESEHT KNVRDWKEVF  120
DFVPREPPPP AAVADGELVF ENKWPEDLPG FRVAFEEYAK AMEELAFKLL ELIARSLGLT  180
PDRLNGFFKD HQTTFIRLNH YPPCPSPDLA LGVGRHKDAG ALTVLYQDDV GGLDVRHRSD  240
GEWWRVRPVP DSYVINVGDI IQVWSNDRYE SAEHRVSVNS DKERFSMPYF FNPGSDAMVE  300
PLEEMVSDER PARYDAYNWG HFFSTRKNSN FKKLDVENVQ IAHFRKLHL              349

SEQ ID NO: 119          moltype = DNA  length = 1963
FEATURE                 Location/Qualifiers
source                  1..1963
                        mol_type = unassigned DNA
                        organism = Sorghum bicolor
SEQUENCE: 119
tataaatacc acgccatgta cttctctgct tctacacttc tccagcttct ctcatgccat   60
accactagtg caaggtccta gatttacact tggtgctaca gcttcttcct ccctccctcc  120
cctctctagg cagctagcac gcagcgcagc acacgaaaca tctattgacc ggccgcctcc  180
gccggggatc cataattact atactaccaa tcggccagcg tcatgccgac gccgtcgcac  240
ctcgcgaacc cgcgctactt cgacttccgt gcggcgcggc gggtgccgga gacgcacgcc  300
tggccggggc tgcacgacca ccccgtcgtg gacggcggcg cgccggggcc agacgccgtc  360
cccgtggtgg acctcgcggg ggcggcggac gagccgagcc ccggtggt gggcccaagtg  420
gcgcgcgccg ccgagcaatg gggcgcgttc ctgctcacgg ggcacggtgg ccccgcggag  480
ctgctggcgc gcgtcgagga ccggatcgcc accatgttcg cgctgccagc ggacgacaag  540
atgcgcgccg tgcgcgggcc tggcgacgcc tgcggctacg ctccccgcc catctcctcc  600
ttcttctcca agtgcatgtg gtcggaggga tacacctctc cgccggccaa cctccgcgcg  660
gacctccgca agtctggcc taaggccggc gacgactaca ccagcttctg tgatgtgatg  720
gaggagttcc acaagcacat gcgtgccctc cgggacaagc tgctggagct gttcctcatg  780
gcgctggggc tcaccgacga caggtcggc ggcgtggagg cggagcggag gatcgccgag  840
acgatgaccg ccaccatgca cctcaactgg taccctcggt gccggaccc cgcgccgcgcg  900
ctggggctga tcgcgcacac cgactcgggc ttcttcaccct tcgtgctgca gagcctcgtc  960
ccggggctgc agctcttccg ccacgccccg gaccggtggg tggcggtgcc ggcggtaccg 1020
ggcgccttcg tcgtcaacgt gggcgacctc ttccacatcc tcaccaacgg ccggttccac 1080
agcgtgtacc accgcgccgt cgtgaaccgg gacctcgaca ggatatctct cggctacttc 1140
ctcggcccgc cgccgcccgg caaggtcggc ccgctaaggg aggccgtgcc gcccggccgg 1200
accccgcgt accgcgccgt cacgtggccc gagtacatgg gcgtccgcaa gaaggccttc 1260
accaccggcg catccgcgct caagatggtc gccctcgccg ccgccgccgc cgccgccgac 1320
ctcgacgatg acgccggtgc tggcgccgcc gccgaacctg tcgtccatca gcagctactc 1380
gtctcgtcgt agccgatcga tcgccgggatc ggtcgagact gatgatgatg atgcatatat 1440
actcgtcgat ggagtagaca gactaatcaa gcaaccctga aactatgaat gcatgcgtgc 1500
gcttcgtgct tgccttgcgca tgcagctagc aggcttcatt ccgttccgca gctgctctgc 1560
tccaacctgc tctgctggat tgatgtatat ggtagaagaa ttaagagatc gatggatgac 1620
ggaggaagaa gaaacgaag acgacgatga ggaaaaggcca acgctgtacg tagctggttc 1680
ttctagtcta gtttacagca ggccggggcgg ccggctgctg cttccaatcg agtttgtcgt 1740
tactgacgat tgttagtgga tcgattaact aatctggaat tctggattat taatataatg 1800
catgtggttt ggcatctggc gtaaagcagg taatggtacc tagccagtag ccagtagcca 1860
ggctggtcaa tgataggtct ataccctgat cctgtactgt tgtttctttc ggtctttctg 1920
agagagaaaa aaaacgaata tatggcgtac tcaattcatc aaa                  1963

SEQ ID NO: 120          moltype = DNA  length = 1170
FEATURE                 Location/Qualifiers
source                  1..1170
                        mol_type = unassigned DNA
                        organism = Sorghum bicolor
SEQUENCE: 120
atgccgacgc cgtcgcacct cgcgaacccg cgctacttcg acttccgtgc ggcgcggcgg   60
gtgccggaga cgcacgcctg gccggggctg cacgaccacc ccgtcgtgga cggcggcgcg  120
ccggggccag acgccgtccc cgtggtggac ctcgcggggg cggcggacga gccgagagcc  180
gcggtggtgg cccaagtggc gcgcgccgcc gagcaatggg gcgcgttcct gctcacgggg  240
cacggcgtcc ccgcggagct gctggcgcgc gtcgaggacc ggatcgccac catgttcgcg  300
ctgccagcgg acgacaagat gcgcgccgtg cgcgggcctg gcgacgcctg cggctacgc  360
tcccccgccca tctcctcctt cttctccaag tgcatgtggt cggagggata cacctctcg  420
ccggccaacc tccgcgccga cctccgcaag ctctggccta aggccggcga cgactacacc  480
agcttctgtg atgtgatgga ggagttccac aagcacatgc gtgccctcgc ggacaagctg  540
ctggagctgt tcctcatggc gctggggctc accgacgagc aggtcggcgg cgtggaggcg  600
gagcggagga tcgccgagac gatgaccgcc accatgcaca tcaactggta ccctcggtgc  660
cggacccgc gccgcgcgct ggggctgatc gcgcacaccg actcgggctt cttcaccttc  720
gtgctgcaga gcctcgtccc ggggctgcag ctcttccgcc acgccccgga ccggtgggtg  780
gcggtgccgg cggtaccggg cgccttcgtc gtcaacgtgg gcgacctctt ccacatcctc  840
accaacggcg ggttccacag cgtgtaccac cgcgccgtcg tgaaccggga cctcgacagg  900
atatctctcg gctacttcct cggcccgccg ccgcacgcca aggtggcgcc gctaagggag  960
```

```
gccgtgccgc  ccggccgcac  ccccgcgtac  cgcgccgtca  cgtgcccga   gtacatgggc   1020
gtccgcaaga  aggccttcac  caccggcgca  tccgcgctca  agatggtcgc  cctcgccgcc   1080
gccgccgccg  ccgccgacct  cgacgatgac  gccggtgctg  gcgccgccgc  cgaacctgtc   1140
gtccatcagc  agctactcgt  ctcgtcgtag                                      1170

SEQ ID NO: 121             moltype = AA   length = 389
FEATURE                    Location/Qualifiers
source                     1..389
                           mol_type = protein
                           organism = Sorghum bicolor
SEQUENCE: 121
MPTPSHLANP RYFDFRAARR VPETHAWPGL HDHPVVDGGA PGPDAVPVVD LAGAADEPRA      60
AVVAQVARAA EQWGAFLLTG HGVPAELLAR VEDRIATMFA LPADDKMRAV RGPGDACGYG     120
SPPISSFFSK CMWSEGYTFS PANLRADLRK LWPKAGDDYT SFCDVMEEFH KHMRALADKL     180
LELFLMALGL TDEQVGGVEA ERRIAETMTA TMHLNWYPRC PDPRRALGLI AHTDSGFFTF     240
VLQSLVPGLQ LFRHAPDRWV AVPAVPGAFV VNVGDLFHIL TNGRFHSVYH RAVVNRDLDR     300
ISLGYFLGPP PHAKVAPLRE AVPPGRTPAY RAVTWPEYMG VRKKAFTTGA SALKMVALAA     360
AAAAADLDDD AGAGAAAEPV VHQQLLVSS                                      389

SEQ ID NO: 122             moltype = DNA   length = 2321
FEATURE                    Location/Qualifiers
source                     1..2321
                           mol_type = unassigned DNA
                           organism = Sorghum bicolor
SEQUENCE: 122
tataaatacc  acgccatgta  cttctctgct  tctacacttc  tccagcttct  ctcatgccat    60
accactagtg  caaggtccta  gatttacact  tggtgctaca  gcttcttcct  ccctccctcc   120
cctctctagg  cagctagcac  gcagcgcagc  acacgaaaca  tctattgacc  ggccgcctcc   180
gccgggggatc cataattact  atactaccaa  tcggccagcg  tcatgccgac  gccgtcgcac   240
ctcgcgaacc  cgcgctactt  cgacttccgt  gcggcgcggc  gggtgccgga  gacgcacgcc   300
tggccggggc  tgcacgacca  ccccgtcgtg  gacggcggac  cgcggggggcc agacgccgtc   360
cccgtggtgg  acctcgcggg  ggcggcggac  gagccgagag  ccgcggtggt  ggcccaagtg   420
gcgcgcgccg  ccgagcaatg  gggcgcgttc  ctgctcacgg  gcacggcgt   ccccgcggag   480
ctgctggcgc  gcgtcgagga  ccggatcgcc  accatgttcg  cgctgccagc  ggacgacaag   540
atgcgccgcg  tgcgcgggcc  tggcgacgcc  tgcggctacg  gctccccgcc  catctcctcc   600
ttcttctcca  agtgcatgtg  gtcggaggga  tacaccttct  cgccggccaa  cctccgcgcc   660
gacctccgca  agctctggcc  taaggccggc  gacgactaca  ccagcttctg  gtacgtgcac   720
ccgccgggcgg  cgcgccgcca  cacaccgtac  ccacacacgt  gcgcgctcgc  gcctagctac   780
tagtagcgtc  tttgctttgc  ttacctttga  ttctcgcctt  tgccatgcat  atgcatgatg   840
cacgtacagg  tactgcaggt  acaacatgtc  acacgcacgc  acgcacgcac  aacccatagt   900
ccgatacgat  acatcatcga  tcgacgtgtc  gtcaccgtct  aaggccatgc  atgcatgcaa   960
gcacacgcct  agaccttttt  agcatgctgg  ctgacgagga  gtatactagc  taataagcta  1020
cttgtcactg  cgcgtcttgc  ttaattacac  tagtgcatat  ttctacagtg  atgtgatgga  1080
ggagttccac  aagcacatgc  gtgccctcgc  ggacaagctg  ctggagctgt  tcctcatggc  1140
gctgggggctc accgacgagc  aggtcggcgg  cgtggaggcg  gagcggagga  tcgccgagac  1200
gatgaccgcc  accatgcacc  tcaactggta  ccctcgggtgc ccggacccgc  gccgcgcgct  1260
gggggctgatc gcgcacaccg  actcgggggctt cttcaccttc  gtgctgcaga  gcctcgtccc  1320
ggggctgcag  ctcttccgcc  acgccccgga  ccggtggggtg gcggtgccgg  cggtaccggg  1380
cgccttcgtc  gtcaacgtgg  gcgacctctt  ccacatcctc  accaacggcc  ggttccacag  1440
cgtgtaccac  cgcgccgtcg  tgaacccggga cctcgacagg  atatctctcg  gctacttcct  1500
cggcccgccg  ccgcacgcca  aggtggcgcc  gctaaggagg  gccgtgccgc  ccggccgcac  1560
ccccgcgtac  cgcgccgtca  cgtgcccga   gtacatgggc  gtccgcaaga  aggccttcac  1620
caccggcgca  tccgcgctca  agatggtcgc  cctcgccgcc  gccgccgccg  ccgccgacct  1680
cgacgatgac  gccggtgctg  gcgccgccgc  cgaacctgtc  gtccatcagc  agctactcgt  1740
ctcgtcgtag  ccgatcgatc  gccggatcgg  tcgagactga  tgatgatgat  gcatatatac  1800
tcgtcgatgg  agtagacaga  ctaatcaagc  aaccctgaaa  ctatgaatgc  atgcgtcgcg  1860
ttcgtgcttg  cttgcgcatg  cagctagcag  gcttcattcc  gttccgcagc  tgctctgctc  1920
caacctgctc  tgctggattg  atgtatatgg  tagaagaatt  aagagatcga  tggatgacgg  1980
aggaagaaga  gacgaagac   gacgatgagg  aaaaggacac  gctgtacgta  gctggttctt  2040
ctagtctagt  ttacagcagg  ccgggcggcc  ggctgctgct  tccaatcgag  tttgtcgtta  2100
ctgacgattg  ttagtggatc  gattaactaa  tctggaattc  tggattatta  atataatgca  2160
tgtggtttgg  catctggcgt  aaagcaggta  atggtaccta  gccagtagcc  agtagccagg  2220
ctggtcaatg  ataggtctat  accctgatcc  tgtactgttg  tttctttcgg  tctttctgag  2280
agagaaaaaa  aacgaatata  tggcgtactc  aattcatcaa  a                      2321

SEQ ID NO: 123             moltype = DNA   length = 1796
FEATURE                    Location/Qualifiers
source                     1..1796
                           mol_type = unassigned DNA
                           organism = Setaria italica
SEQUENCE: 123
actagtgcaa  ggtcctagat  ttacacttgg  tgcttgcttg  tttcttccta  gttgctactg    60
gtagcacgca  gtgctggct   ggccgtaatc  tattgtctgg  gctcgatcgg  tgattaggaa   120
gtagccaaag  caagctaagg  ccgccgccatg ccgacgccgt  cgcacctcaa                180
gaaccccgctc tacttcgact  tccgcgccgc  gcgcgggtg  ccggagtccc  acgcctggcc   240
ggggctcgac  gaccacccccg tggtggacgg  cggggcgcg   ccggggtccc  ggacgccgt    300
gccggtggtg  gacctgcgcg  agccgggcgc  ccgcggcggtg gccgcgtgg   cgcgcgccgc   360
cgagcagtgg  ggcgcgttcc  tgctcaccgg  ccacggcgtc  cccgcggagc  tcctggcgcg   420
cgtcgaggac  cgcgtcgcgt  gcatgttcgc  gctgccggcc  gccgacaaga  tgcgcgccgt   480
```

```
gcgcgggccg ggggacgcct gcggctacgg ctcgccgccc atctcctcct tcttctccaa    540
gtgcatgtgg tccgagggct acaccttctc gccggcctcc ctccgccgcg acctccgcaa    600
gctctggccc aaggccggcg acgactacga cagcttctgt gacgtgatgg aggagttcca    660
caaggagatg cgcgccctcg ccgacaggct cctggagctg ttcctcaggg cgctcgggct    720
caccggcgag caggtcggcg ccgtcgaggc ggagcggagg atcggcgaga cgatgaccgc    780
caccatgcac ctcaactggt atccgaggtg cccggacccg cggcgcgcgc tgggggctgat    840
cgcgcacacg gactcgggct tcttcacctt cgtgctgcag agcctcgtgc cggggctgca    900
gctgttccgg cacggcccca accggtgggg ggcggtgccg ccgtgccggg cgccttcgt    960
cgtcaacgtc ggcgacctct tccacatcct cacgaacggc cgcttccaca gcgtgtacca   1020
ccgcgcgtc gtcaaccggg acctcgaccg gatatcgctc ggctacttcc tcgggcccgc   1080
gccccacgcc aaggtggcgc cgctccggga ggtcgtgccg ccgggccggg ccccccgccta   1140
ccgcgccgtc acgtggcccg agtacatggg cgtccgcaag aaggccttca ccaccggcgc   1200
ctccgcgctc aagatggtcg ccgccgccgc cgccgccacc gaatccgacg acaccgacgc   1260
agccgccgcc gccgttcacc agccgccggt cgtcgtctca tcgtagccga tcgatcgcgg   1320
gaaacacaga cgatgcatac cgtaccccga gcaatctaat caaaacaagg catccattct   1380
cgcgcgcatg cagcggccag ccgggcttcc gcagctgctc ggcctcctct gctggctgtg   1440
gaaatggaaa attttaatct gagatgaaga cgaagacgaa gacgaaacgg agaggaaaag   1500
gacatgctgt agctgtttct tctagttgcg caggccgctc ccagtcgagt ttgtcgttac   1560
tgacgattat tactctgatg aaaactaatc tgaattaatg catgtagttt ggcaatttgg   1620
tactaaaggt aggcacctag ccaggctggt caatgatagg tctataacct gatcctgttc   1680
tctgttgttt tcctttgtct gagaaaaaat ggaaataatt gatccggccg gacgggtgta   1740
ctgataggtg atgctgaatt gctgatgcaa gaggttgcga gctgcagtga gcagca       1796

SEQ ID NO: 124         moltype = DNA   length = 1149
FEATURE                Location/Qualifiers
source                 1..1149
                       mol_type = unassigned DNA
                       organism = Setaria italica
SEQUENCE: 124
atgccgacgc cgtcgcacct caagaacccg ctctacttcg acttccgcgc cgcgcggcgg     60
gtgccggagt cccacgcctg gccggggctc gacgaccacc ccgtggtgga cggcggcggc    120
gcgcgggggt ccccggacgc cgtgccggtg gtggacctgc gcgagccggg cgccgcggcg    180
gtggcccgcg tggcgcgcgc cgccgagcag tggggcgcgt tcctgctcac cggccacggc    240
gtcccgcgcg agctcctggc gcgcgtcgag accgcgtcg cgtgcatgtt cgcgctgccg    300
gccgccgaca agatgcgcgc cgtcgcgcgg ccgggggacg cctgcggcta cggctcgccg    360
cccatctcct ccttcttctc caagtgcatg tggtccgagg gctacacctt ctcgccggcc    420
tccctccgcc gcgacctccg caagctctgg cccaaggccg cgacgactac gacagcttc    480
tgtgacgtga tggaggagtt ccacaaggag atgcgcgccc tcgccgacag gctcctggag    540
ctgttcctca gggcgctcgg gctcaccggc gagcaggtcg gcgccgtcga ggcggagcgg    600
aggatcggcg agacgatgac cgccaccatg cacctcaact ggtatccgag gtgcccggac    660
ccgcggcgcg cgctggggct gatcgcgcac acggactcgg gcttcttcac cttcgtgctg    720
cagagcctcg tgccggggct gcagctgttc ggcacggcc ccaaccggtg ggtggcggtg    780
ccggcgtgc cgggcgcctt cgtcgtcaac gtcggcgacc tcttccacat cctcacgaac    840
ggccgcttcc acagcgtgta ccaccgcgcc gtcgtcaacc gggacctcga ccggatatgc    900
ctcggctact tcctcggccc gccgccccac gccaaggtgg cgccgctccg ggaggtcgtg    960
ccgccgggcc gggcccccgc ctaccgcgcc gtcacgtggc ccgagtacat gggcgtccgc   1020
aagaaggcct tcaccaccgg cgcctccgcg ctcaagatgg tcgccgccgc cgccgccgcc   1080
accgaatccg acgacaccga cgcagccgcc gccgccgttc accagccgcc ggtcgtcgtc   1140
tcatcgtag                                                          1149

SEQ ID NO: 125         moltype = AA    length = 382
FEATURE                Location/Qualifiers
source                 1..382
                       mol_type = protein
                       organism = Setaria italica
SEQUENCE: 125
MPTPSHLKNP LYFDFRAARR VPESHAWPGL DDHPVVDGGG APGSPDAVPV VDLREPGAAA     60
VARVARAAEQ WGAFLLTGHG VPAELLARVE DRVACMFALP AADKMRAVRG PGDACGYGSP    120
PISSFFSKCM WSEGYTFSPA SLRRDLRKLW PKAGDDYDSF CDVMEEFHKE MRALADRLLE    180
LFLRALGLTG EQVGAVEAER RIGETMTATM HLNWYPRCPD PRRALGLIAH TDSGFFTFVL    240
QSLVPGLQLF RHGPNRWVAV PAVPGAFVVN VGDLFHILTN GRFHSVYHRA VVNRDLDRIS    300
LGYFLGPPPH AKVAPLREVV PPGRAPAYRA VTWPEYMGVR KKAFTTGASA LKMVAAAAAA    360
TESDDTDAAA AAVHQPPVVV SS                                            382

SEQ ID NO: 126         moltype = DNA   length = 2146
FEATURE                Location/Qualifiers
source                 1..2146
                       mol_type = unassigned DNA
                       organism = Setaria italica
SEQUENCE: 126
actagtgcaa ggtcctagat ttacacttgg tgcttgcttg tttcttccta gttgctactg     60
gtagcacgca gtggctggct ggccgtaatc tattgtctgg gctcgatcgg tgattaggaa    120
gtagccaaag caagctaagg ccgccgccgc cgccgccatg ccgacgccgt cgcacctcaa    180
gaacccgctc tacttcgact tccgcgccgc gcggcgggtg ccggagtccc acgcctggcc    240
ggggctcgac gaccacccccg tggtggacgg cggcggcgcg ccgggtccc ggacgccgt    300
gccggtggtg gacctgcgcg agccgggcgc cgcggcggtg gccgcgtgg cgcgcgccgc    360
cgagcagtgg ggcgcgttcc tgctcaccgg ccacggcgtc ccgcgggagc tcctggcgcg    420
cgtcgaggac cgcgtcgcgt gcatgttcgc gctgccggcc gccgacaaga tgcgcgccgt    480
gcgcgggccg ggggacgcct gcggctacgg ctcgccgccc atctcctcct tcttctccaa    540
```

```
gtgcatgtgg tccgagggct acaccttctc gccggcctcc ctccgccgcg acctccgcaa    600
gctctggccc aaggccggcg acgactacga cagcttctgg tacgtcgtcg tctatagcta    660
gtagctagcc gccggcacac gtgcgcctga cctgctccgc catgcatggt gcacgtatgc    720
agatcgatca cacgcaccga tcgatcgacg tgtcccggtc aaggccatgc atgcatgcaa    780
gcaaccaaca gcacgcctcc tgatactgct tgttgcttac accgttggta tgtgcctgtt    840
gcctacagtg acgtgatgga ggagttccac aaggagatgc gcgccctcgc cgacaggctc    900
ctggagctgt tcctcagggc gctcgggctc accggcgagc aggtcggcgc cgtcgaggcg    960
gagcggagga tcggcgagac gatgaccgcc accatgcacc tcaactggta tgtgccatgc   1020
catgaccacc tgcgtctatg aactaacgga agcttccatc gcgtgtccat gacgatttag   1080
aagctgtagt ccagagcttg agacaaacga aacgaagctt acatggtggc gtgacgtgtc   1140
gcgtgcaggt atccgaggtg cccggacccg cggcgcgcgc tggggctgat cgcgcacacg   1200
gactcgggct tcttcacctt cgtgctgcag agcctcgtgc cggggctgca gctgttccgg   1260
cacggcccca accggtgggt ggcggtgccg gccgtgccgg gcgccttcgt cgtcaacgtc   1320
ggcgacctct tccacatcct cacgaacggc cgcttccaca gcgtgtacca ccgcgccgtc   1380
gtcaaccggg acctcgaccg gatatcgctc ggctacttcc tcgcccgcc gccccacgcc   1440
aaggtggcgc cgctccggga ggtcgtgccg ccgggccggg cccccgccta ccgcgccgtc   1500
acgtggcccg agtacatggg cgtccgcaag aaggccttca ccaccggcgc ctccgcgctc   1560
aagatggtcg ccgccgaccg cgccgccacc gaatccgaca acaccgacgc agccgcgcc   1620
gccgttcacc agccgccggt cgtcgtctca tcgtagccga tcgatcgccg gaaacacaga   1680
cgatgcatac cgtaccccga gcaattaat caaaacaagg catccattct cgcgcgcatg   1740
cagcggccag ccgggcttcc gcagctgctc ggcctcctct gctggctgtg gaaatggaaa   1800
attttaatct gagatgaaga cgaagacgaa gcgaaacgg agaggaaaag gacatgctgt   1860
agctgtttct tctagttgcg caggccgctc ccagtcgagt ttgtcgttac tgacgattat   1920
tactctgatg aaaactaatc tgaattaatg catgtagttt ggcaatttgg tactaaaggt   1980
aggcacctag ccaggctggt caatgatagg tctataacct gatcctgttc tctgttgttt   2040
tcctttgtct gagaaaaaat ggaaataatt gatccggccg gacgggtgta ctgataggtg   2100
atgctgaatt gctgatgcaa gaggttgcga gctgcagtga gcagca                 2146

SEQ ID NO: 127            moltype = DNA   length = 1933
FEATURE                   Location/Qualifiers
source                    1..1933
                          mol_type = unassigned DNA
                          organism = Oryza sativa
SEQUENCE: 127
actactcatt ccactattgt aaagtcatag aaaaaattta tatagagaga aaaaattagt     60
gttgttattg ttactggctt tctgccagac gagacgagcg agcgcgcgag tgtgttgctc    120
tctggtcatc gtcgtcgtcg tcgcgatgcc gacgccgtcg cacttgaaga acccgctctg    180
cttcgacttc cgggcggcga ggcgggtgcc ggagacgcac gcgtgccgg ggctggacga    240
ccaccggtg gtggacgcg cggcggcg cggcgaggac ggcgtgccgg tggtggacgt    300
cggggcgggc gacgcggcgg cgcgggtggc gcgggcggcg gagcagtggg gcgcgttcct    360
tctggtcggg cacggcgtgc cggcggcgct gctgtcgcgc gtcgaggagc gcgtcgcccg    420
cgtgttctcc ctgccggcgt cggagaagat gcgcgccgtc cgcggcccg gcgagccctg    480
cggctacggc tcgccgccca tctcctcctt ctttctcaag tctcatgtgt ccgagggcta    540
caccttctcc ccttcctccc tccgctccga gctccgccgc ctctggccca agtccggcga    600
cgactacctc ctcttctgtg acgtgatgga ggagtttcac aaggagatgc ggcggctagc    660
cgacgagttg ctgaggttgt tcttgagggc gctgggggctc accggcgagg aggtcgccgg    720
agtcggccg gagaggagga tcggcgagag gatgacggcg accgtcacc tcaactggta    780
cccgaggtgc ccggagccgc ggcgagcgct gggggctcatc gcgcacacgg actcgggctt    840
cttcaccttc gtgctccaga gcctcgtccc ggggctgcag ctgttccgtc gagggcccga    900
ccggtgggtg gcggtgccgg cggtggcggg ggccttcgtc gtcaacgtcg gcgacctctt    960
ccacatcctc accaacggcc gcttccacag cgtctaccac cgccgcgtcg tgaaccggga   1020
ccgcgaccgg gtctgctcg gctacttcct cggcccgccg ccgacgccg aggtggcgcc   1080
gctgccggag gccgtgccgg ccggccggag ccccgcctac cgcgctgtca cgtgccggga   1140
gtacatggcc gtccgcaaga aggccttcgc caccggcggc tccgcctca agatggtctc   1200
caccgacgcc gccgccgccg ccgacgaaca cgacgacgtc gccgccgccg cgacgtcca   1260
cgcataagct atagctacta gctacctcga tctcacgcaa aaaaaaaag aaacaattaa   1320
tagagcaaaa aaaaaagaa gagaaaatgg tggtacttgt gtttaaggtt tcctccatgc   1380
aaaatggttt gcatgcatgc atgcaaagct agcatctgca gctgcaagaa ttacaagagc   1440
agagaagcag acagctagat ggagataatt aattaattaa ttaatctaat taagcatgca   1500
ataattaaga ttattattct gatttcagaa ctgaaaaaaa aagtgtggtt aattaattat   1560
tggttaggct taattttatc tagatgtaga aaaagaatca agatcttcaa gcaagagaga   1620
agaggatcga agaagaagga aaagaaaacg aaaaggacat gctgtgttgt ctcttctagt   1680
tgtaccctgg ctgctgatta agtgctttgt tttgttgctg caagcttgtc gttactgatt   1740
attagttagt tatgcatcta attgattaaa ctaatctgtt gcattttg gctcgagcta   1800
agctatagcc aggctggtca atgataggaa cttgtacaat ttaagcaatt gaacctgatc   1860
ctgtactggc atgtatgtat atatgcaagt gatgagaacc actagctagt atagctagac   1920
atgtatttgt ata                                                     1933

SEQ ID NO: 128            moltype = DNA   length = 1122
FEATURE                   Location/Qualifiers
source                    1..1122
                          mol_type = unassigned DNA
                          organism = Oryza sativa
SEQUENCE: 128
atgccgacgc cgtcgcactt gaagaacccg ctctgcttcg acttccgggc ggcgaggcgg     60
gtgccggaga cgcacgcgtg gccggggctg acgaccacc cggtggtgga cggcggcggc    120
ggcggcggc aggacgcggt gccggtggtg gacgtcgggg cggcgacgc ggcggcgcgg    180
gtggcgcggg cggcggagca gtggggcgcg ttccttctgg tcgggcacgg cgtgccgcg    240
gcgctgctgt cgcgcgtcga ggagcgcgtc gcccgcgtgt tctccctgcc ggcgtcggag    300
```

-continued

```
aagatgcgcg ccgtccgcgg ccccggcgag ccctgcggct acggctcgcc gcccatctcc  360
tccttcttct ccaagctcat gtggtccgag ggctacacct tctccccttc ctccctccgc  420
tccgagctcc gccgcctctg gcccaagtcc ggcgacgact acctcctctt ctgtgacgtg  480
atggaggagt ttcacaagga gatgcggcgg ctagccgacg agttgctgag gttgttcttg  540
agggcgctgg ggctcaccgg cgaggaggtc gccggagtcg aggcggagag gaggatcggc  600
gagaggatga cggcgacggt gcacctcaac tggtacccga ggtgcccgga gccgcggcga  660
gcgctggggc tcatcgcgca cacggactcg ggcttcttca ccttcgtgct ccagagcctc  720
gtcccggggc tgcagctgtt ccgtcgaggg cccgaccggt gggtggcggt gccggcggtg  780
gcgggggcct tcgtcgtcaa cgtcggcgac ctcttccaca tcctcaccaa cggccgcttc  840
cacagcgtct accaccgcgc cgtcgtgaac cgcgaccgcg accgggtctc gctcggctac  900
ttcctcggcc cgccgccgga cgccgaggtg gcgccgctgc cggaggccgt ccggccggcc  960
cggagcccg cctaccgcgc tgtcacgtgg ccggagtaca tggccgtccg caagaaggcc  1020
ttcgccaccg gcggctccgc cctcaagatg gtctccaccg acgccgccgc cgccgccgac  1080
gaaacacgacg acgtcgccgc cgccgccgac gtccacgcat aa                    1122

SEQ ID NO: 129          moltype = AA   length = 373
FEATURE                 Location/Qualifiers
source                  1..373
                        mol_type = protein
                        organism = Oryza sativa
SEQUENCE: 129
MPTPSHLKNP LCFDFRAARR VPETHAWPGL DDHPVVDGGG GGGEDAVPVV DVGAGDAAAR   60
VARAAEQWGA FLLVGHGVPA ALLSRVEERV ARVFSLPASE KMRAVRGPGE PCGYGSPPIS  120
SFFSKLMWSE GYTFSPSSLR SELRRLWPKS GDDYLLFCDV MEEFHKEMRR LADELLRLFL  180
RALGLTGEEV AGVEAERRIG ERMTATVHLN WYPRCPEPRR ALGLIAHTDS GFFTFVLQSL  240
VPGLQLFRRG PDRWVAVPAV AGAFVVNVGD LFHILTNGRF HSVYHRAVVN RDRDRVSLGY  300
FLGPPPDAEV APLPEAVPAG RSPAYRAVTW PEYMAVRKKA FATGGSALKM VSTDAAAAAD  360
EHDDVAAAAD VHA                                                     373

SEQ ID NO: 130          moltype = DNA   length = 2040
FEATURE                 Location/Qualifiers
source                  1..2040
                        mol_type = unassigned DNA
                        organism = Oryza sativa
SEQUENCE: 130
actactcatt ccactattgt aaagtcatag aaaaaattta tatagagaga aaaaattagt   60
gttgttattg ttactggctt tctgccagac gagacgagcg agcgcgcgag tgtgttgctc  120
tctggtcatc gtcgtcgtcg tcgcgatgcc gacgccgtcg cacttgaaga acccgctctg  180
cttcgacttc cgggcggcga ggcggctgcc ggagacgcac gcgttgccgg ggctggacga  240
ccacccggtg gtggacggcg gcggcggcgg cggcgaggac gcggtgccgg tggtggacgt  300
cggggcgggc gacggcggcg gcgggtggc gcggcggcg gagcagtggg gcgcgttcct  360
tctggtcggg cacggcgtgc cggcggcgct gctgtcgcgc gtcgaggagc gcgtcgcccg  420
cgtgttctcc ctgccggcgt cggagaagat gcgcgccggc gaggcccg gcgagccctc  480
cggctacggc tcgccgccca tctcctcctt cttctccaag ctcatgtggt ccgagggcta  540
caccttctcc ccttcctccc tccgtccga gctccgccgc ctctggccca gtccggcga  600
cgactacctc ctcttctggt atatatacat atatactctc ccatgcattc catgcacata  660
cactctacgt atatatctac ctctacgtat atatctactc attgatctac gtataatata  720
cgcagtgacg tgatggagga gttttcacaag gagatgcggc ggctagccga cgagttgctg  780
aggttgttct tgagggcgct ggggctcacc ggcgaggagg tcgccggagt cgaggcggag  840
aggaggatcg gcgagaggat gacggcgacg gtgcacctca actggtaccc gaggtgcccg  900
gagccgcggc gagcgctggg gctcatcgcg cacacggact cgggcttctt caccttcgtg  960
ctccagagcc tcgtcccggg gctgcagctg ttccgtcgag ggcccgaccg gtgggtggcg 1020
gtgccggcgg tggcggggc cttcgtcgtc aacgtcggcg acctcttcca catcctcacc 1080
aacggccgct tccacagcgt ctaccaccgc gccgtcgtga accgcgaccg cgaccgggtc 1140
tcgctcggct acttcctcgg cccgccgccg gacgccgagg tggcgccgct gccggaggcc 1200
gtgccggccg gccggagccc gcctaccgc gctgtcacgt ggccggagta catggccgtc 1260
cgcaagaagg ccttcgccac cggcggctcc gccctcaaga tggtctccac cgacgccgcc 1320
gccgccgccg acgaacacga cgacgtcgcc gccgccgccg acgtccacgc ataagctata 1380
gctactagct acctcgatct cacgcaaaaa aaaaaagaaa caattaatag agcaaaaaaa 1440
aaaagaagag aaaatggtgg tacttgtgtt taaggtttcc tccatgcaaa atggtttgca 1500
tgcatgcatg caaagctagc atctgcagct gcaagaatta caagagcaga gaagcagaca 1560
gctagatgga gataattaat taattaatta atctaattaa gcatgcaata attaagatta 1620
ttattctgat ttcagaactg aaaaaaaaag tgtggttaat taattattgg ttaggcttaa 1680
ttttatctag atgtagaaaa agaatcaaga tcttcaagca agagagaaga ggatcgaaga 1740
agaaggaaaa gaaacgaaa aggacatgct gtgttgtctc ttctagttgt acctggctg 1800
ctgattaagt gctttgtttt gttgctgcaa gcttgtcgtt actgattatt agttagttat 1860
gcatctaatt gattaaacta atctgtttgg cattttggct cgagctaagc tatagccagg 1920
ctggtcaatg ataggaactt gtacaattta agcaattgaa cctgatcctg tactggcatg 1980
tatgtatata tgcaagtgat gagaaccact agctagtata gctagacatg tatttgtata 2040

SEQ ID NO: 131          moltype = DNA   length = 1332
FEATURE                 Location/Qualifiers
source                  1..1332
                        mol_type = unassigned DNA
                        organism = Hordeum vulgare
SEQUENCE: 131
acactcactc ctcaatccat ccgtctccac cattgctcgc tagctcgagc tctactagct   60
agcactgcaa agtcagccgg gccggagttg atttggtcct tgttagcttg accgatcgta  120
tacgtatcgc caggatgccg acgccgtcgc acctgagcaa ggaccgcac tacttcgact  180
```

```
tccgggcggc gcggcgggtg ccggagacac acgcgtggcc ggggctgcac gaccacccgg  240
tggtggacgg cggcggcgcg ggcggagggc cggacgcggt gccggtggtg gacatgcgcg  300
acccgtgcgc cgcggaggcg gtggcgctgg ccgcgcagga ctggggcgcc ttcctcttgc  360
agggccacgg cgtcccgttg gagctgctgg cccgcgtgga ggccgcgata gcgggcatgt  420
tcgcgctgcc ggcgtcggag aagatgcgcg ccgtgcggcg cgcgaccgtc gtgcggct    480
acgggtcgcc gcccatctcc tccttcttct ccaagtgcat gtggtccgag gctacacct   540
tctccccggc caacctccgc tccgacctcc gcaagctctg gcccaaggcc ggccacgact  600
accgccactt ctgtgccgtg atggaggagt tccacaggga gatgcgcgtt ctggccgaca  660
agctgctgga gctgttcctg gtggcccctcg ggctcaccgg cgagcaggtc gccgccgtcg  720
agtcggagca caagatcgcc gagaccatga ccgccacaat gcacctcaac tggtacccca  780
agtgcccgga cccgaagcga gcgctgggcc tgatcgcgca cacggactcg gcttcttca   840
ccttcgtgct ccagagcctg gtgccgggcc tgcagctgtt ccggcacggc cccgaccgtt  900
gggtgacggt gcccgccgtg ccgggcgcca tggtcgtcaa cgtcggcgac ctcttccaca  960
tcctcaccaa tggccgcttc cacagcgtct accaccgcgc cgtcgtcaac cgcgacagcg 1020
accggatatc gctggggtac ttcctcggcc cgccccgcca cgttaaggtg gcgccgctca 1080
gggaggccct cgccggcacg cccgctgcct accgcgccgt cacgtggccc gagtacatgg 1140
gcgtgcgcaa gaaggccttc accaccgcg cctccgcgct caagatggtc gccatctcca 1200
ccgacgacgc cgccgacgtc ctccccgacg tcctctcgtc gtagatcggc gccggccatc 1260
acccggccgg ccaagagacc gatctataca aacaattagt gaacaaaaaa aaaaaaaaaa 1320
aaaaaaaaaa aa                                                    1332

SEQ ID NO: 132         moltype = DNA  length = 1110
FEATURE                Location/Qualifiers
source                 1..1110
                       mol_type = unassigned DNA
                       organism = Hordeum vulgare
SEQUENCE: 132
atgccgacgc cgtcgcacct gagcaaggac ccgcactact tcgacttccg ggcggcgcgg   60
cgggtgccga agacacacgc gtggccgggg ctgcacgacc accggtggt ggacggcggc  120
ggcgcggcgg gagggccgga cgcggtgccg gtggtggaca tgcgcgaccc gtgcgccgcg  180
gaggcggtgg cgctggccgc gcaggactgg ggcgccttcc tcttgcaggg ccacggcgtc  240
ccgttggagc tgctggcccg cgtggaggcc gcgatagcgg gcatgttcgc gctgccggcg  300
tcggagaaga tgcgcgccgt gcggcggccc ggcgactcgt gcggctacgg gtcgccgccc  360
atctcctcct tcttctccaa gtgcatgtgg tccgagggct acacttccg cccggccaac  420
ctccgctccg acctccgcaa gctctggccc aaggccgccc acgactaccg ccacttctgt  480
gccgtgatgg aggagttcca cagggagatg cgcgttctgg ccgacaagct gctggagctg  540
ttcctggtgg ccctcgggct caccggcgag caggtcgccg ccgtcgagtc ggagcacaag  600
atcgccgaga ccatgaccgc cacaatgcac ctcaactggt accccaagtg cccggaccgg  660
aagcgagcgc tgggcctgat cgcgcacacg gactcggcgt tcttcaccct cgtgctccaa  720
agcctggtgc ccgggctgca gctgttccgg cacgccccg accgttgggt gacggtgccc  780
gccgtgccgg gcgccatggt cgtcaacgtc ggcgacctct ccacatcct caccaatggc  840
cgcttccaca cgtctacca ccgcgccgtc gtcaaccgcg acagcgaccg gatatcgctg  900
gggtacttcc tcggcccgcc cgcccacgtt aaggtgccg cgcccctgca  960
ggcacgcccg ctgcctaccg cgccgtcacg tggcccgagt acatgggcgt gcgcaagaag 1020
gccttcacca ccggcgcctc cgcgctcaag atggtcgcca tctccaccga cgacgccgcc 1080
gacgtcctcc ccgacgtcct ctcgtcgtag                                 1110

SEQ ID NO: 133         moltype = AA  length = 369
FEATURE                Location/Qualifiers
source                 1..369
                       mol_type = protein
                       organism = Hordeum vulgare
SEQUENCE: 133
MPTPSHLSKD PHYFDFRAAR RVPETHAWPG LHDHPVVDGG GAGGGPDAVP VVDMRDPCAA   60
EAVALAAQDW GAFLLQGHGV PLELLARVEA AIAGMFALPA SEKMRAVRRP GDSCGYGSPP  120
ISSFFSKCMW SEGYTFSPAN LRSDLRKLWP KAGHDYRHFC AVMEEFHREM RVLADKLLEL  180
FLVALGLTGE QVAAVESEHK IAETMTATMH LNWYPKCPDP KRALGLIAHT DSGFFTFVLQ  240
SLVPGLQLFR HGPDRWVTVP AVPGAMVVNV GDLFHILTNG RFHSVYHRAV VNRDSDRISL  300
GYFLGPPAHV KVAPLREALA GTPAAYRAVT WPEYMGVRKK AFTTGASALK MVAISTDDAA  360
DVLPDVLSS                                                         369

SEQ ID NO: 134         moltype = DNA  length = 1653
FEATURE                Location/Qualifiers
misc_feature           1594..1600
                       note = n is a, c, g, or t
misc_feature           1641
                       note = n is a, c, g, or t
source                 1..1653
                       mol_type = unassigned DNA
                       organism = Triticum aestivum
SEQUENCE: 134
cacgagatcc atccgtctcc accattgctc gctagctcga gctcctagct agtactgcaa   60
agtcagccgg ggagttgatt tggtccttct tggcttgacc gatcgtacgt gccgccagga  120
tgccgacgcc ggcgcacctg agcaaggacc cgcgctactt cgacttccgg ggcggcgcg   180
gggtgccgga gacgcacgcg tggcccgggc tgcacgacca cccgtggtg gacggcagcg  240
gcgcgggcgg agggccggac gcggtgccgg tgtggacat gcgcgacccg tgcgcggcgg  300
aggcggtggc gctggcggcg caggactggg gcgccttcct cctggagggc cacggcgtcc  360
cgttggagct gctggcgcgc gtggaggccg cgatcgcggg catgttcgcg ctgccggcgt  420
cggagaagat gcgcgccgtg cggcggcccg gcgactcgtg cggctacggg tcgccgccca  480
```

```
tctcctcctt cttctccaag tgcatgtggt ccgagggcta cacctttctcc ccggccaacc    540
tccgctccga cctccgcaag ctctggccca aggccggcca cgactaccgc cacttctgcg    600
ccgtgatgga ggagttccac agggagatgc gcgcgctggc cgacaagctg ctggagctgt    660
tcctggtggc cctcgggctc accggcgagc aggtcgccgc cgtcgagtcc gagcagaaga    720
tcgccgagac catgaccgcc acaatgcacc tcaactggta ccccaagtgc ccggacccgg    780
agcgggcgct gggcctgatc gcgcacacgg actcgggctt cttcaccttc gtgctgcaga    840
gccttgtgcc cgggctgcag ctgttccggc acggccccga ccgtgggtg acggtgcccg    900
ccgtgccggg ggccatggtc gtcaacgtcg gcgacctctt ccagatcctc accaacggcc    960
gcttccacag cgtctaccac cgcgctgtcg tcaaccgcga cagcgaccgg atatcgctcg   1020
gctacttcct cggcccgccc gcccacgtca aggtggcgcc gctcagggag gccctggccg   1080
gcacgcccgc cgcctaccgc gccgtcacgt ggcccgagta catgggcgtg cgcaagaagg   1140
ccttcaccac cggcgcctcc gcgctcaaga tggtcgccat ctccactgac aacgacgccg   1200
ccaaccacac ggacgacctg atctcgtcgt agatcggcgc cggccatcac cggccggcca   1260
agggatcgat ctacacacac aattagtgaa caaaaaaatg ccagagatgg tgcatggtgc   1320
gctggtagct tagctgaggt agctaggagg aagagcgcgc gtgcggctgt cgttcgtgcg   1380
gctgttcccg caaaaaaaaa aaaggttttcc tccatatatg tctccatgca gaactgcaga   1440
tgctggtggt ggatgcgtcc atgcagcagg gaacgaacta attgtaagaa aatcaagcaa   1500
acttagttct acatctgtaa ttaagtatgc atgccacttg gtttaattca attcaagtgc   1560
agaaaaaatt atgatgggaa aaaaaaagac atgnnnnnnn aaaaaaaaaa aaaaaaaaa    1620
aaaaaaaaaa aaaaaaaaaa naaaaaaaaa aaa                                 1653

SEQ ID NO: 135          moltype = DNA  length = 1113
FEATURE                 Location/Qualifiers
source                  1..1113
                        mol_type = unassigned DNA
                        organism = Triticum aestivum
SEQUENCE: 135
atgccgacgc cggcgcacct gagcaaggac ccgcgctact tcgacttccg ggcggcgcgg    60
cgggtgccgg agacgcacgc gtggcccggg ctgcacgacc accccgtggt ggacggcagc   120
ggcgcgggcg gagggccgga cgcggtgccg gtggtggaca tgcgcgaccc cgtgcgcggcg   180
gaggcggtgg cgctggcgg gcaggactgg ggcgccttcc tcctggaggg ccacgtcgtc   240
ccgttggagc tgctggcgcg cgtggaggcc gcgatcgcgg gcatgttcgc gctgccggcg   300
tcggagaaga tgcgcgccgt gcggcggccc ggcgactcgt gcggctacgg gtcgccgccc   360
atctcctcct tcttctccaa gtgcatgtgg tccgagggct cacctttctc cccggccaac   420
ctccgctccg acctccgcaa gctctggccc aaggccggca cgactaccg ccacttctgc   480
gccgtgatgg aggagttcca cagggagatg cgcgcgctgg ccgacaagct gctggagctg   540
ttcctggtgg ccctcgggct caccggcgag caggtcgccg ccgtcgagtc cgagcagaag   600
atcgccgaga ccatgaccgc cacaatgcac ctcaactggt accccaagtg cccggacccg   660
aagcgggcgc tgggcctgat cgcgcacacg gactcgggct tcttcacctt cgtgctgcag   720
agccttgtgc ccgggctgca gctgttccgg cacggccccg accgtgggt gacggtgccc   780
gccgtgccgg gggccatggt cgtcaacgtc ggcgacctct tccagatcct caccaacgg   840
cgcttccaca gcgtctacca ccgcgccgtc gtcaaccgcg acagcgaccg gatatcgctc   900
ggctacttcc tcggcccgcc cgcccacgtc aaggtggcgc cgctcaggga ggccctggcc   960
ggcacgcccg ccgcctaccg cgccgtcacg tggcccgagt acatgggcgt gcgcaagaag   1020
gccttcacca ccggcgcctc cgcgctcaag atggtcgcca tctccactga caacgacgcc   1080
gccaaccaca cggacgacct gatctcgtcg tag                                 1113

SEQ ID NO: 136          moltype = AA  length = 370
FEATURE                 Location/Qualifiers
source                  1..370
                        mol_type = protein
                        organism = Triticum aestivum
SEQUENCE: 136
MPTPAHLSKD PRYFDFRAAR RVPETHAWPG LHDHPVVDGS GAGGGPDAVP VVDMRDPCAA    60
EAVALAAQDW GAFLLEGHGV PLELLARVEA AIAGMFALPA SEKMRAVRRP GDSCGYGSPP   120
ISSFFSKCMW SEGYTFSPAN LRSDLRKLWP KAGHDYRHFC AVMEEFHREM RALADKLLEL   180
FLVALGLTGE QVAAVESEQK IAETMTATMH LNWYPKCPDP KRALGLIAHT DSGFFTFVLQ   240
SLVPGLQLFR HGPDRWVTVP AVPGAMVVNV GDLFQILTNG RFHSVYHRAV VNRDSDRISL   300
GYFLGPPAHV KVAPLREALA GTPAAYRAVT WPEYMGVRKK AFTTGASALK MVAISTDNDA   360
ANHTDDLISS                                                            370

SEQ ID NO: 137          moltype = DNA  length = 1884
FEATURE                 Location/Qualifiers
source                  1..1884
                        mol_type = unassigned DNA
                        organism = Triticum aestivum
SEQUENCE: 137
tatatataca gctcctctgta cttctctcgt tcttacactc actcctcaat ccatccgtct    60
ccaccattgc tcgctagctc gagctcctag ctagtactgc aaagtcagcc ggggagttga   120
tttggtcctt cttggcttga ccgatcgtac gtgccgccag gatgccgacg ccggcgcacc   180
tgagcaagga cccgcgctac ttcgacttcc gggcggcgcg gcgggtgccg gagacgcacg   240
cgtggcccgg gctgcacgac caccccgtgg tggacggcag cggcgcgggc ggagggccgg   300
acgcggtgcc ggtggtggac atgcgcgacc cgtgcgcggc ggaggcggtg gcgctggcgg   360
gcaggactgg gggcgccttc ctcctggagg gccacgtcgt cccgttggag ctgctggcgc   420
gcgtggaggc cgcgatcgcg ggcatgttcg cgctgccggc gtcggagaag atgcgcgccg   480
tgcggcggcc cggcgactcg tgcggctacg ggtcgccgcc catctcctcc ttcttctcca   540
agtgcatgtg gtccgagggc tacaccttct ccccggccaa cctccgctcc gacctccgca   600
agctctggcc caaggccggc cacgactacc gccacttctg gtacgtacgc cggccgcga   660
tgcgcatata cacgtcatag tacggcacct acctaactgg ctctgccaa ccgtccgtac   720
```

```
acacgtgaag gggcgacgtg tccgactccg accatgcatg catgcacgcg cgcgaaactt   780
gttactcctg ttctgctatg gcagcagcta gccgcgtgtg tccgttcgta ggagtagtta   840
cttacacagt tacacttacg ccgtccgtcg tgttcctcga cgtgcagcgc cgtgatggag   900
gagttccaca gggagatgcg cgcgctggcc gacaagctgc tggagctgtt cctggtggcc   960
ctcgggctca ccggcgagca ggtcgccgcc gtcgagtccg agcagaagat cgccgagacc  1020
atgaccgcca caatgcacct caactggtac gttccactac tactccagta gtacaagtac  1080
aatatataga atacaaatgg cagcagccac gacgacacgt actccaccat gcagcaaagc  1140
atatattgtc ggtgcggcgg ttgacacgga gttgtgtcgt gtcgttgatt cacaggtacc  1200
ccaagtgccc ggacccgaag cgggcgctgg gcctgatcgc gcacacggac tcgggcttct  1260
tcaccttcgt gctgcagagc cttgtgcccg ggctgcagct gttccggcac ggccccgacc  1320
ggtgggtgac ggtgcccgcc gtgccggggg ccatggtcgt caacgtcggc gacctcttcc  1380
agatcctcac caacggccgc ttccacagcg tctaccaccg cgccgtcgtc aaccgcgaca  1440
gcgaccggat atcgctcggc tacttcctcg gcccgcccgc ccacgtcaag gtggcgccgc  1500
tcaggcgaggc cctggccggc acgcccgccg cctaccgcgc cgtcacgtgg cccgagtaca  1560
tgggcgtgcg caagaaggcc ttcaccaccg cgcgcctccgc gctcaagatg gtcgccatct  1620
ccactgacaa cgacgccgcc aaccacacgg acgacctgat ctcgtcgtag atcggcgccg  1680
gccatccacg gccggccaag ggatcgatct acacacacaa ttagtgaaca aaaaaatgcc  1740
agagatggtg catggtgggc tggtagctta gctgaggtag ctaggaggaa gagcgcgcgt  1800
gcggctgtcg ttcgtgcggc tgttcccgca aaaaaaaaaa ggtttcctcc atatakgtcc  1860
ccakscaaaa tsgmaawgct gggg                                         1884

SEQ ID NO: 138           moltype = RNA  length = 20
FEATURE                  Location/Qualifiers
misc_feature             1..20
                         note = suppression oligo
source                   1..20
                         mol_type = other RNA
                         organism = synthetic construct
SEQUENCE: 138
acgggttctt ccaggtgtgc                                                20

SEQ ID NO: 139           moltype = RNA  length = 20
FEATURE                  Location/Qualifiers
misc_feature             1..20
                         note = suppression oligo
source                   1..20
                         mol_type = other RNA
                         organism = synthetic construct
SEQUENCE: 139
cacgggttct tccaggtgtg                                                20

SEQ ID NO: 140           moltype = RNA  length = 20
FEATURE                  Location/Qualifiers
misc_feature             1..20
                         note = suppression oligo
source                   1..20
                         mol_type = other RNA
                         organism = synthetic construct
SEQUENCE: 140
cattgacctc cccgctggca                                                20

SEQ ID NO: 141           moltype = RNA  length = 20
FEATURE                  Location/Qualifiers
misc_feature             1..20
                         note = suppression oligo
source                   1..20
                         mol_type = other RNA
                         organism = synthetic construct
SEQUENCE: 141
ccagcgggga ggtcaatgct                                                20

SEQ ID NO: 142           moltype = RNA  length = 20
FEATURE                  Location/Qualifiers
misc_feature             1..20
                         note = suppression oligo
source                   1..20
                         mol_type = other RNA
                         organism = synthetic construct
SEQUENCE: 142
cccagcattg acctccccgc                                                20

SEQ ID NO: 143           moltype = RNA  length = 20
FEATURE                  Location/Qualifiers
misc_feature             1..20
                         note = suppression oligo
source                   1..20
                         mol_type = other RNA
                         organism = synthetic construct
SEQUENCE: 143
```
cgcgctcgtg tacccggaca                                                    20

SEQ ID NO: 144         moltype = RNA   length = 20
FEATURE                Location/Qualifiers
misc_feature           1..20
                       note = suppression oligo
source                 1..20
                       mol_type = other RNA
                       organism = synthetic construct
SEQUENCE: 144
ctcccggcgc aggtcgaaca                                                    20

SEQ ID NO: 145         moltype = RNA   length = 20
FEATURE                Location/Qualifiers
misc_feature           1..20
                       note = suppression oligo
source                 1..20
                       mol_type = other RNA
                       organism = synthetic construct
SEQUENCE: 145
gtgtacccgg acacggtgcc                                                    20

SEQ ID NO: 146         moltype = RNA   length = 20
FEATURE                Location/Qualifiers
misc_feature           1..20
                       note = suppression oligo
source                 1..20
                       mol_type = other RNA
                       organism = synthetic construct
SEQUENCE: 146
tgcagggaag ctgtccgggc                                                    20

SEQ ID NO: 147         moltype = RNA   length = 20
FEATURE                Location/Qualifiers
misc_feature           1..20
                       note = suppression oligo
source                 1..20
                       mol_type = other RNA
                       organism = synthetic construct
SEQUENCE: 147
ttcttccagg tgtgcgggca                                                    20

SEQ ID NO: 148         moltype = RNA   length = 20
FEATURE                Location/Qualifiers
misc_feature           1..20
                       note = suppression oligo
source                 1..20
                       mol_type = other RNA
                       organism = synthetic construct
SEQUENCE: 148
agatccccgc gccattcctg                                                    20

SEQ ID NO: 149         moltype = RNA   length = 20
FEATURE                Location/Qualifiers
misc_feature           1..20
                       note = suppression oligo
source                 1..20
                       mol_type = other RNA
                       organism = synthetic construct
SEQUENCE: 149
atgcagggaa gctgtccggg                                                    20

SEQ ID NO: 150         moltype = RNA   length = 20
FEATURE                Location/Qualifiers
misc_feature           1..20
                       note = suppression oligo
source                 1..20
                       mol_type = other RNA
                       organism = synthetic construct
SEQUENCE: 150
attcctgtgg ccgcaggaag                                                    20

SEQ ID NO: 151         moltype = RNA   length = 20
FEATURE                Location/Qualifiers
misc_feature           1..20
                       note = suppression oligo
source                 1..20
                       mol_type = other RNA
                       organism = synthetic construct

```
SEQUENCE: 151
cagcggggag gtcaatgctg                                               20

SEQ ID NO: 152          moltype = RNA  length = 20
FEATURE                 Location/Qualifiers
misc_feature            1..20
                        note = suppression oligo
source                  1..20
                        mol_type = other RNA
                        organism = synthetic construct
SEQUENCE: 152
caggaatggc gcgggatct                                                20

SEQ ID NO: 153          moltype = RNA  length = 20
FEATURE                 Location/Qualifiers
misc_feature            1..20
                        note = suppression oligo
source                  1..20
                        mol_type = other RNA
                        organism = synthetic construct
SEQUENCE: 153
gactacttcg tcggcaccct                                               20

SEQ ID NO: 154          moltype = RNA  length = 20
FEATURE                 Location/Qualifiers
misc_feature            1..20
                        note = suppression oligo
source                  1..20
                        mol_type = other RNA
                        organism = synthetic construct
SEQUENCE: 154
gccaggattt cgagccaatg                                               20

SEQ ID NO: 155          moltype = RNA  length = 20
FEATURE                 Location/Qualifiers
misc_feature            1..20
                        note = suppression oligo
source                  1..20
                        mol_type = other RNA
                        organism = synthetic construct
SEQUENCE: 155
ggaacatttg gagggaggcg                                               20

SEQ ID NO: 156          moltype = RNA  length = 20
FEATURE                 Location/Qualifiers
misc_feature            1..20
                        note = suppression oligo
source                  1..20
                        mol_type = other RNA
                        organism = synthetic construct
SEQUENCE: 156
gggaggtcaa tgctggggct                                               20

SEQ ID NO: 157          moltype = RNA  length = 20
FEATURE                 Location/Qualifiers
misc_feature            1..20
                        note = suppression oligo
source                  1..20
                        mol_type = other RNA
                        organism = synthetic construct
SEQUENCE: 157
ttggctcgaa atcctggccg                                               20

SEQ ID NO: 158          moltype = RNA  length = 20
FEATURE                 Location/Qualifiers
misc_feature            1..20
                        note = suppression oligo
source                  1..20
                        mol_type = other RNA
                        organism = synthetic construct
SEQUENCE: 158
acgggttctt ccaggtgtgc                                               20

SEQ ID NO: 159          moltype = RNA  length = 20
FEATURE                 Location/Qualifiers
misc_feature            1..20
                        note = suppression oligo
source                  1..20
                        mol_type = other RNA
```

```
                        organism = synthetic construct
SEQUENCE: 159
cacgggttct tccaggtgtg                                                   20

SEQ ID NO: 160          moltype = RNA   length = 20
FEATURE                 Location/Qualifiers
misc_feature            1..20
                        note = suppression oligo
source                  1..20
                        mol_type = other RNA
                        organism = synthetic construct
SEQUENCE: 160
cattgacctc cccgctggca                                                   20

SEQ ID NO: 161          moltype = RNA   length = 20
FEATURE                 Location/Qualifiers
misc_feature            1..20
                        note = suppression oligo
source                  1..20
                        mol_type = other RNA
                        organism = synthetic construct
SEQUENCE: 161
ccagcgggga ggtcaatgct                                                   20

SEQ ID NO: 162          moltype = RNA   length = 20
FEATURE                 Location/Qualifiers
misc_feature            1..20
                        note = suppression oligo
source                  1..20
                        mol_type = other RNA
                        organism = synthetic construct
SEQUENCE: 162
cccagcattg acctccccgc                                                   20

SEQ ID NO: 163          moltype = RNA   length = 20
FEATURE                 Location/Qualifiers
misc_feature            1..20
                        note = suppression oligo
source                  1..20
                        mol_type = other RNA
                        organism = synthetic construct
SEQUENCE: 163
cgcgctcgtg tacccggaca                                                   20

SEQ ID NO: 164          moltype = RNA   length = 20
FEATURE                 Location/Qualifiers
misc_feature            1..20
                        note = suppression oligo
source                  1..20
                        mol_type = other RNA
                        organism = synthetic construct
SEQUENCE: 164
ctcccggcgc aggtcgaaca                                                   20

SEQ ID NO: 165          moltype = RNA   length = 20
FEATURE                 Location/Qualifiers
misc_feature            1..20
                        note = suppression oligo
source                  1..20
                        mol_type = other RNA
                        organism = synthetic construct
SEQUENCE: 165
gtgtacccgg acacggtgcc                                                   20

SEQ ID NO: 166          moltype = RNA   length = 20
FEATURE                 Location/Qualifiers
misc_feature            1..20
                        note = suppression oligo
source                  1..20
                        mol_type = other RNA
                        organism = synthetic construct
SEQUENCE: 166
tgcagggaag ctgtccgggc                                                   20

SEQ ID NO: 167          moltype = RNA   length = 20
FEATURE                 Location/Qualifiers
misc_feature            1..20
                        note = suppression oligo
source                  1..20
```

```
                           mol_type = other RNA
                           organism = synthetic construct
SEQUENCE: 167
ttcttccagg tgtgcgggca                                                  20

SEQ ID NO: 168             moltype = AA   length = 358
FEATURE                    Location/Qualifiers
source                     1..358
                           mol_type = protein
                           organism = Physcomitrella patens
SEQUENCE: 168
MPKPCDACHV SSAAVFCRAD AAYLCVGCDG KVHGANKLAS RHERVWMCEV CEVAPAVVTC       60
KADAASLCVA CDTDIHSANP LAQRHERVPV TPLFESASPL RGPDFCVLVS ENGCHDLLKG      120
CEDASVVEAV SWLLPHPKIS TNSIIRGSAA ADEMGSSPFH DRPFSPKPKK QKVELPADIF      180
SDVDPFLDLD DATVTGIQPD SLVPVHMPEC SEDTDSLAHS MDPSFTKFPL SAKSGYSYGT      240
STLTQSISCS SLDAAVVPDS SLSDISTPYL DSQSSQDMSA RLPHQTGGPI DTVDREARVL      300
RYKEKRQKRK FEKTIRYASR KAYAESRPRI KGRFAKRTDS DMEQFGSVDS SFGVVPSF        358

SEQ ID NO: 169             moltype = DNA   length = 1077
FEATURE                    Location/Qualifiers
source                     1..1077
                           mol_type = unassigned DNA
                           organism = Physcomitrella patens
SEQUENCE: 169
atgccgaagc cttgtgatgc atgccatgtt ccagcgcgg cggtgttctg ccagcggac         60
gctgcctacc tgtgcgtagg ctgcgatggg aaggtccacg gggcaacaa actagcgtct      120
cgacacgagc gcgtgtggat gtgcgaagtg tgcgaggttg ctccagccgt ggtgacctgc     180
aaggcggatg cggcttctct ctgtgtggcc tgtgacacag acatccactc cgccaacccg     240
ctagcgcagc gtcacgagag agtgccggtg acacctctgt tcgagagtgc gagtcctttg     300
cgtggggcag atttctgcgt gttggtgtca gagaatggcc atgatct gctgaagggc        360
tgtgaggacg cctcggttgt ggaagctgtc tcgtggcttc ttccgcaccc taagatctg     420
accaactcta ttatcagagg cagcgctgca gccgacgaga tgggttcgtc gccttccac     480
gaccggcccc ttagtcccaa gcccaagaaa cagaaggttg aattgccgc ggacatattc      540
tctgatgtgg acccttttcct agacttggac gatgcaaccg ttaccggaat tcaacccgac    600
agcttggtac cagtccatat gccagaatgc tccgaggaca cggattcgct tgctcactcc    660
atggaccctt cgtttactaa atttcctctc tcggcgaaga gcggttacag ctatggcaca    720
tctacccctta ctcagagcat ttcttgttcg tctctagatg ccgccgttgt tccagactcc    780
agtctcagcg acatttccac ccctaccta gactcacaaa gctcccaaga tatgtcagct     840
cgcctgccac accagactgg aggtcccatt gacaccgtcg accgtgaagc tcgcgtgttg    900
cgctacaagg agaagaggca gaagcgcaag tttgagaaaa caattcgcta tgcatcaagg     960
aaggcatatg ctgagagccg gccgaggatc aaaggaaggt tcgctaagag aactgattcc   1020
gacatggagc agtttggctc agtggactca agtttcggag tggttccaag ttttag       1077

SEQ ID NO: 170             moltype = DNA   length = 757
FEATURE                    Location/Qualifiers
source                     1..757
                           mol_type = unassigned DNA
                           organism = Oryza sativa
SEQUENCE: 170
ctcgaggtca ttcatatgct tgagaagaga gtcgggatag tccaaaataa aacaaaggta      60
agattacctg gtcaaaagtg aaaacatcag ttaaaaggtg gtataaagta aaatatcggt     120
aataaaaggt ggcccaaagt gaaatttact cttttctact attataaaaa ttgaggatgt     180
ttttgtcggt actttgatac gtcattttg tatgaattgg ttttaagtt tattcgcttt       240
tggaaatgca tatctgtatt tgagtcgggt tttaagttcg tttgcttttg taaatacaga     300
gggatttgta taagaaatat cttagaaaa acccatatgc taatttgaca taattttga      360
gaaaaatata tattcaggcg aattctcaca atgaacaata ataagattaa aatagctttc    420
ccccgttgca gcgcatgggt attttttcta gtaaaaataa aagataaact tagactcaaa    480
acatttacaa aaacaacccc taagttcct aaagcccaaa gtgctatcca cgatccctag    540
caagcccagc ccaacccaac ccaacccaac ccaccccagt ccagccaact ggacaatagt    600
ctccacaccc ccccactatc accgtgagtt gtccgcagc accgcacgtc tcgcagccaa    660
aaaaaaaag aaaactaaaaa aagaaaaga aaaacagca ggtgggtccg ggtcgtgggg      720
gccggaaacg cgaggaggat cgcgagccag cgacgag                              757

SEQ ID NO: 171             moltype = DNA   length = 333
FEATURE                    Location/Qualifiers
source                     1..333
                           mol_type = unassigned DNA
                           organism = Cauliflower mosaic virus
SEQUENCE: 171
catcgttgaa gatgcctctg ccgacagtgg tcccaaagat ggaccccac ccacgaggag       60
catcgtggaa aaagaagacg ttccaaccac gtcttcaaag caagtggatt gatgtgatat     120
ctccactgac gtaagggatg acgcacaatc ccactatcct tcgaggcctc atcgttgaag    180
atgcctctgc cgacagtggt cccaaagatg accccacc cacgaggagc atcgtggaaa      240
aagaagacgt tccaaccacg tcttcaaagc aagtggattg atgtgatatc tccactgacg    300
taagggatga cgcacaatcc cactatcctt cga                                  333

SEQ ID NO: 172             moltype = DNA   length = 80
FEATURE                    Location/Qualifiers
source                     1..80
```

```
                            mol_type = unassigned DNA
                            organism = Oryza sativa
SEQUENCE: 172
ccctccctcc gcttccaaag aaacgccccc catcgccact atatacatac ccccccctct    60
cctcccatcc ccccaaccct                                                80

SEQ ID NO: 173          moltype = DNA   length = 61
FEATURE                 Location/Qualifiers
source                  1..61
                        mol_type = unassigned DNA
                        organism = Triticum aestivum
SEQUENCE: 173
aaccatcttc cacacactca agccacacta ttggagaaca cacagggaca acacaccata    60
a                                                                    61

SEQ ID NO: 174          moltype = DNA   length = 480
FEATURE                 Location/Qualifiers
source                  1..480
                        mol_type = unassigned DNA
                        organism = Oryza sativa
SEQUENCE: 174
ccgccgccgc cggtaaccac cccgcccctc tcctctttct ttctccgttt ttttttccgt    60
ctcggtctcg atctttggcc ttggtagttt gggtgggcga gaggcggctt cgtgcgcgcc   120
cagatcggtg cgcggggagg gcgggatctc gcggctgggg ctctcgccgg cgtggatccg   180
gcccggatct cgcggggaat ggggctctcg gatgtagatc tgcgatccgc cgttgttggg   240
ggagatgatg gggggtttaa aatttccgcc gtgctaaaca agatcaggaa gagggaaaa    300
gggcactatg gtttatattt ttatatattt ctgctgcttc gtcaggctta gatgtgctag   360
atctttcttt cttctttttg tgggtagaat ttgaatccct cagcattgtt catcggtagt   420
ttttcttttc atgatttgtg acaaatgcag cctcgtgcgg agctttttg taggtagaag    480

SEQ ID NO: 175          moltype = DNA   length = 943
FEATURE                 Location/Qualifiers
source                  1..943
                        mol_type = unassigned DNA
                        organism = Solanum tuberosum
SEQUENCE: 175
accctgcaat gtgaccctag acttgtccat cttctggatt ggccaactta attaatgtat    60
gaaataaaag gatgcacaca tagtgacatg ctaatcacta taatgtgggc atcaaagttg   120
tgtgttatgt gtaattacta attatctgaa taagagaaag agatcatcca tatttcttat   180
cctaaatgaa tgtcacgtgt ctttataatt ctttgatgaa ccagatgcat tttattaacc   240
aattccatat acatataaat attaatcata tataattaat atcaattggg ttagcaaaac   300
aaatctagtc taggtgtgtt ttgctaatta ttgggggata gtgcaaaaag aaatctacgt   360
tctcaataat tcagatagaa aacttaataa agtgagataa tttacataga ttgcttttat   420
cctttgatat atgtgaaacc atgcatgata taaggaaaat agatagaaaa ataattttt    480
acatcgttga atatgtaaac aatttaattc aagaagctag gaatataaat attgaggagt   540
ttatgattat tattattatt ttgatgttca atgaagtttt ttaaatttc atatgaagta    600
tacaaaaatt cttcatagat ttttgtttct atgccgtagt tatctttaat atatttgtgg   660
ttgaagaaat ttattgctag aaacgaatgg attgtcaatt ttttttaaa gcaaatatat    720
atgaaattat actgtatatt attttagtca tgattaaat gtggccttaa ttgaatcatc    780
tttctcattc attttttcaa aagcatatca ggatgattga tatttatcta tttaaaaat    840
taatttaagg gttcaaatta aatttaactt aaaagtgtcc taaccgtagt taaaggttta   900
ctttaaaaaa atactatgaa aaatctaatc ttctatgaat cga                     943

SEQ ID NO: 176          moltype = AA    length = 337
FEATURE                 Location/Qualifiers
source                  1..337
                        mol_type = protein
                        organism = Brassica juncea
SEQUENCE: 176
MLKQESNWAQ TCDTCRSAAC TVYCRPDSAY LCTSCDAQIH EANRLASRHE RVRVCQSCER    60
APAAFFCKAD AASLCTACDS QIHSANPLAR RHQRVPILPI SGSMVTNHSS ETTEAEDIVV   120
VGQEEEEDAE AASWLLPTSV KNCGDNNNNN NNSQDNRFSV GEEYLDLVDY SKYQQDYNVP   180
QRRSYVADGV VPLQVEVSKS LSHMHHEQHN FQFGFTNVSS EASPIHMVSL VPESSLSETT   240
VSNPRSPKAA TEELPEAPVQ MLSPMERKAR VMRYREKKKT RKFEKTIRYA SRKEYAEKRP   300
RIKGRFAKRN EVDAEEEADKA FSSMVMFDTG YGIEPSF                          337

SEQ ID NO: 177          moltype = AA    length = 345
FEATURE                 Location/Qualifiers
source                  1..345
                        mol_type = protein
                        note = Oryza sativa Japonica Group
                        organism = Oryza sativa
SEQUENCE: 177
MASAAAATGA ALGARTARAC DGCMRRRARW HCPADDAFLC QACDSASVHSA NPLARRHHRV    60
RLPSASSSPA SSPRSAAAPR AGSDDPDAPA WLHGLKRRPR TPRTKPGGGG KHDASAATVA   120
AAAASAVPDL EAEESGIVGD TDHDVGEEDD EDLLYRVPGF DDLGFLDDEK PHVKLDLDMD   180
MDFASISPAP APEREERKRK RPEMILKLDY EGVIDSWARD GASPWFHGER PRFDPSESWP   240
DFPAGSRGGL GAAVTAVTGG EREARVSRYR EKRRTRLFAK KIRYEVRKLN AEKRPRMKGR   300
FVKRAAALPP LPLPRHQHPP PPPPRALPPV PMMLAPRGAH GRYRF                   345
```

```
SEQ ID NO: 178          moltype = AA   length = 410
FEATURE                 Location/Qualifiers
source                  1..410
                        mol_type = protein
                        organism = Picea abies
SEQUENCE: 178
MSMPKLCDVC QVSNSVLYCR AHTAQLCLVC DVKIHGGSKA SLCHERVWVC EVCEQAPAVV    60
TCKADAAALC VSCDTDIHSA NPLASRHERA PVIPFYECPN MPNNNTATNA NNDNLDCNVL   120
LNEDGGGDDP LKHDYVDDDY DDYDDDENDH NNLLNHQEDD NDAEICCAEE AATASWLIPE   180
ANRNNLTNIN GGNSEGEDKM VKDKLKFKAY MQSIDFLQDV ENYVDLEYLG TTTTITTPTT   240
PTAHMGADSM VPVHTPEVIE HSSTKVSVET ARSLDVDAAS KCNYVYRTTS LNHCVSSSSI   300
DVGIVPDSNT TTDISTPYHD PRGVFEIPPR VVHPGGHVEV MGREARVLRY REKRKNRRFE   360
KTIRYASRKA YAETRPRIKG RFAKRTEVEV EQIYSSSLLP DQGYGVVPSY              410

SEQ ID NO: 179          moltype = AA   length = 410
FEATURE                 Location/Qualifiers
VARIANT                 152
                        note = X can be any naturally occurring amino acid
VARIANT                 155
                        note = X can be any naturally occurring amino acid
source                  1..410
                        mol_type = protein
                        organism = Picea abies
SEQUENCE: 179
MSMPKLCDVC QVSNSVLYCR AHTAQLCLVC DVKIHGGSKA SLCHERVWVC EVCEQAPAVV    60
TCKADAAALC VSCDTDIHSA NPLASRHERA PVIPFYECPN MPNNNTATNA NNDNLDCNVL   120
LNEDGGGDDP LKHDYVDDDY DDYDDDENDH NXLLXHQEED NDAEICCAEE AATASWLIPE   180
ANRNNLTNIN GGNSEGEDKM VKDKLKFKAY MQSIDFLQDV ENYVDLEYLG TTTTITTPTT   240
PTAHMGADSM VPVHTPEVIE HSSTKVSVET ARSLDVDAAS KCNYVYRTTS LNHCVSSSSI   300
DVGIVPDSNT TTDISTPYHD PRGVFEIPPR VVHPGGHVEV MGREARVLRY REKRKNRRFE   360
KTIRYASRKA YAETRPRIKG RFAKRTEVEV EQIYSSSLLP DQGYGVVPSY              410

SEQ ID NO: 180          moltype = AA   length = 410
FEATURE                 Location/Qualifiers
VARIANT                 245
                        note = X can be any naturally occurring amino acid
VARIANT                 389
                        note = X can be any naturally occurring amino acid
source                  1..410
                        mol_type = protein
                        organism = Picea abies
SEQUENCE: 180
MSMPKLCDVC QVSNSVLYCR AHTAQLCLVC DVKIHGGSKA SLCHERVWVC EVCEQAPAVV    60
TCKADAAALC VACDTDIHSA NPLASRHERA PVIPFYECPN MPNNNTATNA NNDNLDCNVL   120
LNEDGGGDDP LKHDYVDDDY DDYDDDENDH NNLLNHQEDD NDAEICCAEE AATASWLIPE   180
ANRNNLTNIN GGNSEGEDKM VKDKLKFKAY MQSIDFLQDV ENYVDLEYLG TTTTITTPTT   240
PTAHXGADSM VPVHTPEVIE HSSTKVSVET ARSLDVDAAS KCNYVYRTTS LNHCVSSSSI   300
DVGIVPDSNT TTDISTPYHD PRGVFEIPPR VVHPGGHVEV MGREARVLRY REKRKNRRFE   360
KTIRYASRKA YAETRPRIKG RFAKRTEVXV EQIYSSSLLP DQGYGVVPSY              410

SEQ ID NO: 181          moltype = AA   length = 410
FEATURE                 Location/Qualifiers
source                  1..410
                        mol_type = protein
                        organism = Picea abies
SEQUENCE: 181
MSMPKLCDVC QVSNSVLYCR AHTAQLCLVC DVKIHGGSKA SLCHERVWVC EVCEQAPAVV    60
TCKADAAALC VACDTDIHSA NPLASRHERA PVIPFYECPN MPNNNTATNA NNDNLDCNVL   120
LNEDGGGDDP LKHDYVDDDY DDYDDDENDH NNLLNHQEDD NDAEICCAEE AATASWLIPE   180
ANRNNLTNIN GGNSEGEDKM VKDKLKFKAY MQSIDFLQDV ENYVDLEYLG TTTTITTPTT   240
PTAHMGADSM VPVHTPEVIE HSSTKVSVET ARSLDVDAAS KCNYVYRTTS LNHCVSSSSI   300
DVGIVPDSNT TTDISTPYHD PRGVFEIPPR VVHPGGHVEV MGREARVLRY REKRKNRRFE   360
KTIRYASRKA YAETRPRIKG RFAKRTEVEV EQIYSSSLLP DQGYGVVPSY              410

SEQ ID NO: 182          moltype = AA   length = 410
FEATURE                 Location/Qualifiers
source                  1..410
                        mol_type = protein
                        organism = Picea abies
SEQUENCE: 182
MSMPKLCDVC QVSNSVLYCR AHTAQLCLVC DVKIHGGSKA SLCHERVWVC EVCEQAPAVV    60
TCKADAAALC VACDTDIHSA NPLASRHERA PVIPFYECPN MPNNNTATNA NNDNLDCNVL   120
LNEDGGGDDP LKHDYVDDDY DDYDDDENDH NNLLNHQEED NDAEICCAEE AATASWLIPE   180
ANRNNLTNIN GGNSEGEDKM VKDKLKFKAY MQSIDFLQDV ENYVDLEYLG TTTTITTPTT   240
PTAHMGADSM VPVHTPEVIE HSSTKVSVET ARSLDVDAAS KCNYVYRTTS LNHCVSSSSI   300
DVGIVPDSNT TTDISTPYHD PRGVFEIPPR VVHPGGHVEV MGREARVLRY REKRKNRRFE   360
KTIRYASRKA YAETRPRIKG RFAKRTEVEV EQIYSSSLLP DQGYGVVPSY              410
```

```
SEQ ID NO: 183            moltype = AA  length = 410
FEATURE                   Location/Qualifiers
VARIANT                   151..152
                          note = X can be any naturally occurring amino acid
source                    1..410
                          mol_type = protein
                          organism = Picea abies
SEQUENCE: 183
MSMPKLCDVC QVSNSVLYCR AHTAQLCLVC DVKIHGGSKA SLCHERVWVC EVCEQAPAVV    60
TCKADAAALC VACDTDIHSA NPLASRHERA PVIPFYECPN MPNNNTATNA NNDNLDCNVL   120
LNEDGGGDDP LKHDYVDDDY DDYDDDENDH XXLLNHQEED NDAEICCAEE AATASWLIPE   180
ANRNNLTNIN GGNSEGEDKM VKDKLKFKAY MQSIDFLQDV ENYVDLEYLG TTTTITTPTT   240
PTAHMGADSM VPVHTPEVIE HSSTKVSVET ARSLDVDAAS KCNYVYRTTS LNHCVSSSSI   300
DVGIVPDSNT TTDISTPYHD PRGVFEIPPR VVHPGGHVEV MGREARVLRY REKRKNRRFE   360
KTIRYASRKA YAETRPRIKG RFAKRTEVEV EQIYSSSLLP DQGYGVVPSY              410

SEQ ID NO: 184            moltype = AA  length = 410
FEATURE                   Location/Qualifiers
VARIANT                   293
                          note = X can be any naturally occurring amino acid
source                    1..410
                          mol_type = protein
                          organism = Picea abies
SEQUENCE: 184
MSMPKLCDVC QVSNSVLYCR AHTAQLCLVC DVKIHGGSKA SLCHERVWVC EVCEQAPAVV    60
TCKADAAALC VACDTDIHSA NPLASRHERA PVIPFYECPN MPNNNTATNA NNDNLDCNVL   120
LNEDGGGDDP LKHDYVDDDY DDYDDDENDH NNLLNHQEDD NDAEICCAEE AATASWLIPE   180
ANRNNLTNIN GGNSEGEDKM VKDKLKFKAY MQSIDFLQDV ENYVDLEYLG TTTTITTPTT   240
PTAHMGADSM VPVHTPEVIE HSSTKVSVET ARSLDVDAAS KCNYVYRTTS LNXCVSSSSI   300
DVGIVPDSNT TTDISTPYHD PRGVFEIPPR VVHPGGHVEV MGREARVLRY REKRKNRRFE   360
KTIRYASRKA YAETRPRIKG RFAKRTEVEV EQIYSSSLLP DQGYGVVPSY              410

SEQ ID NO: 185            moltype = AA  length = 410
FEATURE                   Location/Qualifiers
VARIANT                   161
                          note = X can be any naturally occurring amino acid
VARIANT                   177
                          note = X can be any naturally occurring amino acid
source                    1..410
                          mol_type = protein
                          organism = Picea abies
SEQUENCE: 185
MSMPKLCDVC QVSNSVLYCR AHTAQLCLVC DVKIHGGSKA SLCHERVWVC EVCEQAPAVV    60
TCKADAAALC VSCDTDIHSA NPLASRHERA PVIPFYECPN MPNNNTATNA NNDNLDCNVL   120
LNEDGGGDDP LKHDYVDDDY DDYDDDENDH NNLLNHQEED XDAEICCAEE AATASWXIPE   180
ANRNNLTNIN GGNSEGEDKM VKDKLKFKAY MQSIDFLQDV ENYVDLEYLG TTTTITTPTT   240
PTAHMGADSM VPVHTPEVIE HSSTKVSVET ARSLDVDAAS KCNYVYRTTS LNHCVSSSSI   300
DVGIVPDSNT TTDISTPYHD PRGVFEIPPR VVHPGGHVEV MGREARVLRY REKRKNRRFE   360
KTIRYASRKA YAETRPRIKG RFAKRTEVEV EQIYSSSLLP DQGYGVVPSY              410

SEQ ID NO: 186            moltype = AA  length = 410
FEATURE                   Location/Qualifiers
source                    1..410
                          mol_type = protein
                          organism = Picea abies
SEQUENCE: 186
MSMPKLCDVC QVSNSVLYCR AHTAQLCLVC DVKIHGGSKA SLCHERVWVC EVCEQAPAVV    60
TCKADAAALC VSCDTDIHSA NPLASRHERA PVIPFYECPN MPNNNTATNA NNDNLDCNVL   120
LNEDGGGDDP LKHDYVDDDY DDYDDDENDH NNLLNHQEED NDAEICCAEE AATASWLIPE   180
ANRNNLTNIN GGNSEGEDKM VKDKLKFKAY MQSIDFLQDV ENYVDLEYLG TTTTITTPTT   240
PTAHMGADSM VPVHTPEVIE HSSTKVSVET ARSLDVDAAS KCNYVYRTTS LNHCVSSSSI   300
DVGIVPDSNT TTDISTPYHD PRGVFEIPPR VVHPGGHVEV MGREARVLRY REKRKNRRFE   360
KTIRYASRKA YAETRPRIKG RFAKRTEVEV EQIYSSSLLP DQGYGVVPSY              410

SEQ ID NO: 187            moltype = AA  length = 410
FEATURE                   Location/Qualifiers
VARIANT                   120
                          note = X can be any naturally occurring amino acid
source                    1..410
                          mol_type = protein
                          organism = Picea abies
SEQUENCE: 187
MSMPKLCDVC QVSNSVLYCR AHTAQLCLVC DVKIHGGSKA SLCHERVWVC EVCEQAPAVV    60
TCKADAAALC VACDTDIHSA NPLASRHERA PVIPFYECPN MPNNNTATNA NNDNLDCNVX   120
LNEDGGGDDP LKHDYVDDDY DDYDDDENDH NNLLNHQEDD NDAEICCAEE AATASWLIPE   180
ANRNNLTNIN GGNSEGEDKM VKDKLKFKAY MQSIDFLQDV ENYVDLEYLG TTTTITTPTT   240
PTAHMGADSM VPVHTPEVIE HSSTKVSVET ARSLDVDAAS KCNYVYRTTS LNHCVSSSSI   300
DVGIVPDSNT TTDISTPYHD PRGVFEIPPR VVHPGGHVEV MGREARVLRY REKRKNRRFE   360
KTIRYASRKA YAETRPRIKG RFAKRTEVEV EQIYSSSLLP DQGYGVVPSY              410
```

```
SEQ ID NO: 188          moltype = AA  length = 410
FEATURE                 Location/Qualifiers
VARIANT                 118
                        note = X can be any naturally occurring amino acid
VARIANT                 159
                        note = X can be any naturally occurring amino acid
source                  1..410
                        mol_type = protein
                        organism = Picea abies
SEQUENCE: 188
MSMPKLCDVC QVSNSVLYCR AHTAQLCLVC DVKIHGGSKA SLCHERVWVC EVCEQAPAVV    60
TCKADAAALC VSCDTDIHSA NPLASRHERA PVIPFYECPN MPNNNTATNA NNDNLDCXVL   120
LNEDGGGDDP LKHDYVDDDY DDYDDDENDH NNLLNHQEXD NDAEICCAEE AATASWLIPE   180
ANRNNLTNIN GGNSEGEDKM VKDKLKFKAY MQSIDFLQDV ENYVDLEYLG TTTTITTPTT   240
PTAHMGADSM VPVHTPEVIE HSSTKVSVET ARSLDVDAAS KCNYVYRTTS LNHCVSSSSI   300
DVGIVPDSNT TTDISTPYHD PRGVFEIPPR VVHPGGHVEV MGREARVLRY REKRKNRRFE   360
KTIRYASRKA YAETRPRIKG RFAKRTEVEV EQIYSSSLLP DQGYGVVPSY             410

SEQ ID NO: 189          moltype = AA  length = 410
FEATURE                 Location/Qualifiers
VARIANT                 179
                        note = X can be any naturally occurring amino acid
VARIANT                 193
                        note = X can be any naturally occurring amino acid
source                  1..410
                        mol_type = protein
                        organism = Picea abies
SEQUENCE: 189
MSMPKLCDVC QVSNSVLYCR AHTAQLCLVC DVKIHGGSKA SLCHERVWVC EVCEQAPAVV    60
TCKADAAALC VSCDTDIHSA NPLASRHERA PVIPFYECPN MPNNNTATNA NNDNLDCNVL   120
LNEDGGGDDP LKHDYVDDDY DDYDDDENDH NNLLNHQEDD NDAEICCAEE AATASWLIXE   180
ANRNNLTNIN GGXSEGEDKM VKDKLKFKAY MQSIDFLQDV ENYVDLEYLG TTTTITTPTT   240
PTAHMGADSM VPVHTPEVIE HSSTKVSVET ARSLDVDAAS KCNYVYRTTS LNHCVSSSSI   300
DVGIVPDSNT TTDISTPYHD PRGVFEIPPR VVHPGGHVEV MGREARVLRY REKRKNRRFE   360
KTIRYASRKA YAETRPRIKG RFAKRTEVEV EQIYSSSLLP DQGYGVVPSY             410

SEQ ID NO: 190          moltype = AA  length = 410
FEATURE                 Location/Qualifiers
VARIANT                 182..183
                        note = X can be any naturally occurring amino acid
VARIANT                 208
                        note = X can be any naturally occurring amino acid
VARIANT                 226
                        note = X can be any naturally occurring amino acid
VARIANT                 233
                        note = X can be any naturally occurring amino acid
VARIANT                 235
                        note = X can be any naturally occurring amino acid
VARIANT                 243
                        note = X can be any naturally occurring amino acid
VARIANT                 248
                        note = X can be any naturally occurring amino acid
VARIANT                 282
                        note = X can be any naturally occurring amino acid
source                  1..410
                        mol_type = protein
                        organism = Picea abies
SEQUENCE: 190
MSMPKLCDVC QVSNSVLYCR AHTAQLCLVC DVKIHGGSKA SLCHERVWVC EVCEQAPAVV    60
TCKADAAALC VACDTDIHSA NPLASRHERA PVIPFYECPN MPNNNTATNA NNDNLDCNVL   120
LNEDGGGDDP LKHDYVDDDY DDYDDDENDH NNLLNHQEDD NDAEICCAEE AATASWLIPE   180
AXXNNLTNIN GGNSEGEDKM VKDKLKFXAY MQSIDFLQDV ENYVDXEYLG TTXTXTTPTT   240
PTXHMGAXSM VPVHTPEVIE HSSTKVSVET ARSLDVDAAS KXNYVYRTTS LNHCVSSSSI   300
DVGIVPDSNT TTDISTPYHD PRGVFEIPPR VVHPGGHVEV MGREARVLRY REKRKNRRFE   360
KTIRYASRKA YAETRPRIKG RFAKRTEVEV EQIYSSSLLP DQGYGVVPSY             410

SEQ ID NO: 191          moltype = AA  length = 417
FEATURE                 Location/Qualifiers
source                  1..417
                        mol_type = protein
                        organism = Ipomoea nil
SEQUENCE: 191
MLKEESCEVL DLDVTIGSSS GSRSGNKQNW ARVCDICRSA ACSVYCRADL AYLCGGCDAR    60
VHGANTVAGR HERVLVCEAC ESAPATVICK ADAASLCAAC DSDIHSANPL ARRHHRVPIL   120
PISGTLYGPP TSNPCRESSM MVGLTGDAAE EDNGFLTQDA EETTMDEDED EAASWLLLNP   180
NPNPNPNPVK SNNSTNMCKG GNNNNNEMSC AVEAVDAYLD LAEFSSCHNN LFEDKYSINQ   240
QQNYSVPQRN MSYRGDSIVP NHGKNQFHYT QGLQQHNHHA IFNCKEWNMR ILTRDMVSIS   300
SMDVGVVPES TLSDTSISHS RASKGTIDLF SGPPIQMPPQ LQLSQMDREA RVLRYREKKK   360
```

```
TRKFEKTIRY ASRKAYAETR PRIKGRFAKR TDVDTEVDQI FYAPLMAESG YGIVPSF      417

SEQ ID NO: 192           moltype = AA   length = 380
FEATURE                  Location/Qualifiers
source                   1..380
                         mol_type = protein
                         organism = Brassica nigra
SEQUENCE: 192
MLKQESNYNI SNRENNRGAR ACDTCRSTIC TVYCHADSAY LCNSCDAEVH SANRVASRHK    60
RVPVCESCER APAAFMCEAD DVSLCTACDS EVHSANPLAR RHQRVPVVPI TGNSCSSLAT    120
THHTAVTEPE KRAVLVQDDE EGKEDAKETA SWMFPYSDKG SPNHNNNNNN NNQNNELLFS    180
DDYLDLADYN SSMDYKFTGQ YNQPQHKQDC TVPQTNYGGD RVVPLQLEET RGNVRHKKEK    240
ITYGSSGSQY NYNDSINHNA YNPSMETDFV PEPTARETTV SHQKTPKIHQ LPEPLVQILS    300
PMDREARVLR YREKKKRRKF EKTIRYASRK AYAERRPRIN GRFAKMSETE VEDQEYNTML    360
MYYDTGYGIV PSFYGQNKEY                                                380

SEQ ID NO: 193           moltype = AA   length = 348
FEATURE                  Location/Qualifiers
source                   1..348
                         mol_type = protein
                         organism = Brassica nigra
SEQUENCE: 193
MLKQESNWAQ ACDTCRSAAC TVYCRADSAY LCTSCDAQIH AANRLASRHE RVRVCESCER    60
APAAFFCKAD AASLCTACDS QIHSANPLAR RHQRVPILPI SGCVATNHHS SETTEPENIV    120
VVGQEEEDEA EAASWLLPSS VKNCGDNNNN NNNNNISENN RFSVGEEYLD LVDYSSSIDK    180
RFTGQTMQYQ QDYNVPQRSY VADGVVPLQV GVANGHMMHE KHNFQFGFTN VSSEASPIHM    240
VSLVPESVTS DATVSHPRSP KAGTEELPEA PVQMLSPMER KARVLRYREK KKTRKFEKRI    300
RYASRKEYAE KRPRIKGRFA KRNEVDADHA LSTMVMFDTG YGIVPSFS                 348

SEQ ID NO: 194           moltype = AA   length = 360
FEATURE                  Location/Qualifiers
source                   1..360
                         mol_type = protein
                         organism = Solanum tuberosum
SEQUENCE: 194
MGTENWSLTA KLCDSCKTTP ATVFCRADSA FLCLGCDCKI HAANKLASRH ARVWVCEVCE    60
QAPAVVTCKA DAAALCVTCD RDIHSANPLA RRHERFPVVP FYDSAVAKSD GGGDADADAA    120
DDEKYFDSTS ENPSQPEEEA EAASWILPIP KEGTDQYKSA DYLFNDMDSY LDIDLMSCEQ    180
KPHIIHHQQH QHGHYSSDGV VPVQNNNNET STHLPGPVVD GFPTYEIDFT GSKPYMYNFT    240
SQSISQSVSS SSLDVGVVPD HSAMTDVSNT FVMNSSAAAG TGTDTEAVPN AVSGLDAGAR    300
VMRYRKKRKN IKIEKTIPYA STKAYAETRP KIKGRFAKRT EIEIDLLIDA DASYGVVPSF    360

SEQ ID NO: 195           moltype = AA   length = 407
FEATURE                  Location/Qualifiers
source                   1..407
                         mol_type = protein
                         note = Oryza sativa Japonica Group
                         organism = Oryza sativa
SEQUENCE: 195
MDALCDFCRE QRSMVYCRSD AASLCLSCDR NVHSANALSR RHTRTLLCDR CVGQPAAVRC    60
LEENTSLCQN CDWNGHGAAS SAAGHKRQTI NCYSGCPSSA ELSRIWSFSM DIPTVAAEPN    120
CEEGINMMSI NDNDVNNHCG APEDGRLLDI ASTALMSDLP TGDKFKPLIG SSSGDGMNLL    180
PLNSDQPAEP VSSTTPKAPCV TDKDMFNDGS VYGDFCVDDA DLTFENYEEL FGTSHVQTEQ   240
LFDDAGIDSY FEMKDVPADE SNEQPKPVQP ECSNVASVDS GMSNPAARAD SSHCIPGRQA    300
ISNISLSFSG LTGESSAGYF QDCGVSSMIL MGEPPWHPPG PESSSAGGSR DNALTRYKEK    360
KKRRKFDKKI RYASRKARAD VRKRVKGRFV KAGEAYDYDP LSQTRSY                  407

SEQ ID NO: 196           moltype = AA   length = 407
FEATURE                  Location/Qualifiers
source                   1..407
                         mol_type = protein
                         note = Oryza sativa Japonica Group
                         organism = Oryza sativa
SEQUENCE: 196
MGALCDFCGE QRSMVYCRSD AASLCLSCDR NVHSANALSR RHTRTLLCDR CASQPAMVRC    60
LVENASLCQN CDWNGHSAGS SAAGHKRQTI NCYSGCPSSS ELSKIWTFVS DIPNVAPEPN    120
CEQGISMMSI SDSGVSNQDN AAGDSSLLDI ASATLMSDLG TAGKPKSLIG SSSEAGVNLL    180
PLATDQMAGS VDSTSAKVPY TADQDMFSKD SIYEDFCVDD VDLSFENYEE LFGTSHIQTE    240
QLFDDAGIDS YFESKEIPSG NSDEPKLMQP VTSNAVSADS GMSIPGAKGD SSLCIPVRQA    300
RSSISLSFSG LTGESSAGDY QDCGVSPVLL MGEPPWHPPG PEGSFAGATR DDAITRYKEK    360
KKRRKFDKKI RYASRKARAD VRKRVKGRFV KAGEAYDYDP LCETRSY                  407

SEQ ID NO: 197           moltype = AA   length = 335
FEATURE                  Location/Qualifiers
source                   1..335
                         mol_type = protein
                         note = Oryza sativa Japonica Group
                         organism = Oryza sativa
SEQUENCE: 197
```

```
MLKLEPEFPG LPQRCDSCRS APCAFYCLAD SAALCATCDA DVHSVNPLAR RHRRVPMGVV    60
AAPGAGGAFV VRPAGGVNSS WPIREGRRCD YDDDDADAAG EEDEEATSWL LFDPLKDSSD   120
QGLPPFGDAL VADFLNLGGG AGEKEDASSS KDCSSSHGKS SEGSHEFAVP GEPVPERQGF   180
GAVSMDITDY DASNFRRGYS FGASLGHSVS MSSLENMSTV PDCGVPDITT SYLRSSKSTI   240
DLFTAAAGSP VAAHSIMSPP QFMGAIDREA RVHRYREKRK TRRFEKTIRY ASRKAYAETR   300
PRIKGRFAKR SDTDLEVDQY FSTTADSSCG VVPTF                             335

SEQ ID NO: 198          moltype = AA  length = 335
FEATURE                 Location/Qualifiers
source                  1..335
                        mol_type = protein
                        note = Brassica oleracea var. alboglabra
                        organism = Brassica oleracea
SEQUENCE: 198
MLKQESNWAQ TCDTCRSAAC TVYCRADSAY LCTNCDAQVH AANRLASRHE RVRVCQSCER    60
APAAFFCKAD AASLCTACDS QIHSANPLAR RHQRVPILPI SGSMVTNHSS ETTETEDIVV   120
VGQEEEDEAE AASWLLPSSL KNSGDNNNNN NNNNSENRFS VGDEYVDLVD YNKYQQDYNV   180
PQRSYVADGV VPLQVGVLKS HMHHEEHNFQ FGFTNVSSEA SPIHMVSLVP ESTLSETTVS   240
HPRSPKVATE ELHDAPVQML SPVERKARVM RYREKKKKRK FEKRIRYASR KEYAEKRPRI   300
KGRFAKRNEV DAEEADKAFS SMVMFDTGYG IVPSF                             335

SEQ ID NO: 199          moltype = AA  length = 366
FEATURE                 Location/Qualifiers
source                  1..366
                        mol_type = protein
                        note = Brassica oleracea var. alboglabra
                        organism = Brassica oleracea
SEQUENCE: 199
MFKQESNNIC NRENNRGAPA CDTCGSTICT VYCHADSAYL CNSCDAQVHS ANRVASRHKR    60
VRVCESCERA PAAFMCEADD VSLCTACDLE VHSANPLARR HQRVPVVPIT GNSCSSLATA   120
NHTTVTEPEK RVVLVQEDAK ETASWLFPKN SDNHNNNNNQ NNELLFSDDY LDLADYNSSM   180
DYKFTSQYNQ PRHKQDCIVP EKNYSGDRVV PLQLEETRGN LRNKQQNITY GSSGSQYNNN   240
GSINHNAYNP SMETDFVPEQ TAPDTTVSHP KTHKGKTAQL PEPLIQILSP MDREARVLRY   300
REKKKRRKFE KTIRYASRKA YAERRPRING RFAKMSETEV EDQEYNTMLM YCDTGYGIVP   360
SFYGQK                                                             366

SEQ ID NO: 200          moltype = AA  length = 413
FEATURE                 Location/Qualifiers
source                  1..413
                        mol_type = protein
                        organism = Solanum tuberosum
SEQUENCE: 200
MLKKEKSGGF DRSSNNWARV CDSCHSATCT VYCRADSAYL CAGCDSRIHA ASLMASRHER    60
VWVCEACERA PAAFLCKADA ASLCASCDAV IHSANPLARR HHRVPIMPIP GTLYGPPAVH   120
TVSGGSMMIG GTTGEGTEDD GFLSLTQDAD DTTIDEEDEN EAASWLLLNP PVKNNNKNNI   180
NNNNNNQNNN YGMLFGGEVV DEYLDLAEYG GDSQFNDQYS VNQQQQHYSV PQKSYVEDSV   240
VPVQNGRKS LILYHQPQQQ QQQQQQSHHL NFQLGMEYDN SNTGYGYPAS LSHSVSISSM   300
DVSVVPESAL SETSNSHPRP PKGTIDLFSG PPIQIPPQLT PMDREARVLR YREKKKNRKF   360
EKTIRYASRK AYAETRPRIK GRFAKRTDVK AEVDQMFSTQ LMTDSSYGIV PSF          413

SEQ ID NO: 201          moltype = AA  length = 444
FEATURE                 Location/Qualifiers
source                  1..444
                        mol_type = protein
                        organism = Populus trichocarpa
SEQUENCE: 201
MICIKSSANA VGGKTARACD SCIKKRARWY CAADDAFLCQ ACDSSVHSAN PLARRHERVR    60
LKTASLKSLD LCSKENSVPS WHGGFTRKAR TPRHGKPVSQ SKIAETIRNI PIPLVPEVGS   120
DEISHEDNEE EHLLYRVPIF DPFVADLCAS TTISNEAGAI VPAGGNDGTD QRVADSNGVE   180
SKILIGAIER RDVESLPGFL PSDMDLAEFA ADMESLLGRG LENESFGMEE LGLMDCKEEK   240
EFEVKGPPLW NGKVKVEDEE NASVERKAVR KCYAGIETDM AKDPIFELSF DYNSSATCGE   300
EDEKVGIEEG DLKNTRGEYE DDDGAKRKIL LSLDYEAVMT AWASQGSPWT NGNRPDFDPD   360
ECWPDCMGIC GAQLHHPYGD MISGLGAHPA MVDGGREARV SRYEKRRTR LFSKKIRYEV   420
RKLNAEKRPR MKGRFVKRTT LAGK                                         444

SEQ ID NO: 202          moltype = AA  length = 416
FEATURE                 Location/Qualifiers
source                  1..416
                        mol_type = protein
                        organism = Arabidopsis thaliana
SEQUENCE: 202
MKSLANAVGA KTARACDSCV KRRARWYCAA DDAFLCQSCD SLVHSANPLA RRHERVRLKT    60
ASPAVVKHSN HSSASPPHEV ATWHHGFTRK ARTPRGSGKK NNSSIFHDLV PDISIEDQTD   120
NYELEEEQLIC QVPVLDPLVS EQFLNDVVEP KIEFPMIRSG LMIEEEEDNA ESCLNGFFPT   180
DMELEEFAAD VETLLGRGLD TESYAMEELG LSNSEMFKIE KDEIEEEVEE IKAMSMDIFD   240
DDRKDVDGTV PFELSPDYES SHKTSEEEVM KNSVESSGECV VKVKEEEHKN VLMLRLNYDS   300
VISTWGGQGP PWSSGEPPER DMDISGWPAF SMVENGGEST HQKQYVGGCL PSSGFGDGGR   360
EARVSRYREK RRTRLFSKKI RYEVRKLNAE KRPRMKGRFV KRASLAAAAS PLGVNY       416
```

```
SEQ ID NO: 203            moltype = AA  length = 405
FEATURE                   Location/Qualifiers
source                    1..405
                          mol_type = protein
                          organism = Arabidopsis thaliana
SEQUENCE: 203
MKSLASAVGG KTARACDSCV KRRARWYCAA DDAFLCHACD GSVHSANPLA RRHERVRLKS    60
ASAGKYRHAS PPHQATWHQG FTRKARTPRG GKKSHTMVFH DLVPEMSTED QAESYEVEEQ   120
LIFEVPVMNS MVEEQCFNQS LEKQNEFPMM PLSFKSSDEE DDDNAESCLN GLFPTDMELA   180
QFTADVETLL GGGDREFHSI EELGLGEMLK IEKEEVEEEG VVTREVHDQD EGDETSPFEI   240
SFDYEYTHKT TFDEGEEDEK EDVMKNVMEM GVNEMSGGIK EEKKEKALML RLDYESVIST   300
WGGQGIPWTA RVPSEIDLDM VCFPTHTMGE SGAEAHHHNH FRGLGLHLGD AGDGGREARV   360
SRYREKRRTR LFSKKIRYEV RKLNAEKRPR MKGRFVKRSS IGVAH                  405

SEQ ID NO: 204            moltype = AA  length = 347
FEATURE                   Location/Qualifiers
source                    1..347
                          mol_type = protein
                          note = Oryza sativa Indica Group
                          organism = Oryza sativa
SEQUENCE: 204
MELGLGRYWG VGGRRCGACA VAPAAVHCRT CDGGGGGGGY LCAGCDAEHG RAGHERVWVC    60
EVCELAPAAV TCKADAAALC AACDSDIHDA NPLARRHERV PGHPIGSSAA PPPDALLLGG   120
ENDAAAAVDG GGGGKEVKLD FLFADFMDPY LGGSPELARF PHADSVVPNH NGSAGPAMEL   180
GFAGGGGAAV KPSYSSYTAA SLGNSGSSSE VGLVPDAICG GGGGGIIELD FAQSKAAYLP   240
YASTPSHSMS SSMDMGVAAP EMSDGAAAAA GRAYAAEGRA ARLMRYREKR KNRRFEKTIR   300
YASRKAYAET RPRVKGRFAK RADDHDAAAP PPQIMLDFAG YGVVPTF                347

SEQ ID NO: 205            moltype = AA  length = 447
FEATURE                   Location/Qualifiers
source                    1..447
                          mol_type = protein
                          note = Oryza sativa Indica Group
                          organism = Oryza sativa
SEQUENCE: 205
MSSKAKAAAA GAVGAKSARA CDGCLRRRAR WYCAADDAFL CQGCDTSVHS ANPLARRHER    60
LRLRPSSPPP LVPPSGSGRR DEAVPAAWFK RKARTPRSHA AKSAAAVGQL LSRRLVVVPE   120
EAAGSGGDSP EERKDEGEIV EEQEQLLYRV PIFDPALSEF CSPPPLEDAA AAVSCCNEDG   180
AVENPTKPSM TTTTATTPPL QFFPDGHANF GPTDAELREF AADMEALLGR GLDDGNDEDS   240
FCMETLGLIE PVDDDAGRVK VEADGDAGMT LAWCHELDTE TSSGEMLDID FDYGSPQAAT   300
TPDEKVGSSG PAAAADDDAQ FQQSSLALSL NYEAIIESWG TSPWTDGERP RVKLDDSWPR   360
DYSGVWMAAA GVFGHGGEEQ ALTPRLGMDG GREARVSRYR EKRRTRLFSK KIRYEVRKLN   420
AEKRPRMKGR FVKRAAAAAA VATACVA                                     447

SEQ ID NO: 206            moltype = AA  length = 448
FEATURE                   Location/Qualifiers
source                    1..448
                          mol_type = protein
                          note = Oryza sativa Japonica Group
                          organism = Oryza sativa
SEQUENCE: 206
MSSTAKAAAA GAVGAKSARA CDGCLRRRAR WYCAADDAFL CQGCDTSVHS ANPLARRHER    60
LRLRPSSPPP LVPPSGSGRR DEAVPAAWFK RKARTPRSHA AKSAAAFGQL LSRRLVVVPE   120
AAAGSGGDSP EERKDEGEIV EEQEQLLYRV PIFDPALSEF CSPPPLEDAA AAVSCCNEDG   180
AVENPTKPSM TTTTATTPPL QFFPDGQANF GPTDAELREF AADMEALLGR GLDDGNDEDS   240
FCMETLGLIE PVDDDAGRVK VEADGDAGMT LAWCHELDTE TSSGEMLDID FDCGSPQAAT   300
TPDEKVGSSG PAAADDDAQL QQSNLALSLN YEAIIESWGT SPWTDGERPH VKLDDSWPRD   360
YSGVWMAAAG VFGHGGEEQA LTPRLGMDGG REARVSRYRE KRRTRLFSKK IRYEVRKLNA   420
EKRPRMKGRF VKRAAAAATA AVATACVA                                    448

SEQ ID NO: 207            moltype = AA  length = 438
FEATURE                   Location/Qualifiers
source                    1..438
                          mol_type = protein
                          organism = Vitis vinifera
SEQUENCE: 207
METTSKSRPS AAVPCDFCDS KTAVVHCRAD SAKLCLLCDR HVHSANALSR KHLRSQICDN    60
CRTEPVSFRC FTDNLALCQS CDWDSHGNCS VPSLHERTPV ESFSGCPSPL ELASVFRVDL   120
KDGNWSSWNF GSVNVQDFVV PGENCYAGCG TKVEKNGISV VYEQLVDLIR SDVDVVRGDV   180
DGDGDEGEDG AELGPGTPGR CANMGNFQGV DLDNGDDEEL LRQQTPFTSL LMLPTPVDAR   240
DTGCGYGCAV EGDAMWDRGH LSYQAPQIWD FHLGRSRICK ETSPEAGYDV DNSGFVIKNY   300
SEITKGSSLT RTKALQGMYE MNCTTTHEDI LSKNSHSNKA LSSQGPTTAE SNNIPIVGPS   360
SESWTAEPNT NSIKSMQFKD LLIGSGTART ETTNVDMELL AQNRGHAIYE KHIRYESRKA   420
RADTRKRVKG RFVKASDS                                               438

SEQ ID NO: 208            moltype = AA  length = 449
FEATURE                   Location/Qualifiers
VARIANT                   108
                          note = X can be any naturally occurring amino acid
```

```
VARIANT                 225
                        note = X can be any naturally occurring amino acid
VARIANT                 275
                        note = X can be any naturally occurring amino acid
VARIANT                 288
                        note = X can be any naturally occurring amino acid
source                  1..449
                        mol_type = protein
                        organism = Vitis vinifera
SEQUENCE: 208
MLKDEGCNAD AAAGGGGWA RVCDTCRSAA CTIYCRADSA YLCAGCDARI HAANRVASQH    60
ERVWVCESCE RAPAAFVCKA DAASLCATCD ADIHSANPLA RRHHRVPXLP IAGCLYGPPA   120
TDPGGTVVRS AAEADNGFLG QEAEETIDEE DEDEAASWLL LNPVKNNNGS SNNQNNGLLF   180
GGEVDEYLDL VEYNSCPENQ FSDQYNQQQP PPHYSVPHKN YGGDXVVPVQ CGEAKGQLHQ   240
QHQQQGFHLG MEYESSKAAY SYNPSISHSV SFFIXVNCLI SLILHDHXAY AFQTHTGLSE   300
SSVSSFILVY GGCLQFIQIH PKFIRSHVSV SSMDVGVVPE ATTMSDISIS ISHPRPPKGT   360
IDLFSGPPIQ MPTQLTPMDR EARVLRYREK KKTRKFEKTI RYASRKAYAE TRPRIKGRFA   420
KRTDVEVEVD QMFSTTLMAE SGYGIVPSF                                    449

SEQ ID NO: 209          moltype = AA   length = 475
FEATURE                 Location/Qualifiers
VARIANT                 37
                        note = X can be any naturally occurring amino acid
VARIANT                 51
                        note = X can be any naturally occurring amino acid
source                  1..475
                        mol_type = protein
                        organism = Vitis vinifera
SEQUENCE: 209
MHDGNEFKLK EEHLDASSTA NALTGGEWLR GVEGETXMKA TIEHANKVYK XVRGIIGNVE    60
TKQQMDLTQA KVANAMGGKT ARACDNCLHK RARWYCGADD AFLCQACDAS VHSANQLAER   120
HERVRLQAAS CKNADSMRDN STPAWHQGFT RKARSPRNVK RTSVQPSKHE NKFPTPPPLV   180
PEIGSEEASP DENEEQFLFR VPTFDPFVAE LNNDGIREIG MENDSKPLSD YGHEEIGDLD   240
SLTGGFLPSEM DLAEFAADVE SYLGAGLDED SCGIKGIGVL DCEQGDMDAC FGDQKVKVKE   300
ERVETDATFH LDPELDMTKE LLAWNLDYES TVMDEEEHEE KMVAAVEMRR KISLSLNYED   360
VITAWASQGS PWTTGNRPEF DPNDYWPDYM GACPTNVHGP CGDVGGVGGN FGGRDGGREA   420
RVLRYREKRR TRLFSKKIRY EVRKLNAEKR PRMKGRFVKR ASFAAGPCFP ILNVK        475

SEQ ID NO: 210          moltype = AA   length = 392
FEATURE                 Location/Qualifiers
source                  1..392
                        mol_type = protein
                        organism = Arabidopsis thaliana
SEQUENCE: 210
MVVDVESRTA SVTGEKMAAR GCDACMKRSR ASWYCPADDA FLCQSCDASI HSANHLAKRH    60
ERVRLQSSSP TETADKTTSV WYEGFRRKAR TPRSKSCAFE KLLQIESNDP LVPELGGDED   120
DGFFSFSSVE ETEESLNCCV PVFDPFSDML IDDINGFCLV PDEVNNTTTN GELGEVEKAI   180
MDDEGFMGFV PLDMDLEDLT MDVESLLEEE QLCLGFKEPN DVGVIKEENK VGFEINCKDL   240
KRVKDEDEEE EEAKCENGGS KDSDREASND KDRKTSLFLR LDYGAVISAW DNHGSPWKTG   300
IKPECMLGGN TCLPHVVGGY EKLMSSDGSV TRQQGRDGGG SDGEREARVL RYEKRRTRL   360
FSKKIRYEVR KLNAEQRPRI KGRFVKRTSL LT                                 392

SEQ ID NO: 211          moltype = AA   length = 332
FEATURE                 Location/Qualifiers
source                  1..332
                        mol_type = protein
                        organism = Arabidopsis thaliana
SEQUENCE: 211
MEAEEGHQRD RLCDYCDSSV ALVYCKADSA KLCLACDKQV HVANQLFAKH FRSLLCDSCN    60
ESPSSLFCET ERSVLCQNCD WQHHTASSSL HSRRPFEGFT GCPSVPELLA IVGLDDLTLD   120
SGLLWESPEI VSLNDLIVSG GSGTHNFRAT DVPPLPKNRH ATCGKYKDEM IRQLRGLSRS   180
EPGCLKFETP DAEIDAGFQF LAPDLFSTCE LESGLKWFDQ QDHEDFPYCS LLKNLSESDE   240
KPENVDRESS VMVPVSGCLN RCEEETVMVP VITSTRSMTH EINSLERNSA LSRYKEKKKS   300
RRYEKHIRYE SRKVRAESRT RIRGRFAKAA DP                                 332

SEQ ID NO: 212          moltype = AA   length = 372
FEATURE                 Location/Qualifiers
source                  1..372
                        mol_type = protein
                        organism = Arabidopsis thaliana
SEQUENCE: 212
MGYMCDFCGE QRSMVYCRSD AACLCLSCDR SVHSANALSK RHSRTLVCER CNAQPATVRC    60
VEERVSLCQN CDWSGHHNSN NNNSSSSSTS PQQHKRQTIS CYSGCPSSSE LASIWSFCLD   120
LAGQSICEQE LGMMNIDDDG PTDKKTCNED KKDVLVGSSS IPETSSVPQG KSSSAKDVGM   180
CEDDFYGNLG MDEVDMALEN YEELFGTAFN PSEELFGHGG IDSLFHKQT APEGGNSVQP   240
AGSNDSFMSS KTEPIICFAS KPAHSNISFS GVTGESSAGD FQECGASSSI QLSGEPPWYP   300
PTLQDNNACS HSVTRNNAVM RYEKKKKARK FDKRVRYASR KARADVRRRV KGRFVKAGEA   360
YDYDPLTPTR SY                                                      372
```

```
SEQ ID NO: 213            moltype = AA   length = 347
FEATURE                   Location/Qualifiers
source                    1..347
                          mol_type = protein
                          organism = Arabidopsis thaliana
SEQUENCE: 213
MLKEESNESG TWARACDTCR SAACTVYCEA DSAYLCTTCD ARVHAANRVA SRHERVRVCQ    60
SCESAPAAFL CKADAASLCT ACDAEIHSAN PLARRHQRVP ILPLSANSCS SMAPSETDAD   120
NDEDDREVAS WLLPNPGKNI GNQNNGFLFG VEYLDLVDYS SSMDNQFEDN QYTHYQRSFG   180
GDGVVPLQVE ESTSHLQQSQ QNFQLGINYG FSSGAHYNNN SLKDLNHSAS VSSMDISVVP   240
ESTASDITVQ HPRTTKETID QLSGPPTQVV QQLTPMEREA RVLRYREKKK TRKFDKTIRY   300
ASRKAYAEIR PRIKGRFAKR IETEAEAEEI FSTSLMSETG YGIVPSF                347

SEQ ID NO: 214            moltype = AA   length = 373
FEATURE                   Location/Qualifiers
source                    1..373
                          mol_type = protein
                          organism = Arabidopsis thaliana
SEQUENCE: 214
MGYMCDFCGE QRSMVYCRSD AACLCLSCDR NVHSANALSK RHSRTLVCER CNAQPASVRC    60
SDERVSLCQN CDWSGHDGKN STTTSHHKRQ TINCYSGCPS SAELSSIWSF CMDLNISSAE   120
ESACEQGMGL MTIDEDGTGE KSGVQKINVE QPETSSAAQG MDHSSVPENS SMAKELGVCE   180
DDFNGNLISD EVDLALENYE ELFGSAFNSS RYLFEHGGIG SLFEKDEAHE GSMQQPALSN   240
NASADSFMTC RTEPIICYSS KPAHSNISFS GITGESNAGD FQDCGASSMK QLSREPQPWC   300
HPTAQDIIAS SHATTRNNAV MRYKEKKKAR KFDKRVRYVS RKERADVRRR VKGRFVKSGE   360
AYDYDPMSPT RSY                                                     373

SEQ ID NO: 215            moltype = AA   length = 373
FEATURE                   Location/Qualifiers
source                    1..373
                          mol_type = protein
                          organism = Arabidopsis thaliana
SEQUENCE: 215
MLKQESNDIG SGENNRARPC DTCRSNACTV YCHADSAYLC MSCDAQVHSA NRVASRHKRV    60
RVCESCERAP AAFLCEADDA SLCTACDSEV HSANPLARRH QRVPILPISG NSFSSMTTTH   120
HQSEKTMTDP EKRLVVDQEE GEEGDKDAKE VASWLFPNSD KNNNNQNNGL LFSDEYLNLV   180
DYNSSMDYKF TGEYSQHQQN CSVPQTSYGG DRVVPLKLEE SRGHQCHNQQ NFQFNIKYGS   240
SGTHYNDNGS INHNAYISSM ETGVVPESTA CVTTASHPRT PKGTVEQQPD PASQMITVTQ   300
LSPMDREARV LRYREKRKTR KFEKTIRYAS RKAYAEIRPR VNGRFAKREI EAEEQGFNTM   360
LMYNTGYGIV PSF                                                     373

SEQ ID NO: 216            moltype = AA   length = 355
FEATURE                   Location/Qualifiers
source                    1..355
                          mol_type = protein
                          organism = Arabidopsis thaliana
SEQUENCE: 216
MLKVESNWAQ ACDTCRSAAC TVYCRADSAY LCSSCDAQVH AANRLASRHE RVRVCQSCER    60
APAAFFCKAD AASLCTTCDS EIHSANPLAR RHQRVPILPI SEYSYSSTAT NHSCETTVTD   120
PENRLVLGQE EEDEDEAEAA SWLLPNSGKN SGNNNGFSIG DEFLNLVDYS SSDKQFTDQS   180
NQYQLDCNVP QRSYGEDGVV PLQIEVSKGM YQEQQNFQLS INCGSWGALR SSNGSLSHMV   240
NVSSMDLGVV PESTTSDATV SNPRSPKAVT DQPPYPPAQM LSPRDREARV LRYREKKKMR   300
KFEKTIRYAS RKAYAEKRPR IKGRFAKKKD VDEEANQAFS TMITFDTGYG IVPSF        355

SEQ ID NO: 217            moltype = AA   length = 397
FEATURE                   Location/Qualifiers
source                    1..397
                          mol_type = protein
                          organism = Zea mays
SEQUENCE: 217
MDYNFDTSVL DEDVAGRGGR EGSCPPAWAR ACDGCRAAPS VVYCHADTAY LCASCDSRVH    60
AANRVASRHE RVRVCEACEC APAVLACRAD AAALCAACDA QVHSANPLAG RHQRVPVLPL   120
PAAAVPAASV LAEATATAAS VAGDKDEEVD SWLLLTKDPD DDDKNHNCSS NNNNNNISSN   180
TSTFYADVDE YFDLVGYSSY CDNHINSNTK QYGMQEQQLL LHKEFGDKEG SEYVVPSQVG   240
QQQSGYHRVI GTEQAASMTP GVSAYTDSIS NSISYSSSME VGIVPDNMAT TDMPSSGILL   300
TPAGAISLFS SGPPLQMPLH LASMDREARV LRYREKKKSR KFEKTIRYAT RKTYAEARPR   360
IKGRFAKRSS DMDDEVDQMF SAALSSDGS YGTVPWF                            397

SEQ ID NO: 218            moltype = AA   length = 398
FEATURE                   Location/Qualifiers
source                    1..398
                          mol_type = protein
                          organism = Zea mays
SEQUENCE: 218
MDYNFDTSVL DEDVAGRGGR EGSCPPAWAR ACDGCRAAPS VVYCHADTAY LCASCDSRVH    60
AANRVASRHE RVRVCEACEC APAVLACRAD AAALCAACDA QVHSANPLAG RHQRVPVLPL   120
PAAAVPAASV LAEAAATAAA VAGDKDEEVD SWLLLTKDPD DDDKNHNCSS NNNNNNISS    180
NTSTFYADVD EYFDLVGYSS YCDNHINSNT KQYGMQEQQL LLHKEFGDKE GSEYVVPSQV   240
GQQQSGYHRV IGTEQAASMT PGVSAYTDSI SNSISFSSSM EVGIVPDNMA TTDMPSSGIL   300
```

```
LTPAGAISLF SSGPPLQMPL HLASMDREAR VLRYREKKKS RKFEKTIRYA TRKTYAEARP    360
RIKGRFAKRS SDMDVEVDQM FSAAALSSDG SYGTVPWF                           398

SEQ ID NO: 219           moltype = AA  length = 410
FEATURE                  Location/Qualifiers
source                   1..410
                         mol_type = protein
                         organism = Chlamydomonas reinhardtii
SEQUENCE: 219
MSSCVVCAAA AVVWCQNDKA LLCKDCDVRI HTSNAVAARH TRFVPCQGCN KAGAALYCKC    60
DAAHMCEACH SSNPLAATHE TEPVAPLPSV EQGAAPEPQV LNMPCESVAQ SAASPAAWFV   120
DDEKMGTTSF FDAPAVLSPS GSEAVVPVMS APIEDEFAFA AAPATFKEIK DKLEFEALDL   180
DNNWLDMGFD FTDILSDGPS DVGLVPTFDA VDEAADAVAD AIVPTFEEEQ PQLQQQEPLV   240
LAPAPEESAA SRKRAAAEEA AEEPAAKVPA LTHQALLQAQ AAAFQAVPQA SALFFQPQML   300
AALPHLPLLQ QPMMPAAVAP APVPKSGSAA ASAALAAGAN LTREQRVARY REKRKNRSFA   360
KTIRYASRKA YAEIRPRIKG RFAKKEEIEA WKAAHGGDDA IVPEVLDAEC              410

SEQ ID NO: 220           moltype = AA  length = 538
FEATURE                  Location/Qualifiers
source                   1..538
                         mol_type = protein
                         note = Physcomitrella patens subsp. patens
                         organism = Physcomitrella patens
SEQUENCE: 220
MATKVASRSM TTAIAIAGRA SRACDVCANK SARWYCGADT AYLCDRCDTQ VHSANALAKR    60
HERVRLTVSG VPMKSSRKVT VTMADHDEDS EMPRKQSSLK KCHSAPVQVM SSRKRSRTSR   120
PHPLKRRASE AKPTSKVSKV EDVKVKEELL TFSDIFDTED FLVDDTQEVP AFITVAQDSS   180
PSSSEFDLSS PELSPEFRSD FYGVCSPSED SFAAYFKGKA AHNDFSDDVM ADQFVVPDGV   240
FDNCLDSGVN ICCDVDSSIS IAGDACFIPG DIPGLDGYED DYSLCFHLAL RDASPDSFGE   300
DSAATATATG RSLEDSPSRV LLCTCFYYFT PSILNNVLKC RKQMYRPECA NADAIPVISY   360
LAVVHPTNNA VSVEADQFGN GPFAKFFAKK PKGEKVLLSP ENIKSEAKEI LRCSLEGLSE   420
EDLRTAPTLR LNYEDVLTAW SDRGEPWVNP ENSTVVPDMG EGGADDDQTG GGREARVLRY   480
KEKRRSRLFS KTIRYEVRKL NAERRPRMKT CGGSDGGGGL RQAATVAAAK SLSILKLS     538

SEQ ID NO: 221           moltype = AA  length = 574
FEATURE                  Location/Qualifiers
source                   1..574
                         mol_type = protein
                         note = Physcomitrella patens subsp. patens
                         organism = Physcomitrella patens
SEQUENCE: 221
MARPKSTAHT NMATAMAIAG RASRACDGCG SQGARWYCEA DNAYLCSRCD RSVHSANALA    60
SRHERVRLNP HGTVSQVPKK ALVDTSGADG NDAHKPHHPR STHTHFLPSR KRSRLCQRPN   120
PHLQHAADIS NPEHRRGKMK TESRNPGESH EVPNFITINI QESPLSFAHD SATGISMAEF   180
CKGRATATAA MYVGVEDAYE ELSSGDSGPD FLVPNGYTED FDSAIGAPTE YHQNAGSPLD   240
SGNGDEDSDN SHEMACVGDG LQLCGSDERY EGYPLEFSDI VGLGNGDAFE EDCENTSGFV   300
DECCEVNGGG LGNGMECSLQ AKMSLEQQKG FSFSKDFYYE VNQECIVPDS YDLIRKEVAD   360
VLRCSLEGEP MKHTPSLLQL NYEDVLSAWS DRCLWTDGKC PQKLPDDSYS EIAGDVGLVP   420
DLSNGCQAVP GGGGDGGREA RVMRYKEKRR TRLFSKKIRY EVRKLNAECR PRMKKPNCAY   480
SLQHPNAAMS QSFRNENNVF LWYLVETGPI REEDTWVLVI RTKAHTSQHG SITVTTYSVW   540
LGGRKSSSGT CDGSADESWF LRGDHANPHL VDIF                               574

SEQ ID NO: 222           moltype = AA  length = 495
FEATURE                  Location/Qualifiers
source                   1..495
                         mol_type = protein
                         note = Physcomitrella patens subsp. patens
                         organism = Physcomitrella patens
SEQUENCE: 222
MTTRTACKSI VTAMAIAGQA SRACDVCMNK SARWYCGADR AYLCEKCDIQ VHSANALAQR    60
HERVPLTPNA ESTILARKDS PDTKNAKEIL LRKPTMSKKL QAPPVNVLPS RKRFRTCRLH   120
PFRQAKHSPG AKHAPNQLEE GDAKMKEDLL MFSETFETEN FLVDVTQKVP SLIVVMQDSS   180
PSSSELDVCS DFFQELRSDS QEVRSSPWSD SLAAFFKGKA AQEDCFPDDD TSDQFFLPDA   240
FDDGINICCD MDGNISVAGD ACFISNDIPG LSGFEDFGSR EFVGDSLSFD FAFHDTLPRA   300
FEGVGADTSE MGGISSKYNL VGAENDQFRT GPFVKFFSKI PRNEKKMHLT PENIKKEAKE   360
ILLCCREGLS EVNLGLAPTL RLNYEDVITA WSDRGEPWFY PHDCTSDATD AGLVPDMAQE   420
GADDCQGSRE ASVMRFKEKR RSRLFSKRIR YEVRKLNAEK RPRMKGRFVK KNSSGFDFRL   480
DPFLSSETHV LAHPH                                                    495

SEQ ID NO: 223           moltype = AA  length = 364
FEATURE                  Location/Qualifiers
source                   1..364
                         mol_type = protein
                         note = Physcomitrella patens subsp. patens
                         organism = Physcomitrella patens
SEQUENCE: 223
MPKSCDACHI SSAVVYCRAD AAYLCAGCDG KVHGANKLAS RHERVWMCEV CEVAVAVVTC    60
KADAASLCVS CDTDIHSANP LAQRHERVPV QPLFDCASSA REAHISVPFP ESECHETLKG   120
VEDSCVAEAG SWLLPHPKIP TNAIIRGSAA ADEAPDSPFR ARPFSPKLKK QKVDLAADIF   180
```

```
SDVDPFLELD DATVTGIQPD SLVPVHIPEG SEDSPSLAHS MEPSFTTDFH LSEKSGYSFG    240
TSTLTHSISC SSVDAAVVPD SSLSDISTPY PLDSQGAQEL SGTRMPQQVS GPIDTVDREA    300
RVMRYKEKRQ KRKFEKTIRY ASRKAYAESR PRIKGRFAKR TDSDVEQLFS SCSMDSSFGV    360
VPSF                                                                 364

SEQ ID NO: 224          moltype = AA  length = 495
FEATURE                 Location/Qualifiers
source                  1..495
                        mol_type = protein
                        note = Physcomitrella patens subsp. patens
                        organism = Physcomitrella patens
SEQUENCE: 224
MPGGGVKDAA TNSVATAMAI AGRASRACDV CGSQRARWYC NADNAYLCYR CDQNVHSANA    60
LALRHERVRL NSQGNISSQS PRKALVVDTS ARKHSRNHTA HAAQSPPSRK RSRLSRRPNP    120
HVSSPVDTLF KPHKASHRGS KVKSESSHEV PNFVTVNIQE SSFSFTHDSA TVMSMAEYCK    180
GRAAAAAAAA MSMSVDVDTY EELSSGDSDQ FLVPTGYLDD FESAAVAPVE DGSSPSEDAE    240
DAPGYEENHH DITDAVDLRD GLELEGGSDD AYRLDFSDIV ALREGDEDAF EGDYGETEGD    300
AFEGECGDTE GDGEVEAAAS NEQSCVDGFP EEQPNCVVPF TKEYLYKVKS ENSVRDGFAL    360
IKKEVAAVLR CSLEGEEAKP AAPSLLRLNF DDVLSAWSDR SLWTDGKRPQ TVPDDSSEAV    420
GGLDLGLVPD LSKGCAQGQP GTGGDRGREA RVLRYREKRR TRLFSKKIRY EVRKLNAERR    480
PRMKGRFVKR TTGCS                                                     495

SEQ ID NO: 225          moltype = AA  length = 646
FEATURE                 Location/Qualifiers
source                  1..646
                        mol_type = protein
                        note = Physcomitrella patens subsp. patens
                        organism = Physcomitrella patens
SEQUENCE: 225
MAGVKGAAHA NVAMAMAIAG RASRACDVCG SQRARWYCEA DNAHLCNRCD QSVHSANALA    60
LRHERVRLNP QDCTTQPLKK VVVDTLDASN KSRKSHHPRP TDKHSLPSRK RSRLSRRPNP    120
HLRPPTSTSK SQHRRGKVKS EGRGAEDSHE VPNFITVNIQ ESPVSFAHDS ATAMSMAEFC    180
KERATAAASV YVDVEDAYEE ISSGDTGPDF LVPNGYMDDF ESAIGAPIGC HEDARSPFDS    240
GNGAMDMNKS HDIMFMRNDL ELCGSDEQYE DYPLDFSDIV GLRDGDAFEG DCGDTSELVD    300
EVGEENKDED GDGDGDGDGD GFECSLDARA QSNVCEDQGL VSYTQDFPYK VKQEYTVPDS    360
YDLIKKEVAA VLRCSLQGEE VKPAPSLLRL NYEDIMSAWS DRSLWTDGKR PQTVPDDSNS    420
ESTVDLGMVP DFGNGCQTVP GGSDGGRGAR IMRYREKRRT RLFSKKIRYE VRKLNAERRP    480
RMKSQLRYDL ALSWVWHYRM TVLTDRNKES MMSKASWKYV PVRSLVRMCD RLVPRELSIL    540
WPLILQPGIH HLDRLEQQYQ KSGSTGGLDW LRMALRLEHL NSVMGCLSFQ SLLPLSVVQT    600
RFQRVTTKRS DSVGEELFND TPSSVIYSLT EGLIVMRTGI LCNCTL                   646

SEQ ID NO: 226          moltype = AA  length = 475
FEATURE                 Location/Qualifiers
source                  1..475
                        mol_type = protein
                        note = Physcomitrella patens subsp. patens
                        organism = Physcomitrella patens
SEQUENCE: 226
MAGGGGIKGA VNNNVATAMA IAGRDSRACD VCGLHRARWY CSVDNAHLCR RCDQNVHSAN    60
ALALHHERVR LDLQGNALHT PRKALKGNTS APQNSLKSAA QMDHAAPSRK SFRQSRRPNT    120
DASPPNSHKI NRRGKEKSDS SHEVPNFVTV NIHESPFSFT HDSATAMSIA EYCKGRAAAA    180
AAMAADVDTN EELSSGDSDQ YLVPNGYLDD FESATVPTPG CRQQGCDPSD DAASNDALDD    240
GEGKDQYDSG AFDQTNGLEF KRGSDQDRIN EKYRLGFSEV VGMRDADDFE GESGYTEGEG    300
EVEDEAYDQS CAYGDPERQR VSPFVKDLKS EYDVLDRLDL IKREVAAVLR CSLEAQEKKS    360
APPPLLRLNF DDVLSAWSDR SLWTDGRRPQ TVPDDSSEAV GGTDVGLVPD INTQYAQGAT    420
LAAGDKGREF RVMRYKEKRR TRLFSKKIRY EVRKLNAERR PRMKGRFVKQ TPGGS         475

SEQ ID NO: 227          moltype = AA  length = 368
FEATURE                 Location/Qualifiers
source                  1..368
                        mol_type = protein
                        note = Physcomitrella patens subsp. patens
                        organism = Physcomitrella patens
SEQUENCE: 227
MPKSCDACQA SSAVVYCRAD AAYLCLGCDG KVHGANKLAS RHERLWMCEV CEVAAAVVTC    60
KADAASLCVS CDTDIHSANP LAQRHERVPV QPLFDCVSQF RGTHFSVLAP KNECNNNLLK    120
GDEDPAVAEA VSWLLPHPKT LSSAILRGIA AADEAPAFPF RERPFSPKLK KLKVEQAADI    180
YSDVDPFLVL DGGNGTGFQP DSMVPVHIPE GPDDSPSLAH STAPSSAINF RASQKSGCSY    240
GTSTLTHSMS CSSVDAAVVP DSSLSDISTP YSKALDSQDS QDLSGALVPH QASKPIDTVD    300
REARVMRYKE KRQKRKFEKT IRYASRKAYA ESRPRIKGRF TKRTDSDVEQ MFSSCTADSG    360
FGVVPSSC                                                             368

SEQ ID NO: 228          moltype = AA  length = 313
FEATURE                 Location/Qualifiers
source                  1..313
                        mol_type = protein
                        organism = Arabidopsis thaliana
SEQUENCE: 228
MISKYQEDVK QPRACELCLN KHAVWYCASD DAFLCHVCDE SVHSANHVAT KHERVCLRTN    60
```

```
EISNDVRGGT TLTSVWHSGF RRKARTPRSR YEKKPQQKID DERRREDPRV PEIGGEVMFF    120
IPEANDDDMT SLVPEFEGFT EMGFFLSNHN GTEETTKQFN FEEEADTMED LYYNGEEEDK    180
TDGAEACPGQ YLMSCKKDYD NVITVSEKTE EIEDCYENNA RHRLNYENVI AAWDKQESPR    240
DVKNNTSSFQ LVPPGIEEKR VRSEREARVW RYRDKRKNRL FEKKIRYEVR KVNADKRPRM    300
KGRFVRRSLA IDS                                                      313

SEQ ID NO: 229          moltype = AA  length = 406
FEATURE                 Location/Qualifiers
source                  1..406
                        mol_type = protein
                        organism = Arabidopsis thaliana
SEQUENCE: 229
MMKSLASAVG GKTARACDSC VKRRARWYCA ADDAFLCHAC DGSVHSANPL ARRHERVRLK     60
SASAGKYRHA SPPHQATWHQ GFTRKARTPR GGKKSHTMVF HDLVPEMSTE DQAESYEVEE    120
QLIFEVPVMN SMVEEQCFNQ SLEKQNEFPM MPLSFKSSDE EDDDNAESCL NGLFPTDMEL    180
AQFTADVETL LGGGDREFHS IEELGLGEML KIEKEEVEEE GVVTREVHDQ DEGDETSPFE    240
ISFDYEYTHK TTFDEGEEDE KEDVMKNVME MGVNEMSGGI KEEKKEKALM LRLDYESVIS    300
TWGGQGIPWT ARVPSEIDLD MVCFPTHTMG ESGAEAHHHN HFRGLGLHLG DAGDGGREAR    360
VSRYEKRRT RLFSKKIRYE VRKLNAEKRP RMKGRFVKRS SIGVAH                    406

SEQ ID NO: 230          moltype = AA  length = 367
FEATURE                 Location/Qualifiers
source                  1..367
                        mol_type = protein
                        note = Beta vulgaris subsp. vulgaris
                        organism = Beta vulgaris
SEQUENCE: 230
MMKEEVSGSD TNSWARVCDT CRAAPCTVYC RADSAFLCTS CDARIHAANQ VASRHERVWV     60
CEACERAPAA FLCKADAASL CATCDAEIHS ANPLARRHQR VPIMPVAGCV YGPQGGRMSE    120
DRFLTLPEGD DHTTDHEGDE DEAASWLLLN PVKNSNNQNT NGFLTGGGEV DEYLDLLEYN    180
SGADNQLCEQ YNQQQEFKVP EKNCGGDSVV PVQCREAKDH QIQYQNFLFG MECETKSGYT    240
YNTSISQSVS VSSMDVGVVP ESAMSDISMS HPRPPKGTID LFSSPPMQVP TQLSPLDREA    300
RVMRYREKKK NRKFEKTIRY ASRKAYAETR PRIKGRFAKR TDVEAEMDQM FTNSLMADSG    360
YGIVPSY                                                             367

SEQ ID NO: 231          moltype = AA  length = 386
FEATURE                 Location/Qualifiers
source                  1..386
                        mol_type = protein
                        organism = Solanum lycopersicum
SEQUENCE: 231
MGIFREAPNC FPGGWNIGAA ARMAKSCEYC HLAAALVFCR TDNTFVCLSC DTRLHARHER     60
VWVCEVCEQA AASVTCRADA AALCVACDRD IHSANPLARR HERVPVVPFY DPVESVVKST    120
AATLLVSING TTTTATTTAT ITPELGKVDT CIGHHENNND PWIPPNTITS KLPLNTEMKG    180
MDFIFTDSEN FLDFDYPACV DTQSQPHYNS SNDSVVPVQA NTPIKSLPFH HQEKHFEIDF    240
TQSHIKSYNT PSLSVSSSSL DVGIVPDGSS ISEISYPYIR TMNNSNSSID LSNSANHQGE    300
KLLGLDREAR VLRYREKKKN RKFEKTIRYA SRKAYAETRP RIKGRFAKRT DGSAGAGEFD    360
DVDGIFSGTD FIAAESRYGV VPSFLT                                        386

SEQ ID NO: 232          moltype = AA  length = 395
FEATURE                 Location/Qualifiers
source                  1..395
                        mol_type = protein
                        organism = Zea mays
SEQUENCE: 232
MDYNFDTSVL DEDVAGRGGR EGSCPPAWAR ACDGCRAAPS VVYCHADTAY LCASCNSRVH     60
AANRVASRHE RVRVCEACEC APAVLACRAD AAALCAACDA QVHSANPLAG RHQRVPVLPL    120
PAAAVPAASV LAEAAATAAA VAGDKDEEVD SWLLLTKDPD DDDKNHNCSS NNNNISSNTS    180
TFYADVDEYF DLVGYSSYCD NHINSNTKQY GMQEQQLLLH KEFGDKEGSE YVVPSQVGQQ    240
QSGYHRVIGT EQAASMTPGV SAYTDSISNS ISFSSSMEVG IVPDNMATTD MPSSGILLTP    300
AGAISLFSSG PPLQMPLHLA SMDREARVLR YREKKKSRKF EKTIRYATRK TYAEARPRIK    360
GRFAKRSSDM DVEVDQMFSA AALSSDGSYG TVPWF                              395

SEQ ID NO: 233          moltype = AA  length = 444
FEATURE                 Location/Qualifiers
source                  1..444
                        mol_type = protein
                        organism = Picea abies
SEQUENCE: 233
MVKEEDKDWH TVEDLHRGSH VDHKEFLRGI GGWRMSMPKL CDVCQVSNSV LYCRAHTAQL     60
CLVCDVKIHG GSKASLCHER VWVCEVCEQA PAVVTCKADA AALCVSCDTD IHSANPLASR    120
HERAPVIPFY ECPNMPNNNT ATNANNDNLD CNVLLNEDGG GDDPLKHDYV DDDYDDDDD     180
ENDHNNLLNH QEDDNDAEIC CAEEAATASW LIPEANRHNL TNINGGNSEG EDKMVKDKLK    240
FKAYMQSIDF LQDVENYVDL EYLGTTTTIT TPTTPTAHMG ADSMVPVHTP EVIEHSSTKV    300
SVETARSLDV DAASKCNYVY RTTSLNHCVS SSSIDVGIVP DSNTTTDIST PYHDPRGVFE    360
IPPRVVHPGG HVEVMGREAR VLRYREKRKN RRFEKTIRYA SRKAYAETRP RIKGRFAKRT    420
EVEVEQIYSS SLLPDQGYGV VPSY                                          444

SEQ ID NO: 234          moltype = AA  length = 339
```

```
FEATURE              Location/Qualifiers
source               1..339
                     mol_type = protein
                     organism = Brassica nigra
SEQUENCE: 234
MLKQESNYNI SNRENNRGPR ACDTCRSTIC TVYCHADSAY LCNSCDAEVH SANRVASRHK  60
RVPVCESCER APAAFMCEAD DVSLCTTCDS EVHSANPLAR RHQRVPVVPI TGNSCSSLAT 120
THHTAVTEPE KRAVLVQDDE EGKEDAKETA SWMFPYSDKG SHNHNNNNQN NELLFSDDYL 180
DLADYNSSMD YKFAGQYNQP QHKQDCTVPQ TNYGGDRVVP LQLEETRGNV RHKKEKITYG 240
SSGSQYNYND SINHNAYNPS METDFVPEPT ARETTVSHQK TPKIHQLPEP LVQILSPMDR 300
EARVLRYREK KKRRKFEKTI RYASRKAYAE RRPRINGRF                       339

SEQ ID NO: 235       moltype = AA   length = 339
FEATURE              Location/Qualifiers
source               1..339
                     mol_type = protein
                     organism = Brassica nigra
SEQUENCE: 235
MLKQESNYNI SNRENNRGPR ACDTCRSTIC TVYCHADSAY LCNSCDAEVH SANRVASRHK  60
RVPVCESCER APAAFMCEAD DVSLCTTCDS EVHSANPLAR RHQRVPVVPI TGNSCSSLAT 120
THHTAVTEPE KRAVLVQDDE EGKEDAKETA SWMFPYSDKG SHNHNNNNQN NELLFSDDYL 180
DLADYNSSMD YKFTGQYNQP QHKQDCTVPQ TNYGGDRVVP LQLEETRGNV RHKKEKITYG 240
SSGSQYNYND SINHNAYNPS METDFVPEPT ARETTVSHQK TPKIHQLPEP LVQILSPMDR 300
EARVLRYREK KKRRKFEKTI RYASRKAYAE RRPRINGRF                       339

SEQ ID NO: 236       moltype = AA   length = 339
FEATURE              Location/Qualifiers
source               1..339
                     mol_type = protein
                     organism = Brassica nigra
SEQUENCE: 236
MLKQESNYNI SNRENNRGPR ACDTCRSTIC TVYCHADSAY LCNSCDAEVH SANRVASRHK  60
RVPVCESCER APAAFMCEAD DVSLCTTCDS EVHSANPLAR RHQRVPVVPI TGNSCSSLAT 120
THHTAVTEPE KRAVLVQDDE EGKEDAKETA SWMFPYSDKG SHNHNNNNQN NELLFSDDYL 180
DLADYNSSMD YKFTGQYNQP QHKQDCTVPQ TNYGGDRVVP LQLEETRGNV RHKKEKITYG 240
SSGSQYNYND SINHNAYNPS METDFVPEPT ARETTVSHQK TPKIHQLPEP LVQILSPMDR 300
EARVLRYREK KKRRKFENTI RYASRKAYAE RRPRINGRF                       339

SEQ ID NO: 237       moltype = AA   length = 339
FEATURE              Location/Qualifiers
source               1..339
                     mol_type = protein
                     organism = Brassica nigra
SEQUENCE: 237
MLKQEINYNI SNRENNRGAR ACDTCRSTIC TVYCHADSAY LCNSCDAEVH SANRVASRHK  60
RVPVCESCER APAAFMCEAD DVSLCTTCDS EVHSANPLAR RHQRVPVVPI TGNSCSSLAT 120
THHTAVTEPE KRAVLVQDDE EGKEDAKETA SWMFPYSDKG SHNHNNNNQN NELLFSDDYL 180
DLADYNSSMD YKFTGQYNQP QHKQDCTVPQ TNYGGDRVVP LQLEETRGNV RHKKEKITYG 240
SSGSQYNYND SINHNAYNPS METDFVPEPT ARETTVSHQK TPKIHQLPEP LVQILSPMDR 300
EARVLRYREK KKRRKFEKTI RYASRKAYAE RRPRINGRF                       339

SEQ ID NO: 238       moltype = AA   length = 343
FEATURE              Location/Qualifiers
source               1..343
                     mol_type = protein
                     organism = Brassica nigra
SEQUENCE: 238
MLKQESNYNI SNRENNRGAR ACDTCRSTIC TVYCHADSAY LCNSCDAEVH SANRVASRHK  60
RVPVCESCER APAAFMCEAD DVSLCTACDS EVHSANPLAR RHQRVPVVPI TGNSCSSLAT 120
THHTAVTEPE KRAVLVQDDE EGKEDAKETA SWMFPYSDKG SPNHNNNNNN NNQNNELLFS 180
DDYLDLADYN SSMDYKFTGQ YNQPQHKQDC TVPQTNYGGD RVVPLQLEET RGNVRHKKEK 240
ITYGSSGSQY NYNDSINHNA YNPSMETDFV PEPTARETTV SHQKTPKIHQ LPEPLVQILS 300
PMDREARVLR YREKKKRRKF EKTIRYASRK AYAERRPRIN GRF                  343

SEQ ID NO: 239       moltype = AA   length = 343
FEATURE              Location/Qualifiers
source               1..343
                     mol_type = protein
                     organism = Brassica nigra
SEQUENCE: 239
MLKQESNYNI SNRENNRGAR ACDTCRSTIC TVYCHADSAY LCNSCDAEVH SANRVASHHK  60
RVPVCESCER APAAFMCEAD DVSLCTACDS EVHSANPLAR RHQRVPVVPI TGNSCSSLAT 120
THHTAVTEPE KRAVLVQDDE EGKEDAKETA SWMFPYSDKG SPNHNNNNNN NNQNNELLFS 180
DDYLDLADYN SSMDYKFTGQ YNQPQHKQDC TVPQTNYGGD RVVPLQLEET RGNVRHKKEK 240
ITYGSSGSQY NYNDSINHNA YNPSMETDFV PEPTARETTV SHQKTPKIHQ LPEPLVQILS 300
PMDREARVLR YREKKKRRKF EKTIRYASRK AYAERRPRIN GRF                  343

SEQ ID NO: 240       moltype = AA   length = 344
FEATURE              Location/Qualifiers
```

```
source                          1..344
                                mol_type = protein
                                organism = Brassica nigra
SEQUENCE: 240
MLKQESNYNI SNRENNRGAR ACDTCRSTIC TVYCHADSAY LCNSCDAEVH SANRVASRHK   60
RVPVCESCER APAAFMCEAD DVSLCTTCDS EVHSANPLAR RHQRVPVVPI TGNSCSSLAT  120
THHTAVTEPE KRAVLVQDDE EGKEDAKETA SWMFPYSDKG SPNHNNNNNN NNNQNNELLF  180
SDDYLDLADY NSSMDYKFTG QYNQPQHKQD CTVPQTNYGG DRVVPLQLEE TRGNVRHKKE  240
KITYGSSGSQ YNYNDSINHN AYNPSMETDF VPEPTARETT VSHQKTPKIH QLPEPLVQIL  300
SPMDREARVL RYREKKKRRK FEKTIRYASR KAYAERRPRI NGRF                  344

SEQ ID NO: 241                  moltype = AA  length = 345
FEATURE                         Location/Qualifiers
source                          1..345
                                mol_type = protein
                                organism = Brassica nigra
SEQUENCE: 241
MLKQESNYNI SNRENNRGAR ACDTCRSTIC TVYCHADSAY LCNSCDAEVH SANRVASRHK   60
RVPVCESCER APAAFMCEAD DVSLCTTCDS EVHSANPLAR RHQRVPVVPI TGNSCSSLAT  120
THHTAVTEPE KRAVLVQDDE EGKEDAKETA SWMFPYSDKG SPNHNNNNNN NNNNQNNELL  180
FSDDYLDLAD YNSSMDYKFT GQYNQPQHKQ DCTVPQTNYG GDRVVPLQLE ETRGNVRHKK  240
EKITYGSSGS QYNYNDSINH NAYNPSMETD FVPEPTARET TVSHQKTPKI HQLPEPLVQI  300
LSPMDREARV LRYEKKKRR KFEKTIRYAS RKAYAERRPR INGRF                  345

SEQ ID NO: 242                  moltype = AA  length = 345
FEATURE                         Location/Qualifiers
source                          1..345
                                mol_type = protein
                                organism = Brassica nigra
SEQUENCE: 242
MLKQESNYNI SNRENNRGPR ACDTCRSTIC TVYCHADSAY LCNSCDAEVH SANRVASRHK   60
RVPVCESCER APAAFMCEAD DVSLCTACDS EVHSANPLAR RHQRVPVVPI TGNSCSSLAT  120
THHTAVTEPE KRAVLVQDDE EGKEDAKETA SWMFPYSDKG SPNHNNNNNN NNNNQNNELL  180
FSDDYLDLAD YNSSIDYKFT GQYNQPQHKQ DCTVPQTNYG GDRVVPLQLE ETRGNVRHKK  240
EKITYGSSGS QYNYNDSINH DAYNPSMETD FVPEPTARET TVSHQKTPKI HQLPEPLVQI  300
LSPMDREARV LRYEKKKRR KFEKTIRYAS RKAYAERRPR INGRF                  345

SEQ ID NO: 243                  moltype = AA  length = 345
FEATURE                         Location/Qualifiers
source                          1..345
                                mol_type = protein
                                organism = Brassica nigra
SEQUENCE: 243
MLKQESNYNI SNRENNRGPR ACDTCRSTIC TVYCHADSAY LCNSCDAEVH SANRVASRHK   60
RVPVCESCER APAAFMCEAD DVSLCTACDS EVHSANPLAR RHQRVPVVPI TGNSCSSLAT  120
THHTAVTEPE KRAVLVQDDE EGKEDAKETA SWMFPYSDKG SPNHNNNNNN NNNNQNNELL  180
FSDDYLDLAD YNSSIDYKFT GQYNQPQHKQ DCTVPQTNYG GDRVVPLQLE ETRGNVRHKK  240
EKITYGSSGS QYNYNDSINH DAYNPSMETD FVPEPTARET TVSHQKMPKI HQLPEPLVQI  300
LSPMDREARV LRYEKKNRR KFEKTIRYAS RKAYAERRPR INGRF                  345

SEQ ID NO: 244                  moltype = AA  length = 345
FEATURE                         Location/Qualifiers
source                          1..345
                                mol_type = protein
                                organism = Brassica nigra
SEQUENCE: 244
MLKQESNYNI SNRENNRGPR ACDTCRSTIC TVYCHADSAY LCNSCDAEVH SANRVASRHK   60
RVPVCESCER APAAFMCEAD DVSLCTACDS EVHSANPLAR RHQRVPVVPI TGNSCSSLAT  120
THHTAVTEPE KRAVLVQDDE EGKEDAKETA SWMFPYSDKG SPNHNNNNNN NNNNQNNELL  180
FSDDYLDLAD YNSSIDYKFT GQYNQPQHKQ DCTVPQTNYG GDRVVPLQLE ETRGNVRHKK  240
EKITYGSSGS QYNYNDSINH NAYNPSMETD FVPEPTARET TVSHQKTPKI HQLPEPLVQI  300
LSPMDREARV LRYEKKKRR KFEKTIRYAS RKAYAERRPR INGRF                  345

SEQ ID NO: 245                  moltype = AA  length = 343
FEATURE                         Location/Qualifiers
source                          1..343
                                mol_type = protein
                                organism = Brassica nigra
SEQUENCE: 245
MLKQESNYNI SNRENNRGAR ACDTCRSTIC TVYCHADSAY LCNSCDAEVH SANRVASRHK   60
RVPVCESCER APAAFMCEAD DVSLCTTCDS EVHSANPLAR RHQRVPVVPI TGNSCSSLAT  120
THHTAVTEPE KRAVLVQDDE EGKEDAKETA SWMFPYSDKG SPNHNNNNNN NNQNNELLFS  180
DDYLDLADYN SSMDYKFTGQ YNQPQHKQDC TVPQTNYGGD RVVPLQLEET GGNVRHKKEK  240
ITYGSSGSQY NYNDSINHDA YNPSMETDFV PEPTARETTS HQKTPKIHQ LPEPLVQILS  300
PMDREARVLR YEKKKRR KF EKTIRYASRK AYAERRPRIN GRF                   343

SEQ ID NO: 246                  moltype = AA  length = 342
FEATURE                         Location/Qualifiers
source                          1..342
```

```
                              mol_type = protein
                              organism = Brassica nigra
SEQUENCE: 246
MLKQESNYNI  SNRENNRGAR  ACDTCRSTIC  TVYCHADSAY  LCNSCDAEVH  SANRVASRHK   60
RVPVCESCER  APAAFMCEAD  DVSLCTACDS  EVHSANPLAR  RHQRVPVVPI  TGNSCSSLAT  120
THHTAVTEPE  KRAVLVQDDE  EGKEDAKETA  SWMFPYSDKG  SPNHNNNNNN  NQNNELLFSD  180
DYLDLADYNS  SMDYKFTGQY  NQPQHKQDCT  VPQTNYGGDR  VVPLQLEETR  GNVRHKKEKI  240
TYGSSGSQYN  YNDSINHNAY  NPSMETDFVP  EPTARETTVS  HQKTPKIHQL  PEPLVQILSP  300
MDREARVLRY  REKKKRRKFE  KTIRYASRRA  YAERRPRING  RF                      342

SEQ ID NO: 247            moltype = AA    length = 347
FEATURE                   Location/Qualifiers
source                    1..347
                          mol_type = protein
                          organism = Brassica nigra
SEQUENCE: 247
MLKQESNYNI  SNRENNRGAR  ACDTCRSTIC  TVYCHADSAY  LCNSCDAEVH  SANRVASRHK   60
RVPVCESCER  APAAFMCEAD  DVSLCTACDS  EVHSANPLAR  RHQRVPVVPI  TGNSCSSLAT  120
THHTTVTEPE  KRAVIVQDDE  EGKEDAKETA  SWMFPYSDKG  SHNHHNNNNN  NNNNNNQNNE  180
LLFSDDYLDL  ADYNSSMDYK  FTGQYNQPQH  KQDCTVPQTN  YGGDRVVPLQ  LEETRGNVRH  240
KKEKITYGSS  GSQYNYNDSI  NHNAYNPSME  TDFVPEPTAR  ETTVSHQKTP  KIHQLPEPLV  300
QILSPMDREA  RVLRYEKKK   RRKFEKTIRY  ASRKAYAERR  PRINGRF                 347

SEQ ID NO: 248            moltype = AA    length = 343
FEATURE                   Location/Qualifiers
source                    1..343
                          mol_type = protein
                          organism = Brassica nigra
SEQUENCE: 248
MLKQESNYNI  SNRENNRGAR  ACDTCRSTIC  TVYCHADSAY  LCNSCDAEVH  SANRVASRHK   60
RVPVCESCER  APAAFMCEAD  DVSLCTTCDS  EVHSANPLAR  RHQRVPVVPI  TGNSCSSLAT  120
THHTAVTEPE  KRAVLVQDDE  EGKEDAKETA  SWMFPYSDKG  SPNHNNNNNN  NNNQNNELLF  180
SDDYLDLADY  NSSMDYKFTG  QYNQPQHKQD  CTVPQTNYGG  DRVVPLQLEE  TGNVRHKKEK  240
ITYGSSGSQY  NYNDSINRNA  YNPSMETDFV  PEPTARETTV  SHQKTPKIHQ  LPEPLVQILS  300
PMDREARVLR  YREKKKRRKF  EKTIRYASRK  AYAERRPRIN  GRF                     343

SEQ ID NO: 249            moltype = AA    length = 344
FEATURE                   Location/Qualifiers
source                    1..344
                          mol_type = protein
                          organism = Brassica nigra
SEQUENCE: 249
MLKQESNYNI  SNRENNRGAR  ACDTCRSTIC  TVYCHADSAY  LCNSCDAEVH  SANRVASRHK   60
RVPVCESCER  APAAFMCEAD  DVSLCTACDS  EVHSANPLAR  RHQRVPVVPI  TGNSCSSLAT  120
THHTTVTEPE  KRAVIVQDDE  EGKEDAKETA  SWMFPYSDKG  SHNHHNNNNN  NNNQNNELLF  180
SDDYLDLADY  NSSMDYKFTG  QYNQPQHKQD  CTVPQTNYGG  DRVVPLQLEE  TRGNVRHKKE  240
KITYGSSGSQ  YNYNDSINHN  AYNPSMETDF  VPEPTARETT  VSHQKTPKIH  QLPEPLVQIL  300
SPMDREARVL  RYREKKKRRK  FEKTIRYASR  KAYAERRPRI  NGRF                    344

SEQ ID NO: 250            moltype = AA    length = 343
FEATURE                   Location/Qualifiers
source                    1..343
                          mol_type = protein
                          organism = Brassica nigra
SEQUENCE: 250
MLKQESNWAQ  ACDTCRSAAC  TVYCRADSAY  LCTSCDAQIH  AANRLASRHE  RVRVCESCER   60
APAAFFCKAD  AASLCTACDS  QIHSANPLAR  RHQRVPILPI  SGCVATNHHS  SETTEPENIV  120
VVGQEEEDEA  EAASWLLPSS  VKNCGDNNNN  NSENNRFSVG  EEYLDLVDYS  SSMDKRFTGQ  180
ANQYQQDYNV  PQRSYVADGV  VPLQVGVSKG  HMHHEQHNFQ  FGFTNVSSEA  HQISNGSPIH  240
MVSLVPESVT  SDATVSHQRS  PKSGTEELPE  APVQMLSPME  RKARVLRYRE  KKKTRKFEKR  300
IRYASRKEYA  EKRPRIKGRF  AKRNEVDADQ  AFPTVVMFDT  GYG                     343

SEQ ID NO: 251            moltype = AA    length = 336
FEATURE                   Location/Qualifiers
source                    1..336
                          mol_type = protein
                          organism = Brassica nigra
SEQUENCE: 251
MLKQESNWAQ  ACDTCRSAAC  TVYCRADSAY  LCTSCDAQIH  AANRLASRHE  RVRVCESCER   60
APAAFFCKAD  AASLCTACDS  QIHSANPLAR  RHQRVPILPI  SGCVATNHHS  SETTEPENIV  120
VVGQEEEDEA  EAASWLLPSS  VKNCGDNNNN  TENNRFSVGE  EYLDLVDYSS  SIDKRFTGQT  180
NQYQQDYNVP  QRSYVADGVV  PLQVGVANGH  MHHEKHNFQF  GFTNVSSEAS  PIHMVSLVPE  240
SVTSDATVSH  PRSPKAGTEE  LPEAPVQMLS  PMERKARVLR  YREKKKTRKF  EKRIRYASRK  300
EYAEKRPRIK  GRFAKRNEVD  ADHALSTMVM  FDTGYG                              336

SEQ ID NO: 252            moltype = AA    length = 340
FEATURE                   Location/Qualifiers
source                    1..340
                          mol_type = protein
```

```
                       organism = Brassica nigra
SEQUENCE: 252
MLKQESNWAQ ACDTCRSAAC TVYCRADSAY LCTSCDAQIH AANRLASRHE RVRVCESCER    60
APAAFFCKAD AASLCTACDS QIHSANPLAR RHQRVPILPI SGCVATNHHS SETTEPENIV   120
VVGQEEEDEA EAASWLLPSS VKNCGDNNNN TENNRFSVGE EYLDLVDYSS SIDKRFTGQT   180
NQYQQDYNVP QRSYVADGVV PLQVGVSKGH MHHEQHNFQF GFTNVSSEAH QISNGSPIHM   240
VSLVPESVTS DATVSHQRSP KAGTEELPEA PVQMLSPMER KARVLRYREK KKTRKFEKRI   300
RYASRKEYAE KRPRIKGRFA KRNEVDADQA FPTVVMFDTG                        340

SEQ ID NO: 253            moltype = AA   length = 342
FEATURE                   Location/Qualifiers
source                    1..342
                          mol_type = protein
                          organism = Brassica nigra
SEQUENCE: 253
MLKQESNWAQ ACDTCRSAAC TVYCRADSAY LCTSCDAQIH AANRLASRHE RVRVCESCER    60
APAAFFCKAD AASLCTACDS QIHSANPLAR RHQRVPILPI SGCVATNHHS SETTEPENIV   120
VVGQEEEDEA EAASWLLPSS VKNCGDNNNN NNNNISENN RFSVGEEYLD LVDYSSSIDK    180
RFTGQTNQYQ QDYNVPQRSY VADGVVPLQV GVANGHMMHE KHNFQFGFTN VSSEASPIHM   240
VSLVPESVTS DATVSHPRSP KAGTEELPEA PVQMLSPMER KARVLRYREK KKTRKFEKRI   300
RYASRKEYAE KRPRIKGRFA KRNEVDADHA LSTMVMFDTG YG                     342

SEQ ID NO: 254            moltype = AA   length = 342
FEATURE                   Location/Qualifiers
source                    1..342
                          mol_type = protein
                          organism = Brassica nigra
SEQUENCE: 254
MLKQESNWAQ ACDTCRSAAC TVYCRADSAY LCTSCDAQIH AANRLASRHE RVRVCESCER    60
APAAFFCKAD AASLCTACDS QIHSANPLAR RHQRVPILPI SGCVATNHHS SETTEPENIV   120
VVGQEEEDEA EAASWLLPSS VKNCGDNNNN TENNRFSVGE EYLDLVDYSS SIDKRFTGQT   180
NQYQQDYNVP QRSYVADGVV PLQVGVSKGH MHHEQHNFQF GFTNVSSEAH QISNGSPIHM   240
VSLVPESVTS DATVSHQRSP KAGTEELPEA PVQMLSPMER KARVLRYREK KKTRKFEKRI   300
RYASRKEYAE KRPRIKGRFA KRNEVDADQA FPTVVMFDTG YG                     342

SEQ ID NO: 255            moltype = AA   length = 335
FEATURE                   Location/Qualifiers
source                    1..335
                          mol_type = protein
                          organism = Brassica nigra
SEQUENCE: 255
MLKQESNWAQ ACDTCRSAAC TVYCRADSAY LCTSCDAQIH AANRLASRHE RVRVCESCER    60
APAAFFCKAD AASLCTACDS QIHSANPLAR RHQRVPILPI SGCVATNHSS ETAEPENIVV   120
VGQEEEDEAE AASWLLPSSV KNCGDNNNNS ENNRFSVGEE YLDLVDYSSS IDKRFTGQTN   180
QYQQDYNVPQ RSYVADGVVP LQVGVANGHM HHEQHNFQFG FTNVSSEASP IHMVSLVPES   240
VTSDATVSHP RSPKAGTEEL PEAPVQMLSP MERKARVLRY REKKKTRKFE KRIRYASRKE   300
YAEKRPRIKG RFAKRNEVDA DHALSTMVVF DTGYG                             335

SEQ ID NO: 256            moltype = AA   length = 338
FEATURE                   Location/Qualifiers
source                    1..338
                          mol_type = protein
                          organism = Brassica nigra
SEQUENCE: 256
MLKQESNWAQ ACDTCRSAAC TVYCRADSAY LCTSCDAQIH AANRLASRHE RVRVCESCER    60
APAAFFCKAD AASLCTACDS QIHSANPLAR RHQRVPILPI SGCVATNHHS SETTEPENIV   120
VVGQEEEDEA EAASWLLPSS VKNCGDNNNN NNSENNRFSV GEEYLDLVDY SSSMDKRFTG   180
QSNQYQQDYN VPQRSYVADG VVPLQVGVAN GHMHHEQHNF QFGFTNVSSE ASPIHMVSLV   240
PESVTSDATV SHPRSPKAGT EELPEAPVQM LSPMERKARV LRYREKKKTR KFEKRIRYAS   300
RKEYAEKRPR IKGRFAKRNE VDADHALSTM VVFDTGYG                          338

SEQ ID NO: 257            moltype = AA   length = 339
FEATURE                   Location/Qualifiers
source                    1..339
                          mol_type = protein
                          organism = Brassica nigra
SEQUENCE: 257
MLKQESNWAQ ACDTCRSAAC TVYCRADSAY LCTSCDAQIH AANRLASRHE RVRVCESCER    60
APAAFFCKAD AASLCTACDS QIHSANPLAR RHQRVPILPI SGCVATNHHS SETTEPENIV   120
VVGQEEEDEA EAASWLLPSS VKNCGDNNNN NNNSENNRFS VGEEYLDLVD YSSSMDKRFT   180
GQSNQYQQDY NVPQRSYVAD GVVPLQVGVA NGHMHHEQHN FQFGFTNVSS EASPIHMVSL   240
VPESVTSDAT VSHPRSPKAG TEELPEAPVQ MLSPMERKAR VLRYREKKKT RKFEKRIRYA   300
SRKEYAEKRP RIKGRFAKRN EVDADHALST MVVFDTGYG                         339

SEQ ID NO: 258            moltype = AA   length = 345
FEATURE                   Location/Qualifiers
source                    1..345
                          mol_type = protein
                          organism = Brassica nigra
```

```
SEQUENCE: 258
MLKQESNWAQ ACDTCRSAAC TVYCRADSAY LCTSCDAQIH AANRLASRHE RVRVCESCER    60
APAAFFCKAD AASLCTACDS QIHSANPLAR RHQRVPILPI SGCVATNHSS KTTEPENIVV   120
VGQEEEDEAE AASWLLPSSV KNCGDNNNNN NNNSENNRFS VGEEYLDLVD YSSSIDKRFT   180
GQSNQYQQDY NVPQRSYVAD GVVPLQVGVA NGHMHHEQHN FQFGFTNVSS EAHQISNGSP   240
IHMVSLVPES VTSDATVSHP RSPKAGTEEL PEAPVQMLSP MERKARVLRY REKKKTRKFE   300
KRIRYASRKE YAEKRPRIKG RFAKRNEVDA DHALSTMVVF DTGYG                   345

SEQ ID NO: 259          moltype = AA   length = 335
FEATURE                 Location/Qualifiers
source                  1..335
                        mol_type = protein
                        organism = Brassica nigra
SEQUENCE: 259
MLKQESNWAQ ACDTCRSAAC TVYCRADSAY LCTSCDAQIH AANRLASRHE RVRVCESCER    60
APAAFFCKAD AASLCTACDS QIHSANPLAR RHQRVPILPI SGCVATNHSS ETAEPENIVV   120
VGQEEEDEAE AASWLLPSSV KNCGDNNNNS ENNRFSVGEE YLDLVDYSSS IDKRFTGQTN   180
QYQQDYNVPQ RSYVADGVVP LQVGVANGHM HHEKHNFQFG FTNVSSEASP IHMVSLVPES   240
VTSDATVSHP RSPKAGTEEL PEAPVQMLSP MERKARVLRY REKKKTRKFE KRIRYASRKE   300
YAEKRPRIKG RFAKRNEVDA DHALSTMVVF DTGYG                              335

SEQ ID NO: 260          moltype = AA   length = 338
FEATURE                 Location/Qualifiers
source                  1..338
                        mol_type = protein
                        organism = Brassica nigra
SEQUENCE: 260
MLKQESNWAQ ACDTCRSAAC TVYCRADSAY LCTSCDAQIH AANRLASRHE RVRVCESCER    60
APAAFFCKAD AASLCTACDS QIHSANPLAR RHQRVPILPI SGCVATNHHS SETTEPENIV   120
VVGQEEEDEA EAASWLLPSS VKNCGDHNNN NNSENNRFSV SSSMDKRFTG              180
QSNQYQQDYN VPQRSYVADG VVPLQVGVAN GHMHHEKHNF QFGFTNVSSE ASPIHMVSLV   240
PESVTSDATV SHPRSPKAGT EELPEAPVQM LSPMERKARV LRYEKKKTR KFEKRIRYAS    300
RKEYAEKRPR IKGRFAKRNE VDADHALSTM VVFDTGYG                           338

SEQ ID NO: 261          moltype = AA   length = 339
FEATURE                 Location/Qualifiers
source                  1..339
                        mol_type = protein
                        organism = Brassica nigra
SEQUENCE: 261
MLKQESNWAQ ACDTCRSAAC TVYCRADSAY LCTSCDAQIH AANRLASRHE RVRVCESCER    60
APAAFFCKAD AASLCTACDS QIHSANPLAR RHQRVPILPI SGCVATNHSS KTTEPENIVV   120
VGQEEEDEAE AASWLLPSSV KNCGDNNNNN NNNSENNRFS VGEEYLDLVD YSSSIDKRFT   180
GQSNQYQQDY NVPQRSYVAD GVVPLQVGVA NGHMHHEQHN FQFGFTNVSS EASPIHMVSL   240
VPESVTSDAT VSHPRSPKAG TEELPEAPVQ MLSPMERKAR VLRYEKKKT RKFEKRIRYA    300
SRKEYAEKRP RIKGRFAKRN EVDADHALST MVVFDTGYG                          339

SEQ ID NO: 262          moltype = AA   length = 339
FEATURE                 Location/Qualifiers
source                  1..339
                        mol_type = protein
                        organism = Brassica nigra
SEQUENCE: 262
MLKQESNWAQ ACDTCRSAAC TVYCRADSAY LCTSCDAQIH AANRLASRHE RVRVCESCER    60
APAAFFCKAD AASLCTACDS QIHSANPLAR RHQRVPILPI SGCVATNHSS KTTEPENIVV   120
VGQEEEDEAE AASWLLPSSV KNCGDNNNNN NNNSENNRFS VGEEYLDLVD YSSSIDKRFT   180
GQSNQYQQDY NVPQRSYVAD GVVPLQVGVA NGHMHHEQHN FQFGFTNVSS EASPIHMVSL   240
VPESVTSDAT VSHPRSPKAG TEELPEAPVR MLSPMERKAR VLRYEKKKT RKFEKRIRYA    300
SRKEYAEKRP RIKGRFAKRN EVDADHALST MVVFDTGYG                          339

SEQ ID NO: 263          moltype = AA   length = 336
FEATURE                 Location/Qualifiers
source                  1..336
                        mol_type = protein
                        organism = Brassica nigra
SEQUENCE: 263
MLKQESNWAQ ACDTCRSAAC TVYCRADSAY LCTSCDAQIH AANRLASRHE RVRVCESCER    60
APAAFFCKAD AASLCTACDS QIHSANPLAR RHQRVPILPI SGCVATNHHS SETTEPENIV   120
VVGQEEEDEA EAASWLLPSS VKNCGDNNNN SENNRFSVGE EYLDLVDYSS SIDKRFTGQT   180
NQYQQDYNVP QRSYVADGVV PLQVGVANGH MHHEKHNFQF GFTNVSSEAS PIHMVSLVPE   240
SVTSDATVSH PRSPKAGTEE LPEAPVQMLS PMERKARVLR YREKKKTRKF EKRIRYASRK   300
EYAEKRPRIK GRFAKRNEVD ADHALSTMVV FDTGYG                             336

SEQ ID NO: 264          moltype = AA   length = 338
FEATURE                 Location/Qualifiers
source                  1..338
                        mol_type = protein
                        organism = Brassica nigra
SEQUENCE: 264
```

```
MLKQESNWAQ ACDTCRSAAC TVYCRADSAY LCTSCDAQIH AANRLASRHE RVRVCESCER    60
APAAFFCKAD AASLCTACDS QIHSANPLAR RHQRVPILPI SGCVATNHSS KTTEPENIVV   120
VGQEEEDEAE AASWLLPSSV KNCGDNNNNN NNSENNRFSV GEEYLDLVDY SSSIDKRFTG   180
QSNQYQQDYN VPQRSYVADG VVPLQVGVAN GHMHHEQHNF QFGFTNVSSE ASPIHMVSLV   240
PESVTSDATV SHPRSPKAGT EELPEAPVQM LSPMERKARV LRYREKKKTR KFEKRIRYAS   300
RKEYAEKRPR IKGRFAKRNE VDADHALSTM VVFDTGYG                          338

SEQ ID NO: 265          moltype = AA  length = 338
FEATURE                 Location/Qualifiers
source                  1..338
                        mol_type = protein
                        organism = Brassica nigra
SEQUENCE: 265
MLKQESNWAQ ACDTCRSAAC TVYCRADSAY LCTSCDAQIH AANRLASRHE RVRVCESCER    60
APAAFFCKAD AASLCTACDS QIHSANPLAR RHQRVPILPI SGCVATNHSS KTTEPENIVV   120
VGQEEEDEAE AASWLLPSSV KNCGDNNNNN NNSENNRFSV GEEYLDLVDY SSSIDKRFTG   180
QSNQYQQDYN VPQRSYVADG VVPLQVGVAN GHMHHEQHNF QFGFTNVSSE ASPIHMVSLV   240
PETVTSDATV SHPRSPKAGT EELPEAPVQM LSPMERKARV LRYREKKKTR KFEKRIRYAS   300
RKEYAEKRPR IKGRFAKRNE VDADHALSTM VVFDTGYG                          338

SEQ ID NO: 266          moltype = AA  length = 417
FEATURE                 Location/Qualifiers
source                  1..417
                        mol_type = protein
                        organism = Arabidopsis thaliana
SEQUENCE: 266
MMKSLANAVG AKTARACDSC VKRRARWYCA ADDAFLCQSC DSLVHSANPL ARRHERVRLK    60
TASPAVVKHS NHSSASPPHE VATWHHGFTR KARTPRGSGK KNNSSIFHDL VPDISIEDQT   120
DNYELEEQLI CQVPVLDPLL SEQFLNDVVE PKIEFPMIRS GLMIEEEEDN AESCLNGFFP   180
TDMELEEFAA DVETLLGRGL DTESYAMEEL ELSNSEMPKI EKDEIEEEVE EIKAMSMDIF   240
DDDRKDVDGT VPFELSFDYE SSHKTSEEEV MKNVESSGEC VVKVKEEEHK NVLMLRLNYD   300
SVISTWGGQG PPWSSGEPPE RDMDISGWPA FSMVENGGES THQKQYVGGC LPSSGFGDGG   360
REARVSRYRE KRRTRLFSKK IRYEVRKLNA EKRPRMKGRF VKRASLAAAA SPLGVNY     417

SEQ ID NO: 267          moltype = AA  length = 406
FEATURE                 Location/Qualifiers
source                  1..406
                        mol_type = protein
                        organism = Zea mays
SEQUENCE: 267
MVPLCGFCGK QRSMIYCRSD AASLCLSCDR SVHSANALSR RHRRTLLCDR CGLQPASVRC    60
LEDNTSLCQN CDWNGHDAAS GASGHKRQAI NCYSGCPSSA ELSRIWSFII DIPTVAAEPN   120
CEDGLSMMTI DDSDVTNHHG ASDDKRLLEI ANTALMSDPP SPDKLKPLIG SSSGDGFDVL   180
PLATDQPAGP VSATPKVPYA RDDNKFNDGM YEDLCVDDAD LTFENYEELF GTSHIRIEEL   240
FDDAGIDSYF EMKETPPFDF NEQPKIVQLQ CSDVVPADCA MSNTGERADS SLCIPVRQVR   300
SSISHPLSGL TGESSAGDHQ DCGVSPILLM GEPPWYSPGP EGSLAGGSRD SALTRYKEKK   360
KKRMFDKKIR YASRKARADV RKRVKGRFIK AGEAYDYDPL SQTRSY                 406

SEQ ID NO: 268          moltype = AA  length = 405
FEATURE                 Location/Qualifiers
source                  1..405
                        mol_type = protein
                        organism = Arabidopsis thaliana
SEQUENCE: 268
MKSLASAVGG KTARACDSCV KRRARWYCAA DDAFLCHACD GSVHSANPLA RRHERVRLKS    60
ASAGKYRHAS PPHQATWHQG FTRKARTPRG GKKSHTMVFH DLVPEMSTED QAESYEVEEQ   120
LIFEVPVMNS MVEEQCFNQS LEKQNEFPMM PLSFKSSDEE DDDNAESCLN GLFPTDMELA   180
QFTADVETLL GGGDREFHSI EELGLGEMLK IEKEEVEEEG VVTREVHDQD EGDETSPFEI   240
SPFDYEYTHKT TFDEGEEDEK EDVMKNVMEM GVNEMSGGIK EKKKEKALML RLDYESVIST   300
WGGQGIPWTA RVPSEIDLDM VCFPTHTMGE SGAEAHHHNH FRGLGLHLGD AGDGGREARV   360
SRYREKRRTR LFSKKIRYEV RKLNADKRPR MKGRFVKRSS IGVAH                  405

SEQ ID NO: 269          moltype = AA  length = 373
FEATURE                 Location/Qualifiers
source                  1..373
                        mol_type = protein
                        organism = Chrysanthemum X morifolium
SEQUENCE: 269
MLKQESNDIG SGENNRARPC DTCRSNACTV YCHADSAYLC TSCDAQVHSA NRVASRHKRV    60
RVCESCERAP AAFLCEADDA SLCTACDSEV HSANPLARRH QRVPILPISG NSFSSMTTTH   120
HQSEKTMTDP EKRLVVDQEE GEEGDKDAKE VASWLFPNSD KNNNNQNNGL LFSDEYLNLV   180
DYNSSMDYKF TGEYSQHQQN CSVPQTSYGG DRVVPLKLEE SRGHQCHNQQ NFQFNIKYGS   240
SGTHYNDNGS INHNAYISSM ETGVVPESTA CVTTASHPRT PKGTVEQQPD PASQMITVTQ   300
LSPMDREARV LRYREKRKTR KFEKTIRYAS RKAYAEIRPR VNGRFAKREI EAEEQGFNTM   360
LMYNTGYGIV PSF                                                    373

SEQ ID NO: 270          moltype = AA  length = 408
FEATURE                 Location/Qualifiers
source                  1..408
```

```
                        mol_type = protein
                        note = Oryza sativa Japonica Group
                        organism = Oryza sativa
SEQUENCE: 270
MGALCDFCGE QRSMVYCRSD AASLCLSCDR NVHSANALSR RHTRTLLCDR CASQPAMVRC    60
LVENASLCQN CDWNGHSAGS SAAGHKRQTI NCYSGCPSSS ELSKIWTFVS DIPNVAPEPN   120
CEQGISMMSI SDSGVSNQDN AAGDSSLLDI ASATLMSDLG TAGKPKSLIG SSSEAGVNLL   180
PLATDQMAGS VDSTSAKVPY TADQDMFSKD SIYEDFCVDD VDLSFENYEE LFGTSHIQTE   240
QLFDDAGIDS YFESKEIPSG NSDEQPKLMQ PVTSNAVSAD SGMSIPGAKG DSSLCIPVRQ   300
ARSSISLSFS GLTGESSAGD YQDCGVSPVL LMGEPPWHPP GPEGSFAGAT RDDAITRYKE   360
KKKRRKFDKK IRYASRKARA DVRKRVKGRF VKAGEAYDYD PLCETRSY                408

SEQ ID NO: 271          moltype = AA  length = 368
FEATURE                 Location/Qualifiers
source                  1..368
                        mol_type = protein
                        note = Hordeum vulgare subsp. vulgare
                        organism = Hordeum vulgare
SEQUENCE: 271
MNCNFNSDLL EKEAGRTSFP WARPCDGCHA APSAVYCCAD AAYLCSSCDT QVHSANRVAS    60
RHERVRVCET CESTPAVLAC HADAAALCTA CDAQVHSANP IAQRHQRVPV LPLPAVAIPA   120
ASGFAEAEAS VTAHGDKEGG EEVDSWLLRR NSDDNNCANK IDRYFNLVGY NMYYDNITCD   180
PRPQEQYRMQ EQQHVQNRYR EKEGCECVVP PQVVMASEQQ GSNYGTIGAG QAASVTAMAS   240
TYTASISNDI SFSSMEVGIV PDNTRPNISN RNILTSSEAI ELSGHSLQMP VHFSSMDREA   300
RVLRYKEKKQ ARKFQKTIRY ATRKAYAEAR PRIKGRFAKR SDIEHEENHM LSPPALPDTS   360
SYNTVPWF                                                            368

SEQ ID NO: 272          moltype = AA  length = 329
FEATURE                 Location/Qualifiers
source                  1..329
                        mol_type = protein
                        note = Hordeum vulgare subsp. vulgare
                        organism = Hordeum vulgare
SEQUENCE: 272
MIKAEPDLRG QLRGSAGVGG MQLQQRCDSC RSAPCAFYCR ADSAALCAAC DADVHSANTL    60
ASRHRRVPMG AVAPASPAGG AFVVRPGGVN SSWPIREGRR SYYDDREGEE EEATSWLLLD   120
PLRGSEADAP AFGDALVADF LDLGRAGEKE ASSKDYHGHG MESNEGSHDH ELVVPGEPVA   180
QLHERQGFTA EMAYDAQNSN HGYGFGATFE RSLSMSSSPD NSSTVQDVSS SYMRRSESSV   240
DLFSTAAHTS PQFMGMAMDR EARVHRYREK RKMRRFEKTI RYASRKAYAE TRPRIKGRFA   300
KRADADLEVD QYFSAAALSD SSCGVVPTF                                     329

SEQ ID NO: 273          moltype = AA  length = 329
FEATURE                 Location/Qualifiers
source                  1..329
                        mol_type = protein
                        note = Hordeum vulgare subsp. vulgare
                        organism = Hordeum vulgare
SEQUENCE: 273
MIKAEPDLRG QLRGSAGVGG MQLQQRCDSC RSAPCAFYCR ADSAALCAAC DADVHSANTL    60
ASRHRRVPMG AVAPASPAGG AFVVRPGGVN SSWPIREGRR SYYDDREGEE EEATSWLLLD   120
PLRGSEADAP AFGDALVADF LDLGRAGQKE ASSKDYHGHG MESNEGSHDH ELVVPGEPVA   180
QLHERQGFTA EMAYDAQNSN HGYGFGATFE RSLSMSSSPD NSSTVQDVSS SYMRRSESSV   240
DLFSTAAHTS PQFMGMAMDR EARVHRYREK RKMRRFEKTI RYASRKAYAE TRPRIKGRFA   300
KRADADLEVD QYFSAAALSD SSCGVVPTF                                     329

SEQ ID NO: 274          moltype = AA  length = 441
FEATURE                 Location/Qualifiers
source                  1..441
                        mol_type = protein
                        note = Oryza sativa Indica Group
                        organism = Oryza sativa
SEQUENCE: 274
MNYNFGGNVF DQEVGVGGEG GGGGEGSGCP WARPCDGCRA APSVVYCRAD AAYLCASCDA    60
RVHAANRVAS RHERVRVCEA CERAPAALAC RADAAALCVA CDVQHSANP LARRHQRVPV   120
APLPAITIPA TSVLAEAVVA TATVLGDKDE EVDSWLLLSK DSDNNNNNNN NNDNDNKDNN   180
NSNSSNNGMY FGEVDEYFDL VGYNSYYDNR IENNQDQQYG MHEQQEQQQQ QQEMQKEFAE   240
KEGSECVVPS QITMLSEQQH SGYGVVGADQ AASMTAGVSA YTDSISNSIS FSSMEAGIVP   300
DSTVIDMPNS RILTPAGAIN LFSGPSLQMS LHFSSMDREA RVLRYEKKKK ARKFEKTIRY   360
ETRRMQRHDP GSRAVSPRDQ MCRSKWTRCS PLQLYLTVAM VLFHGSDGTH ETLSYRHIYG   420
DLLSSNNIDP VGVVLDNLCY E                                             441

SEQ ID NO: 275          moltype = AA  length = 380
FEATURE                 Location/Qualifiers
source                  1..380
                        mol_type = protein
                        organism = Olea europaea
SEQUENCE: 275
MLKEKSRGVH GGNTSSHWAR ICDTCQSAVC TMYCRADSAY LCTGCDSRIH RTSPEASRHQ    60
RMWVCEACER APAAFLCKAD AASLCITCDS DIHSAQPLAR RHQRVPILPI PGMLCGTPSA   120
```

```
PYPSGLVMGP TGVAAKIEFL TQDEDQTIHE EEDEDEAASW PLFNHVKNIC NQSNNIGRFF      180
GGEVDEYLDL DEYNSYQDNQ FSNQDNNQLQ PYDVSQKSYG SDNVVPIQYG KSKDQIHNHG      240
FQLGREYEAS KNVYDNPASI SHTVSFSSLD VGVVPESTTS EVSVPHPRPP KGTIDLFSSP      300
PIPMPTQLSP MDREARVLRY REKKKARKFE KTIRYASRKA YAETRPRIKG RFAKRTDVRA      360
NQMFSSTLIE EGGYGIVPSF                                                 380

SEQ ID NO: 276           moltype = AA   length = 372
FEATURE                  Location/Qualifiers
source                   1..372
                         mol_type = protein
                         organism = Sinapis alba
SEQUENCE: 276
MLKPESYNIS NRENNRGARA CDTCQLTICT VYCHADSAYL CTSCDAQVHS ANRVASRHKR       60
VRVCESCERA PAAFMCEADD VSLCTACDSE VHSANPLARR HQRVPVVPIT GNSCSSLATH      120
HTTVTEPEKR AVLVQDDQEG KEDAKETASW MFPYSDKSNH NHNNNNNNQN NELLFSDGYL      180
DLADYNSSMD YKFTGQYNQH QNKQDCTVPQ TNYGGDRVVP LQLEETKGNL RHKEHNITYG      240
SSGSQYNYNG SINHNAYNPS VETDYVPEPT ARDTTVSHQK TPKGAIHKQP EPLIQILSPM      300
DREARVLRYR EKKKRRKFEK TIRYASRKAY AERRPRINGR FAKMSETEAE DQDFNTMLMY      360
YDTGYGIVPS FY                                                         372

SEQ ID NO: 277           moltype = AA   length = 330
FEATURE                  Location/Qualifiers
source                   1..330
                         mol_type = protein
                         organism = Arabidopsis thaliana
SEQUENCE: 277
MEARCDFCGT EKALIYCKSD SAKLCLNCDV NVHSANPLSQ RHTRSLLCEK CSLQPTAVHC       60
MNENVSLCQG CQWTASNCTG LGHRLQSLNP YSDCPSPSDF GKIWSSTLEP SVTSLVSPFS      120
DTLLQELDDW NGSSTSVVTQ TQNLKDYSSF FPMESNLPKV IEEECSGLDL CEGINLDDAP      180
LNFNASNDII GCSSLDNTKC YEYEDSFKEE NNIGLPSLLL PTLSGNVVPN MSLSMSNLTG      240
ESNATDYQDC GISPGFLIGD SPWESNVEVS FNPKLRDEAK KRYKQKKSKR MFGKQIRYAS      300
RKARADTRKR VKGRFVKSGE TFEYDPSLVM                                       330

SEQ ID NO: 278           moltype = AA   length = 444
FEATURE                  Location/Qualifiers
source                   1..444
                         mol_type = protein
                         organism = Populus trichocarpa
SEQUENCE: 278
MVTHKSKTKE TVPCDFCSEQ TAVLYCRADS AKLCLFCDQH VHSANLLSRK HVRSQICDNC       60
STEPVSFRCS TDNLVLCQEC DWDAHGSCSV SASHDRTTIE GFSGCPSALD LASIWGFDLE      120
EKKPEPLIEN WSNNSCGVIH DLVNEPWVYD KSSGNLTFQD LMVPNENNNN GNRNIDNSPS      180
CGKYKHVICK QLFELFKRDL IGGGVEGEGC GFGDGEGCGF GGGDGGGETL VTQSRSGWRS      240
GVKGVQFGNG NDGERISCVF NNDSGLLLLQ VWDFPHLGQLR NHDESGQLEI EYVANDAGFV      300
IKDFGELMKE TSSTSPKMLG DMYQMNCSTA HDDMTQGPAT SESNNLPIVR SGFSKPRCSS      360
SSNDVQFMEQ SILIRGEGLK MEAATKVDME LLARNRGDAM QRYKEKKKNR RYDKHIRYES      420
RKARADTRKR VKGRFVKTTE APDS                                             444

SEQ ID NO: 279           moltype = AA   length = 447
FEATURE                  Location/Qualifiers
source                   1..447
                         mol_type = protein
                         organism = Populus trichocarpa
SEQUENCE: 279
MICNKSLANA VGGRTARACD SCIKKRASWY CAADDAFLCQ ACDSSVHSAN LLARRHERVR       60
LKSASLKSSD AGSKENSMPS WHGGFTRKAR TPRHGKPVSR SKIEETTRNI PIPLVPEVGS      120
DEISLEDNEE EHLLYRVPIF DPFAAELCTS TTVSNEAGAV VPAGGTDTDQ RAADSSGTES      180
KVLLGGSEGK DVESLHGFLP SDMDLAEFAA DMESLLGRGL ENESFGMEEL GLMDCKEENE      240
LGVKGYPLGN GKVKVEEEED AGMEEKAVRE CHADIEIDIA KDPPFELSFD YDSPATCVEE      300
DEKVGIEEGD LKNSDGEYED DGGAKKKRRT LLSLDYEAVM TAWASQGSPW TNGYRPDFDA      360
DECWPDADCM GICGAQLHHP YGDVSGLGAH PAALVDGGRE ARVSRYREKR RTRLFSKKIR      420
YEVRKLNAEK RPRMKGRFVK RTTFAGK                                          447

SEQ ID NO: 280           moltype = AA   length = 393
FEATURE                  Location/Qualifiers
source                   1..393
                         mol_type = protein
                         organism = Populus trichocarpa
SEQUENCE: 280
MISGRKAANA MGGKTARACD SCLRKRARWF CVADDAFLCQ ACDASVHSAN QLASRHQRVR       60
LETASSYRIS SSLNTDQDYS PPAWHQGFTR KARTPRHNSN KSLLVQQLLK DDREKVLNPL      120
PLVPEIGSEE EPNMAPDENE DDQLLCRVPV FDPFAAKMCD IVTSEDENMV VEVYGQEGAC      180
GLDNLPGFLP SDMDLAEFAA DLLDCSKGED EGQFCFADKV VKMKDEQEME TIIDCHFDQD      240
FNMARESLLD EEVEEKKVPV PETEMMNSTG YKEMKRNVSL RLDYESVIIA WANQGCPWTT      300
GSRPELNPDD SWTDSMGACP KDVNNPYGGL GSHTRGGDGE REARVMRYKE KRRTRLFSKK      360
IRYEVRKLNA EKRPRMKGRF VKRTSLMGTT DFP                                   393

SEQ ID NO: 281           moltype = AA   length = 379
FEATURE                  Location/Qualifiers
```

```
source                       1..379
                             mol_type = protein
                             organism = Populus trichocarpa
SEQUENCE: 281
MGYVCDFCGE QRSMVYCRSD AASLCLSCDR NVHSANALSK RHSRTLLCER CNSQPALVRC    60
AEERISLCQN CDWIGHGTST SASTHRRQTI NSYSGCPSAS ELSSIWSFVL DFPSRGESTC   120
EQELGLMSIA ENSTTDSWGP TENTIGQNAS GVVEVNDRRE IAKSGVWLGS SSIPESSSVP   180
NNLDQTTRSA NTSLPKDFNM DEMDLSLENY EELFGVTLNN SEELLENGGI DSLFGTKDMS   240
VVNAVQPASS NAASADSMMS NKTEPILCFT EKQGHSSLSF SGLNVESSAA DYQDCGASSM   300
LLMGEPPWCP PCPESPFSSA NRSDAVMRYK EKKKTRMFEK KVRYASRKAR ADVRRRVKGR   360
FVKAGEAYDY DPLSQTRSF                                                379

SEQ ID NO: 282               moltype = AA length = 432
FEATURE                      Location/Qualifiers
source                       1..432
                             mol_type = protein
                             organism = Vitis vinifera
SEQUENCE: 282
MISEKNVANA VGGKTARACD SCIRKRARFY CAADDAFLCQ ACDMSVHSAN PLARRHERVR    60
LKTASLKLPG ADSLENSMPS WHQGFTRKAR TPRHGKPAAH PAFKSDELTR NPLPFVPEIG   120
ADETSYDDNE EQLLYRVPIF DPFVAELCAS TNSNEAVTTV ANDTETADVT GSETKALVAG   180
RGHDVDSLHG FLPSDMDLAE FAADVESLLG KGLDNESFGM EGLGLIDCKE KESVEYSLHS   240
GRVKLEEEED IGGVMACQAD AEIDMTREPF ELNFDYGSPA TCEEEEEKVA VGAMDMNNKV   300
DDPKKKNKIL LRLDYEAIIT AWASQGSPWT NGHRPELDPD DCWPDCLGTC GIQVHHPYGE   360
FGGMGEQQAA MGDGGREARV SRYREKRRTR LFSKKIRYEV RKLNAEKRPR MKGRFVKRAS   420
FGGPAAFPLL NK                                                       432

SEQ ID NO: 283               moltype = AA length = 474
FEATURE                      Location/Qualifiers
source                       1..474
                             mol_type = protein
                             organism = Vitis vinifera
SEQUENCE: 283
MVSPKPSNGE RVPCDFCSGQ IAVLYCRADS AKLCLFCDQH VHSANALSRK HLRSQICDNC    60
SSEPVSVRCS TDNMVLCQEC DWDAHGSCSV SAAHDRKPVE GFSGCPSAVQ LSSIWGLDIE   120
EKKAPLPPPP SMAVDSWVYK SNTLTFQDLM VPNGNAVAFP DALGGEVSKR QSPSCGKHKQ   180
VIFKQLVELF RRDLLAGNGG GGGIVGDDED DGGGGVCGGG ENLVTGWQGH VGESIGIENG   240
GVLDVDHQAL EQQTPFTSLL MLPNRATTGG VILWDNNPSD QSTQIWDFHL GHSRGYEECG   300
LLEAEYGVND AGFVIKSYSE LMKETSFTNT KVVGEMYDIN YSMTHEDITS FNNNSNNPTA   360
SQGAATSESN NLPIARPSSG SAFAKPKSFS GSKDIELTEQ SILMRGESGR TAATTKVDLE   420
QLAQNRGNAM LRYKEKKKTR RYDKHIRYES RKARADTRKR VKGRFVKATE APDG         474

SEQ ID NO: 284               moltype = AA length = 529
FEATURE                      Location/Qualifiers
source                       1..529
                             mol_type = protein
                             organism = Vitis vinifera
SEQUENCE: 284
METTSKSRPS AAVPCDFCDS KTAVVHCRAD SAKLCLLCDR HVHSANALSR KHLRSQICDN    60
CRTEPVSFRC FTDNLALCQS CDWDSHGNCS VPSLHERTPV ESFSGCPSPL ELASVFRVDL   120
KDGNWSSWNF GSVNVQDFVV PGENCYAGCG TKVEKNGISV VYEQLVDLIR SDVDVVRGDV   180
DGDGDEGEDG AELGPGTPGR CANMGNFQGV DLDNGDDEEL LRQQTPFTSL LMLPTPVDAR   240
DTGCGYGCAV EGDAMWDRGH LSYQAPQSQI WDFHLGRSRI CKETSPEAGY DVDNSGFVIK   300
NYSEITKGSS LTRTKALQGM YEMNCTTTHE DILSKNCPLG HGSMIYSKTG GLGTPLNHVA   360
ICKGLEFCSC CPFEKHTSHY CCEFSEDTGT PDGGNGIGVI VAPFLKNVNK QRLYSHSNKA   420
LSSQGPTTAE SNNIPIVGPS SESWTAEPNT NSIKSMQFKD LLIGSGTART ETTNVDMELL   480
AQNRGHAMLR YKEKKKTRRY EKHIRYESRK ARADTRKRVK GRFVKASDS              529

SEQ ID NO: 285               moltype = AA length = 391
FEATURE                      Location/Qualifiers
source                       1..391
                             mol_type = protein
                             organism = Vitis vinifera
SEQUENCE: 285
MLKDEGCNAD AAAGGGGWA RVCDTCRSAA CTIYCRADSA YLCAGCDARI HAANRVASQH     60
ERVWVCESCE RAPAAFVCKA DAASLCATCD ADIHSANPLA RRHHRVPVLP IAGCLYGPPA   120
TDPGGTVVRS AAEEADNGFLG QEAEETIDEE DEDEAASWLL LNPVKNNNGS SNNQNNGLLF   180
GGEVDEYLDL VEYNSCPENQ FSDQYNQQQP PPHYSVPHHN YGGEAKGQLHQ CGEAKGQLHQ   240
QHQQQGFHLG MEYESSKAAY SYNPSISHSV SVSSMDVGVV PEATTMSDIS ISISHPRPPK   300
GTIDLFSGPP IQMPTQLTPM DREARVLRYR EKKKTRKFEK TIRYASRKAY AETRPRIKGR   360
FAKRTDVEVE VDQMFSTTLM AESGYGIVPS F                                 391

SEQ ID NO: 286               moltype = AA length = 410
FEATURE                      Location/Qualifiers
source                       1..410
                             mol_type = protein
                             organism = Vitis vinifera
SEQUENCE: 286
MITDKKVANA MGGKTARACD NCLHKRARWY CGADDAFLCQ ACDASVHSAN QLAERHERVR    60
```

```
LQAASCKNAD SMRDNSTPAW HQGFTRKARS PRNVKRTSVQ PSKHENKFPT PPPLVPEIGS    120
EEASPDENEE QFLFRVPTFD PFVAELNNDG IREIGMENDS KPLSDYGHEE IGDLDSLTGF    180
LPSEMDLAEF AADVESYLGA GLDEDSCGIK GIGVLDCEQG DMDACFGDQK VKVKEERVET    240
DATFHLDPEL DMTKELLAWN LDYESTVMDE EEHEEKMVAA VEMRRKISLS LNYEDVITAW    300
ASQGSPWTTG NRPEFDPNDY WPDYMGACPT NVHGPCGDVG GVGGNFGGRD GGREARVLRY    360
REKRRTRLFS KKIRYEVRKL NAEKRPRMKG RFVKRASFAA GPCFPILNVK               410

SEQ ID NO: 287           moltype = AA  length = 401
FEATURE                  Location/Qualifiers
source                   1..401
                         mol_type = protein
                         organism = Vitis vinifera
SEQUENCE: 287
MGQLCDFCGD QRSMVYCRSD AACLCLSCDR NVHSANALSR RHSRTLLCER CNSQPATVRC    60
VEEKISLCQN CNWIGHGSTT SASDHKRQTI NCYSGCPSAA ELSRIWSFVL EFLSVDDSNC    120
EQGMVLMSLT ENSVGSCSLP PVNNNINDST VAGRTNAQEN VDKSDLWMAS SPVPALNPIS    180
SSVDQPTDLV NSPTTKLCCS GICDDDDLLY EDFSMADVDL SIENYEELFG VSQNHSEQLL    240
ENGGIDSLFG IGNLPAGSCQ EPLTMQPACS NPISADSIIS SKTDPNLCFP PRQAHSSLSL    300
SFSGLTGESS TGDYQDCGVS SMLLMGEPPW CSPCPENSLP SANRDSAVLR YKEKKKARKF    360
EKKIRYASRK ARADVRKRVK GRFVKAGDAY DYDPLNQTRS F                        401

SEQ ID NO: 288           moltype = AA  length = 410
FEATURE                  Location/Qualifiers
source                   1..410
                         mol_type = protein
                         note = Solanum tuberosum subsp. andigena
                         organism = Solanum tuberosum
SEQUENCE: 288
MLKKEKSGGF DGSSNNWARV CDSCHSATCT VYCRADSAYL CAGCDSRIHA ASLMASRHER    60
VWVCEACERA PAAFLCKADA ASLCASCDAD IHSANPLARR HHRVPIMPIP GTLYGPPAVH    120
TVSGGSMMIG GTTGEGTEDD GFLSLTQDAD DTTIDEEDEN EAASWLLLNP PVKNNNKNNI    180
NNNNNNQNNN YGMLFGGEVV DDYLDLAEYG GDSQFNDQYS VNQQQQRYSV PQKSYVEDSV    240
VPVQNGQRKS LILYHQPQQQ QQQSHHLNFQ LGMEYDNSNT GYGYPASLSH SVSISSMDVS    300
VVPESALSET SNSHPRPPKG TIDLFSGPPI QIPPQLTPMD REARVLRYRE KKKNRKFEKT    360
IRYASRKAYA ETRPRIKGRF AKRTDVEAEV DQMFSTQLMT DSSYGIVPSF               410

SEQ ID NO: 289           moltype = AA  length = 413
FEATURE                  Location/Qualifiers
source                   1..413
                         mol_type = protein
                         organism = Zea mays
SEQUENCE: 289
MTSAGAATGA ALGARTARSC DGCMRRRARW HCPADDAFLC QTCDVSVHSA NPLARRHHRV    60
RLPSASCSSP PRDPDAPTWL HGLKRRPRTP RSKPGGSKSN KHEATPSFIA AAASSAAVPD    120
LEAEESGSGI LGGNDDHHGF LQDDDEDLLY RVPVFDPMLA EFYNPVADEG EQKPACSLLM    180
PSLAETSPEF ASGGSAEADG LSVSFHVPDM ELASFAADME SLLMGVDDDG FDCLGFLDEE    240
KPQVNADLDA IVAPAPEPED KKRKRPEMIL KLNYEGVIAS WVRDGGSPWF HGERPHLDCH    300
ELWSDDFTTG SRELLGGAVT PVTGGEREAR VSRYREKRRT RLFAKKIRYE VRKLNAEKRP    360
RMKGRFVKRA TLPPLPRPPP PQQQQQQKQL PRAPPHVGMV LPPPPPVSNGR LWF          413

SEQ ID NO: 290           moltype = AA  length = 452
FEATURE                  Location/Qualifiers
source                   1..452
                         mol_type = protein
                         organism = Zea mays
SEQUENCE: 290
MIATTRGSSA KAAAAVGGKA ARACDGCLRR RARWYCAADD AFLCQGCDTS VHSANPLARR    60
HERLRLCPAS PLQTPPDRSA AAAATATNKR ERHDEVAVPA WFGRKARTPR GGHAKSVGQV    120
ALSRRLVVPH AAGGSDSPD ERNGGEEEQL LYRVPILDPA LAEFCSPPPL EDAAGLALDA    180
SVCNEDGAIE DPAKPDPAAP LAQFCPVSGH FNFGPTDAEL REFAADMEAL LGHGLDDGNE    240
EDSSFYMETL GLLDPMEVGD DATQVKVETD GSSACCEASG TLACGLELDL EASDEMLDID    300
FDYASPQDTA TDERAASSDT GADAQFLQTS LSLTLNYEAI IQSWGSSPWT GGGERPHVKL    360
DTRWPHDYTN MWVVGGVVGH GGEDLPGTPR LGMDGGREAR VSRYREKRRT RLFSKKIRYE    420
VRKLNAEKRP RMKGRFVKRA TAGGSLAIAG LA                                  452

SEQ ID NO: 291           moltype = AA  length = 364
FEATURE                  Location/Qualifiers
source                   1..364
                         mol_type = protein
                         organism = Zea mays
SEQUENCE: 291
MELHKYWGVG GRRCGSCEGA PAAVHCRTCV GGSFLCTTCD ARPAHARLGH ERVWMCEVCE    60
LAPAAVTCKA DAAVLCAACD SDIHDANPLA RRHARVPVAP IGSEAAAAAV EAMLFGTGEA    120
AASEADEQHA AAEHAHAHAL NLNVEAKDMK LDYLFSELDP YLSVEIPRFQ HADSVVPNGA    180
GAAVELDFTC GIGVKHSSYS SYTATSLAHS GSSSEVGVVP EAFGGSGSGG GSFELDFTRP    240
KPQAYMPYTG TPQSHSVPSA DVEVVPERGD LAAVRPVPLM GESREARLMR YREKRKNRRF    300
EKTIRYASRK AYAETRPRIK GRFAKRADHD GDADADDAEA EAEAEAAVPM SYVLDFGYGV    360
VPSF                                                                 364
```

```
SEQ ID NO: 292            moltype = AA   length = 407
FEATURE                   Location/Qualifiers
source                    1..407
                          mol_type = protein
                          organism = Zea mays
SEQUENCE: 292
MGALCDFCGE QRSMVYCRSD AASLCLSCDR NVHSANALSR RHTRTLLCDR CASQPAMVRC    60
LAENASLCQN CDWNGHIAGS SSAGHKRQTI NCYSGCPSSA ELSRIWSFVS DIPNVAPEPN   120
CEQGISMMSI SDSGVSNQDN AAGDSILLDI ASATLVSDIG TCDKLLVGSS SGAGVNLLPL   180
VTGQTETAGS VDSTPDKVPY TPDKDMFSKD SIYEDFCVDD ADLAFENYEE LFGTSHIQTE   240
QLFDDAGIDI YFEMKEAPAG NSTESKLKQP ANSNAVSADS GMSNPGVKGD SSVCTPLRQA   300
RSSLSLSFAG LTGESSAGDN QDCVVSSLLL MGEPPWQPPG PEGSIAGGSR DSALTRYKEK   360
KMRRKFDKKI RYASRKARAD VRKRVKGRFV KAGEAYDYDP LCQTRSY                 407

SEQ ID NO: 293            moltype = AA   length = 456
FEATURE                   Location/Qualifiers
source                    1..456
                          mol_type = protein
                          organism = Zea mays
SEQUENCE: 293
MIATTTTGSS AKAAAVGGKE ARACDACLRR RARWYCAADD AFLCQACDTS VHSANSLARR    60
HERLRLRPTS PLQTPPPPTP ASAKRESHDE VVPAWFKRKA RTPRGGRAKS DVRTLSRRLV   120
VPHAAGGDSP DGRNDEGEFE AEEPEEEVLY RVPVFDPALA EFCSPQPLED AAALASSCNE   180
DGAVEDPAKT DRETPAAAPL VQFFPDGGHA NFGPTDAELR EFAADMEALL GYGLDDGNEE   240
SSSFCMETLG LLEPVEVGED ASRVKVETDA GSACEASGTL ACALELLDPD ASDEMLDIDF   300
NYGSPQDTTT TENAASSSHT GTDGQFLQTS LSLTLNYEAI IQSWGSSPWT GGAERPHVKL   360
DDSWPHDCTN MWVVGRGMVG HGGEDLLGTP RLGQGMDDVG REARVSRYRE KRRTRLFSKK   420
IRYEVRKLNA EKRPRMKGRF VKRATAGGSL TIAGLA                             456

SEQ ID NO: 294            moltype = AA   length = 348
FEATURE                   Location/Qualifiers
source                    1..348
                          mol_type = protein
                          organism = Brassica nigra
SEQUENCE: 294
MLKQESNWAQ ACDTCRSAAC TVYCRADSAY LCTSCDAQIH AANRLASRHE RVRVCESCER    60
APAAFFCKAD AASLCTACDS QIHSANPLAR RHQRVPILPI SGCVATNHHS SETTEPENIV   120
VVGQEEEDEA EAASWLLPSS VKNCGDNNNN TENNRFSVGE EYLDLVDYSS SIDKRFTGQT   180
NQYQQDYNVP QRSYVADGVV PLQVGVSKGH MHHEQHNFQF GFTNVSSEAH QISNGSPIHM   240
VSLVPESVTS DATVSHQRSP KAGTEELPEA PVQMLSPMER KARVLRYREK KKTRKFEKRI   300
RYASRKEYAE KRPRIKGRFA KRNEVDADQA FPTVVMFDTG YGIVPSFS                348

SEQ ID NO: 295            moltype = AA   length = 348
FEATURE                   Location/Qualifiers
VARIANT                   321
                          note = X can be any naturally occurring amino acid
source                    1..348
                          mol_type = protein
                          organism = Brassica nigra
SEQUENCE: 295
MLKQESNWAQ ACDTCRSAAC TVYCRADSAY LCTSCDAQIH AANRLASRHE RVRVCESCER    60
APAAFFCKAD AASLCTACDS QIHSANPLAR RHQRVPILPI SGCVATNHHS SETTEPENIV   120
VVGQEEEDEA EAASWLLPSS VKNCGDNNNN TENNRFSVGE EYLDLVDYSS SIDKRFTGQT   180
NQYQQDYNVP QRSYVADGVV PLQVGVSKGH MHHEQHNFQF GFTNVSSEAH QISNGSPIHM   240
VSLVPESVTS DATVSHQRSP KAGTEELPEA PVQMLSPMER KARVLRYREK KKTRKFEKRI   300
RYASRKEYAE KRPRIKGRFA XRNEVDADQA FPTVVMFDTG YGIVPSFS                348

SEQ ID NO: 296            moltype = AA   length = 348
FEATURE                   Location/Qualifiers
source                    1..348
                          mol_type = protein
                          organism = Brassica nigra
SEQUENCE: 296
MLKQESNWAQ ACDTCRSAAC TVYCRADSAY LCTSCDAQIH AANRLASRHE RVRVCESCER    60
APAAFFCKAD AASLCTACDS QIHSANPLAR RHQRVPILPI SGCVATNHHS SETTEPENIV   120
VVGQEEEDEA EAASWLLPSS VKNCGDNNNN TENNRFSVGE EYLDLVDYSS SIDKRFTGQT   180
NQYQQDYNVP QRSYVADGVV PLQVGVSKGH MHHEQHNFQF GFTNVSSEAH QISNGSPIHM   240
VSLVPESVTS DATVSHQRSP KAGTEELPEA PVQMLSPMER KARVLRYREK KKTRKFEKRI   300
RYASRKEYAE KRPRIKGRFA KRNEVDADQA FPTVVMFDTG YGIVPSFS                348

SEQ ID NO: 297            moltype = AA   length = 348
FEATURE                   Location/Qualifiers
source                    1..348
                          mol_type = protein
                          organism = Brassica nigra
SEQUENCE: 297
MLKQESNWAQ ACDTCRSAAC TVYCRADSAY LCTSCDAQIH AANRLASRHE RVRVCESCER    60
APAVFFCQAD AASLCTACDS QIHSANPLAR RHQRVPILPI SGCVATNHHS SETTEPENIV   120
VVGQEEEDEA EAASWLLPSS VKNCGDNNNN TENNRFSVGE EYLDLVDYSS SIDKRFTGQT   180
```

```
NQYQQDYNVP QRSYVADGVV PLQVGVSKGH MHHEQHNFQF GFTNVSSEAH QISNGSPIHM    240
VSLVPESVTS DATVSHQRSP KAGTEELPEA PVQMLSPMER KARVLRYREK KKTRKFEKRI    300
RYASRKEYAE KRPRIKGRFA KRNEVDADQA FPTVVMFDTG YGIVPSFS                348

SEQ ID NO: 298          moltype = AA   length = 342
FEATURE                 Location/Qualifiers
source                  1..342
                        mol_type = protein
                        organism = Brassica nigra
SEQUENCE: 298
MLKQESNWAQ ACDTCRSAAC TVYCRADSAY LCTSCDAQIH AANRLASRHE RVRVCESCER    60
APAAFFCKAD AASLCTACDS QIHSANPLAR RHQRVPILPI SGCVATNHHS SETTEPENIV    120
VVGQEEEDEA EAASWLLPSS VKNCGDNNNN TENNRFSVGE EYLDLVDYSS SIDKRFTGQT    180
NQYQQDYNVP QRSYVADGVV PLQVGVANGH MHHEKHNFQF GFTNVSSEAS PIHMVSLVPE    240
SVTSDATVSH PRSPKAGTEE LPEAPVQMLS PMERKARVLR YREKKKTRKF EKRIRYASRK    300
EYAEKRPRIK GRFAKRNEVD ADHALSTMVM FDTGYGIVPS FS                      342

SEQ ID NO: 299          moltype = AA   length = 342
FEATURE                 Location/Qualifiers
source                  1..342
                        mol_type = protein
                        organism = Brassica nigra
SEQUENCE: 299
MLKQESNWAQ ACDTCRSAAC TVYCRADSAY LCTSCDAQIH AANRLASRHE RVRVCESCER    60
APAAFFCKAD AASLCTACDS QIHSANPLAR RHQRVPILPI SGCVATNHHS SETTEPENIV    120
VVGQEEEDEA EAASWLLPSS VKNCGDNNNN TENNRFSVGE EYLDLVDYSS IIDKRFTGQT    180
NQYQQDYNVP QRSYVADGVV PLQVGVANGH MHHEKHNFQF GFTNVSSEAS PIHMVSLVPE    240
SVTSDATVSH PRSPKAGTEE LPEAPVQMLS PMERKARVLR YREKKKTRKF EKRIRYASRK    300
EYAEKRPRIK GRFAKRNEVD ADHALSTMVM FDTGYGIVPS FS                      342

SEQ ID NO: 300          moltype = AA   length = 345
FEATURE                 Location/Qualifiers
source                  1..345
                        mol_type = protein
                        organism = Brassica nigra
SEQUENCE: 300
MLKQESNWAQ ACDTCRSAAC TVYCRADSAY LCTSCDAQIH AANRLASRHE RVRVCESCER    60
APAAFFCKAD AASLCTACDS QIHSANPLAR RHQRVPILPI SGCVATNHSS ETTEPENIVV    120
VGQEEEDEAE AASWLLPSSV KNCGDNNNNN NNSENNRFS VGEEYLDLVD YSSSIDKRFT     180
GQSNQYQQDY NVPQRSYVAD GVVPLQVGVA NGHMHHEQHN FQFGFTNVSS EASPIHMVSL    240
VPESVTSDAT VSHPRSPKAG TEELPEAPVQ MLSPMERKAR VLRYREKKKT RKFEKRIRYA    300
SRKEYAEKRP RIKGRFAKRN EVDADHALST MVVFDTGYGI VPSFS                   345

SEQ ID NO: 301          moltype = AA   length = 345
FEATURE                 Location/Qualifiers
source                  1..345
                        mol_type = protein
                        organism = Brassica nigra
SEQUENCE: 301
MLKQESNWAQ ACDTCRSAAC TVYCRADSAY LCTSCDAQIH AANRLASRHE RVRVCESCER    60
APAAFFCKAD AASLCTACDS QIHSANPLAR RHQRVPILPI SGCVATNHSS KTTEPENIVV    120
VGQEEEDEAE AASWLLPSSV KNCGDNNNNN NNSENNRFS VGEEYLDLVD YSSSIDKRFT     180
GQSNQYQQDY NVPQRSYVAD GVVPLQVGVA NGHMHHEQHN FQFGFTNVSS EASPIHMVSL    240
VPESVTSDAT VSHPRSPKAG TEELPEAPVQ MLSPMERKAR VLRYREKKKT RKFEKRIRYA    300
SRKEYAEKRP RIKGRFAKRN EVDADHALST MVVFDTGYGI VPSFS                   345

SEQ ID NO: 302          moltype = AA   length = 345
FEATURE                 Location/Qualifiers
source                  1..345
                        mol_type = protein
                        organism = Brassica nigra
SEQUENCE: 302
MLKQESNWAQ ACDTCRSAAC TVYCRADSAY LCTSCDAQIH AANRLASRHE RVRVCESCER    60
APAAFFCKAD AASLCTACDS QIHSANPLAR RHQRVPILPI SGCVATNHSS KTTEPENIVV    120
VGQEEEDEAE AASWLLPSSV KNCGDNNNNN NNSENNRFS VGEEYLDLVD YSSSIDKRFT     180
GQSNQYQQDY NVPQRSYVAD GVVPLQVGVA NGHMHHEQHN FQFGFTNVSS EASPIHMVSL    240
VPESVTSDAT VSHPRSPKAG TEELPEAPVQ MLSPMERKAR VLRYREKKKT RKFEKRIRYA    300
SRKEYAEKRP RIKGRFAKRN EVDADQALST MVVFDTGYGI VPSFS                   345

SEQ ID NO: 303          moltype = AA   length = 342
FEATURE                 Location/Qualifiers
VARIANT                 15
                        note = X can be any naturally occurring amino acid
VARIANT                 31
                        note = X can be any naturally occurring amino acid
VARIANT                 40
                        note = X can be any naturally occurring amino acid
VARIANT                 113
                        note = X can be any naturally occurring amino acid
```

```
VARIANT                    315
                           note = X can be any naturally occurring amino acid
source                     1..342
                           mol_type = protein
                           organism = Brassica nigra
SEQUENCE: 303
MLKQESNWAQ ACDTXRSAAC TVYCRADSAY XCTSCDAQIX AANRLASRHE RVRVCESCER    60
APAAFFCKAD AASLCTACDS QIHSANPLAR RHQRVPILPI SGCVATNHHS SEXTEPENIV   120
VVGQEEEDEA EAASWLLPSS VKNCGDNNNN TENNRFSVGE EYLDLVDYSS SIDKRFTGQT   180
NQYQQDYNVP QRSYVADGVV PLQVGVANGH MHHEKHNFQF GFTNVSSEAS PIHMVSLVPE   240
SVTSDATVSH PRSPKAGTEE LPEAPVQMLS PMERKAVLR YREKKKTRKF EKRIRYASRK    300
EYAEKRPRIK GRFAXRNEVD ADHALSTMVM FDTGYGIVPS FS                      342

SEQ ID NO: 304             moltype = AA   length = 345
FEATURE                    Location/Qualifiers
source                     1..345
                           mol_type = protein
                           organism = Brassica nigra
SEQUENCE: 304
MLKQESNWAQ ACDTCRSAAC TVYCRADSAY LCTSCDAQIH AANRLASRHE RVRVCESCER    60
APAAFFCKAD AASLCTACDS QIHSANPLAR RHQRVPILPI SGCVATNHHS SETTEPENIV   120
VVGQEEEDEA EAASWLLPSS VKNCGDNNNN NNNSENNRFS VGEEYLDLVD YSSSMDKRFT   180
GQSNQYQQDY NVPQRSYVAD GVVPLQVGVA NGHMHHEQHN FQFGFTNVSS EASPIHMVSL   240
VPESVTSDAT VSHPRSPKAG TEELPEAPVQ MLSPMERKAR VLRYEKKKT RKFEKRIRYA    300
SRKEYAEKRP RIKGRFAKRN EVDADHALST MVVFDTGYGI VPSFS                   345

SEQ ID NO: 305             moltype = AA   length = 348
FEATURE                    Location/Qualifiers
source                     1..348
                           mol_type = protein
                           organism = Brassica nigra
SEQUENCE: 305
MLKQESNWAQ ACDTCRSAAC TVYCRADSAY LCTSCDAQIH AANRLASRHE RVRVCESCER    60
APAAFFCKAD AASLCTACDS QIHSANPLAR RHQRVPILPI SGCVATNHHS SETTEPENIV   120
VVGQEEEDEA EAASWLLPSS VKNCGDNNNN NNNNNISENN RFSVGEEYLD LVDYSSSIDK   180
RFTGQTNQYQ QDYNVPQRSY VADGVVPLQV GVANGHMHHE KHNFQFGFTN VSSEASPIHM   240
VSLVPESVTS DATVSHPRSP KAGTEELPEA PVQMLSPMER KARVLRYREK KKTRKFEKRI   300
RYASRKEYAE KRPRIKGRFA KRNEVDADHA LSTMVMVDTG YGIVPSFS                348

SEQ ID NO: 306             moltype = AA   length = 342
FEATURE                    Location/Qualifiers
VARIANT                    177
                           note = X can be any naturally occurring amino acid
source                     1..342
                           mol_type = protein
                           organism = Brassica nigra
SEQUENCE: 306
MLKQESNWAQ ACDTCRSAAC TVYCRADSAY LCTSCDAQIH AANRLASRHE RVRVCESCER    60
APAAFFCKAD AASLCTACDS QIHSANPLAR RHQRVPILPI SGCVATNHHS SETTEPENIV   120
VVGQEEEDEA EAASWLLPSS VKNCGDNNNN TENNRFSVGE EYLDLVDYSS SIDKRFXGQT   180
NQYQQDYNVP QRSYVADGVV PLQVGVANGH MHHEKHNFQF GFTNVSSEAS PIHMVSLVPE   240
SVTSDATVSH PRSPKAGTEE LPEAPVQMLS PMERKARVLR YREKKKTRKF EKRIRYASRK   300
EYAEKRPRIK GRFAKRNEVD ADHALSTMVM FDTGYGIVPS FS                      342

SEQ ID NO: 307             moltype = AA   length = 344
FEATURE                    Location/Qualifiers
source                     1..344
                           mol_type = protein
                           organism = Brassica nigra
SEQUENCE: 307
MLKQESNWAQ ACDTCRSAAC TVYCRADSAY LCTSCDAQIH AANRLASRHE RVRVCESCER    60
APAAFFCKAD AASLCTACDS QIHSANPLAR RHQRVPILPI SGCVATNHHS SETTEPENIV   120
VVGQEEEDEA EAASWLLPSS VKNCGDHNNN NNSENNRFSV GEEYLDLVDY SSSMDKRFTG   180
QSIQYQQDYN VPQRSYVADG VVPLQVGVAN GHMHHKKHNF QFGFTNVSSE ASPIHMVSLV   240
PESVTSDATV SHPRSPKAGT EELPEAPVQM LSPMERKARV LRYEKKKTR KFEKRIRYAS    300
RKEYAEKRPR IKGRFAKRNE VDADHALSTM VVFDTGYGIV PSFS                    344

SEQ ID NO: 308             moltype = AA   length = 342
FEATURE                    Location/Qualifiers
source                     1..342
                           mol_type = protein
                           organism = Brassica nigra
SEQUENCE: 308
MLKQESNWAQ ACDTCRSAAC TVYCRADSAY LCTSCDAQIH AANRLASRHE RVRVCESCER    60
APAAFFCKAD AASLCTACDS QIHSANPLAR RHQRVPILPI SGCVATNHHS SETTEPENIV   120
VVGQEEEDEA EAASWLLPSS VKNCGDNNNN TENNRFSVGE EYLDLVDYSS SIDKRFTGQT   180
NQYQQDYNVP QRSYVADGVV PLQVGVANGH MHHEKHNFQF GFTNVSSEAS PIHMVSLVPE   240
SVTSDATVSH PRSPKAGTEE LPEAPVQMLS PMERKARVLR YREKKKTRKF EKRIRYASRK   300
EYAEKRPRIK GRFAKRNEVD ANHALSTMVM SDTGYGIVPS FS                      342
```

```
SEQ ID NO: 309            moltype = AA  length = 345
FEATURE                   Location/Qualifiers
VARIANT                   344
                          note = X can be any naturally occurring amino acid
source                    1..345
                          mol_type = protein
                          organism = Brassica nigra
SEQUENCE: 309
MLKQESNWAQ ACDTCRSAAC TVYCRADSAY LCTSCDAQIH AANRLASRHE RVRVCESCER    60
APAAFFCKAD AASLCTACDS QIHSANPLAR RHQRVPILPI SGCVATNHSS KTTEPENIVV   120
VGQEEEDEAE AASWLLPSSV KNCGDNNNNN NNNSENNRFS VGEEYLDLVD YSSSIDKRFT   180
GQSNQYQQDY NVPQRSYVAD GVVPLQVGVA NGHMHHEQHN FQFGFTNVSS EASPIHMVSL   240
VPESVTSDAT VSHPRSPKAG TEELPEAPVQ MLSPMERKAR VLRYREKKKT RKFEKRIRYA   300
SRKEYAEKRP RIKGRFAKRN EVDADHALST MVVFDTGYGI VPSXS                  345

SEQ ID NO: 310            moltype = AA  length = 345
FEATURE                   Location/Qualifiers
source                    1..345
                          mol_type = protein
                          organism = Brassica nigra
SEQUENCE: 310
MLKQESNWAQ ACDTCRSAAC TVYCRADSAY LCTSCDAQIH AANRLASRHE RVRVCESCER    60
APAAFFCKAD AASLCTACDS QIHSANPLAR RHQRVPILPI SGCVATNHSS KTTEPENIVV   120
VGQEEEDEAE AASWLLPSSV KNCGDNNNNN NNNSENNRFS VGEEYLDLVD YSSSIDKRFT   180
GQSNQYQQDY NVPQRSYVAD GVVPLQVGVA NGHMHHEQHN FQFGFTNVSS EASPIHMVSL   240
VPESVTSDAT VSHPRSPKAG TEELPEAPVQ MLSPMERKAR VLRYREKKKT RKFEKRIRYA   300
SRKEYAEKRP RIKGRFAKRN EVDADHALST MVMFDTGYGI VPSFS                  345

SEQ ID NO: 311            moltype = AA  length = 345
FEATURE                   Location/Qualifiers
source                    1..345
                          mol_type = protein
                          organism = Brassica nigra
SEQUENCE: 311
MLKQESNWAQ ACDTCRSAAC TVYCRADSAY LCTSCDAQIH AANRLASRHE RVRVCESCER    60
APAAFFCKAD AASLCTACDS QIHSANPLAR RHQRVPILPI SGCVATNHSS KTTEPENIVV   120
VGQEEEDEAE AASWLLPSSV KNCGDNNNNN NNNSENNRFS VGEEYLDLVD YSSSIDKRFT   180
GLSNQYQQDY NVPQRSYVAD GVVPLQVGVA NGHMHHEQHN FQFGFTNVSS EASPIHMVSL   240
VPESVTSDAT VSHPRSPKAG TEELPEAPVQ MLSPMERKAR VLRYREKKKT RKFEKRIRYA   300
SRKEYAEKRP RIKGRFAKRN EVDADHALST MVVFDTGYGI VPSFS                  345

SEQ ID NO: 312            moltype = AA  length = 420
FEATURE                   Location/Qualifiers
source                    1..420
                          mol_type = protein
                          organism = Sorghum bicolor
SEQUENCE: 312
MTTSAGAAAG AALGARTARS CDGCMRRRAR WHCPADDAFL CQTCDVSVHS ANPLARRHHR    60
VRLPSASCSS PPCDPDAPTW LHGLKRRPRT PRSKPGGGKH EATTPNSMAA AASAAVPDLE   120
AEESGSGIVG DNDDHGFLVD DDEDLLYRVP VFDPMLAEFY NPVADEGEQK PLAEFYNLVA   180
DEGEQKPACL MPPLVETSPE FASGGLAEAD GLSGFDVPDM ELASFAADME SLLMGVHDGF   240
DDLGFLDEEK PQVNADAYLE AMAAPVPERE DKKRKRPEMI LKLNYDGVIA SWVRDGGSPW   300
FHGERPHLDP YELWSDFPAG SRGLLGGAVT AVTGGEREAR VSRYREKRRT RLFAKKIRYE   360
VRKVNAEKRP RMKGRFVKRT TLPPLPRPPP QQQQKQLPRA LPHVGMVLAP PPGANGRFQF   420

SEQ ID NO: 313            moltype = AA  length = 376
FEATURE                   Location/Qualifiers
source                    1..376
                          mol_type = protein
                          organism = Sorghum bicolor
SEQUENCE: 313
MEALVAGRYW GVGGRRCEAC GGSPAAVHCR TCPGGGAYLC AGCDAGHARA GHERVWVCEV    60
CERAPAAVTC RADAAALCAA CDADIHDANP LARRHERVPV QPIGAAAAAP AAETLLFGAA   120
AEENQDDDDG AAAAAKVVGV DAGKLADFLF ADVMDPFFGQ DFTGILRRRV ALWTLTFGGG   180
VAAAAVAAKP SYSSYTAASL GHSGSSSEVG LVPDAMCGRG GSVTGGVIEL DFAQSKAAYL   240
PYAATPTHSM SSLDVGAVPE RGDGVMAGRV ATPPAAAAAE SREARLMRYR EKRKNRRFEK   300
TIRYASRKAY AESRPRIKGR FAKRADDNDA DADADFDFDA GAAAATAPAR SRSQQQQPSY   360
PYVLDFAAGY GVVPTF                                                  376

SEQ ID NO: 314            moltype = AA  length = 488
FEATURE                   Location/Qualifiers
source                    1..488
                          mol_type = protein
                          organism = Sorghum bicolor
SEQUENCE: 314
MSSSKHAAAG AGAVGGKAAR ACDSCLRRRA RWYCAADDAF LCQGCDASVH SANPLARRHE    60
RLRLRPMTSP PDPAHSTLEA GGVGVASTST WKKRQQQQQQ VAPAWSKRKA RTRRPHVKSV   120
GQLLSRKLVV VPEVATVESS EERKVEEEDE EEEEEEEQLL YCVPTFDRAL AELCTPPPPL   180
```

```
DDPTATASSS CCRDNDVDGA VDNAKAAPPA VVVAESPVQQ LPDSFAGFGP TDAELREFAA    240
DMEALLGQGL GDSNELDESF YMESLGLMTT TQQAEDVDVG RVKMEPNGSV ISRSRGEGAP    300
GFGPAELMKP EASSAEVLVL DIDFNCSSPT VMMDHEDEDS FEHKASASNG DAAAAGTQFL    360
KRSLDLSLNY EAIIESWGSS PWTDGQRPNV QLDDFWPHAH LTGWMAGGGR LGGEAAAVSP    420
RLGMVGGREA RVTRYREKRR TRLFAKKIRY EVRKLNAEKR PRMKGRFVKR PAAAGGGGAA    480
IAAPCAVT                                                            488

SEQ ID NO: 315           moltype = AA  length = 406
FEATURE                  Location/Qualifiers
source                   1..406
                         mol_type = protein
                         organism = Sorghum bicolor
SEQUENCE: 315
MASLCDFCGK QRSMIYCRSD AASLCLSCDR NVHSANALSR RHTRTLLCDR CGSQPASVRC     60
LEDNASLCQN CDWNGHDAAS GASGHKRQAI NCYSGCPSSA ELSRIWSFIM DIPTVPAEPN    120
CEDGLSMMTI DDSDVTNHHD ASDDKRLLEI ANTTLMSDPP SADKPKPLIS SSSGDGFDVL    180
PLATDQPAGS VSVTPKVPYA RDDDNFNDGM YEDLCVDDAD MTFENYEELF GTSHIRTEEL    240
FDDAGIDSYF EMKETQPFDF NEEPKTMQLE CSNVVSADCG MLNPGARADS SLCIPVRQVR    300
SSISHSLSGL TGESSAGDHQ DCGVSPMLLM GEPPWHSPGP EGSVAGGSRD SALTRYKEKK    360
KRRKFDKKIR YASRKARADV RKRVKGRFIK AGEAYDYDPL SQTRSY                   406

SEQ ID NO: 316           moltype = AA  length = 329
FEATURE                  Location/Qualifiers
source                   1..329
                         mol_type = protein
                         organism = Sorghum bicolor
SEQUENCE: 316
MEGDEKSAGG APAYWGLGAR PCDACGADAA RLYCRADSAF LCAGCDARAH GAGSPNARVW     60
LCEVCEHAPA AVTCRADAAA LCASCDADIH SANPLARRHE RLPVAPFFGA LADAPKPFAS    120
SAAAVPPKAT AGADDDGSSE AEAASWLLPE PDHGHKEEGA TTEVFFADSD PYLDLDFARS    180
MDDIKTIGVQ GGPPELDLNG AKLFYSDHSM NHSVSSSEEA VVPDAAAGAA PVVAVVSRGL    240
EREEARLMRYR EKRKSRRFEK TIRYASRKAY AETRPRIKGR FAKRTPGAGE DPLEEHEEMY   300
SSAAAAVAAL MAPGGADADY GVDGVVPTY                                     329

SEQ ID NO: 317           moltype = AA  length = 474
FEATURE                  Location/Qualifiers
source                   1..474
                         mol_type = protein
                         organism = Sorghum bicolor
SEQUENCE: 317
MIATTGSSAK TAAAAAVGGK SARACDGCLR RRARWYCAAD DAFLCQGCDT SVHSANPLAR     60
RHERLRLQPA AASSSPLHTP PRTGAAANNK RERHDEVVPA WFRRKARTPR GGHAKSVGGQ    120
ALSRSRRLGV VVPHAAAGGG DSPDDGRSAE GEFEAEEEQL LYRVPIFDPA LAEFCSPPPA    180
PLEDAAALAS SCNEDGAVED PANSKPDPGP ATPAPAPVVQ FFPDSGHANF EPTDAELREF    240
AADMEALLGH GLDDGNEEDS SFYMETLGLL DPVEVGDDAT RVKVETDGGS ACGEASGTLA    300
CALELLDPAE VSDEMLDIDF NYGSPLDTMM DDEKAASSDT GGADDAQFLQ TSLSLTLNYE    360
AIIQSWGSSP WTAGGERPHV KLDDSWPHTN MWVVGGVAGH GGEDLLLGTA RLGMDGGREA    420
RVSRYREKRR TRLFSKKIRY EVRKLNAEKR PRMKGRFVKR ATAGGSSLAI AGLA          474

SEQ ID NO: 318           moltype = AA  length = 411
FEATURE                  Location/Qualifiers
source                   1..411
                         mol_type = protein
                         organism = Sorghum bicolor
SEQUENCE: 318
MNYNFSSNAL DEEEVAGRGG EGGSCAAAPA WARPCDGCRA APSVVYCHAD AAYLCASCDV     60
RVHAANRVAS RHERVRVCEA CERAPAVLAC RADAAALCVV CDAQVHSANP LAGRHQRVPV    120
LPLPVAAIPA ASVLAEAAAT AVAVGDKQEE EVDSWLLLTN TKDPVSDNNN CNCSSSSNNN    180
ISSSNTSTFY ADVDEYFDLV GYNSYCDNHI NSNPKQYGMQ RERQQQQQLLL QKEFGDKEGS   240
EHVVPASQVA MANEQQQSGY GVIGVEQAAS MTAAVSAYTD SITNSISFSS SMEVGIVPDN    300
MATTTDMPNS GILLTPAEAI SLFSSGSSLQ MPLHLTSMDR EARVLRYKEK KKSRKFAKTI    360
RYATRKTYAE ARPRIKGRFA KRSSDMEIEV DQMFSSAALS SDGSYGTVLW F             411

SEQ ID NO: 319           moltype = AA  length = 406
FEATURE                  Location/Qualifiers
source                   1..406
                         mol_type = protein
                         organism = Sorghum bicolor
SEQUENCE: 319
MGALCDFCGE QRSMVYCRSD AASLCLSCDR NVHSANALSR RHTRTLLCDR CASQPAMVRC     60
LAENASLCQN CDWNGHIAGS SAAGHKRQTI NCYSGCPSSA ELSRIWSFVS DIPNVAPEPN    120
CEQGISMMSI SDSGVSSQDN AAGDNNLLDI ASETLISDLG TCDKPLVGSS SGAGVNLLPL    180
ATDQTAGSVD SPPPDKVPYTP DKDMFSKDSI YEDFCVDDVD LAFENYEELF GTSHIQTEQL   240
FDDAGIDSYF EVKEAPAGNS TEQSKLKQPA NSNAVSADSG MSNPGVKADS SVCIPLRQAR    300
SSLSLSFSGL TGESSAGDHQ DCVVSSLLLM GEPPWQPPGP EGSIAGGSRD SAITRYKEKK    360
KRRKFDKKIR YASRKARADV RKRVKGRFVK VGEAYDYDPL CQTRSY                   406

SEQ ID NO: 320           moltype = AA  length = 426
FEATURE                  Location/Qualifiers
```

```
source                  1..426
                        mol_type = protein
                        organism = Ricinus communis
SEQUENCE: 320
MEEYSDSAPR NSLFVRLCDF CNSEAAILYC RADSAKLCLF CDQQVHSANA LSLNHFRSLN    60
CDKCGAEPAS VQCSVINDNN NNDLVLCQDC DFDCSVSLSL LKRAHINGFM GCPNAVELGE   120
ILGFDLKKTK LFASSDSGSD LYDQEMDNMQ DLLVPSGNSS RNCRQEMYKQ LLELGKRERV   180
KVNGDGDGEE LRPETPPSRC GQQGNLVNLQ MKNGNEEEFH HQERPFASML MLPNLEDVRE   240
SDGAADGVLL WDCNPTYQAA QVWDLDLGKT RDCAEPGEEE ANYDATDPGF TFNNHRISKD   300
SAFNIIKVCS KQQVLQSTME TGGGKDTLLV EQSSDSLLAE AKSNNSPRHV EVVEKSHLAW   360
VGTDDDMETSK ADVELFAQNR GNAMLRYMEK KKTRRYDKHI RYESRKARAD TRERVKGRFV   420
KASENC                                                             426

SEQ ID NO: 321          moltype = AA  length = 468
FEATURE                 Location/Qualifiers
source                  1..468
                        mol_type = protein
                        organism = Ricinus communis
SEQUENCE: 321
MISNKNVANA VAGKTARACD SCVRKRARWY CAADDAFLCQ SCDSSVHSAN PLARRHERVR    60
LKISSLKSLD IISKGSSVIT VPSWHQGFTR KARTPRNGHG NKPLLSLLKI EEKSRNPIPL   120
VPEVGSDDQI SHEDNNEEEQ LLYRVPIFDP FVAELCTPTT ISNEADQTTT APFTAGGGNG   180
NDTDQTVAGA NGIESKASYL HGFLPSETDL ADFAADVESL LGRGLENESF GMEDLGLVDC   240
KEEKQFKMQE REFSLASGQV IKLEEEEKEE EEAVRECHID TEIDMAKEPP FELSFDYDSA   300
TCGEEDEKVA TPQRDIKSNN GEYKDNTRSK NDNKKKRKIL LSLDYEAVIT AWATQGTSPW   360
TDGTRRDVDP DECWQDCMGT CGAEFHHPYG DTNGLGGVGG GGNPAMAGGG REARVSRYRE   420
KRRTRLFSKK IRYEVRKLNA EKRPRMKGRF VKRATFAGGP SAFPLHAK                468

SEQ ID NO: 322          moltype = AA  length = 378
FEATURE                 Location/Qualifiers
source                  1..378
                        mol_type = protein
                        organism = Ricinus communis
SEQUENCE: 322
MLKEENTGGG GGNNWARVCD TCRAAACTVY CKADSAYLCA TCDARIHAAN RVASRHGRVW    60
VCEACERAPA AFLCKADAAS LCATCDADIH SANPLARRHQ RVPIHPISGC LHGPQAGPVG   120
GGGETTTEDM FMTEDGEDGV GEEEEDEAAS WLLLNPVKNG NSQNNGTNGF LFGGEVEEYL   180
DLFEYNSNSC GENQYADNHQ HYSGTVHQKS HEGDSVVPVR CGDGAGKDHV HQQYHNFQLG   240
LEFESSKAAY SYNGSISHSV SISPMDVGVV PDSTMSEASI SHPRPPKGTI DLFSGPPIQM   300
PSQLSPRDRE ARVLRYREKK KTRKFEKTIR YASRKAYAET RPRIKGRFAK RTDVEVEVDQ   360
IFSTALMAET GYGIVPSF                                                378

SEQ ID NO: 323          moltype = AA  length = 430
FEATURE                 Location/Qualifiers
source                  1..430
                        mol_type = protein
                        organism = Ricinus communis
SEQUENCE: 323
MTNDRKAANA LSGKTARACD GCSRKRARWF CAADDAFLCQ ACDDSVHSAN QLASRHERVR    60
LETASSKISG SRNTVDSVPA WHQGFIRKAR TPRNSSNKQQ LKDEDKVLVM NPLPLVPEIG   120
GEEEGNSTFA DEDDDRLLYR VPVFDPYASE LCTDDMVTCG EGTEITMGNE EGNIVFDGYN   180
GQEGTCDDLD ILPEFFSSDM DLAEFAADVE NLLGVNEDSP DIEDLCLLHC KEEEDDQKCF   240
FDDQDKVVMK VKDEQEVEAC DHFDQAFERE SLDWSFNYES PTITADEVEE KKRVPVAINS   300
QQKKETKSTA SLLRLNYEDV INAWASQGSP WTSGSRPELN SDDCWPDCMD ICLKDGHHHP   360
YGGMGGHTRG GNGAREARVL RYKEKRRTRL FSKKIRYEVR KLNAEKRPRM KGRFVKRTSF   420
MGNGFPYMNK                                                         430

SEQ ID NO: 324          moltype = AA  length = 365
FEATURE                 Location/Qualifiers
source                  1..365
                        mol_type = protein
                        organism = Magnolia virginiana
SEQUENCE: 324
MDGDSSTRRW ARVCDSCRSA ACTAYCRADA AYLCAGCDSR THAANRVASR HERVWVCESC    60
ERAPAAVSCK ADAAALCTAC DVDIHSANPL ARRHHRTPIL PISGQLYSSP HESVHDREPG   120
GAHEEDEDED GDGDDEAASW LLLNPVKNSN QNNGYGYGGE VDEYLDLVGY NNSCNENQNE   180
GQSIQLHQNL GKNEGDDSVV PVQFLAGDEQ QQQQQQQQNL QLDLDMEFEE SKAGYNYTAS   240
MSQSVSYSSM DASVVPDATA MTDISNSHVR PPKGTIDLFA GPPLQMMPAQ FSPMDREARV   300
LRYREKKKTR KFEKTIRYAS RKAYAETRPR IKGRFAKRTD VEVEVHQMFS TTVMAESRYS   360
IVPSF                                                              365

SEQ ID NO: 325          moltype = AA  length = 407
FEATURE                 Location/Qualifiers
source                  1..407
                        mol_type = protein
                        organism = Zea mays
SEQUENCE: 325
MASLCDFCGK QRSMIYCRSD AASLCLSCDR NVHSANALSR RHTRTLLCDR CGSQPASVRC    60
LEDNASLCQN CDWNGHDAES GASGHKRQAI NCYSGCPSSA ELSRIWSFIT DIPTVAAEPD   120
```

```
YEDGLSMMTI DGSDVTNRHD TSDDKRLLEI ANTTLMSDPP SADKLKSPTG SSSGDGFDVM    180
TLATDQPAGP VSATPKVPNA RDDDKFNDGM YEDLCVDDAD LTFEDYEELF GTSHIRTEEL    240
FDDAGIDGYF ELKETPPFYF NEQPKAMQIE CGNVVSADCA MSNPGARADS SLCIPVRQVR    300
SSISHSLSGL TGESSAGDHH DCGVSPMLLM GEPPWHSPGG PEGSVAGGSR DSALTRYKEK    360
KKRRKFDKKI RYASRKARAD VRKRVKGRFI KAGEAYDYDP LSQTRSY                 407

SEQ ID NO: 326          moltype = AA  length = 374
FEATURE                 Location/Qualifiers
source                  1..374
                        mol_type = protein
                        organism = Glycine max
SEQUENCE: 326
MGIERGGFKG FRSAWSVPPK PCDSCKLASA ALFCRPDSAF LCIACDSNIH CSNKLASRHE     60
RVWMCEVCEQ APAAVTCKAD AAALCVTCDS DIHSANPLAQ RHERVPVEPF FDSAESIVKA    120
SAAATFGFIV PSDDGGASDA FAPDDSDAAA WLIPNPNFGS KLMDAPEIKS KEIFFSEMDP    180
FLDFDYSNSF QNNNSAGNDS VVPVQKPSLA PPLINNHHHH QSETCFDVDF CRSKLSSFNY    240
PSNSLSQSVS SSSLDVGVVP DGNTVSDMSY SFGRNSSDSS GIVVVSGNSV GQGATQLCGM    300
DREARVLRYR EKRKNRKFEK TIRYASRKAY AETRPRIKGR FAKRTEIDSD VERLYSPGPA    360
VLMLDTPYGV VPSF                                                     374

SEQ ID NO: 327          moltype = AA  length = 365
FEATURE                 Location/Qualifiers
source                  1..365
                        mol_type = protein
                        organism = Glycine max
SEQUENCE: 327
MGIERGGLKG FRSGWSVPPK KPCDSCKLAS AALFCHLDSA FLCIACDSKI HCANKLASRH     60
ERVWMCEVCE QAPASVTCKA DAAALCVTCD SDIHSANPLA QRHERVPVEP FFDSAESIVK    120
ASATASFGFV VPSDDGAASD VFAPDDSDSA AWLIPNPNFG SKLMDAPEIK SKEIFFSEMD    180
PPLDFDYSNS PQNHNSAVND SVVPVQTKPS LAPPPINNHQ HHHQSETCFD IDFCRSKLSS    240
FNYPSQSLSQ SVSSSSLDVG VVPDGNTVSD MSYSSGIVVS GGQGATQLCG MDREARVLRY    300
REKRKNRKFE KTIRYASRKA YAETRPRIKG RFAKRTEIDS DVERLYSPGA AALMLDTPYG    360
VVPTF                                                                365

SEQ ID NO: 328          moltype = AA  length = 366
FEATURE                 Location/Qualifiers
source                  1..366
                        mol_type = protein
                        organism = Glycine max
SEQUENCE: 328
MKDAGALGGK TARACDSCVS RRARWFCAAD DAFLCHGCDT LVHSANQLAS RHERVRLQTA     60
SSKVTTTHAW HSGFTRKART PRHNSKHFAL QQRLKDEVLF NNTSVLPLVP ELGGEEQEPV    120
VVDNDETEEQ MLCRVPVFDP FDVRTDDLDS FSDMDFAEFA ADVESLLDKE DDEISACVGG    180
GEGEGEGVQG AMVKVKDEEE IDGDVACYLE SVFDDAFHWN NIESVLSDAR EEKEGVVACD    240
VGVGDEEGGT KRDIFLRLNY DEVITAWSSQ GSSPWTTSNP PKFNSDYDFS LGLSGVGGEV    300
RSLRGHLDGG REARVSRYRE KRRTRLFAKK IRYEVRKLNA EKRPRMKGRF VKRTCFVGAN    360
AFPAYH                                                               366

SEQ ID NO: 329          moltype = AA  length = 411
FEATURE                 Location/Qualifiers
source                  1..411
                        mol_type = protein
                        organism = Oryza sativa
SEQUENCE: 329
MNYNFGGNVF DQEVGVGGEG GGGGEGSGCP WARPCDGCRA APSVVYCRAD AAYLCASCDA     60
RVHAANRVAS RHERVRVCEA CERAPAALAC RADAAALCVA CDVQVHSANP LARRHQRVPV    120
APLPAITIPA TSVLAEAVVA TATVLGDKDE EVDSWLLLSK DSDNNNNNNN NDNDNDNDNN    180
NSNSSNNGMY FGEVDEYFDL VGYNSYYDNR IENNQDQQYG MHEQQEQQQQ QQEMQKEFAE    240
KEGSECVVPS QITMLSEQQH SGYGVVGADQ AASMTAGVSA YTDSISNSVS SSISFSSMEA    300
GIVPDSTVID MPNSRILTPA GAINLFSGPS LQMSLHFSSM DREARVLRYR EKKKARKFEK    360
TIRYETRKAY AEARPRIKGR FAKRSDVQIE VDQMFSTAAL SDGSYGTVPW F             411

SEQ ID NO: 330          moltype = AA  length = 411
FEATURE                 Location/Qualifiers
source                  1..411
                        mol_type = protein
                        organism = Oryza sativa
SEQUENCE: 330
MNYNFGGNVF DQEVGVGGEG GGGGEGSGCP WARPCDGCRA APSVVYCRAD AAYLCASCDA     60
RVHAANRVAS RHERVRVCEA CERAPAALAC RADAAALCVA CDVQVHSANP LARRHQRVPV    120
APLPAITIPA TSVLAEAVVA TATVLGDKDE EVDSWLLLSK DSDNNNNNNN NDNDNDKDNN    180
NSNSSNNGMY FGEVDEYFDL VGYNSYYDNR IENNQDQQYG MHEQQEQQQQ QQEMQKEFAE    240
KEGSECVVPS QITMLSEQQH SGYGVVGADQ AASMTAGVSA YTDSISNSVS SSISFSSMEA    300
GIVPDSTVID MPNSRILTPA GAINLFSGPS LQMSLHFSSM DREARVLRYR EKKKARKFEK    360
TIRYETRKAY AEARPRIKGR FAKRSDVQIE VDQMFSTAAL SDGSYGTVPW F             411

SEQ ID NO: 331          moltype = AA  length = 291
FEATURE                 Location/Qualifiers
source                  1..291
```

```
                            mol_type = protein
                            organism = Oryza sativa
SEQUENCE: 331
MNYNFGGNVF DQEVGVGGEG GGGGEGSGCP WARPCDGCRA APSVVYCRAD AAYLCASCDA    60
RVHAANRVAS RHERVRVCEA CEQAPAALAC RADAAALCVA CDVQVHSANP LARRHQRVPF   120
APLPAITIPA TSVLAEAVVA TATVLGGKDE EVDSWIILSK DSNNNNNNNN SNISFSSMEA   180
GIVPDSTVID MPNSSILTPA GAINLFSGPS LQMSLHFSSM DREARVLRYR EKKKARKFEK   240
TIRYETRKAY AEARPRIKGR FAKRSDVQIE VDQMFSTAAL SDSSYGTVPW F            291

SEQ ID NO: 332          moltype = AA  length = 451
FEATURE                 Location/Qualifiers
source                  1..451
                        mol_type = protein
                        organism = Oryza sativa
SEQUENCE: 332
MNYNFGGNVF DQEVGVGGEG GGGGEGSGCP WARPCDGCRA APSVVYCRAD AAYLCASCDA    60
RVHAANRVAS RHERVRVCEA CEQAPAALAC RADAAALCVA CDVQVHSANP LARRHQRVPV   120
APLPAITIPA TSVLAEAVVA TATVLGGKDE EVDSWIILSK DSNNNNNNNN SNSSNNGMYF   180
GEVDEYFDLV RYNSYYDNNN NDNSNSNSSN NDNDNDNDNN NNSNSSNNGM YFGEVDEYFD   240
LVGYNSYYDN RIENNQDQQY GMHEQQEQQQ QQQEMQKEFA EKEGSECVVP SQITMLSEQQ   300
HSGYGVVGAD QAASMTAGVS AYTDSISNSV SSSISFSSME AGIVPDSTVI DMPNSSILTP   360
AGAINLFSGP SLQMSLHFSS MDREARVLRY REKKARKFEK TIRYETRKAY AEARPRIKGR   420
FAKRSDVQIE VDQMFSTAAL SDSSYGTVPW F                                  451

SEQ ID NO: 333          moltype = AA  length = 413
FEATURE                 Location/Qualifiers
source                  1..413
                        mol_type = protein
                        organism = Oryza sativa
SEQUENCE: 333
MNYNFGGNVF DQEVGVRGEG GGGGEGSGCP WARPCDGCRA APSVVYCRAD AAYLCASCDA    60
RVHAANRVAS RHERVRVCEA CERAPAALAC RADAAALCVA CDVQVHSANP LARRHQRVPV   120
APLPAITIPA TSVLAEAVVA TATVLGDKDE EVDSWLLLSK DSNNNNNNNN NNDNDNDNND   180
NNNSNSNSNG MYFGEVDEYF DLVGYNSYYD NRIENNQDQQ YGMHEQQEQQ QQQQEMQKEF   240
AEKEGSECVV PSQITMLSEQ QHSGYGVVGA DQAASMTAGV SAYTDSISNR VSSSISFSSM   300
EAGIVPDSTV IDMPNSSILT PAGAINLFSG PSLQMSLHFS SMDREARVLR YREKKKARKF   360
EKTIRYETRK AYAEARPRIK GRFAKRSDVQ IEVDQMFSTA ALSDGSYGTV PWF           413

SEQ ID NO: 334          moltype = AA  length = 412
FEATURE                 Location/Qualifiers
source                  1..412
                        mol_type = protein
                        organism = Oryza rufipogon
SEQUENCE: 334
MNYNFGGNVF DQEVGVGGEG GGGGEGSGCP LARPCDGCRA APSVVYCRAD AAYLCASCDA    60
RVHAANRVAS RHERVRVCEA CERAPAALAC RADAAALCVA CDVQVHSANP LARRHQRVPV   120
APLPAITIPA TSVLAEAVVA TATVLGDKDE EVDSWLLLSK DSNNNNNNNN NNNDNDNDNN   180
DNNNSNSSNN GMYFGEVDEY FDLVGYNSYY DNRIENNQDQ QYGMHEQQEQ QQQQQEMQKV   240
FAEKEGSECV VPSQITMLSE QQHSGYGVVG ADQAASMTAG VSAYTDSISN SVSSSISFSS   300
MEAGIVPDST VIDMPNSSIL TLAGAINLFS GPSLQMSLHF SSMDREARVL RYREKKKARK   360
FEKTIRYETR KAYAEARPRI KGRFAKRSDV QIEVDQMFST AALSDGSYGT VP           412

SEQ ID NO: 335          moltype = AA  length = 415
FEATURE                 Location/Qualifiers
source                  1..415
                        mol_type = protein
                        organism = Oryza barthii
SEQUENCE: 335
MNYNFGGNVF DQEVGVGGEG GGGGEGSGCP WARPCDGCRA ALSVVYCRAD AAYLCASCDA    60
RVHAANRVAS RHERVRVCEA CERAPAALAC RADAAALCVA CDVQVHSANP LARRHQRVPV   120
APLPAITIPA TSILAEAVVA TATVLGDKDE EVDSWLLLSK DSDNNNNNNN NNDNDNDNNN   180
NSNSNSNSSS NGMYFGEVDE YFDLVGYNSY YDNRIENNQD QQYGMHEQQE QQQQQEMQK    240
EFAEKEGSEC VVPSQITMLS EQQHSDYGVV GADQAASMTA GVSACTDSIS NRVSSSISFS   300
SMEASIVPDS TVIDMPNSSI LTPAGAINLF SGPSLQMSLH FSSMDREARV LRYREKKKAR   360
KFEKTIRYET RKAYAEARPR IKGRFAKRSD VQIEVDQMFS TAALSDGSYG TVPWF         415

SEQ ID NO: 336          moltype = AA  length = 407
FEATURE                 Location/Qualifiers
source                  1..407
                        mol_type = protein
                        organism = Oryza longistaminata
SEQUENCE: 336
MNYNFGGNVF DQEVGGGEGA AGGGGCPWAR PCDGCRAAPS VVYCRADAAY LCASCDARVH    60
AANRVVSRHE RVRVCEACER APAALACRAD AAALCVACDV QVHSANPLAR RHQRVPAPL   120
PAVAIPATSV LAEAVVATAT VLGDKDEEVD SWLLLTKDPD NKNNDDDNNN NNNNKNNNNN   180
NSNNGMYYGE VDEYFDLVGY NSYDNRIEN  SQDQQYGMHE QQEQQQQQQQ QQEMQKEFAE   240
KEGSECVVPS QITMLSEQQH SGYGVVGADQ AASMTAGVSA YTDSISNSIS FSSMEVGIVP   300
DSTVIDMPNS SILTPAGAIN LFSGPSLQMS LHFSSMDREA RVLRYEKKKK ARKFEKTIRY   360
ATRKAYAEAR PRIKGRFAKR SDVEIEVDQM FSTAALSDGS YGTVPWF                 407
```

```
SEQ ID NO: 337          moltype = AA  length = 366
FEATURE                 Location/Qualifiers
source                  1..366
                        mol_type = protein
                        organism = Brassica napus
SEQUENCE: 337
MFKQESNNIG SEENNTGPRA CDTCGSTICT VYCHADSAYL CNSCDAQVHS ANRVASRHKR   60
VRVCESCERA PAAFMCEADD VSLCTACDLE VHSANPLARR HQRVPVVPIT GNSCSSLATA  120
NHTTVTEPEK RVVLVQEDAK ETASWLFPKN SDNHNNNNQN NELLFSDDYL DLADYNSSMD  180
YKFTGQYNQP TQHKQDCTVP EKNYGGDRVV PLQLEETRGN LHHKQHNITY GSSGSHYNNN  240
GSINHNAYNP SMETDFVPEQ TAPDKTVSHP KTHKGKIEKL PEPLIQILSP MDREARVLRY  300
REKKKRRKFE KTIRYASRKA YAERRPRING RFAKISETEV EDQEYNTMLM YYDTGYGIVP  360
SFYGQK                                                            366

SEQ ID NO: 338          moltype = AA  length = 366
FEATURE                 Location/Qualifiers
source                  1..366
                        mol_type = protein
                        organism = Brassica napus
SEQUENCE: 338
MFKQESNNIC NRENNRGARA CDTCGSTICT VYCHADSAYL CNSCDAQVHS ANRVASRHKR   60
VRVCESCERA PAAFMCEADD VSLCTACDLE VHSANPLARR HQRVPVVPII GNSCSSLATA  120
NHTTVTEPEK RVVLVQEDAK ETASWLFPKN SDYHNNNNNQ NNELLFSDDY LDLADYNSSM  180
DYKFTSQYNQ PRHKQDCIVP EKNYSGDRVV PLQLEETRGN LRNKQQNITY GSSGSQYNNN  240
GSINHNAYNP SMETDFVPEQ TAPDTTVSHP KTHKGKTAQL PEPLIQILSP MDREARVLRY  300
REKKKRRKFE KTIRYASRKA YAERRPRING RFAKMSETEV EDQEYNTMLM YCDTGYGIVP  360
SFYGQK                                                            366

SEQ ID NO: 339          moltype = AA  length = 368
FEATURE                 Location/Qualifiers
source                  1..368
                        mol_type = protein
                        organism = Brassica napus
SEQUENCE: 339
MFKQESNNNI CNRENNRGAR ACDTCGSTIC TVYCHADSAY LCNSCDAQVH SANRVASRHK   60
RVRVCESCER APAAFMCEAD DVSLCTACDL EVHSANPLAR RHQRVPVVPI TGNSCSSLAT  120
ANHTTVTEPE KRVVLVQEDA KETASWLFPK NSDNHNNNNN QNNELLFSDD YLDLADYNSS  180
MDYKFTGQYN QPTQHKQDCT VPEKNYGGDR VVPLQLEETR GNLHHKQHNI TYGSSGSHYN  240
NNGSINHNAY NPSMETDFVP EQTAPDKTVS HPKTHKGKIE KLPEPLIQIL SPMDREARVL  300
RYREKKKRRK FEKTIRYASR KAYAERRPRI NGRFAKISET EVEDQEYNTM LMYYDTGYGI  360
VPSFYGQK                                                          368

SEQ ID NO: 340          moltype = AA  length = 343
FEATURE                 Location/Qualifiers
source                  1..343
                        mol_type = protein
                        organism = Vitis vinifera
SEQUENCE: 340
MALLYCRADS AKLCLSCDRE VHSTNQLFTK HTRSRLCDVC DASPASILCS TDNLVLCQNC   60
DWAKHGRSLS SAHDRRPLEG FSGQPSVTEL LAFVGFEDLG KKSLFCGDES EFSDFLVWDT  120
PAVVNLDDLI VSTACDHNFQ AMGVPPLPKN RGAPCGQHKA EIIHQLRQLA KIELSFDFDH  180
GDAKPPIGFQ SHIPKQLIQK ENECNSCDHE VEFVFPTYEA SAFQWCSDGS EAANQVLPSV  240
LLGSCADEKC LVPRKHSDIG GSVSHTNGSD EGKSECPVVT KTLPALPKVS VHELNSQERD  300
SAISRYKEKK KTRRYEKHIR YESRKARAES RIRIKGRFAK MDH                   343

SEQ ID NO: 341          moltype = AA  length = 448
FEATURE                 Location/Qualifiers
source                  1..448
                        mol_type = protein
                        note = Oryza sativa Japonica Group
                        organism = Oryza sativa
SEQUENCE: 341
MNYNFGGNVF DQEVGVGGEG GGGGEGSGCP WARPCDGCRA APSVGYCRAD AAYLCASCDA   60
RVHAANRVAS RHERVRVCEA CEQAPAALAC RADAAALCVA CDVQVHSANP LARRHQRVPV  120
APLPAITIPA TSVLAEAVVA TATVLGGKDE EVDSWIILSK DSNNNNNNNN SNSSNNGMYF  180
GEVDEYFDLV GYNSYYDNNN NDNSNSNSSN NDNDNDNDNN NNSNSSNNGM YFGEVDEYFD  240
LVGYNSYYDN RIENNQDQQY GMHEQQEQQQ QQQEMQKEFA EKEGSECVVP SQITMLSEQQ  300
HSGYGVVGAD QAASMTAGVS AYTDSISNSI SFSSMEAGIV PDSTVIDMPN SSILTPAGAI  360
NLFSGPSLQM SLHFSSMDRE ARVLRYREKK KARKFEKTIR YETRKAYAEA RPRIKGRFAK  420
RSDVQIEVDQ MFSTAALSDS SYGTVPWF                                    448

SEQ ID NO: 342          moltype = AA  length = 501
FEATURE                 Location/Qualifiers
source                  1..501
                        mol_type = protein
                        note = Oryza sativa Japonica Group
                        organism = Oryza sativa
SEQUENCE: 342
```

```
MNYNFGGNVF DQEVGVGGEG GGGGGEGSGC PWARPCDGCR AAPSVVYCRA DAAYLCASCD    60
ARVHAANRVA SRHERVRVCE ACEQAPAALA CRADAAALCV ACDVQVHSAN PLARRHQRVP   120
VAPLPAITIP ATSVLAEAVV ATATVLGGKD EEVDSWIILS KDSNNNNNNN NSNSSNNGMY   180
FGEVDEYFDL VRYNSYYDNN NNDNSNSNSS NNDNDNDNDN NNNSNSSNNG MYFGEVDEYF   240
DLVRYNSYYD NNNNDNSNSN SSNNDNDNDN DNNNNSNSSN NGMYFGEVDE YFPDLVGYNSY  300
YDNRIENNQD QQYGMHEQQE QQQQQQEMQK EFAEKEGSEC VVPSQITMLS EQQHSGYGVV   360
GADQAASMTA GVSAYTDSIS NSISFSSMEA GIVPDSTVID MPNSSILTPA GAINLFSGPS   420
LQMSLHFSSM DREARVLRYR EKKKARKFEK TIRYETRKAY AEARPRIKGR FAKRSDVQIE   480
VDQMFSTAAL SDSSYGTVPW F                                             501

SEQ ID NO: 343           moltype = AA  length = 481
FEATURE                  Location/Qualifiers
source                   1..481
                         mol_type = protein
                         note = Oryza sativa Japonica Group
                         organism = Oryza sativa
SEQUENCE: 343
MSSTAKAAAA GAVGAKSARA CDGCLRRRAR WYCAADDAFL CQGCDTSVHS ANPLARRHER    60
LRLRPSSPPP LVPPSGSGRR DEAVPAAWFK RKARTPRSHA AKSAAAFGQL LSRRLVVVPE   120
AAAGSGGDSP EERKDEGEIV EEQEQLLYRV PIFDPALSEF CSPPPLEDAA AAVSCCNEDG   180
AVENPTKPSM TTTTATTPPL QFFPDGQANF GPTDAELREF AADMEALLGR GLDDGNDEDS   240
FCMETLGLIE PVDDDAGRVK VEADGDAGMT LAWCHELDTE TSSGEMLDID FDCGSPQAAT   300
TPDEKVGSSG PAAADDDAQL QQSNLALSLN YEAIIESWGT SPWTDGERPH VKLDDSWPRD   360
YSVRATPCTP YASSHRILHN LAGTDDLLRR RAAVQGVWMA AAGVFGHGGE EQALTPRLGM   420
DGGREARVSR YREKRRTRLF SKKIRYEVRK LNAEKRPRMK GRFVKRAAAA ATAAVATACV   480
A                                                                  481

SEQ ID NO: 344           moltype = AA  length = 379
FEATURE                  Location/Qualifiers
source                   1..379
                         mol_type = protein
                         note = Arabidopsis lyrata subsp. lyrata
                         organism = Arabidopsis lyrata
SEQUENCE: 344
MGYMCDFCDE QRSMVYCRSD AACLCLSCDR NVHSANALSK RHSRTLVCER CNAQPASVRC    60
SDERVSLCQN CDWLGHDGKN STTTTSNHKR QTINCYSGCP SSAELSSIWS FFMDLNISSA   120
GESACEQGMG LMTIDEDSTG EKSGVLNVNV DQPETSSAAQ GMDRSSVPEN SSLAKELGVC   180
EDDFNGNLIT DEVDLALENY EELFGSAFNS SRYLFEHGGI SSLFEKDEAP EGSNKGNEMQ   240
QPAVNNNASA DSFMTCRTEP IICYSSKPTH SNISFSGITG ESNAGDFQDC GASSMKQLLR   300
EPQPWCHPTA QDIIASSHAT TRNNAVMRYK EKKKARKFDK RVRYVSRKER ADVRRRVKGR   360
FVKSGEAYDY DPMSPTRSY                                                379

SEQ ID NO: 345           moltype = AA  length = 330
FEATURE                  Location/Qualifiers
source                   1..330
                         mol_type = protein
                         note = Arabidopsis lyrata subsp. lyrata
                         organism = Arabidopsis lyrata
SEQUENCE: 345
MEARCDYCET EKALIYCKSD LAKLCLNCDV NIHSANPLSQ RHTRTLLCEK CFLQPTVIHC    60
MNEKVSLCQG CQWTATNCTG LGHRLQNLNP YSGCPSPSDF AKIWSSILEP SVSNWVSPFP   120
DTLLQELDDW NGSSTSVITQ TQNLKDYSSF FSMESNLPKV IEEECSGLDL CEGINLDDAP   180
LNFNASNDII GCSSLDNTKC YQYEESFKEE NNIGIPSLLL PALSGNVVPS MSISMSNITG   240
ENSATDYQDC GISPGFLIGD SPWESNVEVS FNPKSRDEAK KRYKQKKSKR MFGKQIRYAS   300
RKARADTRKR VKGRFVKSGE TFEYDPSLVM                                    330

SEQ ID NO: 346           moltype = AA  length = 360
FEATURE                  Location/Qualifiers
source                   1..360
                         mol_type = protein
                         note = Arabidopsis lyrata subsp. lyrata
                         organism = Arabidopsis lyrata
SEQUENCE: 346
MASKLCDSCK SATAALYCRP DAAFLCLSCD SKVHAANKLA SRHARVWMCE VCEQAPAHVT    60
CKADAAALCV TCDRDIHSAN PLARRHERVP VTPFYDSVSS DGSVKHTAVN FLDDCYLSDI   120
DGNGSREEEE EEAASWLLPN PKTTTTATAG MVAVTAAEEV PGDSPEMNTG QQYLFSDPDP   180
YLDLDYGSVD PKVESLEQNS SGTDGVVPVE NRTVRVPTVN ENCYEMDFTG GSKGFAYGGY   240
NCISHSVSSS SMEVGVVPDG GSVADVSYPY GGPATSGADP GSQRAVPLTS AEREARVMRY   300
REKRKNRKFE KTIRYASRKA YAEMRPRIKG RFAKRTDTSE SSDVVGHGGI FSGFGLVPTF   360

SEQ ID NO: 347           moltype = AA  length = 371
FEATURE                  Location/Qualifiers
source                   1..371
                         mol_type = protein
                         note = Arabidopsis lyrata subsp. lyrata
                         organism = Arabidopsis lyrata
SEQUENCE: 347
MLKQESNEID SEENNRARAC DTCRSNACTV YCHADSAYLC MSCDAQVHSA NRVASRHKRV    60
RVCESCERAP AAFLCEADDA SLCIACDSEV HSANPLSRRH QRVPILPISG NSFSSMATHH   120
```

```
QSETTMTDPE KRLVVDQEKG EEGDEDAKEV ASWLFPNSDK NINNQNNGLL FSDEYLDLVD    180
YNSSMDYKFT GQYHQHQQNC GVPQTSYGGD GVVPLQLEES RRHQCHNQQN FQFDIKYDSS    240
GSHYNDNCSL NHNVYILSME TGVVPESTAR DKTASPPRTP KKTTDQLPDP PIQMITQLSP    300
MDREARVLRY REKKKTRKFE KTIRYASRKA YAEIRPRVNG RFAKRREIEA EDQVFNTMLM    360
YDTGYGIVPS C                                                       371

SEQ ID NO: 348           moltype = AA   length = 348
FEATURE                  Location/Qualifiers
source                   1..348
                         mol_type = protein
                         note = Arabidopsis lyrata subsp. lyrata
                         organism = Arabidopsis lyrata
SEQUENCE: 348
MMKVESNWGQ ACDTCRSAAC TVYCRADSAY LCTSCDAQVH AANRLASRHE RVRVCQSCER    60
APAAFFCKAD AASLCTTCDS EIHSANPLAR RHQRVPILPI SENSYSSTAT NHSCETTVTD    120
PENRLVLGQG EEDEDEAEAA SWLLPNSGKN NGNNNGFSIG DEFLDLVDYS SSDKQFTDQS    180
NQYQLDCNVP QRSYEDGVVP LQVEVSKGHM NHEQQNFQLS ITCGSPRAHR SSNGSLSHMV    240
HVSSIDLGVV PESTNPRSPK AVTDQLPDPP AQMLSPRDRE ARVLRYREKK KMRKFEKTIR    300
YASRKAYAEK RPRIKGRFAK RNEVDAEANE AFSTIITFDT GYGIVPSF                348

SEQ ID NO: 349           moltype = AA   length = 400
FEATURE                  Location/Qualifiers
source                   1..400
                         mol_type = protein
                         note = Arabidopsis lyrata subsp. lyrata
                         organism = Arabidopsis lyrata
SEQUENCE: 349
MGGSTRESVV ACEFCGERTA VLFCRADTAK LCLPCDQHVH SANLLSRKHV RSQICDNCSK    60
EPVAVRCFTD NLVLCQDCDW DVHGSCSSSA THERSAVEGF SGCPSVLELA AVWGIDLEGK    120
KKEDEEDQLT KNFGMALDSW GSGSNSGQDL IVPYDVSIKK QSFSLGRSKK VVFKQLELLK    180
RGFVGGDGGG EIMVPERING GGSICQPSPM SAESQSHCGN AMQWNATNHS STLPIIAIWD    240
FNLGQSRNPE EPSPVETKGS TFTFNEVTHV KNDTRATNVK APFKETYQDD SIRSTSTKGQ    300
ETSKSNNIPA AIHSHKSSND SSDLHCMEHI AMTSNRATRL VAATNADLER LAQNRDNAMQ    360
RYKEKKKTRR YDKTIRYETR KARAETRLRV KGRFVKATDP                         400

SEQ ID NO: 350           moltype = AA   length = 366
FEATURE                  Location/Qualifiers
source                   1..366
                         mol_type = protein
                         note = Arabidopsis lyrata subsp. lyrata
                         organism = Arabidopsis lyrata
SEQUENCE: 350
MGYMCDFCGE QRSMVYCRSD AACLCLSCDR SVHSANALSK RHSRTLVCER CNAQPATVRC    60
VEERVSLCQN CDWSGHNNNS SSSSTSPQQH KRQTISCYSG CPSSSELASI WSFCLDLAGQ    120
SICEQEMGMM NIDDDGPTDN KNCNEDKKDV FVSIPETSSA AKGKSSSAKD VGVCEDDFYG    180
NLGMDEVDMA LENYEELFGT AFNPSEELFG HGGIDSLFQK HQTKAPEGGN SVHPAGSNDS    240
FMSSKTEPII CYTSKPAQSN ISFSGVTGES SAGDFQECGA SSSIQLSGEP PWYPPTSQEN    300
NACSHSVTRN NAVMRYKEKK KARKFDKRVR YASRKARADV RRRVKGRFVK AGEAYDYDPL    360
TPTRSY                                                              366

SEQ ID NO: 351           moltype = AA   length = 377
FEATURE                  Location/Qualifiers
source                   1..377
                         mol_type = protein
                         note = Arabidopsis lyrata subsp. lyrata
                         organism = Arabidopsis lyrata
SEQUENCE: 351
MEPKCDHCAT SQAVIYCKSD LAKLCQNCDF HVHSANPLSH RHSRSLICQK CFSQPAVIRC    60
LGEKVSYCQR CHWHASNCSD LGHRVQRLNP FSGCPSPTDF VKMWSSILEP SVSSLVSPFV    120
GSLPLNDPNN TMFGMAKINE LDGLIGSPYS MVPHSFNVTQ NFSDQLSFFS VESKGYPDLV    180
LKLEEGEEDL CEGLNFDNAP LNFDVGDDII GCSLEEPIEP DHTVPNCLLI DKNNTSVTAS    240
NFTIDNTSAS SPGQQMNINT GLPLPLSPVL FGQIHPSLNI SNVTGESNAA DYQDCGMPPG    300
FITSEAPWES NLEVSCPQAR TQAKLRYMEK KLKRSFGKQI RYASRKARAD TRKRVKGRFV    360
KAGDNYDYDP SSPTTNN                                                  377

SEQ ID NO: 352           moltype = AA   length = 347
FEATURE                  Location/Qualifiers
source                   1..347
                         mol_type = protein
                         note = Arabidopsis lyrata subsp. lyrata
                         organism = Arabidopsis lyrata
SEQUENCE: 352
MLKEESNESG TWARACDTCR SAACTVYCEA DSAYLCTTCD ARVHAANRVA SRHERVRVCQ    60
SCESAPAAFL CKADAASLCT ACDAEIHSAN PLARRHQRVP ILPLSANSCS SMAASETDAD    120
NDEDDREVAS WLLPNPGKNS GNQNNGFLFG VEYLDLVDYS SSMDNQFEDH QYSHQRSFG    180
GDGVVPLQVE ESTSHLQQSQ HNFQLGINYG FSSGANYNNN FLKDLNHSAS VSSMDISVVP    240
ESTASDITVQ HPRTTKETTD QLAGPPTQVV QQLTPMEREA RVLRYREKKK TRKFDKTIRY    300
ASRKAYAEIR PRIKGRFAKR IEIEAEAEEI FSTSLMSETG YGIVPSF                 347
```

```
SEQ ID NO: 353            moltype = AA  length = 391
FEATURE                   Location/Qualifiers
source                    1..391
                          mol_type = protein
                          note = Arabidopsis lyrata subsp. lyrata
                          organism = Arabidopsis lyrata
SEQUENCE: 353
MVVDVERRAA SVPGGKMVAR GCDACMKRSR ASWYCPADDA FLCQSCDSSI HSANHLAKRH   60
ERVRLQSSSW TETTEKTTSV WYEGFRRKAR TPRNKGLASE KLLQMEANDP LVPDLGGEEE  120
EVFFSFSSVE ENEESLNCCV PVFDPFSDMV IDDINGFCLV PDEVINNTTN GEELGELERE  180
VIDDEGFIGF LPLDMDLEDL TMDVERLLKE GQLCLGLKEP NDIGVIKEEN NVGFEIDCKD  240
LKRVKDEEEE EAKCENGRSK DSDGEASKDE DRKTSLFLSL DYEAVITAWD NHGSPWKTGI  300
KSECLLGGNT CPSHAVGGFD ELVSTVGSVT RQQVKDGGGS DGEREARVLR YKEKRRTRLF  360
SKKIRYEVRK LNAEQRPRIK GRFVKRTSLL T                                391

SEQ ID NO: 354            moltype = AA  length = 412
FEATURE                   Location/Qualifiers
source                    1..412
                          mol_type = protein
                          note = Arabidopsis lyrata subsp. lyrata
                          organism = Arabidopsis lyrata
SEQUENCE: 354
MMKSLASAVG GKTARACDSC VKRRARWYCA ADDAFLCHAC DGSVHSANPL ARRHERVRLK   60
SASSGKHRHA SSSSPSHQST WHQGFTRKAR TPRGGKKSHT MVFHDLVPEM STENQAESYE  120
VEVEEQLIFE VPVMNPMVKE QCFHQSVETK VEFPMMPLSF KCSDEEDEDN AESCLNGLFP  180
TDMELAQFTA DVETLLGGGM EREPHSIEEL GLGEVLKIEK EEVEEEEGVV TREVYDLDEA  240
EETSPFEISF DYEYAHKTTY EEEEEDEKED VMKNRMDVGV NEMSGRIKEE NKEKALMLRL  300
DYESVISTWN GQGIPWTDRE PSEIDLDMVC CPTHSLGESG EAHHHNHPFRG LGLHMGEAGD  360
GGREARVSRY REKRRTRLFS KKIRYEVRKL NAEKRPRMKG RFVKRSSIGV AL          412

SEQ ID NO: 355            moltype = AA  length = 419
FEATURE                   Location/Qualifiers
source                    1..419
                          mol_type = protein
                          note = Arabidopsis lyrata subsp. lyrata
                          organism = Arabidopsis lyrata
SEQUENCE: 355
MKSLANAVGA KTARACDSCV KRRARWYCAA DDAFLCQSCD SLVHSANPLA RRHERVRLKT   60
ASPAVVKHSN HSSSSPPHEA ATWHHGFTRK ARTPRGSGKK NNSSIFHDLV PEISVEDQTD  120
SYELEEQLIC QVPVLDPLVA EQFLNDVVEP KIEFPMMRSG VMIEEEEDNA ESCLNGFFPT  180
DMELEEFAAD VETLLGRGLD SESYPMEELG LSNSEMFKLE KDEIEEEVEE RKAMNMEIFD  240
DDRRDGDGTV PFELSFDYES SHKTSKEEVM KNVESSGECV VKVKEEEQKN VLLLRLNYDS  300
VISTWGGQGP PWSSGVPPER DMDISGWPAV SMGENGGECT HKKQYVGGCL PSSGFGDGGR  360
EARVSRYREK RRTRLFSKKI RYEVRKLNAE KRPRMKGRFV KRASLAASAA AISPLGVNY   419

SEQ ID NO: 356            moltype = AA  length = 326
FEATURE                   Location/Qualifiers
source                    1..326
                          mol_type = protein
                          note = Arabidopsis lyrata subsp. lyrata
                          organism = Arabidopsis lyrata
SEQUENCE: 356
MIWENQTDVK QQRACELCKN KHAVWYCASD DAFLCHVCDE SVHSANHVAT KHERVCLRTN   60
EISNYVLRGT TSNPVWHSGF RRKARTPRVR CEKKPQEKID DERRIEDPRV PEIGGEVMFF  120
IPEPNDDDMT SLVPEFEGFT EMGFFLNNHN GTEETTKQFN FEDEIDAKED LCYNGEDEEE  180
VKTDGAEACP EQYLMSCKKD YDNVITVSAK TEEIEDCYEN KARQRNMLLK LNYENVIAAW  240
DKQESPINQT EFNNTSNLQL VPPLQGIEEK RVSNRSEREA RVWRYRDKRK NRLFEKKIRY  300
EVRKVNADKR PRIKGRFVRR SLAMDS                                      326

SEQ ID NO: 357            moltype = AA  length = 438
FEATURE                   Location/Qualifiers
source                    1..438
                          mol_type = protein
                          organism = Vitis vinifera
SEQUENCE: 357
MADTCLAPHL GAEFAFTSVA RNMESDACHS KGFSTTPTCL FRLPTVTSSP PFVHCAPETQ   60
TYAHSHSLTH MLKDEGCNAD AAAGGGGGWA RVCDTCRSAA CTIYCRADSA YLCAGCDARI  120
HAANRVASQH ERVWVCESCE RAPAAFVCKA DAASLCATCD ADIHSANPLA RRHHRVPVLP  180
IAGCLYGPPA TDPGGTEDED EAASWLLLNP VKNNNGSSNN QNNGLLFGGE VDEYLDLVEY  240
NSCPENQFSD QYNQQQPPPH YSVPHKNYGG DRVVPQCGE AKGQLHQQHQ QQGFHLGMEY   300
ESSKAAYSYN PSISHSVSVS SMDVGVVPEA TTMSDISISI SHPRPPKGTI DLFSGPPIQM  360
PTQLTPMDRE ARVLRYREKK KTRKFEKTIR YASRKAYAET RPRIKGRFAK RTDVEVEVDQ  420
MFSTTLMAES GYGIVPSF                                               438

SEQ ID NO: 358            moltype = AA  length = 342
FEATURE                   Location/Qualifiers
source                    1..342
                          mol_type = protein
                          organism = Brassica rapa
```

```
SEQUENCE: 358
MGYMCDFCGE QRSMVYCRSD AACLCLSCDR SVHSANALSK RHSRTLVCER CNSQPATVRC    60
VEERVSLCQN CDWSSHNNNN NSSSSSNNHK RQTISCYSGC PSSSELASIW SFCLDLAGQS   120
GCEQEMGMMN IDGDGQNNQN CNEEKKDVVA GSSSRPETSS AAPATSAFPK DVRVCEDDFY   180
GNLGMDEVDL ALENYEELFG TAFNTSGELF GQGGIDCLFR KHHQGAAPEG GNLVQPAESN   240
DDSFMSSKTE PIICFTSKPA HSNISFSGVT GDSSAGDFQE CGASSSMQLS GEPPWYPQTS   300
QDNNASSHSV TRNNAVMRYK EKEKARKFDK TVRYASRKQE LM                     342

SEQ ID NO: 359          moltype = AA  length = 484
FEATURE                 Location/Qualifiers
source                  1..484
                        mol_type = protein
                        organism = Malus domestica
SEQUENCE: 359
MVSPKSGGVE GVPCDFCSDQ PAVLYCRADS AKLCLFCDQH VHSANLLSRK HVRSQICDNC    60
SSEAVSVRCS TDNLVLCQEC DWDAHGSCSV TAAHDRTPLE GFSGCPSALE LASLLGLDLQ   120
DKNLPARPDP QLQNWDMGLP SVDPSWNGFG MQDLMVPIQN GVVDLTGDMK RQNSGGISGK   180
QKQGIQKQLL ELLKRDLGGG RGGGGSGSEN LVPGTQTRNG WQEENGKGNG DVEGLASIDV   240
RNENGGVGGV AARAASLETV LQQQTPFSTM LMMPEENRDG DMLWDSNPHG QTQIWDFNLG   300
RLRDHEESGP LKVTYGSNVS GFMIKDFSEL MKESSLTDTK MLRDIYQMNS PVGHDDIKFN   360
ITSNNPEGSL GPATSESNNV PIGQPLSGSV FGDDKGSGAS NDISFMEQSF LMRGDSISMR   420
TVGTKADMEL LAQNRGNAML RYKEKKKTRR YDKHIRYESR KARADTRKRV KGRFVKATTE   480
SPDG                                                               484

SEQ ID NO: 360          moltype = AA  length = 364
FEATURE                 Location/Qualifiers
source                  1..364
                        mol_type = protein
                        organism = Malus domestica
SEQUENCE: 360
MCEVCDQAPA AVTCKADAAA LCVACDADIH SANPLARRHE RVPVEPFYDS AESIIVKSTA    60
AAPSSAGAAI NYLVPNGDVL SKTKDVNNDP ASNWLIPNPN FNSKLQMDIA PDITKSSGDL   120
FFPEMDLLLE LDYPNSIHTI SGPGTDGVVP VQTDPIPPPS LKMNHNISGP ADQNCFDMDF   180
CSSKFSSSFS YPTQSLSQSV SSFSLDVGVV PDQNSLSDIS YTFGRTACNG VSEPGDVSYS   240
FGQKASNNVS EPGDISYPFG RKASNNVSEP GAPVSATPAS QPATQLCGLN REARVLRYRE   300
KRKNRKFQKT IRYASRKAYA ETRPRIKGRF AKRTKTETET FDLIYGSGSA TFISDPQFGV   360
VPTF                                                               364

SEQ ID NO: 361          moltype = AA  length = 393
FEATURE                 Location/Qualifiers
source                  1..393
                        mol_type = protein
                        organism = Malus domestica
SEQUENCE: 361
MLKEDQSNGT ATANNWARVC DTCRAAACTV YCRADSAYLC SGCDATIHAA NRVASRHERV    60
WVCEACERAP AAFLCKADAA SLCTACDADI HSANPLARRH QRVPILPISG CLYSSQATEQ   120
GEMGVAVSAG AETEDGFLSQ EGDDTIYEED EDEAASWLLL NPVKNNNNNN NTNTQNNGFF   180
FGAEVDEYLD LVEYNTCADQ NNQFTDHHQQ HDQQQQQQYG VPYKNYGGDS VVPIHQGEV    240
GKAHQLQKQS FHQLGLEYES SKAAYSYNGS LSHSVSVSSM DVGVVPDSTM SDISISHPRT   300
PKGTIDLFSG PTIQMPTQLS PMDREARVLR YREKKKTRKF EKTIRYASRK AYAETRPRIK   360
GRFAKRTEME VEVDQMFATS LMAENGYGIV PSF                                393

SEQ ID NO: 362          moltype = AA  length = 409
FEATURE                 Location/Qualifiers
source                  1..409
                        mol_type = protein
                        organism = Malus domestica
SEQUENCE: 362
MGYMCDYCQV QRSMVHCRSD AACLCLSCDR NVHSANALSR RHLRTLICER CNSQPALVRC    60
TEERVSLCQN CDWMGHQAST SASGHKRQTL NCYSGCPSSA ELSSIWSFVS DLPSNGESAC   120
EQEMGLMSIA ENSTRSEWSQ TESNTRQSAS GADEVNPAHS MEKSGILVGS SSVPERSHAR   180
HVVGQLSGSV NASLPKLYSH GGKGTGLPED DDLYDDLDMD EMELNLENYD ELFGVSLNHS   240
EELFKNGGID SLFGAKNVSR DCQDAVAAEG SSFGLGNAPQ PACSNAASAD SVMSTKTDPV   300
ICFPAKQAHS NLSFSGITGE SSAGDCQDCG ASSTPWYPPC PESSMQSANR SNAVMRYKEK   360
KKARKFEKRV RYASRKARAD VRKRVKGRFI KAGEAYDYDP LNQARTRSY              409

SEQ ID NO: 363          moltype = AA  length = 448
FEATURE                 Location/Qualifiers
source                  1..448
                        mol_type = protein
                        organism = Selaginella moellendorffii
SEQUENCE: 363
MEKASSTSKS SSNLAATAMA IAGRALRPCD VCGRERAKWF CKADEAYLCE NCDGSVHGAN    60
AVSLRHERFR MGPNGMLMKN VKRVSKFQLA EDISPTNSAA AVTAACAKDS HCPPRKKPRS   120
SRSHSLGSNS SKESGKVKAE PKSPKEYAAE FQPCQESSHE VPIFDPLLED FAASDDNSLG   180
CTVPCATPPD EDDEEMCFTV PDDCDLDGFL DSEADLGVMD GIISGTIEMD GIADLGDVLG   240
ESECKTFTHD SFGIDFPAIF HSPSPNSDGS VADAFDSADA VKVKTEEAEE LDKIKLEVDE   300
MLGFAFSSAS TVKEEEVEKK ITLKLDYEDV LNAWSDRGPF WTEGPRPQTV PDDSLFDPAS   360
TLDYGLVPDF CMESTEVEAV GQVPVVNFGE DRLTPQGGRE ARVMRYREKR RTRLFSKKIR   420
```

```
YEVRKLNAER RPRLKGRFVK RTNSTPHA                                        448

SEQ ID NO: 364          moltype = AA  length = 287
FEATURE                 Location/Qualifiers
source                  1..287
                        mol_type = protein
                        organism = Selaginella moellendorffii
SEQUENCE: 364
MAKRPNCDVC EMQRASLYCE ADEAYLCHEC DASVHGANTL ASRHKRISFK QEQEEEEEEE     60
NLEEENDGVCP AHNFADSSFS LSRPSTVDYP LGGVRIGDVT YARVSSHTGS GGASLIAPRR   120
KEDEELHQVP RFVPVAQELP SLEPPRFHAL ASNGRASPVR STRFMSLLEG EATDADENHG   180
APDEDGAQEN QELGVVPDLV SPRTVEPAAA KPVAALPKGG PRLDKEREAR VNRYREKRRT   240
RMFSKKIRYE VRKIYAENRP RLKGRFVRRT NEIESLQCLW SEDQVRN                 287

SEQ ID NO: 365          moltype = AA  length = 448
FEATURE                 Location/Qualifiers
source                  1..448
                        mol_type = protein
                        organism = Selaginella moellendorffii
SEQUENCE: 365
MEKASSTSKS SSNLAATAMA IAGRALRPCD VCGRERAKWF CKADEAYLCE NCDGSVHGAN    60
AVSLRHERFR MGPNGMLMKN VKRVSKFQLA EDISPTNSAA AVTAACAKDS HCPPRKKPRS   120
SRSHSLGSNS SKESGKVKAE PKSPKEYAAE FQPCQESSHE VPIFDPLLED FAASDDNSLG   180
CTVPCATPPD EDDEEMCFTV PDDCDLDGFL DSEADLGVMD GIISGTIEMD GIADLGDVLG   240
ESECKTFTHD SFGIDFPEIF HSPSPNSDVS DADAFDSADA VKVKTEEVEE LDKIKLEVDE   300
MLGFAFSSAS TVKEEEVEKK ITLKLDYEDV LNAWSDRGPF WTEGPRPQTV PDDSLFDPAS   360
TLDYGLVPDF CMESTEVEAV GQVPVVNFGE DRLTPRGGRE ARVMRYREKR RTRLFSKKIR   420
YEVRKLNAER RPRLKGRFVK RTNSTPHA                                     448

SEQ ID NO: 366          moltype = AA  length = 452
FEATURE                 Location/Qualifiers
source                  1..452
                        mol_type = protein
                        organism = Selaginella moellendorffii
SEQUENCE: 366
MERPCDFCGD ERATVYCKAD AALLCLSCDR NVHDANALSR RHSRTLVCDM CVVQPAVVRC    60
GAESKAFCQA CDGKRHAEYR AMHHKRRAIV SYTGCPSSAE LARLWYCDVS DEPGGNGSGN   120
GSGKGSTSKC LETFQGWVPA SSQSQQQLHH PSTPQSREKK IFQQLMILQN RPPQQGLGHQ   180
QREKAITQAQ TLMPPPPPRP STSSSNGVAE IQYQTAQLGL HSPSSKPESG EIFPQQGENA   240
WKAASPDQQL WNNAQDMGID DICKALTADD VNVFDNYEDL FLSAQDAAGT PFQDIGIACP   300
SMAPAMSSKS MQNGCSSMDT ANSLQSDASE SACRGPFHPA AAAGNVQFSP RPACSSGVSG   360
DSSGTEYADC ASVFYSAGEL WSSTSSDPAA ASEARGNAML RYKEKRKTRK YEKRIRYESR   420
KTRADTRRRI KGRFVKAGQV YDYDPLSTTR SY                                 452

SEQ ID NO: 367          moltype = AA  length = 363
FEATURE                 Location/Qualifiers
source                  1..363
                        mol_type = protein
                        organism = Selaginella moellendorffii
SEQUENCE: 367
MTKPCDACQS GNAVIYCRAD AAFLCCSCDN KVHCANKLAS RHERVLVCEV CEHAPAAVTC    60
KADAAALCVT CDSDIHSANP LARRHERVPI TPFVDSSDGG AAPPPAPPIL HDTGNANHDD   120
EEEESSAAEAA SWLLPQPNNL AKSDGEKLGG GVESTDFYST LKPSAPPPLR IEKLLLKSQA   180
AANFDLFSDE DSYLDMDFLG ALHSVTDSLV PIHTTGGALH SSSPVGSNAD SYDLDVHDKS   240
PPHAYCPGLS LSASSIDVGV VPDASLSDIS TPQSRPTSSS VFGSGEAQAA APLHHATPL   300
EPIAREARVL RYREKRKNRK FEKTIRYASR KAYAETRPRI KGRFAKRGEM DSYDASFGVV   360
PSF                                                                363

SEQ ID NO: 368          moltype = AA  length = 453
FEATURE                 Location/Qualifiers
source                  1..453
                        mol_type = protein
                        organism = Selaginella moellendorffii
SEQUENCE: 368
MERPCDFCGD ERATVYCKAD AALLCLSCDR NVHEANALSR RHSRTLVCDM CVVQPAVVRC    60
GAESKAFCQA CDGKRHAEYR AMHHKRRAIV SYTGCPSSAE LARLWYCDVS DEPGSGSGSG   120
NGSGKGSTSK SLETLQGWLP ASSQSQQQLH HPSTPQSREK KIFQQLMILQ SRPPQQALGH   180
QQREKAITQA QTLMPPPPPR PSTSSSSGVA EIQNQTAQLG LHSPSSKPES GEIFPQQGEN   240
AWKAASPDQQ LWNNAQDMGI DDICKALTAD DVNVFDNYED LFLSAQDAAG TPFQDIGIAC   300
PSMAPAMSSK SMQNGCSSMD TANSLQSDAS ESACRGPFHP AAAAGNVQFS PRPACSSGVS   360
GDSSGTEYAD CASVFYAAGE LWSSTSSDPA AASEARGNAM LRYKEKRKTR KYEKRIRYES   420
RKTRADTRRR IKGRFVKAGQ VYDYDPLSTT RSY                                453

SEQ ID NO: 369          moltype = AA  length = 405
FEATURE                 Location/Qualifiers
source                  1..405
                        mol_type = protein
                        note = Volvox carteri f. nagariensis
                        organism = Volvox carteri
```

```
SEQUENCE: 369
MACVVCAAQA SVYCENDKAL LCKDCDVRIH MSNAVAARHV RRIPCEGGCS KGASLFCRCD    60
NAYMCEACHC ANPLAATHET EPTAPLPLME QENAVAEQPH ATGPCESVAQ SAASPVAWFV   120
DDEKPSLGSF EEPIMLSPAG SEAVVPVMSA PADDFTFTEP ATFKEIKDKL EFESLEFDNS   180
WMELNFDFTD ILSDGPSDVG LVPTFDLEGV DPVADATVPS VAEEVVVAES DAATEIHRKR   240
TAEPSDEEPA AKLPAISEAA TTALGLHAAF QMTQPASLFF QSAVAQPSLL PPMVPPAVIS   300
PLATTAAAPP LQPPPTAVQS KSSAAYNTAL AAGANLTREQ RVARYREKRK NRKFEKTIRY   360
ASRKAYAEIR PRIKGRFAKK EEIEAWKAAH GGEDAVVPEI LDGEF                  405

SEQ ID NO: 370          moltype = AA  length = 402
FEATURE                 Location/Qualifiers
source                  1..402
                        mol_type = protein
                        organism = Arabidopsis thaliana
SEQUENCE: 370
MGTSTTESVV ACEFCGERTA VLFCRADTAK LCLPCDQHVH SANLLSRKHV RSQICDNCSK    60
EPVSVRCFTD NLVLCQECDW DVHGSCSSSA THERSAVEGF SGCPSVLELA AVWGIDLKGK   120
KKEDDEDELT KNFGMGLDSW GSGSNIVQEL IVPYDVSCKK QSFSFGRSKQ VVFEQLELLK   180
RGFVEGEGEI MVPEGINGGG SISQPSPTTS FTSLLMSQSL CGNGMQWNAT NHSTGQNTQI   240
WDFNLGQSRN PDEPSPVETK GSTFTFNNVT HLKNDTRTTN MNAFKESYQQ EDSVHSTSTK   300
GQETSKSNNI PAAIHSKSS NDSCGLHCTE HIAITSNRAT RLVAVTNADL EQMAQNRDNA    360
MQRYKEKKKT RRYDKTIRYE TRKARAETRL RVKGRFVKAT DP                     402

SEQ ID NO: 371          moltype = AA  length = 417
FEATURE                 Location/Qualifiers
source                  1..417
                        mol_type = protein
                        organism = Arabidopsis thaliana
SEQUENCE: 371
MMKSLANAVG AKTARACDSC VKRRARWYCA ADDAFLCQSC DSLVHSANPL ARRHERVRLK    60
TASPAVVKHS NHSSASPPHE VATWHHGFTR KARTPRGSGK KNNSSIFHDL VPDISIEDQT   120
DNYELEEQLI CQVPVLDPLV SEQFLNDVVE PKIEFPMIRS GLMIEEEEDN AESCLNGFFP   180
TDMELEEEFA DVETLLGRGL DTESYAMEEL GLSNSEMFKI EKDEIEEEVE EIKAMSMDIF   240
DDDRKDVDGT VPFELSFDYE SSHKTSEEEV MKNVESSGEC VVKVKEEEHK NVLMLRLNYD   300
SVISTWGGQG PPWSSGEPPE RDMDISGWPA FSMVENGGES THQKQYVGGC LPSSGFGDGG   360
REARVSRYRE KRRTRLFSKK IRYEVRKLNA EKRPRMKGRF VKRASLAAAA SPLGVNY     417

SEQ ID NO: 372          moltype = AA  length = 406
FEATURE                 Location/Qualifiers
source                  1..406
                        mol_type = protein
                        organism = Arabidopsis thaliana
SEQUENCE: 372
MDPTWIDSLT RSCEANSNTN HKRKRERETL KHREKKKKRF RERKMASKLC DSCKSATAAL    60
YCRPDAAFLC LSCDSKVHAA NKLASRHARV WMCEVCEQAP AHVTCKADAA ALCVTCDRDI   120
HSANPLARRH ERVPVTPFYD SVSSDGSVKH TAVNFLDDCY FSDIDGNGSR EEEEEEAASW   180
LLLPNPKTTT TATAGIVAVT SAEEVPGDSP EMNTGQQYEF SDPDPYLDLD YGNVDPKVES   240
LEQNSSGTDG VVPVENRTVR IPTVNENCFE MDFTGGSKGF TYGGGYNCIS HSVSSSSMEV   300
GVVPDGGSVA DVSYPYGGPA TSGADPGTQR AVPLTSAERE ARVMRYREKR KNRKFEKTIR   360
YASRKAYAEM RPRIKGRFAK RTDTNESNDV VGHGGIFSGF GLVPTF                 406

SEQ ID NO: 373          moltype = AA  length = 326
FEATURE                 Location/Qualifiers
source                  1..326
                        mol_type = protein
                        organism = Arabidopsis thaliana
SEQUENCE: 373
MTSHQNIKIS EKIMISKYQE DVKQPRACEL CLNKHAVWYC ASDDAFLCHV CDESVHSANH    60
VATKHERVCL RTNEISNDVR GGTTLTSVWH SGFRRKARTP RSRYEKKPQQ KIDDERRED    120
PRVPEIGGEV MFFIPEANDD DMTSLVPEFE GFTEMGFFLS NHNGTEETTK QFNFEEEADT   180
MEDLYYNGEE EDKTDGAEAC PGQYLMSCKK DYDNVITVSE KTEEIEDCYE NNARHRLNYE   240
NVIAAWDKQE SPRDVKNNTS SFQLVPPGIE EKRVRSEREA RVWRYRDKRK NRLFEKKIRY   300
EVRKVNADKR PRMKGRFVRR SLAIDS                                      326

SEQ ID NO: 374          moltype = AA  length = 385
FEATURE                 Location/Qualifiers
source                  1..385
                        mol_type = protein
                        organism = Helianthus annuus
SEQUENCE: 374
MLDHTGTLCL KTSTTWARVC DTCRSAPCTI YCRPDAAYLC TACDARIHAA NKLQSSQHER    60
VWVCEACEQA PAAFICKADA ASLCTTCDAD IHSANPLARR HHRVPVMPIP GALYGPQGAG   120
PDPRAVMGLG VGVDSQSGFL SNDGGGDEED ESEAASWLLF DGPVVVNKNS QSQSGGGGKD   180
SGFLFSGEGG EEDEYLEFME FGSDVQAQCY ANKVNDQKMS YADADSVPV QSQSGGGGKD   240
FQLGVDEYGA AAGATGGYGY PQLTHSVSMS SMEVGVVPDS TITEASFSHP RPSKGTIDLF   300
SNPPVQVATQ LTPMDREARV LRYREKKKTR KFEKTIRYAS RKAYAETRPR IKGRFAKRTN   360
ADVDVDQMFP TNHMLEGGYG IVPSF                                       385

SEQ ID NO: 375          moltype = AA  length = 385
```

```
FEATURE                 Location/Qualifiers
VARIANT                 246
                        note = X can be any naturally occurring amino acid
VARIANT                 337
                        note = X can be any naturally occurring amino acid
VARIANT                 361
                        note = X can be any naturally occurring amino acid
source                  1..385
                        mol_type = protein
                        organism = Helianthus annuus
SEQUENCE: 375
MLDHTGTLCL KTSTTWARVC DTCRSAPCTI YCRPDAAYLC TACDARIHAA NKLQSSQHER   60
VWVCEACEQA PAAFICKADA ASLCTTCDAD IHSANPLARR HHRVPVMPIP GALYGPQGAG  120
PDPRAVMGLG VGVDSQSGFL SNDGGGDEED ESEAASWLLF DGPVVVNKNS QSQSGGGGKD  180
SGFLFSGEGG EEDEYLEFME FGSDVQAQCY ANKVNDQKMS YADADSVVPV QKNHEFQNHK  240
FQLGVXYEGA AAGATGGYGY PQLTHSVSMS SMEVGVVPDS TITEASLSHS RPSKGTIDLF  300
SNPPVQVATQ LTPMDREARV LRYREKKKTR KFEKTIXYAS RKAYAETRPR IKGRFAKRTN  360
XDVDVDQMFP TNHMLEGGYG IVPSF                                       385

SEQ ID NO: 376          moltype = AA  length = 388
FEATURE                 Location/Qualifiers
source                  1..388
                        mol_type = protein
                        organism = Helianthus annuus
SEQUENCE: 376
MLNEDLTSTL CLKNSTTRAR LCDTCHLLPG TIFCEADLAY LCTACDLHVH AANKLSSRHK   60
RVRVCDACEQ APAAFICKAD AASLCTTCDA VIHSANPLSR RHHRVPVMPI LGSSVYNNNN  120
NNEPWSVIGL GFQPQDSADQ ATLDHHNHHQ DEDEAASWLI FHDSPPKNNG QGQSQTNEFV  180
SNGDEYLELV DYNSCQDTPF SDDLKFDDDN KYMHDGINNN IQQQQRYGGC DADSLVPGQK  240
YHQLQHQHNF QNQKFQLGMD YETSNGGYGY SASLGDSVSM SSMEVGIAVD STITEASIDL  300
FSNPSIQMPT QLTPIDREAR VLRYREKKKT RKFEKTIRYA SRKAYAETRP RIQGRFAKRT  360
NLDIDIEVDQ MFSTSLITQD GSCTFPSF                                    388

SEQ ID NO: 377          moltype = AA  length = 386
FEATURE                 Location/Qualifiers
VARIANT                 213
                        note = X can be any naturally occurring amino acid
source                  1..386
                        mol_type = protein
                        organism = Helianthus annuus
SEQUENCE: 377
MLNEDLTSTL CLKNSTTRAR LCDTCHLLPG TIFCEADLAY LCTACDLHVH AANKLSSRHK   60
RVRVCDACEQ APAAFICKAD AASLCTTCDA VIHSANPLSR RHHRVPVMPI LGSSVYNNNN  120
NNNNEPWSVI GLGFQPQDSA DQATLDHHNH HQDEDEAASW LIFHDSPPKN NGHGQSQTNE  180
FVSNGDEYLE LVDYNSCQDT PFSDDLKFDD DNXYIQQQQQ QQQRYGGCDA DSLVPGQKYH  240
QLQHQHNFQN QKFQLGMDYE TSNGGYGYSA SLGDSVSMSS MEVGIAVDST ITEASIDLFS  300
NPSIQMPTQL TPIDREARVL RYREKKKTRK FEKTIRYASR KAYAETRPRI QGRFAKRTNL  360
DIDIEVDQMF STSLITQDGS CTFPSF                                      386

SEQ ID NO: 378          moltype = AA  length = 337
FEATURE                 Location/Qualifiers
source                  1..337
                        mol_type = protein
                        organism = Brassica napus
SEQUENCE: 378
MLKQEGNWAQ TCDTCRSAAC TVYCRADSAY LCTSCDAQIH AANRLASRHE RVRVCQSCER   60
APAAFFCKAD AASLYTACDS QIHSANPLAR RHQRVPILPI SGSMVTNRSS ETTEAEDIVV  120
VGQEEEDEAE AASWLLPTSV KNCGDNNNNN NNSQDNRFSV GEEYLDLVDY SKYQQDYNVP  180
QRRSYVADGV VPLQVEVSKS LSHMHHEQHN FQFGFTNVSS EASPIHMVSL VPESTLSETT  240
VSNPRSPKAA TEELPEAPVQ MLSPMERKAR VMRYREKKKT RKFEKTIRYA SRKEYAEKRP  300
RIKGRFAKRN EVDAEEADKA FSSMVMFDTG YGIVPSF                          337

SEQ ID NO: 379          moltype = AA  length = 369
FEATURE                 Location/Qualifiers
source                  1..369
                        mol_type = protein
                        organism = Triticum aestivum
SEQUENCE: 379
MFMNCNFNSN LLENEAGRIS FPWARPCDGC HAAPSAVYCC ADAAYLCASC DTQVHSANRV   60
ASRHERVRVC ETCESAPAVL ACHADAAALC TACDAQVHSA NPIAQRHQRV PVLPLPAVAI  120
PAASGFAEAE ASVTAHGDKE EGEEVDSWRL RRNSDDNNCA NKIDRYYNLV GYNMYYNNIT  180
CDPRPEEQYR MQEQRVQNRY IEKQGCECVV PPQVVMASEQ QESDYGTRGA GQAASVTAIT  240
STYTASISND ISFSSMEVGI IPDNTRPDIS NSNILTGSEA MELSGHSLQM PVHFSSMDRE  300
ARVLRYKEKK QTRKFQKTIR YATRKAYAEA RPRIKGRFAK RSDIEHEEDH MLSPPALPDT  360
SSYNTVPWF                                                         369

SEQ ID NO: 380          moltype = AA  length = 370
FEATURE                 Location/Qualifiers
source                  1..370
```

```
                         mol_type = protein
                         organism = Triticum aestivum
SEQUENCE: 380
MFMNCNFNSN LLEKEAGRTS FPWARPCDGC HAAPSAVYCC ADAAYLCASC DTQVHSANRV   60
ASRHERVRVC ETCESAPAVL ACHADAAALC TACDAQVHSA NPIAQRHQRV PVLPLPAVAL  120
PAASGFVEAE ASVTAHGDKE EGEEVDSWLL RRNSDDNNCA NKIDRYFNLV GYNMYYDNIT  180
CDPRPEEQYR MQEQQHVQNR YIEKEGCECV VPPQVVMASE QQESDYGTIG AGQAASVTAM  240
TSTYTASISN DISFSSMEVG IVPDNTRPDI SNSNILTSSE AMELSGHSLQ MPVHFNSMDR  300
EARVLRYKEK KQTRKFQKTI RYATRKAYAE ARPRIKGRFA KRSDIEHEED HMLSPPALQD  360
TSSYNTAPWF                                                        370

SEQ ID NO: 381           moltype = AA   length = 369
FEATURE                  Location/Qualifiers
source                   1..369
                         mol_type = protein
                         organism = Triticum aestivum
SEQUENCE: 381
MFMNCNFNSN LLENEAGRIS FPWARPCDGC HAAPSTVYCC ADAAYLCASC DTQVHSANRV   60
ASRHERVRVC ETCESAPAVL ACHADAAALC TACDAQVHSA NPIAQRHQRV PVLPLPAVAI  120
PAASGFAEAE ASVTAHGDKE EGEEVDSWLL RRNSDDNNCA NKIDRYYNLV GYNMYYDNIT  180
CDPRPEEQYR MQEQHVQNRY IEKEGCECVV PPQVVMASEQ QESDYGTIGA GQAASVTAMT  240
STYTASISND ISFSSMEVGI VPDNSRPDIS NSNILTSSEA MELSGHSLQM PVHFSSMDRE  300
ARVLRYKEKK QTRKFQKTIR YATRKAYAEA RPRIKGRFAK RSDIEHEEDH MLSPPALPDT  360
SSYNTVPWF                                                         369

SEQ ID NO: 382           moltype = AA   length = 321
FEATURE                  Location/Qualifiers
source                   1..321
                         mol_type = protein
                         organism = Brassica rapa
SEQUENCE: 382
MLKEESNESG GTRACDTCRS AACTIYREAD STYLCTTCDA RVHAAKRVRV CDSCESAPAA   60
FFCKADAAPL CTACDAEIHS ANPLARRHQR VPITSNSCGS MATDGDNNVM MVSEEKEDAD  120
EVASWLMLNP GKNNQNNGFL FGVEYLDLVD YSSSIDNNER DQYNHYQRSF GGGEDGVVPL  180
QLEESTSHMQ QSQHNFHLGV NYGFSTEPHY SYISVVPEST SSDTTVQHAK ETMDQVSGPP  240
TQMVQQLTPA DREARVLRYR EKKKRRKFEK TIRYASRKAY AEVRPRIKGR FAKRIDMEAD  300
AEQLFSTSLM SNTSYGIVPS F                                           321

SEQ ID NO: 383           moltype = AA   length = 422
FEATURE                  Location/Qualifiers
source                   1..422
                         mol_type = protein
                         organism = Populus deltoides
SEQUENCE: 383
MPRFTSLILS SPLVFFLQVS LILATNAHSL SYIAKDSIIE IGIGREREEV MLKEESGGSG   60
GVVNNWARVC DTCRAAACTV YCRADSAYLC AGCDARVHAA NRVASRHERV RVCEACERAP  120
AALLCKADAA SLCTACDADI HSANPLARRH QRVPILPISG YLYGTQVGPA AGETEDQFMT  180
QEGEETIGEE DEDEAASWLL LNPAKNSNNQ NNNGFLFGGE VDEYLDIVEY NSCAENQYSD  240
QYNQQHYSVP PKSCGGDSVV PIQYGEGKDH QQQQQQQYHN FQLGLEYEPA KAAYSYDGSV  300
SQGVSMSSMD VGVVPESAMS EISISHQSAS RGTIDLFSSP PIQMPSQLSP MEREARVLRY  360
REKKKARKFE KTIRYASRKA YAETRPRIKG RFAKRTDVDV EVDQMFSSTL MAETAYGIVP  420
SF                                                                422

SEQ ID NO: 384           moltype = AA   length = 372
FEATURE                  Location/Qualifiers
source                   1..372
                         mol_type = protein
                         organism = Populus deltoides
SEQUENCE: 384
MLKQESSGSG GGDNRARLCD TCRAAACTVY CRADSAYLCA GCDARVHAAN RVASRHERVW   60
VCESCERAPA ALLCKADAAS LCTACDADIH SANPLARRHQ RVPILPISGC LHGSQVGPAA  120
GETEDRFTTQ EGEETISEEE EEEDEAASW LLLNPVKNSK NQNNNGFLFE GEVDEYLDLV  180
EYNSCTENQC SDQYNQQHYC VPPKSYGGDR VVPIQYGEGK DHQQQRQYHN FQLGLEYEPS  240
KAAYSYNGLI SQSVSMSSMD VGVVPESTMS EISISQHRTP KRTIELFSST AIQMPSQLSP  300
MDREARVLRY REKKKTRKFE KTIRYASRKA YAETRPRVKG RFAKRKDVEV EDDRTFSSTL  360
MAGTGCGIVP SF                                                     372

SEQ ID NO: 385           moltype = AA   length = 401
FEATURE                  Location/Qualifiers
source                   1..401
                         mol_type = protein
                         organism = Arabidopsis thaliana
SEQUENCE: 385
MGTSTTESVV ACEFCGERTA VLFCRADTAK LCLPCDQHVH SANLLSRKHV RSQICDNCSK   60
EPVSVRCFTD NLVLCQECDW DVHGSCSSSA THERSAVEGF SGCPSVLELA AVWGIDLKGK  120
KKEDDEDELT KNFGMGLDSW GSGSNIVQEL IVPDYVSCKK QSFSFGRSKQ VVFEQLELLK  180
RGFVEGEGEI MVPEGINGGG SISQPSPTTS FTSLLMSQSL CGNGMQWNAT NHSTGQNTQI  240
WDFNLGQSRN PDEPSPVETK GSTFTFNNVT HLKNDTRTTN MNAFKESYQE DSVHSTSTKG  300
QETSKSNNIP AAIHSHKSSN DSCGLHCTEH IAITSNRATR LVAVTNADLE QMAQNRDNAM  360
```

```
QRYKEKKKTR RYDKTIRYET RKARAETRLR VKGRFVKATD P                                401

SEQ ID NO: 386           moltype = AA  length = 391
FEATURE                  Location/Qualifiers
source                   1..391
                         mol_type = protein
                         organism = Solanum lycopersicum
SEQUENCE: 386
MLKKENSNNW ARVCDSCHSA TCTVYCRADS AYLCAGCDAR IHTASLMASR HERVWVCEAC            60
ERAPAAFLCK ADAASLCASC DADIHSANPL ARRHHRVPIM PIPGTIYGPP AVHTITGGSM            120
MIGGTTGEGT EDDGFLSLNQ DADDTTIDEE DEDEAASWLL LNPPVKNNNK NNNYGMLFGG            180
EVVDDYLDLA EYGGDSQFND QYSVNQQQQH YSVPQKSYVE DSVVPVQNGQ RKSLILYQTP            240
QQQQSHHLNF QLGMEYDNSN TGYGYPASLS HSVSISSMDV SVVPESAQSE TSNSHPRPPK            300
GTIDLFSGPP IQIPPQLTPM DREARVLRYR EKKKNRKFEK TIRYASRKAY AETRPRIKGR            360
FAKRTDVEAE VDQMFSTQLM TDSNYGIVPS F                                          391

SEQ ID NO: 387           moltype = AA  length = 438
FEATURE                  Location/Qualifiers
source                   1..438
                         mol_type = protein
                         organism = Pinus radiata
SEQUENCE: 387
MVLENFGGVG AREASCRIRH ELRGIGGWRM SMPKLCDVCQ VSSSVIYCRA HTAQLCLVCD            60
AKIHGGSKAS LCHERVWVCE VCEQAPAVVT CKADAAALCV ACDTDIHSAN PLASRHERAP            120
VIPFYECPNM PTNNTVTHAN NDNLDCNVLL NEDGGGDDPL KHDYVDDDYG DYDDDENDQN            180
NLLNNQEDNN DAEICCAEEA ATASWLIPEA NRNNLTIING GNSEGEDKMV KDKLKFKAYM            240
QSMDFLQDVD NYADLEYLGT TTITTPINPT ANMGADSMVP VHTPEVIEHS STKVSIDTAG            300
SMDVDAASKC NHVYRTTSLN HCVSSSPIDV GIVPDSNITS DISTPYHDPR GVFEIPPRVV            360
HPGGQGEVMG REARVLRYRE KRKNRRFEKT IRYASRKAYA ETRPRIKGRF AKRTEVEVEQ            420
IYSSSLLPDQ GYGVVPSY                                                         438

SEQ ID NO: 388           moltype = AA  length = 452
FEATURE                  Location/Qualifiers
source                   1..452
                         mol_type = protein
                         note = Oryza sativa Japonica Group
                         organism = Oryza sativa
SEQUENCE: 388
MSCSSEKAAG AVGGKAARAC DSCLRRRARW YCAADDAFLC QGCDTSVHSA NPLARRHERL            60
RLRVSSPPPL TARASVEEEA AAAVGTTTTT TSKREGGVTP AWSKRKARTR RPQVKSVGQL            120
LSRRLVVPEM AVESSDERKA DEDGAHEELE GQLLYRVPVF DPSLAEFCSP PPIDDAAAAS            180
SSCFKEDAAD GAVEDAKYPA AAASSPVQQL PDSFVNFEPT DAELREFAAD MEALLGQGLD            240
DSNELQDSFY METLGLITPP VEESGRVKME LDGGVASNSR VSLPSCRAHP KPEDVESADV            300
LDIDFNCTSP DEQKSSASNG AAADSQFFHR SLDLRLNYEA IIESWGNSPW TDGRPPHGQL            360
DDFWPNDHHY SGLWAAGGGG HGAEVGMMTV RPRMDGPGRE ARVTRYREKR RTRLFSKKIR            420
YEVRKLNAEK RPRMKGRFVK RPSAAAAPCA VT                                         452

SEQ ID NO: 389           moltype = AA  length = 362
FEATURE                  Location/Qualifiers
source                   1..362
                         mol_type = protein
                         organism = Arabidopsis thaliana
SEQUENCE: 389
MASKLCDSCK SATAALYCRP DAAFLCLSCD SKVHAANKLA SRHARVWMCE VCEQAPAHVT            60
CKADAAALCV TCDRDIHSAN PLARRHERVP VTPFYDSVSS DGSVKHTAVN FLDDCYFSDI            120
DGNGSREEEE EEAASWLLLP NPKTTTTATA GIVAVTSAEE VPGDSPEMNT GQQYLFSDPD            180
PYLDLDYGNV DPKVESLEQN SSGTDGVVPV ENRTVRIPTV NENCFEMDFT GGSKGFTYGG            240
GYNCISHSVS SSSMEVGVVP DGGSVADVSY PYGGPATSGA DPGTQRAVPL TSAEREARVM            300
RYREKRKNRK FEKTIRYASR KAYAEMRPRI KGRFAKRTDT NESNDVVGHG GIFSGFGLVP            360
TF                                                                          362

SEQ ID NO: 390           moltype = AA  length = 405
FEATURE                  Location/Qualifiers
source                   1..405
                         mol_type = protein
                         organism = Pisum sativum
SEQUENCE: 390
MLEQKFLTTT SATVRSAVTW PRTCDTCRSA PCAVFCRADS AYLCAGCDAR IHAANRVASR            60
HERVWVCEAC ERAPAAFLCK ADAASLCSSC DADIHSANPL ASRHQRVPIL PISGYLGPP             120
TTLLGADDEG FVRGGGDAEE EEDEGADMED ENEAASWLLL NPLKNNHHNI NNHNNNNNSN            180
DHNQEGNNNG FLFSGEVDEY LDLVDCNSCG GGENTFTTNN THDHDYSRDQ QQQRQDHYGV            240
PQKNYVGDSV VPVQQQHLQN FQLGLEFESS KAGFSYNGAS ISQSVSVSSM DVGVVPESTM            300
RDATTMSYSR PSKGTIDLFS APPIQMTSHF SPMDREARVL RYLEKKKTRK FEKTIRYASR            360
KAYAETRPRI KGRFAKRTDV EAEVDQMFST TLITEVGYGI VPSFV                           405

SEQ ID NO: 391           moltype = AA  length = 368
FEATURE                  Location/Qualifiers
source                   1..368
                         mol_type = protein
```

```
                            organism = Physcomitrella patens
SEQUENCE: 391
MPKSCDACQA SSAVVYCRAD AAYLCLGCDG KVHGANKLAS RHERLWMCEV CEVAAAVVTC    60
KADAASLCVS CDTDIHSANP LAQRHERVPV QPLFDCVSQF RGTHFSVLAP KNECNNNLLK   120
GDEDPAVAEA VSWLLPHPKT LSSAILRGIA AADEAPAPPF RERPFSPKLK KLKVEQAADI   180
YSDVDPFLVL DGGNGTGFQP DSLVPVHIPE GPDDSPSLAN STAPSSAINF RASQKSGCSY   240
GTSTLTHSMS CSSVDAAVVP DSSLSDISTP YSKALDSQDS QDLSGALVPH QASKPIDTVD   300
REARVMRCKE KRQKRKFEKT IRYASRKAYA ESRPRIKGRF TKRTDSDVEQ MFSSCTADSG   360
FGVVPSSC                                                            368

SEQ ID NO: 392          moltype = AA   length = 407
FEATURE                 Location/Qualifiers
source                  1..407
                        mol_type = protein
                        note = Oryza sativa Indica Group
                        organism = Oryza sativa
SEQUENCE: 392
MNYNFGGNVF DQEVGVGGEG GGGGEGSGCP WARPCDGCRA APSVVYCRAD AAYLCASCDA    60
RVHAANRVAS RHERVRVCEA CERAPAALAC RADAAALCVA CDVQVHSANP LARRHQRVPV   120
APLPAITIPA TSVLAEAVVA TATVLGDKDE EVDSWLLLSK DSDNNNNNNN NNDNDNKDNN   180
NSNSSNNGMY FGEVDEYFDL VGYNSYYDNR IENNQDQQYG MHEQQEQQQQ QQEMQKEFAE   240
KEGSECVVPS QITMLSEQQH SGYGVVGADQ AASMTAGVSA YTDSISNSIS FSSMEAGIVP   300
DSTVIDMPNS RILTPAGAIN LFSGPSLQMS LHFSSMDREA RVLRYREKKK ARKFEKTIRY   360
ETRKAYAEAR PRIKGRFAKR SDVQIEVDQM FSTAALSDGS YGTVPWF                 407

SEQ ID NO: 393          moltype = AA   length = 319
FEATURE                 Location/Qualifiers
source                  1..319
                        mol_type = protein
                        organism = Arabidopsis thaliana
SEQUENCE: 393
MFCAEIMISK YQEDVKQPRA CELCLNKHAV WYCASDDAFL CHVCDESVHS ANHVATKHER    60
VCLRTNEISN DVRGGTTLTS VWHSGFRRKA RTPRSRYEKK PQQKIDDERR REDPRVPEIG   120
GEVMFFIPEA NDDDMTSLVP EFEGFTEMGF FLSNHNGTEE TTKQFNFEEE ADTMEDLYYN   180
GEEEDKTDGA EACPGQYLMS CKKDYDNVIT VSEKTEEIED CYENNARHRL NYENVIAAWD   240
KQESPRDVKN NTSSFQLVPP GIEEKRVRSE REARVWRYRD KRKNRLFEKK IRYEVRKVNA   300
DKRPRMKGRF VRRSLAIDS                                                319

SEQ ID NO: 394          moltype = AA   length = 348
FEATURE                 Location/Qualifiers
source                  1..348
                        mol_type = protein
                        organism = Glycine max
SEQUENCE: 394
MLDGEATMGT WARMCDTCRS APSSVFCRAH TAFLCATCDA RLHASLTWHE RVWVCEACER    60
APAAFLCKAD AASLCASCDA DIHAANPLAS RHHRVPILPI AAAPGNNDND NVDDADLDDD   120
DETASWLLLN PVKSASVPNN NNTNNGFSYN GEVDEYLDLV DDCDNHHFAS VATTTDHYSH   180
QHQHFGVVSH KSYAGDSVVP VQHHQHFQLG LEFDNSKAAF SYNASVNQSV SVSSMDIGVV   240
PESPMRDVSI GHTRTPKGTI DLFSGPPIQV PSHFSPMDRE ARVLRYREKK KTRKFEKTIR   300
YASRKAYAET RPRIKGRFAK RTDVEAEVDQ MFSTTLITEV GYGIVPSF                348

SEQ ID NO: 395          moltype = AA   length = 328
FEATURE                 Location/Qualifiers
source                  1..328
                        mol_type = protein
                        organism = Glycine max
SEQUENCE: 395
MLEGQATTPT WPRMCDTCRS VPSTVFCRSH TAFLCATCDT RLHVSLTWHE RVWVCEACER    60
APAAFLCKAD AASLCASCDA DIHAANPLAS RHHRVPILPI AAANNNNNDD DDVADVDDED   120
ETASWLLLNP IKSATVPNTN NNNNNNGFLY NAAATTDHYA QHQHFAGVSQ KSYAGDSVVP   180
VQQHQHFQLG LDFDNSKPAF SYNGSVSQSV SVSSMDIGVV PESPMRDVSI AHTRPPKGTI   240
DLFSGPPIQV PSHFSPMDRE ARVLRYREKK KMRKFEKTIR YASRKAYAET RPRIKGRFAK   300
RTDVEAEVDQ MFSTTLITEV GYGIVPSF                                      328

SEQ ID NO: 396          moltype = AA   length = 352
FEATURE                 Location/Qualifiers
source                  1..352
                        mol_type = protein
                        organism = Glycine max
SEQUENCE: 396
MLEGQATTPT WPRMCDTCRS VPSTVFCRSH TAFLCATCDT RLHVSLTWHE RVWVCEACER    60
APAAFLCKAD AASLCASCDA DIHAANPLAS RHHRVPILPI AAANNNNNDD DDVADVDDED   120
ETASWLLLNP IKSATVPNTN NNNNNGFLY NGEVDEYLDL VDNCNSCGDN NHFASAAATT    180
DHYAQHQHFA GVSQKSYAGD SVVPVQQHQH FQLGLDFDNS KPAFSYNGSV SQSVSVSSMD   240
IGVVPESPMR DVSIAHTRPP KGTIDLFSGP PIQVPSHFSP MDREARVLRY REKKKMRKFE   300
KTIRYASRKA YAETRPRIKG RFAKRTDVEA EVDQMFSTTL ITEVGYGIVP SF            352

SEQ ID NO: 397          moltype = AA   length = 381
FEATURE                 Location/Qualifiers
```

```
source                        1..381
                              mol_type = protein
                              organism = Cleome spinosa
SEQUENCE: 397
MLKEERTSGG ETGENNWARI CDTCRSAACT VYCRADSAYL CTSCDARVHA ANHVASRHER    60
VWVCESCERA PAAFLCKADA ASLCAACDAE IHSANPLARR HHRVPILPIS GSMSGPMANH   120
HPSETAMTDT ENDMVVGREE AEDEDEDDEE AASWLLLNPG KNSGNNNNQN NGFFFDGEAD   180
EYLDLVEYNS SMENQFSDQY SQYHQDCGVP QKSFGGDGVV PLQVEESRGQ LHHEQQSFQL   240
AITYGSPGAL YGSYNGSMNH SVSMSSMDIV VVPESTASDM AVVSQLRAPK GTTDLLIGPP   300
IQMMPQLSPM DREARVLRYR EKKKTRKFEK TIRYASRKAY AETRPRIKGR FAKRTDIEAE   360
VDQAFSTTLM QESGYGIVPS F                                            381

SEQ ID NO: 398               moltype = AA  length = 317
FEATURE                      Location/Qualifiers
source                        1..317
                              mol_type = protein
                              organism = Medicago sativa
SEQUENCE: 398
MATKLCDSCK SSKATLFCRS DSAFLCLTCD SNIHAANKLA SRHHRVTLCQ VCEQAPAHVT    60
CKADAAALCI SCDHDIHSAN PLARRHERVP LTTFHHHNNN SQQQSFFSEN DHDATNEEAG   120
AASWLLQTPS NPKFPDLNYS HYSYPEIDDF VTVNAKTDTP EQNSPGTTAD GVVPVQSQSK   180
TTTEHQHEHY SDINIDFSNS KPFTYNFNHT VSSPSMEVGV VPDGNVMTEI SYCGYQTTAT   240
ETAPMTVAVP MTAVEREARV SRYREKRKNR KFEKTIRYAS RKAYAETRPR IKGRFAKRSD   300
LNMNLIAEDE YGVVPSC                                                 317

SEQ ID NO: 399               moltype = AA  length = 332
FEATURE                      Location/Qualifiers
source                        1..332
                              mol_type = protein
                              note = Oryza sativa Japonica Group
                              organism = Oryza sativa
SEQUENCE: 399
MEAVEDKAMV GVGGAVAAGY SSSSWGLGTR ACDSCGGEAA RLYCRADGAF LCARCDARAH    60
GAGSRHARVW LCEVCEHAPA AVTCRADAAA LCAACDADIH SANPLARRHE RLPVAPFFGP   120
LADAPQPFPF SQAAADAAAA REEDADDDRS NEAEAASWLL PEPDDNSHED SAAAADAFFA   180
DTGAYLGVDL DFARSMDGIK AIGVPVAPPE LDLTAGSLFY PEHSMAHSLS SSEVAIVPDA   240
LSAGSAAPPM VVVVASKGKE REARLMRYRE KRKNRRFDKT IRYASRKAYA ETRPRIKGRF   300
AKRTADADDD DEAPCSPAFS ALAASDGVVP SF                                332

SEQ ID NO: 400               moltype = AA  length = 333
FEATURE                      Location/Qualifiers
source                        1..333
                              mol_type = protein
                              note = Oryza sativa Japonica Group
                              organism = Oryza sativa
SEQUENCE: 400
MEGDDKSAVV GGAYWGLAAR ACDACGGEAA RLFCRADAAF LCAGCDARAH GPGSRHARVW    60
LCEVCEHAPA AVTCRADAAA LCAACDADIH SANPLARRHE RLPVAPFFGA LADAPKPGSG   120
AHGGDAAAAD DDGSNDAEAA SWLLPEPDHG QKDGAVGATD ELYADSDPYL DLDFARSMDD   180
IKAIGVQNGP PELDITGGKL FYSDHSMNHS VSSSEAAVVP DAAAGGGAPM PVVSRGRERE   240
ARLMRYREKR KSRRFEKTIR YASRKAYAET RPRIKGRFAK RTKGGAGADA DADADADGED   300
EEMYSSAAAA VAALMAPGGS DADYGVDGVV PTF                               333

SEQ ID NO: 401               moltype = AA  length = 331
FEATURE                      Location/Qualifiers
source                        1..331
                              mol_type = protein
                              note = Oryza sativa Indica Group
                              organism = Oryza sativa
SEQUENCE: 401
MEGDDKSAVV GGAYWGLAAR ACDACGGEAA RLFCRADAAF LCAGCDARAH GPGSRHARVW    60
LCEVCEHAPA AVTCRADAAA LCAACDADIH SANPLARRHE RLPVAPFFGA LADAPKPGSG   120
AHGGDAAAAD DDGSNDAEAA SWLLPEPDHG QKDGAVGATD ELYADSDPYL DLDFARSMDD   180
IKAIGVQNGP PELDITGGKL FYSDHSMNHS VSSSEAAVVP DAAAGGGAPM PVVSRGRERE   240
ARLMRYREKR KSRRFEKTIR YASRKAYAET RPRIKGRFAK RTKGGAGADA DADADGEDEE   300
MYSSAAAAVA ALMAPGGSDA DYGVDGVVPT F                                 331

SEQ ID NO: 402               moltype = AA  length = 384
FEATURE                      Location/Qualifiers
source                        1..384
                              mol_type = protein
                              organism = Picea sitchensis
SEQUENCE: 402
MVKEEDCKVP KEAGIVKEFQ AWTMPKPCNV CRIASASLYC RADSAYLCSG CDVKVHGANK    60
LASRHERVWL CEVCEQAPAA VTCKADAASL CVSCDADIHS ANPLARRHDR VPIVPFYECA   120
SVAKTFLPPP PPPTSSLQD SDVVGTLDYE DHDDDDEIYA AEAASWLLPN PKSSAEGTKN   180
CDDGGSCFGV DAGPPVNKAA GGYFSVVDLF PDVDPYLDLD YASPLEATGG TDSVVPQSN   240
VSSQDGAVST PSDCFDTEKV TYSYTTTTSL SHSVSSSSLD VGVVPDATLS DMPRPLNRGV   300
FELANPGVVN VGIQYVQLDR EARVLRYKEK RKNRKFEKTI RYASRKAYAE TRPRIKGRFA   360
```

```
KRVDADVAQM YTSAELSYGL VPSF                                             384

SEQ ID NO: 403          moltype = AA  length = 350
FEATURE                 Location/Qualifiers
source                  1..350
                        mol_type = protein
                        note = Populus trichocarpa x Populus deltoides
                        organism = Populus sp.
SEQUENCE: 403
MASKLCDSCK SATATLFCRA DSAFLCISCD SKIHAANKLA SRHARVSVCE VCEQAPAHFT        60
CKADAAALCV TCDRDIHSAN PLASRHERVP ITPFFDSSST VHGGGAAVNL LEDRYFDEVD       120
GGRGDVSREE AEAESWLLPN PGGGTAKGVD SMDLNTGQYV FGSEMDPYLD LDPYVDPKVE       180
VQEQNSSGTT DGVVPVQSNK LGFQAPALVN DNCCYELDFS TGSKSFGGGY GYNSLSHSVS       240
SSSLDVGVVP DGSGSTLTDI SNPYCSRSVS NGMESANQTV QLSAVDREAR VLRYREKRKN       300
RKFEKTIRYA SRKAYAETRP RIKGRFAKRT DTEVEVDRSS LYGFGVVPSF                  350

SEQ ID NO: 404          moltype = AA  length = 332
FEATURE                 Location/Qualifiers
source                  1..332
                        mol_type = protein
                        note = Oryza sativa Indica Group
                        organism = Oryza sativa
SEQUENCE: 404
MEAVEDKAMV GVGGAVAAGY SSSSWGLGTR ACDSCGGEAA RLYCRADGAF LCARCDARAH        60
GAGSRHARVW LCEVCEHAPA AVTCRADAAA LCAACDADIH SANPLARRHE RLPVAPFFGP       120
LADAPQPFTF SQAAADAAGA REEDADDDRS NEAEAASWLL PEPDDNSHED SAAAADAFFA       180
DTGAYLGVDL DFARSMDGIK AIGVPVAPPE LDLTAGSLFY PEHSMAHSLS SSEVAIVPDA       240
LSAGAAAPPM VVVASKGKE REARLMRYRE KRKNRRFDKT IRYASRKAYA ETRPRIKGRF       300
AKRTADADDD DEAPCSPAFS ALAASDGVVP SF                                    332

SEQ ID NO: 405          moltype = AA  length = 384
FEATURE                 Location/Qualifiers
source                  1..384
                        mol_type = protein
                        organism = Picea abies
SEQUENCE: 405
MVKEEDCKVP KEAGIVKEFQ AWTMPKPCNV CRIASASLYC RADSAYLCSG CDVKVHGANK        60
LASRHERVWL CEVCEQAPAA VTCKADAASL CVSCDADIHS ANPLARRHDR VPIVPFYECA       120
SVAKTFLPPP PPPTSSLQD SDVVGTLDYE DDDEDDEIYA AEAASWLLPN PKSSAEGAKN        180
CDDGGSCFGV DAGPPVNKAA GGYFSVVDLF PDVDPYLDLD YASPLEATGG TDSVVPQSN        240
VSSQDGAVST PSDCFDTEKA TYSYTTTSL SHSVSSSSLD VGVVPDATLS DMSRPLNRGV       300
FELANPGVVN VGIQYVQLDR EARVLRYKEK RKNRKFEKTI RYASRKAYAE TRPRIKGRFA       360
KRVDADVAQM YTSAELSYGL VPSF                                              384

SEQ ID NO: 406          moltype = AA  length = 294
FEATURE                 Location/Qualifiers
source                  1..294
                        mol_type = protein
                        organism = Arabidopsis thaliana
SEQUENCE: 406
MASSSRLCDS CKSTAATLFC RADAAFLCGD CDGKIHTANK LASRHERVWL CEVCEQAPAH        60
VTCKADAAAL CVTCDRDIHS ANPLSRRHER VPITPFYDAV GPAKSASSSV NFVDEDGGDV       120
TASWLLAKEG IEITNLFSDL DYPKIEVTSE ENSSGNDGVV PVQNKLFNLE DYFNDDLSAS       180
KISQQGFNFI NQTVSTRTID VPLVPESGGV TAEMTNTETP AVQLSPAERE ARVLRYREKR       240
KNRKFEKTIR YASRKAYAEM RPRIKGRFAK RTDSRENDGG DVGVYGGFGV VPSF             294

SEQ ID NO: 407          moltype = AA  length = 362
FEATURE                 Location/Qualifiers
source                  1..362
                        mol_type = protein
                        organism = Chenopodium rubrum
SEQUENCE: 407
MMKKEVPGGD NNSWARVCDT CRSAPCTVYC KEDSAFLCTS CDARIHAVNQ MASRHERVWV        60
CEACEREPAA FLCKADAASL CATCDADIHS ANPLARRHHR VPIMPVGCVY GPSDGRMSED       120
GFLDLPDRDD QTTDHEGDED EAASWLLLNP GKNSNNQTTN GFLTGGGEVD EYLDLFEYNS       180
GADNQFCEQY NQQQEFSVPE KNCGGDSVVP VQCREVKDHQ IQYQNFLFGM ECETKSEYTY       240
NTSISHSVSV SSLDVGVVPE STMSDMSVSH SRPPKGTIDL FSSTPMQVPT QLSPLDREAR       300
VMRYEKKKN RKFEKTIRYA SRKAYAETRP RIKGRFAKRT DVEAERTNSL MSDGGYGIVP       360
SF                                                                      362

SEQ ID NO: 408          moltype = AA  length = 336
FEATURE                 Location/Qualifiers
source                  1..336
                        mol_type = protein
                        organism = Chenopodium rubrum
SEQUENCE: 408
MMKKEVPGGD NNSWARVCDT CRSAPCTVYC KEDSAFLCTS CDARIHAVNQ VASRHERVWV        60
CEACEREPAA FLCKADAASL CATCDADIHS ANPLARRHHR VPIMPVGCVY GPSDGRMSEE       120
GFLDLPDGDD QTTDHEGDED EAASWLLLNP GADNQFCEQY SQQQEFSVPE KNCGGDSVVP       180
```

```
VQCREVKDHQ IQYQKFLFGM ECETKSEYNY NTSISHSVSV SSLDVGVVPE STMSDMSVSH   240
SRPPKGTIDL FSSPPMQVPT QLSPLDREAR VMRYREKKKN RKFEKTIRYA SRKAYAETRP   300
RIKGRFAKRT DVEAEMDQMF TNSLMSDGGY GIVPSF                            336

SEQ ID NO: 409            moltype = AA  length = 355
FEATURE                   Location/Qualifiers
source                    1..355
                          mol_type = protein
                          organism = Arabidopsis thaliana
SEQUENCE: 409
MGFGLESIKS ISGGWGAAAR SCDACKSVTA AVFCRVDSAF LCIACDTRIH SFTRHERVWV    60
CEVCEQAPAA VTCKADAAAL CVSCDADIHS ANPLASRHER VPVETFFDSA ETAVAKISAS   120
STFGILGSST TVDLTAVPVM ADDLGLCPWL LPNDFNEPAK IEIGTENMKG SSDFMFSDFD   180
RLIDFEFPNS FNHHQNNAGG DSLVPVQTKT EPLPLTNNDH CFDIDFCRSK LSAFTYPSQS   240
VSHSVSTSSI EYGVVPDGNT NNSVNRSTIT SSTTGGDHQA SSMDREARVL RYREKRKNRK   300
FEKTIRYASR KAYAESRPRI KGRFAKRTET ENDDIFLSHV YASAAHAQYG VVPTF        355

SEQ ID NO: 410            moltype = AA  length = 348
FEATURE                   Location/Qualifiers
source                    1..348
                          mol_type = protein
                          note = Beta vulgaris subsp. vulgaris
                          organism = Beta vulgaris
SEQUENCE: 410
MGGGLMAAKL CDSCKSATAT IFCRADTAYL CISCDAKIHA ANKLASRHAR VWVCEVCEHA    60
PATVTCKADA AHLCATCDRD IHSANPLARR HERVPLTPFY DPLSPPNTTN NNNDDSDSSA   120
TAAAAAKSAA INKLFGDEYY SDADEAEAAS WLLPNPNKTD EPKSIDYLFS SSGNGDDDID   180
PYLDLDFGAE AKPDPDLSSD GVVPDPDQKG VHHHHLTTLQ HPAASMFSLS SYHHHHHHHH   240
VSNNNGHFDG FENSSAACKP FALSSYHTQP SLSHSVSSSS LDFGVVPDAS NITDVASTGF   300
DKQQQMKIIG MDREARVLRY REKRKNRKFE KTIRYASRKA YAETRPRI                348

SEQ ID NO: 411            moltype = AA  length = 340
FEATURE                   Location/Qualifiers
source                    1..340
                          mol_type = protein
                          organism = Malus domestica
SEQUENCE: 411
MALKLCDSCK SATGTLFCRA DSAFLCVNCD SKIHAANKLA SRHARVWLCE VCEQAPAHVT    60
CKADDAALCV TCDRDIHSAN PLSRRHERVP VTPFYDSVNS ATDSVPAVKS AVNFLNDRYF   120
SDVDGEIEAR REEEAEAASWL LPNPKAMENP DLNSGQYLFP EMDPYMDLDY GHVDPKLEDA   180
QEQNSCITDG VVPEQSKNMQ PQLVNDHSFE IDFSAASKPF VYGYHHAQCL RQSVSSSSMD   240
VSIVPDDNAM TDDSNPYNKS MTSAVESSHP AVQLSSADRE ARVLRYREKR KNRKFEKTIR   300
YASRKAYAET RPRIKGRFAK RTEVEIEAEP MCRYGIVPSF                         340

SEQ ID NO: 412            moltype = AA  length = 339
FEATURE                   Location/Qualifiers
source                    1..339
                          mol_type = protein
                          organism = Brassica nigra
SEQUENCE: 412
MLKQKSNNID GEENNRARAC DTCMSTVCTV YCHADSAYLC TSCDAEVHSA NRVASRHKRV    60
PVCESCECAP AAFLCEADDA SLCTACDSEV HSANAIARRH HRVPVLPVSG NSYISMETHH   120
QTETTEAEPE KRLVIHQEED EARETASWLL PKDKNSNQNN ELLLSDEYLD LADYNSNMDN   180
KFTGQYSHHQ QEGDVPQTNY VGDRVVPIQI QESNGSLRHK QQNMTYGSSD INSGSINHNN   240
GYDTSMETDF VPEPTTPDTA DGYTTDGKID QPPEPPVKMI IQLTPMDREA RVLRYREKRK   300
TRKFEKTIRY ASRKAYAERR PRINGRFAKM GETEDYDVD                          339

SEQ ID NO: 413            moltype = AA  length = 338
FEATURE                   Location/Qualifiers
source                    1..338
                          mol_type = protein
                          organism = Brassica nigra
SEQUENCE: 413
MLKQKSNNID SEENNRARAC DTCMSTVCTV YCHADSAYLC TSCDAEVHSA NRVASRHKRV    60
PVCESCECAP AAFLCEADDA SLCTACDSEV HSANAIARRH HRVPVLPVSG NSYISMDTHH   120
QTETTEAEPE KRLVIHQEED EARETASWLL PKDKNSNQNN ELLLSDEYLD LADYNSNMDN   180
KFTGQYNHHQ QEGDVPQTNY VGDRVVPIQI QESNGNLRHK QQNMTYSSDI NSGSINHNNG   240
YDTSMETDFV PEPTTLDTAD GDTTGKIDQ PPEPPVKMII QLSPMDREAR VLRYREKRKT   300
RKFEKTIRYA SRKAYAERRP RINGRFAKIG KTEDYDVD                           338

SEQ ID NO: 414            moltype = AA  length = 339
FEATURE                   Location/Qualifiers
source                    1..339
                          mol_type = protein
                          organism = Brassica nigra
SEQUENCE: 414
MLKQKSNNID GEENNRARAC DTCMSTVCTV YCHADSAYLC TSCDAEVHSA NRVASRHKRV    60
PVCESCECAP AAFLCEADDA SLCTACDSEV HSANAIARRH HRVPVLPVSG NSYISMETHH   120
QTETTEAEPE KRLVIHQEED EARETASWLL PKDKNSNQNN ELLLSDEYLD LADYNSNMDN   180
```

```
KFTGQYSHHQ QEGDVPQTNY VGDRVVPIQI QESNGNLRHK QQNMTYGSSD INSGSINHNN    240
GYDTSMETDF VPEPTTPDTA DGYTTDGKID QPPEPPVKMI IQLTPMDREA RVLRYREKRK    300
TRKFEKTIRY ASRKAYAERR PRINGRFAKM GETEDYDVD                          339

SEQ ID NO: 415           moltype = AA   length = 339
FEATURE                  Location/Qualifiers
source                   1..339
                         mol_type = protein
                         organism = Brassica nigra
SEQUENCE: 415
MLKQKSNNID SEENNRARAC DTCMSTVCTV YCHADSAYLC TSCDAEVHSA NRVASRHKRV    60
PVCESCECAP AAFLCEADDA SLCTACDSEV HSANAIGRRH HRVPVLPVSG NSYISMDTHH    120
QTETTEAEPE KRLVIHQEED EARETASWLL PKDKNSNQNN ELLLSDEYLD LADYNSNMDN    180
KFTGQYNHHQ QEGDVPQTNY VGDRVVPIQI QESDGNLRHK QQNMTYGSSD INSGSINHNN    240
GYDTSMETDF VPEPTTLDTA DGDTTDGKID QPPEPPVKMI IQLSPMDREA RVLRYREKRK    300
TKKFEKTIRY ASRKAYAERR PRINGRFAKM GETEDYDVD                          339

SEQ ID NO: 416           moltype = AA   length = 339
FEATURE                  Location/Qualifiers
source                   1..339
                         mol_type = protein
                         organism = Brassica nigra
SEQUENCE: 416
MLKQKSNNID SEENNRARAC DTCMSTVCTV YCHADSAYLC TSCDAEVHSA NRVASRHKRV    60
PVCESCECAP AAFLCEADDA SLCTACDSEV HSANAIARRH HRVPVLPVSG NSYISMDTHH    120
QTETTEAEPE KRLVIHQEED EARETASWLL PKDKNSNQNN ELLLSDEYLD LADYNSNMDN    180
KFTGQYNHHQ QEGDVPQTNY VGDRVVPIQI QESDGNLRHK QQNMTYGSSD INSGSINHNN    240
GYDTSMETDF VPEPTTLDTA DGDTTDGKID QPPEPPVKMI IQLSPMDREA RVLRYREKRK    300
TKKFEKTIRY ASRKAYAERR PRINGRFAKM GETEDYDVD                          339

SEQ ID NO: 417           moltype = AA   length = 339
FEATURE                  Location/Qualifiers
source                   1..339
                         mol_type = protein
                         organism = Brassica nigra
SEQUENCE: 417
MLKQKSNNID SEENNRARAC DTCMSTVCTV YCHADSAYLC TSCDAEVHSA NRVASRHKRV    60
PVCESCECAP AAFLCEADDA SLCTACDSEV HSANAIARRH HRVPVLPVSG NSYISMDTHH    120
QTETTEAEPE KRLVIHQEED EARETASWLL PKDKNSNQNN ELLLSDEYLD LADYNSNMDN    180
KFTGQYNRHQ QEGDVPQTNY VGDRVVPIQI QESDGNLRHK QQNMTYGSSD INSGSINHNN    240
GYDTSMETDF VPEPTTLDTA DGDTTDGKID QPPEPPVKMI IQLSPMDREA RVLRYREKRK    300
TKKFEKTIRY ASRKAYAERR PRINGRFAKM GETEDYDVD                          339

SEQ ID NO: 418           moltype = AA   length = 343
FEATURE                  Location/Qualifiers
source                   1..343
                         mol_type = protein
                         organism = Prunus persica
SEQUENCE: 418
MASKLCDSCK SATATLFCRA DSAFLCVNCD SKIHAANKLA SRHARVWLCE VCEQAPAHVT    60
CKADDAALCV TCDRDIHSAN PLSRRHERVP VTPFYDSGNS AANSAPVVKS VVNFLDDRYF    120
SDVDGQDAET EVSREEAEAA SWLLPNPKAM ENPDLNSGEY FLPEMDPYLD LDYGHVDPKL    180
EDAQEQNSCG TDGVVPVQSK SVQPQLVNDH SFEIDFSAAS KPYVVGFHAQ CLSQSVSSSS    240
MDVSVVPDGN TTMTDVCDPY TKSMSAAVES THQAVQISSA DREARVLRYR EKRKNRKFEK    300
TIRYASRKAY AETRPRIKGR FAKRTEVEIE AERLCRYGVV PSF                     343

SEQ ID NO: 419           moltype = AA   length = 384
FEATURE                  Location/Qualifiers
source                   1..384
                         mol_type = protein
                         organism = Fragaria X ananassa
SEQUENCE: 419
MLKEESNGAA AANSWARVCD TCRSAPCTVY CRADSAYLCS GCDATIHAAN RVASRHERVS    60
VCEACERAPA AFLCKADAAS LCTACDADIH SANPLARRHQ RVPILPISGC QIMVGSTPAD    120
TTEDGFLSQE GDEEVMDEED EDEAASWLLL NPVKNSNNHN SNNNNPNNNN NGFLFGVEVD    180
EYLDLVEYNS SDQNQFSGTT ATNDQHNYGV PHKISYGGDS VVPVQYGEGK VTQMQMQQKH    240
NFHQLGMEYE SSKAAYGYDG SISHTVSVSS MDVGVVPDST MSEMSVCHPR TPKGTIDLFN    300
GPTIQMPTQL SPMDREARVL RYREKKKTRK FEKTIRYASR KAYAETRPRI KGRFAKRTDI    360
EVEVDQMFST SLMGETGYGI VPSY                                          384

SEQ ID NO: 420           moltype = AA   length = 294
FEATURE                  Location/Qualifiers
source                   1..294
                         mol_type = protein
                         organism = Arabidopsis thaliana
SEQUENCE: 420
MASSSRLCDS CKSTAATLFC RADAAFLCGN CDGKIHTANK LASRHERVWL CEVCEQAPAH    60
VTCKADAAAL CVTCDRDIHS ANPLSRRHER VPITPFYDAV GPAKSASSSV NFVDEDGGDV    120
TASWLLAKEG IEITNLFSDL DYPKIEVTSE ENSSGNDGVV PVQNKLFLNE DYFNFDLSAS    180
```

```
KISQQGFNFI NQTVSTRTID VPLVPESGGV TAEMTNTETP AVQLSPAERE ARVLRYREKR    240
KNRKFEKTIR YASRKAYAEM RPRIKGRFAK RTDSRENDGG DVGVYCGFGV VPSF           294

SEQ ID NO: 421          moltype = AA  length = 355
FEATURE                 Location/Qualifiers
source                  1..355
                        mol_type = protein
                        organism = Arabidopsis thaliana
SEQUENCE: 421
MGFGLESIKS ISGGWGAAAR SCDACKSVTA AVFCRVDSAF LCIACDTRIH SFTRHERVWV     60
CEVCEQAPAA VTCKADAAAL CVTCDADIHS ANPLASRHER VPVETFFDSA ETAVAKISAS    120
STFGILGSST TVDLTAVPVM ADDLGLCPWL LPNDFNEPAK IEIGTENMKG SSDFMFSDFD    180
RLIDFEFPNS FNHHQNNAGG DSLVPVQTKT EPLPLTNNDH CFDIDFCRSK LSAFTYPSQS    240
VSHSVSTSSI EYGVVPDGNT NNSVNRSTIT SSTTGGDHQA SSMDREARVL RYREKRKNRK    300
FEKTIRYASR KAYAESRPRI KGRFAKRTET ENDDIFLSHV YASAAHAQYG VVPTF          355

SEQ ID NO: 422          moltype = AA  length = 323
FEATURE                 Location/Qualifiers
source                  1..323
                        mol_type = protein
                        note = Hordeum vulgare subsp. vulgare
                        organism = Hordeum vulgare
SEQUENCE: 422
MEGEEKPVVG GAYWGVGARA CDSCATEAAR LFCRADAAFL CAGCDARAHG SGSRHARVWL     60
CEVCEHAPAA VTCKADAAVL CASCDADIHA ANPLARRHER VPVAPFFGAA ADAHKPFPSS    120
GAQAGAAASA EDDGSNDAEA ASWLLPEPDH KDGANGATAD VFFADSDHYL DLDFARSMDD    180
IKAISVQLNG QPEIDLNGGN KGFYSDHSMN HSLSSSEAAV VPDAAAAPVV SRGREREARL    240
MRYREKRKSR RFEKTIRYAS RKAYAETRPR VKGRFAKRTG TADADALEEH EEMYSSAAAA    300
VAALMAPGPD HDYGVDGVVP TLV                                            323

SEQ ID NO: 423          moltype = AA  length = 498
FEATURE                 Location/Qualifiers
source                  1..498
                        mol_type = protein
                        organism = Populus trichocarpa
SEQUENCE: 423
MEKCLNSKQK KDCFLFLPCE FCNSKAAILY CRADSAKLCL PCDQQIHSSN TLSLKHVRSQ     60
ICDNCRAEPA SIHCSNDNLF LCQDCDWDSH NSSFSVSSLH NRNPVEGFMG CPPVVELASL    120
FGFDFKSDFF VDSDPGSCSF EQEAVNFQDF AVSSDDFSVL SSSGKSRQEV YKQLVEMGKR    180
GMVRVNGDGA ELGPDTPPSR CAVQWNLESL ELENGDEELL HQQTPFTSLL MLPNHVDASE    240
NDCVSDLGFM WDCNYTHQGA QAWDFQLGTS LDCTIPGPQE EGYDVKDPGF MVKNYVDFTE    300
DGAFATQKVL DDGHVTSCCS STCEDNLSKN SCSNQQLSRY KPPTENCNNT PLLGLSPGSM    360
PGEPNAHIQV MEQPSLTWFE TLNEVRQKGD AGLFAQNRGN AMLRYDKRIR YESRKARADT    420
RKRVKGRGKP VFLGKASPLM LWPELVVTCN PLDHINGEWS FNKHSLQKSL ERSSYSDRNN    480
ASLSFASTMT VTMLHLRL                                                  498

SEQ ID NO: 424          moltype = AA  length = 369
FEATURE                 Location/Qualifiers
source                  1..369
                        mol_type = protein
                        organism = Populus trichocarpa
SEQUENCE: 424
MLKQESSGGG GGDNRARVCD TCRAAPCTVY CRADSAYLCA GCDARVHAAN RVASRHERVS     60
VCEACERAPA ALLCKADAAS LCTACDADIH SANPLARRHQ RVPILPISGC LHGSPVGPAA    120
GETEDRFTTQ EGEETISEEE EDEAASWLLL NPVKNSKNQN NNGFLFGGEV DEYLDLVEYN    180
SCTENQCSDQ YNQQHYCVPP KSYGGDRAVP IQYGEGKDHQ QQRQYHNFQL GLEYEPSKAA    240
CSYNGSISQS VSMSSMDVGV VPESTMSEIS ISQHRPPKGT MELFSSTAIQ MPSQLSPMDR    300
EARVLRYREK KKTRKFEKTI RYASRKAYAE TRPRIKGRFA KRKDVEVEDD QMFSSTLMAE    360
TGYGIVPSF                                                            369

SEQ ID NO: 425          moltype = AA  length = 348
FEATURE                 Location/Qualifiers
source                  1..348
                        mol_type = protein
                        organism = Populus trichocarpa
SEQUENCE: 425
MASKLCDSCK SATATLFCRA DSAFLCVSCD SKIHAANKLA SRHARVWVCE VCEQAPAHVT     60
CKADAALCV TCDRDIHSAN PLAQRHERVP VTPFFDSSSA AHGGGAAVNF LEYRYLDDVN    120
GGDDVSREEA EAESWLLPNP GGGNTKGVDS LDLNTGQYVF GAEMHPYLDL DRYVDQKVEV    180
EVQEQNSSGT TDGVVPVQSN KLGFQAPALV NDNCCFELDF SAGSKTFAGG YGYNSLSHSV    240
SSSSLDVGVV PDGSTLTDIS NPYSRSVSNG MESANQTVQL SAVDREARVL RYREKRKNRK    300
FEKTIRYASR KAYAETRPRI KGRFAKRTDS GVEVDRSSIY GFGVVPSF                 348

SEQ ID NO: 426          moltype = AA  length = 339
FEATURE                 Location/Qualifiers
source                  1..339
                        mol_type = protein
                        organism = Populus trichocarpa
SEQUENCE: 426
```

```
MGIEVESLKN LTGGWSVAAK RCDSCKTAAA AAFCRADSAF LCLNCDTKIH HSGVNSKIMS    60
RHERVWMCEV CEQAPAAVTC KADAAALCVT CDADIHSANP LARRHERVPV EPFYDSAESI   120
VKTSSAFNFL TGDMFFCEMD PFLDFEYQNS MDGRYKQSHG GGGAGADSVV PVQNKPAPLP   180
VIDHKNCFDI DFCRSKLTSF SSYPSQSLSH SVSSSSLDVG VVPDGNSMSD ISYPFGRSMN   240
TYTDPSMPIS GSTTNQAAAQ LAGIDREARV LRYREKRKNR KFEKTIRYAS RKAYAETRPR   300
IKGRFAKRTE MESDMDTLYN SPSSVPFLAD THYGVVPSF                         339

SEQ ID NO: 427          moltype = AA  length = 362
FEATURE                 Location/Qualifiers
source                  1..362
                        mol_type = protein
                        organism = Populus trichocarpa
SEQUENCE: 427
MGIEVESLKN LTGGWSVAAK RCDSCKTAAA AAFCRADSAF LCLNCDTKIH HSQVNSKIMS    60
RHERVWMCEV CEQAPAAVTC KADAAALCVT CDADIHSANP LARRHERVPI EPFYNSAESI   120
VKTSTAFNIL IPGENGVSGY DQNDDVEGVS WLLQSNHTTH DHNSKLQIEN PVVKTGDMFF   180
SEIDPFLELE YQNSIDASYE KIHGGAGADS VVPVQTKPAP LPVINHESCF DIDFCRSKLT   240
SFSYSSQSLS HSVSSSSLDV GVVPDGNSIM PLSGWTANQA ATQLAGIDRE ARVLRYRERR   300
KNRKFEKTIR YASRKAYAET RPRIKGRFAK RTEMESDMDN LYNSPSSVPF MADTQYGVVP   360
SF                                                                 362

SEQ ID NO: 428          moltype = AA  length = 350
FEATURE                 Location/Qualifiers
source                  1..350
                        mol_type = protein
                        organism = Populus trichocarpa
SEQUENCE: 428
MASKLCDSCK SATATLFCRA DSAFLCISCD SKIHAANKLA SRHARVSVCE VCEQAPAHFT    60
CKADAAALCV TCDRDIHSAN PLASRHERVP ITPFFDSSST VHGGGEAVNL LEDRYFDEVD   120
GGRGDVSREE AEAESWLLPN PGGGTTKGVD SMDLNTGQYV FGSEMDPYLD LDPYVDPKLE   180
VQEQNSSGTT DGVVPVQSNK LGFQSPALVN DHCCYELDFS TGSKSFGGGY GYNSLSQSVS   240
SSSSLDVGVVP DGSGSTLTDI SNPYCSRSVC NGMESANQTV QLSAVDREAR VLRYREKRKN   300
RKFEKTIRYA SRKAYAETRP RIKGRFAKRT DTEVEVDRSS LYGFGVVPSF             350

SEQ ID NO: 429          moltype = AA  length = 322
FEATURE                 Location/Qualifiers
source                  1..322
                        mol_type = protein
                        organism = Mangifera indica
SEQUENCE: 429
MASKLCDSCK SATATLFCRA DSAFLCVSCD TKIHTANKLA SRHARVWVCE VCEQAPAHVT    60
CKADAAALCV ACDHDIHSAN PLARRHERVP VTPFYDSVNS ADKHNGVVNF FDDVEGGGDA   120
SREEAAASW LLPNPKVVED GPEMNTGQYV FSDMDPYLDL DYGPVDPKLE AQEQNSSGTD   180
GVVPVQSQTA PVPLVNDHCF DLDFSGPKSF GYGYNNTQCL SHSVSSSSLD VGVVPDGSAT   240
TESTNQTVQL SSADREARVL RYREKRKNKK FEKTIRYASR KAYAEMRPRI KGRFAKRTDM   300
DVEADRSSNS SSIYGFGVVP SY                                           322

SEQ ID NO: 430          moltype = AA  length = 347
FEATURE                 Location/Qualifiers
source                  1..347
                        mol_type = protein
                        organism = Vitis vinifera
SEQUENCE: 430
MVVEVESWRM ASKLCDSCKS APPTLFCRAD SAFLCVACDS KVHAANKLAS RHARVWMCEV    60
CEQAPAHVTC KADAAALCVT CDRDIHSANP LARRHERVPV VPFYDSAAAA AKSNAVNLLV   120
DDRYYSDPDG DASREEAEAA SWLLPNPNPK LAESSDLNSS HYMFSDIDPY LDLDYPSMDP   180
KLQSQQQQQS SGTDGVVPVQ NKSVQAPLVN DNCFDMDFSG SKSFYNGQSL SQSVSSSSLE   240
VGVVPDGNAM VDVTNPFGRS MNTGSESANQ TAQISSGIDR EARVLRYREK RKNRKFEKTI   300
RYASRKAYAE TRPRIKGRFA KRSEIEVDYS SSGALTADSG YGVVPSF                347

SEQ ID NO: 431          moltype = AA  length = 394
FEATURE                 Location/Qualifiers
source                  1..394
                        mol_type = protein
                        organism = Vitis vinifera
SEQUENCE: 431
MSDSPGDNLH HRHEEEGQKM TIQNRLCDFC GDSMALLYCR ADSAKLCLSC DREVHSTNQL    60
FTKHTRSRLC DVCDASPASI LCSTDNLVLC QNCDWAKHGR SLSSAHDRRP LEGFSGQPSV   120
TELLAFVGFE DLGKKSLFCG DESEVNEFLG CGVYESVGVD EEFSDFLVWD TPAVVNLDDL   180
IVSTACDHNF QAMGVPPLPK NRGAPCGQHK AEIIHQLRQL AKIELSFDFD HGDAKPPIGF   240
QSHIPKQLIQ KENECNSCDH EVEFVFPTYE ASAFQWCSDG SEAANQVLPS VLLGSCADEK   300
CLVPRKHSDI GGSVSHTNGS DEGKSECPVV TKTLPALPKV SVHELNSQER DSAISRYKEK   360
KKTRRYEKHI RYESRKARAE SRIRIKGRFA KMDH                              394

SEQ ID NO: 432          moltype = AA  length = 349
FEATURE                 Location/Qualifiers
source                  1..349
                        mol_type = protein
                        organism = Vitis vinifera
```

```
SEQUENCE: 432
MTIQNRLCDF CGDSMALLYC RADSAKLCLS CDREVHSTNQ LFTKHTRSRL CDVCDASPAS    60
ILCSTDNLVL CQNCDWAKHG RSLSSAHDRR PLEGFSGQPS VTELLAFVGF EDLGKKSLFY   120
FLVWDTPAVV NLDDLIVSTA CDHNFQAMGV PPLPKNRGAP CGQHKAEIIH QLRQLAKIEL   180
SFDFDHGDAK PPIGFQSHIP KQLIQKENEC NSCDHEVEFV FPTYEASAFQ WCSDGSEAAN   240
QVLPSVLLGS CADEKCLVPR KHSDIGGSVS HTNGSDEGKS ECPVVTKTLP ALPKVSVHEL   300
NSQERDSAIS RYKEKKKTRR YEKHIRYESR KARAESRIRI KGRFAKMDH               349

SEQ ID NO: 433          moltype = AA  length = 361
FEATURE                 Location/Qualifiers
source                  1..361
                        mol_type = protein
                        organism = Vitis vinifera
SEQUENCE: 433
MGFQELNGKT FSAATWALAA KPCDSCKSAA ALLFCRADSA FLCVGCDSKI HGANKLASRH    60
ERVWMCEVCE QAPASVTCKA DAAALCVTCD RDIHSANPLA RRHDRVPVVP FYDSAESLVK   120
STAAAVGFLV PGGAGDEEDS EAASWLLPNP KLPEGPEVKS GEVFFSDIDP FLDFDYPDAK   180
FPHHHHHHCG GNDGVVPVQA KDPSPPVTNH PADNCFELDF SRSKLSAYNY TAQSLSQSIS   240
SSDVGVVPDG NCNSMSDTSY PSMKQVSGGG GGGSTGSQAT QLSGMDREAR VLRYREKRKN   300
RKFEKTIRYA SRKAYAETRP RIKGRFAKRT EMESEMVDHI YNSASAAAFM VDAGYGVVPS   360
Y                                                                  361

SEQ ID NO: 434          moltype = AA  length = 339
FEATURE                 Location/Qualifiers
source                  1..339
                        mol_type = protein
                        organism = Zea mays
SEQUENCE: 434
MDTAAELELG LELEQKPAAG YWSVVGARPC DACAAEPARL HCRADGAFLC PGCDARAHGA    60
GSRHARVWLC EVCEHAPAVV TCRADAAALC AACDADIHSA NPLARRHERL PIAPLFGALA   120
DAPQPFPSPA LAAAAGAEAP APTPAQGEAV AEDYGSSEAE AASWLLPEPD NSHEDSAADT   180
FFAESDAYLG ADLDFARCMD GVKAIGVPVA PPELDIGAGS FCYPEHSMNH ILSSSSEVAV   240
VPDAQAAGLP VVVVVSRGEE REARLMRYRE KRKNRRFDKT IRYASRKAYA ETRPRIKGRF   300
AKRRSAEGED EALEHEEGAC FSPAGSAPAA SDGVVPSLC                          339

SEQ ID NO: 435          moltype = AA  length = 336
FEATURE                 Location/Qualifiers
source                  1..336
                        mol_type = protein
                        organism = Sorghum bicolor
SEQUENCE: 435
MDTAVELELE QKPAVGYWSV VGARPCDACA AEPARLHCRE DGAFLCPGCD ARAHGAGSRH    60
ARVWLCEVCE HAPAVTCRA DAAALCAACD ADIHSANPLA RRHERLPVAP FFGALADAPQ   120
PFPSPAFAAA AAAGGQAQGE AAAADNDDDD GSNEAEAASW LLAEPDNSHE DSAAATAADT   180
LFAESDAYLG VDLDFARCMD GVKAIGVPVA PPELDIAAGS FFYPEHSMNH SLSSSEVAVV   240
PDAQAAGVPA VVSRGKEREA RLMRYREKRK NRRFDKTIRY ASRKAYAETR PRIKGRFAKR   300
CSAEADDDAL EHDEGACFSP AGSAHAASDG VVPSFC                             336

SEQ ID NO: 436          moltype = AA  length = 317
FEATURE                 Location/Qualifiers
source                  1..317
                        mol_type = protein
                        organism = Allium cepa
SEQUENCE: 436
MAVNYWGLTA KHCANCVSSP AVMYCRTDAT YLCSTCEARS HSSHVRVWLC EVCEQAPAAV    60
TCKADAATLC VTCDADIHAA NPLARRHERV PVVPVGNPTV QVKEDLFGED GEGDTWKGMM   120
VDLNCFGGFS NELVDPYLDL DGNGDGLVPV QEKHVGYGY RQEKGTMMPK GTVDIDFGAV   180
GKGDGYGCGH GGYTVGVQSM SHSTTVSSSE AGVVPDNSSS MAVADVSNPY SRPLPNPMDA   240
MDREARVMRY REKRKNRKFE KTIRYASRKA YAETRPRIKG RFAKRVDNDS YADPMHSVIN   300
ASTAFMNDSG YGVVPSF                                                  317

SEQ ID NO: 437          moltype = AA  length = 332
FEATURE                 Location/Qualifiers
source                  1..332
                        mol_type = protein
                        organism = Ricinus communis
SEQUENCE: 437
MASKLCDSCK SATATLFCRP DSAFLCINCD SKIHAANKLA SRHARVLICE VCEQAPAHVT    60
CKADAAALCV TCDRDIHSAN PLARRHERVP ITPFYDSVSS VNNKPNAVNL LDDRYFSDVD   120
GDAADVSREE AEAASWLLPN PPNTKLVENS DPNTGQYVFS DMDPYLDLDY GPGDPKLEAQ   180
EQNSSGTDGV VPVKSSKNVQ APFVNDNCFE LDFTGSKPFP YGYNAQCLSN SVSSSSLDVG   240
VVPDGGDISN PYSKSTMESV QQLSAVDREA RVLRYREKRK NRKFEKTIRY ASRKAYAETR   300
PRIKGRFAKR TDIDVEADRS SSINAFGVVP SF                                 332

SEQ ID NO: 438          moltype = AA  length = 411
FEATURE                 Location/Qualifiers
source                  1..411
                        mol_type = protein
                        organism = Ricinus communis
```

```
SEQUENCE: 438
MSDFGRTPDE QQTMMTQQHH QQERLCDYCN DTTALLYCRA DSAKLCISCD REVHSTNQLF    60
SKHTRSLLCD SCDASPASIF CETEHSVFCQ NCDWEKHNLS LSSVHNRRPI EGFSGFPSVS   120
ELVSILGFED LGDKKDKKAL LFNEGDNGLA SSGPDGSGFE DGYSDLLIWE TPAVVSIDDL   180
IVSSDSGPNF PALGVPPLPK AIVFRFSLFY FSCKSQNRNA VCGQHFKEEIL RQLRELAGLE   240
PDPNCHNPET EPTYVFQSAA GENMQTRMTH KCCEPVARPI SSPSYEENIF NWLSDNGEAG   300
NQVSVPCTLP RSHLEESPVV PDKQSNIDGS ASYANGSHEG EPQYPASTGL ISVFPKVVSH   360
DINSQERDSA ISRYKEKRKT RRYDKHIRYE SRKARAESRT RIRGRFAKMD R            411

SEQ ID NO: 439          moltype = AA   length = 388
FEATURE                 Location/Qualifiers
source                  1..388
                        mol_type = protein
                        organism = Ricinus communis
SEQUENCE: 439
MGIEMESLKS LTGGWTVAAR RCDSCKTAAA AVFCRADSAF LCLNCDAKIH AANKLVSRHE    60
RVWMCEVCEQ APAAVTCKAD AAALCVTCDA DIHSANPLAR RHERVPVEPF FDSAGSIVKS   120
SPFNFLVPTD HNGAGSAAFN HQQHEDDDVE GVSWLLPNPS STMINSKLGG IENHEMKSGH   180
GGGGGSGDLF FTEMDPFLDL EFHQNNNHSS AANDSVVPVQ ITKPAAASSI PVMNNDICYD   240
IDFCRTKLSS FNYPTQSLSQ SVSSSSLDVG VVPDGSSTSD ISYPFGRNMN TCTDPSGPIS   300
GNSTNQAAQM CGINREARVL RYREKRKNRK FEKTIRYASR KAYAETRPRI KGRFAKRTEI   360
DTDMDRLYNS PSSVSYLGDA QYGVVPTF                                      388

SEQ ID NO: 440          moltype = AA   length = 351
FEATURE                 Location/Qualifiers
source                  1..351
                        mol_type = protein
                        organism = Glycine max
SEQUENCE: 440
MSGAEARPCD YCGNSTALLY CRADSAKLCF SCDREVHSTN QLFSKHTRTL LCDACDDSPA    60
TILCSTDTSV LCQNCDWENH NPALSDSLHE RRPLEGFTGC PSVSELLSIV GFSDISKKSL   120
LFSPQGSVAD GFFGASEIEG LSDMFVWDAP SFVTLDDLIS SSPSSHSFQA MKVPPLPKNR   180
KAACGQHKEE ILSQLRELAK SEPLDLEPYV QSGNLSLGFE RDPEADIFPS HEWHRESSEP   240
MHQVVPPDPS MGTYTEEIPV KHSTSAVGEN HTYGDNEGKP SISLKSETLS TTPKAAACEL   300
TSQERDSALL RYKQKKKTRR FDKHIRYESR KVRAESRVRV KGRFAKMGHE H            351

SEQ ID NO: 441          moltype = AA   length = 382
FEATURE                 Location/Qualifiers
source                  1..382
                        mol_type = protein
                        organism = Phyllostachys edulis
SEQUENCE: 441
MNYNFGGNVY EQEVAGGEGS CPWARPCDGC NAAPSVVYCR ADAAYLCASC DSRVHAANRV    60
ATRHERVRVC EACERAPAVL ACRADAAVLC VSCDAQVHSA NPLARRHQRV PVVPLPAAAI   120
PAASVLAEAA AAATTVLGDK EEEVDSWLLL SKDSDNQNCS SNNNNNSMYF GEVDEYFDLV   180
GYNSYYDNRI DNNQEQYGMQ EQQQQQQQEM QKEFAEKEGS ECVVPSQVAM VSEQQQQSGY   240
VGAEQAASMT AGVSAYTDSI SNSISFSSME VGIVPDNTVI DMPNSSILTP AGAINLFSGP   300
SLQMPLHLST MDREARVLRY KEKKKTRKFE KTIRYATRKA YAEARPRIKG RFAKRSDVDI   360
EVDQMFSSAA LSDCSYGTVP WF                                            382

SEQ ID NO: 442          moltype = AA   length = 307
FEATURE                 Location/Qualifiers
source                  1..307
                        mol_type = protein
                        organism = Vitis vinifera
SEQUENCE: 442
MASKLCDSCK SAPPTLFCRA DSAFLCVACD SKVHAANKLA SRHARVWMCE VCEQAPAHVT    60
CKADAAALCV TCDRDIHSAN PLARRHERVP VVPFYDSAAA AKSNAVNLL LAESSDLNSS   120
HYMFSDIDPY LDLDYPSMDP KLQSQQQQQS SGTDGVVPVQ NKSVQAPLVN DNCFDMDFSG   180
SKSFYNGQSL SQSVSSSSLE VGVVPDGNAM VDVTNPFGRS MNTGSESANQ TAQISSGIDR   240
EARVLRYREK RKNRKFEKTI RYASRKAYAE TRPRIKGRFA KRSEIEVDYS SSGALTADSG   300
YGVVPSF                                                             307

SEQ ID NO: 443          moltype = AA   length = 343
FEATURE                 Location/Qualifiers
source                  1..343
                        mol_type = protein
                        note = Arabidopsis lyrata subsp. lyrata
                        organism = Arabidopsis lyrata
SEQUENCE: 443
MGFGLESIKS ISGGWGAAAR SCDACKSVTA AVFCRLDSAF LCISCDTRIH SFTRHERVWV    60
CDVCEQAPAA VTCKADAAAL CVTCDSDIHS ANPLASRHER VPVESFFDSA ETAVAKISPS   120
STFGILGSST TVDLTAVPVM GDDLGLCPCS SEFMFADFDR LIDFEFPNSF NHPSNNDAGG   180
DSLVPVQTKT EPLPLTNNDH CFDIDFCRSK LSAFTYPSQS VSHSVSTSSI EYGVVPSNNT   240
NNSVSEISIP FNRSMITTST AASTGDHQTS SMDREARVLR YREKRKNRKF EKTIRYASRK   300
AYAESRPRIK GRFAKRTETE NDDVFLSHVY ASAATQYGVV PTF                     343

SEQ ID NO: 444          moltype = AA   length = 291
FEATURE                 Location/Qualifiers
```

```
source                         1..291
                               mol_type = protein
                               note = Arabidopsis lyrata subsp. lyrata
                               organism = Arabidopsis lyrata
SEQUENCE: 444
MASSRLCDSC KSTTATLFCR ADAAFLCGVC DGKIHTANKL ASRHERVWLC EVCEQAPAHV        60
TCKADAAALC VTCDRDIHSA NPLSSRHERV PITPFYDTSP AKSASSSINF VDEDGGDVSA       120
SWLLHKEGIE ITNLFSDLDY PKMEVTSENN SSGNDGVVPV QSKMFLNEDY FNFDLSASKI       180
SSNGFNFINQ TVSRSIDVAL VPESGGVTAE ITNTATVTPA VQLSPAEREA RVLRYREKRK       240
NRKFEKTIRY ASRKAYAEMR PRIKGRFAKR TDSRENDGGD VGVYGGFGVV P                291

SEQ ID NO: 445                 moltype = AA   length = 342
FEATURE                        Location/Qualifiers
source                         1..342
                               mol_type = protein
                               organism = Brassica rapa
SEQUENCE: 445
MGFGLESIKP LSGGWGAAAR SCDACKSASA AVYCRFDSAF LCVTCDTSIH SFTRHERVYL        60
CEVCEQAPAA VTCKADAASL CVTCDSDIHS ANPLASRHER VPVESFFDSA VAKISPSTFG       120
VLGDSTTVDL TAVPVIGNAD ELGLCPWLLP NDFNEPAKIE TVTELKSSEF MFSDFDRLID       180
FEYPNTFGAD SLVPVQTKTE PLPVTNNDHC FDIDFCRSKL STFTYPTQSI SHSVSTSSLE       240
YGVVPDGTTS VPFNRSTITT STGTTGEQPS SMDREARVLR YREKRKNRKF EKTIRYASRK       300
AYAESRPRIK GRFAKRTETE NDDVFFSQVY ASAGQYGVVP TF                         342

SEQ ID NO: 446                 moltype = AA   length = 307
FEATURE                        Location/Qualifiers
source                         1..307
                               mol_type = protein
                               organism = Raphanus sativus
SEQUENCE: 446
MASRLCDSCR SAAATLYCRA DAAFLCGECD GKIHTANKLA SRHERVLLCQ ICEQAPAHVT        60
CEADAAALCV TCDRDIHSAN PLSRRHERVS VTPFYDAPAQ GGSPATTKSA ASSNLFGEDA       120
DVSMEAVSWL LPNPSVKEGV VVEIPNLFAD LDYSAVDPKM EASENSSGND GVVPVQTKAL       180
FLNEDYFNFD VSASKTTFPH GYSCINQTVS STSLEVPLVP EGGAVTTTNA TPAVQLSPAE       240
REARVLRYRE KRKNRKFEKT IRYASRKAYA EVRPRIKGRF AKRTDSRVND GGGDVGVYGG       300
FGVVPSF                                                                 307

SEQ ID NO: 447                 moltype = AA   length = 340
FEATURE                        Location/Qualifiers
source                         1..340
                               mol_type = protein
                               organism = Malus domestica
SEQUENCE: 447
MALKLCDSCK SATGTLFCRA DSAFLCVNCD SKIHAANKLA SRHARVWLCE VCEQAPAHVT        60
CKADDAALCV TCDRDIHSAN PLSHADERVP VTPFYDSVNS ATDSVPAVKS AVNFLNDRYF       120
SDVDGEIEAR REEAEAASWL LPNPKAMENP DLNSGQYLFP EMDPYMDLDY GHVDPKLEDA       180
QEQNSCITDG VVPEQSKNMQ PQLVNDHSFE IDFSAASKPF VYGYHHAQCL RQSVSSSSMD       240
VSIVPDDNAM TDDSNPYNKS MTSAVESSHP AVQLSSADRE ARVLRYREKR KNRKFEKTIR       300
YASRKAYAET RPRIKGRFAK RTEVEIEAEP MCRYGIVPSF                             340

SEQ ID NO: 448                 moltype = AA   length = 329
FEATURE                        Location/Qualifiers
source                         1..329
                               mol_type = protein
                               organism = Malus domestica
SEQUENCE: 448
MASKLCDSCQ SATATLFCRA DSAFLCVNCD SKIHAANKLA SRHPRVWLCE VCEQAPAHVT        60
CKADDAALCV TCDRDIHSAN PLSSRHDRVP VTPFYDSVNS AANSVPVVKS VVNFLDDRYL       120
SDVDGETEVS REEAEAASWL LPNPKAMENP DLNSGQYLFQ EMDPYLDLDY GHVDPKLEEA       180
QEQNSCGADG VVPVQSKNMQ PLLVNDQSFE LDFSAGSKPF VYGYHHARCL SQSVSSSSMD       240
ISVVPDGNAV TAAVETSQPA VQLSSVDRVA RVLRYREKRK NRKFEKTIRY ASRKAYAETR       300
PRIKGRFAKR TEVEIEAERM CRYGVVPSF                                         329

SEQ ID NO: 449                 moltype = AA   length = 409
FEATURE                        Location/Qualifiers
source                         1..409
                               mol_type = protein
                               organism = Solanum lycopersicum
SEQUENCE: 449
MLKKENSGGL DGSSNYWARV CDSCRSVTCT IYCQADSAYL CADCDARIHA ASLVTSRHKR        60
VWVCEACERA PAAFLCKADA ASLCASCDAD IHSANPLAHR HHRIPIITIP GTLYGPPAVE       120
TVGGDSMMIS GSTGEGTEDD GFLSLTQDAD DTIIDEEDED EDEAASWLLL NHPVKNNNKN       180
NVNNNNNQTN NYDMLFGGEV VDDYLDLAEY GGDSQFNDQY NVNQQQQQYF VPQMSYGGDS       240
VVPVQDGQGK PLIFYQQQQQ QQQSHHQNFQ LGMEYDNSNT RLGLPASMSH SVSVVSMDVS       300
VVPESALCET SNSQPRPQKG TIELFSGHPI QIPLLTPMDR EARVLRYREK KKNRKFEKTI       360
RYASRKAYAE TRPRIKGRFA KRTDVEAEVD QMFSTQLMTD SSYRIVPSF                   409

SEQ ID NO: 450                 moltype = AA   length = 312
FEATURE                        Location/Qualifiers
```

```
source                  1..312
                        mol_type = protein
                        organism = Pisum sativum
SEQUENCE: 450
MATKLCDSCK STKATLFCRS DSAFLCITCD SNIQAANKLA SRHHRVTLCE VCEQAPAHVT    60
CKADAAALCV SCDHDIHSAN PPASRHERIP LNTFHHNSKQ QFFSESDPDA DVSTEEAEAA   120
SWLLQTPANP KGPDLNSSHY SFTEIDATDL NFVCVDAKTD SPEQHSPGTA DGVVPVQSHS   180
KTVTEHYSDI NNDFSTSKPF TYNYNHSVSS SSLEVGVVPD GNVMSEMSYC GYGRTEAVQI   240
TAADREARVM RYREKRKNRR FEKTIRYASR KAYAETRPRI KGRFAKRTDL NMNVNLIGED   300
ESYDGYGVVP SC                                                       312

SEQ ID NO: 451          moltype = AA  length = 312
FEATURE                 Location/Qualifiers
source                  1..312
                        mol_type = protein
                        organism = Pisum sativum
SEQUENCE: 451
MATKLCDSCK STKATLFCRS DSAFLCITCD SNIHAANKLA SRHHRVTLCE VCEQAPAHVT    60
CKADAAALCV SCDHDIHSAN PLASRHERIP LNTFHHNSKQ QFFSESDPDA DVSTEEAEAA   120
SWLLQTPANP KGPDLNSSHY SFTEIDATDL NFVCVDAKTD SPEQHSPGTA DGVVPVQSHS   180
KTVTEHYSDI NNDFSTSKPF TYNYNHSVSS PSLEVGVVPD GNVMSEMSYC GYGRTEAVQI   240
TAADREARVM RYREKRKNRR FEKTIRYASR KAYAETRPRI KGRFAKRTDL NMNVNLIGED   300
ESYDGYGVVP SC                                                       312

SEQ ID NO: 452          moltype = AA  length = 351
FEATURE                 Location/Qualifiers
source                  1..351
                        mol_type = protein
                        organism = Arabidopsis thaliana
SEQUENCE: 452
MGFGLESIKS ISGGWGAAAR SCDACKSVTA AVFCRVDSAF LCIACDTRIH SFTRHERVWV    60
CEVCEQAPAA VTCKADAAAL CVSCDADIHS ANPLASRHER VPVETFFDSA ETAVAKISAS   120
STFGILGSST TVDLTAVPVM ADDLGLCPWL LPNDFNEPAK IEIGTENMKG SSDFMFSDFD   180
RLIDFEFPNS FNHHQNNAGG DSLVPVQTKT EPLPLTNNDH CFDIDFCRSK LSAFTYPSQS   240
VSTSSIEYGV VPDGNTNNSV NRSTITSSTT GGDHQASSMD REARVLRYRE KRKNRKFEKT   300
IRYASRKAYA ESRPRIKGRF AKRTETENDD IFLSHVYASA AHAQYGVVPT F            351
```

COMPOSITIONS AND METHODS FOR IMPROVING CROP YIELDS THROUGH TRAIT STACKING

CROSS-REFERENCE TO RELATED APPLICATION

This application is a Divisional of U.S. application Ser. No. 16/276,616, filed Feb. 15, 2019, which claims benefit under 35 U.S.C. § 119 (e) of U.S. Provisional Appln. No. 62/631,344, filed Feb. 15, 2018, the contents of each of which are incorporated by reference herein in their entirety.

REFERENCE TO AN ELECTRONIC SEQUENCE LISTING

The contents of the electronic sequence listing (777052058510SEQLIST.xml; Size: 691,674 bytes; Date of Creation: Aug. 19, 2022) are herein incorporated by reference in their entirety.

FIELD

The present disclosure relates to transgenic and/or genome edited or mutated corn plants that are semi-dwarf and have one or more improved ear traits relative to a control plant, as well as methods for producing transgenic and/or genome edited or mutated corn plants through stacking.

BACKGROUND

Cereal crop yields have been steadily increasing over the past decades due to improved agronomic practices and traits. However, there continues to be a need in the art for improved corn yield through intrinsic yield gains and/or reduced yield losses from improved lodging resistance, stress tolerances and other traits.

SUMMARY

Figure 1:
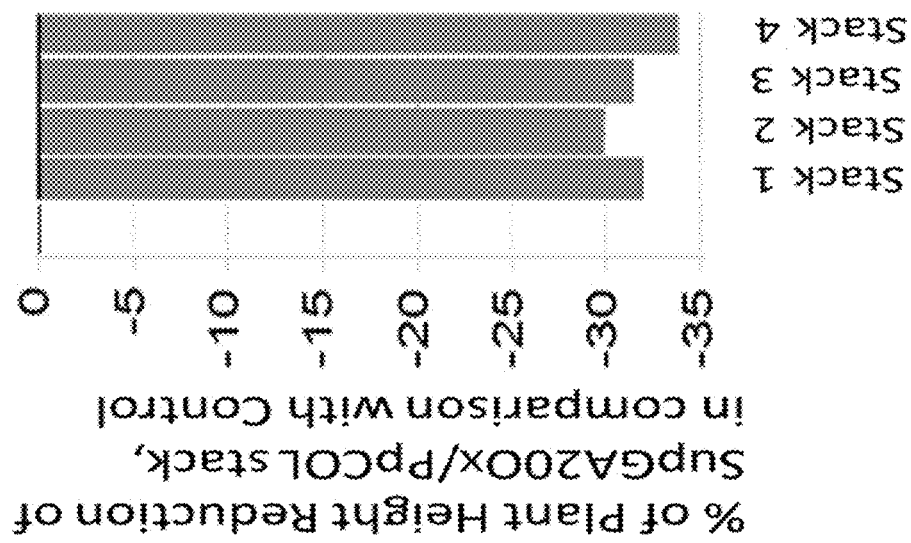
FIG. 1 shows plant heights of stacked transgenic corn plants ("GA20Ox_SUP/PpCOL stack") comprising a transgene encoding *Physcomitrella patens* CONSTANS-like 1 (PpCOL1) polypeptide and a DNA sequence encoding a miRNA for the suppression of GA20 oxidase (GA20Ox_SUP) across four transformation events, relative to control plants.

The present specification provides a modified corn plant or a plant part thereof comprising 1) a first recombinant expression cassette comprising a transcribable DNA sequence encoding a non-coding RNA for suppression of one or more gibberellic acid 20 (GA20) oxidase genes and/or one or more gibberellic acid 3 (GA3) oxidase genes, and 2) a second recombinant expression cassette comprising a DNA sequence encoding a CONSTANS (CO) or CONSTANS-like (COL) polypeptide.

The present specification also provides A plurality of modified corn plants in a field, each modified corn plant comprising 1) a first recombinant expression cassette comprising a transcribable DNA sequence encoding a non-coding RNA for suppression of one or more gibberellic acid 20 (GA20) oxidase genes and/or one or more gibberellic acid 3 (GA3) oxidase genes, and 2) a second recombinant expression cassette comprising a DNA sequence encoding a CO or COL polypeptide.

Also provided by the present specification is a method for producing a modified corn plant, the method comprising: a) introducing into a corn cell a first recombinant expression cassette comprising a DNA sequence encoding a CO or COL polypeptide, wherein the corn cell comprises a second recombinant expression cassette comprising a transcribable DNA sequence encoding a non-coding RNA for suppression of one or more GA3 oxidase genes and/or one or more GA20 oxidase genes; and b) regenerating or developing a modified corn plant from the corn cell, wherein the modified corn plant comprises the first and second recombinant expression cassettes.

Further provided by the present specification is a method for producing a modified corn plant, the method comprising: a) introducing into a corn cell a first recombinant expression cassette comprising a transcribable DNA sequence encoding a non-coding RNA for suppression of one or more GA3 oxidase genes and/or GA20 oxidase genes, wherein the corn cell comprises a second recombinant expression cassette comprising a DNA sequence encoding a CO and/or COL polypeptide; and b) regenerating or developing a modified corn plant from the corn cell, wherein the modified corn plant comprises the first and second recombinant expression cassettes.

In an aspect, the present specification provides a method for producing a modified corn plant, the method comprising a) introducing into a corn cell 1) a first recombinant expression cassette comprising a transcribable DNA sequence encoding a non-coding RNA for suppression of one or more GA3 oxidase genes and/or GA20 oxidase genes and 2) a second recombinant expression cassette comprising a DNA sequence encoding a CO or COL polypeptide; and b) regenerating or developing a modified corn plant from the corn cell, wherein the modified corn plant comprises the first and second recombinant expression cassettes.

In another aspect, the present specification provides a method for producing a modified corn plant, the method comprising a) introducing into a corn cell a first recombinant expression cassette comprising a transcribable DNA sequence encoding a non-coding RNA for suppression of one or more GA3 oxidase genes and/or GA20 oxidase genes; b) introducing into the corn cell of step (a) a second recombinant expression cassette comprising a DNA sequence encoding a CO or COL polypeptide to create a modified corn cell; and c) regenerating or developing a modified corn plant from the modified corn cell of step (b), wherein the modified corn plant comprises the first and second recombinant expression cassettes.

In an still another aspect, the present specification provides a method for producing a modified corn plant, the method comprising a) introducing into a corn cell a first recombinant expression cassette comprising a DNA sequence encoding a CO or COL polypeptide; b) introducing into the corn cell of step (a) a second recombinant expression cassette comprising a transcribable DNA sequence encoding a non-coding RNA for suppression of one or more GA3 oxidase genes and/or GA20 oxidase genes to create a modified corn cell; and c) regenerating or developing a modified corn plant from the modified corn cell of step (b), wherein the modified corn plant comprises the first and second recombinant expression cassettes.

The present specification provides a method for producing a modified corn plant, the method comprising: a) crossing a first modified corn plant with a second modified corn plant, wherein the expression or activity of one or more endogenous GA3 oxidase genes and/or GA20 oxidase genes is reduced in the first modified corn plant relative to a wildtype control, and wherein the second modified corn plant comprises a recombinant expression cassette comprising a DNA sequence encoding a CO or COL polypeptide; and b) producing a progeny corn plant comprising the recombinant expression cassette and has the reduced expression of the one or more endogenous GA3 oxidase genes and/or GA20 oxidase genes.

The present specification also provides A method for producing a modified corn plant, the method comprising: a) introducing into a corn cell a recombinant expression cassette comprising a DNA sequence encoding a CO or COL polypeptide, wherein the DNA sequence is operably linked to a plant-expressible promoter, and wherein the corn cell comprises one or more mutations and/or edits in one or more endogenous GA3 oxidase and/or GA20 oxidase genes; and b) regenerating or developing a modified corn plant from the corn cell, wherein the modified corn plant comprises the recombinant expression cassette and the one or more mutations and/or edits, and wherein the level of expression or activity of the one or more endogenous GA3 oxidase and/or GA20 oxidase genes in the modified corn plant is reduced relative to a control plant not having the one or more mutations and/or edits.

Also provided by the present specification is A method for producing a modified corn plant, the method comprising: a) mutating or editing one or more endogenous GA3 oxidase genes and/or one or more GA20 oxidase genes in a corn cell, wherein the corn cell comprises a recombinant expression cassette encoding a CO or COL polypeptide, wherein the DNA sequence is operably linked to a plant-expressible promoter; and b) regenerating or developing a modified corn plant from the corn cell, wherein the modified corn plant comprises the recombinant expression cassette and the one or more mutations and/or edits, and wherein the level of expression or activity of the one or more endogenous GA3 oxidase and/or GA20 oxidase genes in the modified corn plant is reduced relative to a control plant not having the one or more mutations and/or edits.

Further provided by the present specification is a modified corn plant comprising 1) one or more mutations or edits at or near one or more endogenous GA20 oxidase and/or GA3 oxidase genes, wherein the expression or activity of the one or more endogenous GA20 oxidase and/or GA3 oxidase genes is reduced relative to a wildtype control plant, and 2) a recombinant expression cassette comprising a DNA sequence encoding a CO or COL polypeptide, wherein the DNA sequence is operably linked to a plant-expressible promoter.

In an aspect, the present specification provides a plurality of modified corn plants in a field, each modified corn plant comprising 1) one or more mutations or edits at or near one or more endogenous GA20 oxidase and/or GA3 oxidase genes, wherein the expression of the one or more endogenous GA20 oxidase and/or GA3 oxidase genes are reduced relative to a wildtype control plant, and 2) a recombinant expression cassette comprising a DNA sequence encoding a CO or COL polypeptide, wherein the DNA sequence is operably linked to a plant-expressible promoter.

In another aspect, the present specification provides a recombinant DNA construct comprising 1) a first expression cassette comprising a transcribable DNA sequence encoding a non-coding RNA for suppression of one or more GA20 oxidase or one or more GA3 oxidase genes, and 2) a second expression cassette comprising a DNA sequence encoding a CO or COL polypeptide, wherein the DNA sequence is operably linked to a plant-expressible promoter.

In still another aspect, the present specification provides A recombinant DNA donor template molecule for site directed integration of an insertion sequence into the genome of a corn plant comprising an insertion sequence and at least one homology sequence, wherein the homology sequence is at least 70%, at least 75%, at least 80%, at least 85%, at least 90%, at least 95%, at least 96%, at least 97%, at least 99% or 100% complementary to at least 20, at least 25, at least 30, at least 35, at least 40, at least 45, at least 50, at least 60, at least 70, at least 80, at least 90, at least 100, at least 150, at least 200, at least 250, at least 500, at least 1000, at least 2500, or at least 5000 consecutive nucleotides of a target DNA sequence in the genome of a corn plant cell, and wherein the insertion sequence comprises an expression cassette comprising a DNA sequence encoding a CO or COL polypeptide, wherein the DNA sequence is operably linked to a plant-expressible promoter.

DESCRIPTION

Definitions

Unless defined otherwise herein, terms are to be understood according to conventional usage by those of ordinary skill in the relevant art. Examples of resources describing many of the terms related to molecular biology used herein can be found in Alberts et al., Molecular Biology of The Cell, 5th Edition, Garland Science Publishing, Inc.: New York, 2007; Rieger et al., Glossary of Genetics: Classical and Molecular, 5th edition, Springer-Verlag: New York, 1991; King et al, A Dictionary of Genetics, 6th ed., Oxford University Press: New York, 2002; and Lewin, Genes IX, Oxford University Press: New York, 2007.

Any references cited herein, including, e.g., all patents, published patent applications, and non-patent publications, are incorporated by reference in their entirety. To facilitate understanding of the disclosure, several terms and abbreviations as used herein are defined below as follows:

The term "and/or" when used in a list of two or more items, means that any one of the listed items can be employed by itself or in combination with any one or more of the listed items. For example, the expression "A and/or B" is intended to mean either or both of A and B—i.e., A alone, B alone, or A and B in combination. The expression "A, B and/or C" is intended to mean A alone, B alone, C alone, A and B in combination, A and C in combination, B and C in combination, or A, B, and C in combination.

The term "about" as used herein, is intended to qualify the numerical values that it modifies, denoting such a value as variable within a margin of error. When no particular margin of error, such as a standard deviation to a mean value, is recited, the term "about" should be understood to mean that range which would encompass the recited value and the range which would be included by rounding up or down to that figure, taking into account significant figures.

As used herein, a "plant" includes an explant, plant part, seedling, plantlet or whole plant at any stage of regeneration or development. The term "cereal plant" as used herein refers to a monocotyledonous (monocot) crop plant that is in the Poaceae or Gramineae family of grasses and is typically harvested for its seed, including, for example, wheat, corn, rice, millet, barley, sorghum, oat and rye. As commonly understood, a "corn plant" or "maize plant" refers to any plant of species Zea mays and includes all plant varieties that can be bred with corn, including wild maize species.

As used herein, a "plant part" can refer to any organ or intact tissue of a plant, such as a meristem, shoot organ/structure (e.g., leaf, stem or node), root, flower or floral organ/structure (e.g., bract, sepal, petal, stamen, carpel, anther and ovule), seed (e.g., embryo, endosperm, and seed coat), fruit (e.g., the mature ovary), propagule, or other plant tissues (e.g., vascular tissue, dermal tissue, ground tissue, and the like), or any portion thereof. Plant parts of the present disclosure can be viable, nonviable, regenerable, and/or non-regenerable. A "propagule" can include any plant part that can grow into an entire plant.

As used herein, a "transgenic plant" refers to a plant whose genome has been altered by the integration or insertion of a recombinant DNA molecule, construct, cassette or sequence for expression of a non-coding RNA molecule, mRNA and/or protein in the plant. A transgenic plant includes an $R_0$ plant developed or regenerated from an originally transformed plant cell(s) as well as progeny transgenic plants in later generations or crosses from the $R_0$ transgenic plant that comprise the recombinant DNA molecule, construct, cassette or sequence. A plant having an integrated or inserted recombinant DNA molecule, construct, cassette or sequence is considered a transgenic plant even if the plant also has other mutation(s) or edit(s) that would not themselves be considered transgenic.

A plant cell is a biological cell of a plant, taken from a plant or derived through culture from a cell taken from a plant. As used herein, a "transgenic plant cell" refers to any plant cell that is transformed with a stably-integrated recombinant DNA molecule, construct, cassette, or sequence. A transgenic plant cell can include an originally-transformed plant cell, a transgenic plant cell of a regenerated or developed $R_0$ plant, a transgenic plant cell cultured from another transgenic plant cell, or a transgenic plant cell from any progeny plant or offspring of the transformed $R_0$ plant, including cell(s) of a plant seed or embryo, or a cultured plant cell, callus cell, etc.

As used herein, the term "transcribable DNA sequence" refers to a DNA sequence that can be transcribed into an RNA molecule. The RNA molecule can be coding or non-coding and may or may not be operably linked to a promoter and/or other regulatory sequences.

For purposes of the present disclosure, a "non-coding RNA molecule" is a RNA molecule that does not encode a protein. Non-limiting examples of a non-coding RNA molecule include a microRNA (miRNA), a miRNA precursor, a small interfering RNA (siRNA), a siRNA precursor, a small RNA (18-26 nt in length) and precursors encoding the same, a heterochromatic siRNA (hc-siRNA), a Piwi-interacting RNA (piRNA), a hairpin double strand RNA (hairpin dsRNA), a trans-acting siRNA (ta-siRNA), a naturally occurring antisense siRNA (nat-siRNA), a CRISPR RNA (crRNA), a tracer RNA (tracrRNA), a guide RNA (gRNA), and a single-guide RNA (sgRNA).

The terms "suppressing"/"suppression" or "reduced"/"reduction" when used in reference to a gene(s), refers to a lowering, reduction, or elimination of the expression level of a mRNA and/or protein encoded by the gene(s), and/or a lowering, reduction, or elimination of the activity of a protein encoded by the gene(s) in a plant, plant cell or plant tissue, at one or more stage(s) of plant development, as compared to the expression level of such target mRNA and/or protein, and/or the activity of such encoded protein in a wild-type or control plant, cell or tissue at the same stage(s) of plant development.

As used herein, the term "consecutive" in reference to a polynucleotide or protein sequence means without deletions or gaps in the sequence.

As commonly understood in the art, a "mutation" refers to any alteration of the nucleotide sequence of the genome, extrachromosomal DNA, or other genetic element of an organism (e.g., a gene or regulatory element operably linked to a gene in a plant), such as a nucleotide insertion, deletion, inversion, substitution, duplication, etc.

The terms "percent identity" or "percent identical" as used herein in reference to two or more nucleotide or protein sequences is calculated by (i) comparing two optimally aligned sequences (nucleotide or protein) over a window of comparison, (ii) determining the number of positions at which the identical nucleic acid base (for nucleotide sequences) or amino acid residue (for proteins) occurs in both sequences to yield the number of matched positions, (iii) dividing the number of matched positions by the total number of positions in the window of comparison, and then (iv) multiplying this quotient by 100% to yield the percent identity. For purposes of calculating "percent identity" between DNA and RNA sequences, a uracil (U) of a RNA sequence is considered identical to a thymine (T) of a DNA sequence. If the window of comparison is defined as a region of alignment between two or more sequences (i.e., excluding nucleotides at the 5' and 3' ends of aligned polynucleotide sequences, or amino acids at the N-terminus and C-terminus of aligned protein sequences, that are not identical between the compared sequences), then the "percent identity" can also be referred to as a "percent alignment identity". If the "percent identity" is being calculated in relation to a reference sequence without a particular comparison window being specified, then the percent identity is determined by dividing the number of matched positions over the region of alignment by the total length of the reference sequence. Accordingly, for purposes of the present disclosure, when two sequences (query and subject) are optimally aligned (with allowance for gaps in their alignment), the "percent identity" for the query sequence is equal to the number of identical positions between the two sequences divided by the total number of positions in the query sequence over its length (or a comparison window), which is then multiplied by 100%.

It is recognized that residue positions of proteins that are not identical often differ by conservative amino acid substitutions, where amino acid residues are substituted for other amino acid residues with similar size and chemical properties (e.g., charge, hydrophobicity, polarity, etc.), and therefore may not change the functional properties of the molecule. When sequences differ in conservative substitutions, the percent sequence similarity can be adjusted upwards to correct for the conservative nature of the non-identical substitution(s). Sequences that differ by such conservative substitutions are said to have "sequence similarity" or "similarity." Thus, "percent similarity" or "percent similar" as used herein in reference to two or more protein sequences is calculated by (i) comparing two optimally aligned protein sequences over a window of comparison, (ii) determining the number of positions at which the same or similar amino acid residue occurs in both sequences to yield the number of matched positions, (iii) dividing the number of matched positions by the total number of positions in the window of comparison (or the total length of the reference or query protein if a window of comparison is not specified), and then (iv) multiplying this quotient by 100% to yield the percent similarity. Conservative amino acid substitutions for proteins are known in the art.

For optimal alignment of sequences to calculate their percent identity or similarity, various pair-wise or multiple sequence alignment algorithms and programs are known in the art, such as ClustalW, or Basic Local Alignment Search Tool® (BLAST®), etc., that can be used to compare the sequence identity or similarity between two or more nucleotide or protein sequences. Although other alignment and comparison methods are known in the art, the alignment between two sequences (including the percent identity ranges described above) can be as determined by the ClustalW or BLAST® algorithm, see, e.g., Chenna R. et al., "Multiple sequence alignment with the Clustal series of programs," *Nucleic Acids Research* 31: 3497-3500 (2003); Thompson J D et al., "Clustal W: Improving the sensitivity of progressive multiple sequence alignment through sequence weighting, position-specific gap penalties and weight matrix choice," *Nucleic Acids Research* 22: 4673-4680 (1994); and Larkin M A et al., "Clustal W and Clustal X version 2.0," *Bioinformatics* 23: 2947-48 (2007); and Altschul, S. F., Gish, W., Miller, W., Myers, E. W. & Lipman, D. J. (1990) "Basic local alignment search tool." *J. Mol. Biol.* 215:403-410 (1990), the entire contents and disclosures of which are incorporated herein by reference.

The terms "percent complementarity" or "percent complementary", as used herein in reference to two nucleotide sequences, is similar to the concept of percent identity but refers to the percentage of nucleotides of a query sequence that optimally base-pair or hybridize to nucleotides of a subject sequence when the query and subject sequences are linearly arranged and optimally base paired without secondary folding structures, such as loops, stems or hairpins. Such a percent complementarity can be between two DNA strands, two RNA strands, or a DNA strand and a RNA strand. The "percent complementarity" is calculated by (i) optimally base-pairing or hybridizing the two nucleotide sequences in a linear and fully extended arrangement (i.e., without folding or secondary structures) over a window of comparison, (ii) determining the number of positions that base-pair between the two sequences over the window of comparison to yield the number of complementary positions, (iii) dividing the number of complementary positions by the total number of positions in the window of comparison, and (iv) multiplying this quotient by 100% to yield the percent complementarity of the two sequences. Optimal base pairing of two sequences can be determined based on the known pairings of nucleotide bases, such as G-C, A-T, and A-U, through hydrogen bonding. If the "percent complementarity" is being calculated in relation to a reference sequence without specifying a particular comparison window, then the percent identity is determined by dividing the number of complementary positions between the two linear sequences by the total length of the reference sequence. Thus, for purposes of the present disclosure, when two sequences (query and subject) are optimally base-paired (with allowance for mismatches or non-base-paired nucleotides but without folding or secondary structures), the "percent complementarity" for the query sequence is equal to the number of base-paired positions between the two sequences divided by the total number of positions in the query sequence over its length (or by the number of positions in the query sequence over a comparison window), which is then multiplied by 100%.

The term "operably linked" refers to a functional linkage between a promoter or other regulatory element and an associated transcribable DNA sequence or coding sequence of a gene (or transgene), such that the promoter, etc., operates or functions to initiate, assist, affect, cause, and/or promote the transcription and expression of the associated transcribable DNA sequence or coding sequence, at least in certain cell(s), tissue(s), developmental stage(s), and/or condition(s).

As commonly understood in the art, the term "promoter" can generally refer to a DNA sequence that contains an RNA polymerase binding site, transcription start site, and/or TATA box and assists or promotes the transcription and expression of an associated transcribable polynucleotide sequence and/or gene (or transgene). A promoter can be synthetically produced, varied or derived from a known or naturally occurring promoter sequence or other promoter sequence. A promoter can also include a chimeric promoter comprising a combination of two or more heterologous sequences. A promoter of the present disclosure can thus include variants of promoter sequences that are similar in composition, but not identical to, other promoter sequence (s) known or provided herein. A promoter can be classified according to a variety of criteria relating to the pattern of expression of an associated coding or transcribable sequence or gene (including a transgene) operably linked to the promoter, such as constitutive, developmental, tissue-specific, inducible, etc. Promoters that drive expression in all or most tissues of the plant are referred to as "constitutive" promoters. Promoters that drive expression during certain periods or stages of development are referred to as "developmental" promoters. Promoters that drive enhanced expression in certain tissues of the plant relative to other plant tissues are referred to as "tissue-enhanced" or "tissue-preferred" promoters. Thus, a "tissue-preferred" promoter causes relatively higher or preferential expression in a specific tissue(s) of the plant, but with lower levels of expression in other tissue(s) of the plant. Promoters that express within a specific tissue(s) of the plant, with little or no expression in other plant tissues, are referred to as "tissue-specific" promoters. An "inducible" promoter is a promoter that initiates transcription in response to an environmental stimulus such as cold, drought or light, or other stimuli, such as wounding or chemical application. A promoter can also be classified in terms of its origin, such as being heterologous, homologous, chimeric, synthetic, etc.

As used herein, a "plant-expressible promoter" refers to a promoter that can initiate, assist, affect, cause, and/or promote the transcription and expression of its associated transcribable DNA sequence, coding sequence or gene in a corn plant cell or tissue.

As used herein, a "heterologous plant-expressible promoter" refers to a plant-expressible promoter which does not naturally occur adjacent to or associated with the referenced gene or nucleic acid sequence in its natural environment, but which is positioned by laboratory manipulation.

As used herein, a "vascular promoter" refers to a plant-expressible promoter that drives, causes or initiates expression of a transcribable DNA sequence or transgene operably linked to such promoter in one or more vascular tissue(s) of the plant, even if the promoter is also expressed in other non-vascular plant cell(s) or tissue(s). Such vascular tissue(s) can comprise one or more of the phloem, vascular parenchymal, and/or bundle sheath cell(s) or tissue(s) of the plant. A "vascular promoter" is distinguished from a constitutive promoter in that it has a regulated and relatively more limited pattern of expression that includes one or more vascular tissue(s) of the plant. A vascular promoter includes both vascular-specific promoters and vascular-preferred promoters.

As used herein, a "leaf promoter" refers to a plant-expressible promoter that drives, causes or initiates expression of a transcribable DNA sequence or transgene operably linked to such promoter in one or more leaf tissue(s) of the plant, even if the promoter is also expressed in other non-leaf plant cell(s) or tissue(s). A leaf promoter includes both leaf-specific promoters and leaf-preferred promoters. A "leaf promoter" is distinguished from a vascular promoter in that it is expressed more predominantly or exclusively in leaf tissue(s) of the plant relative to other plant tissues, whereas a vascular promoter is expressed in vascular tissue(s) more generally including vascular tissue(s) outside of the leaf, such as the vascular tissue(s) of the stem, or stem and leaves, of the plant.

The term "heterologous" in reference to a promoter or other regulatory sequence in relation to an associated polynucleotide sequence (e.g., a transcribable DNA sequence or coding sequence or gene) is a promoter or regulatory sequence that is not operably linked to such associated polynucleotide sequence in nature—e.g., the promoter or regulatory sequence has a different origin relative to the associated polynucleotide sequence and/or the promoter or regulatory sequence is not naturally occurring in a plant species to be transformed with the promoter or regulatory sequence.

The term "recombinant" in reference to a polynucleotide (DNA or RNA) molecule, protein, construct, vector, etc., refers to a polynucleotide or protein molecule or sequence that is man-made and not normally found in nature, and/or is present in a context in which it is not normally found in nature, including a polynucleotide (DNA or RNA) molecule, protein, construct, etc., comprising a combination of two or more polynucleotide or protein sequences that would not naturally occur together in the same manner without human intervention, such as a polynucleotide molecule, protein, construct, etc., comprising at least two polynucleotide or protein sequences that are operably linked but heterologous with respect to each other. For example, the term "recombinant" can refer to any combination of two or more DNA or protein sequences in the same molecule (e.g., a plasmid, construct, vector, chromosome, protein, etc.) where such a combination is man-made and not normally found in nature. As used in this definition, the phrase "not normally found in nature" means not found in nature without human introduction. A recombinant polynucleotide or protein molecule, construct, etc., can comprise polynucleotide or protein sequence(s) that is/are (i) separated from other polynucleotide or protein sequence(s) that exist in proximity to each other in nature, and/or (ii) adjacent to (or contiguous with) other polynucleotide or protein sequence(s) that are not naturally in proximity with each other. Such a recombinant polynucleotide molecule, protein, construct, etc., can also refer to a polynucleotide or protein molecule or sequence that has been genetically engineered and/or constructed outside of a cell. For example, a recombinant DNA molecule can comprise any engineered or man-made plasmid, vector, etc., and can include a linear or circular DNA molecule. Such plasmids, vectors, etc., can contain various maintenance elements including a prokaryotic origin of replication and selectable marker, as well as one or more transgenes or expression cassettes perhaps in addition to a plant selectable marker gene, etc.

As used herein, the term "isolated" refers to at least partially separating a molecule from other molecules typically associated with it in its natural state. In an aspect, the term "isolated" refers to a DNA molecule that is separated from the nucleic acids that normally flank the DNA molecule in its natural state. For example, a DNA molecule encoding a protein that is naturally present in a bacterium would be an isolated DNA molecule if it was not within the DNA of the bacterium from which the DNA molecule encoding the protein is naturally found. Thus, a DNA molecule fused to or operably linked to one or more other DNA molecule(s) with which it would not be associated in nature, for example as the result of recombinant DNA or plant transformation techniques, is considered isolated herein. Such molecules are considered isolated even when integrated into the chromosome of a host cell or present in a nucleic acid solution with other DNA molecules.

As used herein, an "encoding region" or "coding region" refers to a portion of a polynucleotide that encodes a functional unit or molecule (e.g., without being limiting, a mRNA, protein, or non-coding RNA sequence or molecule).

As used herein, "modified" in the context of a plant, plant seed, plant part, plant cell, and/or plant genome, refers to a plant, plant seed, plant part, plant cell, and/or plant genome comprising an engineered change in the expression level and/or coding sequence of one or more gene(s) relative to a wild-type or control plant, plant seed, plant part, plant cell, and/or plant genome, such as via a transgenic event or a genome editing event or mutation affecting the expression level or activity of one or more genes. Modified plants, plant parts, seeds, etc., can be subjected to or created by mutagenesis, genome editing or site-directed integration (e.g., without being limiting, via methods using site-specific nucleases), genetic transformation (e.g., without being limiting, via methods of *Agrobacterium* transformation or microprojectile bombardment), or a combination thereof. Such "modified" plants, plant seeds, plant parts, and plant cells include plants, plant seeds, plant parts, and plant cells that are offspring or derived from "modified" plants, plant seeds, plant parts, and plant cells that retain the molecular change (e.g., change in expression level and/or activity) to the one or more genes. A modified seed provided herein can give rise to a modified plant provided herein. A modified plant, plant seed, plant part, plant cell, or plant genome provided herein can comprise a recombinant DNA construct or vector or genome edit as provided herein. A "modified plant product" can be any product made from a modified plant, plant part, plant cell, or plant chromosome provided herein, or any portion or component thereof.

As used herein, the term "control plant" (or likewise a "control" plant seed, plant part, plant cell and/or plant genome) refers to a plant (or plant seed, plant part, plant cell and/or plant genome) that is used for comparison to a modified plant (or modified plant seed, plant part, plant cell and/or plant genome) and has the same or similar genetic background (e.g., same parental lines, hybrid cross, inbred line, testers, etc.) as the modified plant (or plant seed, plant part, plant cell and/or plant genome), except for a transgene, expression cassette, mutation, and/or genome edit affecting one or more genes. For purposes of comparison to a modified plant, plant seed, plant part, plant cell and/or plant genome, a "wild-type plant" (or likewise a "wild-type" plant seed, plant part, plant cell and/or plant genome) refers to a non-transgenic, non-mutated, and non-genome edited control plant, plant seed, plant part, plant cell and/or plant genome. Alternatively as can be specified herein, such a "control plant" (or likewise a "control" plant seed, plant part, plant cell and/or plant genome) can refer to a plant (or plant seed, plant part, plant cell and/or plant genome) that (i) is used for comparison to a modified plant (or modified plant seed, plant part, plant cell and/or plant genome) having a stack of two or more transgene(s), expression cassette(s), mutation(s) and/or genome edit(s), (ii) has the same or similar genetic background (e.g., same parental lines, hybrid cross, inbred line, testers, etc.) as the modified plant (or plant seed, plant part, plant cell and/or plant genome), but (iii) lacks at least one of the two or more transgene(s), expression cassette(s), mutation(s) and/or genome edit(s) of the modified plant (e.g., a stack in comparison to a single of one of the members of the stack). As used herein, such a "control" plant, plant seed, plant part, plant cell and/or plant genome can also be a plant, plant seed, plant part, plant cell and/or plant genome having a similar (but not the same or identical) genetic background to a modified plant, plant seed, plant part, plant cell and/or plant genome, if deemed sufficiently similar for comparison of the characteristics or traits to be analyzed.

As used herein, "crossed" or "cross" means to produce progeny via fertilization (e.g., cells, seeds or plants) and includes crosses between plants (sexual) and self-fertilization (selfing).

As used herein, "ear trait" of a corn plant refers to a characteristic of an ear of a corn plant. In an aspect, an ear trait can include, but is not limited to, ear area, single kernel weight, ear fresh weight, and/or number of florets. In another aspect, an ear trait can include, but is not limited to, ear diameter, ear length, ear tip void, ear void, ear volume, kernel number, kernel number per row, kernel number per ear, kernels per field area, kernel rank, kernel row number, kernel weight, single kernel weight, yield, and/or grain yield estimate. In yet another aspect, an ear trait can include, but is not limited to, ear attitude, ear cob color, ear cob diameter, ear cob strength, ear dry husk color, ear fresh husk color, ear husk bract, ear husk cover, ear husk opening, ear number per stalk, ear shank length, ear shelling percent, ear silk color, ear taper, ear weight, ear rot rating, kernel aleurone color, kernel cap color, kernel endosperm color, kernel endosperm type, kernel grade, kernel length, kernel pericarp color, kernel row direction, kernel side color, kernel thickness, kernel type, kernel width, cob weight, and/or prolificacy. A modified or genome edited/mutated corn plant of the present disclosure exhibits one or more improved ear trait compared to a control corn plant. In an aspect, a modified or genome edited/mutated corn plant exhibits an increased ear area relative to a control corn plant. In an aspect, a modified or genome edited/mutated corn plant exhibits increased kernel weight relative to a control corn plant. In an aspect, a modified or genome edited/mutated corn plant exhibits an increased ear fresh weight relative to a control corn plant.

As used herein, "yield" refers to the total amount of an agricultural product (e.g., seeds, fruit, etc.) produced or harvested from a plurality of crop plants per unit area of land cultivation (e.g., a field of crop plants) as understood in the art. Yield can be measured or estimated in a greenhouse, in a field, or under specific environment, treatment and/or stress conditions. For example, as known and understood in the art, yield can be measured in units of kilograms per hectare, bushels per acre, or the like. Indeed, yield can be measured in terms of "broad acreage yield" or "BAY" as known and understood in the art.

As used herein, "comparable conditions" for plants refers to the same or similar environmental conditions and agronomic practices for growing and making meaningful comparisons between two or more plant genotypes so that neither environmental conditions nor agronomic practices would significantly contribute to, or explain, any differences observed between the two or more plant genotypes. Environmental conditions include, for example, light, temperature, water, humidity, soil, and nutrition (e.g., nitrogen and phosphorus).

As used herein, a "targeted genome editing technique" refers to any method, protocol, or technique that allows the precise and/or targeted editing of a specific location in a genome of a plant (i.e., the editing is largely or completely non-random) using a site-specific nuclease, such as a meganuclease, a zinc-finger nuclease (ZFN), an RNA-guided endonuclease (e.g., the CRISPR/Cas9 system), a TALE-endonuclease (TALEN), a recombinase, or a transposase.

As used herein, "editing" or "genome editing" refers to generating a targeted mutation, deletion, inversion or substitution of at least 1, at least 2, at least 3, at least 4, at least 5, at least 6, at least 7, at least 8, at least 9, at least 10, at least 15, at least 20, at least 25, at least 30, at least 35, at least 40, at least 45, at least 50, at least 75, at least 100, at least 250, at least 500, at least 1000, at least 2500, at least 5000, at least 10,000, or at least 25,000 nucleotides of an endogenous plant genome nucleic acid sequence using a targeted genome editing technique. As used herein, "editing" or "genome editing" also encompasses the targeted insertion or site-directed integration of at least 1, at least 2, at least 3, at least 4, at least 5, at least 6, at least 7, at least 8, at least 9, at least 10, at least 15, at least 20, at least 25, at least 30, at least 35, at least 40, at least 45, at least 50, at least 75, at least 100, at least 250, at least 500, at least 750, at least 1000, at least 1500, at least 2000, at least 2500, at least 3000, at least 4000, at least 5000, at least 10,000, or at least 25,000 nucleotides into the endogenous genome of a plant using a targeted genome editing technique.

As used herein, a "target site" for genome editing refers to the location of a polynucleotide sequence within a plant genome that is targeted and cleaved by a site-specific nuclease introducing a double stranded break (or single-stranded nick) into the nucleic acid backbone of the polynucleotide sequence and/or its complementary DNA strand. A site-specific nuclease can bind to a target site, such as via a non-coding guide RNA (e.g., without being limiting, a CRISPR RNA (crRNA) or a single-guide RNA (sgRNA) as described further below). A non-coding guide RNA provided herein can be complementary to a target site (e.g., complementary to either strand of a double-stranded nucleic acid molecule or chromosome at the target site). A "target site" also refers to the location of a polynucleotide sequence within a plant genome that is bound and cleaved by another site-specific nuclease that may not be guided by a non-coding RNA molecule, such as a meganuclease, zinc finger nuclease (ZFN), or a transcription activator-like effector nuclease (TALEN), to introduce a double stranded break (or single-stranded nick) into the polynucleotide sequence and/or its complementary DNA strand. As used herein, a "target region" or a "targeted region" refers to a polynucleotide sequence or region that is flanked by two or more target sites. Without being limiting, in some aspects a target region can be subjected to a mutation, deletion, insertion or inversion. As used herein, "flanked" when used to describe a target region of a polynucleotide sequence or molecule, refers to two or more target sites of the polynucleotide sequence or molecule surrounding the target region, with one target site on each side of the target region.

Apart from genome editing, the term "target site" can also be used in the context of gene suppression to refer to a portion of a mRNA molecule (e.g., a "recognition site") that is complementary to at least a portion of a non-coding RNA molecule (e.g., a miRNA, siRNA, etc.) encoded by a suppression construct. As used herein, a "target site" for a RNA-guided nuclease can comprise the sequence of either complementary strand of a double-stranded nucleic acid (DNA) molecule or chromosome at the target site. It will be appreciated that perfect identity or complementarity may not be required for a non-coding guide RNA to bind or hybridize to a target site. For example, at least 1, at least 2, at least 3, at least 4, at least 5, at least 6, at least 7, or at least 8 mismatches (or more) between a target site and a non-coding RNA can be tolerated.

As used herein, a "donor molecule", "donor template", or "donor template molecule" (collectively a "donor template"), which can be a recombinant DNA donor template, is defined as a nucleic acid molecule having a nucleic acid template or insertion sequence for site-directed, targeted insertion or recombination into the genome of a plant cell via repair of a nick or double-stranded DNA break in the genome of a plant cell. For example, a "donor template" can be used for site-directed integration of a transgene or suppression construct, or as a template to introduce a mutation, such as an insertion, deletion, etc., into a target site within the genome of a plant. A targeted genome editing technique provided herein can comprise the use of one or more, two or more, three or more, four or more, or five or more donor molecules or templates. A donor template can be a single-stranded or double-stranded DNA or RNA molecule or plasmid. A donor template can also have at least one homology sequence or homology arm, such as two homology arms, to direct the integration of a mutation or insertion sequence into a target site within the genome of a plant via homologous recombination, wherein the homology sequence or homology arm(s) are identical or complementary, or have a percent identity or percent complementarity, to a sequence at or near the target site within the genome of the plant. When a donor template comprises homology arm(s) and an insertion sequence, the homology arm(s) will flank or surround the insertion sequence of the donor template. Further, the donor template can be linear or circular, and can be single-stranded or double-stranded. A donor template can be delivered to the cell as a naked nucleic acid (e.g., via particle bombardment), as a complex with one or more delivery agents (e.g., liposomes, proteins, poloxamers, T-strand encapsulated with proteins, etc.), or contained in a bacterial or viral delivery vehicle, such as, for example, *Agrobacterium tumefaciens* or a geminivirus, respectively.

An insertion sequence of a donor template can comprise one or more genes or sequences that each encode a transcribed non-coding RNA or mRNA sequence and/or a translated protein sequence. A transcribed sequence or gene of a donor template can encode a protein or a non-coding RNA molecule. An insertion sequence of a donor template can comprise a polynucleotide sequence that does not comprise a functional gene or an entire gene sequence (e.g., the donor template can simply comprise regulatory sequences, such as a promoter sequence, or only a portion of a gene or coding sequence), or may not contain any identifiable gene expression elements or any actively transcribed gene sequence. An insertion sequence of a donor template provided herein can comprise a transcribable DNA sequence that can be transcribed into an RNA molecule, which can be non-coding and may or may not be operably linked to a promoter and/or other regulatory sequence.

As used herein, the term "guide RNA" or "gRNA" is a short RNA sequence comprising (1) a structural or scaffold RNA sequence necessary for binding or interacting with an RNA-guided nuclease and/or with other RNA molecules (e.g., tracrRNA), and (2) an RNA sequence (referred to herein as a "guide sequence") that is identical or complementary to a target sequence or a target site. A "single-chain guide RNA" (or "sgRNA") is a RNA molecule comprising a crRNA covalently linked a tracrRNA by a linker sequence, which can be expressed as a single RNA transcript or molecule. The guide RNA comprises a guide or targeting sequence (a "guide sequence") that is identical or complementary to a target site within the plant genome, such as at or near a GA oxidase gene. A protospacer-adjacent motif (PAM) can be present in the genome immediately adjacent and upstream to the 5' end of the genomic target site sequence complementary to the targeting sequence of the guide RNA—i.e., immediately downstream (3') to the sense (+) strand of the genomic target site (relative to the targeting sequence of the guide RNA) as known in the art. The genomic PAM sequence on the sense (+) strand adjacent to the target site (relative to the targeting sequence of the guide RNA) can comprise 5'-NGG-3'. However, the corresponding sequence of the guide RNA (i.e., immediately downstream (3') to the targeting sequence of the guide RNA) can generally not be complementary to the genomic PAM sequence. The guide RNA can typically be a non-coding RNA molecule that does not encode a protein.

As used herein, an "RNA-guided nuclease" refers to an RNA-guided DNA endonuclease associated with the CRISPR system. Non-limiting examples of RNA-guided nucleases include Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, Cpf1, homologs thereof, or modified versions thereof. In an aspect, the RNA-guided nuclease is Cas9. In an aspect, the RNA-guided nuclease comprises the N and C terminal nuclear localization sequences (NLS).

Description

The present disclosure provides certain stacked combinations of transgenes and/or mutations or edits in corn plants, plant parts, etc., comprising a transgene that encodes one or more CONTANS (CO) or CONSTANS-like (COL) polypeptides, such as *Physcomitrella patens* CONSTANS-like 1 (PpCOL1), in addition to a reduction in the expression level of one or more GA20 and/or GA3 oxidase genes through suppression, mutation and/or editing of the GA oxidase genes, wherein the corn plants have a semi-dwarf phenotype and one or more improved traits related to yield, lodging resistance, and/or stress tolerance. As described in co-pending PCT Application No. PCT/US2017/047405, the entire contents and disclosure of which are incorporated herein by reference, reducing the level of active GAs in corn or other cereal plants, such as through suppression, mutation or editing of one or more GA20 and/or GA3 oxidase genes, can result in a semi-dwarf phenotype with improved agronomic traits, such as lodging resistance and/or increased yield. However, it is proposed herein that lower active GA levels can be combined with an expression cassette or transgene encoding a CONTANS (CO) or CONSTANS-like (COL) protein, such as PpCOL1, to produce a semi-dwarf corn plant having positive ear traits leading to further increased yield, thus providing greater agronomic benefits than either CO/COL expression or lower active GA levels alone.

Gibberellins (gibberellic acids or GAs) are plant hormones that regulate a number of major plant growth and developmental processes. Manipulation of GA levels in semi-dwarf wheat, rice and sorghum plant varieties led to increased yield and reduced lodging in these cereal crops during the 20th century, which was largely responsible for the Green Revolution. However, successful yield gains in other cereal crops, such as corn, have not been realized through manipulation of the GA pathway. Corn or maize is unique among the grain-producing grasses in that it forms separate male (tassel) and female (ear) inflorescences, and mutations in the GA pathway in corn have been shown to negatively impact reproductive development. Indeed, some mutations in the GA pathway genes in corn have been associated with various off-types that are incompatible with yield, which has led researchers away from finding semi-dwarf, high-yielding corn varieties via manipulation of the GA pathway.

Despite these prior difficulties in achieving higher grain yields in corn through manipulation of the GA pathway, co-pending PCT Application No. PCT/US2017/047405 describes a way to manipulate active GA levels in corn plants in a manner that reduces overall plant height and stem internode length and increases resistance to lodging, but does not cause the reproductive off-types previously associated with mutations of the GA pathway in corn. Further evidence indicates that these short stature or semi-dwarf corn plants with reduced GA levels can also have one or more additional yield and/or stress tolerance traits, including increased stem diameter, reduced green snap, deeper roots, increased leaf area, earlier canopy closure, higher stomatal conductance, lower ear height, increased foliar water content, improved drought tolerance, increased nitrogen use efficiency, increased water use efficiency, reduced anthocyanin content and area in leaves under normal or nitrogen or water limiting stress conditions, increased ear weight, increased kernel number, increased kernel weight, increased yield, and/or increased harvest index.

Active or bioactive gibberellic acids (i.e., "active gibberellins" or "active GAs") are known in the art for a given plant species, as distinguished from inactive GAs. For example, active GAs in corn and higher plants include the following: GA1, GA3, GA4, and GA7. Thus, an "active GA-producing tissue" is a plant tissue that produces one or more active GAs.

Certain biosynthetic enzymes (e.g., GA20 oxidase and GA3 oxidase) and catabolic enzymes (e.g., GA2 oxidase) in the GA pathway participate in GA synthesis and degradation, respectively, to affect active GA levels in plant tissues. Thus, in addition to suppression of certain GA20 oxidase genes, it is further proposed that suppression of a GA3 oxidase gene in a constitutive or tissue-specific or tissue-preferred manner can also produce corn plants having a short stature phenotype and increased lodging resistance, with possible increased yield, but without off-types in the ear.

Without being bound by theory, it is proposed that incomplete suppression of GA20 or GA3 oxidase gene(s) and/or targeting of a subset of one or more GA oxidase gene(s) can be effective in achieving a short stature, semi-dwarf phenotype with increased resistance to lodging, but without reproductive off-types in the ear. It is further proposed, without being limited by theory, that restricting the suppression of GA20 and/or GA3 oxidase gene(s) to certain active GA-producing tissues, such as the vascular and/or leaf tissues of the plant, can be sufficient to produce a short-stature plant with increased lodging resistance, but without significant off-types in reproductive tissues. Expression of a GA20 or GA3 oxidase suppression element in a tissue-specific or tissue-preferred manner can be sufficient and effective at producing plants with the short stature phenotype, while avoiding potential off-types in reproductive tissues that were previously observed with GA mutants in corn (e.g., by avoiding or limiting the suppression of the GA20 oxidase gene(s) in those reproductive tissues). For example, GA20 and/or GA3 oxidase gene(s) can be targeted for suppression using a vascular promoter, such as a rice tungro bacilliform virus (RTBV) promoter, that drives expression in vascular tissues of plants. The expression pattern of the RTBV promoter is enriched in vascular tissues of corn plants relative to non-vascular tissues, which is sufficient to produce a semi-dwarf phenotype in corn plants when operably linked to a suppression element targeting GA20 and GA3 oxidase gene(s). Lowering of active GA levels in tissue(s) of a corn plant that produce active GAs can reduce plant height and increase lodging resistance, and off-types can be avoided in those plants if active GA levels are not also significantly impacted or lowered in reproductive tissues, such as the developing female organ or ear of the plant. If active GA levels could be reduced in the stalk, stem, or internode(s) of corn or cereal plants without significantly affecting GA levels in reproductive tissues (e.g., the female or male reproductive organs or inflorescences), then corn or cereal plants having reduced plant height and increased lodging resistance could be created without off-types in the reproductive tissues of the plant.

Without being limited by theory, it is further proposed that short stature, semi-dwarf phenotypes in corn plants can result from a sufficient level of expression of a suppression construct targeting certain GA oxidase gene(s) in active GA-producing tissue(s) of the plant. For targeted suppression of certain GA20 oxidase genes in corn, restricting the pattern of expression to avoid reproductive ear tissues may not be necessary to avoid reproductive off-types in the developing ear. However, expression of a GA20 oxidase suppression construct at low levels, and/or in a limited number of plant tissues, can be insufficient to cause a significant short stature, semi-dwarf phenotype. Given that the observed semi-dwarf phenotype with targeted GA20 oxidase suppression is the result of shortening the stem internodes of the plant, it was surprisingly found that suppression of GA20 oxidase genes in at least some stem tissues was not sufficient to cause shortening of the internodes and reduced plant height. Without being bound by theory, it is proposed that suppression of certain GA oxidase gene(s) in tissue(s) and/or cell(s) of the plant where active GAs are produced, and not necessarily in stem or internode tissue(s), can be sufficient to produce semi-dwarf plants, even though the short stature trait is due to shortening of the stem internodes. Given that GAs can migrate through the vasculature of the plant, manipulating GA oxidase genes in plant tissue(s) where active GAs are produced can result in a short stature, semi-dwarf plant, even though this can be largely achieved by suppressing the level of active GAs produced in non-stem tissues (i.e., away from the site of action in the stem where reduced internode elongation leads to the semi-dwarf phenotype). Indeed, suppression of certain GA20 oxidase genes in leaf tissues causes a moderate semi-dwarf phenotype in corn plants. Given that expression of a GA20 oxidase suppression construct with several different "stem" promoters did not produce the semi-dwarf phenotype in corn, it is noteworthy that expression of the same GA20 oxidase suppression construct with a vascular promoter was effective at consistently producing the semi-dwarf phenotype with a high degree of penetrance across events and germplasms. A semi-dwarf phenotype was also observed with expression of the same GA20 oxidase suppression construct using other vascular promoters and with various constitutive promoters without any observable off-types.

By targeting a subset of one or more endogenous GA3 or GA20 oxidase genes for suppression within a plant, a more pervasive pattern of expression (e.g., with a constitutive promoter) can be used to produce semi-dwarf plants without significant reproductive off-types and/or other undesirable traits in the plant, even with expression of the suppression construct in reproductive tissue(s). Indeed, suppression elements and constructs are provided herein that selectively target the GA20 oxidase_3 and/or GA20 oxidase_5 genes for suppression, which can be operably linked to a vascular, leaf and/or constitutive promoter.

Thus, recombinant DNA constructs and modified corn plants are provided herein comprising a GA20 or GA3 oxidase suppression element or sequence operably linked to a plant expressible promoter, which can be a constitutive or tissue-specific or tissue-preferred promoter. Such a tissue-specific or tissue-preferred promoter can drive expression of its associated GA oxidase suppression element or sequence in one or more active GA-producing tissue(s) of the plant to suppress or reduce the level of active GAs produced in those tissue(s). Such a tissue-specific or tissue-preferred promoter can drive expression of its associated GA oxidase suppression construct or transgene during one or more vegetative stage(s) of development. Such a tissue-specific or tissue-preferred promoter can also have little or no expression in one or more cell(s) or tissue(s) of the developing female organ or ear of the plant to avoid the possibility of off-types in those reproductive tissues. According to an aspect, the tissue-specific or tissue-preferred promoter is a vascular promoter, such as the RTBV promoter. The sequence of the RTBV promoter is provided herein as SEQ ID NO: 65, and a truncated version of the RTBV promoter is further provided herein as SEQ ID NO: 66. However, other types of tissue-specific or tissue preferred promoters can potentially be used for GA3 oxidase suppression in active GA-producing tissues of a corn or cereal plant to produce a semi-dwarf phenotype without significant off-types. As introduced above, instead of suppressing one or more GA oxidase gene(s), active GA levels can also be reduced in a corn plant by mutation or editing of one or more GA20 and/or GA3 oxidase gene(s).

Corn has a family of at least nine GA20 oxidase genes that includes GA20 oxidase_1, GA20 oxidase_2, GA20 oxidase_3, GA20 oxidase_4, GA20 oxidase_5, GA20 oxidase_6, GA20 oxidase_7, GA20 oxidase_8, and GA20 oxidase_9. However, there are only two GA3 oxidases in corn, GA3 oxidase_1 and GA3 oxidase_2. The DNA and protein sequences by SEQ ID NOs for each of these GA20 oxidase genes are provided in Table 1, and the DNA and protein sequences by SEQ ID NOs for each of these GA3 oxidase genes are provided in Table 2.

TABLE 1

DNA and protein sequences by sequence identifier for GA20 oxidase genes in corn.

| GA20 oxidase Gene | cDNA | Coding Sequence (CDS) | Protein |
|---|---|---|---|
| GA20 oxidase_1 | SEQ ID NO: 1 | SEQ ID NO: 2 | SEQ ID NO: 3 |
| GA20 oxidase_2 | SEQ ID NO: 4 | SEQ ID NO: 5 | SEQ ID NO: 6 |
| GA20 oxidase_3 | SEQ ID NO: 7 | SEQ ID NO: 8 | SEQ ID NO: 9 |
| GA20 oxidase_4 | SEQ ID NO: 10 | SEQ ID NO: 11 | SEQ ID NO: 12 |
| GA20 oxidase_5 | SEQ ID NO: 13 | SEQ ID NO: 14 | SEQ ID NO: 15 |
| GA20 oxidase_6 | SEQ ID NO: 16 | SEQ ID NO: 17 | SEQ ID NO: 18 |
| GA20 oxidase_7 | SEQ ID NO: 19 | SEQ ID NO: 20 | SEQ ID NO: 21 |
| GA20 oxidase_8 | SEQ ID NO: 22 | SEQ ID NO: 23 | SEQ ID NO: 24 |
| GA20 oxidase_9 | SEQ ID NO: 25 | SEQ ID NO: 26 | SEQ ID NO: 27 |

TABLE 2

DNA and protein sequences by sequence identifier for GA3 oxidase genes in corn.

| GA3 oxidase Gene | cDNA | Coding Sequence (CDS) | Protein |
|---|---|---|---|
| GA3 oxidase_1 | SEQ ID NO: 28 | SEQ ID NO: 29 | SEQ ID NO: 30 |
| GA3 oxidase_2 | SEQ ID NO: 31 | SEQ ID NO: 32 | SEQ ID NO: 33 |

In addition to lowering active GA levels in corn plants through suppression, mutation or editing of GA oxidase gene(s), such corn plants as provided herein can further comprise an ectopically expressed CONSTANS (CO) or CONSTANS-like (COL) transgene. CONSTANS (CO) and its paralogous CONSTANS-like (COL) polypeptides are transcriptional regulators of the photoperiodic control of flowering in plants. In *Arabidopsis*, the CO gene, when mutated, delayed the flowering under long days, which is the inductive condition for flowering in this species. See Putterill et al., "The CO gene of *Arabidopsis* promotes flowering and encodes a protein showing similarities to zinc finger transcription factors," *Cell*, 80: 847-857 (1995). While not being limited by any scientific theory, CO protein expression is believed to be modulated by the circadian clock and day length to control flowering. See Suarez-Lopez et al., "CONSTANS mediates between the circadian clock and the control of flowering in *Arabidopsis*," *Nature*, 410: 1116-1120 (2001).

CO and COL are both zinc-finger transcription factors with characteristic domains and are found in monocot and dicot plant species. The N-terminal part of CO and COL proteins typically contain one or two tandem Zn finger domain(s), which are also called B-boxes involved in protein-protein interaction, and a C-terminal CCT (CO, CO-like, TOC1) domain, which can also include a nuclear import signal. See Khanna et al., "The *Arabidopsis* B-box zinc finger family," *Plant Cell*, 21:3416-3420 (2009); see also Robson et al., "Functional importance of conserved domains in the flowering-time gene CONSTANS demonstrated by analysis of mutant alleles and transgenic plants," *Plant J.*, 28:619-631 (2001). In addition to one or two B-boxes and the CCT domain, the CO and COL proteins can also contain a conserved six-amino acid motif (G-I/V-V-P-S/T-F) in their C-termini. See Datta et al., "*Arabidopsis* CONSTANS-LIKE3 is a positive regulator of red light signaling and root growth," *Plant Cell*, 18: 70-84 (2006).

*Physcomitrella patens* CONSTANS-like 1 (PpCOL1) is a zinc finger transcription factor derived from the *Physcomitrella patens* moss species. The expression of PpCOL1 is shown to be photoperiodically regulated in this moss species, suggesting a role for PpCOL1 in the photoperiodic control of reproduction. See Shimizu et al., "Photoperiod-regulated expression of the PpCOL1 gene encoding a homolog of CO/COL protein in the moss *Physcomitrella patens*,". *Biochem. Biophys. Res. Commun.*, 324:1296-1301 (2004). Transgenic expression of PpCOL1 in corn plants has been shown to improve drought, salt, and/or cold tolerance. See U.S. Pat. No. 7,439,417. Transgenic expression of the PpCOL1 gene in corn plants also improves ear traits or metrics, such as single kernel weight, ear area, ear size, ear weight, and grain yield estimate.

The CONSTANS (CO) or CONSTANS-like (COL) transgene can comprise a coding sequence of any known CO or COL gene expected to have a similar function to PpCOL1. The CO/COL transgene can be a Group I, Group II, or Group III CONSTANS (CO) or CONSTANS-like (COL) gene. See, e.g., Cal, D et al., "Identification and characterization of CONSTANS-like (COL) gene family in upland cotton (*Gossypium hirsutum*)", PLOS ONE 12(6): e0179038, the entire contents and disclosure of which are incorporated by reference. The CO/COL transgene can comprise one or two B-box domain(s), a CCT domain, and possibly an additional VP motif and/or a diverged zinc-finger. See also, e.g., Khanna et al., "The *Arabidopsis* B-Box Zinc Finger Family," *Plant Cell* 21(11): 3416-3420 (2009), the entire contents and disclosure of which are incorporated by reference. In an aspect, a CO or COL polypeptide of the present disclosure is a *Physcomitrella patens* COL (PpCOL) polypeptide or homologs, orthologs, and/or paralogs thereof. In an aspect, a CO or COL polynucleotide provided herein comprises an amino acid sequence comprising SEQ ID NOs: 168, and homologs, orthologs, and paralogs thereof. In another aspect, a CO or COL polynucleotide provided herein comprises an amino acid sequence selected from the group consisting of SEQ ID NOs: 176-452, and homologs, orthologs, and paralogs thereof.

According to an aspect, a modified corn plant or plant part is provided comprising (1) a first expression cassette comprising a transcribable DNA sequence encoding a non-coding RNA for suppression of one or more GA20 oxidase genes and/or one or more GA3 oxidase genes, and (2) a second expression cassette comprising a DNA sequence encoding a CONSTANS (CO) or CONSTANS-like (COL) polypeptide. Alternatively, a modified corn plant or plant part is provided comprising (1) one or more mutated or edited GA20 oxidase genes and/or one or more mutated or edited GA3 oxidase genes, and (2) an expression cassette comprising a DNA sequence encoding a CONSTANS (CO) or CONSTANS-like (COL) polypeptide.

According to another aspect, a modified corn plant or a plant part thereof is provided comprising 1) a first recombinant expression cassette (or a construct) comprising a transcribable DNA sequence encoding a non-coding RNA for suppression of one or more gibberellic acid 20 (GA20) oxidase genes and/or one or more gibberellic acid 3 (GA3) oxidase genes, and 2) a second recombinant expression cassette (or a construct) comprising a DNA sequence encoding a CONSTANS (CO) or CONSTANS-like (COL) polypeptide.

According to another aspect, a plurality of modified corn plants in a field, each modified corn plant comprising 1) a first recombinant expression cassette comprising a transcribable DNA sequence encoding a non-coding RNA for suppression of one or more gibberellic acid 20 (GA20) oxidase genes and/or one or more gibberellic acid 3 (GA3) oxidase genes, and 2) a second recombinant expression cassette comprising a DNA sequence encoding a CONSTANS (CO) or CONSTANS-like (COL) polypeptide. In an aspect, the modified corn plants have increased yield relative to control corn plants. In another aspect, the modified corn plants have an increase in yield that is at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, or at least 25% greater than control corn plants.

Such modified corn plants can have semi-dwarf plant height in addition to one or more improved yield-related traits as described further herein, relative to control corn plant(s) that do not have the first and second expression cassettes or the combination of CO/COL transgene and edited/mutated GA oxidase gene(s). Modified corn plants comprising a combination of the first and second expression cassettes, or a combination of an expression cassette comprising a CO or COL transgene and one or more mutated or edited GA oxidase genes, can each be referred to as a "stack" or "stacked" combination. Such stacked combinations for the reduction of active GA levels and expression of a CO/COL transgene can be brought together in the same corn plant, or population of corn plants, by (1) crossing a first plant comprising a GA oxidase suppression element(s), edit(s) and/or mutation(s) to a second plant comprising a CO/COL transgene, (2) co-transformation of a plant or plant part with a GA oxidase suppression element(s) and a CO/COL transgene, (3) transformation of a plant or plant part already having a GA oxidase suppression element(s), edit(s) and/or mutation(s) with a CO/COL transgene, (4) transformation of a plant or plant part already having a CO/COL transgene with a GA oxidase suppression element(s), or (5) editing or mutating a GA oxidase gene(s) in a plant or plant part already having a CO/COL transgene, each of which can be followed by further crosses to obtain a desired genotype, plant parts can be regenerated, grown or developed into plants, and plant parts can be taken from any of the foregoing plants.

As provided above, a corn plant or plant part can comprise a first expression cassette comprising a first sequence encoding a non-coding RNA molecule that targets one or more GA20 or GA3 oxidase gene(s) for suppression. In an aspect, the non-coding RNA molecule can target one or more GA20 oxidase gene(s) for suppression, such as a GA20 oxidase_3 gene, a GA20 oxidase_4 gene, a GA20 oxidase_5 gene, or any combination thereof. According to an aspect, the first expression cassette comprises a first transcribable DNA sequence encoding a non-coding RNA targeting a GA20 oxidase_3 gene for suppression. According to another aspect, the first expression cassette comprises a first transcribable DNA sequence encoding a non-coding RNA targeting a GA20 oxidase_5 gene for suppression. According to another aspect, the first expression cassette comprises a first transcribable DNA sequence encoding a non-coding RNA that targets both the GA20 oxidase_3 gene and the GA20 oxidase_5 gene for suppression. In addition to targeting a mature mRNA sequence (including either or both of the untranslated or exonic sequences), a non-coding RNA molecule can also target the intronic sequences of a GA20 oxidase gene or transcript.

A genomic DNA sequence of GA20 oxidase_3 is provided in SEQ ID NO: 34, and the genomic DNA sequence of GA20 oxidase_5 is provided in SEQ ID NO: 35. For the GA20 oxidase_3 gene, SEQ ID NO: 34 provides 3000 nucleotides upstream of the GA20 oxidase_3 5'-UTR; nucleotides 3001-3096 correspond to the 5'-UTR; nucleotides 3097-3665 correspond to the first exon; nucleotides 3666-3775 correspond to the first intron; nucleotides 3776-4097 correspond to the second exon; nucleotides 4098-5314 correspond to the second intron; nucleotides 5315-5584 correspond to the third exon; and nucleotides 5585-5800 correspond to the 3'-UTR. SEQ ID NO: 34 also provides 3000 nucleotides downstream of the end of the 3'-UTR (nucleotides 5801-8800). For the GA20 oxidase_5 gene, SEQ ID NO: 35 provides 3000 nucleotides upstream of the GA20 oxidase_5 start codon (nucleotides 1-3000); nucleotides 3001-3791 correspond to the first exon; nucleotides 3792-3906 correspond to the first intron; nucleotides 3907-4475 correspond to the second exon; nucleotides 4476-5197 correspond to the second intron; nucleotides 5198-5473 correspond to the third exon; and nucleotides 5474-5859 correspond to the 3'-UTR. SEQ ID NO: 35 also provides 3000 nucleotides downstream of the end of the 3'-UTR (nucleotides 5860-8859).

A genomic DNA sequence of GA20 oxidase_4 is provided in SEQ ID NO: 38. For the GA oxidase_4 gene, SEQ ID NO: 38 provides nucleotides 1-1416 upstream of the 5'-UTR; nucleotides 1417-1543 of SEQ ID NO: 38 correspond to the 5'-UTR; nucleotides 1544-1995 of SEQ ID NO: 38 correspond to the first exon; nucleotides 1996-2083 of SEQ ID NO: 38 correspond to the first intron; nucleotides 2084-2411 of SEQ ID NO: 38 correspond to the second exon; nucleotides 2412-2516 of SEQ ID NO: 38 correspond to the second intron; nucleotides 2517-2852 of SEQ ID NO: 38 correspond to the third exon; nucleotides 2853-3066 of SEQ ID NO: 38 correspond to the 3'-UTR; and nucleotides 3067-4465 of SEQ ID NO: 38 corresponds to genomic sequence downstream of to the 3'-UTR.

For the GA20 oxidase_5 gene, SEQ ID NO: 35 provides 3000 nucleotides upstream of the GA20 oxidase_5 start codon (nucleotides 1-3000); nucleotides 3001-3791 correspond to the first exon; nucleotides 3792-3906 correspond to the first intron; nucleotides 3907-4475 correspond to the second exon; nucleotides 4476-5197 correspond to the second intron; nucleotides 5198-5473 correspond to the third exon; and nucleotides 5474-5859 correspond to the 3'-UTR. SEQ ID NO: 35 also provides 3000 nucleotides downstream of the end of the 3'-UTR (nucleotides 5860-8859).

For suppression of a GA20 oxidase_3 gene, a first transcribable DNA sequence comprises a sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical or complementary to at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, or at least 60 consecutive nucleotides of a sequence as set forth in SEQ ID NOs: 7 and 8.

For suppression of a GA20 oxidase_4 gene, a first transcribable DNA sequence comprises a sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical or complementary to at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, or at least 60 consecutive nucleotides of a sequence as set forth in SEQ ID NOs: 10 and 11.

For suppression of a GA20 oxidase_5 gene, a first transcribable DNA sequence comprises a sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical or complementary to at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, or at least 60 consecutive nucleotides of a sequence as set forth in SEQ ID NOs: 13 and 14.

For suppression of a GA20 oxidase_3 gene and a GA20 oxidase_5 gene, a transcribable DNA sequence comprises a sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical or complementary to at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, or at least 60 consecutive nucleotides of a sequence as set forth in SEQ ID NOs: 7 and 8; and the transcribable DNA sequence comprises a sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical or complementary to at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, or at least 60 consecutive nucleotides of a sequence as set forth in SEQ ID NOs: 13 and 14.

In an aspect, a non-coding RNA molecule encoded by a transcribable DNA sequence comprises (i) a sequence that is at least 95%, at least 96%, at least 97%, at least 98%, at least 99%, at least 99.5%, or 100% complementary to SEQ ID NO: 39, 41, 43 or 45, and/or (ii) a sequence or suppression element encoding a non-coding RNA molecule comprising a sequence that is at least 95%, at least 96%, at least 97%, at least 98%, at least 99%, at least 99.5%, or 100% identical to SEQ ID NO: 40, 42, 44 or 46. According to an aspect, the non-coding RNA molecule encoded by a transcribable DNA sequence can comprise a sequence with one or more mismatches, such as 1, 2, 3, 4, 5 or more complementary mismatches, relative to the sequence of a target or recognition site of a targeted GA20 oxidase gene mRNA, such as a sequence that is nearly complementary to SEQ ID NO: 40 but with one or more complementary mismatches relative to SEQ ID NO: 40. According to a particular aspect, the non-coding RNA molecule encoded by the transcribable DNA sequence comprises a sequence that is 100% identical to SEQ ID NO: 40, which is 100% complementary to a target sequence within the cDNA and coding sequences of the GA20 oxidase_3 (i.e., SEQ ID NOs: 7 and 8, respectively), and/or to a corresponding sequence of a mRNA encoded by an endogenous GA20 oxidase_3 gene. However, the sequence of a non-coding RNA molecule encoded by a transcribable DNA sequence that is 100% identical to SEQ ID NO: 40, 42, 44 or 46 may not be perfectly complementary to a target sequence within the cDNA and coding sequences of the GA20 oxidase_5 gene (i.e., SEQ ID NOs: 13 and 14, respectively), and/or to a corresponding sequence of a mRNA encoded by an endogenous GA20 oxidase_5 gene. For example, the closest complementary match between the non-coding RNA molecule or miRNA sequence in SEQ ID NO: 40 and the cDNA and coding sequences of the GA20 oxidase_5 gene can include one mismatch at the first position of SEQ ID NO: 39 (i.e., the "C" at the first position of SEQ ID NO: 39 is replaced with a "G"; i.e., GTCCATCATGCGGTGCAACTA). However, the non-coding RNA molecule or miRNA sequence in SEQ ID NO: 40 can still bind and hybridize to the mRNA encoded by the endogenous GA20 oxidase_5 gene despite this slight mismatch.

For suppression of a GA20 oxidase_1 gene, a first transcribable DNA sequence comprises a sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical or complementary to at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, or at least 60 consecutive nucleotides of a sequence as set forth in SEQ ID NOs: 1 and 2.

For suppression of a GA20 oxidase_2 gene, a first transcribable DNA sequence comprises a sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical or complementary to at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, or at least 60 consecutive nucleotides of a sequence as set forth in SEQ ID NOs: 4 and 5.

For suppression of a GA2 oxidase 6, a first transcribable DNA sequence comprises a sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical or complementary to at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, or at least 60 consecutive nucleotides of a sequence as set forth in SEQ ID NOs: 16 and 17.

For suppression of a GA20 oxidase 7 gene, a first transcribable DNA sequence comprises a sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical or complementary to at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, or at least 60 consecutive nucleotides of a sequence as set forth in SEQ ID NOs: 19 and 20.

For suppression of a GA20 oxidase_8 gene, a first transcribable DNA sequence comprises a sequence that is at least at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical or complementary to at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, or at least 60 consecutive nucleotides of a sequence as set forth in SEQ ID NOs: 22 and 23.

For suppression of a GA20 oxidase_9 gene, a first transcribable DNA sequence comprises a sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical or complementary to at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, or at least 60 consecutive nucleotides of a sequence as set forth in SEQ ID NOs: 25 and 26.

A non-coding RNA can target an intron sequence of a GA20 oxidase gene instead of, or in addition to, an exonic, 5' UTR or 3' UTR of the GA20 oxidase gene. Thus, a non-coding RNA targeting the GA20 oxidase_3 gene for suppression can comprise a sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of SEQ ID NO: 34, and/or of nucleotides 3666-3775 or 4098-5314 of SEQ ID NO: 34.

In another aspect, a non-coding RNA molecule targeting the GA20 oxidase_5 gene for suppression can comprise a sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of SEQ ID NO: 35, and/or of nucleotides 3792-3906 or 4476-5197 of SEQ ID NO: 35.

In another aspect, a non-coding RNA molecule targeting the GA20 oxidase_4 gene for suppression can comprise a sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of SEQ ID NO: 38, and/or of nucleotides 1996-2083 or 2412-2516 of SEQ ID NO: 38.

In another aspect, a first expression cassette comprises a first transcribable DNA sequence encoding a non-coding RNA targeting a GA3 oxidase gene(s) for suppression in corn, such as a GA3 oxidase_1 gene or a GA3 oxidase_2 gene. In another aspect, a first transcribable DNA sequence encoding a non-coding RNA targets both the GA3 oxidase_1 gene and the GA3 oxidase_2 gene for suppression. In addition to targeting a mature mRNA sequence (including either or both of the untranslated or exonic sequences), a non-coding RNA molecule can also target the intronic sequences of a GA3 oxidase gene or transcript.

The genomic DNA sequence of GA3 oxidase_1 is provided in SEQ ID NO: 36, and the genomic DNA sequence of GA3 oxidase_2 is provided in SEQ ID NO: 37. For the GA3 oxidase_1 gene, nucleotides 1-29 of SEQ ID NO: 36 correspond to the 5'-UTR; nucleotides 30-514 of SEQ ID NO: 36 correspond to the first exon; nucleotides 515-879 of SEQ ID NO: 36 correspond to the first intron; nucleotides 880-1038 of SEQ ID NO: 36 correspond to the second exon; nucleotides 1039-1158 of SEQ ID NO: 36 correspond to the second intron; nucleotides 1159-1663 of SEQ ID NO: 36 correspond to the third exon; and nucleotides 1664-1788 of SEQ ID NO: 36 correspond to the 3'-UTR. For the GA3 oxidase_2 gene, nucleotides 1-38 of SEQ ID NO: 37 correspond to the 5-UTR; nucleotides 39-532 of SEQ ID NO: 37 correspond to the first exon; nucleotides 533-692 of SEQ ID NO: 37 correspond to the first intron; nucleotides 693-851 of SEQ ID NO: 37 correspond to the second exon; nucleotides 852-982 of SEQ ID NO: 37 correspond to the second intron; nucleotides 983-1445 of SEQ ID NO: 37 correspond to the third exon; and nucleotides 1446-1698 of SEQ ID NO: 37 correspond to the 3'-UTR.

For suppression of a GA3 oxidase_1 gene, a first transcribable DNA sequence comprises a sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical or complementary to at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, or at least 60 consecutive nucleotides of a sequence as set forth in SEQ ID NOs: 28 and 29.

As mentioned above, a non-coding RNA molecule can target an intron sequence of a GA3 oxidase gene instead of, or in addition to, an exonic, 5' UTR or 3' UTR of the GA oxidase gene. Thus, a non-coding RNA molecule targeting the GA3 oxidase_1 gene for suppression can comprise a sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of SEQ ID NO: 36, and/or of nucleotides 515-879 or 1039-1158 of SEQ ID NO: 36.

For suppression of a GA3 oxidase_2 gene, a first transcribable DNA sequence comprises a sequence that is at least at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical or complementary to at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, or at least 60 consecutive nucleotides of a sequence as set forth in SEQ ID NOs: 31 and 32.

As mentioned above, a non-coding RNA molecule can target an intron sequence of a GA3 oxidase gene instead of, or in addition to, an exonic, 5' UTR or 3' UTR of the GA3 oxidase gene. Thus, a non-coding RNA molecule targeting the GA3 oxidase_2 gene for suppression can comprise a sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of SEQ ID NO: 37, and/or of nucleotides 533-692 or 852-982 of SEQ ID NO: 37.

For suppression of a GA3 oxidase_1 gene and a GA3 oxidase_2 gene, a transcribable DNA sequence comprises a sequence that is at least at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical or complementary to at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, or at least 60 consecutive nucleotides of a sequence as set forth in SEQ ID NOs: 28 and 29; and the transcribable DNA sequence comprises a sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical or complementary to at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, or at least 60 consecutive nucleotides of a sequence as set forth in SEQ ID NOs: 31 and 32.

In an aspect, a transcribable DNA sequence for the suppression of a GA20 oxidase gene and/or a GA3 oxidase comprises a sequence selected from the group consisting of SEQ ID NOs: 47, 49, 51, 53, 55, 57, 59, 61, and 63. In another aspect, a transcribable DNA sequence for the suppression of a GA20 oxidase gene and/or a GA3 oxidase encodes a non-coding RNA sequence, wherein the non-coding RNA sequence comprises a sequence selected from the group consisting of SEQ ID NOs: 48, 50, 52, 54, 56, 58, 60, 62, and 64.

In an aspect, an expression cassette is provided comprising a second DNA sequence encoding a CO or COL polypeptide. In another aspect, the second DNA sequence encodes a protein that comprises a sequence that is at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to an amino acid sequence selected from the group consisting of SEQ ID NOs: 176-397. In another aspect, the second DNA sequence encodes a protein that comprises a sequence that is at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to an amino acid sequence selected from the group consisting of SEQ ID NOs: 398-452. The second DNA sequence encoding a CO or COL polypeptide is operatively linked to a constitutive or tissue-specific promoter.

In an aspect, an expression cassette is provided comprising a second DNA sequence encoding PpCOL1. In another aspect, the second DNA sequence comprises a sequence that is at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to a sequence selected from the group consisting of SEQ ID NO: 169. In another aspect, the second DNA sequence comprises a sequence encoding a polypeptide that is at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 168, or a functional fragment thereof.

In addition to targeting a mature mRNA sequence, a non-coding RNA molecule can instead target an intronic sequence of a GA oxidase gene or mRNA transcript, or a GA oxidase mRNA sequence overlapping coding and non-coding sequences. According to other aspects, a recombinant DNA molecule, vector or construct is provided comprising a transcribable DNA sequence encoding a non-coding RNA (precursor) molecule that is cleaved or processed into a mature non-coding RNA molecule that binds or hybridizes to a target mRNA in a plant cell, wherein the target mRNA molecule encodes a GA20 or GA3 oxidase protein, and wherein the transcribable DNA sequence is operably linked to a constitutive or tissue-specific or tissue-preferred promoter.

Any method known in the art for suppression of a target gene can be used to suppress GA oxidase gene(s) according to aspects of the present disclosure including expression of antisense RNAs, double stranded RNAs (dsRNAs) or inverted repeat RNA sequences, or via co-suppression or RNA interference (RNAi) through expression of small interfering RNAs (siRNAs), short hairpin RNAs (shRNAs), trans-acting siRNAs (ta-siRNAs), or micro RNAs (miRNAs). Furthermore, sense and/or antisense RNA molecules can be used that target the non-coding genomic sequences or regions within or near a gene to cause silencing of the gene. Accordingly, any of these methods can be used for the targeted suppression of an endogenous GA oxidase gene(s) in a tissue-specific or tissue-preferred manner. See, e.g., U.S. Patent Application Publication Nos. 2009/0070898, 2011/0296555, and 2011/0035839, the contents and disclosures of which are incorporated herein by reference.

In an aspect, an expression level(s) of one or more endogenous GA20 oxidase and/or GA3 oxidase gene(s) is/are reduced or eliminated in the modified corn plant, thereby suppressing the endogenous GA20 oxidase and/or GA3 oxidase gene(s).

According to an aspect, a modified or transgenic plant is provided having the expression level(s) of one or more GA20 oxidase gene(s) reduced in at least one plant tissue by at least 5%, at least 10%, at least 20%, at least 25%, at least 30%, at least 40%, at least 50%, at least 60%, at least 70%, at least 75%, at least 80%, at least 90%, or 100%, as compared to a control plant.

According to an aspect, a modified or transgenic plant is provided having the expression level(s) of one or more GA3 oxidase gene(s) reduced in at least one plant tissue by at least 5%, at least 10%, at least 20%, at least 25%, at least 30%, at least 40%, at least 50%, at least 60%, at least 70%, at least 75%, at least 80%, at least 90%, or 100%, as compared to a control plant.

According to an aspect, a modified or transgenic plant is provided having the expression level(s) of one or more GA20 oxidase gene(s) reduced in at least one plant tissue by 5%-20%, 5%-25%, 5%-30%, 5%-40%, 5%-50%, 5%-60%, 5%-70%, 5%-75%, 5%-80%, 5%-90%, 5%-100%, 75%-100%, 50%-100%, 50%-90%, 50%-75%, 25%-75%, 30%-80%, or 10%-75%, as compared to a control plant.

According to an aspect, a modified or transgenic plant is provided having the expression level(s) of one or more GA3 oxidase gene(s) reduced in at least one plant tissue by 5%-20%, 5%-25%, 5%-30%, 5%-40%, 5%-50%, 5%-60%, 5%-70%, 5%-75%, 5%-80%, 5%-90%, 5%-100%, 75%-100%, 50%-100%, 50%-90%, 50%-75%., 25%-75%, 30%-80%, or 10%-75%, as compared to a control plant.

According to an aspect, the at least one tissue of a modified or transgenic plant having a reduced expression level of a GA20 oxidase and/or GA3 oxidase gene(s) includes one or more active GA producing tissue(s) of the plant, such as the vascular and/or leaf tissue(s) of the plant, during one or more vegetative stage(s) of development.

In an aspect, the non-coding RNA is a precursor miRNA or siRNA capable of being processed or cleaved to form a mature miRNA or siRNA.

In an aspect, suppression of an endogenous GA20 oxidase gene or a GA3 oxidase gene is tissue-specific (e.g., only in leaf and/or vascular tissue). Suppression of a GA20 oxidase gene can be constitutive and/or vascular or leaf tissue specific or preferred. In other aspects, suppression of a GA20 oxidase gene or a GA3 oxidase gene is constitutive and not tissue-specific. According to an aspect, expression of an endogenous GA20 oxidase gene and/or a GA3 oxidase gene is reduced in one or more tissue types (e.g., in leaf and/or vascular tissue(s)) of a modified or transgenic plant as compared to the same tissue(s) of a control plant.

Engineered miRNAs can be useful for targeted gene suppression with increased specificity. See, e.g., Parizotto et al., *Genes Dev.* 18:2237-2242 (2004), and U.S. Patent Application Publication Nos. 2004/0053411, 2004/0268441, 2005/0144669, and 2005/0037988, the contents and disclosures of which are incorporated herein by reference. miRNAs are non-protein coding RNAs. When a miRNA precursor molecule is cleaved, a mature miRNA is formed that is typically from about 19 to about 25 nucleotides in length (commonly from about 20 to about 24 nucleotides in length in plants), such as 19, 20, 21, 22, 23, 24, or 25 nucleotides in length, and has a sequence corresponding to the gene targeted for suppression and/or its complement. Mature miRNA hybridizes to target mRNA transcripts and guides the binding of a complex of proteins to the target transcripts, which can function to inhibit translation and/or result in degradation of the transcript, thus negatively regulating or suppressing expression of the targeted gene. miRNA precursors are also useful in plants for directing in-phase production of siRNAs, trans-acting siRNAs (ta-siRNAs), in a process that requires a RNA-dependent RNA polymerase to cause suppression of a target gene. See, e.g., Allen et al., *Cell,* 121:207-221 (2005), Vaucheret, *Science STKE,* 2005: pe43 (2005), and Yoshikawa et al. *Genes Dev.,* 19:2164-2175 (2005), the contents and disclosures of which are incorporated herein by reference.

Without being limited by any scientific theory, plant miRNAs regulate their target genes by recognizing and binding to a complementary or near-perfectly complementary sequence (miRNA recognition site) in the target mRNA transcript, followed by cleavage of the transcript by RNase III enzymes, such as ARGONAUTE 1. In plants, certain mismatches between a given miRNA recognition site and the corresponding mature miRNA are typically not tolerated, particularly mismatched nucleotides at positions 10 and 11 of the mature miRNA. Positions within the mature miRNA are given in the 5' to 3' direction. Perfect complementarity between a given miRNA recognition site and the corresponding mature miRNA is usually required at positions 10 and 11 of the mature miRNA. See, for example, Franco-Zorrilla et al. (2007) *Nature Genetics,* 39:1033-1037; and Axtell et al. (2006) *Cell,* 127:565-577.

Many microRNA genes (MIR genes) have been identified and made publicly available in a database ("miRBase", available on line at microrna.sanger.ac.uk/sequences; also see Griffiths-Jones et al. (2003) *Nucleic Acids Res.,* 31:439-441). MIR genes have been reported to occur in intergenic regions, both isolated and in clusters in the genome, but can also be located entirely or partially within introns of other genes (both protein-coding and non-protein-coding). For a review of miRNA biogenesis, see Kim (2005) *Nature Rev. Mol. Cell. Biol.,* 6:376-385. Transcription of MIR genes can be, at least in some cases, under promotional control of a MIR gene's own promoter. The primary transcript, termed a "pri-miRNA", can be quite large (several kilobases) and can be polycistronic, containing one or more pre-miRNAs (foldback structures containing a stem-loop arrangement that is processed to the mature miRNA) as well as the usual 5' "cap" and polyadenylated tail of an mRNA. See, for example, FIG. 1 in Kim (2005) *Nature Rev. Mol. Cell. Biol.,* 6:376-385.

Transgenic expression of miRNAs (whether a naturally occurring sequence or an artificial sequence) can be employed to regulate expression of the miRNA's target gene or genes. Recognition sites of miRNAs have been validated in all regions of a mRNA, including the 5' untranslated region, coding region, intron region, and 3' untranslated region, indicating that the position of the miRNA target or recognition site relative to the coding sequence may not necessarily affect suppression (see, e.g., Jones-Rhoades and Bartel (2004). *Mol. Cell,* 14:787-799, Rhoades et al. (2002) *Cell,* 110:513-520, Allen et al. (2004) *Nat. Genet.,* 36:1282-1290, Sunkar and Zhu (2004) Plant Cell, 16:2001-2019). miRNAs are important regulatory elements in eukaryotes, and transgenic suppression with miRNAs is a useful tool for manipulating biological pathways and responses. A description of native miRNAs, their precursors, recognition sites, and promoters is provided in U.S. Patent Application Publication No. 2006/0200878, the contents and disclosures of which are incorporated herein by reference.

Designing an artificial miRNA sequence can be achieved by substituting nucleotides in the stem region of a miRNA precursor with a sequence that is complementary to the intended target, as demonstrated, for example, by Zeng et al. (2002) *Mol. Cell,* 9:1327-1333. According to many aspects, the target can be a sequence of a GA20 oxidase gene or a GA3 oxidase gene. One non-limiting example of a general method for determining nucleotide changes in a native miRNA sequence to produce an engineered miRNA precursor for a target of interest includes the following steps: (a)

selecting a unique target sequence of at least 18 nucleotides specific to the target gene, e.g., by using sequence alignment tools such as BLAST (see, for example, Altschul et al. (1990) *J. Mol. Biol.,* 215:403-410; Altschul et al. (1997) *Nucleic Acids Res.,* 25:3389-3402); cDNA and/or genomic DNA sequences can be used to identify target transcript orthologues and any potential matches to unrelated genes, thereby avoiding unintentional silencing or suppression of non-target sequences; (b) analyzing the target gene for undesirable sequences (e.g., matches to sequences from non-target species), and score each potential target sequence for GC content, Reynolds score (see Reynolds et al. (2004) *Nature Biotechnol.,* 22:326-330), and functional asymmetry characterized by a negative difference in free energy ("ΔΔG") (see Khvorova et al. (2003) *Cell,* 115:209-216). Preferably, target sequences (e.g., 19-mers) can be selected that have all or most of the following characteristics: (1) a Reynolds score >4, (2) a GC content between about 40% to about 60%, (3) a negative ΔΔG, (4) a terminal adenosine, (5) lack of a consecutive run of 4 or more of the same nucleotide; (6) a location near the 3' terminus of the target gene; (7) minimal differences from the miRNA precursor transcript. In an aspect, a non-coding RNA molecule used here to suppress a target gene (e.g., a GA20 or GA3 oxidase gene) is designed to have a target sequence exhibiting one or more, two or more, three or more, four or more, or five or more of the foregoing characteristics. Positions at every third nucleotide of a suppression element can be important in influencing RNAi efficacy; for example, an algorithm, "siExplorer" is publicly available at rna.chem.t.u-tokyo.ac.jp/siexplorer.htm (see Katoh and Suzuki (2007) *Nucleic Acids Res.,* 10.1093/nar/gk11120); (c) determining a reverse complement of the selected target sequence (e.g., 19-mer) to use in making a modified mature miRNA. Relative to a 19-mer sequence, an additional nucleotide at position 20 can be matched to the selected target or recognition sequence, and the nucleotide at position 21 can be chosen to either be unpaired to prevent spreading of silencing on the target transcript or paired to the target sequence to promote spreading of silencing on the target transcript; and (d) transforming the artificial miRNA into a plant.

Multiple sense and/or anti-sense suppression elements for more than one GA oxidase target can be arranged serially in tandem or arranged in tandem segments or repeats, such as tandem inverted repeats, which can also be interrupted by one or more spacer sequence(s), and the sequence of each suppression element can target one or more GA oxidase gene(s). Furthermore, a sense or anti-sense sequence of the suppression element may not be perfectly matched or complementary to the targeted GA oxidase gene sequence, depending on the sequence and length of the suppression element. Even shorter RNAi suppression elements from about 19 nucleotides to about 27 nucleotides in length can have one or more mismatches or non-complementary bases, yet still be effective at suppressing the target GA oxidase gene. Accordingly, a sense or anti-sense suppression element sequence can be at least 80%, at least 85%, at least 90%, at least 95%, at least 96%, at least 97%, at least 98%, at least 99%, at least 99.5% or 100% identical to a corresponding sequence of at least a segment or portion of the targeted GA oxidase gene, or its complementary sequence, respectively.

For suppression of GA oxidase gene(s) using an inverted repeat or a transcribed dsRNA, a transcribable DNA sequence or suppression element can comprise a sense sequence that comprises a segment or portion of a targeted GA oxidase gene and an anti-sense sequence that is complementary to a segment or portion of the targeted GA oxidase gene, where the sense and anti-sense DNA sequences are arranged in tandem. The sense and/or anti-sense sequences, respectively, can each be less than 100% identical or complementary to a segment or portion of the targeted GA oxidase gene as described above. A sense and anti-sense sequences can be separated by a spacer sequence, such that the RNA molecule transcribed from the suppression element forms a stem, loop or stem-loop structure between the sense and anti-sense sequences. A suppression element can instead comprise multiple sense and anti-sense sequences that are arranged in tandem, which can also be separated by one or more spacer sequences. Suppression elements comprising multiple sense and anti-sense sequences can be arranged as a series of sense sequences followed by a series of anti-sense sequences, or as a series of tandemly arranged sense and anti-sense sequences. Alternatively, one or more sense DNA sequences can be expressed separately from the one or more anti-sense sequences (i.e., one or more sense DNA sequences can be expressed from a first transcribable DNA sequence, and one or more anti-sense DNA sequences can be expressed from a second transcribable DNA sequence, wherein the first and second transcribable DNA sequences are expressed as separate transcripts).

For suppression of GA oxidase gene(s) using a microRNA (miRNA), the transcribable DNA sequence or suppression element can comprise a DNA sequence derived from a miRNA sequence native to a virus or eukaryote, such as an animal or plant, or modified or derived from such a native miRNA sequence. Such native or native-derived miRNA sequences can form a fold back structure and serve as a scaffold for the precursor miRNA (pre-miRNA), and can correspond to the stem region of a native miRNA precursor sequence, such as from a native (or native-derived) primary-miRNA (pri-miRNA) or pre-miRNA sequence. However, in addition to these native or native-derived miRNA scaffold or preprocessed sequences, engineered or synthetic miRNAs of the present aspects further comprise a sequence corresponding to a segment or portion of the targeted GA oxidase gene(s). Thus, in addition to the pre-processed or scaffold miRNA sequences, the suppression element can further comprise a sense and/or anti-sense sequence that corresponds to a segment or portion of a targeted GA oxidase gene, and/or a sequence that is complementary thereto, although one or more sequence mismatches can be tolerated.

GA oxidase gene(s) can also be suppressed using one or more small interfering RNAs (siRNAs). The siRNA pathway involves the non-phased cleavage of a longer double-stranded RNA intermediate ("RNA duplex") into small interfering RNAs (siRNAs). The size or length of siRNAs ranges from about 19 to about 25 nucleotides or base pairs, but common classes of siRNAs include those containing 21 or 24 base pairs. Thus, a transcribable DNA sequence or suppression element can encode a RNA molecule that is at least about 19 to about 25 nucleotides (or more) in length, such as at least 19, 20, 21, 22, 23, 24, or 25 nucleotides in length. For siRNA suppression, a recombinant DNA molecule, construct or vector can be provided comprising a transcribable DNA sequence and suppression element encoding a siRNA molecule for targeted suppression of a GA oxidase gene(s). A transcribable DNA sequence and suppression element can be at least 19 nucleotides in length and have a sequence corresponding to one or more GA oxidase gene(s), and/or a sequence complementary to one or more GA oxidase gene(s).

GA oxidase gene(s) can also be suppressed using one or more trans-acting small interfering RNAs (ta-siRNAs). In the ta-siRNA pathway, miRNAs serve to guide in-phase processing of siRNA primary transcripts in a process that requires an RNA-dependent RNA polymerase for production of a double-stranded RNA precursor. ta-siRNAs are defined by lack of secondary structure, a miRNA target site that initiates production of double-stranded RNA, requirements of DCL4 and an RNA-dependent RNA polymerase (RDR6), and production of multiple perfectly phased ~P21-nt small RNAs with perfectly matched duplexes with 2-nucleotide 3' overhangs (see Allen et al. (2005) Cell, 121:207-221). The size or length of ta-siRNAs ranges from about 20 to about 22 nucleotides or base pairs, but are mostly commonly 21 base pairs. A transcribable DNA sequence or suppression element of the present invention can encode a RNA molecule that is at least about 20 to about 22 nucleotides in length, such as 20, 21, or 22 nucleotides in length. For ta-siRNA suppression, a recombinant DNA molecule, construct or vector is thus provided comprising a transcribable DNA sequence or suppression element encoding a ta-siRNA molecule for targeted suppression of a GA oxidase gene(s). Such a transcribable DNA sequence and suppression element can be at least 20 nucleotides in length and have a sequence corresponding to one or more GA oxidase gene(s) and/or a sequence complementary to one or more GA oxidase gene(s). For methods of constructing suitable ta-siRNA scaffolds, see, e.g., U.S. Pat. No. 9,309,512, which is incorporated herein by reference in its entirety.

According to an aspect of the present disclosure, a seed of the modified corn plant is produced, in which the seed comprises a first expression cassette and DNA sequence encoding a non-coding RNA for suppression of one more GA20 oxidase genes and/or one or more GA3 oxidase genes, or one or more mutated or edited GA20 and/or GA3 oxidase genes, and a second expression cassette and DNA sequence encoding one or more CO or COL polypeptides. In an aspect, a progeny plant grown from the seed is semi-dwarf and has one or more improved ear traits, relative to a control corn plant that does not have the suppression element, mutation or edit and the CO/COL transgene. In another aspect, a commodity or commodity product is produced from the seed of the modified corn plant comprising the first transcribable DNA sequence encoding a non-coding RNA for suppression of one more GA20 oxidase genes and/or one or more GA3 oxidase genes, or one or more mutated or edited GA20 and/or GA3 oxidase genes, and the second DNA sequence encoding one or more CO or COL polypeptides.

A transgenic plant can be produced by any suitable transformation method as provided herein to produce a transgenic $R_0$ plant, which can then be selfed or crossed to other plants to generate $R_1$ seed and subsequent progeny generations and seed through additional crosses, etc. Aspects of the present disclosure further include a plant cell, tissue, explant, plant part, etc., comprising one or more transgenic cells having a transformation event or genomic insertion of a recombinant DNA or polynucleotide sequence comprising a transcribable DNA sequence encoding a non-coding RNA molecule that targets an endogenous GA3 or GA20 oxidase gene for suppression and a transgene encoding a CO or COL polypeptide Transgenic plants, plant cells, seeds, and plant parts of the present disclosure can be homozygous or hemizygous for a transgenic event or insertion in at least one plant cell thereof, or a targeted genome editing event or mutation, and plants, plant cells, seeds, and plant parts of the present disclosure can contain any number of copies of such transgenic event(s), insertion(s) mutation(s), and/or edit(s). The dosage or amount of expression of a transgene or transcribable DNA sequence can be altered by its zygosity and/or number of copies, which can affect the degree or extent of phenotypic changes in the transgenic plant, etc.

Transgenic plants provided herein can include a variety of monocot cereal plants, including crop plants, such as corn, wheat, rice and sorghum. Indeed, recombinant DNA molecules or constructs of the present disclosure can be used to create beneficial traits in cereal plants such as corn without off-types using only a single copy of the transgenic event, insertion or construct.

Aspects of the present disclosure further include methods for making or producing transgenic plants, such as by transformation, crossing, etc., wherein the method comprises introducing a recombinant DNA molecule, construct or sequence into a plant cell, and then regenerating or developing the transgenic plant from the transformed or edited plant cell, which can be performed under selection pressure favoring a transgenic event.

Provided in the present disclosure is a method for producing a modified corn plant, the method comprising: introducing into a corn cell a first recombinant expression cassette comprising a DNA sequence encoding a CO or COL polypeptide, wherein the corn cell comprises a second recombinant expression cassette comprising a transcribable DNA sequence encoding a non-coding RNA for suppression of one or more GA3 oxidase genes and/or one or more GA20 oxidase genes; and regenerating or developing a modified corn plant from the corn cell, wherein the modified corn plant comprises the first and second recombinant expression cassettes.

Also provided in the present disclosure is a method for producing a transgenic corn plant, the method comprising: (a) introducing into a first corn cell a transgene that encodes one or more CO or COL polypeptides to create a transgenic corn cell, wherein the first corn cell comprises a transcribable DNA sequence encoding a non-coding RNA for suppression of one or more GA3 oxidase genes or GA20 oxidase genes; and (b) generating a transgenic corn plant from the transgenic corn cell. In an aspect, the method further comprises identifying a transgenic corn plant with a desired trait. In another aspect, the identified transgenic corn plant is semi-dwarf and has one or more improved ear traits, relative to a control corn plant not having both the transgene and the DNA sequence.

Also provided in the present disclosure is a method for producing a modified corn plant, the method comprising: introducing into a corn cell a first recombinant expression cassette comprising a transcribable DNA sequence encoding a non-coding RNA for suppression of one or more GA3 oxidase genes and/or GA20 oxidase genes, wherein the corn cell comprises a second recombinant expression cassette comprising a DNA sequence encoding a CO and/or COL polypeptide; and regenerating or developing a modified corn plant from the corn cell, wherein the modified corn plant comprises the first and second recombinant expression cassettes.

Also provided in the present disclosure is a method for producing a transgenic corn plant, the method comprising: (a) introducing into a first corn cell a transcribable DNA sequence encoding a non-coding RNA for suppression of one or more GA3 oxidase genes or GA20 oxidase genes to create a transgenic corn cell, wherein the first corn cell comprises a transgene that encodes one or more CO or COL polypeptides; and (b) generating a transgenic corn plant from the transgenic corn cell. In an aspect, the method further comprises identifying a transgenic corn plant with a desired trait. In another aspect, the identified transgenic corn plant is semi-dwarf and has one or more improved ear traits, relative to a control corn plant not having both the transgene and the DNA sequence.

Also provided in the present disclosure is a method for producing a modified corn plant, the method comprising introducing into a corn cell 1) a first recombinant expression cassette comprising a transcribable DNA sequence encoding a non-coding RNA for suppression of one or more GA3 oxidase genes and/or GA20 oxidase genes and 2) a second recombinant expression cassette comprising a DNA sequence encoding a CO or COL polypeptide; and regenerating or developing a modified corn plant from the corn cell, wherein the modified corn plant comprises the first and second recombinant expression cassettes.

Also provided in the present disclosure is a method for producing a transgenic corn plant, the method comprising (a) introducing into a first corn cell 1) a transcribable DNA sequence encoding a non-coding RNA for suppression of one or more GA3 oxidase genes or GA20 oxidase genes and 2) a transgene that encodes one or more CO or COL polypeptides, to create a transgenic corn cell; and (b) generating a transgenic corn plant from the transgenic corn cell. In an aspect, the method further comprises identifying a transgenic corn plant with a desired trait. In another aspect, the identified transgenic corn plant is semi-dwarf and has one or more improved ear traits, relative to a control corn plant not having both the transgene and the DNA sequence.

Also provided in the present disclosure is a method for producing a modified corn plant, the method comprising introducing into a corn cell a first recombinant expression cassette comprising a transcribable DNA sequence encoding a non-coding RNA for suppression of one or more GA3 oxidase genes and/or GA20 oxidase genes; introducing into the corn cell of step (a) a second recombinant expression cassette comprising a DNA sequence encoding a CO or COL polypeptide to create a modified corn cell; and regenerating or developing a modified corn plant from the modified corn cell of step (b), wherein the modified corn plant comprises the first and second recombinant expression cassettes.

Also provided in the present disclosure is a method for producing a modified corn plant, the method comprising introducing into a corn cell a first recombinant expression cassette comprising a DNA sequence encoding a CO or COL polypeptide; introducing into the corn cell of step (a) a second recombinant expression cassette comprising a transcribable DNA sequence encoding a non-coding RNA for suppression of one or more GA3 oxidase genes and/or GA20 oxidase genes to create a modified corn cell; and regenerating or developing a modified corn plant from the modified corn cell of step (b), wherein the modified corn plant comprises the first and second recombinant expression cassettes.

Also provided in the present disclosure is a method for producing a transgenic corn plant, the method comprising (a) introducing into a first corn cell a transcribable DNA sequence encoding a non-coding RNA for suppression of one or more GA3 oxidase genes and/or one or more GA20 oxidase genes to create a transgenic corn cell, wherein the first corn cell is genome edited or mutated and comprises a transgene that encodes one or more CO or COL polypeptides; and (b) generating a transgenic corn plant from the transgenic corn cell. In an aspect, the method further comprises identifying a transgenic corn plant with a desired trait. In another aspect, the identified transgenic corn plant is semi-dwarf and has one or more improved ear traits, relative to a control corn plant not having both the DNA sequence and the transgene.

Also provided in the present disclosure is a method for producing a transgenic corn plant, the method comprising (a) introducing into a first corn cell a DNA sequence that encodes one or more CO or COL polypeptides to create a transgenic corn cell, wherein the first corn cell is genome edited or mutated and has a reduced expression of one or more endogenous GA3 oxidase genes and/or one or more GA20 oxidase genes; and (b) generating a transgenic corn plant from the transgenic corn cell. In an aspect, the first corn cell comprises one or more mutation(s) or edit(s) at or near one or more endogenous GA20 oxidase and/or GA3 oxidase gene(s) (e.g., a mutation or edit in two or more endogenous GA20 oxidase and/or GA3 oxidase gene(s), wherein the expression of the endogenous GA20 oxidase and/or GA3 oxidase gene(s) is reduced relative to a wildtype control. In an aspect, the method further comprises identifying a transgenic corn plant with a desired trait. In another aspect, the identified transgenic corn plant is semi-dwarf and has one or more improved ear traits, relative to a control corn plant not having both the DNA sequence and the reduced expression of the one or more endogenous GA3 oxidase and/or GA20 oxidase genes.

Also provided in the present disclosure is a method for producing a modified corn plant, the method comprising: crossing a first modified corn plant with a second modified corn plant, wherein the expression or activity of one or more endogenous GA3 oxidase genes and/or GA20 oxidase genes is reduced in the first modified corn plant relative to a wildtype control, and wherein the second modified corn plant comprises a recombinant expression cassette comprising a DNA sequence encoding a CO or COL polypeptide; and producing a progeny corn plant comprising the recombinant expression cassette and has the reduced expression of the one or more endogenous GA3 oxidase genes and/or GA20 oxidase genes.

Also provided in the present disclosure is a method for producing a transgenic corn plant, the method comprising (a) crossing a first corn plant with a second corn plant to create a modified corn plant, wherein the expression of one or more endogenous GA3 oxidase gene(s) and/or one or more GA20 oxidase gene(s) is reduced in the first corn plant relative to a wildtype control, and wherein the second corn plant comprises a transgene encoding one or more CO or COL polypeptides; and (b) producing an offspring of the transgenic corn plant of step (a). In an aspect, the method further comprises identifying a modified corn plant with a desired trait. In another aspect, the identified modified corn plant is semi-dwarf and has one or more improved ear traits, relative to a control corn plant not having both the transgene and a reduced expression of the one or more endogenous GA3 oxidase and/or GA20 oxidase gene(s).

According to an aspect of the present disclosure, methods are provided for transforming a cell, tissue or explant with a recombinant DNA molecule or construct comprising DNA sequences or transgenes operably linked to one or more promoters to produce a transgenic or genome edited cell. According to other aspects of the present disclosure, methods are provided for transforming a plant cell, tissue or explant with a recombinant DNA molecule or construct comprising transcribable DNA sequences or transgenes operably linked to one or more plant-expressible promoters to produce a transgenic or genome edited plant or plant cell.

Numerous methods for transforming chromosomes or plastids in a plant cell with a recombinant DNA molecule or construct are known in the art, which can be used according to methods of the present disclosure to produce a transgenic plant cell and plant. Any suitable method or technique for transformation of a plant cell known in the art can be used according to present methods.

Effective methods for transformation of plants include bacterially mediated transformation, such as *Agrobacterium*-mediated or *Rhizobium*-mediated transformation and microprojectile particle bombardment-mediated transformation. A variety of methods are known in the art for transforming explants with a transformation vector via bacterially mediated transformation or microprojectile particle bombardment and then subsequently culturing, etc., those explants to regenerate or develop transgenic plants.

In an aspect, the methods for producing a transgenic or modified corn plant disclosed in the present disclosure comprise obtaining the first corn cell and the transgenic corn cell via *Agrobacterium*-mediated transformation.

In another aspect, the methods for producing a transgenic or modified corn plant disclosed in the present disclosure comprise obtaining the first corn cell and the transgenic corn cell via microprojectile particle bombardment-mediated transformation.

In yet another aspect, the methods for producing a transgenic corn plant disclosed in the present disclosure comprises (1) introducing into a first corn cell a transgene via site-directed integration to create a modified or mutated corn cell, wherein the transgene encodes one or more CO or COL polypeptides, and (2) introducing into the modified or mutated corn cell a transcribable DNA sequence via transformation to create a transgenic corn cell, wherein the transcribable DNA sequence encodes a non-coding RNA for suppression of one or more GA3 oxidase genes and/or one or more GA20 oxidase genes. In an aspect, the transformation can be *Agrobacterium*-mediated transformation or microprojectile particle bombardment-mediated transformation.

In still another aspect, the methods for producing a transgenic corn plant disclosed in the present disclosure comprise (1) obtaining a modified corn cell via genome editing, wherein the modified corn cell has a reduced expression of one or more GA3 oxidase genes and/or one or more GA20 oxidase genes; and (2) introducing into the modified corn cell a transgene via transformation to create a transgenic corn cell, wherein the transgene encodes one or more CO or COL polypeptides. In an aspect, the transformation can be *Agrobacterium*-mediated transformation or microprojectile particle bombardment-mediated transformation.

Other methods for plant transformation, such as microinjection, electroporation, vacuum infiltration, pressure, sonication, silicon carbide fiber agitation, PEG-mediated transformation, etc., are also known in the art. Transgenic plants produced by these transformation methods can be chimeric or non-chimeric for the transformation event depending on the methods and explants used.

Methods of transforming plant cells are well known by persons of ordinary skill in the art. For instance, specific instructions for transforming plant cells by microprojectile particle bombardment with particles coated with recombinant DNA are found in U.S. Pat. Nos. 5,550,318; 5,538,880 6,160,208; 6,399,861; and 6,153,812 and *Agrobacterium*-mediated transformation is described in U.S. Pat. Nos. 5,159,135; 5,824,877; 5,591,616; 6,384,301; 5,750,871; 5,463,174; and 5,188,958, all of which are incorporated herein by reference. Additional methods for transforming plants can be found in, for example, Compendium of Transgenic Crop Plants (2009) Blackwell Publishing. Any appropriate method known to those skilled in the art can be used to transform a plant cell with any of the nucleic acid molecules provided herein.

In an aspect, described herein are methods of integrating an insertion sequence encoding one or more CO or COL polypeptides into the genome of a plant cell via site-directed integration. Such methods comprise creating a double-stranded break (DSB) in the genome of the plant cell such that the insertion sequence is integrated at the site of the DSB. In an aspect, the insertion/donor sequence encoding one or more CO or COL polypeptides can be integrated in a targeted manner into the genome of a cell at the location of a DSB. DSBs can be created by any mechanism, including but are not limited to, zinc finger nucleases (ZFN), transcription activator-like effector nuclease (TALEN), meganucleases, recombinases, transposases, and RNA-guided nucleases (e.g., Cas9 and Cpf1) in a CRISPR based genome editing system.

When Cas9 cleaves targeted DNA, endogenous double stranded break (DSB) repair mechanisms are activated. DSBs can be repaired via non-homologous end joining (NHEJ), which can incorporate insertions or deletions (indels) into the targeted locus. If two DSBs flanking one target region are created, the breaks can be repaired by reversing the orientation of the targeted DNA. Alternatively, if an insertion sequence of a donor template with homology to the target DNA sequence is provided, the DSB can be repaired via homology-directed repair or homologous recombination (HR). This repair mechanism allows for the precise integration of an insertion sequence into the targeted DNA sequence.

As used herein, an "insertion sequence" of a donor template is a sequence designed for targeted insertion into the genome of a plant cell, which can be of any suitable length. For example, an insertion sequence can be between 2 and 50,000, between 2 and 10,000, between 2 and 5000, between 2 and 1000, between 2 and 500, between 2 and 250, between 2 and 100, between 2 and 50, between 2 and 30, between 15 and 50, between 15 and 100, between 15 and 500, between 15 and 1000, between 15 and 5000, between 18 and 30, between 18 and 26, between 20 and 26, between 20 and 50, between 20 and 100, between 20 and 250, between 20 and 500, between 20 and 1000, between 20 and 5000, between 20 and 10,000, between 50 and 250, between 50 and 500, between 50 and 1000, between 50 and 5000, between 50 and 10,000, between 100 and 250, between 100 and 500, between 100 and 1000, between 100 and 5000, between 100 and 10,000, between 250 and 500, between 250 and 1000, between 250 and 5000, or between 250 and 10,000 nucleotides or base pairs in length.

According to some aspects, a donor template may not comprise a sequence for insertion into a genome, and instead comprise one or more homology sequences that include(s) one or more mutations, such as an insertion, deletion, substitution, etc., relative to the genomic sequence at a target site within the genome of a plant. Alternatively, a donor template can comprise a sequence that does not comprise a coding or transcribable DNA sequence, wherein the insertion sequence is used to introduce one or more mutations into a target site within the genome of a plant.

A donor template provided herein can comprise at least one, at least two, at least three, at least four, at least five, at least six, at least seven, at least eight, at least nine, or at least ten genes or transcribable DNA sequences. Alternatively, a donor template can comprise no genes. Without being limiting, a gene or transcribable DNA sequence of a donor template can include, for example, an insecticidal resistance gene, an herbicide tolerance gene, a nitrogen use efficiency gene, a water use efficiency gene, a nutritional quality gene, a DNA binding gene, a selectable marker gene, an RNAi or suppression construct, a site-specific genome modification enzyme gene, a single guide RNA of a CRISPR/Cas9 system, a geminivirus-based expression cassette, or a plant viral expression vector system. A donor template can comprise a promoter, such as a tissue-specific or tissue-preferred promoter, a constitutive promoter, or an inducible promoter. A donor template can comprise a leader, enhancer, promoter, transcriptional start site, 5'-UTR, one or more exon(s), one or more intron(s), transcriptional termination site, region or sequence, 3'-UTR, and/or polyadenylation signal. The leader, enhancer, and/or promoter can be operably linked to a gene or transcribable DNA sequence encoding a non-coding RNA, a guide RNA, an mRNA and/or protein.

In an aspect, an insertion sequence of a donor template of the present disclosure comprises a DNA sequence encoding a CO or COL polypeptide, wherein the CO or COL polypeptide is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to a sequence selected from the group consisting of SEQ ID NOs: 176-452 and a functional fragment thereof.

In an aspect, an insertion sequence of a donor template of the present disclosure comprises a DNA sequence encoding a PpCOL polypeptide, wherein the DNA sequence is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 169.

In an aspect, a "modified plant(s)," "modified corn plant(s)," "transgenic plant(s)," or "transgenic corn plant(s)" produced according to a method disclosed in the present disclosure comprises (1) a first transcribable DNA sequence encoding a non-coding RNA for suppression of one or more GA20 oxidase genes and/or one or more GA3 oxidase genes, and (2) a second DNA sequence encoding one or more CO or COL polypeptides.

In another aspect, a "modified plant(s)," "modified corn plant(s)," "transgenic plant(s)," or "transgenic corn plant(s)" produced according to a method disclosed in the present disclosure comprises (1) a DNA sequence encoding one or more CO or COL polypeptides, and (2) a reduced expression of one or more endogenous GA3 oxidase genes or GA20 oxidase genes relative to a wildtype control. In an aspect, the reduced expression of the one or more endogenous GA20 oxidase genes or GA3 oxidase genes is caused by a mutation or edit at or near the one or more endogenous GA20 oxidase genes or GA3 oxidase genes.

Transgenic or modified plants produced by transformation methods can be chimeric or non-chimeric for the transformation event depending on the methods and explants used. Methods are further provided for expressing a non-coding RNA molecule that targets an endogenous GA oxidase gene for suppression in one or more plant cells or tissues under the control of a plant-expressible promoter, such as a constitutive, tissue-specific, tissue-preferred, vascular and/or leaf promoter as provided herein. Such methods can be used to create transgenic cereal or corn plants having a shorter, semi-dwarf stature, reduced internode length, increased stalk/stem diameter, and/or improved lodging resistance. Such transgenic cereal or corn plants can further have other traits that can be beneficial for yield, such as reduced green snap, deeper roots, increased leaf area, earlier canopy closure, improved drought tolerance, increased nitrogen use efficiency, increased water use efficiency, higher stomatal conductance, lower ear height, increased foliar water content, reduced anthocyanin content and/or area in leaves under normal or nitrogen or water limiting stress conditions, increased ear weight, increased seed or kernel number, increased seed or kernel weight, increased yield, and/or increased harvest index, relative to a wild type or control plant. As used herein, "harvest index" refers to the mass of the harvested grain divided by the total mass of the above-ground biomass of the plant over a harvested area.

Alternatively, nucleotide sequences of the disclosure can be introduced into an organism and allowed to undergo recombination with homologous regions of the organism's genome. Such homologous recombination approaches are well known to those of ordinary skill in the art and can be used to stably incorporate sequences of the disclosure into an organism. In an aspect, nucleotide sequences of the disclosure can be used to introduce "knockout mutations" into a specific gene of an organism that shares substantial homology to the sequences of the disclosure. A knockout mutation is any mutation in the sequence of a gene that eliminates or substantially reduces the function or the level of the product encoded by the gene. Methods involving transformation of an organism followed by homologous recombination to stably integrate the sequences of the disclosure into the genome organism are encompassed by the disclosure. The disclosure is particularly directed to methods where sequences of the disclosure are utilized to alter the growth of an organism. Such methods encompass use of the sequences of the disclosure to interfere with the function of one or more GA20 oxidase genes or GA3 oxidase genes. In an aspect, a knockout mutation of one or more GA20 oxidase or GA3 oxidase genes can be introduced into a corn cell via recombination to reduce the expression of the one or more of GA20 oxidase or GA3 oxidase genes in the corn cell.

Cells that have been transformed can be grown into plants in accordance with conventional ways. See, for example, McCormick et al. (1986) *Plant Cell Reports* 5:81-84. These plants can then be grown, and either pollinated with the same transformed strain or different strains, and the resulting hybrid having constitutive expression of the desired phenotypic characteristic identified. Two or more generations can be grown to ensure that constitutive expression of the desired phenotypic characteristic is stably maintained and inherited and then seeds harvested to ensure constitutive expression of the desired phenotypic characteristic has been achieved.

In an aspect, the methods for producing a transgenic or modified corn plant further comprises culturing the transgenic corn plant of step (b) or a plant part thereof in the presence of a selection agent. In another aspect, the selection agent is kanamycin.

Recipient cell or explant targets for transformation include, but are not limited to, a seed cell, a fruit cell, a leaf cell, a cotyledon cell, a hypocotyl cell, a meristem cell, an embryo cell, an endosperm cell, a root cell, a shoot cell, a stem cell, a pod cell, a flower cell, an inflorescence cell, a stalk cell, a pedicel cell, a style cell, a stigma cell, a receptacle cell, a petal cell, a sepal cell, a pollen cell, an anther cell, a filament cell, an ovary cell, an ovule cell, a pericarp cell, a phloem cell, a bud cell, or a vascular tissue cell. In another aspect, this disclosure provides a plant chloroplast. In a further aspect, this disclosure provides an epidermal cell, a stomata cell, a trichome cell, a root hair cell, a storage root cell, or a tuber cell. In another aspect, this disclosure provides a protoplast. In another aspect, this disclosure provides a plant callus cell.

Transformation of a target plant material or explant can be practiced in tissue culture on nutrient media, for example a mixture of nutrients that allow cells to grow in vitro or cell culture. Transformed explants, cells or tissues can be subjected to additional culturing steps, such as callus induction, selection, regeneration, etc., as known in the art. Transformation can also be carried out without creation or use of a callus tissue. Transformed cells, tissues or explants containing a recombinant DNA sequence insertion or event can be grown, developed or regenerated into transgenic plants in culture, plugs, or soil according to methods known in the art. Transgenic plants can be further crossed to themselves or other plants to produce transgenic seeds and progeny. A transgenic plant can also be prepared by crossing a first plant comprising the recombinant DNA sequence or transformation event with a second plant lacking the insertion. For example, a recombinant DNA construct or sequence can be introduced into a first plant line that is amenable to transformation, which can then be crossed with a second plant line to introgress the recombinant DNA construct or sequence into the second plant line. Progeny of these crosses can be further back crossed into the more desirable line multiple times, such as through 6 to 8 generations or back crosses, to produce a progeny plant with substantially the same genotype as the original parental line, but for the introduction of the recombinant DNA construct or sequence.

Any cell from which a fertile plant can be regenerated is contemplated as a useful recipient cell for practice of this disclosure. Callus can be initiated from various tissue sources, including, but not limited to, immature embryos or parts of embryos, seedling apical meristems, microspores, and the like. Those cells which are capable of proliferating as callus can serve as recipient cells for transformation. Practical transformation methods and materials for making transgenic plants of this disclosure (e.g., various media and recipient target cells, transformation of immature embryos, and subsequent regeneration of fertile transgenic plants) are disclosed, for example, in U.S. Pat. Nos. 6,194,636 and 6,232,526 and U. S. Patent Application Publication 2004/0216189, all of which are incorporated herein by reference.

Transformed explants, cells or tissues can be subjected to additional culturing steps, such as callus induction, selection, regeneration, etc., as known in the art. Transformed cells, tissues or explants containing a recombinant DNA insertion can be grown, developed or regenerated into transgenic plants in culture, plugs or soil according to methods known in the art. In an aspect, this disclosure provides plant cells that are not reproductive material and do not mediate the natural reproduction of the plant. In another aspect, this disclosure also provides plant cells that are reproductive material and mediate the natural reproduction of the plant. In another aspect, this disclosure provides plant cells that cannot maintain themselves via photosynthesis. In another aspect, this disclosure provides somatic plant cells. Somatic cells, contrary to germline cells, do not mediate plant reproduction.

Transgenic plants can be further crossed to themselves or other plants to produce transgenic seeds and progeny. A transgenic plant can also be prepared by crossing a first plant comprising the recombinant DNA sequence or transformation event with a second plant lacking the insertion. For example, a recombinant DNA construct or sequence can be introduced into a first plant line that is amenable to transformation, which can then be crossed with a second plant line to introgress the recombinant DNA construct or sequence into the second plant line. Progeny of these crosses can be further back crossed into the more desirable line multiple times, such as through 6 to 8 generations or back crosses, to produce a progeny plant with substantially the same genotype as the original parental line but for the introduction of the recombinant DNA construct or sequence.

A plant, cell, or explant provided herein can be of an elite variety or an elite line. An elite variety or an elite line refers to any variety that has resulted from breeding and selection for superior agronomic performance. A plant, cell, or explant provided herein can be a hybrid plant, cell, or explant. As used herein, a "hybrid" is created by crossing two plants from different varieties, lines, or species, such that the progeny comprises genetic material from each parent. Skilled artisans recognize that higher order hybrids can be generated as well. For example, a first hybrid can be made by crossing Variety C with Variety D to create a C×D hybrid, and a second hybrid can be made by crossing Variety E with Variety F to create an E×F hybrid. The first and second hybrids can be further crossed to create the higher order hybrid (C×D)×(E×F) comprising genetic information from all four parent varieties.

For *Agrobacterium*-mediated transformation, the transformation vector can comprise an engineered transfer DNA (or T-DNA) segment or region having two border sequences, a left border (LB) and a right border (RB), flanking at least a transcribable DNA sequence or transgene, such that insertion of the T-DNA into the plant genome will create a transformation event for the transcribable DNA sequence, transgene or expression cassette. In other words, the transgene, a transcribable DNA sequence, transgene or expression cassette encoding the site-specific nuclease(s), and/or sgRNA(s) or crRNA(s) would be located between the left and right borders of the T-DNA, perhaps along with an additional transgene(s) or expression cassette(s), such as a plant selectable marker transgene and/or other gene(s) of agronomic interest that can confer a trait or phenotype of agronomic interest to a plant.

A plant selectable marker transgene in a transformation vector or construct of the present disclosure can be used to assist in the selection of transformed cells or tissue due to the presence of a selection agent, such as an antibiotic or herbicide, wherein the plant selectable marker transgene provides tolerance or resistance to the selection agent. Thus, the selection agent can bias or favor the survival, development, growth, proliferation, etc., of transformed cells expressing the plant selectable marker gene, such as to increase the proportion of transformed cells or tissues in the $R_0$ plant.

A plant selectable marker transgene in a transformation vector or construct of the present disclosure can be used to assist in the selection of transformed cells or tissue due to the presence of a selection agent, such as an antibiotic or herbicide, wherein the plant selectable marker transgene provides tolerance or resistance to the selection agent. Thus, the selection agent can bias or favor the survival, development, growth, proliferation, etc., of transformed cells expressing the plant selectable marker gene, such as to increase the proportion of transformed cells or tissues in the $R_O$ plant. Commonly used plant selectable marker genes include, for example, those conferring tolerance or resistance to antibiotics, such as kanamycin and paromomycin (val), hygromycin B (aph IV), streptomycin or spectinomycin (aadA) and gentamycin (aac3 and aacC4), or those conferring tolerance or resistance to herbicides such as glufosinate (bar or pat), dicamba (DMO) and glyphosate (aroA or EPSPS). Plant screenable marker genes can also be used, which provide an ability to visually screen for transformants, such as luciferase or green fluorescent protein (GFP), or a gene expressing a beta glucuronidase or uidA gene (GUS) for which various chromogenic substrates are known. In some aspects, a vector or polynucleotide provided herein comprises at least one selectable marker gene selected from the group consisting of nptII, aph IV, aadA, aac3, aacC4, bar, pat, DMO, EPSPS, aroA, GFP, and GUS. Plant transformation can also be carried out in the absence of selection during one or more steps or stages of culturing, developing or regenerating transformed explants, tissues, plants and/or plant parts.

An aspect of the present disclosure relate to screening cells, tissues or plants for mutations, targeted edits or transgenes and selecting cells or plants comprising targeted edits or transgenes. Nucleic acids can be isolated using techniques routine in the art. For example, nucleic acids can be isolated using any method including, without limitation, recombinant nucleic acid technology, and/or the polymerase chain reaction (PCR). General PCR techniques are described, for example in PCR Primer: A Laboratory Manual, Dieffenbach & Dveksler, Eds., Cold Spring Harbor Laboratory Press, 1995. Recombinant nucleic acid techniques include, for example, restriction enzyme digestion and ligation, which can be used to isolate a nucleic acid. Isolated nucleic acids also can be chemically synthesized, either as a single nucleic acid molecule or as a series of oligonucleotides. Polypeptides can be purified from natural sources (e.g., a biological sample) by known methods such as DEAE ion exchange, gel filtration, and hydroxyapatite chromatography. A polypeptide also can be purified, for example, by expressing a nucleic acid in an expression vector. In addition, a purified polypeptide can be obtained by chemical synthesis. The extent of purity of a polypeptide can be measured using any appropriate method, e.g., column chromatography, polyacrylamide gel electrophoresis, or HPLC analysis.

In an aspect, this disclosure provides methods of detecting recombinant nucleic acids and polypeptides in plant cells. Without being limiting, nucleic acids also can be detected using hybridization. Hybridization between nucleic acids is discussed in detail in Sambrook et al. (1989, Molecular Cloning: A Laboratory Manual, 2nd Ed., Cold Spring Harbor Laboratory Press, Cold Spring Harbor, NY).

Polypeptides can be detected using antibodies. Techniques for detecting polypeptides using antibodies include enzyme linked immunosorbent assays (ELISAs), Western blots, immunoprecipitations and immunofluorescence. An antibody provided herein can be a polyclonal antibody or a monoclonal antibody. An antibody having specific binding affinity for a polypeptide provided herein can be generated using methods well known in the art. An antibody provided herein can be attached to a solid support such as a microtiter plate using methods known in the art.

Detection (e.g., of an amplification product, of a hybridization complex, of a polypeptide) can be accomplished using detectable labels. The term "label" is intended to encompass the use of direct labels as well as indirect labels. Detectable labels include enzymes, prosthetic groups, fluorescent materials, luminescent materials, bioluminescent materials, and radioactive materials.

The screening and selection of modified or transgenic plants or plant cells can be through any methodologies known to those having ordinary skill in the art. Examples of screening and selection methodologies include, but are not limited to, Southern analysis, PCR amplification for detection of a polynucleotide, Northern blots, RNase protection, primer-extension, RT-PCR amplification for detecting RNA transcripts, Sanger sequencing, Next Generation sequencing technologies (e.g., Illumina, PacBio, Ion Torrent, 454) enzymatic assays for detecting enzyme or ribozyme activity of polypeptides and polynucleotides, marker genotyping, and protein gel electrophoresis, Western blots, immunoprecipitation, and enzyme-linked immunoassays to detect polypeptides. Other techniques such as in situ hybridization, enzyme staining, and immunostaining also can be used to detect the presence or expression of polypeptides and/or polynucleotides. Methods for performing all of the referenced techniques are known.

Modified corn plants of the present disclosure having a reduced plant height and improved ear traits relative to a wild-type or control plant can comprise a mutation (e.g., an insertion, deletion, substitution, etc.) introduced through other plant mutagenesis technique or genome editing, wherein expression of one or more GA20 or GA3 oxidase gene is reduced or eliminated in one or more tissues of the modified plant. Modified corn plants of the present disclosure having a reduced plant height and improved ear traits relative to a wild-type or control plant can comprise a transgene encoding one or more CO or COL polypeptides. The transgene can be introduced through other plant mutagenesis technique or genome editing.

Plant mutagenesis techniques (excluding genome editing) can include chemical mutagenesis (i.e., treatment with a chemical mutagen, such as an azide, hydroxylamine, nitrous acid, acridine, nucleotide base analog, or alkylating agent—e.g., EMS (ethylmethane sulfonate), MNU (N-methyl-N-nitrosourea), etc.), physical mutagenesis (e.g., gamma rays, X-rays, UV, ion beam, other forms of radiation, etc.), and insertional mutagenesis (e.g., transposon or T-DNA insertion). Plants or various plant parts, plant tissues or plant cells can be subjected to mutagenesis. Treated plants can be reproduced to collect seeds or produce a progeny plant, and treated plant parts, plant tissues or plant cells can be developed or regenerated into plants or other plant tissues. Mutations generated with chemical or physical mutagenesis techniques can include a frameshift, missense or nonsense mutation leading to loss of function or expression of a targeted gene, such as a GA3 or GA20 oxidase gene.

One method for mutagenesis of a gene is called "TILLING" (for targeting induced local lesions in genomes), in which mutations are created in a plant cell or tissue, preferably in the seed, reproductive tissue or germline of a plant, for example, using a mutagen, such as an EMS treatment. The resulting plants are grown and self-fertilized, and the progeny are used to prepare DNA samples. PCR amplification and sequencing of a nucleic acid sequence of a GA20 or GA3 oxidase gene can be used to identify whether a mutated plant has a mutation in the GA oxidase gene. Plants having mutations in the GA20 or GA3 oxidase gene can then be tested for an altered trait, such as reduced plant height. Alternatively, mutagenized plants can be tested for an altered trait, such as reduced plant height, and then PCR amplification and sequencing of a nucleic acid sequence of a GA20 or GA3 oxidase gene can be used to determine whether a plant having the altered trait also has a mutation in the GA oxidase gene. See, e.g., Colbert et al., 2001, *Plant Physiol* 126:480-484; and McCallum et al., 2000, *Nat. Biotechnol.*, 18:455-457. TILLING can be used to identify mutations that alter the expression a gene or the activity of proteins encoded by a gene, which can be used to introduce and select for a targeted mutation in a GA20 or GA3 oxidase gene of a corn or cereal plant.

Provided in the present disclosure is a recombinant DNA construct comprising 1) a first expression cassette comprising a transcribable DNA sequence encoding a non-coding RNA for suppression of one or more GA20 oxidase or one or more GA3 oxidase genes, and 2) a second expression cassette comprising a DNA sequence encoding a CO or COL polypeptide, wherein the DNA sequence is operably linked to a plant-expressible promoter. In an aspect, the first and second expression cassettes are in a single T-DNA segment of a transformation vector. In another aspect, the first and second expression cassettes are in two different T-DNA segments of a transformation vector.

In an aspect, the transcribable DNA sequence encodes a non-coding RNA for suppression of a GA3 oxidase_1 gene, a GA3 oxidase_2 gene, or both. In another aspect, the transcribable DNA sequence comprises a sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of one or more of SEQ ID NOs: 28, 29, 31, 32, 36, and 37. In another aspect, the transcribable DNA sequence encodes a non-coding RNA comprising a sequence that is 80% complementary to at least 15 consecutive nucleotides of one or more of SEQ ID NOs: 28, 29, 31, 32, 36, and 37.

In another aspect, the transcribable DNA sequence encodes a non-coding RNA for suppression of a GA20 oxidase_3 gene, a GA20 oxidase_4 gene, a GA20 oxidase_5 gene, or a combination thereof. In another aspect, the transcribable DNA sequence comprises a sequence that is at least 80% complementary to at least 15 consecutive nucleotides of SEQ ID NO: 39, 53, or 55. In another aspect, the transcribable DNA sequence encodes a sequence that is at least 80% complementary to at least 15 consecutive nucleotides of SEQ ID NO: 40, 54, or 56.

In another aspect, the non-coding RNA comprises a sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous GA oxidase protein in a corn plant or plant cell, the endogenous GA oxidase protein being at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 9, 12, 15, 30, or 33.

In another aspect, the non-coding RNA comprises a sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of SEQ ID NO: 7, 8, 10, 11, 13, 14, 28, 29, 31, or 32.

In an aspect, the DNA sequence comprised in the second expression cassette comprises a sequence that encodes a protein having an amino acid sequence that is at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to one or more of SEQ ID NOs: 176-397. In another aspect, the DNA sequence comprised in the second expression cassette comprises a sequence that encodes a protein having an amino acid sequence that is at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to one or more of SEQ ID NOs: 398-452.

In an aspect, the DNA sequence comprised in the second expression cassette encodes a *Physcomitrella patens* CONSTANS-like 1 (PpCOL1) polypeptide. In another aspect, the CO or COL polypeptide comprises an amino acid sequence that is at least 60% identical to SEQ ID NO: 168, or a functional fragment thereof. In another aspect, the DNA sequence comprises a sequence that is at least 60% identical to SEQ ID NO: 169.

Also provided herein is a recombinant DNA construct comprising 1) a first transcribable DNA sequence encoding a non-coding RNA for suppression of one or more GA20 oxidase or one or more GA3 oxidase genes, and 2) a second DNA sequence encoding one or more CO or COL polypeptides.

In an aspect, a recombinant DNA construct of the present disclosure comprises a transcribable DNA sequence encoding a non-coding RNA for suppression of one or more GA20 oxidase or one or more GA3 oxidase genes, wherein the DNA sequence is operably linked to a plant-expressible promoter. Such a recombinant DNA construct can be used to transform a corn plant cell expressing a transgene encoding one or more CO or COL polypeptides to create a transgenic corn plant with desired traits. In another aspect, desired traits comprise semi-dwarf and improved ear traits as compared to a control corn plant not having the transgene and the DNA sequence.

In an aspect, a recombinant DNA construct of the present disclosure comprises a DNA sequence encoding one or more CO or COL polypeptides, wherein the DNA sequence is operably linked to a plant-expressible promoter. Such a recombinant DNA construct can be used to transform a corn plant cell having a reduced expression of one or more GA20 oxidase genes and/or one or more GA3 oxidase genes to create a transgenic corn plant with desired traits. In another aspect, desired traits comprise semi-dwarf and improved ear traits as compared to a control corn plant not having the DNA sequence and the reduced expression of the one or more GA20 oxidase genes and/or GA3 oxidase genes.

Also provided in the present disclosure is a transgenic corn plants comprising the recombinant DNA construct. In an aspect, the first and second DNA sequences are in a single T-DNA molecule. In another aspect, the first and second DNA sequences are in two different T-DNA molecules. In an aspect, the first transcribable DNA sequence is operably linked to a plant-expressible promoter.

In an aspect, a recombinant DNA construct of the present disclosure comprises a transcribable DNA sequence encoding a non-coding RNA molecule, wherein the non-coding RNA comprises a sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous GA oxidase protein, the endogenous GA oxidase protein being at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 9, 12, 15, 30 or 33, and wherein the transcribable DNA sequence is operably linked to a plant-expressible promoter. In another aspect, the non-coding RNA comprises a sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of SEQ ID NO: 7, 8, 10, 11, 13, 14, 28, 29, 31 or 32.

In another aspect, the non-coding RNA comprises a sequence that is at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous GA20 oxidase protein, the endogenous GA20 oxidase protein being at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 15. In yet another aspect, the non-coding RNA comprises a sequence that is at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of SEQ ID NO: 13 or SEQ ID NO: 14.

In another aspect, the non-coding RNA molecule comprises a sequence that is (i) at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous GA20 oxidase protein, the endogenous GA20 oxidase protein being at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 9; and/or (ii) at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous GA20 oxidase protein, the endogenous GA20 oxidase protein being at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 15.

In another aspect, the non-coding RNA molecule comprises a sequence that is (i) at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of SEQ ID NO: 7 or 8; and/or (ii) at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of SEQ ID NO: 13 or 14.

In another aspect, the non-coding RNA comprises a sequence that is at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous GA20 oxidase protein, the endogenous GA20 oxidase protein being at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 12.

In another aspect, the non-coding RNA comprises a sequence that is at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of SEQ ID NO: 10 or 11.

In another aspect, the non-coding RNA comprises a sequence that is at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous GA3 oxidase protein, the endogenous GA3 oxidase protein being at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 30 or 33.

In another aspect, the non-coding RNA comprises a sequence that is at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of SEQ ID NO: 28, 29, 31 or 32.

In an aspect, the non-coding RNA comprises a sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous GA oxidase protein, the endogenous GA oxidase protein being at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to one or more of SEQ ID NOs: 3, 6, 9, 12, 15, 18, 21, 24, 27, 30 and 33.

In another aspect, the non-coding RNA molecule comprises a sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of one or more of SEQ ID NOs: 1, 2, 4, 5, 7, 8, 10, 11, 13, 14, 16, 17, 19, 20, 22, 23, 25, 26, 28, 29, 31, and 32.

In an aspect, a recombinant DNA molecule, vector or construct is provided for suppression of an endogenous GA oxidase (or GA oxidase-like) gene in a corn or cereal plant, the recombinant DNA molecule, vector or construct comprising a transcribable DNA sequence encoding a non-coding RNA molecule, wherein the non-coding RNA molecule comprises a sequence that is (i) at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of any one or more of SEQ ID NO: 84, 85, 87, 88, 89, 91, 92, 93, 95, 96, 98, 99, 100, 102, 103, 105, 106, 107, 109, 110, 111, 113, 114, 115, 117, 119, 120, 122, 123, 124, 126, 127, 128, 130, 131, 132, 134, 135, and/or 137, and/or (ii) at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding a protein in the cereal plant that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to any one or more of SEQ ID NO: 86, 90, 94, 97, 101, 104, 108, 112, 116, 118, 121, 125, 129, 133, and/or 136. Likewise, a non-coding RNA molecule can target an endogenous GA oxidase (or GA oxidase-like) gene in a cereal plant having a percent identity to the GA oxidase gene(s) shown to affect plant height in corn. Thus, a non-coding RNA molecule is further provided comprising a sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous protein in a cereal plant that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to any one or more of SEQ ID NO: 9, 12, 15, 30, and/or 33. As mentioned above, the non-coding RNA molecule can target an exon, intron and/or UTR sequence of a GA oxidase (or GA oxidase-like) gene.

A recombinant DNA construct of the present disclosure can comprise or be included within a DNA transformation vector for use in transformation of a target plant cell, tissue or explant. Such a transformation vector of the present disclosure can generally comprise sequences or elements necessary or beneficial for effective transformation in addition to at least one selectable marker gene, at least one expression cassette and/or transcribable DNA sequence encoding one or more site-specific nucleases, and, optionally, one or more sgRNAs or crRNAs.

According to an aspect of the present disclosure, suitable tissue-specific or tissue preferred promoters can include those promoters that drive or cause expression of its associated suppression element or sequence at least in the vascular and/or leaf tissue(s) of a corn or cereal plant, or possibly other tissues.

Expression of the GA oxidase suppression element or construct with a tissue-specific or tissue-preferred promoter can also occur in other tissues of the cereal or corn plant outside of the vascular and leaf tissues, but active GA levels in the developing reproductive tissues of the plant (particularly in the female reproductive organ or ear) are preferably not significantly reduced or impacted (relative to wild type or control plants), such that development of the female organ or ear can proceed normally in the transgenic plant without off-types in the ear and a loss in yield potential.

According to some aspects, constructs and transgenes are provided comprising the first transcribable DNA sequence and the second DNA sequence that are operably linked to a constitutive or tissue-specific or tissue-preferred promoter, such as a vascular or leaf promoter.

In an aspect, the plant-expressible promoter is a vascular promoter. Any vascular promoters known in the art can potentially be used as the tissue-specific or tissue-preferred promoter. Examples of vascular promoters include the RTBV promoter, a known sucrose synthase gene promoter, such as a corn sucrose synthase-1 (Sus1 or Sh1) promoter, a corn Sh1 gene paralog promoter, a barley sucrose synthase promoter (Ss1) promoter, a rice sucrose synthase-1 (RSs1) promoter, or a rice sucrose synthase-2 (RSs2) promoter, a known sucrose transporter gene promoter, such as a rice sucrose transporter promoter (SUT1), or various known viral promoters, such as a *Commelina* yellow mottle virus (CoYMV) promoter, a wheat dwarf geminivirus (WDV) large intergenic region (LIR) promoter, a maize streak geminivirus (MSV) coat protein (CP) promoter, or a rice yellow stripe 1 (YS1)-like or OsYSL2 promoter, and any functional sequence portion or truncation of any of the foregoing promoters with a similar pattern of expression, such as a truncated RTBV promoter.

In another aspect, the vascular promoter comprises a DNA sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to one or more of SEQ ID NO: 67, SEQ ID NO: 68, SEQ ID NO: 69, SEQ ID NO: 70, or SEQ ID NO: 71, or a functional portion thereof.

In another aspect, the plant-expressible promoter is a rice tungro bacilliform virus (RTBV) promoter. In an aspect, the RTBV promoter comprises a DNA sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to one or more of SEQ ID NO: 65 or SEQ ID NO: 66, or a functional portion thereof.

In another aspect, the plant-expressible promoter is a leaf promoter. Any leaf promoters known in the art can potentially be used as the tissue-specific or tissue-preferred promoter. Examples of leaf promoters include a corn pyruvate phosphate dikinase or PPDK promoter, a corn fructose 1,6 bisphosphate aldolase or FDA promoter, and a rice Nadh-Gogat promoter, and any functional sequence portion or truncation of any of the foregoing promoters with a similar pattern of expression. Other examples of leaf promoters from monocot plant genes include a ribulose biphosphate carboxylase (RuBisCO) or RuBisCO small subunit (RBCS) promoter, a chlorophyll a/b binding protein gene promoter, a phosphoenolpyruvate carboxylase (PEPC) promoter, and a Myb gene promoter, and any functional sequence portion or truncation of any of these promoters with a similar pattern of expression.

In another aspect, the leaf promoter comprises a DNA sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to one or more of SEQ ID NO: 72, SEQ ID NO: 73 or SEQ ID NO: 74, or a functional portion thereof.

In another aspect, the plant-expressible promoter is a constitutive promoter. Examples of constitutive promoters that can be used in monocot plants, such as cereal or corn plants, include, for example, various actin gene promoters, such as a rice Actin 1 promoter (see, e.g., U.S. Pat. No. 5,641,876) and a rice Actin 2 promoter (see, e.g., U.S. Pat. No. 6,429,357), a CaMV 35S or 19S promoter (see, e.g., U.S. Pat. No. 5,352,605), a maize ubiquitin promoter (see, e.g., U.S. Pat. No. 5,510,474), a *Coix lacryrna-jobi* polyubiquitin promoter, a rice or maize Gos2 promoter (see, e.g., Pater et al., *Plant J.,* 2(6): 837-44 1992), a FMV 35S promoter (see, e.g., U.S. Pat. No. 6,372,211), a dual enhanced CMV promoter (see, e.g., U.S. Pat. No. 5,322, 938), a MMV promoter (see, e.g., U.S. Pat. No. 6,420,547), a PCLSV promoter (see, e.g., U.S. Pat. No. 5,850,019), an Emu promoter (see, e.g., Last et al., *Theor. Appl. Genet.,* 81:581 (1991); and Mcelroy et al., *Mol. Gen. Genet.,* 231: 150 (1991)), a tubulin promoter from maize, rice or other species, a nopaline synthase (nos) promoter, an octopine synthase (ocs) promoter, a mannopine synthase (mas) promoter, or a plant alcohol dehydrogenase (e.g., maize Adh1) promoter, any other promoters including viral promoters known or later-identified in the art to provide constitutive expression in a cereal or corn plant, any other constitutive promoters known in the art that can be used in monocot or cereal plants, and any functional sequence portion or truncation of any of the foregoing promoters.

In another aspect, the constitutive promoter comprises a DNA sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to one or more of SEQ ID NOs: 75, SEQ ID NO: 76, SEQ ID NO: 77, SEQ ID NO: 78, SEQ ID NO: 79, SEQ ID NO: 80, SEQ ID NO: 81, SEQ ID NO: 82 or SEQ ID NO: 83, or a functional portion thereof.

Tissue-specific and tissue-preferred promoters that drive, etc., a moderate or strong level of expression of their associated transcribable DNA sequence in active GA-producing tissue(s) of a plant can be preferred. Furthermore, such tissue-specific and tissue-preferred should drive, etc., expression of their associated transcribable DNA sequence during one or more vegetative stage(s) of plant development when the plant is growing and/or elongating including one or more of the following vegetative stage(s): $V_E$, V1, V2, V3, V4, V5, V6, V7, V8, V9, V10, V11, V12, V13, V14, Vn, $V_T$, such as expression at least during V3-V12, V4-V12, V5-V12, V6-V12, V7-V12, V8-V12, V3-V14, V5-V14, V6-V14, V7-V14, V8-V14, V9-V14, V10-V14, etc., or during any other range of vegetative stages when growth and/or elongation of the plant is occurring.

According to an aspect, the plant-expressible promoter can preferably drive expression constitutively or in at least a portion of the vascular and/or leaf tissues of the plant. Different promoters driving expression of a suppression element targeting the endogenous GA20 oxidase_3 and/or GA20 oxidase_5 gene(s), the GA20 oxidase_4 gene, the GA3 oxidase_1 and/or GA3 oxidase_2 gene(s) in corn, or similar genes and homologs in other cereal plants, can be effective at reducing plant height and increasing lodging resistance to varying degrees depending on their particular pattern and strength of expression in the plant. However, some tissue-specific and tissue-preferred promoters driving expression of a GA20 or GA3 oxidase suppression element in a plant may not produce a short stature or anti-lodging phenotypes due to the spatial-temporal pattern of expression of the promoter during plant development, and/or the amount or strength of expression of the promoter being too low or weak. Furthermore, some suppression constructs can only reduce and not eliminate expression of the targeted GA20 or GA3 oxidase gene(s) when expressed in a plant, and thus depending on the pattern and strength of expression with a given promoter, the pattern and level of expression of the GA20 or GA3 oxidase suppression construct with such a promoter may not be sufficient to produce an observable plant height and lodging resistance phenotype in plants.

Any other vascular and/or leaf promoters known in the art can also be used, including promoter sequences from related genes (e.g., sucrose synthase, sucrose transporter, and viral gene promoter sequences) from the same or different plant species or virus that have a similar pattern of expression. Further provided are promoter sequences with a high degree of homology to any of the foregoing. Examples of vascular and/or leaf promoters can further include other known, engineered and/or later-identified promoter sequences shown to have a pattern of expression in vascular and/or leaf tissue(s) of a cereal or corn plant. Furthermore, any known or later-identified constitutive promoter can also be used for expression of a GA20 oxidase or GA3 oxidase suppression element.

In addition to its associated promoter, a transcribable DNA sequence or a transgene can also be operatively linked to one or more additional regulatory element(s), such as an enhancer(s), leader, transcription start site (TSS), linker, 5' and 3' untranslated region(s) (UTRs), intron(s), polyadenylation signal, termination region or sequence, etc., that are suitable, necessary or preferred for strengthening, regulating or allowing expression of the transcribable DNA sequence in a plant cell. Such additional regulatory element(s) can be optional and/or used to enhance or optimize expression of the transgene or transcribable DNA sequence. As provided herein, an "enhancer" can be distinguished from a "promoter" in that an enhancer typically lacks a transcription start site, TATA box, or equivalent sequence and is thus insufficient alone to drive transcription. As used herein, a "leader" can be defined generally as the DNA sequence of the 5'-UTR of a gene (or transgene) between the transcription start site (TSS) and 5' end of the transcribable DNA sequence or protein coding sequence start site of the transgene.

In an aspect, the second DNA sequence encoding one or more CO or COL polypeptides comprised in a recombinant DNA construct of the present application is operably linked to a plant-expressible promoter, such as a constitutive or tissue-specific promoter. According to an aspect, the plant-expressible promoter is a medium or high-constitutive promoter with a high-constitutive promoter having a relatively more robust or strong constitutive expression. In an aspect, the plant-expressible promoter is a constitutive promoter, which can be selected from the group consisting of an actin promoter, a Cauliflower mosaic virus (CaMV) 35S or 19S promoter, a plant ubiquitin promoter, a plant Gos2 promoter, a Figwort mosaic virus (FMV) promoter, a cytomegalovirus (CMV) promoter, a mirabilis mosaic virus (MMV) promoter, a peanut chlorotic streak caulimovirus (PCLSV) promoter, an Emu promoter, a tubulin promoter, a nopaline synthase promoter, an octopine synthase promoter, a mannopine synthase promoter, or a maize alcohol dehydrogenase, a functional portion thereof, and a combination thereof.

In an aspect, a transformation vector comprising the recombinant DNA construct is produced. In another aspect, a transgenic corn plant or a plant part thereof comprising the recombinant DNA construct is produced. In still another aspect, the transgenic corn plant is semi-dwarf and has one or more improved ear traits, relative to a control corn plant not having both the first transcribable DNA sequence and the second DNA sequence.

A recombinant DNA molecule or construct of the present disclosure can comprise or be included within a DNA transformation vector for use in transformation of a target plant cell, tissue or explant. Such a transformation vector can generally comprise sequences or elements necessary or beneficial for effective transformation in addition to at least one transgene, expression cassette and/or transcribable DNA sequence.

For *Agrobacterium*-mediated, *Rhizobia*-mediated or other bacteria-mediated transformation, the transformation vector can comprise an engineered transfer DNA (or T-DNA) segment or region having two border sequences, a left border (LB) and a right border (RB), flanking at least a transcribable DNA sequence or transgene, such that insertion of the T-DNA into the plant genome will create a transformation event for the transcribable DNA sequence, transgene or expression cassette. Thus, a transcribable DNA sequence, transgene or expression cassette can be located between the left and right borders of the T-DNA, perhaps along with an additional transgene(s) or expression cassette(s), such as a plant selectable marker transgene and/or other gene(s) of agronomic interest that can confer a trait or phenotype of agronomic interest to a plant. According to alternative aspects, the transcribable DNA sequence, transgene or expression cassette encoding a non-coding RNA molecule targeting an endogenous GA oxidase gene for suppression and the plant selectable marker transgene (or other gene of agronomic interest) can be present in separate T-DNA segments on the same or different recombinant DNA molecule(s), such as for co-transformation. A transformation vector or construct can further comprise prokaryotic maintenance elements, which can be located in the vector outside of the T-DNA region(s).

The present disclosure provides a modified corn plant with a semi-dwarf phenotype and one or more improved ear traits relative to a control plant. The modified corn plant has its expression of one or more GA20 oxidase genes and/or one or more GA3 oxidase genes reduced and comprises a transgene expressing one or more CO or COL polypeptides. In an aspect, the reduced expression of the one or more GA20 oxidase genes and/or one or more GA3 oxidase genes is caused by a mutation or edit at or near the one or more GA20 oxidase genes and/or GA3 oxidase genes introduced via genome editing. In another aspect, the reduced expression of one or more GA20 oxidase genes and/or one or more GA3 oxidase genes is caused by a site-directed integration of a transcribable DNA sequence encoding a non-coding RNA for suppression of the one or more GA20 oxidase genes and/or one or more GA3 oxidase genes. In an aspect, the site-directed integration is mediated by genome editing. In an aspect, the introduction of the transgene expressing one or more CO or COL polypeptides is caused by a site-directed integration of a sequence comprising the transgene. In another aspect, the site-directed integration is mediated by genome editing.

In an aspect, a genome editing system provided herein comprises a CRISPR system. The CRISPR systems are based on RNA-guided engineered nucleases that use complementary base pairing to recognize DNA sequences at target sites. In an aspect, a vector provided herein can comprise any combination of a nucleic acid sequence encoding a RNA-guided nuclease.

In an aspect, a method and/or composition provided herein comprises one or more, two or more, three or more, four or more, or five or more Cas9 nucleases. In an aspect, a method and/or composition provided herein comprises one or more polynucleotides encoding one or more, two or more, three or more, four or more, or five or more Cas9 nucleases. In another aspect, a Cas9 nuclease provided herein is capable of generating a targeted DSB. In an aspect, a method and/or composition provided herein comprises one or more, two or more, three or more, four or more, or five or more Cpf1 nucleases. In an aspect, a method and/or composition provided herein comprises one or more polynucleotides encoding one or more, two or more, three or more, four or more, or five or more Cpf1 nucleases. In another aspect, a Cpf1 nuclease provided herein is capable of generating a targeted DSB.

In an aspect, a vector or construct provided herein comprises polynucleotides encoding at least 1, at least 2, at least 3, at least 4, at least 5, at least 6, at least 7, at least 8, at least 9, or at least 10 site-specific nuclease. In another aspect, a cell provided herein already comprises a site-specific nuclease. In an aspect, a polynucleotide encoding a site-specific nuclease provided herein is stably transformed into a cell. In another aspect, a polynucleotide encoding a site-specific nuclease provided herein is transiently transformed into a cell. In another aspect, a polynucleotide encoding a site-specific nuclease is under the control of a regulatable promoter, a constitutive promoter, a tissue specific promoter, or any promoter useful for expression of the site-specific nuclease.

In an aspect, vectors comprising polynucleotides encoding a site-specific nuclease, and optionally one or more, two or more, three or more, or four or more sgRNAs are provided to a plant cell by transformation methods known in the art (e.g., without being limiting, particle bombardment, PEG-mediated protoplast transfection or *Agrobacterium*-mediated transformation). In an aspect, vectors comprising polynucleotides encoding a Cas9 nuclease, and optionally one or more, two or more, three or more, or four or more sgRNAs are provided to a plant cell by transformation methods known in the art (e.g., without being limiting, particle bombardment, PEG-mediated protoplast transfection or *Agrobacterium*-mediated transformation). In another aspect, vectors comprising polynucleotides encoding a Cpf1 and, optionally one or more, two or more, three or more, or four or more crRNAs are provided to a cell by transformation methods known in the art (e.g., without being limiting, viral transfection, particle bombardment, PEG-mediated protoplast transfection or *Agrobacterium*-mediated transformation).

In an aspect, a vector comprises in cis a cassette encoding a site-specific nuclease and an insertion sequence such that when contacted with the genome of a cell, the site-specific nuclease enables site-specific integration of the insertion sequence. In an aspect, a first vector comprises a cassette encoding a site-specific nuclease and a second vector comprises an insertion sequence such that when contacted with the genome of a cell, the site-specific nuclease provided in trans enables site-specific integration of the insertion sequence.

Site-specific nucleases provided herein can be used as part of a targeted editing technique. Non-limiting examples of site-specific nucleases used in methods and/or compositions provided herein include meganucleases, zinc finger nucleases (ZFNs), transcription activator-like effector nucleases (TALENs), RNA-guided nucleases (e.g., Cas9 and Cpf1), a recombinase (without being limiting, for example, a serine recombinase attached to a DNA recognition motif, a tyrosine recombinase attached to a DNA recognition motif), a transposase (without being limiting, for example, a DNA transposase attached to a DNA binding domain), or any combination thereof. In an aspect, a method provided herein comprises the use of one or more, two or more, three or more, four or more, or five or more site-specific nucleases to induce one, two, three, four, five, or more than five DSBs at one, two, three, four, five, or more than five target sites.

In an aspect, a genome editing system provided herein (e.g., a meganuclease, a ZFN, a TALEN, a CRISPR/Cas9 system, a CRISPR/Cpf1 system, a recombinase, a transposase), or a combination of genome editing systems provided herein, is used in a method to introduce one or more insertions, deletions, substitutions, or inversions to a locus in a cell to introduce a mutation, or generate a dominant negative allele or a dominant positive allele.

Site-specific nucleases, such as meganucleases, ZFNs, TALENs, Argonaute proteins (non-limiting examples of Argonaute proteins include *Thermus thermophilus* Argonaute (TtAgo), *Pyrococcus furiosus* Argonaute (PfAgo), Natronobacterium gregoryi Argonaute (NgAgo), homologs thereof, or modified versions thereof), Cas9 nucleases (non-limiting examples of RNA-guided nucleases include Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, Cpf1, homologs thereof, or modified versions thereof), induce a double-strand DNA break at the target site of a genomic sequence that is then repaired by the natural processes of HR or NHEJ. Sequence modifications then occur at the cleaved sites, which can include inversions, deletions, or insertions that result in gene disruption in the case of NHEJ, or integration of nucleic acid sequences by HR.

In an aspect, a site-specific nuclease provided herein is selected from the group consisting of a zinc-finger nuclease, a meganuclease, an RNA-guided nuclease, a TALE-nuclease, a recombinase, a transposase, or any combination thereof. In another aspect, a site-specific nuclease provided herein is selected from the group consisting of a Cas9 or a Cpf1.

In another aspect a site-specific nuclease provided herein is selected from the group consisting of a Cas1, a Cas1B, a Cas2, a Cas3, a Cas4, a Cas5, a Cas6, a Cas7, a Cas8, a Cas9, a Cas10, a Csy1, a Csy2, a Csy3, a Cse1, a Cse2, a Csc1, a Csc2, a Csa5, a Csn2, a Csm2, a Csm3, a Csm4, a Csm5, a Csm6, a Cmr1, a Cmr3, a Cmr4, a Cmr5, a Cmr6, a Csb1, a Csb2, a Csb3, a Csx17, a Csx14, a Csx10, a Csx16, a CsaX, a Csx3, a Csx1, a Csx15, a Csf1, a Csf2, a Csf3, a Csf4, a Cpf1, a homolog thereof, or a modified version thereof. In another aspect, an RNA-guided nuclease provided herein is selected from the group consisting of a Cas9 or a Cpf1.

In another aspect an RNA guided nuclease provided herein is selected from the group consisting of a Cas1, a Cas1B, a Cas2, a Cas3, a Cas4, a Cas5, a Cas6, a Cas7, a Cas8, a Cas9, a Cas10, a Csy1, a Csy2, a Csy3, a Cse1, a Cse2, a Csc1, a Csc2, a Csa5, a Csn2, a Csm2, a Csm3, a Csm4, a Csm5, a Csm6, a Cmr1, a Cmr3, a Cmr4, a Cmr5, a Cmr6, a Csb1, a Csb2, a Csb3, a Csx17, a Csx14, a Csx10, a Csx16, a CsaX, a Csx3, a Csx1, a Csx15, a Csf1, a Csf2, a Csf3, a Csf4, a Cpf1, a homolog thereof, or a modified version thereof.

In another aspect, a method and/or a composition provided herein comprises at least one, at least two, at least three, at least four, at least five, at least six, at least seven, at least eight, at least nine, or at least ten site-specific nucleases. In yet another aspect, a method and/or a composition provided herein comprises at least one, at least two, at least three, at least four, at least five, at least six, at least seven, at least eight, at least nine, or at least ten polynucleotides encoding at least one, at least two, at least three, at least four, at least five, at least six, at least seven, at least eight, at least nine, or at least ten site-specific nucleases.

In an aspect, an RNA-guided nuclease provided herein is selected from the group consisting of Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, Cpf1, homologs thereof, or modified versions thereof, an Argonaute (non-limiting examples of Argonaute proteins include *Thermus thermophilus* Argonaute (TtAgo), *Pyrococcus furiosus* Argonaute (PfAgo), Natronobacterium gregoryi Argonaute (NgAgo), homologs thereof, modified versions thereof), a DNA guide for an Argonaute protein, and any combination thereof. In another aspect, an RNA-guided nuclease provided herein is selected from the group consisting of Cas9 and Cpf1.

In another aspect, an RNA-guided nuclease provided herein comprises Cas9. In an aspect, an RNA-guided nuclease provided herein is selected from the group consisting of Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, Cpf1, homologs thereof, or modified versions thereof. In an aspect a site-specific nuclease is selected from the group consisting of Cas1, Cas1B, Cas2, Cas3, Cas4, Cas5, Cas6, Cas7, Cas8, Cas9, Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, Cpf1, TtAgo, PfAgo, and NgAgo. In another aspect, an RNA-guided nuclease is selected from the group consisting of Cas1, Cas1B, Cas2, Cas3, Cas4, Cas5, Cas6, Cas7, Cas8, Cas9, Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, Cpf1, TtAgo, PfAgo, and NgAgo.

A target site can be positioned in a polynucleotide sequence encoding a leader, an enhancer, a transcriptional start site, a promoter, a 5'-UTR, an exon, an intron, a 3'-UTR, a polyadenylation site, or a termination sequence. It will be appreciated that a target site can also be positioned upstream or downstream of a sequence encoding a leader, an enhancer, a transcriptional start site, a promoter, a 5'-UTR, an exon, an intron, a 3'-UTR, a polyadenylation site, or a termination sequence. In an aspect, a target site is positioned within 10, within 20, within 30, within 40, within 50, within 75, within 100, within 125, within 150, within 200, within 250, within 300, within 400, within 500, within 600, within 700, within 800, within 900, within 1000, within 1250, within 1500, within 2000, within 2500, within 5000, within 10,000, or within 25,000 nucleotides of a polynucleotide encoding a leader, an enhancer, a transcriptional start site, a promoter, a 5'-UTR, an exon, an intron, a 3'-UTR, a polyadenylation site, a gene, or a termination sequence.

In an aspect, a target site bound by an RNA-guided nuclease is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical or complementary to at least 20, at least 25, at least 30, at least 35, at least 40, at least 45, at least 50, at least 60, at least 70, at least 80, at least 90, at least 100, at least 150, at least 200, at least 250, at least 500, at least 1000, at least 2500, or at least 5000 consecutive nucleotides of SEQ ID NO: 34, 35, 36, 37, or 38, or a sequence complementary thereto.

In an aspect, a targeted genome editing technique described herein can comprise the use of a recombinase. In an aspect, a tyrosine recombinase attached to a DNA recognition motif is selected from the group consisting of a Cre recombinase, a Gin recombinase a Flp recombinase, and a Tnp 1 recombinase. In an aspect, a Cre recombinase or a Gin recombinase provided herein is tethered to a zinc-finger DNA binding domain. The Flp-FRT site-directed recombination system comes from the 2µ plasmid from the baker's yeast Saccharomyces cerevisiae. In this system, Flp recombinase (flippase) recombines sequences between flippase recognition target (FRT) sites. FRT sites comprise 34 nucleotides. Flp binds to the "arms" of the FRT sites (one arm is in reverse orientation) and cleaves the FRT site at either end of an intervening nucleic acid sequence. After cleavage, Flp recombines nucleic acid sequences between two FRT sites. Cre-lox is a site-directed recombination system derived from the bacteriophage P1 that is similar to the Flp-FRT recombination system. Cre-lox can be used to invert a nucleic acid sequence, delete a nucleic acid sequence, or translocate a nucleic acid sequence. In this system, Cre recombinase recombines a pair of lox nucleic acid sequences. Lox sites comprise 34 nucleotides, with the first and last 13 nucleotides (arms) being palindromic. During recombination, Cre recombinase protein binds to two lox sites on different nucleic acids and cleaves at the lox sites. The cleaved nucleic acids are spliced together (reciprocally translocated) and recombination is complete. In another aspect, a lox site provided herein is a loxP, lox 2272, loxN, lox 511, lox 5171, lox71, lox66, M2, M3, M7, or M11 site.

In another aspect, a serine recombinase attached to a DNA recognition motif provided herein is selected from the group consisting of a PhiC31 integrase, an R4 integrase, and a TP-901 integrase. In another aspect, a DNA transposase attached to a DNA binding domain provided herein is selected from the group consisting of a TALE-piggyBac and TALE-Mutator.

Several site-specific nucleases, such as recombinases, zinc finger nucleases (ZFNs), meganucleases, and TALENs, are not RNA-guided and instead rely on their protein structure to determine their target site for causing the DSB or nick, or they are fused, tethered or attached to a DNA-binding protein domain or motif.

ZFNs are synthetic proteins consisting of an engineered zinc finger DNA-binding domain fused to the cleavage domain of the FokI restriction nuclease. ZFNs can be designed to cleave almost any long stretch of double-stranded DNA for modification of the zinc finger DNA-binding domain. ZFNs form dimers from monomers composed of a non-specific DNA cleavage domain of FokI nuclease fused to a zinc finger array engineered to bind a target DNA sequence.

DNA-binding domain of a ZFN is typically composed of 3-4 zinc-finger arrays. The amino acids at positions −1, +2, +3, and +6 relative to the start of the zinc finger ∞-helix, which contribute to site-specific binding to the target DNA, can be changed and customized to fit specific target sequences. The other amino acids form the consensus backbone to generate ZFNs with different sequence specificities. Rules for selecting target sequences for ZFNs are known in the art.

FokI nuclease domain requires dimerization to cleave DNA and therefore two ZFNs with their C-terminal regions are needed to bind opposite DNA strands of the cleavage site (separated by 5-7 bp). The ZFN monomer can cut the target site if the two-ZF-binding sites are palindromic. The term ZFN, as used herein, is broad and includes a monomeric ZFN that can cleave double stranded DNA without assistance from another ZFN. The term ZFN is also used to refer to one or both members of a pair of ZFNs that are engineered to work together to cleave DNA at the same site.

Without being limited by any scientific theory, because the DNA-binding specificities of zinc finger domains can be re-engineered using one of various methods, customized ZFNs can theoretically be constructed to target nearly any target sequence (e.g., at or near a GA oxidase gene in a plant genome). Publicly available methods for engineering zinc finger domains include Context-dependent Assembly (CoDA), Oligomerized Pool Engineering (OPEN), and Modular Assembly. In an aspect, a method and/or composition provided herein comprises one or more, two or more, three or more, four or more, or five or more ZFNs. In another aspect, a ZFN provided herein is capable of generating a targeted DSB or nick. In an aspect, vectors comprising polynucleotides encoding one or more, two or more, three or more, four or more, or five or more ZFNs are provided to a cell by transformation methods known in the art (e.g., without being limiting, viral transfection, particle bombardment, PEG-mediated protoplast transfection, or *Agrobacterium*-mediated transformation). The ZFNs can be introduced as ZFN proteins, as polynucleotides encoding ZFN proteins, and/or as combinations of proteins and protein-encoding polynucleotides.

In an aspect, a method and/or composition provided herein comprises one or more, two or more, three or more, four or more, or five or more ZFNs. In another aspect, a ZFN provided herein is capable of generating a targeted DSB. In an aspect, vectors comprising polynucleotides encoding one or more, two or more, three or more, four or more, or five or more ZFNs are provided to a cell by transformation methods known in the art (e.g., without being limiting, viral transfection, particle bombardment, PEG-mediated protoplast transfection or *Agrobacterium*-mediated transformation).

Meganucleases, which are commonly identified in microbes, such as the LAGLIDADG family of homing endonucleases, are unique enzymes with high activity and long recognition sequences (>14 bp) resulting in site-specific digestion of target DNA. Engineered versions of naturally occurring meganucleases typically have extended DNA recognition sequences (for example, 14 to 40 bp). According to some aspects, a meganuclease can comprise a scaffold or base enzyme selected from the group consisting of I-CreI, I-CeuI, I-MsoI, I-SceI, I-AniI, and I-DmoI. The engineering of meganucleases can be more challenging than ZFNs and TALENs because the DNA recognition and cleavage functions of meganucleases are intertwined in a single domain. Specialized methods of mutagenesis and high-throughput screening have been used to create novel meganuclease variants that recognize unique sequences and possess improved nuclease activity. Thus, a meganuclease can be selected or engineered to bind to a genomic target sequence in a plant, such as at or near the genomic locus of a GA oxidase gene. In an aspect, a method and/or composition provided herein comprises one or more, two or more, three or more, four or more, or five or more meganucleases. In another aspect, a meganuclease provided herein is capable of generating a targeted DSB. In an aspect, vectors comprising polynucleotides encoding one or more, two or more, three or more, four or more, or five or more meganucleases are provided to a cell by transformation methods known in the art (e.g., without being limiting, viral transfection, particle bombardment, PEG-mediated protoplast transfection or *Agrobacterium*-mediated transformation).

TALENs are artificial restriction enzymes generated by fusing the transcription activator-like effector (TALE) DNA binding domain to a FokI nuclease domain. When each member of a TALEN pair binds to the DNA sites flanking a target site, the FokI monomers dimerize and cause a double-stranded DNA break at the target site. Besides the wild-type FokI cleavage domain, variants of the FokI cleavage domain with mutations have been designed to improve cleavage specificity and cleavage activity. The FokI domain functions as a dimer, requiring two constructs with unique DNA binding domains for sites in the target genome with proper orientation and spacing. Both the number of amino acid residues between the TALEN DNA binding domain and the FokI cleavage domain and the number of bases between the two individual TALEN binding sites are parameters for achieving high levels of activity.

TALENs are artificial restriction enzymes generated by fusing the transcription activator-like effector (TALE) DNA binding domain to a nuclease domain. In some aspects, the nuclease is selected from a group consisting of PvuII, MutH, TevI and FokI, AlwI, MlyI, SbfI, SdaI, StsI, CleDORF, Clo051, Pept071. When each member of a TALEN pair binds to the DNA sites flanking a target site, the FokI monomers dimerize and cause a double-stranded DNA break at the target site.

The term TALEN, as used herein, is broad and includes a monomeric TALEN that can cleave double stranded DNA without assistance from another TALEN. The term TALEN is also used to refer to one or both members of a pair of TALENs that work together to cleave DNA at the same site.

Transcription activator-like effectors (TALEs) can be engineered to bind practically any DNA sequence. TALE proteins are DNA-binding domains derived from various plant bacterial pathogens of the genus *Xanthomonas*. The X pathogens secrete TALEs into the host plant cell during infection. The TALE moves to the nucleus, where it recognizes and binds to a specific DNA sequence in the promoter region of a specific DNA sequence in the promoter region of a specific gene in the host genome. TALE has a central DNA-binding domain composed of 13-28 repeat monomers of 33-34 amino acids. The amino acids of each monomer are highly conserved, except for hypervariable amino acid residues at positions 12 and 13. The two variable amino acids are called repeat-variable diresidues (RVDs). The amino acid pairs NI, NG, HD, and NN of RVDs preferentially recognize adenine, thymine, cytosine, and guanine/adenine, respectively, and modulation of RVDs can recognize consecutive DNA bases. This simple relationship between amino acid sequence and DNA recognition has allowed for the engineering of specific DNA binding domains by selecting a combination of repeat segments containing the appropriate RVDs.

Besides the wild-type FokI cleavage domain, variants of the FokI cleavage domain with mutations have been designed to improve cleavage specificity and cleavage activity. The FokI domain functions as a dimer, requiring two constructs with unique DNA binding domains for sites in the target genome with proper orientation and spacing. Both the number of amino acid residues between the TALEN DNA binding domain and the FokI cleavage domain and the number of bases between the two individual TALEN binding sites are parameters for achieving high levels of activity. PvuII, MutH, and TevI cleavage domains are useful alternatives to FokI and FokI variants for use with TALEs. PvuII functions as a highly specific cleavage domain when coupled to a TALE (see Yank et al. 2013. *PLoS One*. 8: e82539). MutH is capable of introducing strand-specific nicks in DNA (see Gabsalilow et al. 2013. *Nucleic Acids Research*. 41: e83). TevI introduces double-stranded breaks in DNA at targeted sites (see Beurdeley et al., 2013. *Nature Communications*. 4: 1762).

The relationship between amino acid sequence and DNA recognition of the TALE binding domain allows for designable proteins. Software programs such as DNA Works can be used to design TALE constructs. Other methods of designing TALE constructs are known to those of skill in the art. See Doyle et al., *Nucleic Acids Research* (2012) 40: W117-122; Cermak et al., *Nucleic Acids Research* (2011). 39:e82; and tale-nt.cac.cornell.edu/about.

In an aspect, a method and/or composition provided herein comprises one or more, two or more, three or more, four or more, or five or more TALENs. In another aspect, a TALEN provided herein is capable of generating a targeted DSB. In an aspect, vectors comprising polynucleotides encoding one or more, two or more, three or more, four or more, or five or more TALENs are provided to a cell by transformation methods known in the art (e.g., without being limiting, viral transfection, particle bombardment, PEG-mediated protoplast transfection or *Agrobacterium*-mediated transformation).

As used herein, a "targeted genome editing technique" refers to any method, protocol, or technique that allows the precise and/or targeted editing of a specific location in a genome of a plant (i.e., the editing is largely or completely non-random) using a site-specific nuclease, such as a meganuclease, a zinc-finger nuclease (ZFN), an RNA-guided endonuclease (e.g., the CRISPR/Cas9 system), a TALE-endonuclease (TALEN), a recombinase, or a transposase.

Provided in the present disclosure is a modified corn plant comprising 1) one or more mutations or edits at or near one or more endogenous GA20 oxidase and/or GA3 oxidase genes, wherein the expression or activity of the one or more endogenous GA20 oxidase and/or GA3 oxidase genes is reduced relative to a wildtype control plant, and 2) a recombinant expression cassette comprising a DNA sequence encoding a CO or COL polypeptide, wherein the DNA sequence is operably linked to a plant-expressible promoter. In an aspect, the modified corn plant is semi-dwarf and has one or more improved ear traits, relative to a control corn plant that does not comprise both the one or more mutations or edits and the recombinant expression cassette. In another aspect, the one or more mutations or edits are selected from the group consisting of an insertion, a substitution, an inversion, a deletion, a duplication, and a combination thereof. In yet another aspect, the one or more mutations or edits are introduced using a meganuclease, a zinc-finger nuclease (ZFN), a RNA-guided endonuclease, a TALE-endonuclease (TALEN), a recombinase, or a transposase.

Also provided is a plurality of modified corn plants in a field, each modified corn plant comprising one or more mutations or edits at or near one or more endogenous GA20 oxidase and/or GA3 oxidase genes, wherein the expression of the one or more endogenous GA20 oxidase and/or GA3 oxidase genes are reduced relative to a wildtype control plant, and a recombinant expression cassette comprising a DNA sequence encoding a CO or COL polypeptide, wherein the DNA sequence is operably linked to a plant-expressible promoter. In an aspect, the modified corn plants have increased yield relative to control corn plants. In another aspect, the modified corn plants have an increase in yield that is at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, or at least 25% greater than control corn plants.

Also provided is a genome edited or mutated corn plant comprising (1) a mutation or edit at or near an endogenous GA20 oxidase or GA3 oxidase gene, wherein the expression of the endogenous GA20 oxidase or GA3 oxidase gene is reduced relative to a wildtype control, and (2) a heterologous DNA sequence encoding a CO or COL polypeptide. In an aspect, the genome edited or mutated corn plant is semi-dwarf and has one or more improved ear traits, relative to a control corn plant that does not comprise both the mutation and the heterologous DNA sequence. In an aspect, a genome edited or mutated corn cell is obtained via a CRISPR based genome editing system.

Aspects of the present disclosure further include methods for making or producing modified plants, such as by genome editing, crossing, etc., wherein the method comprises editing the genomic locus of an endogenous GA3 or GA20 oxidase gene and introducing a transgene encoding one or more CO or COL polypeptide, and then regenerating or developing the modified plant from the edited plant cell.

In an aspect, a method comprises introducing a mutation or edit via CRISPR based genome editing at or near one or more endogenous GA3 or GA20 oxidase genes to reduce the expression of the one or more endogenous GA3 or GA20 oxidase genes. The method comprises creating a double-stranded break (DSB) in the genome of the plant cell, wherein a mutation or edit is introduced therein, thereby reducing the expression of the one or more endogenous GA3 or GA20 oxidase genes. In an aspect, the mutation or edit can be created (or integrated with a donor template) in a targeted manner into the genome of a cell at the location of a DSB via RNA-guided nucleases (e.g., Cas9 and Cpf1). In another aspect, a guide RNA recognizes a target site and acts in association with an RNA-guided nuclease that creates a DSB at the target site, wherein a mutation or edit is created (or integrated with a donor template) into the target site. In another aspect, the target site is near or at one or more endogenous GA3 or GA20 oxidase genes.

In an aspect, a method comprises introducing an insertion sequence encoding one or more CO or COL polypeptides into the genome of a plant cell via site-directed integration. Such a method comprises creating a DSB in the genome of the plant cell such that the insertion sequence is integrated at the site of the DSB. In an aspect, the insertion sequence encoding one or more CO or COL polypeptides can be inserted or integrated in a targeted manner into the genome of a cell at the location of a DSB via RNA-guided nucleases (e.g., Cas9 and Cpf1) in a CRISPR based genome editing system. In another aspect, a guide RNA recognizes a target site and acts in association with an RNA-guided nuclease that creates a double-stranded break at the target site, wherein the insertion sequence encoding one or more CO or COL polypeptides inserts or integrates into the target site.

In an aspect, an insertion sequence of a donor template of the present disclosure comprises a DNA sequence encoding a CO or COL polypeptide, wherein the CO or COL polypeptide sequence is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to a sequence selected from the group consisting of SEQ ID NOs: 176-452 and a functional fragment thereof.

In an aspect, an insertion sequence of a donor template of the present disclosure comprises a DNA sequence encoding a PpCOL1 polypeptide, wherein the DNA sequence is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 169. In another aspect, an insertion sequence of the present disclosure comprises a DNA sequence encoding a polypeptide comprising an amino acid sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to a polypeptide or amino acid sequence selected from the group consisting of SEQ ID NO: 168, or a functional fragment thereof.

Provided in the present disclosure is a method for producing a modified corn plant, the method comprising: introducing into a corn cell a recombinant expression cassette comprising a DNA sequence encoding a CO or COL polypeptide, wherein the DNA sequence is operably linked to a plant-expressible promoter, and wherein the corn cell comprises one or more mutations and/or edits in one or more endogenous GA3 oxidase and/or GA20 oxidase genes; and regenerating or developing a modified corn plant from the corn cell, wherein the modified corn plant comprises the recombinant expression cassette and the one or more mutations and/or edits, and wherein the level of expression or activity of the one or more endogenous GA3 oxidase and/or GA20 oxidase genes in the modified corn plant is reduced relative to a control plant not having the one or more mutations and/or edits. In an aspect, the method further comprises introducing a recombinant DNA construct encoding a guide RNA that targets the one or more endogenous GA3 oxidase and/or GA20 oxidase genes.

In another aspect, the guide RNA comprises a guide sequence that is at least 95%, at least 96%, at least 97%, at least 99% or 100% complementary to at least 10, at least 11, at least 12, at least 13, at least 14, at least 15, at least 16, at least 17, at least 18, at least 19, at least 20, at least 21, at least 22, at least 23, at least 24, or at least 25 consecutive nucleotides of a target DNA sequence at or near the genomic locus of one or more endogenous GA3 oxidase and/or GA20 oxidase genes. In another aspect, In yet another aspect, the guide RNA comprises a guide sequence that is at least 95%, at least 96%, at least 97%, at least 99% or 100% complementary to at least 10, at least 11, at least 12, at least 13, at least 14, at least 15, at least 16, at least 17, at least 18, at least 19, at least 20, at least 21, at least 22, at least 23, at least 24, or at least 25 consecutive nucleotides of SEQ ID NO: 34, 35, 36, 37, or 38, or a sequence complementary thereto. In an aspect, the guide RNA is a CRISPR RNA (crRNA) or a single-chain guide RNA (sgRNA), or the guide RNA comprises a sequence complementary to a protospacer adjacent motif (PAM) sequence present in the genome of the corn cell immediately adjacent to a target DNA sequence at or near the genomic locus of the one or more endogenous GA3 oxidase and/or GA20 oxidase genes.

Also provided is a method for producing a genome edited or mutated corn plant, the method comprising: (a) introducing into a first corn cell a transgene that encodes one or more CO or COL polypeptides to create a genome edited or mutated corn cell, wherein the first corn cell has its expression of one or more endogenous GA3 oxidase genes or GA20 oxidase genes reduced relative to a wildtype control; and (b) generating a genome edited or mutated corn plant from the genome edited or mutated corn cell. In an aspect, the method further comprises identifying a genome edited or mutated corn plant with a desired trait. In another aspect, the identified genome edited or mutated corn plant is semi-dwarf and has one or more improved ear traits, relative to a control corn plant not having both the transgene and a reduced expression of one or more endogenous GA3 oxidase genes or GA20 oxidase genes.

In another aspect, the first corn cell of step (a) is obtained by being provided with a first guide RNA and a first RNA-guided nuclease, and wherein the genome edited or mutated corn cell of step (b) is obtained by being provided with a second guide RNA, an insertion sequence, and a second RNA-guided nuclease.

In another aspect, the first guide RNA recognizes a target site in a GA20 oxidase, wherein the first guide RNA acts in association with the first RNA-guided nuclease that creates a double-stranded break at the target site, and whereby the expression of the endogenous GA20 oxidase is reduced.

In another aspect, the method further comprises integrating into the double-stranded break at least one insertion, at least one substitution, at least one inversion, at least one deletion, at least one duplication, or a combination thereof.

In yet another aspect, the second guide RNA recognizes a target site and acts in association with the second RNA-guided nuclease that creates a double-stranded break at the target site, wherein the insertion sequence integrates into the target site, and wherein the donor/insertion sequence encodes a CO or COL polypeptide, such as PpCOL1 polypeptide.

Provided in the present disclosure is A method for producing a modified corn plant, the method comprising: mutating or editing one or more endogenous GA3 oxidase genes and/or one or more GA20 oxidase genes in a corn cell, wherein the corn cell comprises a recombinant expression cassette encoding a CO or COL polypeptide, wherein the DNA sequence is operably linked to a plant-expressible promoter; and regenerating or developing a modified corn plant from the corn cell, wherein the modified corn plant comprises the recombinant expression cassette and the one or more mutations and/or edits, and wherein the level of expression or activity of the one or more endogenous GA3 oxidase and/or GA20 oxidase genes in the modified corn plant is reduced relative to a control plant not having the one or more mutations and/or edits.

In an aspect, the mutating or editing is obtained by using a site-specific nuclease selected from the group consisting of a RNA-guided endonuclease, a meganuclease, a zinc-finger nuclease (ZFN), a TALE-endonuclease (TALEN), a recombinase, and a transposase. In another aspect, a method further comprises introducing a recombinant DNA construct encoding a guide RNA that targets the one or more endogenous GA3 oxidase and/or GA20 oxidase genes. In another aspect, the guide RNA comprises a guide sequence that is at least 95%, at least 96%, at least 97%, at least 99% or 100% complementary to at least 10, at least 11, at least 12, at least 13, at least 14, at least 15, at least 16, at least 17, at least 18, at least 19, at least 20, at least 21, at least 22, at least 23, at least 24, or at least 25 consecutive nucleotides of a target DNA sequence at or near the genomic locus of one or more endogenous GA3 oxidase and/or GA20 oxidase genes.

In another aspect, the guide RNA comprises a guide sequence that is at least 95%, at least 96%, at least 97%, at least 99% or 100% complementary to at least 10, at least 11, at least 12, at least 13, at least 14, at least 15, at least 16, at least 17, at least 18, at least 19, at least 20, at least 21, at least 22, at least 23, at least 24, or at least 25 consecutive nucleotides of SEQ ID NO: 34, 35, 36, 37, or 38, or a sequence complementary thereto. In another aspect, the guide RNA is a CRISPR RNA (crRNA) or a single-chain guide RNA (sgRNA). In yet another aspect, the guide RNA comprises a sequence complementary to a protospacer adjacent motif (PAM) sequence present in the genome of the corn cell immediately adjacent to a target DNA sequence at or near the genomic locus of the one or more endogenous GA3 oxidase and/or GA20 oxidase genes.

Also provided is a method for producing a genome edited or mutated corn plant, the method comprising: (a) reducing the expression of one or more endogenous GA3 oxidase genes or GA20 oxidase genes in a first corn cell to create a genome edited or mutated corn cell, wherein the first corn cell comprises a transgene that encodes one or more CO or COL polypeptides; and (b) generating a genome edited or mutated corn plant from the genome edited or mutated corn cell. In an aspect, the method further comprises identifying a genome edited or mutated corn plant with a desired trait. In another aspect, the identified genome edited or mutated corn plant is semi-dwarf and has one or more improved ear traits, relative to a control corn plant not having both the transgene and a reduced expression of one or more endogenous GA3 oxidase genes or GA20 oxidase genes.

In an aspect, the first corn cell of step (a) is obtained by being provided with a first guide RNA, an insertion sequence, and a first RNA-guided nuclease, and wherein the genome edited or mutated corn cell of step (b) is obtained by being provided with a second guide RNA and a second RNA-guided nuclease.

In another aspect, the first guide RNA recognizes a target site and acts in association with the first RNA-guided nuclease that creates a double-stranded break at the target site, wherein the insertion sequence integrates into the target site, and wherein the insertion sequence encodes a PpCOL1 polypeptide.

In another aspect, the second guide RNA recognizes a target site in a GA20 oxidase, wherein the second guide RNA acts in association with the second RNA-guided nuclease that creates a double-stranded break at the target site, and whereby the expression level of the endogenous GA20 oxidase is reduced.

The gRNA can be transformed or introduced into a plant cell or tissue (perhaps along with a nuclease, or nuclease-encoding DNA molecule, construct or vector) as a gRNA molecule, or as a recombinant DNA molecule, construct or vector comprising a transcribable DNA sequence encoding the guide RNA operably linked to a plant-expressible promoter. The guide sequence of the guide RNA can be at least 10 nucleotides in length, such as 12-40 nucleotides, 12-30 nucleotides, 12-20 nucleotides, 12-35 nucleotides, 12-30 nucleotides, 15-30 nucleotides, 17-30 nucleotides, or 17-25 nucleotides in length, or about 12, 13, 14, 15, 16, 17, 18, 19, 20, 21, 22, 23, 24, 25 or more nucleotides in length. The guide sequence can be at least 95%, at least 96%, at least 97%, at least 99% or 100% identical or complementary to at least 10, at least 11, at least 12, at least 13, at least 14, at least 15, at least 16, at least 17, at least 18, at least 19, at least 20, at least 21, at least 22, at least 23, at least 24, at least 25, or more consecutive nucleotides of a DNA sequence at the genomic target site.

For genome editing at or near the GA20 oxidase_3 gene with an RNA-guided endonuclease, a guide RNA can be used comprising a guide sequence that is at least 90%, at least 95%, at least 96%, at least 97%, at least 99% or 100% identical or complementary to at least 10, at least 11, at least 12, at least 13, at least 14, at least 15, at least 16, at least 17, at least 18, at least 19, at least 20, at least 21, at least 22, at least 23, at least 24, at least 25, or more consecutive nucleotides of SEQ ID NO: 34 or a sequence complementary thereto (e.g., 12, 13, 14, 15, 16, 17, 18, 19, 20, 21, 22, 23, 24, 25 or more consecutive nucleotides of SEQ ID NO: 34 or a sequence complementary thereto).

For genome editing at or near the GA20 oxidase_4 gene with an RNA-guided endonuclease, a guide RNA can be used comprising a guide sequence that is at least 90%, at least 95%, at least 96%, at least 97%, at least 99% or 100% identical or complementary to at least 10, at least 11, at least 12, at least 13, at least 14, at least 15, at least 16, at least 17, at least 18, at least 19, at least 20, at least 21, at least 22, at least 23, at least 24, at least 25, or more consecutive nucleotides of SEQ ID NO: 38 or a sequence complementary thereto (e.g., 12, 13, 14, 15, 16, 17, 18, 19, 20, 21, 22, 23, 24, 25 or more consecutive nucleotides of SEQ ID NO: 38 or a sequence complementary thereto).

For genome editing at or near the GA20 oxidase_5 gene with an RNA-guided endonuclease, a guide RNA can be used comprising a guide sequence that is at least 90%, at least 95%, at least 96%, at least 97%, at least 99% or 100% identical or complementary to at least 10, at least 11, at least 12, at least 13, at least 14, at least 15, at least 16, at least 17, at least 18, at least 19, at least 20, at least 21, at least 22, at least 23, at least 24, at least 25, or more consecutive nucleotides of SEQ ID NO: 35 or a sequence complementary thereto (e.g., 10, 11, 12, 13, 14, 15, 16, 17, 18, 19, 20, 21, 22, 23, 24, 25 or more consecutive nucleotides of SEQ ID NO: 35 or a sequence complementary thereto).

In an aspect, a guide RNA for targeting an endogenous GA20 oxidase_3 and/or GA20 oxidase_5 gene is provided comprising a guide sequence that is at least 90%, at least 95%, at least 96%, at least 97%, at least 99% or 100% identical or complementary to at least 10, at least 11, at least 12, at least 13, at least 14, at least 15, at least 16, at least 17, at least 18, at least 19, at least 20, or at least 21 consecutive nucleotides of any one or more of SEQ ID NOs: 138-167.

For genome editing at or near the GA3 oxidase_1 gene with an RNA-guided endonuclease, a guide RNA can be used comprising a guide sequence that is at least 90%, at least 95%, at least 96%, at least 97%, at least 99% or 100% identical or complementary to at least 10, at least 11, at least 12, at least 13, at least 14, at least 15, at least 16, at least 17, at least 18, at least 19, at least 20, at least 21, at least 22, at least 23, at least 24, at least 25, or more consecutive nucleotides of SEQ ID NO: 36 or a sequence complementary thereto (e.g., 10, 11, 12, 13, 14, 15, 16, 17, 18, 19, 20, 21, 22, 23, 24, 25 or more consecutive nucleotides of SEQ ID NO: 36 or a sequence complementary thereto).

For genome editing at or near the GA3 oxidase_2 gene with an RNA-guided endonuclease, a guide RNA can be used comprising a guide sequence that is at least 90%, at least 95%, at least 96%, at least 97%, at least 99% or 100% identical or complementary to at least 10, at least 11, at least 12, at least 13, at least 14, at least 15, at least 16, at least 17, at least 18, at least 19, at least 20, at least 21, at least 22, at least 23, at least 24, at least 25, or more consecutive nucleotides of SEQ ID NO: 37 or a sequence complementary thereto (e.g., 10, 11, 12, 13, 14, 15, 16, 17, 18, 19, 20, 21, 22, 23, 24, 25 or more consecutive nucleotides of SEQ ID NO: 37 or a sequence complementary thereto).

In an aspect, a guide RNA comprises a guide sequence that is at least 95%, at least 96%, at least 97%, at least 99% or 100% complementary to at least 10, at least 11, at least 12, at least 13, at least 14, at least 15, at least 16, at least 17, at least 18, at least 19, at least 20, at least 21, at least 22, at least 23, at least 24, or at least 25 consecutive nucleotides of SEQ ID NO: 87, 91, 95, 98, 105, 109, 113, 117, 122, 126, 130 or 137, or a sequence complementary thereto.

In an aspect, a guide RNA comprises a sequence complementary to a protospacer adjacent motif (PAM) sequence present in the genome of a corn plant immediately adjacent to a target DNA sequence at or near the genomic locus of one or more endogenous GA20 or GA3 oxidase gene.

In addition to the guide sequence, a guide RNA can further comprise one or more other structural or scaffold sequence(s), which can bind or interact with an RNA-guided endonuclease. Such scaffold or structural sequences can further interact with other RNA molecules (e.g., tracrRNA). Methods and techniques for designing targeting constructs and guide RNAs for genome editing and site-directed integration at a target site within the genome of a plant using an RNA-guided endonuclease are known in the art.

Mutations such as deletions, insertions, inversions and/or substitutions can be introduced at a target site via imperfect repair of the DSB or nick to produce a knock-out or knock-down of a GA oxidase gene. Such mutations can be generated by imperfect repair of the targeted locus even without the use of a donor template molecule. A "knock-out" of a GA oxidase gene can be achieved by inducing a DSB or nick at or near the endogenous locus of the GA oxidase gene that results in non-expression of the GA oxidase protein or expression of a non-functional protein, whereas a "knock-down" of a GA oxidase gene can be achieved in a similar manner by inducing a DSB or nick at or near the endogenous locus of the GA oxidase gene that is repaired imperfectly at a site that does not affect the coding sequence of the GA oxidase gene in a manner that would eliminate the function of the encoded GA oxidase protein.

For example, the site of the DSB or nick within the endogenous locus can be in the upstream or 5' region of the GA oxidase gene (e.g., a promoter and/or enhancer sequence) to affect or reduce its level of expression. Similarly, such targeted knock-out or knock-down mutations of a GA oxidase gene can be generated with a donor template molecule to direct a particular or desired mutation at or near the target site via repair of the DSB or nick.

The donor template molecule can comprise a homologous sequence with or without an insertion sequence and comprising one or more mutations, such as one or more deletions, insertions, inversions and/or substitutions, relative to the targeted genomic sequence at or near the site of the DSB or nick. For example, targeted knock-out mutations of a GA oxidase gene can be achieved by deleting or inverting at least a portion of the gene or by introducing a frame shift or premature stop codon into the coding sequence of the gene. A deletion of a portion of a GA oxidase gene can also be introduced by generating DSBs or nicks at two target sites and causing a deletion of the intervening target region flanked by the target sites.

Provided herein is a recombinant DNA donor template molecule for site directed integration of an insertion sequence into the genome of a corn plant comprising an insertion sequence and at least one homology sequence, wherein the homology sequence is at least 70%, at least 75%, at least 80%, at least 85%, at least 90%, at least 95%, at least 96%, at least 97%, at least 99% or 100% complementary to at least 20, at least 25, at least 30, at least 35, at least 40, at least 45, at least 50, at least 60, at least 70, at least 80, at least 90, at least 100, at least 150, at least 200, at least 250, at least 500, at least 1000, at least 2500, or at least 5000 consecutive nucleotides of a target DNA sequence in the genome of a corn plant cell, and wherein the insertion sequence comprises an expression cassette comprising a DNA sequence encoding a CO or COL polypeptide, wherein the DNA sequence is operably linked to a plant-expressible promoter.

In an aspect, the DNA donor template molecule comprises two of the homology sequences, wherein the two homology sequences flank the insertion sequence. In another aspect, the CO or COL polypeptide comprises an amino acid sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to one or more of SEQ ID NOs: 176-397. In another aspect, the CO or COL polypeptide comprises an amino acid sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to one or more of SEQ ID NOs: 398-452.

In another aspect, the CO or COL polypeptide comprises a *Physcomitrella patens* CONSTANS-like 1 (PpCOL1) polypeptide. In another aspect, the DNA sequence comprised in the expression cassette comprises a sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 169. In another aspect, the CO or COL polypeptide comprises an amino acid sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 168, or a functional fragment thereof. In another aspect, a plant-expressible promoter comprises a DNA sequence that is at least 80%, at least 85%, at least 90%, at least 95%, at least 96%, at least 97%, at least 98%, at least 99%, at least 99.5% or 100% identical to one or more of SEQ ID NOs: 170-172 or a functional portion thereof.

In another aspect, a DNA donor template molecule further comprises a transcribable DNA sequence encoding a non-coding RNA for suppression of one or more GA20 oxidase genes and/or one or more GA3 oxidase genes, wherein the transcribable DNA sequence is operably linked to a promoter.

In an aspect, a donor template comprising at least one homology sequence or homology arm, wherein the at least one homology sequence or homology arm is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% complementary to at least 20, at least 25, at least 30, at least 35, at least 40, at least 45, at least 50, at least 60, at least 70, at least 80, at least 90, at least 100, at least 150, at least 200, at least 250, at least 500, at least 1000, at least 2500, or at least 5000 consecutive nucleotides of a target DNA sequence, wherein the target DNA sequence is a genomic sequence at or near the genomic locus of an endogenous GA oxidase gene of a corn or cereal plant.

In another aspect, the at least one homology sequence is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical or complementary to at least 20, at least 25, at least 30, at least 35, at least 40, at least 45, at least 50, at least 60, at least 70, at least 80, at least 90, at least 100, at least 150, at least 200, at least 250, at least 500, at least 1000, at least 2500, or at least 5000 consecutive nucleotides of SEQ ID NO: 34, 35, 36, 37, or 38, or a sequence complementary thereto.

In an aspect, a donor template comprising two homology arms including a first homology arm and a second homology arm, wherein the first homology arm comprises a sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% complementary to at least 20, at least 25, at least 30, at least 35, at least 40, at least 45, at least 50, at least 60, at least 70, at least 80, at least 90, at least 100, at least 150, at least 200, at least 250, at least 500, at least 1000, at least 2500, or at least 5000 consecutive nucleotides of a first flanking DNA sequence, wherein the second homology arm comprises a sequence that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% complementary to at least 20, at least 25, at least 30, at least 35, at least 40, at least 45, at least 50, at least 60, at least 70, at least 80, at least 90, at least 100, at least 150, at least 200, at least 250, at least 500, at least 1000, at least 2500, or at least 5000 consecutive nucleotides of a second flanking DNA sequence, and wherein the first flanking DNA sequence and the second flanking DNA sequence are genomic sequences at or near the genomic locus of an endogenous GA oxidase gene of a corn or cereal plant.

In another aspect, each of the two homology arms is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical or complementary to at least 20, at least 25, at least 30, at least 35, at least 40, at least 45, at least 50, at least 60, at least 70, at least 80, at least 90, at least 100, at least 150, at least 200, at least 250, at least 500, at least 1000, at least 2500, or at least 5000 consecutive nucleotides of SEQ ID NO: 34, 35, 36, 37, or 38, or a sequence complementary thereto.

In another aspect, the method further comprises integrating into the double-stranded break at least one insertion, at least one substitution, at least one inversion, at least one deletion, at least one duplication, or a combination thereof.

In yet another aspect, an insertion sequence of a donor template comprises a sequence encoding a protein that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to a sequence selected from the group consisting of SEQ ID NOs: 168 and 176-452 and a functional fragment thereof.

Further provided is a method for producing a modified corn plant, the method comprising: (a) crossing a first corn plant with a second corn plant to create a modified corn plant, wherein the expression of one or more endogenous GA3 oxidase genes or GA20 oxidase genes is reduced in the first corn plant relative to a wildtype control, and wherein the second corn plant comprising a transgene encoding one or more CO or COL polypeptides; and (b) producing an offspring of the modified corn plant of step (a). In an aspect, the method further comprises identifying a modified corn plant with a desired trait. In another aspect, the identified modified corn plant is semi-dwarf and has one or more improved ear traits, relative to a control corn plant not having both the transgene and a reduced expression of one or more endogenous GA3 oxidase genes or GA20 oxidase genes.

In an aspect, a target site can comprise at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 29, or at least 30 consecutive nucleotides.

In an aspect, the target site is a GA3 oxidase_1 gene. In another aspect, the target site is a GA3 oxidase_2 gene. In yet another aspect, the target site is a combination of the GA3 oxidase_1 and GA3 oxidase_2 genes. In still another aspect, the target site is within the open reading frame of the GA3 oxidase_1 or GA3 oxidase_2 gene. In still another aspect, the target site is within the promoter/enhancer of the GA3 oxidase_1 or GA3 oxidase_2 gene. In still another aspect, the target site is within the intron of the GA3 oxidase_1 or GA3 oxidase_2 gene. In still another aspect, the target site is within the 5'UTR of the GA3 oxidase_1 or GA3 oxidase_2 gene. In still another aspect, the target site is within the 3'UTR of the GA3 oxidase_1 or GA3 oxidase_2 gene.

In an aspect, the target site is a GA20 oxidase_3 gene. In another aspect, the target site is a GA20 oxidase_4 gene. In another aspect, the target site is a GA20 oxidase_5 gene. In yet another aspect, the target site is a combination of the GA20 oxidase_3 gene, GA20 oxidase_4 gene, and GA20 oxidase_5 gene. In still another aspect, the target site is within the open reading frame of the GA20 oxidase_3, GA20 oxidase_4, or GA20 oxidase_5 gene. In still another aspect, the target site is within the promoter/enhancer of the GA20 oxidase_3, GA20 oxidase_4, or GA20 oxidase_5 gene. In still another aspect, the target site is within the intron of the GA20 oxidase_3, GA20 oxidase_4, or GA20 oxidase_5 gene. In still another aspect, the target site is within the 5'UTR of the GA20 oxidase_3, GA20 oxidase_4, or GA20 oxidase_5 gene. In still another aspect, the target site is within the 3'UTR of the GA20 oxidase_3, GA20 oxidase_4, or GA20 oxidase_5 gene.

In an aspect, the target site comprises a nucleotide sequence selected from the group consisting of SEQ ID NOs: 34, 35, and 38.

A targeted genome editing technique provided herein can comprise the use of one or more, two or more, three or more, four or more, or five or more donor molecules or templates. A "donor template" can be a single-stranded or double-stranded DNA or RNA molecule or plasmid.

According to other aspects, an insertion sequence of a donor template can comprise a transcribable DNA sequence that encodes a non-coding RNA molecule, which targets one or more GA oxidase gene(s), such as a GA3 oxidase or GA20 oxidase gene(s), for suppression. In an aspect, the transcribable DNA sequence that encodes a non-coding RNA for the suppression of the GA3 oxidase and/or GA20 oxidase gene(s) is selected from the group consisting of SEQ ID NOs: 35-38. In another aspect, an insertion sequence of a donor template can comprise a DNA sequence encoding one or more CO or COL polypeptides, wherein the DNA sequence encodes protein that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to a sequence selected from the group consisting of SEQ ID NOs: 168 and a functional fragment thereof. In another aspect, an insertion sequence of a donor template can comprise a DNA sequence encoding one or more CO or COL polypeptides, wherein the DNA sequence encodes protein that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to a sequence selected from the group consisting of SEQ ID NOs: 176-452 and a functional fragment thereof. In yet another aspect, an insertion sequence of a donor template can comprise a first transcribable DNA sequence encoding a non-coding RNA molecule for the suppression of the one or more GA3 oxidase or GA20 oxidase gene(s), wherein the first transcribable DNA sequence is selected from the group consisting of SEQ ID NOs: 35-38; and an insertion sequence of a donor template can comprise a second DNA sequence encoding one or more CO or COL polypeptides, wherein the second DNA sequence encodes a protein that is at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to a sequence selected from the group consisting of SEQ ID NOs: 168, 176-452, and a functional fragment thereof.

An insertion sequence provided herein can be of any length. For example, a donor or insertion sequence provided herein is between 2 and 50,000, between 2 and 10,000, between 2 and 5000, between 2 and 1000, between 2 and 500, between 2 and 250, between 2 and 100, between 2 and 50, between 2 and 30, between 15 and 50, between 15 and 100, between 15 and 500, between 15 and 1000, between 15 and 5000, between 18 and 30, between 18 and 26, between 20 and 26, between 20 and 50, between 20 and 100, between 20 and 250, between 20 and 500, between 20 and 1000, between 20 and 5000 or between 20 and 10,000 nucleotides in length.

In an aspect, a sequence can be inserted into a double-stranded break created by a CRISPR based genome editing system without the presence of a donor template. In an aspect, at least one insertion, at least one substitution, at least one deletion, at least one duplication, and/or at least one inversion can be inserted/introduced into a double-stranded break created by a CRISPR based genome editing system via non-homologous end joining (NHEJ) without a donor template. In an aspect, at least one insertion, at least one substitution, at least one deletion, at least one duplication, and/or at least one inversion can be inserted/introduced into a double-stranded break created by a CRISPR based genome editing system via homologous recombination (HR) with a donor template.

According to other aspects, at least one insertion is integrated into the double-stranded break at the GA3 oxidase or GA20 oxidase locus and introduces a premature stop codon therein which leads to truncation of the GA3 oxidase or GA20 oxidase proteins and subsequent suppression of the GA3 oxidase or GA20 oxidase genes. In an aspect, the at least one insertion is a single nucleobase insertion. In another aspect, the single nucleobase insertion is selected from the group consisting of guanine, cytosine, adenine, thymine, and uracil. In an aspect, the at least one insertion is inserted within the open reading frame of the GA3 oxidase or GA20 oxidase gene. In another aspect, the at least one insertion is inserted within the promoter/enhancer, intron, 5'UTR, 3'UTR, or a combination thereof.

In another aspect, the at least one insertion at the GA3 oxidase or GA20 oxidase locus comprises at least 2 nucleotides, at least 3 nucleotides, at least 4 nucleotides, at least 5 nucleotides, at least 6 nucleotides, at least 7 nucleotides, at least 8 nucleotides, at least 9 nucleotides, at least 10 nucleotides, at least 11 nucleotides, at least 12 nucleotides, at least 13 nucleotides, at least 14 nucleotides, at least 15 nucleotides, at least 16 nucleotides, at least 17 nucleotides, at least 18 nucleotides, at least 19 nucleotides, or at least 20 nucleotides.

According to an aspect, at least one substitution is integrated into the double-stranded break at the GA3 oxidase or GA20 oxidase locus that leads to the suppression of the GA3 oxidase or GA20 oxidase gene. In an aspect, the at least one substitution is integrated within the open reading frame of the GA3 oxidase or GA20 oxidase gene. In another aspect, the at least one substitution is integrated within the promoter/enhancer, intron, 5'UTR, 3'UTR, or a combination thereof.

According to an aspect, at least one deletion is introduced into the double-stranded break at the GA3 oxidase or GA20 oxidase locus that leads to the suppression of the GA3 oxidase or GA20 oxidase gene. In an aspect, the at least one deletion is introduced within the open reading frame of the GA3 oxidase or GA20 oxidase gene. In another aspect, the at least one deletion is introduced within the promoter/enhancer, intron, 5'UTR, 3'UTR, or a combination thereof.

According to an aspect, at least one duplication is introduced into the double-stranded break at the GA3 oxidase or GA20 oxidase locus that leads to the suppression of the GA3 oxidase or GA20 oxidase gene. In an aspect, the at least one duplication is introduced within the open reading frame of the GA3 oxidase or GA20 oxidase gene. In another aspect, the at least one duplication is introduced within the promoter/enhancer, intron, 5'UTR, 3'UTR, or a combination thereof.

According to an aspect, at least one inversion is integrated into the double-stranded break at the GA3 oxidase or GA20 oxidase locus that leads to the suppression of the GA3 oxidase or GA20 oxidase gene. In an aspect, the at least one inversion is integrated within the open reading frame of the GA3 oxidase or GA20 oxidase gene. In another aspect, the at least one inversion is integrated within the promoter/enhancer, intron, 5'UTR, 3'UTR, or a combination thereof.

According to an aspect, a recombinant DNA construct or vector can comprise a first polynucleotide sequence encoding a site-specific nuclease and a second polynucleotide sequence encoding a guide RNA that can be introduced into a plant cell together via plant transformation techniques. Alternatively, two recombinant DNA constructs or vectors can be provided including a first recombinant DNA construct or vector and a second DNA construct or vector that can be introduced into a plant cell together or sequentially via plant transformation techniques, where the first recombinant DNA construct or vector comprises a polynucleotide sequence encoding a site-specific nuclease and the second recombinant DNA construct or vector comprises a polynucleotide sequence encoding a guide RNA.

According to an aspect, a recombinant DNA construct or vector comprising a polynucleotide sequence encoding a site-specific nuclease can be introduced via plant transformation techniques into a plant cell that already comprises (or is transformed with) a recombinant DNA construct or vector comprising a polynucleotide sequence encoding a guide RNA. Alternatively, a recombinant DNA construct or vector comprising a polynucleotide sequence encoding a guide RNA can be introduced via plant transformation techniques into a plant cell that already comprises (or is transformed with) a recombinant DNA construct or vector comprising a polynucleotide sequence encoding a site-specific nuclease. According to yet further aspects, a first plant comprising (or transformed with) a recombinant DNA construct or vector comprising a polynucleotide sequence encoding a site-specific nuclease can be crossed with a second plant comprising (or transformed with) a recombinant DNA construct or vector comprising a polynucleotide sequence encoding a guide RNA. Such recombinant DNA constructs or vectors can be transiently transformed into a plant cell or stably transformed or integrated into the genome of a plant cell.

In an aspect, vectors comprising polynucleotides encoding a site-specific nuclease, and optionally one or more, two or more, three or more, or four or more gRNAs are provided to a plant cell by transformation methods known in the art (e.g., without being limiting, particle bombardment, PEG-mediated protoplast transfection or *Agrobacterium*-mediated transformation). In an aspect, vectors comprising polynucleotides encoding a Cas9 nuclease, and optionally one or more, two or more, three or more, or four or more gRNAs are provided to a plant cell by transformation methods known in the art (e.g., without being limiting, particle bombardment, PEG-mediated protoplast transfection or *Agrobacterium*-mediated transformation). In another aspect, vectors comprising polynucleotides encoding a Cpf1 and, optionally one or more, two or more, three or more, or four or more crRNAs are provided to a cell by transformation methods known in the art (e.g., without being limiting, viral transfection, particle bombardment, PEG-mediated protoplast transfection or *Agrobacterium*-mediated transformation).

Dwarf or semi-dwarf corn disclosed herein can have characteristics that make it suitable for grain and forage production, especially, production in short-season environments. In particular, limited heat units in short-season environments reduce grain yield and lessen the probability of the crop reaching physiological maturity in a given year. The disclosed dwarf or semi-dwarf corn plants require fewer heat units (e.g., required 10%) than conventional hybrids to reach anthesis and generally reach physiological maturity earlier than conventional cultivars. Semi-dwarf corn plants disclosed herein are less prone to stalk and root lodging due to the shorter stalks and lower ear placement. Corn plants disclosed herein also have the potential to produce high-quality forage due to its high ear-to-stover ratio.

Short stature or semi-dwarf corn plants can also have one or more additional traits, including, but not limited to, increased stem diameter, reduced green snap, deeper roots, increased leaf area, earlier canopy closure, higher stomatal conductance, lower ear height, increased foliar water content, improved drought tolerance, increased nitrogen use efficiency, increased water use efficiency, reduced anthocyanin content and area in leaves under normal or nitrogen or water limiting stress conditions, increased ear weight, increased kernel number, increased kernel weight, increased yield, increased seed number, increased seed weight, and increased prolificacy, and/or increased harvest index.

According to aspects of the present disclosure, modified, transgenic, or genome edited/mutated cereal or corn plants are provided that have at least one beneficial agronomic trait and at least one female reproductive organ or ear that is substantially or completely free of off-types. The beneficial agronomic trait can include, but is not limited to, shorter plant height, shorter internode length in one or more internode(s), larger (thicker) stem or stalk diameter, increased lodging resistance, improved drought tolerance, increased nitrogen use efficiency, increased water use efficiency, deeper roots, larger leaf area, earlier canopy closure, and/or increased harvestable yield. As used herein, "harvest index" refers to the mass of the harvested grain divided by the total mass of the above-ground biomass of the plant over a harvested area.

In an aspect, a modified, transgenic, or genome edited/mutated corn plant exhibits improved lodging resistance, reduced green snap, or both, relative to a control corn plant.

In an aspect, the height at maturity of a modified, transgenic, or genome edited/mutated corn plant exhibiting semi-dwarf phenotype is reduced by at least 1%, at least 2%, at least 5%, at least 10%, at least 15%, at least 20%, at least 25%, at least 30%, at least 35%, at least 40%, at least 45%, at least 50%, at least 55%, at least 60%, at least 65%, at least 70%, or at least 75%, relative to a control corn plant grown under comparable conditions.

According to another aspect of the present disclosure, a modified, transgenic, or genome edited/mutated corn plant provided herein comprises a height that is between 1% and 75%, between 1% and 70%, between 1% and 65%, between 1% and 60%, between 1% and 55%, between 1% and 50%, between 1% and 45%, between 1% and 40%, between 1% and 35%, between 1% and 30%, between 1% and 25%, between 1% and 20%, between 1% and 15%, between 1% and 10%, between 1% and 5%, or between 1% and 2%, of that of a control plant grown under comparable conditions.

According to another aspect of the present disclosure, a modified, transgenic, or genome edited/mutated corn plant provided herein comprises a height that is between 2% and 75%, between 5% and 75%, between 10% and 75%, between 15% and 75%, between 20% and 75%, between 25% and 75%, between 30% and 75%, between 35% and 75%, between 40% and 75%, between 45% and 75%, between 50% and 75%, between 55% and 75%, between 60% and 75%, between 65% and 75%, or between 70% and 75%, of that of a control plant grown under comparable conditions.

According to another aspect of the present disclosure, a modified, transgenic, or genome edited/mutated corn plant provided herein comprises a height that is between 2% and 70%, between 5% and 65%, between 10% and 60%, between 15% and 55%, between 20% and 50%, between 25% and 45%, or between 30% and 40%, of that of a control plant grown under comparable conditions.

According to another aspect of the present disclosure, a modified, transgenic, or genome edited/mutated corn plant provided herein comprises a height that is between 1% and 10%, between 10% and 20%, between 20% and 30%, between 30% and 40%, between 40% and 50%, between 50% and 60%, between 60% and 70%, or between 70% and 80%, of that of a control plant grown under comparable conditions.

In an aspect, the stalk or stem diameter of a transgenic corn plant or genome edited/mutated corn plant is increased by at least 0.1%, at least 0.2%, at least 0.5%, at least 1%, at least 1.5%, at least 2%, at least 2.5%, at least 3%, at least 3.5%, at least 4%, at least 4.5%, at least 5%, at least 6%, at least 7%, at least 8%, at least 9%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, relative to a control corn plan grown under comparable conditions.

According to another aspect of the present disclosure, a modified, transgenic, or genome edited/mutated corn plant provided herein comprises a stalk or stem diameter that is between 0.1% and 100%, between 0.2% and 100%, between 0.5% and 100%, between 1% and 100%, between 1.5% and 100%, between 2% and 100%, between 2.5% and 100%, between 3% and 100%, between 3.5% and 100%, between 4% and 100%, between 4.5% and 100%, between 5% and 100%, between 6% and 100%, between 7% and 100%, between 8% and 100%, between 9% and 100%, between 10% and 100%, between 15% and 100%, between 20% and 100%, between 25% and 100%, between 30% and 100%, between 35% and 100%, between 40% and 100%, between 45% and 100%, between 50% and 100%, between 55% and 100%, between 60% and 100%, between 65% and 100%, between 70% and 100%, between 75% and 100%, between 80% and 100%, between 85% and 100%, between 90% and 100%, or between 95% and 100%, greater than that of a control corn plan grown under comparable conditions.

According to another aspect of the present disclosure, a modified, transgenic, or genome edited/mutated corn plant provided herein comprises a stalk or stem diameter that is between 0.1% and 95%, between 0.1% and 90%, between 0.1% and 85%, between 0.1% and 80%, between 0.1% and 75%, between 0.1% and 70%, between 0.1% and 65%, between 0.1% and 60%, between 0.1% and 55%, between 0.1% and 50%, between 0.1% and 45%, between 0.1% and 40%, between 0.1% and 35%, between 0.1% and 30%, between 0.1% and 25%, between 0.1% and 20%, between 0.1% and 15%, between 0.1% and 10%, between 0.1% and 9%, between 0.1% and 8%, between 0.1% and 7%, between 0.1% and 6%, between 0.1% and 5%, between 0.1% and 4.5%, between 0.1% and 4%, between 0.1% and 3.5%, between 0.1% and 3%, between 0.1% and 2.5%, between 0.1% and 2%, between 0.1% and 1.5%, between 0.1% and 1%, between 0.1% and 0.5%, or between 0.1% and 0.2%, greater than that that of a control corn plan grown under comparable conditions.

According to another aspect of the present disclosure, a modified, transgenic, or genome edited/mutated corn plant provided herein comprises a stalk or stem diameter that is between 0.2% and 95%, between 0.5% and 90%, between 1% and 85%, between 1.5% and 80%, between 2% and 75%, between 2.5% and 70%, between 3% and 65%, between 3.5% and 60%, between 4% and 55%, between 4.5% and 50%, between 5% and 45%, between 6% and 40%, between 7% and 35%, between 8% and 30%, between 9% and 25%, or between 10% and 20%, greater than that that of a control corn plan grown under comparable conditions.

According to another aspect of the present disclosure, a modified, transgenic, or genome edited/mutated corn plant provided herein comprises a stalk or stem diameter that is between 0.1% and 1%, between 1% and 5%, between 6% and 10%, between 20% and 30%, between 30% and 40%, between 40% and 50%, between 50% and 60%, between 60% and 70%, between 70% and 80%, between 80% and 90%, between 90% and 100%, greater than that that of a control corn plan grown under comparable conditions.

In another aspect, the yield of a modified, transgenic, or genome edited/mutated exhibiting semi-dwarf phenotype is equal to or more then the yield of a control plant grown under comparable conditions.

In another aspect, a modified, transgenic, or genome edited/mutated corn plant exhibiting semi-dwarf phenotype requires about 5%, 10%, 15%, 20%, or 25% fewer heat units than a control plant to reach anthesis.

In yet another aspect, a modified, transgenic, or genome edited/mutated corn plant exhibiting semi-dwarf phenotype has a relative maturity of about 10%, 15%, 20%, 25%, 30%, 35%, 40%, or 45% fewer days than the relative maturity of a control plant grown under comparable conditions.

According to an aspect of the present disclosure, a modified, transgenic, or genome edited/mutated corn plant provided herein comprises a height of less than 2000 mm, less than 1950 mm, less than 1900 mm, less than 1850 mm, less than 1800 mm, less than 1750 mm, less than 1700 mm, less than 1650 mm, less than 1600 mm, less than 1550 mm, less than 1500 mm, less than 1450 mm, less than 1400 mm, less than 1350 mm, less than 1300 mm, less than 1250 mm, less than 1200 mm, less than 1150 mm, less than 1100 mm, less than 1050 mm, or less than 1000 mm and an average stem diameter of at least 17.5 mm, at least 18 mm, at least 18.5 mm, at least 19 mm, at least 19.5 mm, at least 20 mm, at least 20.5 mm, at least 21 mm, at least 21.5 mm, or at least 22 mm. According to another aspect the modified corn plant further comprises at least one ear that is substantially free of mature male reproductive tissue.

According to aspects of the present disclosure, modified, transgenic, or genome edited/mutated corn plants are provided that comprise a plant height during late vegetative and/or reproductive stages of development (e.g., at R3 stage) of between 1000 mm and 1800 mm, between 1000 mm and 1700 mm, between 1050 mm and 1700 mm, between 1100 mm and 1700 mm, between 1150 mm and 1700 mm, between 1200 mm and 1700 mm, between 1250 mm and 1700 mm, between 1300 mm and 1700 mm, between 1350 mm and 1700 mm, between 1400 mm and 1700 mm, between 1450 mm and 1700 mm, between 1000 mm and 1500 mm, between 1050 mm and 1500 mm, between 1100 mm and 1500 mm, between 1150 mm and 1500 mm, between 1200 mm and 1500 mm, between 1250 mm and 1500 mm, between 1300 mm and 1500 mm, between 1350 mm and 1500 mm, between 1400 mm and 1500 mm, between 1450 mm and 1500 mm, between 1000 mm and 1600 mm, between 1100 mm and 1600 mm, between 1200 mm and 1600 mm, between 1300 mm and 1600 mm, between 1350 mm and 1600 mm, between 1400 mm and 1600 mm, between 1450 mm and 1600 mm, of between 1000 mm and 2000 mm, between 1200 mm and 2000 mm, between 1200 mm and 1800 mm, between 1300 mm and 1700 mm, between 1400 mm and 1700 mm, between 1400 mm and 1600 mm, between 1400 mm and 1700 mm, between 1400 mm and 1800 mm, between 1400 mm and 1900 mm, between 1400 mm and 2000 mm, or between 1200 mm and 2500 mm, and/or an average stem diameter of between 17.5 mm and 22 mm, between 18 mm and 22 mm, between 18.5 and 22 mm, between 19 mm and 22 mm, between 19.5 mm and 22 mm, between 20 mm and 22 mm, between 20.5 mm and 22 mm, between 21 mm and 22 mm, between 21.5 mm and 22 mm, between 17.5 mm and 21 mm, between 17.5 mm and 20 mm, between 17.5 mm and 19 mm, between 17.5 mm and 18 mm, between 18 mm and 21 mm, between 18 mm and 20 mm, or between 18 mm and 19 mm. A modified corn plant can be substantially free of off-types, such as male reproductive tissues or structures in one or more ears of the modified corn plant.

According to an aspect of the present disclosure a modified, transgenic, or genome edited/mutated corn plant provided herein comprises a height of between 1000 mm and 1600 mm, 1000 mm and 1500 mm, between 1050 mm and 1500 mm, between 1100 mm and 1500 mm, between 1150 mm and 1500 mm, between 1200 mm and 1500 mm, between 1250 mm and 1500 mm, between 1300 mm and 1500 mm, between 1350 mm and 1500 mm, between 1400 mm and 1500 mm, between 1450 mm and 1500 mm, between 1000 mm and 1600 mm, between 1100 mm and 1600 mm, between 1200 mm and 1600 mm, between 1300 mm and 1600 mm, or between 1000 mm and 1300 mm, and an average stem diameter of between 17.5 mm and 22 mm, between 18 mm and 22 mm, between 18.5 and 22 mm, between 19 mm and 22 mm, between 19.5 mm and 22 mm, between 20 mm and 22 mm, between 20.5 mm and 22 mm, between 21 mm and 22 mm, between 21.5 mm and 22 mm, between 17.5 mm and 21 mm, between 17.5 mm and 20 mm, between 17.5 mm and 19 mm, between 17.5 mm and 18 mm, between 18 mm and 21 mm, between 18 mm and 20 mm, or between 18 mm and 19 mm. According to another aspect the modified corn plant further comprises at least one ear that is substantially free of mature male reproductive tissue.

According to an aspect of the present disclosure, a modified, transgenic, or genome edited/mutated corn plant provided herein comprises a height that is at least 5%, at least 10%, at least 15%, at least 20%, at least 25%, at least 30%, at least 35%, at least 40%, at least 45%, at least 50%, at least 55%, at least 60%, at least 65%, at least 70%, or at least 75% less than the height of a control plant and a stalk or stem diameter that is at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% greater than the stem diameter of a control plant.

According to an aspect of the present disclosure, a modified, transgenic, or genome edited/mutated corn plant provided herein comprises a fresh ear weight that is at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% greater than the fresh ear weight of a control plant.

According to an aspect of the present disclosure, a population of modified, transgenic, or genome edited/mutated corn plants provided herein comprises a lodging frequency that is at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or 100% lower as compared to a population of unmodified control plants. According to another aspect of the present disclosure, a population of modified corn plants provided herein comprises a lodging frequency that is between 5% and 100%, between 5% and 95%, between 5% and 90%, between 5% and 85%, between 5% and 80%, between 5% and 75%, between 5% and 70%, between 5% and 65%, between 5% and 60%, between 5% and 55%, between 5% and 50%, between 5% and 45%, between 5% and 40%, between 5% and 35%, between 5% and 30%, between 5% and 25%, between 5% and 20%, between 5% and 15%, between 5% and 10%, between 10% and 100%, between 10% and 75%, between 10% and 50%, between 25% and 75%, between 25% and 50%, or between 50% and 75% lower as compared to a population of control plants.

According to an aspect of the present disclosure, modified, transgenic, or genome edited/mutated corn plants are provided that comprise an average internode length (or a minus-2 internode length and/or minus-4 internode length relative to the position of the ear) that is at least 5%, at least 10%, at least 15%, at least 20%, at least 25%, at least 30%, at least 35%, at least 40%, at least 45%, at least 50%, at least 55%, at least 60%, at least 65%, at least 70%, or at least 75% less than the same or average internode length of a control plant.

The "minus-2 internode" of a corn plant refers to the second internode below the ear of the plant, and the "minus-4 internode" of a corn plant refers to the fourth internode below the ear of the plant. According to many aspects, modified, transgenic, or genome edited/mutated corn plants are provided that have an average internode length (or a minus-2 internode length and/or minus-4 internode length relative to the position of the ear) that is between 5% and 75%, between 5% and 50%, between 10% and 70%, between 10% and 65%, between 10% and 60%, between 10% and 55%, between 10% and 50%, between 10% and 45%, between 10% and 40%, between 10% and 35%, between 10% and 30%, between 10% and 25%, between 10% and 20%, between 10% and 15%, between 10% and 10%, between 10% and 75%, between 25% and 75%, between 10% and 50%, between 20% and 50%, between 25% and 50%, between 30% and 75%, between 30% and 50%, between 25% and 50%, between 15% and 50%, between 20% and 50%, between 25% and 45%, or between 30% and 45% less than the same or average internode length of a control plant.

A modified, transgenic, or genome edited/mutated corn plant can have a harvest index that is at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 20%, at least 25%, at least 30%, at least 35%, at least 40%, at least 45%, or at least 50% greater than the harvest index of a wild-type or control plant. A modified corn plant can have a harvest index that is between 1% and 45%, between 1% and 40%, between 1% and 35%, between 1% and 30%, between 1% and 25%, between 1% and 20%, between 1% and 15%, between 1% and 14%, between 1% and 13%, between 1% and 12%, between 1% and 11%, between 1% and 10%, between 1% and 9%, between 1% and 8%, between 1% and 7%, between 1% and 6%, between 1% and 5%, between 1% and 4%, between 1% and 3%, between 1% and 2%, between 5% and 15%, between 5% and 20%, between 5% and 30%, or between 5% and 40% greater than the harvest index of a control plant.

According to an aspect of the present disclosure, modified, transgenic, or genome edited/mutated corn plants are provided that have an increase in harvestable yield of at least 1 bushel per acre, at least 2 bushels per acre, at least 3 bushels per acre, at least 4 bushels per acre, at least 5 bushels per acre, at least 6 bushels per acre, at least 7 bushels per acre, at least 8 bushels per acre, at least 9 bushels per acre, or at least 10 bushels per acre, relative to a wild-type or control plant. A modified corn plant can have an increase in harvestable yield between 1 and 10, between 1 and 8, between 2 and 8, between 2 and 6, between 2 and 5, between 2.5 and 4.5, or between 3 and 4 bushels per acre. A modified corn plant can have an increase in harvestable yield that is at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 20%, or at least 25% greater than the harvestable yield of a wild-type or control plant. A modified corn plant can have a harvestable yield that is between 1% and 25%, between 1% and 20%, between 1% and 15%, between 1% and 14%, between 1% and 13%, between 1% and 12%, between 1% and 11%, between 1% and 10%, between 1% and 9%, between 1% and 8%, between 1% and 7%, between 1% and 6%, between 1% and 5%, between 1% and 4%, between 1% and 3%, between 1% and 2%, between 5% and 15%, between 5% and 20%, between 5% and 25%, between 2% and 10%, between 2% and 9%, between 2% and 8%, between 2% and 7%, between 2% and 6%, between 2% and 5%, or between 2% and 4% greater than the harvestable yield of a control plant.

According to an aspect, the present disclosure provides a population of a modified, transgenic, or genome edited/mutated corn plants, where the population of a modified, transgenic, or genome edited/mutated corn plants shares ancestry with a single a modified, transgenic, or genome edited/mutated corn plant, where the population of a modified, transgenic, or genome edited/mutated corn plants comprises an average height of 1500 mm or less, wherein the population of a modified, transgenic, or genome edited/mutated corn plants comprises an average stalk or stem diameter of 18 mm or more, wherein less than 5%, less than 10%, less than 15%, less than 20%, or less than 25% of the population of modified, transgenic, or genome edited/mutated corn plants comprises a height of greater than 1500 mm, and where less than 5%, less than 10%, less than 15%, less than 20%, or less than 25% of the population of a modified, transgenic, or genome edited/mutated corn plants comprises at least one ear comprising mature male reproductive tissue. In another aspect the population of a modified, transgenic, or genome edited/mutated corn plants comprises an average height of 1200 mm or less.

According to an aspect, the present disclosure provides a population of a modified, transgenic, or genome edited/mutated corn plants, where the population of a modified, transgenic, or genome edited/mutated corn plants share ancestry with a single modified corn plant, where the population of a modified, transgenic, or genome edited/mutated corn plants comprises an average height of 1500 mm or less, where less than 5%, less than 10%, less than 15%, less than 20%, or less than 25% of the population of modified corn plants comprises a height of greater than 1500 mm, and where the population of a modified, transgenic, or genome edited/mutated corn plants comprises a lodging frequency that is at least 5%, at least 10%, at least 20%, at least 30%, at least 40%, at least 50%, at least 60%, at least 70% at least 80%, at least 90%, or 100% lower as compared to a population of control corn plants.

According to an aspect, the present disclosure provides a modified, transgenic, or genome edited/mutated corn plant comprising a height of 1500 mm or less, where the a modified, transgenic, or genome edited/mutated corn plant further comprises a stalk or stem diameter of 18 mm or more, and where at least one ear of the a modified, transgenic, or genome edited/mutated corn plant is substantially free of mature male reproductive tissue.

According to an aspect, the present disclosure provides a modified, transgenic, or genome edited/mutated corn plant comprising a height of 1500 mm or less, wherein the a modified, transgenic, or genome edited/mutated corn plant further comprises a harvest index of at least 0.58, and where the a modified, transgenic, or genome edited/mutated corn plant further comprises at least one ear that is substantially free of mature male reproductive tissue.

According to an aspect of the present disclosure, modified, transgenic, or genome edited/mutated corn plants are provided having a significantly reduced or eliminated expression level of one or more GA3 oxidase and/or GA20 oxidase gene transcript(s) and/or protein(s) in one or more tissue(s), such as one or more stem, internode, leaf and/or vascular tissue(s), of the modified, transgenic, or genome edited/mutated plants, as compared to the same tissue(s) of wild-type or control plants. In an aspect, the level of one or more GA3 oxidase and/or GA20 oxidase gene transcript(s) and/or protein(s), or one or more GA oxidase (or GA oxidase-like) gene transcript(s) and/or protein(s), in one or more stem, internode, leaf and/or vascular tissue(s) of a modified corn plant can be at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% less or lower than in the same tissue(s) of a control corn or cereal plant.

According to an aspect of the present disclosure, modified, transgenic, or genome edited/mutated cereal or corn plants are provided that have at least one beneficial agronomic trait and at least one female reproductive organ or ear that is substantially or completely free of off-types. The beneficial agronomic trait can include, for example, shorter plant height, shorter internode length in one or more internode(s), larger (thicker) stem or stalk diameter, increased lodging resistance, improved drought tolerance, increased nitrogen use efficiency, increased water use efficiency, deeper roots, larger leaf area, earlier canopy closure, and/or increased harvestable yield. A modified, transgenic, or genome edited/mutated cereal or corn plant can have a female reproductive organ or ear that appears normal relative to a control or wild-type plant. Indeed, modified, transgenic, or genome edited/mutated cereal or corn plants are provided that comprise at least one reproductive organ or ear that does not have or exhibit, or is substantially or completely free of, off-types including male sterility, reduced kernel or seed number, and/or masculinized structure(s) in one or more female organs or ears.

A modified, transgenic, or genome edited/mutated cereal or corn plant is provided herein that lacks significant off-types in the reproductive tissues of the plant. Off-types can include male (tassel or anther) sterility, reduced kernel or seed number, and/or the presence of one or more masculinized or male (or male-like) reproductive structures in the female organ or ear (e.g., anther ear) of the plant.

As used herein, a female organ or ear of a plant, such as corn, is "substantially free" of male reproductive structures if male reproductive structures are absent or nearly absent in the female organ or ear of the plant based on visual inspection of the female organ or ear at later reproductive stages. A female organ or ear of a plant, such as corn, is "completely free" of mature male reproductive structures if male reproductive structures are absent or not observed or observable in the female organ or ear of the plant, such as a corn plant, by visual inspection of the female organ or ear at later reproductive stages.

In an aspect, a modified, transgenic, or genome edited/mutated corn plant exhibits increased ear area relative to a control corn plant.

According to an aspect of the present disclosure, a modified, transgenic, or genome edited/mutated corn plant exhibits an increase in ear area by at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, relative to a control corn plant grown under comparable conditions.

According to an aspect of the present disclosure, a modified, transgenic, or genome edited/mutated corn plant exhibits an ear area that is between 1% and 100%, between 2% and 100%, between 3% and 100%, between 4% and 100%, between 5% and 100%, between 6% and 100%, between 7% and 100%, between 8% and 100%, between 9% and 100%, between 10% and 100%, between 11% and 100%, between 12% and 100%, between 13% and 100%, between 14% and 100%, between 15% and 100%, between 16% and 100%, between 17% and 100%, between 18% and 100%, between 19% and 100%, between 20% and 100%, between 25% and 100%, between 30% and 100%, between 35% and 100%, between 40% and 100%, between 45% and 100%, between 50% and 100%, between 55% and 100%, between 60% and 100%, between 65% and 100%, between 70% and 100%, between 75% and 100%, between 80% and 100%, between 85% and 100%, between 90% and 100%, or between 95% and 100% greater than that of a control corn plant grown under comparable conditions.

According to an aspect of the present disclosure, a modified, transgenic, or genome edited/mutated corn plant exhibits an ear area that is between 1% and 95%, between 1% and 90%, between 1% and 85%, between 1% and 80%, between 1% and 75%, between 1% and 70%, between 1% and 65%, between 1% and 60%, between 1% and 55%, between 1% and 50%, between 1% and 45%, between 1% and 40%, between 1% and 35%, between 1% and 30%, between 1% and 25%, between 1% and 20%, between 1% and 19%, between 1% and 18%, between 1% and 17%, between 1% and 16%, between 1% and 15%, between 1% and 14%, between 1% and 13%, between 1% and 12%, between 1% and 11%, between 1% and 10%, between 1% and 9%, between 1% and 8%, between 1% and 7%, between 1% and 6%, between 1% and 5%, between 1% and 4%, between 1% and 3%, or between 1% and 2% greater than that of a control corn plant grown under comparable conditions.

According to an aspect of the present disclosure, a modified, transgenic, or genome edited/mutated corn plant exhibits an ear area that is between 2% and 90%, between 3% and 85%, between 4% and 80%, between 5% and 75%, between 6% and 70%, between 7% and 65%, between 8% and 60%, between 9% and 55%, between 10% and 50%, between 11% and 45%, between 12% and 40%, between 13% and 35%, between 14% and 30%, or between 15% and 25% greater than that of a control corn plant grown under comparable conditions.

According to an aspect of the present disclosure, a modified, transgenic, or genome edited/mutated corn plant exhibits an ear area that is between 1% and 5%, between 5% and 10%, between 10% and 20%, between 20% and 30%, between 30% and 40%, between 40% and 50%, between 50% and 60%, between 60% and 70%, between 70% and 80%, between 80% and 90%, or between 90% and 100% greater than that of a control corn plant grown under comparable conditions.

In an aspect, a modified, transgenic, or genome edited/mutated corn plant exhibits increased ear volume relative to a control corn plant grown under comparable conditions.

According to an aspect of the present disclosure, a modified, transgenic, or genome edited/mutated corn plant exhibits an increase in ear volume by at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, relative to a control corn plant grown under comparable conditions.

According to an aspect of the present disclosure, a modified, transgenic, or genome edited/mutated corn plant exhibits an ear volume that is between 1% and 100%, between 2% and 100%, between 3% and 100%, between 4% and 100%, between 5% and 100%, between 6% and 100%, between 7% and 100%, between 8% and 100%, between 9% and 100%, between 10% and 100%, between 11% and 100%, between 12% and 100%, between 13% and 100%, between 14% and 100%, between 15% and 100%, between 16% and 100%, between 17% and 100%, between 18% and 100%, between 19% and 100%, between 20% and 100%, between 25% and 100%, between 30% and 100%, between 35% and 100%, between 40% and 100%, between 45% and 100%, between 50% and 100%, between 55% and 100%, between 60% and 100%, between 65% and 100%, between 70% and 100%, between 75% and 100%, between 80% and 100%, between 85% and 100%, between 90% and 100%, or between 95% and 100% greater than that of a control corn plant grown under comparable conditions.

According to an aspect of the present disclosure, a modified, transgenic, or genome edited/mutated corn plant exhibits an ear volume that is between 1% and 95%, between 1% and 90%, between 1% and 85%, between 1% and 80%, between 1% and 75%, between 1% and 70%, between 1% and 65%, between 1% and 60%, between 1% and 55%, between 1% and 50%, between 1% and 45%, between 1% and 40%, between 1% and 35%, between 1% and 30%, between 1% and 25%, between 1% and 20%, between 1% and 19%, between 1% and 18%, between 1% and 17%, between 1% and 16%, between 1% and 15%, between 1% and 14%, between 1% and 13%, between 1% and 12%, between 1% and 11%, between 1% and 10%, between 1% and 9%, between 1% and 8%, between 1% and 7%, between 1% and 6%, between 1% and 5%, between 1% and 4%, between 1% and 3%, or between 1% and 2% greater than that of a control corn plant grown under comparable conditions.

According to an aspect of the present disclosure, a modified, transgenic, or genome edited/mutated corn plant exhibits an ear volume that is between 2% and 90%, between 3% and 85%, between 4% and 80%, between 5% and 75%, between 6% and 70%, between 7% and 65%, between 8% and 60%, between 9% and 55%, between 10% and 50%, between 11% and 45%, between 12% and 40%, between 13% and 35%, between 14% and 30%, or between 15% and 25% greater than that of a control corn plant grown under comparable conditions.

According to an aspect of the present disclosure, a modified, transgenic, or genome edited/mutated corn plant exhibits an ear volume that is between 1% and 5%, between 5% and 10%, between 10% and 20%, between 20% and 30%, between 30% and 40%, between 40% and 50%, between 50% and 60%, between 60% and 70%, between 70% and 80%, between 80% and 90%, or between 90% and 100% greater than that of a control corn plant grown under comparable conditions.

In an aspect, a modified, transgenic, or genome edited/mutated corn plant exhibits increased ear diameter relative to a control corn plant grown under comparable conditions.

According to an aspect of the present disclosure, a modified, transgenic, or genome edited/mutated corn plant exhibits an ear diameter that is at least 0.2%, at least 0.4%, at least 0.6%, at least 0.8%, at least 1.0%, at least 1.2%, at least 1.4%, at least 1.6%, at least 1.8%, at least 2.0%, at least 2.2%, at least 2.4%, at least 2.6%, at least 2.8%, at least 3.0%, at least 3.2%, at least 3.4%, at least 3.6%, at least 3.8%, at least 4.0%, at least 4.5%, at least 5.0%, at least 5.5%, at least 6.0%, at least 6.5%, at least 7.0%, at least 7.5%, at least 8.0%, at least 8.5%, at least 9.0%, at least 9.5%, at least 10.0%, relative to a control corn plant.

According to an aspect of the present disclosure, a modified, transgenic, or genome edited/mutated corn plant exhibits an ear diameter that is between 0.2% and 10.0%, between 0.4% and 10.0%, between 0.6% and 10.0%, between 0.8% and 10.0%, between 1.0% and 10.0%, between 1.2% and 10.0%, between 1.4% and 10.0%, between 1.6% and 10.0%, between 1.8% and 10.0%, between 2.0% and 10.0%, between 2.2% and 10.0%, between 2.4% and 10.0%, between 2.6% and 10.0%, between 2.8% and 10.0%, between 3.0% and 10.0%, between 3.2% and 10.0%, between 3.4% and 10.0%, between 3.6% and 10.0%, between 3.8% and 10.0%, between 4.0% and 10.0%, between 4.5% and 10.0%, between 5.0% and 10.0%, between 5.5% and 10.0%, between 6.0% and 10.0%, between 6.5% and 10.0%, between 7.0% and 10.0%, between 7.5% and 10.0%, between 8.0% and 10.0%, between 8.5% and 10.0%, between 9.0% and 10.0%, or between 9.5% and 10.0%, greater than that of a control corn plant grown under comparable conditions.

According to an aspect of the present disclosure, a modified, transgenic, or genome edited/mutated corn plant exhibits an ear diameter that is between 0.2% and 9.5%, between 0.2% and 9.0%, between 0.2% and 8.5%, between 0.2% and 8.0%, between 0.2% and 7.5%, between 0.2% and 7.0%, between 0.2% and 6.5%, between 0.2% and 6.0%, between 0.2% and 5.5%, between 0.2% and 5.0%, between 0.2% and 4.5%, between 0.2% and 4.0%, between 0.2% and 3.8%, between 0.2% and 3.6%, between 0.2% and 3.4%, between 0.2% and 3.2%, between 0.2% and 3.0%, between 0.2% and 2.8%, between 0.2% and 2.6%, between 0.2% and 2.4%, between 0.2% and 2.2%, between 0.2% and 2.0%, between 0.2% and 1.8%, between 0.2% and 1.6%, between 0.2% and 1.4%, between 0.2% and 1.2%, between 0.2% and 1.0%, between 0.2% and 0.8%, between 0.2% and 0.6%, or between 0.2% and 0.4%, greater than that of a control corn plant grown under comparable conditions.

According to an aspect of the present disclosure, a modified, transgenic, or genome edited/mutated corn plant exhibits an ear diameter that is between 0.4% and 9.5%, between 0.6% and 9.0%, between 0.8% and 8.5%, between 1.0% and 8.0%, between 1.2% and 7.5%, between 1.4% and 7.0%, between 1.6% and 6.5%, between 1.8% and 6.0%, between 2.0% and 5.5%, between 2.2% and 5.0%, between 2.4% and 4.5%, between 2.6% and 4.0%, between 2.8% and 3.8%, between 3.0% and 3.6%, or between 3.2% and 3.4%, greater than that of a control corn plant grown under comparable conditions.

According to an aspect of the present disclosure, a modified, transgenic, or genome edited/mutated corn plant exhibits an ear diameter that is between 0.2% and 0.6%, between 0.6% and 1.0%, between 1.0% and 1.4%, between 1.4% and 1.8%, between 1.8% and 2.2%, between 2.2% and 2.6%, between 2.6% and 3.0%, between 3.0% and 3.5%, between 3.5% and 4.0%, between 4.0% and 4.5%, between 4.5% and 5.0%, between 5.0% and 5.5%, between 5.5% and 6.0%, between 6.0% and 6.5%, between 6.5% and 7.0%, between 7.0% and 7.5%, between 7.5% and 8.0%, between 8.0% and 8.5%, between 8.5% and 9.0%, between 9.0% and 9.5%, or between 9.5% and 10.0%, greater than that of a control corn plant grown under comparable conditions.

In an aspect, a modified, transgenic, or genome edited/mutated corn plant exhibits increased ear length relative to a control corn plant grown under comparable conditions.

According to an aspect of the present disclosure, a modified, transgenic, or genome edited/mutated corn plant exhibits an increase in ear length by at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, relative to a control corn plant grown under comparable conditions.

According to an aspect of the present disclosure, a modified, transgenic, or genome edited/mutated corn plant exhibits an ear length that is between 1% and 100%, between 2% and 100%, between 3% and 100%, between 4% and 100%, between 5% and 100%, between 6% and 100%, between 7% and 100%, between 8% and 100%, between 9% and 100%, between 10% and 100%, between 11% and 100%, between 12% and 100%, between 13% and 100%, between 14% and 100%, between 15% and 100%, between 16% and 100%, between 17% and 100%, between 18% and 100%, between 19% and 100%, between 20% and 100%, between 25% and 100%, between 30% and 100%, between 35% and 100%, between 40% and 100%, between 45% and 100%, between 50% and 100%, between 55% and 100%, between 60% and 100%, between 65% and 100%, between 70% and 100%, between 75% and 100%, between 80% and 100%, between 85% and 100%, between 90% and 100%, or between 95% and 100% greater than that of a corn plant grown under comparable conditions.

According to an aspect of the present disclosure, a modified, transgenic, or genome edited/mutated corn plant exhibits an ear length that is between 1% and 95%, between 1% and 90%, between 1% and 85%, between 1% and 80%, between 1% and 75%, between 1% and 70%, between 1% and 65%, between 1% and 60%, between 1% and 55%, between 1% and 50%, between 1% and 45%, between 1% and 40%, between 1% and 35%, between 1% and 30%, between 1% and 25%, between 1% and 20%, between 1% and 19%, between 1% and 18%, between 1% and 17%, between 1% and 16%, between 1% and 15%, between 1% and 14%, between 1% and 13%, between 1% and 12%, between 1% and 11%, between 1% and 10%, between 1% and 9%, between 1% and 8%, between 1% and 7%, between 1% and 6%, between 1% and 5%, between 1% and 4%, between 1% and 3%, or between 1% and 2% greater than that of a control corn plant grown under comparable conditions.

According to an aspect of the present disclosure, a modified, transgenic, or genome edited/mutated corn plant exhibits an ear length that is between 2% and 90%, between 3% and 85%, between 4% and 80%, between 5% and 75%, between 6% and 70%, between 7% and 65%, between 8% and 60%, between 9% and 55%, between 10% and 50%, between 11% and 45%, between 12% and 40%, between 13% and 35%, between 14% and 30%, or between 15% and 25% greater than that of a control corn plant grown under comparable conditions.

According to an aspect of the present disclosure, a modified, transgenic, or genome edited/mutated corn plant exhibits an ear length that is between 1% and 5%, between 5% and 10%, between 10% and 20%, between 20% and 30%, between 30% and 40%, between 40% and 50%, between 50% and 60%, between 60% and 70%, between 70% and 80%, between 80% and 90%, or between 90% and 100% greater than that of a control corn plant grown under comparable conditions.

In an aspect, a modified, transgenic, or genome edited/mutated corn plant exhibits decreased ear tip void relative to a control corn plant grown under comparable conditions.

According to an aspect of the present disclosure, a modified, transgenic, or genome edited/mutated corn plant exhibits an decrease in ear tip void by at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, relative to a control corn plant grown under comparable conditions.

According to an aspect of the present disclosure, a modified, transgenic, or genome edited/mutated corn plant exhibits an ear tip void that is between 1% and 100%, between 2% and 100%, between 3% and 100%, between 4% and 100%, between 5% and 100%, between 6% and 100%, between 7% and 100%, between 8% and 100%, between 9% and 100%, between 10% and 100%, between 11% and 100%, between 12% and 100%, between 13% and 100%, between 14% and 100%, between 15% and 100%, between 16% and 100%, between 17% and 100%, between 18% and 100%, between 19% and 100%, between 20% and 100%, between 25% and 100%, between 30% and 100%, between 35% and 100%, between 40% and 100%, between 45% and 100%, between 50% and 100%, between 55% and 100%, between 60% and 100%, between 65% and 100%, between 70% and 100%, between 75% and 100%, between 80% and 100%, between 85% and 100%, between 90% and 100%, or between 95% and 100% less than that of a control corn plant grown under comparable conditions.

According to an aspect of the present disclosure, a modified, transgenic, or genome edited/mutated corn plant exhibits an ear tip void that is between 1% and 95%, between 1% and 90%, between 1% and 85%, between 1% and 80%, between 1% and 75%, between 1% and 70%, between 1% and 65%, between 1% and 60%, between 1% and 55%, between 1% and 50%, between 1% and 45%, between 1% and 40%, between 1% and 35%, between 1% and 30%, between 1% and 25%, between 1% and 20%, between 1% and 19%, between 1% and 18%, between 1% and 17%, between 1% and 16%, between 1% and 15%, between 1% and 14%, between 1% and 13%, between 1% and 12%, between 1% and 11%, between 1% and 10%, between 1% and 9%, between 1% and 8%, between 1% and 7%, between 1% and 6%, between 1% and 5%, between 1% and 4%, between 1% and 3%, or between 1% and 2% less than that of a control corn plant grown under comparable conditions.

According to an aspect of the present disclosure, a modified, transgenic, or genome edited/mutated corn plant exhibits an ear tip void that is between 2% and 90%, between 3% and 85%, between 4% and 80%, between 5% and 75%, between 6% and 70%, between 7% and 65%, between 8% and 60%, between 9% and 55%, between 10% and 50%, between 11% and 45%, between 12% and 40%, between 13% and 35%, between 14% and 30%, or between 15% and 25% less than that of a control corn plant grown under comparable conditions.

According to an aspect of the present disclosure, a modified, transgenic, or genome edited/mutated corn plant exhibits an ear tip void that is between 1% and 5%, between 5% and 10%, between 10% and 20%, between 20% and 30%, between 30% and 40%, between 40% and 50%, between 50% and 60%, between 60% and 70%, between 70% and 80%, between 80% and 90%, or between 90% and 100% less than that of a control corn plant grown under comparable conditions.

In an aspect, a modified, transgenic, or genome edited/mutated corn plant exhibits an increased number of kernels per ear relative to a control corn plant grown under comparable conditions.

According to an aspect of the present disclosure, a modified, transgenic, or genome edited/mutated corn plant exhibits an increase in number of kernels per ear by at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, relative to a control corn plant grown under comparable conditions.

According to an aspect of the present disclosure, a modified, transgenic, or genome edited/mutated corn plant exhibits kernels per ear that is between 1% and 100%, between 2% and 100%, between 3% and 100%, between 4% and 100%, between 5% and 100%, between 6% and 100%, between 7% and 100%, between 8% and 100%, between 9% and 100%, between 10% and 100%, between 11% and 100%, between 12% and 100%, between 13% and 100%, between 14% and 100%, between 15% and 100%, between 16% and 100%, between 17% and 100%, between 18% and 100%, between 19% and 100%, between 20% and 100%, between 25% and 100%, between 30% and 100%, between 35% and 100%, between 40% and 100%, between 45% and 100%, between 50% and 100%, between 55% and 100%, between 60% and 100%, between 65% and 100%, between 70% and 100%, between 75% and 100%, between 80% and 100%, between 85% and 100%, between 90% and 100%, or between 95% and 100% greater than that of a control corn plant grown under comparable conditions.

According to an aspect of the present disclosure, a modified, transgenic, or genome edited/mutated corn plant exhibits kernels per ear that is between 1% and 95%, between 1% and 90%, between 1% and 85%, between 1% and 80%, between 1% and 75%, between 1% and 70%, between 1% and 65%, between 1% and 60%, between 1% and 55%, between 1% and 50%, between 1% and 45%, between 1% and 40%, between 1% and 35%, between 1% and 30%, between 1% and 25%, between 1% and 20%, between 1% and 19%, between 1% and 18%, between 1% and 17%, between 1% and 16%, between 1% and 15%, between 1% and 14%, between 1% and 13%, between 1% and 12%, between 1% and 11%, between 1% and 10%, between 1% and 9%, between 1% and 8%, between 1% and 7%, between 1% and 6%, between 1% and 5%, between 1% and 4%, between 1% and 3%, or between 1% and 2% greater than that of a control corn plant grown under comparable conditions.

According to an aspect of the present disclosure, a modified, transgenic, or genome edited/mutated corn plant exhibits kernels per ear that is between 2% and 90%, between 3% and 85%, between 4% and 80%, between 5% and 75%, between 6% and 70%, between 7% and 65%, between 8% and 60%, between 9% and 55%, between 10% and 50%, between 11% and 45%, between 12% and 40%, between 13% and 35%, between 14% and 30%, or between 15% and 25% greater than that of a control corn plant grown under comparable conditions.

According to an aspect of the present disclosure, a modified, transgenic, or genome edited/mutated corn plant exhibits kernels per ear that is between 1% and 5%, between 5% and 10%, between 10% and 20%, between 20% and 30%, between 30% and 40%, between 40% and 50%, between 50% and 60%, between 60% and 70%, between 70% and 80%, between 80% and 90%, or between 90% and 100% greater than that of a control corn plant grown under comparable conditions.

In an aspect, a modified, transgenic, or genome edited/mutated corn plant exhibits increased single kernel weight relative to a control corn plant grown under comparable conditions.

According to an aspect of the present disclosure, a modified, transgenic, or genome edited/mutated corn plant exhibits an increase in single kernel weight by at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, relative to a control corn plant grown under comparable conditions.

According to an aspect of the present disclosure, a modified, transgenic, or genome edited/mutated corn plant exhibits a single kernel weight that is between 1% and 100%, between 2% and 100%, between 3% and 100%, between 4% and 100%, between 5% and 100%, between 6% and 100%, between 7% and 100%, between 8% and 100%, between 9% and 100%, between 10% and 100%, between 11% and 100%, between 12% and 100%, between 13% and 100%, between 14% and 100%, between 15% and 100%, between 16% and 100%, between 17% and 100%, between 18% and 100%, between 19% and 100%, between 20% and 100%, between 25% and 100%, between 30% and 100%, between 35% and 100%, between 40% and 100%, between 45% and 100%, between 50% and 100%, between 55% and 100%, between 60% and 100%, between 65% and 100%, between 70% and 100%, between 75% and 100%, between 80% and 100%, between 85% and 100%, between 90% and 100%, or between 95% and 100% greater than that of a control corn plant grown under comparable conditions.

According to an aspect of the present disclosure, a modified, transgenic, or genome edited/mutated corn plant exhibits a single kernel weight that is between 1% and 95%, between 1% and 90%, between 1% and 85%, between 1% and 80%, between 1% and 75%, between 1% and 70%, between 1% and 65%, between 1% and 60%, between 1% and 55%, between 1% and 50%, between 1% and 45%, between 1% and 40%, between 1% and 35%, between 1% and 30%, between 1% and 25%, between 1% and 20%, between 1% and 19%, between 1% and 18%, between 1% and 17%, between 1% and 16%, between 1% and 15%, between 1% and 14%, between 1% and 13%, between 1% and 12%, between 1% and 11%, between 1% and 10%, between 1% and 9%, between 1% and 8%, between 1% and 7%, between 1% and 6%, between 1% and 5%, between 1% and 4%, between 1% and 3%, or between 1% and 2% greater than that of a control corn plant grown under comparable conditions.

According to an aspect of the present disclosure, a modified, transgenic, or genome edited/mutated corn plant exhibits a single kernel weight that is between 2% and 90%, between 3% and 85%, between 4% and 80%, between 5% and 75%, between 6% and 70%, between 7% and 65%, between 8% and 60%, between 9% and 55%, between 10% and 50%, between 11% and 45%, between 12% and 40%, between 13% and 35%, between 14% and 30%, or between 15% and 25% greater than that of a control corn plant grown under comparable conditions.

According to an aspect of the present disclosure, a modified, transgenic, or genome edited/mutated corn plant exhibits a single kernel weight that is between 1% and 5%, between 5% and 10%, between 10% and 20%, between 20% and 30%, between 30% and 40%, between 40% and 50%, between 50% and 60%, between 60% and 70%, between 70% and 80%, between 80% and 90%, or between 90% and 100% greater than that of a control corn plant grown under comparable conditions.

According to an aspect of the present disclosure, a modified, transgenic, or genome edited/mutated corn plant exhibits a single kernel weight that is between 1% and 2%, between 2% and 3%, between 3% and 4%, between 4% and 5%, between 5% and 6%, between 6% and 7%, between 7% and 8%, between 8% and 9%, or between 9% and 10% greater than that of a control corn plant grown under comparable conditions.

In an aspect, a modified, transgenic, or genome edited/mutated corn plant exhibits increased ear fresh weight relative to a control corn plant.

According to an aspect of the present disclosure, a modified, transgenic, or genome edited/mutated corn plant exhibits an increased ear fresh weight by at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, at least 25%, at least 26%, at least 27%, at least 28%, at least 29%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% relative to a control corn plant grown under comparable conditions.

According to an aspect of the present disclosure, a modified, transgenic, or genome edited/mutated corn plant exhibits an ear fresh weight that is between 1% and 100%, between 2% and 100%, between 3% and 100%, between 4% and 100%, between 5% and 100%, between 6% and 100%, between 7% and 100%, between 8% and 100%, between 9% and 100%, between 10% and 100%, between 11% and 100%, between 12% and 100%, between 13% and 100%, between 14% and 100%, between 15% and 100%, between 16% and 100%, between 17% and 100%, between 18% and 100%, between 19% and 100%, between 20% and 100%, between 21% and 100%, between 22% and 100%, between 23% and 100%, between 24% and 100%, between 25% and 100%, between 26% and 100%, between 27% and 100%, between 28% and 100%, between 29% and 100%, between 30% and 100%, between 35% and 100%, between 40% and 100%, between 45% and 100%, between 50% and 100%, between 55% and 100%, between 60% and 100%, between 65% and 100%, between 70% and 100%, between 75% and 100%, between 80% and 100%, between 85% and 100%, between 90% and 100%, or between 95% and 100% greater than that of a control corn plant grown under comparable conditions.

According to an aspect of the present disclosure, a modified, transgenic, or genome edited/mutated corn plant exhibits an ear fresh weight that is between 1% and 95%, between 1% and 90%, between 1% and 85%, between 1% and 80%, between 1% and 75%, between 1% and 70%, between 1% and 65%, between 1% and 60%, between 1% and 55%, between 1% and 50%, between 1% and 45%, between 1% and 40%, between 1% and 35%, between 1% and 30%, between 1% and 29%, between 1% and 28%, between 1% and 27%, between 1% and 26%, between 1% and 25%, between 1% and 24%, between 1% and 23%, between 1% and 22%, between 1% and 21%, between 1% and 20%, between 1% and 19%, between 1% and 18%, between 1% and 17%, between 1% and 16%, between 1% and 15%, between 1% and 14%, between 1% and 13%, between 1% and 12%, between 1% and 11%, between 1% and 10%, between 1% and 9%, between 1% and 8%, between 1% and 7%, between 1% and 6%, between 1% and 5%, between 1% and 4%, between 1% and 3%, or between 1% and 2% greater than that of a control corn plant grown under comparable conditions.

According to an aspect of the present disclosure, a modified, transgenic, or genome edited/mutated corn plant exhibits an ear fresh weight that is between 2% and 90%, between 3% and 85%, between 4% and 80%, between 5% and 75%, between 6% and 70%, between 7% and 65%, between 8% and 60%, between 9% and 55%, between 10% and 50%, between 11% and 45%, between 12% and 40%, between 13% and 35%, between 14% and 30%, or between 15% and 25% greater than that of a control corn plant grown under comparable conditions.

According to an aspect of the present disclosure, a modified, transgenic, or genome edited/mutated corn plant exhibits an ear fresh weight that is between 1% and 5%, between 5% and 10%, between 10% and 15%, between 15% and 20%, between 20% and 25%, between 25% and 30%, between 30% and 40%, between 40% and 50%, between 50% and 60%, between 60% and 70%, between 70% and 80%, between 80% and 90%, or between 90% and 100% greater than that of a control corn plant grown under comparable conditions.

According to an aspect of the present disclosure, a modified, transgenic, or genome edited/mutated corn plant exhibits an ear fresh weight that is between 1% and 2%, between 2% and 3%, between 3% and 4%, between 4% and 5%, between 5% and 6%, between 6% and 7%, between 7% and 8%, between 8% and 9%, between 9% and 10%, between 10% and 11%, between 11% and 12%, between 12% and 13%, between 13% and 14%, between 14% and 15%, between 15% and 16%, between 16% and 17%, between 17% and 18%, between 18% and 19%, between 19% and 20%, between 20% and 21%, between 21% and 22%, between 22% and 23%, between 23% and 24%, between 24% and 25%, between 25% and 26%, between 26% and 27%, between 27% and 28%, between 28% and 29%, between 29% and 30%, greater than that of a control corn plant grown under comparable conditions.

In an aspect, a modified, transgenic, or genome edited/mutated corn plant exhibits an increased yield relative to a control corn plant.

According to an aspect of the present disclosure, a modified, transgenic, or genome edited/mutated corn plant exhibits an increased yield by at least 1%, at least 3%, at least 5%, at least 7%, at least 9%, at least 11%, at least 13%, at least 15%, at least 17%, at least 19%, at least 21%, at least 23%, at least 25%, at least 27%, at least 29%, at least 31%, at least 33%, at least 35%, at least 37%, at least 39%, at least 41%, at least 43%, at least 45%, at least 47%, at least 49%, at least 50%, at least 55%, at least 60%, at least 65%, at least 70%, at least 75%, at least 80%, at least 85%, at least 90%, at least 95%, at least 100%, relative to a control corn plant grown under comparable conditions.

According to an aspect of the present disclosure, a modified, transgenic, or genome edited/mutated corn plant exhibits a yield that is between 1% and 100%, between 3% and 100%, between 5% and 100%, between 7% and 100%, between 9% and 100%, between 11% and 100%, between 13% and 100%, between 15% and 100%, between 17% and 100%, between 19% and 100%, between 21% and 100%, between 23% and 100%, between 25% and 100%, between 27% and 100%, between 29% and 100%, between 31% and 100%, between 33% and 100%, between 35% and 100%, between 37% and 100%, between 39% and 100%, between 41% and 100%, between 43% and 100%, between 45% and 100%, between 47% and 100%, between 49% and 100%, between 50% and 100%, between 55% and 100%, between 60% and 100%, between 65% and 100%, between 70% and 100%, between 75% and 100%, between 80% and 100%, between 85% and 100%, between 90% and 100%, between 95% and 100%, greater than that of a control corn plant grown under comparable conditions.

According to an aspect of the present disclosure, a modified, transgenic, or genome edited/mutated corn plant exhibits a yield that is between 1% and 95%, between 1% and 90%, between 1% and 85%, between 1% and 80%, between 1% and 75%, between 1% and 70%, between 1% and 65%, between 1% and 60%, between 1% and 55%, between 1% and 50%, between 1% and 49%, between 1% and 47%, between 1% and 45%, between 1% and 43%, between 1% and 41%, between 1% and 39%, between 1% and 37%, between 1% and 35%, between 1% and 33%, between 1% and 31%, between 1% and 29%, between 1% and 27%, between 1% and 25%, between 1% and 23%, between 1% and 21%, between 1% and 19%, between 1% and 17%, between 1% and 15%, between 1% and 13%, between 1% and 11%, between 1% and 9%, between 1% and 7%, between 1% and 5%, or between 1% and 3%, greater than that of a control corn plant grown under comparable conditions.

According to an aspect of the present disclosure, a modified, transgenic, or genome edited/mutated corn plant exhibits a yield that is between 3% and 95%, between 5% and 90%, between 7% and 85%, between 9% and 80%, between 11% and 75%, between 13% and 70%, between 15% and 65%, between 17% and 60%, between 19% and 55%, between 21% and 50%, between 23% and 49%, between 25% and 47%, between 27% and 45%, between 29% and 43%, between 31% and 41%, between 33% and 39%, or between 35% and 37%, greater than that of a control corn plant grown under comparable conditions.

According to an aspect of the present disclosure, a modified, transgenic, or genome edited/mutated corn plant exhibits a yield that is between 1% and 7%, between 7% and 13%, between 13% and 19%, between 19% and 25%, between 25% and 31%, between 31% and 37%, between 37% and 43%, between 43% and 49%, between 49% and 55%, between 55% and 60%, between 60% and 65%, between 65% and 70%, between 70% and 75%, between 75% and 80%, between 80% and 85%, between 85% and 90%, between 90% and 95%, or between 95% and 100%, greater than that of a control corn plant grown under comparable conditions.

In an aspect, modified, transgenic, or genome edited/mutated corn plants exhibit increased kernels per field area relative to control corn plants.

According to an aspect of the present disclosure, modified, transgenic, or genome edited/mutated corn plants exhibit increased kernels per field area by at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, at least 25%, at least 26%, at least 27%, at least 28%, at least 29%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, relative to control corn plants.

According to an aspect of the present disclosure, modified, transgenic, or genome edited/mutated corn plants exhibit kernels per field area that is between 1% and 100%, between 2% and 100%, between 3% and 100%, between 4% and 100%, between 5% and 100%, between 6% and 100%, between 7% and 100%, between 8% and 100%, between 9% and 100%, between 10% and 100%, between 11% and 100%, between 12% and 100%, between 13% and 100%, between 14% and 100%, between 15% and 100%, between 16% and 100%, between 17% and 100%, between 18% and 100%, between 19% and 100%, between 20% and 100%, between 21% and 100%, between 22% and 100%, between 23% and 100%, between 24% and 100%, between 25% and 100%, between 26% and 100%, between 27% and 100%, between 28% and 100%, between 29% and 100%, between 30% and 100%, between 35% and 100%, between 40% and 100%, between 45% and 100%, between 50% and 100%, between 55% and 100%, between 60% and 100%, between 65% and 100%, between 70% and 100%, between 75% and 100%, between 80% and 100%, between 85% and 100%, between 90% and 100%, or between 95% and 100% greater than that of control corn plants grown under comparable conditions.

According to an aspect of the present disclosure, modified, transgenic, or genome edited/mutated corn plants exhibit kernels per field area that is between 1% and 95%, between 1% and 90%, between 1% and 85%, between 1% and 80%, between 1% and 75%, between 1% and 70%, between 1% and 65%, between 1% and 60%, between 1% and 55%, between 1% and 50%, between 1% and 45%, between 1% and 40%, between 1% and 35%, between 1% and 30%, between 1% and 29%, between 1% and 28%, between 1% and 27%, between 1% and 26%, between 1% and 25%, between 1% and 24%, between 1% and 23%, between 1% and 22%, between 1% and 21%, between 1% and 20%, between 1% and 19%, between 1% and 18%, between 1% and 17%, between 1% and 16%, between 1% and 15%, between 1% and 14%, between 1% and 13%, between 1% and 12%, between 1% and 11%, between 1% and 10%, between 1% and 9%, between 1% and 8%, between 1% and 7%, between 1% and 6%, between 1% and 5%, between 1% and 4%, between 1% and 3%, or between 1% and 2% greater than that of control corn plants grown under comparable conditions.

According to an aspect of the present disclosure, modified, transgenic, or genome edited/mutated corn plants exhibit kernels per field area that is between 2% and 90%, between 3% and 85%, between 4% and 80%, between 5% and 75%, between 6% and 70%, between 7% and 65%, between 8% and 60%, between 9% and 55%, between 10% and 50%, between 11% and 45%, between 12% and 40%, between 13% and 35%, between 14% and 30%, or between 15% and 25% greater than that of control corn plants grown under comparable conditions.

According to an aspect of the present disclosure, modified, transgenic, or genome edited/mutated corn plants exhibit kernels per field area that is between 1% and 5%, between 5% and 10%, between 10% and 20%, between 20% and 30%, between 30% and 40%, between 40% and 50%, between 50% and 60%, between 60% and 70%, between 70% and 80%, between 80% and 90%, or between 90% and 100% greater than that of control corn plants grown under comparable conditions.

According to an aspect of the present disclosure, modified, transgenic, or genome edited/mutated corn plants exhibit kernels per field area that is between 1% and 3%, between 3% and 5%, between 5% and 7%, between 7% and 9%, between 9% and 11%, between 11% and 13%, between 13% and 15%, between 15% and 17%, between 17% and 19%, between 19% and 21%, between 21% and 23%, between 23% and 25%, between 25% and 27%, between 27% and 29%, or between 29% and 30% greater than that of control corn plants grown under comparable conditions.

In an aspect, a modified, transgenic, or genome edited/mutated corn plant exhibits increased number of florets relative to a control corn plant.

According to an aspect of the present disclosure, a modified, transgenic, or genome edited/mutated corn plant exhibits increased number of florets by at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, at least 25%, at least 26%, at least 27%, at least 28%, at least 29%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, relative to a control corn plant.

According to an aspect of the present disclosure, a modified, transgenic, or genome edited/mutated corn plant exhibits a number of florets that is between 1% and 100%, between 2% and 100%, between 3% and 100%, between 4% and 100%, between 5% and 100%, between 6% and 100%, between 7% and 100%, between 8% and 100%, between 9% and 100%, between 10% and 100%, between 11% and 100%, between 12% and 100%, between 13% and 100%, between 14% and 100%, between 15% and 100%, between 16% and 100%, between 17% and 100%, between 18% and 100%, between 19% and 100%, between 20% and 100%, between 21% and 100%, between 22% and 100%, between 23% and 100%, between 24% and 100%, between 25% and 100%, between 26% and 100%, between 27% and 100%, between 28% and 100%, between 29% and 100%, between 30% and 100%, between 35% and 100%, between 40% and 100%, between 45% and 100%, between 50% and 100%, between 55% and 100%, between 60% and 100%, between 65% and 100%, between 70% and 100%, between 75% and 100%, between 80% and 100%, between 85% and 100%, between 90% and 100%, or between 95% and 100% greater than that of a control corn plant grown under comparable conditions.

According to an aspect of the present disclosure, a modified, transgenic, or genome edited/mutated corn plant exhibits a number of florets that is between 1% and 95%, between 1% and 90%, between 1% and 85%, between 1% and 80%, between 1% and 75%, between 1% and 70%, between 1% and 65%, between 1% and 60%, between 1% and 55%, between 1% and 50%, between 1% and 45%, between 1% and 40%, between 1% and 35%, between 1% and 30%, between 1% and 29%, between 1% and 28%, between 1% and 27%, between 1% and 26%, between 1% and 25%, between 1% and 24%, between 1% and 23%, between 1% and 22%, between 1% and 21%, between 1% and 20%, between 1% and 19%, between 1% and 18%, between 1% and 17%, between 1% and 16%, between 1% and 15%, between 1% and 14%, between 1% and 13%, between 1% and 12%, between 1% and 11%, between 1% and 10%, between 1% and 9%, between 1% and 8%, between 1% and 7%, between 1% and 6%, between 1% and 5%, between 1% and 4%, between 1% and 3%, or between 1% and 2% greater than that of a control corn plant grown under comparable conditions.

According to an aspect of the present disclosure, a modified, transgenic, or genome edited/mutated corn plant exhibits a number of florets that is between 2% and 90%, between 3% and 85%, between 4% and 80%, between 5% and 75%, between 6% and 70%, between 7% and 65%, between 8% and 60%, between 9% and 55%, between 10% and 50%, between 11% and 45%, between 12% and 40%, between 13% and 35%, between 14% and 30%, or between 15% and 25% greater than that of a control corn plant grown under comparable conditions.

According to an aspect of the present disclosure, a modified, transgenic, or genome edited/mutated corn plant exhibits a number of florets that is between 1% and 5%, between 5% and 10%, between 10% and 20%, between 20% and 30%, between 30% and 40%, between 40% and 50%, between 50% and 60%, between 60% and 70%, between 70% and 80%, between 80% and 90%, or between 90% and 100% greater than that of a control corn plant grown under comparable conditions.

According to an aspect of the present disclosure, a modified, transgenic, or genome edited/mutated corn plant exhibits a number of florets that is between 1% and 3%, between 3% and 5%, between 5% and 7%, between 7% and 9%, between 9% and 11%, between 11% and 13%, between 13% and 15%, between 15% and 17%, between 17% and 19%, between 19% and 21%, between 21% and 23%, between 23% and 25%, between 25% and 27%, between 27% and 29%, or between 29% and 30% greater than that of a control corn plant grown under comparable conditions.

A modified, transgenic, or genome edited/mutated corn plant disclosed in the present disclosure can display a positive trait interaction in which a trait, such as a positive or negative trait, attributable to a transgene (or mutation or edit) can be enhanced, out-performed, neutralized, offset or mitigated due to the presence of a second transgene (or mutation or edit). Such a transgenic and/or genome edited/mutated corn plant can exhibit improved ear traits as compared to a control corn plant comprising only one transgene (or mutation or edit). For example, GA20Ox_SUP/PpCOL stack plants may have enhanced traits and/or positive trait interactions relative to PpCOL single and/or GA20Ox_SUP single plants, in terms of increased ear area, number of florets per ear, single kernel weight, ear fresh weight, and/or yield.

In another aspect, a modified, transgenic, or genome edited/mutated corn plant of the present disclosure exhibits a trait selected from the group consisting of deeper roots, increased leaf area, earlier canopy closure, higher stomatal conductance, lower ear height, increased foliar water content, improved drought tolerance, improved nitrogen use efficiency, reduced anthocyanin content and area in leaves under normal or nitrogen-limiting or water-limiting stress conditions, increased ear weight, increased harvest index, increased seed number, increased seed weight, increased prolificacy, and a combination thereof, relative to a control corn plant.

In yet another aspect, a modified, transgenic, or genome edited/mutated corn plant of the present disclosure does not have any significant off-types in at least one female organ or ear.

According to an aspect of the present disclosure, a modified, transgenic, or genome edited/mutated corn plant has no or reduced adverse effect over a trait or phenotype selected from the group consisting of senescence, delayed flowering, fungal infection, and a combination thereof, relative to a control corn plant.

Short stature or semi-dwarf corn plants can also have one or more additional traits, including increased stem diameter, reduced green snap, deeper roots, increased leaf area, earlier canopy closure, higher stomatal conductance, lower ear height, increased foliar water content, improved drought tolerance, increased nitrogen use efficiency, increased water use efficiency, reduced anthocyanin content and area in leaves under normal or nitrogen or water limiting stress conditions, increased ear weight, increased kernel number, increased kernel weight, increased yield, and/or increased harvest index.

According to an aspect of the present disclosure, a modified, transgenic, or genome edited/mutated corn plant provided herein comprises a harvest index of at least 0.57, at least 0.58, at least 0.59, at least 0.60, at least 0.61, at least 0.62, at least 0.63, at least 0.64, or at least 0.65. According to another aspect of the present disclosure a modified, transgenic, or genome edited/mutated corn plant provided herein comprises a harvest index of between 0.57 and 0.65, between 0.57 and 0.64, between 0.57 and 0.63, between 0.57 and 0.62, between 0.57 and 0.61, between 0.57 and 0.60, between 0.57 and 0.59, between 0.57 and 0.58, between 0.58 and 0.65, between 0.59 and 0.65, or between 0.60 and 0.65. According to yet another aspect of the present disclosure, a modified, transgenic, or genome edited/mutated corn plant provided herein comprises a harvest index that is at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 20%, at least 25%, at least 30%, at least 35%, at least 40%, at least 45%, or at least 50% greater as compared to an unmodified control plant. According to still another aspect of the present disclosure, a modified, transgenic, or genome edited/mutated corn plant provided herein comprises a harvest index that is between 1% and 45%, between 1% and 40%, between 1% and 35%, between 1% and 30%, between 1% and 25%, between 1% and 20%, between 1% and 15%, between 1% and 14%, between 1% and 13%, between 1% and 12%, between 1% and 11%, between 1% and 10%, between 1% and 9%, between 1% and 8%, between 1% and 7%, between 1% and 6%, between 1% and 5%, between 1% and 4%, between 1% and 3%, between 1% and 2%, between 5% and 15%, between 5% and 20%, between 5% and 30%, or between 5% and 40% greater as compared to a control plant.

According to another aspect of the present disclosure, methods are provided for planting a modified or transgenic plant(s) provided herein at a normal/standard or high density in field. According to some aspects, the yield of a crop plant per acre (or per land area) can be increased by planting a modified or transgenic plant(s) of the present disclosure at a higher density in the field. As described herein, modified or transgenic plants expressing a transcribable DNA sequence that encodes a non-coding RNA molecule targeting one or more endogenous GA20 and/or GA3 oxidase gene for suppression and a transgene encoding one or more CO or COL polypeptide, can have reduced plant height, shorter internode(s), increased stalk/stem diameter, and/or increased lodging resistance. Modified or transgenic plants described herein can tolerate high density planting conditions since an increase in stem diameter can resist lodging and the shorter plant height can allow for increased light penetrance to the lower leaves under high density planting conditions. Thus, modified or transgenic plants provided herein can be planted at a higher density to increase the yield per acre (or land area) in the field. For row crops, higher density can be achieved by planting a greater number of seeds/plants per row length and/or by decreasing the spacing between rows. In an aspect, the row spacing for high density planting of the modified, transgenic, or genome edited/mutated corn plants is less than or equal to 40 inches. In an aspect, the row spacing for high density planting of the modified, transgenic, or genome edited/mutated corn plants is less than or equal to 30 inches. In another aspect, the row spacing for high density planting of the modified, transgenic, or genome edited/mutated corn plants is less than or equal to 20 inches.

According to an aspect, seeds of a modified or transgenic crop plants can be planted at a density in the field (plants per land/field area) that is at least 5%, 10%, 15%, 20%, 25%, 50%, 75%, 100%, 125%, 150%, 175%, 200%, 225%, or 250% higher than the normal planting density for that crop plant according to standard agronomic practices. A modified or transgenic crop plant can be planted at a density in the field of at least 38,000 plants per acre, at least 40,000 plants per acre, at least 42,000 plants per acre, at least 44,000 plants per acre, at least 45,000 plants per acre, at least 46,000 plants per acre, at least 48,000 plants per acre, 50,000 plants per acre, at least 52,000 plants per acre, at least 54,000 per acre, or at least 56,000 plants per acre.

As an example, seeds of corn plants can be planted at a higher density, such as in a range from about 38,000 plants per acre to about 60,000 plants per acre, or about 40,000 plants per acre to about 58,000 plants per acre, or about 42,000 plants per acre to about 58,000 plants per acre, or about 40,000 plants per acre to about 45,000 plants per acre, or about 45,000 plants per acre to about 50,000 plants per acre, or about 50,000 plants per acre to about 58,000 plants per acre, or about 52,000 plants per acre to about 56,000 plants per acre, or about 38,000 plants per acre, about 42,000 plant per acre, about 46,000 plant per acre, or about 48,000 plants per acre, about 50,000 plants per acre, or about 52,000 plants per acre, or about 54,000 plant per acre, as opposed to a standard density range, such as about 18,000 plants per acre to about 38,000 plants per acre.

Exemplary Embodiments

The following are exemplary embodiments of the present specification.

1. A modified corn plant or a plant part thereof comprising 1) a first recombinant expression cassette comprising a transcribable DNA sequence encoding a non-coding RNA for suppression of one or more gibberellic acid 20 (GA20) oxidase genes and/or one or more gibberellic acid 3 (GA3) oxidase genes, and 2) a second recombinant expression cassette comprising a DNA sequence encoding a CON-STANS (CO) or CONSTANS-like (COL) polypeptide.

2. The modified corn plant of embodiment 1, wherein the first and second recombinant expression cassettes are stably integrated into the genome of the corn plant or plant part thereof.

3. The modified corn plant or plant part thereof of embodiment 1, wherein the modified corn plant is semi-dwarf and has one or more improved ear traits, relative to a control corn plant that does not have the first or second recombinant expression cassettes.

4. The modified corn plant or plant part thereof of embodiment 1, 2, or 3, wherein the transcribable DNA sequence encodes a non-coding RNA for suppression of a GA3 oxidase gene.

5. The modified corn plant or plant part thereof of embodiment 4, wherein the transcribable DNA sequence encodes a non-coding RNA for suppression of a GA3 oxidase_1 gene, a GA3 oxidase_2 gene, or both.

6. The modified corn plant or plant part thereof of embodiment 5, wherein the transcribable DNA sequence comprises a sequence that is at least 80%, at least 85%, at least 90%, at least 95%, at least 96%, at least 97%, at least 98%, at least 99%, at least 99.5%, or 100% identical or complementary to at least 15, at least 16, at least 17, at least 18, at least 19, at least 20, at least 21, at least 22, at least 23, at least 24, at least 25, at least 26, or at least 27 consecutive nucleotides of one or more of SEQ ID NOs: 28, 29, 31, 32, 36, and 37.

7. The modified corn plant or plant part thereof of embodiment 5, wherein the transcribable DNA sequence encodes a non-coding RNA comprising a sequence that is 80% complementary to at least 15 consecutive nucleotides of one or more of SEQ ID NOs: 28, 29, 31, 32, 36, and 37.

8. The modified corn plant or plant part thereof of embodiment 1, 2, or 3, wherein the transcribable DNA sequence encodes a non-coding RNA for suppression of a GA20 oxidase gene.

9. The modified corn plant or plant part thereof of embodiment 8, wherein the transcribable DNA sequence encodes a non-coding RNA for suppression of a GA20 oxidase_3 gene, a GA20 oxidase_4 gene, a GA20 oxidase_5 gene, or a combination thereof.

10. The modified corn plant or plant part thereof of embodiment 8, wherein the transcribable DNA sequence encodes a non-coding RNA for suppression of a GA20 oxidase_3 gene, a GA20 oxidase_5 gene, or both.

11. The modified corn plant or plant part thereof of embodiment 10, wherein the transcribable DNA sequence comprises a sequence that is at least 60% identical or complementary to at least 15 consecutive nucleotides of SEQ ID NO: 39, 53, or 55.

12. The modified corn plant or plant part thereof of embodiment 10, wherein the transcribable DNA sequence encodes a sequence that is at least 60% identical or complementary to at least 15 consecutive nucleotides of SEQ ID NO: 40, 54, or 56.

13. The modified corn plant or plant part thereof of any one of embodiments 4 to 10, wherein the non-coding RNA comprises a sequence that is at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous GA oxidase protein in a corn plant or plant cell, the endogenous GA oxidase protein being at least 80%, at least 85%, at least 90%, at least 95%, at least 96%, at least 97%, at least 98%, at least 99%, at least 99.5%, or 100% identical to SEQ ID NO: 9, 12, 15, 30, or 33.

14. The modified corn plant or plant part thereof of any one of embodiments 4 to 10, wherein the non-coding RNA comprises a sequence that is at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of SEQ ID NO: 7, 8, 10, 11, 13, 14, 28, 29, 31, or 32.

15. The modified corn plant or plant part thereof of embodiment 1, 2, or 3, wherein the second recombinant expression cassette comprises a DNA sequence encoding a CO or COL polypeptide.

16. The modified corn plant or plant part thereof of embodiment 15, wherein the CO or COL polypeptide comprises an amino acid sequence that is at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to one or more of SEQ ID NOs: 176-397.

17. The modified corn plant or plant part thereof of embodiment 15, wherein the CO or COL polypeptide comprises an amino acid sequence that is at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to one or more of SEQ ID NOs: 398-452.

18. The modified corn plant or plant part thereof of any one of embodiments 1 to 3, wherein the CO or COL polypeptide comprises a *Physcomitrella patens* CONSTANS-like 1 (PpCOL1) polypeptide.

19. The modified corn plant or plant part thereof of any one of embodiments 1 to 17, wherein the DNA sequence comprised in the second recombinant expression cassette comprises a sequence that is at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 169.

20. The modified corn plant or plant part thereof of any one of embodiments 1 to 17, wherein the CO or COL polypeptide comprises an amino acid sequence that is at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 168

21. The modified corn plant or plant part thereof of embodiment 1 or 3, wherein the expression level of an endogenous GA20 oxidase or GA3 oxidase gene is reduced or eliminated in the modified corn plant or plant part thereof.

22. The modified corn plant or plant part thereof of embodiment 1 or 3, wherein the transcribable DNA sequence is operably linked to a heterologous plant-expressible promoter.

23. The modified corn plant or plant part thereof of embodiment 22, wherein the heterologous plant-expressible promoter is a vascular promoter.

24. The modified corn plant or plant part thereof of embodiment 23, wherein the vascular promoter is selected from the group consisting of a sucrose synthase promoter, a sucrose transporter promoter, a Sh1 promoter, *Commelina* yellow mottle virus (CoYMV) promoter, a wheat dwarf geminivirus (WDV) large intergenic region (LIR) promoter, a maize streak geminivirus (MSV) coat polypeptide (CP) promoter, a rice yellow stripe 1 (YS1)-like promoter, a rice yellow stripe 2 (OsYSL2) promoter, and a combination thereof.

25. The modified corn plant or plant part thereof of embodiment 24, wherein the vascular promoter comprises a DNA sequence that is at least 80%, at least 85%, at least 90%, at least 95%, at least 96%, at least 97%, at least 98%, at least 99%, at least 99.5% or 100% identical to one or more of SEQ ID NO: 67, SEQ ID NO: 68, SEQ ID NO: 69, SEQ ID NO: 70 or SEQ ID NO: 71, or a functional portion thereof.

26. The modified corn plant or plant part thereof of embodiment 22, wherein the heterologous plant-expressible promoter is a rice tungro bacilliform virus (RTBV) promoter.

27. The modified corn plant or plant part thereof of embodiment 26, wherein RTBV promoter comprises a DNA sequence that is at least 80%, at least 85%, at least 90%, at least 95%, at least 96%, at least 97%, at least 98%, at least 99%, at least 99.5% or 100% identical to one or more of SEQ ID NO: 65 or SEQ ID NO: 66, or a functional portion thereof.

28. The modified corn plant or plant part thereof of embodiment 22, wherein the heterologous plant-expressible promoter is a leaf promoter.

29. The modified corn plant or plant part thereof of embodiment 28, wherein the leaf promoter is selected from the group consisting of a RuBisCO promoter, a pyruvate phosphate dikinase (PPDK) promoter, a fructose 1-6 bisphosphate aldolase (FDA) promoter, a Nadh-Gogat promoter, a chlorophyll a/b binding polypeptide gene promoter, a phosphoenolpyruvate carboxylase (PEPC) promoter, a Myb gene promoter, and a combination thereof.

30. The modified corn plant or plant part thereof of embodiment 29, wherein the leaf promoter comprises a DNA sequence that is at least 80%, at least 85%, at least 90%, at least 95%, at least 96%, at least 97%, at least 98%, at least 99%, at least 99.5% or 100% identical to one or more of SEQ ID NO: 72, SEQ ID NO: 73 or SEQ ID NO: 74, or a functional portion thereof.

31. The modified corn plant or plant part thereof of embodiment 22, wherein the heterologous plant-expressible promoter is a constitutive promoter.

32. The modified corn plant or plant part thereof of embodiment 31, wherein the constitutive promoter is selected from the group consisting of an actin promoter, a Cauliflower mosaic virus (CaMV) 35S or 19S promoter, a plant ubiquitin promoter, a plant Gos2 promoter, a Figwort mosaic virus (FMV) promoter, a cytomegalovirus (CMV) promoter, a mirabilis mosaic virus (MMV) promoter, a peanut chlorotic streak caulimovirus (PCLSV) promoter, an Emu promoter, a tubulin promoter, a nopaline synthase promoter, an octopine synthase promoter, a mannopine synthase promoter, or a maize alcohol dehydrogenase, a functional portion thereof, and a combination thereof.

33. The modified corn plant or plant part thereof of embodiment 32, wherein the constitutive promoter comprises a DNA sequence that is at least 80%, at least 85%, at least 90%, at least 95%, at least 96%, at least 97%, at least 98%, at least 99%, at least 99.5% or 100% identical to one or more of SEQ ID NOs: 75, SEQ ID NO: 76, SEQ ID NO: 77, SEQ ID NO: 78, SEQ ID NO: 79, SEQ ID NO: 80, SEQ ID NO: 81, SEQ ID NO: 82 or SEQ ID NO: 83, or a functional portion thereof 34. The modified corn plant or plant part thereof of embodiment 1 or 3, wherein the non-coding RNA is a precursor miRNA or siRNA capable of being processed or cleaved to form a mature miRNA or siRNA.

35. The modified corn plant or plant part thereof of embodiment 1 or 3, wherein the DNA sequence comprised in the second recombinant expression cassette is operably linked to a heterologous plant-expressible promoter.

36. The modified corn plant or plant part thereof of embodiment 35, wherein the heterologous plant-expressible promoter is a constitutive promoter.

37. The modified corn plant or plant part thereof of embodiment 36, wherein the constitutive promoter is selected from the group consisting of an actin promoter, a Cauliflower mosaic virus (CaMV) 35S or 19S promoter, a plant ubiquitin promoter, a plant Gos2 promoter, a Figwort mosaic virus (FMV) promoter, a cytomegalovirus (CMV) promoter, a mirabilis mosaic virus (MMV) promoter, a peanut chlorotic streak caulimovirus (PCLSV) promoter, an Emu promoter, a tubulin promoter, a nopaline synthase promoter, an octopine synthase promoter, a mannopine synthase promoter, or a maize alcohol dehydrogenase, a functional portion thereof, and a combination thereof.

38. The modified corn plant or plant part thereof of embodiment 35, wherein the heterologous plant-expressible promoter comprises a DNA sequence that is at least 80%, at least 85%, at least 90%, at least 95%, at least 96%, at least 97%, at least 98%, at least 99%, at least 99.5% or 100% identical to SEQ ID NO: 172 or a functional portion thereof.

39. The modified corn plant or plant part thereof of any one of embodiments 1 to 38 wherein the height at maturity of the modified corn plant is reduced by at least 1%, at least 2%, at least 5%, at least 10%, at least 15%, at least 20%, at least 25%, at least 30%, at least 35%, at least 40%, at least 45%, at least 50%, at least 55%, at least 60%, at least 65%, or at least 70%, relative to a control corn plant.

40. The modified corn plant or plant part thereof of any one of embodiments 1 to 39, wherein the stalk or stem diameter of the modified corn plant is increased by at least 0.1%, at least 0.2%, at least 0.5%, at least 1%, at least 1.5%, at least 2%, at least 2.5%, at least 3%, at least 3.5%, at least 4%, at least 4.5%, at least 5%, at least 6%, at least 7%, at least 8%, at least 9%, at least 10%, at least 15%, at least 20%, at least 25%, at least 30%, at least 35%, at least 40%, at least 45%, or at least 50%, relative to a control corn plant.

41. The modified corn plant or plant part thereof of any one of embodiments 1 to 40, wherein the modified corn plant exhibits improved lodging resistance, reduced green snap, or both, relative to a control corn plant.

42. The modified corn plant or plant part thereof of any one of embodiments 1 to 41, wherein the modified corn plant exhibits increased ear area relative to a control corn plant.

43. The modified corn plant or plant part thereof of any one of embodiments 1 to 42, wherein the modified corn plant exhibits an increase in ear area by at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, or at least 20%, relative to a control corn plant.

44. The modified corn plant or plant part thereof of any one of embodiments 1 to 43, wherein the modified corn plant exhibits increased single kernel weight relative to a control corn plant.

45. The modified corn plant or plant part thereof of any one of embodiments 1 to 44, wherein the modified corn plant exhibits an increase in singe kernel weight by at least at least 1%, at least 2%, at least 3%, at least 4%, at least 5%, at least 6%, at least 7%, at least 8%, at least 9%, or at least 10%, relative to a control corn plant.

46. The modified corn plant or plant part thereof of any one of embodiments 1 to 45, wherein the modified corn plant exhibits increased ear fresh weight relative to a control corn plant.

47. The modified corn plant or plant part thereof of any one of embodiments 1 to 46, wherein the modified corn plant exhibits increased ear fresh weight by at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, or at least 20%, relative to a control corn plant.

48. The modified corn plant or plant part thereof of any one of embodiments 1 to 47, wherein the modified corn plant exhibits increased number of florets relative to a control corn plant.

49. The modified corn plant or plant part thereof of any one of embodiments 1 to 48, wherein the modified corn plant exhibits increased number of florets by at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, at least 25%, at least 26%, at least 27%, at least 28%, at least 29%, or at least 30%, relative to a control corn plant.

50. The modified corn plant or plant part thereof of any one of embodiments 1 to 49, wherein the modified corn plant exhibits a trait selected from the group consisting of deeper roots, increased leaf area, earlier canopy closure, higher stomatal conductance, lower ear height, increased foliar water content, improved drought tolerance, improved nitrogen use efficiency, reduced anthocyanin content and area in leaves under normal or nitrogen-limiting or water-limiting stress conditions, increased ear weight, increased harvest index, increased yield, increased seed number, increased seed weight, increased prolificacy, and a combination thereof, relative to the control corn plant.

51. The modified corn plant or plant part thereof of any one of embodiments 1 to 50, wherein the modified corn plant does not have any significant off-types in at least one female organ or ear.

52. A seed of the modified corn plant of any one of embodiments 1 to 51, wherein the seed comprises the first and second recombinant expression cassettes.

53. The seed of embodiment 52, wherein a progeny plant grown from the seed is semi-dwarf and has one or more improved ear traits, relative to a control corn plant that does not comprise the first or second recombinant expression cassette.

54. A commodity or commodity product produced from the seed of embodiment 52, comprising the first and second DNA sequence recombinant expression cassettes.

55. A method comprising planting the seed of embodiment 52 in a growth medium or soil.

56. The method of embodiment 55, further comprising planting a plurality of the seeds with a row spacing of less than or equal to 40 inches.

57. The method of embodiment 55, further comprising planting a plurality of the seeds with a row spacing of less than or equal to 30 inches.

58. The method of embodiment 57, wherein the row spacing is less than or equal to 20 inches.

59. The method of embodiment 55, further comprising growing a corn plant from the seed.

60. The method of embodiment 59, further comprising harvesting a seed from the corn plant.

61. The method of any one of embodiments 57 to 60, wherein the seed is planted at a density selected from the group consisting of at least 38,000 plants per acre, at least 40,000 plants per acre, at least 42,000 plants per acre, at least 44,000 plants per acre, at least 45,000 plants per acre, at least 46,000 plants per acre, at least 48,000 plants per acre, 50,000 plants per acre, at least 52,000 plants per acre, at least 54,000 per acre, and at least 56,000 plants per acre.

62. A plurality of modified corn plants in a field, each modified corn plant comprising
   a. a first recombinant expression cassette comprising a transcribable DNA sequence encoding a non-coding RNA for suppression of one or more gibberellic acid 20 (GA20) oxidase genes and/or one or more gibberellic acid 3 (GA3) oxidase genes, and
   b. a second recombinant expression cassette comprising a DNA sequence encoding a CO or COL polypeptide.

63. The plurality of modified corn plants of embodiment 62, wherein the modified corn plants have increased yield relative to control corn plants.

64. The plurality of modified corn plants of embodiment 62 or 63, wherein the modified corn plants have an increase in yield that is at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, or at least 25% greater than control corn plants.

65. A method for producing a modified corn plant, the method comprising:
   a. introducing into a corn cell a first recombinant expression cassette comprising a DNA sequence encoding a CO or COL polypeptide, wherein the corn cell comprises a second recombinant expression cassette comprising a transcribable DNA sequence encoding a non-coding RNA for suppression of one or more GA3 oxidase genes and/or one or more GA20 oxidase genes; and
   b. regenerating or developing a modified corn plant from the corn cell, wherein the modified corn plant comprises the first and second recombinant expression cassettes.

66. The method of embodiment 65, wherein the introducing is via site-directed integration using a site-specific nuclease.

67. The method of embodiment 66, wherein the site-specific nuclease is selected from the group consisting of a RNA-guided endonuclease, a meganuclease, a zinc-finger nuclease (ZFN), a TALE-endonuclease (TALEN), a recombinase, and a transposase.

68. The method of embodiment 65, wherein the introducing is via *Agrobacterium*-mediated transformation.

69. The method of embodiment 65, wherein the introducing is via particle bombardment.

70. The method of any one of embodiments 65 to 69, wherein the transcribable DNA sequence encodes a non-coding RNA for suppression of a GA3 oxidase_1 gene, a GA3 oxidase_2 gene, or both.

71. The method of embodiment 70, wherein the transcribable DNA sequence comprises a sequence that is at least 80%, at least 85%, at least 90%, at least 95%, at least 96%, at least 97%, at least 98%, at least 99%, at least 99.5%, or 100% identical or complementary to at least 15, at least 16, at least 17, at least 18, at least 19, at least 20, at least 21, at least 22, at least 23, at least 24, at least 25, at least 26, or at least 27 consecutive nucleotides of one or more of SEQ ID NOs: 28, 29, 31, 32, 36, and 37.

72. The method of embodiment 70, wherein the transcribable DNA sequence encodes a non-coding RNA comprising a sequence that is 80% complementary to at least 15 consecutive nucleotides of one or more of SEQ ID NOs: 28, 29, 31, 32, 36, and 37.

73. The method of any one of embodiments 65 to 69, wherein the transcribable DNA sequence encodes a non-coding RNA for suppression of a GA20 oxidase gene.

74. The method of embodiment 73, wherein the transcribable DNA sequence encodes a non-coding RNA for suppression of a GA20 oxidase_3 gene, a GA20 oxidase_4 gene, a GA20 oxidase_5 gene, or a combination thereof.

75. The method of embodiment 74, wherein the non-coding RNA comprises a sequence that is at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous GA oxidase protein in a corn plant or plant cell, the endogenous GA oxidase protein being at least 80%, at least 85%, at least 90%, at least 95%, at least 96%, at least 97%, at least 98%, at least 99%, at least 99.5%, or 100% identical to SEQ ID NO: 9, 12, 15, 30, or 33.

76. The method of embodiment 74, wherein the non-coding RNA comprises a sequence that is at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of SEQ ID NO: 7, 8, 10, 11, 13, 14, 28, 29, 31, or 32.

77. The method of any one of embodiments 65 to 76, wherein the CO or COL polypeptide comprises an amino acid sequence that is at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to one or more of SEQ ID NOs: 176-397.

78. The method of any one of embodiments 65 to 76, wherein the CO or COL polypeptide comprises an amino acid sequence that is at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to one or more of SEQ ID NOs: 398-452.

79. The method of any one of embodiments 65 to 76, wherein the CO or COL polypeptide comprises a *Physcomitrella patens* CONSTANS-like 1 (PpCOL1) polypeptide.

80. The method of any one of embodiments 65 to 76, wherein the DNA sequence comprised in the first recombinant expression cassette comprises a sequence that is at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 169.

81. The method of any one of embodiments 65 to 76, wherein the CO or COL polypeptide comprises an amino acid sequence that is at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 168.

82. The modified corn plant of embodiment 65, wherein the first and second recombinant expression cassettes are stably integrated into the genome of the corn cell.

83. The method of embodiment 65, further comprising selecting a modified corn plant having a desired trait.

84. The method of embodiment 83, wherein the selected modified corn plant is semi-dwarf and has one or more improved ear traits, relative to a control corn plant not having the first or the second recombinant expression cassettes.

85. The method of embodiment 83 or 84, wherein the selecting a modified corn plant having a desired trait comprises the use of one or more molecular techniques.

86. The method of embodiment 85, wherein the one or more molecular techniques are selected from the group consisting of Southern analysis, polymerase chain reaction (PCR) amplification, Northern blots, RNase protection, primer extension, reverse transcription PCR (RT-PCR), Sanger sequencing, Next Generation sequencing technologies, enzymatic assays, protein gel electrophoresis, Western blots, immunoprecipitation, enzyme-linked immunoassays, in situ hybridization, enzyme staining, immunostaining, marker genotyping, and a combination thereof.

87. The method of any one of embodiments 65 to 86, wherein the height at maturity of the modified corn plant is reduced by at least 1%, at least 2%, at least 5%, at least 10%, at least 15%, at least 20%, at least 25%, at least 30%, at least 35%, at least 40%, at least 45%, at least 50%, at least 55%, at least 60%, at least 65%, or at least 70%, relative to a control corn plant.

88. The method of any one of embodiments 65 to 87, wherein the stalk or stem diameter of the modified corn plant is increased by at least 0.1%, at least 0.2%, at least 0.5%, at least 1%, at least 1.5%, at least 2%, at least 2.5%, at least 3%, at least 3.5%, at least 4%, at least 4.5%, at least 5%, at least 6%, at least 7%, at least 8%, at least 9%, at least 10%, at least 15%, at least 20%, at least 25%, at least 30%, at least 35%, at least 40%, at least 45%, or at least 50%, relative to a control corn plant.

89. The method of any one of embodiments 65 to 88, wherein the modified corn plant exhibit an ear trait selected from the group consisting of increased ear area, increased single kernel weight, increased ear fresh weight, increased number of florets, and a combination thereof, relative to a control corn plant.

90. The method of any one of embodiments 65 to 88, wherein the modified corn plant exhibits a trait selected from the group consisting of deeper roots, increased leaf area, earlier canopy closure, higher stomatal conductance, lower ear height, increased foliar water content, improved drought tolerance, improved nitrogen use efficiency, reduced anthocyanin content and area in leaves under normal or nitrogen-limiting or water-limiting stress conditions, increased ear weight, increased harvest index, increased yield, increased seed number, increased seed weight, increased prolificacy, and a combination thereof, relative to a control corn plant.

91. A method for producing a modified corn plant, the method comprising:
   a. introducing into a corn cell a first recombinant expression cassette comprising a transcribable DNA sequence encoding a non-coding RNA for suppression of one or more GA3 oxidase genes and/or GA20 oxidase genes, wherein the corn cell comprises a second recombinant expression cassette comprising a DNA sequence encoding a CO and/or COL polypeptide; and
   b. regenerating or developing a modified corn plant from the corn cell, wherein the modified corn plant comprises the first and second recombinant expression cassettes.

92. The method of embodiment 91, wherein the introducing is via site-directed integration using a site-specific nuclease.

93. The method of embodiment 92, wherein the site-specific nuclease is selected from the group consisting of a RNA-guided endonuclease, a meganuclease, a zinc-finger nuclease (ZFN), a TALE-endonuclease (TALEN), a recombinase, and a transposase.

94. The method of embodiment 91, wherein the introducing is via *Agrobacterium*-mediated transformation.

95. The method of embodiment 91, wherein the introducing is via particle bombardment.

96. The method of any one of embodiments 91 to 95, wherein the transcribable DNA sequence encodes a non-coding RNA for suppression of a GA3 oxidase_1 gene, a GA3 oxidase_2 gene, or both.

97. The method of embodiment 96, wherein the transcribable DNA sequence comprises a sequence that is at least 80%, at least 85%, at least 90%, at least 95%, at least 96%, at least 97%, at least 98%, at least 99%, at least 99.5%, or 100% identical or complementary to at least 15, at least 16, at least 17, at least 18, at least 19, at least 20, at least 21, at least 22, at least 23, at least 24, at least 25, at least 26, or at least 27 consecutive nucleotides of one or more of SEQ ID NOs: 28, 29, 31, 32, 36, and 37.

98. The method of embodiment 96, wherein the transcribable DNA sequence encodes a non-coding RNA comprising a sequence that is 80% complementary to at least 15 consecutive nucleotides of one or more of SEQ ID NOs: 28, 29, 31, 32, 36, and 37.

99. The method of any one of embodiments 91 to 95, wherein the transcribable DNA sequence encodes a non-coding RNA for suppression of a GA20 oxidase gene.

100. The method of embodiment 99, wherein the transcribable DNA sequence encodes a non-coding RNA for suppression of a GA20 oxidase_3 gene, a GA20 oxidase_4 gene, a GA20 oxidase_5 gene, or a combination thereof.

101. The method of embodiment 100, wherein the non-coding RNA comprises a sequence that is at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous GA oxidase protein in a corn plant or plant cell, the endogenous GA oxidase protein being at least 80%, at least 85%, at least 90%, at least 95%, at least 96%, at least 97%, at least 98%, at least 99%, at least 99.5%, or 100% identical to SEQ ID NO: 9, 12, 15, 30, or 33.

102. The method of embodiment 100, wherein the non-coding RNA comprises a sequence that is at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of SEQ ID NO: 7, 8, 10, 11, 13, 14, 28, 29, 31, or 32.

103. The method of any one of embodiments 91 to 102, wherein the CO or COL polypeptide comprises an amino acid sequence that is at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to one or more of SEQ ID NOs: 176-397.

104. The method of any one of embodiments 91 to 102, wherein the CO or COL polypeptide comprises an amino acid sequence that is at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to one or more of SEQ ID NOs: 398-452.

105. The method of any one of embodiments 91 to 102, wherein the CO or COL polypeptide comprises a *Physcomitrella patens* CONSTANS-like 1 (PpCOL1) polypeptide.

106. The method of any one of embodiments 91 to 102, wherein the DNA sequence comprised in the second recombinant expression cassette comprises a sequence that is at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 169.

107. The method of any one of embodiments 91 to 102, wherein the CO or COL polypeptide comprises an amino acid sequence that is at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 168.

108. The modified corn plant of embodiment 91, wherein the first and second recombinant expression cassettes are stably integrated into the genome of the corn cell.

109. The method of embodiment 91, further comprising selecting a modified corn plant having a desired trait.

110. The method of embodiment 109, wherein the selected modified corn plant is semi-dwarf and has one or more improved ear traits, relative to a control corn plant not having the first or the second recombinant expression cassette.

111. The method of embodiment 109 or 110, wherein the selecting a modified corn plant having a desired trait comprises the use of one or more molecular techniques.

112. The method of embodiment 111, wherein the one or more molecular techniques are selected from the group consisting of Southern analysis, PCR amplification, Northern blots, RNase protection, primer extension, RT-PCR, Sanger sequencing, Next Generation sequencing technologies, enzymatic assays, protein gel electrophoresis, Western blots, immunoprecipitation, enzyme-linked immunoassays, in situ hybridization, enzyme staining, immunostaining, marker genotyping, and a combination thereof.

113. The method of any one of embodiments 91 to 112, wherein the height at maturity of the modified corn plant is reduced by at least 1%, at least 2%, at least 5%, at least 10%, at least 15%, at least 20%, at least 25%, at least 30%, at least 35%, at least 40%, at least 45%, at least 50%, at least 55%, at least 60%, at least 65%, or at least 70%, relative to a control corn plant.

114. The method of any one of embodiments 91 to 113, wherein the stalk or stem diameter of the modified corn plant is increased by at least 0.1%, at least 0.2%, at least 0.5%, at least 1%, at least 1.5%, at least 2%, at least 2.5%, at least 3%, at least 3.5%, at least 4%, at least 4.5%, at least 5%, at least 6%, at least 7%, at least 8%, at least 9%, at least 10%, at least 15%, at least 20%, at least 25%, at least 30%, at least 35%, at least 40%, at least 45%, or at least 50%, relative to a control corn plant.

115. The method of any one of embodiments 91 to 114, wherein the modified corn plant exhibit an ear trait selected from the group consisting of increased ear area, increased single kernel weight, increased ear fresh weight, increased number of florets, and a combination thereof, relative to a control corn plant.

116. The method of any one of embodiments 91 to 115, wherein the modified corn plant exhibits a trait selected from the group consisting of deeper roots, increased leaf area, earlier canopy closure, higher stomatal conductance, lower ear height, increased foliar water content, improved drought tolerance, improved nitrogen use efficiency, reduced anthocyanin content and area in leaves under normal or nitrogen-limiting or water-limiting stress conditions, increased ear weight, increased harvest index, increased yield, increased seed number, increased seed weight, increased prolificacy, and a combination thereof, relative to a control corn plant.

117. A method for producing a modified corn plant, the method comprising
  a. introducing into a corn cell 1) a first recombinant expression cassette comprising a transcribable DNA sequence encoding a non-coding RNA for suppression of one or more GA3 oxidase genes and/or GA20 oxidase genes and 2) a second recombinant expression cassette comprising a DNA sequence encoding a CO or COL polypeptide; and
  b. regenerating or developing a modified corn plant from the corn cell, wherein the modified corn plant comprises the first and second recombinant expression cassettes.

118. A method for producing a modified corn plant, the method comprising
  a. introducing into a corn cell a first recombinant expression cassette comprising a transcribable DNA sequence encoding a non-coding RNA for suppression of one or more GA3 oxidase genes and/or GA20 oxidase genes;
  b. introducing into the corn cell of step (a) a second recombinant expression cassette comprising a DNA sequence encoding a CO or COL polypeptide to create a modified corn cell; and
  c. regenerating or developing a modified corn plant from the modified corn cell of step (b), wherein the modified corn plant comprises the first and second recombinant expression cassettes.

119. A method for producing a modified corn plant, the method comprising
  a. introducing into a corn cell a first recombinant expression cassette comprising a DNA sequence encoding a CO or COL polypeptide;
  b. introducing into the corn cell of step (a) a second recombinant expression cassette comprising a transcribable DNA sequence encoding a non-coding RNA for suppression of one or more GA3 oxidase genes and/or GA20 oxidase genes to create a modified corn cell; and
  c. regenerating or developing a modified corn plant from the modified corn cell of step (b), wherein the modified corn plant comprises the first and second recombinant expression cassettes.

120. A method for producing a modified corn plant, the method comprising:
  a. crossing a first modified corn plant with a second modified corn plant, wherein the expression or activity of one or more endogenous GA3 oxidase genes and/or GA20 oxidase genes is reduced in the first modified corn plant relative to a wildtype control, and wherein the second modified corn plant comprises a recombinant expression cassette comprising a DNA sequence encoding a CO or COL polypeptide; and
  b. producing a progeny corn plant comprising the recombinant expression cassette and has the reduced expression of the one or more endogenous GA3 oxidase genes and/or GA20 oxidase genes.

121. The method of embodiment 120, wherein the first and second modified corn plants are obtained via site-directed integration using a site-specific nuclease.

122. The method of embodiment 121, wherein the site-specific nuclease is selected from the group consisting of a RNA-guided endonuclease, a meganuclease, a zinc-finger nuclease (ZFN), a TALE-endonuclease (TALEN), a recombinase, and a transposase.

123. The method of embodiment 120, wherein the first and second modified corn plants are obtained via *Agrobacterium*-mediated transformation.

124. The method of embodiment 120, wherein the first and second modified corn plants are obtained via particle bombardment.

125. The method of embodiment 120 to 124, wherein the first modified corn plant and the progeny corn plant comprise a transcribable DNA sequence encoding a non-coding RNA for suppression of a GA3 oxidase_1 gene, a GA3 oxidase_2 gene, or both.

126. The method of embodiment 125, wherein the transcribable DNA sequence comprises a sequence that is at least 80%, at least 85%, at least 90%, at least 95%, at least 96%, at least 97%, at least 98%, at least 99%, at least 99.5%, or 100% identical or complementary to at least 15, at least 16, at least 17, at least 18, at least 19, at least 20, at least 21, at least 22, at least 23, at least 24, at least 25, at least 26, or at least 27 consecutive nucleotides of one or more of SEQ ID NOs: 28, 29, 31, 32, 36, and 37.

127. The method of embodiment 125, wherein the transcribable DNA sequence encodes a non-coding RNA comprising a sequence that is 80% complementary to at least 15 consecutive nucleotides of one or more of SEQ ID NOs: 28, 29, 31, 32, 36, and 37.

128. The method of any one of embodiments 120 to 124, wherein the transcribable DNA sequence encodes a non-coding RNA for suppression of a GA20 oxidase gene.

129. The method of embodiment 128, wherein the transcribable DNA sequence encodes a non-coding RNA for suppression of a GA20 oxidase_3 gene, a GA20 oxidase_4 gene, a GA20 oxidase_5 gene, or a combination thereof.

130. The method of embodiment 129, wherein the non-coding RNA comprises a sequence that is at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous GA oxidase protein in a corn plant or plant cell, the endogenous GA oxidase protein being at least 80%, at least 85%, at least 90%, at least 95%, at least 96%, at least 97%, at least 98%, at least 99%, at least 99.5%, or 100% identical to SEQ ID NO: 9, 12, 15, 30, or 33.

131. The method of embodiment 129, wherein the non-coding RNA comprises a sequence that is at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of SEQ ID NO: 7, 8, 10, 11, 13, 14, 28, 29, 31, or 32.

132. The method of any one of embodiments 120 to 131, wherein the second modified corn plant and the progeny corn plant comprise a recombinant expression cassette comprising a DNA sequence encoding a CO or COL polypeptide.

133. The method of embodiment 132, wherein the CO or COL polypeptide comprises an amino acid sequence that is at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to one or more of SEQ ID NOs: 176-397.

134. The method of embodiment 132, wherein the CO or COL polypeptide comprises an amino acid sequence that is at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to one or more of SEQ ID NOs: 398-452.

135. The method of any one of embodiments 120 to 131, wherein the CO or COL polypeptide comprises a *Physcomitrella patens* CONSTANS-like 1 (PpCOL1) polypeptide.

136. The method of any one of embodiments 120 to 131, wherein the DNA sequence comprised in the second modified corn plant comprises a sequence that is at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 169.

137. The method of any one of embodiments 120 to 131, wherein the CO or COL polypeptide comprises an amino acid sequence that is at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 168.

138. The method of embodiment 120, further comprising selecting a progeny corn plant having a desired trait.

139. The method of embodiment 138, wherein the selected progeny corn plant is semi-dwarf and has one or more improved ear traits, relative to a control corn plant.

140. The method of embodiment 138 or 139, wherein the selecting a progeny corn plant having a desired trait comprises the use of one or more molecular techniques.

141. The method of embodiment 140, wherein the one or more molecular techniques are selected from the group consisting of Southern analysis, PCR amplification, Northern blots, RNase protection, primer extension, RT-PCR, Sanger sequencing, Next Generation sequencing technologies, enzymatic assays, protein gel electrophoresis, Western blots, immunoprecipitation, enzyme-linked immunoassays, in situ hybridization, enzyme staining, immunostaining, marker genotyping, and a combination thereof.

142. The method of any one of embodiments 120 to 141, wherein the height at maturity of the progeny corn plant is reduced by at least 1%, at least 2%, at least 5%, at least 10%, at least 15%, at least 20%, at least 25%, at least 30%, at least 35%, at least 40%, at least 45%, at least 50%, at least 55%, at least 60%, at least 65%, or at least 70%, relative to a control corn plant.

143. The method of any one of embodiments 120 to 142, wherein the stalk or stem diameter of the progeny corn plant is increased by at least 0.1%, at least 0.2%, at least 0.5%, at least 1%, at least 1.5%, at least 2%, at least 2.5%, at least 3%, at least 3.5%, at least 4%, at least 4.5%, at least 5%, at least 6%, at least 7%, at least 8%, at least 9%, at least 10%, at least 15%, at least 20%, at least 25%, at least 30%, at least 35%, at least 40%, at least 45%, or at least 50%, relative to a control corn plant.

144. The method of any one of embodiments 120 to 143, wherein the progeny corn plant exhibit an ear trait selected from the group consisting of increased ear area, increased single kernel weight, increased ear fresh weight, increased number of florets, and a combination thereof, relative to a control corn plant.

145. The method of any one of embodiments 120 to 144, wherein the progeny corn plant exhibits a trait selected from the group consisting of deeper roots, increased leaf area, earlier canopy closure, higher stomatal conductance, lower ear height, increased foliar water content, improved drought tolerance, improved nitrogen use efficiency, reduced anthocyanin content and area in leaves under normal or nitrogen-limiting or water-limiting stress conditions, increased ear weight, increased harvest index, increased yield, increased seed number, increased seed weight, increased prolificacy, and a combination thereof, relative to a control corn plant.

146. A method for producing a modified corn plant, the method comprising:
  a. introducing into a corn cell a recombinant expression cassette comprising a DNA sequence encoding a CO or COL polypeptide, wherein the DNA sequence is operably linked to a plant-expressible promoter, and wherein the corn cell comprises one or more mutations and/or edits in one or more endogenous GA3 oxidase and/or GA20 oxidase genes; and b. regenerating or developing a modified corn plant from the corn cell, wherein the modified corn plant comprises the recombinant expression cassette and the one or more mutations and/or edits, and wherein the level of expression or activity of the one or more endogenous GA3 oxidase and/or GA20 oxidase genes in the modified corn plant is reduced relative to a control plant not having the one or more mutations and/or edits.

147. The method of embodiment 146, further comprising introducing a recombinant DNA construct encoding a guide RNA that targets the one or more endogenous GA3 oxidase and/or GA20 oxidase genes.

148. The method of embodiment 147, wherein the guide RNA comprises a guide sequence that is at least 95%, at least 96%, at least 97%, at least 99% or 100% complementary to at least 10, at least 11, at least 12, at least 13, at least 14, at least 15, at least 16, at least 17, at least 18, at least 19, at least 20, at least 21, at least 22, at least 23, at least 24, or at least 25 consecutive nucleotides of a target DNA sequence at or near the genomic locus of one or more endogenous GA3 oxidase and/or GA20 oxidase genes.

149. The method of embodiment 148, wherein the guide RNA comprises a guide sequence that is at least 95%, at least 96%, at least 97%, at least 99% or 100% complementary to at least 10, at least 11, at least 12, at least 13, at least 14, at least 15, at least 16, at least 17, at least 18, at least 19, at least 20, at least 21, at least 22, at least 23, at least 24, or at least 25 consecutive nucleotides of SEQ ID NO: 34, 35, 36, 37, or 38, or a sequence complementary thereto.

150. The method of any one of embodiments 147 to 149, wherein the guide RNA is a CRISPR RNA (crRNA) or a single-chain guide RNA (sgRNA).

151. The method of any one of embodiments 147 to 150, wherein the guide RNA comprises a sequence complementary to a protospacer adjacent motif (PAM) sequence present in the genome of the corn cell immediately adjacent to a target DNA sequence at or near the genomic locus of the one or more endogenous GA3 oxidase and/or GA20 oxidase genes.

152. The method of any one of embodiments 147 to 151, wherein the one or more endogenous GA3 oxidase and/or GA20 oxidase genes encode a protein that is at least 80%, at least 85%, at least 90%, at least 95%, at least 96%, at least 97%, at least 98%, at least 99%, at least 99.5%, or 100% identical to SEQ ID NO: 9, 12, 15, 30, or 33.

153. The method of embodiment 146, wherein the introducing is via *Agrobacterium*-mediated transformation or particle bombardment.

154. The method of embodiment 153, wherein the CO or COL polypeptide comprises an amino acid sequence that is at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to one or more of SEQ ID NOs: 176-397.

155. The method of embodiment 153, wherein the CO or COL polypeptide comprises an amino acid sequence that is at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to one or more of SEQ ID NOs: 398-452.

156. The method of embodiment 153, wherein the CO or COL polypeptide comprises a *Physcomitrella patens* CONSTANS-like 1 (PpCOL1) polypeptide.

157. The method of any one of embodiments 146 to 156, wherein the DNA sequence comprises a sequence that is at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 169.

158. The method of any one of embodiments 146 to 156, wherein the CO or COL polypeptide comprises an amino acid sequence that is at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 168.

159. A method for producing a modified corn plant, the method comprising:

a. mutating or editing one or more endogenous GA3 oxidase genes and/or one or more GA20 oxidase genes in a corn cell, wherein the corn cell comprises a recombinant expression cassette encoding a CO or COL polypeptide, wherein the DNA sequence is operably linked to a plant-expressible promoter; and b. regenerating or developing a modified corn plant from the corn cell, wherein the modified corn plant comprises the recombinant expression cassette and the one or more mutations and/or edits, and wherein the level of expression or activity of the one or more endogenous GA3 oxidase and/or GA20 oxidase genes in the modified corn plant is reduced relative to a control plant not having the one or more mutations and/or edits.

160. The method of embodiment 159, wherein the mutating or editing is obtained by using a site-specific nuclease selected from the group consisting of a RNA-guided endonuclease, a meganuclease, a zinc-finger nuclease (ZFN), a TALE-endonuclease (TALEN), a recombinase, and a transposase.

161. The method of embodiment 159 or 160, further comprising introducing a recombinant DNA construct encoding a guide RNA that targets the one or more endogenous GA3 oxidase and/or GA20 oxidase genes.

162. The method of embodiment 161, wherein the guide RNA comprises a guide sequence that is at least 95%, at least 96%, at least 97%, at least 99% or 100% complementary to at least 10, at least 11, at least 12, at least 13, at least 14, at least 15, at least 16, at least 17, at least 18, at least 19, at least 20, at least 21, at least 22, at least 23, at least 24, or at least 25 consecutive nucleotides of a target DNA sequence at or near the genomic locus of one or more endogenous GA3 oxidase and/or GA20 oxidase genes.

163. The method of embodiment 162, wherein the guide RNA comprises a guide sequence that is at least 95%, at least 96%, at least 97%, at least 99% or 100% complementary to at least 10, at least 11, at least 12, at least 13, at least 14, at least 15, at least 16, at least 17, at least 18, at least 19, at least 20, at least 21, at least 22, at least 23, at least 24, or at least 25 consecutive nucleotides of SEQ ID NO: 34, 35, 36, 37, or 38, or a sequence complementary thereto.

164. The method of any one of embodiments 161 to 163, wherein the guide RNA is a CRISPR RNA (crRNA) or a single-chain guide RNA (sgRNA).

165. The method of any one of embodiments 161 to 164, wherein the guide RNA comprises a sequence complementary to a protospacer adjacent motif (PAM) sequence present in the genome of the corn cell immediately adjacent to a target DNA sequence at or near the genomic locus of the one or more endogenous GA3 oxidase and/or GA20 oxidase genes.

166. The method of any one of embodiments 161 to 165, wherein the one or more endogenous GA3 oxidase and/or GA20 oxidase genes encode a protein that is at least 80%, at least 85%, at least 90%, at least 95%, at least 96%, at least 97%, at least 98%, at least 99%, at least 99.5%, or 100% identical to SEQ ID NO: 9, 12, 15, 30, or 33.

167. The method of embodiment 159, wherein the CO or COL polypeptide comprises an amino acid sequence that is at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to one or more of SEQ ID NOs: 176-397.

168. The method of embodiment 159, wherein the CO or COL polypeptide comprises an amino acid sequence that is at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to one or more of SEQ ID NOs: 398-452.

169. The method of embodiment 159, wherein the recombinant expression cassette encodes a *Physcomitrella patens* CONSTANS-like 1 (PpCOL1) polypeptide.

170. The method of embodiment 159, wherein the recombinant expression cassette comprises a sequence that is at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 169.

171. The method of embodiment 159, wherein the CO or COL polypeptide comprises an amino acid sequence that is at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 168.

172. The method of any one of embodiments 159 to 171, further comprising selecting a modified corn plant having a desired trait.

173. The method of embodiment 172, wherein the height at maturity of the modified corn plant is reduced by at least 1%, at least 2%, at least 5%, at least 10%, at least 15%, at least 20%, at least 25%, at least 30%, at least 35%, at least 40%, at least 45%, at least 50%, at least 55%, at least 60%, at least 65%, or at least 70%, relative to a control corn plant.

174. The method of embodiment 173, wherein the stalk or stem diameter of the modified corn plant is increased by at least 0.1%, at least 0.2%, at least 0.5%, at least 1%, at least 1.5%, at least 2%, at least 2.5%, at least 3%, at least 3.5%, at least 4%, at least 4.5%, at least 5%, at least 6%, at least 7%, at least 8%, at least 9%, at least 10%, at least 15%, at least 20%, at least 25%, at least 30%, at least 35%, at least 40%, at least 45%, or at least 50%, relative to a control corn plant.

175. The method of any one of embodiments 172 to 174, wherein the modified corn plant exhibit an ear trait selected from the group consisting of increased ear area, increased single kernel weight, increased ear fresh weight, increased number of florets, and a combination thereof, relative to a control corn plant.

176. The method of any one of embodiments 172 to 175, wherein the modified corn plant exhibits a trait selected from the group consisting of deeper roots, increased leaf area, earlier canopy closure, higher stomatal conductance, lower ear height, increased foliar water content, improved drought tolerance, improved nitrogen use efficiency, reduced anthocyanin content and area in leaves under normal or nitrogen-limiting or water-limiting stress conditions, increased ear weight, increased harvest index, increased yield, increased seed number, increased seed weight, increased prolificacy, and a combination thereof, relative to a control corn plant.

177. A modified corn plant comprising 1) one or more mutations or edits at or near one or more endogenous GA20 oxidase and/or GA3 oxidase genes, wherein the expression or activity of the one or more endogenous GA20 oxidase and/or GA3 oxidase genes is reduced relative to a wildtype control plant, and 2) a recombinant expression cassette comprising a DNA sequence encoding a CO or COL polypeptide, wherein the DNA sequence is operably linked to a plant-expressible promoter.

178. The modified corn plant of embodiment 177, wherein the modified corn plant is semi-dwarf and has one or more improved ear traits, relative to a control corn plant that does not comprise both the one or more mutations or edits and the recombinant expression cassette.

179. The modified corn plant of embodiment 177 or 178, wherein the one or more mutations or edits are selected from the group consisting of an insertion, a substitution, an inversion, a deletion, a duplication, and a combination thereof.

180. The modified corn plant of any one of embodiments 177 to 179, wherein the one or more mutations or edits are introduced using a meganuclease, a zinc-finger nuclease (ZFN), a RNA-guided endonuclease, a TALE-endonuclease (TALEN), a recombinase, or a transposase.

181. The modified corn plant of any one of embodiments 177 to 180, wherein the CO or COL polypeptide comprises an amino acid sequence that is at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to one or more of SEQ ID NOs: 176-397.

182. The modified corn plant of any one of embodiments 177 to 180, wherein the CO or COL polypeptide comprises an amino acid sequence that is at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to one or more of SEQ ID NOs: 398-452.

183. The modified corn plant of any one of embodiments 177 to 180, wherein CO or COL polypeptide comprises a *Physcomitrella patens* CONSTANS-like 1 (PpCOL1) polypeptide.

184. The modified corn plant of any one of embodiments 177 to 180, wherein the DNA sequence comprises a sequence that is at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 169.

185. The modified corn plant of any one of embodiments 177 to 180, the CO or COL polypeptide comprises an amino acid sequence that is at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 168.

186. The modified corn plant of any one of embodiments 177 to 185, wherein the recombinant expression cassette is stably integrated into the genome of the modified corn plant.

187. The modified corn plant of any one of embodiments 177 to 186, wherein the height at maturity of the modified corn plant is reduced by at least 1%, at least 2%, at least 5%, at least 10%, at least 15%, at least 20%, at least 25%, at least 30%, at least 35%, at least 40%, at least 45%, at least 50%, at least 55%, at least 60%, at least 65%, or at least 70%, relative to a control corn plant.

188. The modified corn plant of any one of embodiments 177 to 187, wherein the stalk or stem diameter of the modified corn plant is increased by at least 0.1%, at least 0.2%, at least 0.5%, at least 1%, at least 1.5%, at least 2%, at least 2.5%, at least 3%, at least 3.5%, at least 4%, at least 4.5%, at least 5%, at least 6%, at least 7%, at least 8%, at least 9%, at least 10%, at least 15%, at least 20%, at least 25%, at least 30%, at least 35%, at least 40%, at least 45%, or at least 50%, relative to a control corn plant.

189. The modified corn plant of any one of embodiments 177 to 188, wherein the modified corn plant exhibits improved lodging resistance, reduced green snap, or both, relative to the control corn plant.

190. The modified corn plant of any one of embodiments 177 to 189, wherein the modified corn plant exhibits increased ear area relative to a control corn plant.

191. The modified corn plant of any one of embodiments 177 to 190, wherein the modified corn plant exhibits increased single kernel weight relative to a control corn plant.

192. The modified corn plant of any one of embodiments 177 to 191, wherein the modified corn plant exhibits increased ear fresh weight relative to a control corn plant.

193. The modified corn plant of any one of embodiments 177 to 192, wherein the modified corn plant exhibits increased number of florets relative to a control corn plant.

194. The modified corn plant of any one of embodiments 177 to 193, wherein the modified corn plant exhibits a trait selected from the group consisting of deeper roots, increased leaf area, earlier canopy closure, higher stomatal conductance, lower ear height, increased foliar water content, improved drought tolerance, improved nitrogen use efficiency, reduced anthocyanin content and area in leaves under normal or nitrogen-limiting or water-limiting stress conditions, increased ear weight, increased harvest index, increased yield, increased seed number, increased seed weight, increased prolificacy, and a combination thereof, relative to a control corn plant.

195. The modified corn plant of any one of embodiments 177 to 194, wherein the modified corn plant does not have any significant off-types in at least one female organ or ear.

196. A plurality of modified corn plants in a field, each modified corn plant comprising
   a. one or more mutations or edits at or near one or more endogenous GA20 oxidase and/or GA3 oxidase genes, wherein the expression of the one or more endogenous GA20 oxidase and/or GA3 oxidase genes are reduced relative to a wildtype control plant, and
   b. a recombinant expression cassette comprising a DNA sequence encoding a CO or COL polypeptide, wherein the DNA sequence is operably linked to a plant-expressible promoter.

197. The plurality of modified corn plants of embodiment 196, wherein the modified corn plants have increased yield relative to control corn plants.

198. The plurality of modified corn plants of embodiment 196 or 197, wherein the modified corn plants have an increase in yield that is at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, or at least 25% greater than control corn plants.

199. A recombinant DNA construct comprising 1) a first expression cassette comprising a transcribable DNA sequence encoding a non-coding RNA for suppression of one or more GA20 oxidase or one or more GA3 oxidase genes, and 2) a second expression cassette comprising a DNA sequence encoding a CO or COL polypeptide, wherein the DNA sequence is operably linked to a plant-expressible promoter.

200. The recombinant DNA construct of embodiment 199, wherein the first and second expression cassettes are in a single T-DNA segment of a transformation vector.

201. The recombinant DNA construct of embodiment 199, wherein the first and second expression cassettes are in two different T-DNA segments of a transformation vector.

202. The recombinant DNA construct of any one of embodiments 199 to 201, wherein the transcribable DNA sequence encodes a non-coding RNA for suppression of a GA3 oxidase gene.

203. The recombinant DNA construct of embodiment 202, wherein the transcribable DNA sequence encodes a non-coding RNA for suppression of a GA3 oxidase_1 gene, a GA3 oxidase_2 gene, or both.

204. The recombinant DNA construct of embodiment 203, wherein the transcribable DNA sequence comprises a sequence that is at least 80%, at least 85%, at least 90%, at least 95%, at least 96%, at least 97%, at least 98%, at least 99%, at least 99.5%, or 100% identical or complementary to at least 15, at least 16, at least 17, at least 18, at least 19, at least 20, at least 21, at least 22, at least 23, at least 24, at least 25, at least 26, or at least 27 consecutive nucleotides of one or more of SEQ ID NOs: 28, 29, 31, 32, 36, and 37.

205. The recombinant DNA construct of embodiment 203, wherein the transcribable DNA sequence encodes a non-coding RNA comprising a sequence that is 80% complementary to at least 15 consecutive nucleotides of one or more of SEQ ID NOs: 28, 29, 31, 32, 36, and 37.

206. The recombinant DNA construct of embodiment 202, wherein the transcribable DNA sequence encodes a non-coding RNA for suppression of a GA20 oxidase gene.

207. The recombinant DNA construct of embodiment 206, wherein the transcribable DNA sequence encodes a non-coding RNA for suppression of a GA20 oxidase_3 gene, a GA20 oxidase_4 gene, a GA20 oxidase_5 gene, or a combination thereof.

208. The recombinant DNA construct of embodiment 206, wherein the transcribable DNA sequence encodes a non-coding RNA for suppression of a GA20 oxidase_3 gene, a GA20 oxidase_5 gene, or both.

209. The recombinant DNA construct of embodiment 208, wherein the transcribable DNA sequence comprises a sequence that is at least 80% identical or complementary to at least 15 consecutive nucleotides of SEQ ID NO: 39, 53, or 55.

210. The recombinant DNA construct of embodiment 209, wherein the transcribable DNA sequence encodes a sequence that is at least 80% identical or complementary to at least 15 consecutive nucleotides of SEQ ID NO: 40, 54, or 56.

211. The recombinant DNA construct of any one of embodiments 199 to 210, wherein the non-coding RNA comprises a sequence that is at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of a mRNA molecule encoding an endogenous GA oxidase protein in a corn plant or plant cell, the endogenous GA oxidase protein being at least 80%, at least 85%, at least 90%, at least 95%, at least 96%, at least 97%, at least 98%, at least 99%, at least 99.5%, or 100% identical to SEQ ID NO: 9, 12, 15, 30, or 33.

212. The recombinant DNA construct of any one of embodiments to 199 to 211, wherein the non-coding RNA comprises a sequence that is at least 80%, at least 85%, at least 90%, at least 95%, at least 96%, at least 97%, at least 98%, at least 99%, at least 99.5%, or 100% complementary to at least 15, at least 16, at least 17, at least 18, at least 19, at least 20, at least 21, at least 22, at least 23, at least 24, at least 25, at least 26, or at least 27 consecutive nucleotides of SEQ ID NO: 7, 8, 10, 11, 13, 14, 28, 29, 31, or 32.

213. The recombinant DNA construct of any one of embodiments 199 to 212, wherein the DNA sequence comprised in the second expression cassette comprises a sequence that encodes a protein having an amino acid sequence that is at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to one or more of SEQ ID NOs: 176-397.

214. The recombinant DNA construct of any one of embodiments 199 to 212, wherein the DNA sequence comprised in the second expression cassette comprises a sequence that encodes a protein having an amino acid sequence that is at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to one or more of SEQ ID NOs: 398-452.

215. The recombinant DNA construct of any one of embodiments 199 to 212, wherein the DNA sequence comprised in the second expression cassette encodes a *Physcomitrella patens* CONSTANS-like 1 (PpCOL1) polypeptide.

216. The recombinant DNA construct of any one of embodiments 199 to 212, wherein the CO or COL polypeptide comprises an amino acid sequence that is at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 168.

217. The recombinant DNA construct of any one of embodiments 199 to 212, wherein the DNA sequence comprises a sequence that is at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 169.

218. The recombinant DNA construct of any one of embodiments 199 to 215, the plant-expressible promoter is a vascular promoter.

219. The recombinant DNA construct of embodiment 218, wherein the vascular promoter is selected from the group consisting of a sucrose synthase promoter, a sucrose transporter promoter, a Sh1 promoter, CoYMV promoter, a WDV large intergenic region (LIR) promoter, a MSV coat polypeptide (CP) promoter, a rice yellow stripe 1 (YS1)-like promoter, a rice yellow stripe 2 (OsYSL2) promoter, and a combination thereof.

220. The recombinant DNA construct of any one of embodiments 199 to 215, wherein the plant-expressible promoter is an RTBV promoter.

221. The recombinant DNA construct of any one of embodiments 199 to 215, wherein the plant-expressible promoter is a leaf promoter.

222. The recombinant DNA construct of embodiment 221, wherein the leaf promoter is selected from the group consisting of a RuBisCO promoter, a PPDK promoter, a FDA promoter, a Nadh-Gogat promoter, a chlorophyll a/b binding polypeptide gene promoter, a PEPC promoter, a Myb gene promoter, and a combination thereof.

223. The recombinant DNA construct of any one of embodiments 199 to 215, wherein the plant-expressible promoter is a constitutive promoter.

224. The recombinant DNA construct of embodiment 223, wherein the constitutive promoter is selected from the group consisting of an actin promoter, a CaMV 35S or 19S promoter, a plant ubiquitin promoter, a plant Gos2 promoter, a FMV promoter, a CMV promoter, a MMV promoter, a PCLSV promoter, an Emu promoter, a tubulin promoter, a nopaline synthase promoter, an octopine synthase promoter, a mannopine synthase promoter, or a maize alcohol dehydrogenase, a functional portion thereof, and a combination thereof.

225. The recombinant DNA construct of any one of embodiments 199 to 215, wherein the plant-expressible promoter comprises a DNA sequence that is at least 80%, at least 85%, at least 90%, at least 95%, at least 96%, at least 97%, at least 98%, at least 99%, at least 99.5% or 100% identical to SEQ ID NO: 172 or a functional portion thereof.

226. The recombinant DNA construct of embodiment 199, wherein the non-coding RNA is a precursor miRNA or siRNA capable of being processed or cleaved to form a mature miRNA or siRNA.

227. A transformation vector comprising the recombinant DNA construct of any one of embodiments 199 to 226.

228. A modified corn plant or a plant part thereof comprising the recombinant DNA construct of embodiment 227.

229. The modified corn plant of embodiment 228, wherein the modified corn plant is semi-dwarf and has one or more improved ear traits, relative to a control corn plant not having both the first and second expression cassettes.

230. The modified corn plant of embodiment 229, wherein the height at maturity of the modified corn plant is reduced by at least 1%, at least 2%, at least 5%, at least 10%, at least 15%, at least 20%, at least 25%, at least 30%, at least 35%, at least 40%, at least 45%, at least 50%, at least 55%, at least 60%, at least 65%, or at least 70%, relative to the control corn plant.

231. The modified corn plant of embodiment 229, wherein the stalk or stem diameter of the modified corn plant is increased by at least 0.1%, at least 0.2%, at least 0.5%, at least 1%, at least 1.5%, at least 2%, at least 2.5%, at least 3%, at least 3.5%, at least 4%, at least 4.5%, at least 5%, at least 6%, at least 7%, at least 8%, at least 9%, at least 10%, at least 15%, at least 20%, at least 25%, at least 30%, at least 35%, at least 40%, at least 45%, or at least 50%, relative to the control corn plant.

232. The modified corn plant of embodiment 229, wherein the modified corn plant exhibits improved lodging resistance, reduced green snap, or both, relative to the control corn plant.

233. The modified corn plant of embodiment 229, wherein the modified corn plant exhibits increased ear area relative to the control corn plant.

234. The modified corn plant of embodiment 229, wherein the modified corn plant exhibits increased single kernel weight relative to the control corn plant.

235. The modified corn plant of embodiment 229, wherein the modified corn plant exhibits increased ear fresh weight relative to the control corn plant.

236. The modified corn plant of embodiment 229, wherein the modified corn plant exhibits increased number of florets relative to the control corn plant.

237. The modified corn plant of embodiment 229, wherein the modified corn plant exhibits a trait selected from the group consisting of deeper roots, increased leaf area, earlier canopy closure, higher stomatal conductance, lower ear height, increased foliar water content, improved drought tolerance, improved nitrogen use efficiency, reduced anthocyanin content and area in leaves under normal or nitrogen-limiting or water-limiting stress conditions, increased ear weight, increased harvest index, increased yield, increased seed number, increased seed weight, increased prolificacy, and a combination thereof, relative to the control corn plant.

238. The modified corn plant of embodiment 229, wherein the modified corn plant does not have any significant off-types in at least one female organ or ear.

239. A recombinant DNA donor template molecule for site directed integration of an insertion sequence into the genome of a corn plant comprising an insertion sequence and at least one homology sequence, wherein the homology sequence is at least 70%, at least 75%, at least 80%, at least 85%, at least 90%, at least 95%, at least 96%, at least 97%, at least 99% or 100% complementary to at least 20, at least 25, at least 30, at least 35, at least 40, at least 45, at least 50, at least 60, at least 70, at least 80, at least 90, at least 100, at least 150, at least 200, at least 250, at least 500, at least 1000, at least 2500, or at least 5000 consecutive nucleotides of a target DNA sequence in the genome of a corn plant cell, and wherein the insertion sequence comprises an expression cassette comprising a DNA sequence encoding a CO or COL polypeptide, wherein the DNA sequence is operably linked to a plant-expressible promoter.

240. The recombinant DNA donor template molecule of embodiment 239, comprising two of the homology sequences, wherein the two homology sequences flank the insertion sequence.

241. The recombinant DNA donor template molecule of embodiment 239 or 240, wherein the CO or COL polypeptide comprises an amino acid sequence that is at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to one or more of SEQ ID NOs: 176-397.

242. The recombinant DNA donor template molecule of embodiment 239 or 240, wherein the CO or COL polypeptide comprises an amino acid sequence that is at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to one or more of SEQ ID NOs: 398-452.

243. The recombinant DNA donor template molecule of embodiment 239 or 240, wherein the CO or COL polypeptide comprises a *Physcomitrella patens* CONSTANS-like 1 (PpCOL1) polypeptide.

244. The recombinant DNA donor template molecule of embodiment 239 or 240, wherein the DNA sequence comprised in the expression cassette comprises a sequence that is at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 169.

245. The recombinant DNA donor template molecule of embodiment 239 or 240, wherein the CO or COL polypeptide comprises an amino acid sequence that is at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% identical to SEQ ID NO: 168.

246. The recombinant DNA donor template molecule of any one of embodiments 239 to 245, wherein the plant-expressible promoter comprises a DNA sequence that is at least 80%, at least 85%, at least 90%, at least 95%, at least 96%, at least 97%, at least 98%, at least 99%, at least 99.5% or 100% identical to SEQ ID NO: 172 or a functional portion thereof.

247. The recombinant DNA donor template molecule of any one of embodiments 239 to 246, further comprising a transcribable DNA sequence encoding a non-coding RNA for suppression of one or more GA20 oxidase genes and/or one or more GA3 oxidase genes, wherein the transcribable DNA sequence is operably linked to a promoter.

248. The recombinant DNA donor template molecule of embodiment 247, wherein the promoter is a vascular promoter.

249. The recombinant DNA donor template molecule of embodiment 248, wherein the vascular promoter is selected from the group consisting of a sucrose synthase promoter, a sucrose transporter promoter, a Sh1 promoter, *Commelina* yellow mottle virus (CoYMV) promoter, a wheat dwarf geminivirus (WDV) large intergenic region (LIR) promoter, a maize streak geminivirus (MSV) coat polypeptide (CP) promoter, a rice yellow stripe 1 (YS1)-like promoter, a rice yellow stripe 2 (OsYSL2) promoter, and a combination thereof.

250. The recombinant DNA donor template molecule of embodiment 249, wherein the vascular promoter comprises a DNA sequence that is at least 80%, at least 85%, at least 90%, at least 95%, at least 96%, at least 97%, at least 98%, at least 99%, at least 99.5% or 100% identical to one or more of SEQ ID NO: 67, SEQ ID NO: 68, SEQ ID NO: 69, SEQ ID NO: 70, or SEQ ID NO: 71, or a functional portion thereof.

251. The recombinant DNA donor template molecule of any one of embodiments 239 to 245, wherein the promoter is a rice tungro bacilliform virus (RTBV) promoter.

252. The recombinant DNA donor template molecule of embodiment 251, wherein the RTBV promoter comprises a DNA sequence that is at least 80%, at least 85%, at least 90%, at least 95%, at least 96%, at least 97%, at least 98%, at least 99%, at least 99.5% or 100% identical to one or more of SEQ ID NO: 65 or SEQ ID NO: 66, or a functional portion thereof.

253. The recombinant DNA donor template molecule of any one of embodiments 239 to 245, wherein the promoter is a leaf promoter.

254. The recombinant DNA donor template molecule of embodiment 253, wherein the leaf promoter is selected from the group consisting of a RuBisCO promoter, a pyruvate phosphate dikinase (PPDK) promoter, a fructose 1-6 bisphosphate aldolase (FDA) promoter, a Nadh-Gogat promoter, a chlorophyll a/b binding polypeptide gene promoter, a phosphoenolpyruvate carboxylase (PEPC) promoter, a Myb gene promoter, and a combination thereof.

255. The recombinant DNA donor template molecule of embodiment 254, wherein the leaf promoter comprises a DNA sequence that is at least 80%, at least 85%, at least 90%, at least 95%, at least 96%, at least 97%, at least 98%, at least 99%, at least 99.5% or 100% identical to one or more of SEQ ID NO: 72, SEQ ID NO: 73 or SEQ ID NO: 74, or a functional portion thereof.

256. The recombinant DNA donor template molecule of any one of embodiments 239 to 245, wherein the promoter is a constitutive promoter.

257. The recombinant DNA donor template molecule of embodiment 256, wherein the constitutive promoter is selected from the group consisting of an actin promoter, a Cauliflower mosaic virus (CaMV) 35S or 19S promoter, a plant ubiquitin promoter, a plant Gos2 promoter, a Figwort mosaic virus (FMV) promoter, a cytomegalovirus (CMV) promoter, a mirabilis mosaic virus (MMV) promoter, a peanut chlorotic streak caulimovirus (PCLSV) promoter, an Emu promoter, a tubulin promoter, a nopaline synthase promoter, an octopine synthase promoter, a mannopine synthase promoter, or a maize alcohol dehydrogenase, a functional portion thereof, and a combination thereof.

258. The recombinant DNA donor template molecule of embodiment 257, wherein the constitutive promoter comprises a DNA sequence that is at least 80%, at least 85%, at least 90%, at least 95%, at least 96%, at least 97%, at least 98%, at least 99%, at least 99.5% or 100% identical to one or more of SEQ ID NOs: 75, SEQ ID NO: 76, SEQ ID NO: 77, SEQ ID NO: 78, SEQ ID NO: 79, SEQ ID NO: 80, SEQ ID NO: 81, SEQ ID NO: 82 or SEQ ID NO: 83, or a functional portion thereof.

259. The modified corn plant of embodiment 1, wherein the first recombinant expression cassette comprises SEQ ID NO: 39, and the second recombinant expression cassette comprises SEQ ID NO: 169.

260. The modified corn plant of embodiment 259, wherein the modified corn plant is semi-dwarf and exhibits one or more improved ear traits, relative to a control plant that does not comprise the first or second recombinant expression cassette.

261. The modified corn plant of embodiment 260, wherein the one or more improved ear traits are selected from the group consisting of ear area, ear volume, ear diameter, ear length, kernels per ear, single kernel weight, grain yield estimate, broad acreage yield, and a combination thereof.

262. A modified corn plant or a plant part thereof comprising 1) a first transcribable DNA sequence comprising SEQ ID NO: 39, and 2) a second transcribable DNA sequence comprising SEQ ID NO: 169.

263. The modified corn plant of embodiment 262, wherein the modified corn plant is semi-dwarf and has one or more improved ear traits, relative to a control corn plant that does not have the first or second transcribable DNA sequence.

264. The modified corn plant of embodiment 263, wherein the one or more improved ear traits are selected from the group consisting of ear area, ear volume, ear diameter, ear length, kernels per ear, single kernel weight, grain yield estimate, broad acreage yield, and a combination thereof.

265. A method for producing a modified corn plant, the method comprising
   a. introducing into a corn cell a recombinant expression cassette comprising a first transcribable DNA sequence comprising SEQ ID NO: 39, and a second transcribable DNA sequence comprising SEQ ID NO: 169;
   b. regenerating or developing a modified corn plant from the corn cell, wherein the modified corn plant comprises the first and second transcribable DNA sequences.

266. The method of embodiment 265, wherein the modified corn plant is semi-dwarf and has one or more improved ear traits, relative to a control corn plant that does not have the first or second transcribable DNA sequence.

267. The method of embodiment 266, wherein the one or more improved ear traits are selected from the group consisting of ear area, ear volume, ear diameter, ear length, kernels per ear, single kernel weight, grain yield estimate, broad acreage yield, and a combination thereof.

268. A recombinant expression cassette comprising 1) a first transcribable DNA sequence comprising SEQ ID NO: 39, and 2) a second transcribable DNA sequence comprising SEQ ID NO: 169.

EXAMPLES

Example 1. Generation of the GA20Ox_SUP/PpCOL Stack Plants

An inbred corn plant line was transformed via *Agrobacterium*-mediated transformation with a transformation vector having an expression construct comprising a miRNA-encoding DNA sequence (SEQ ID NO: 39) encoding a targeting sequence (SEQ ID NO: 40) under the control of a rice tungro bacilliform virus (RTBV) promoter (SEQ ID NO: 65) known to cause expression in vascular tissues of plants. The miRNA encoded by the construct comprises an RNA sequence that targets the GA20 oxidase_3 and GA20 oxidase_5 genes in corn plants. Several transformation events were generated therefrom. The resulting transformed/transgenic inbred line is herein referred to as GA20Ox_SUP or GA20Ox_SUP single.

Similarly, an inbred corn plant line was transformed via *Agrobacterium*-mediated transformation with a transformation vector having an expression construct comprising a transgene (SEQ ID NO: 169) encoding *Physcomitrella patens* CONSTANS-like (PpCOL) polypeptide (SEQ ID NO: 168). The expression construct comprises an *Oryza sativa* enhancer (SEQ ID NO: 170), a CaMV 35S enhancer (SEQ ID NO: 171), an *Oryza sativa* promoter (SEQ ID NO: 172), a leader sequence (SEQ ID NO: 173), an intron sequence (SEQ ID NO: 174), and a terminator sequence (SEQ ID NO: 175) Several transformation events were generated therefrom. The resulting transformed/transgenic inbred line is herein referred to as PpCOL, PpCOL transgenic plant, or PpCOL single. PpCOL1 and PpCOL are used interchangeably.

The parental GA20Ox_SUP and PpCOL singles were crossed to create a stacked transgenic progeny plant comprising both the PpCOL transgene and the miRNA-encoding DNA sequence for the suppression of GA20 oxidase_3 and GA20 oxidase_5 genes. The resulting stacked transgenic line is herein referred to as GA20Ox_SUP/PpCOL stack. The GA20Ox_SUP/PpCOL stack can be inbred stack if the parental lines are of the same inbred line origin, or hybrid when the parental lines are of different inbreds.

For each type of transgenic single and stack plants, the corresponding control plants were also produced for comparison having the same inbred line or same parental line combination, but without the transgenic GA20Ox_SUP and PpCOL constructs.

Example 2. Reduced Height of the GA20Ox_SUP/PpCOL Stack Plants

GA20Ox_SUP/PpCOL stack plants were grown to maturity in a field under standard agronomic practice and their heights are measured. Plant height was measured as the plot average from the soil line to the base of highest collared leaf at the R3 stage. A sufficient number of plants were measured to meet statistical significance with p-value≤0.2. Control plants of the same parental inbred lines but without the GA20Ox_SUP and PpCOL transgenic constructs were also grown under similar conditions.

Average plant height reduction for each of four breeding or crossing stack event combinations of the GA20Ox_SUP/PpCOL transgenes ("Stack-1" to "Stack-4") is shown in FIG. 1 relative to control plants. As shown in FIG. 1, a statistically significant reduction in plant height averaging between 30 to 35% was consistently observed in GA20Ox_SUP/PpCOL stack plants relative to control plants.

Example 3. Enhanced Ear Traits of PpCOL Single Plants

Transgenic single and stack plants, along with control plants as described in Example 1, were grown under standard agronomic practice. For GA20Ox_SUP and PpCOL singles, plants of two to four transformation events were chosen, with corresponding event combinations in the GA20Ox_SUP/PpCOL stack. Several corn ear traits were measured at the R6 stage.

Ear area is measured as the plot average of the size of the area of an ear from a two-dimensional view. The measurement is conducted via imaging of the ear, including kernels and void. Typically, 10 representative ears are measured per plot. Ear fresh weight is measured as the plot average of the ear weight of a plant at the R6 stage.

Grain yield estimate is measured as the conversion from hand-harvested grain weight per area, collected from a small section of a plot, to the equivalent of bushels per acre, including adjustment to a standard moisture level.

Single kernel weight is measured as the plot average of weight per kernel, calculated as the ratio of (sample kernel weight adjusted to a standard moisture level)/(sample kernel number). The sample kernel number ranges from 350 to 850.

Figure 2:
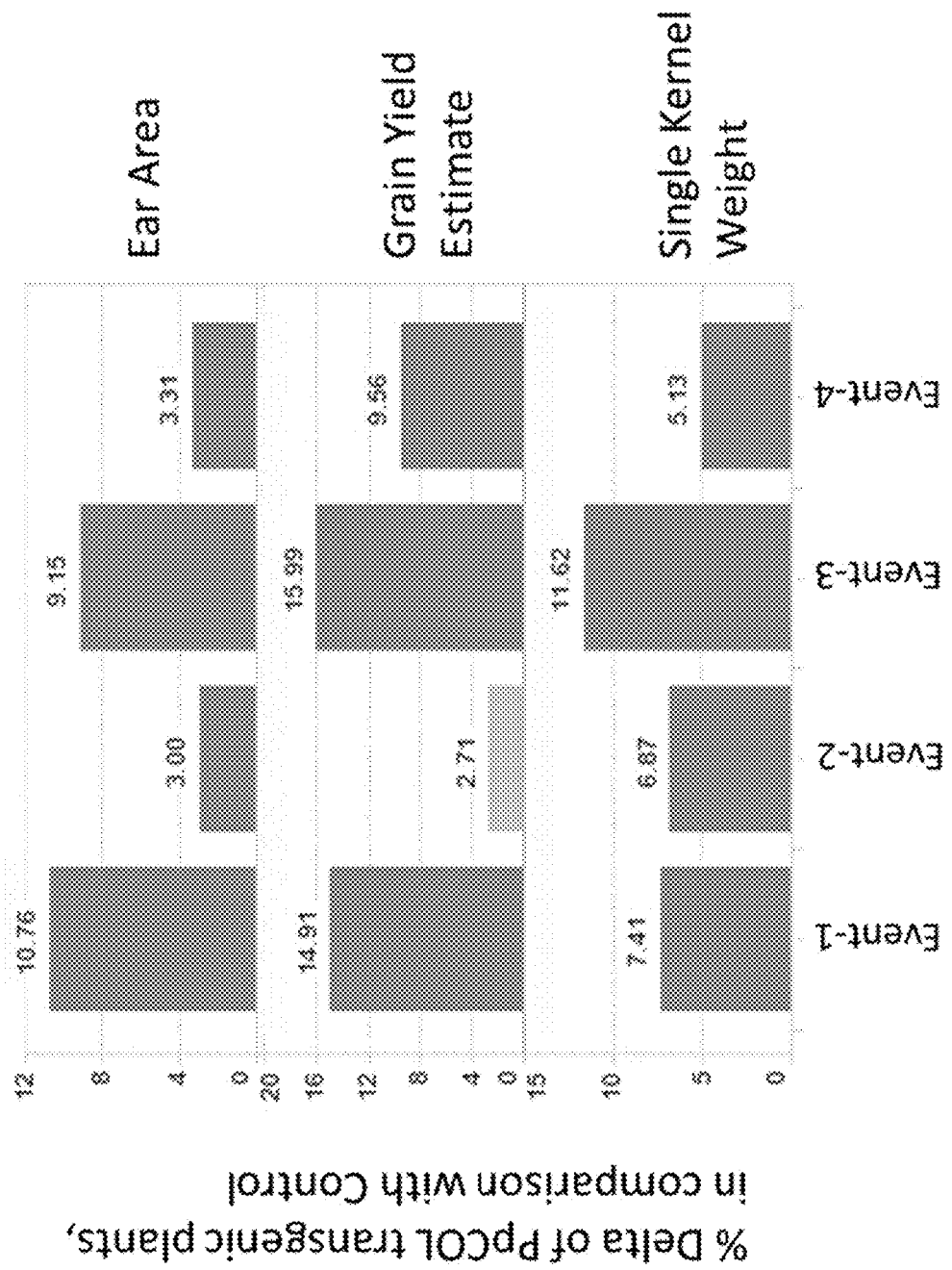
FIG. 2 shows ear traits of stacked GA20Ox_SUP/PpCOL plants across four transformation events including ear area, grain yield estimate, and single kernel weight, relative to control plants.

FIG. 2 shows ear trait results for PpCOL single plants from four transformation events in one growing season. Results were shown as percent difference (delta) between PpCOL single plants and control plants of the same inbred without the PpCOL transgenic construct. The dark gray bars in FIG. 2 are indicative of a statistically significant difference in ear area, grain yield estimate, and single kernel weight relative to control plants (p-value≤0.2). The light gray bar is indicative of numerically positive improvement in grain yield estimate.

As shown in FIG. 2, statistically significant improvements or increases in ear area, grain yield estimate, and single kernel weight relative to control plants were observed in all four PpCOL single transformation events ("Event-1" to "Event-4"), with the exception that Event-2 showed a non-statistically positive trend or increase in grain yield estimate.

Figure 3:
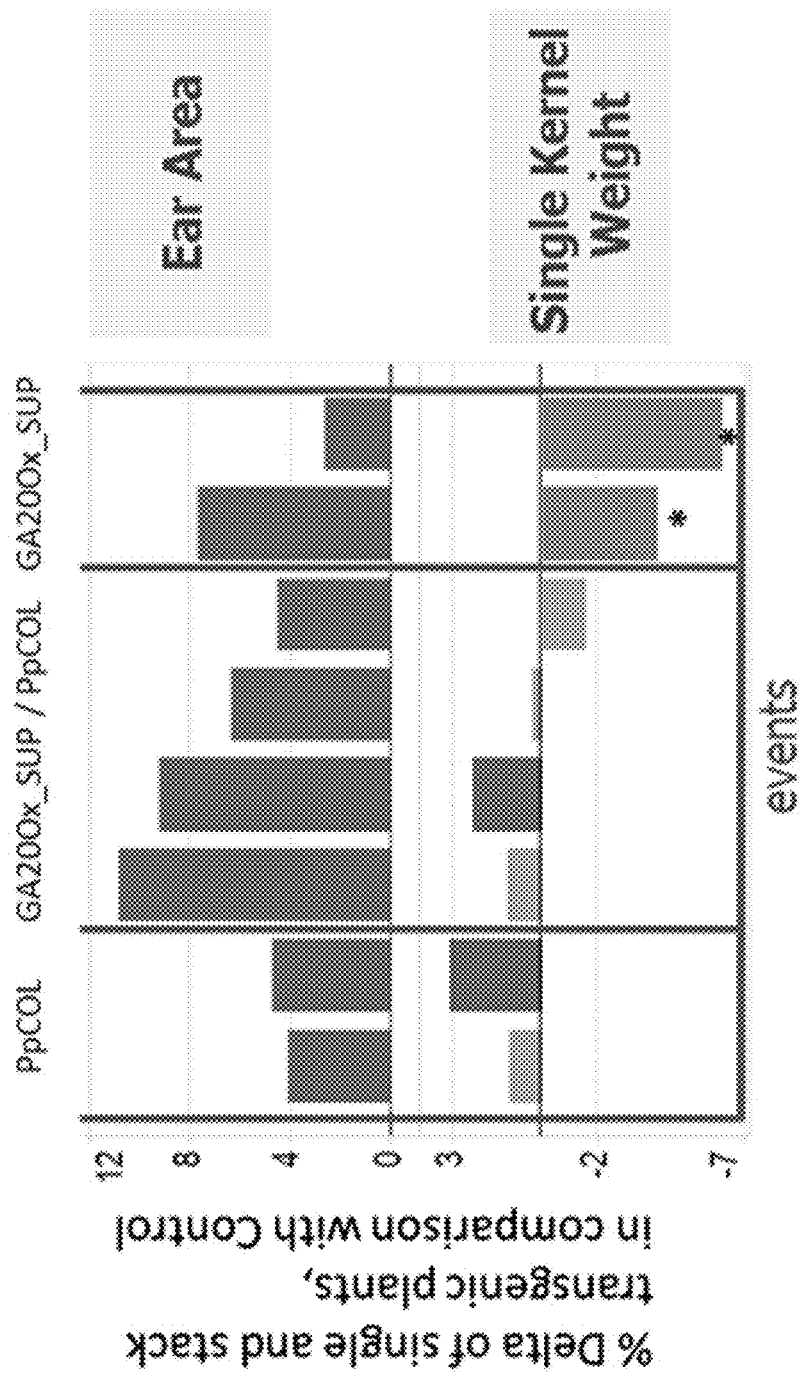
FIG. 3 shows ear area and single kernel weight of stacked GA20Ox_SUP/PpCOL plants relative to control plants.

Example 4. Enhanced Ear Area and Single Kernel Weight of GA20Ox_SUP/PpCOL Stack Plants Ear traits were measured with GA20Ox_SUP single, PpCOL single, and GA20Ox_SUP/PpCOL stack plants, and positive effects or traits were observed when both the GA20Ox_SUP and PpCOL constructs were present in a plant. As shown in FIG. 3, ear area and single kernel weight were measured in two events of the GA20OX_SUP single, two events of the PpCOL single, and four breeding stack event combinations of the GA20Ox_SUP/PpCOL transgenes grown in a single growing season, with each bar indicating one transformation event. Dark gray bars in FIG. 3 are indicative of statistically significant positive changes (p-value≤0.2), and light gray bars are indicative of numerically, but not statistically significant, positive or negative changes. Asterisk (*) indicates significant negative changes (p-value≤0.2).

Positive effects were observed in the GA20Ox_SUP/PpCOL stack plants. As shown in FIG. 3, PpCOL single events demonstrated improved ear area and single kernel weight relative to control plants. The PpCOL single and GA20Ox_SUP single plants each showed a significantly increased ear area relative to control plants, and PpCOL single plants showed increased single kernel weight relative to control plants. GA20Ox_SUP/PpCOL stack plants also demonstrated a statistically significant increase in ear area relative to control plants. Moreover, the average increase in ear area with the four breeding stack event combinations in GA20Ox_SUP/PpCOL stack plants was greater than that of the PpCOL single or GA20Ox_SUP single plants. Similarly, the GA20Ox_SUP/PpCOL stack plants had an increased single kernel weight relative to control, as compared to the GA20Ox_SUP single plants.

These results show that GA20Ox_SUP/PpCOL stack plants have enhanced ear traits, such as increased ear area and single kernel weight, compared to control plants, PpCOL single plants, and/or GA20Ox_SUP single plants.

Example 5. Increased Ear Fresh Weight of GA20Ox_SUP/PpCOL Stack Plants

Figure 4:
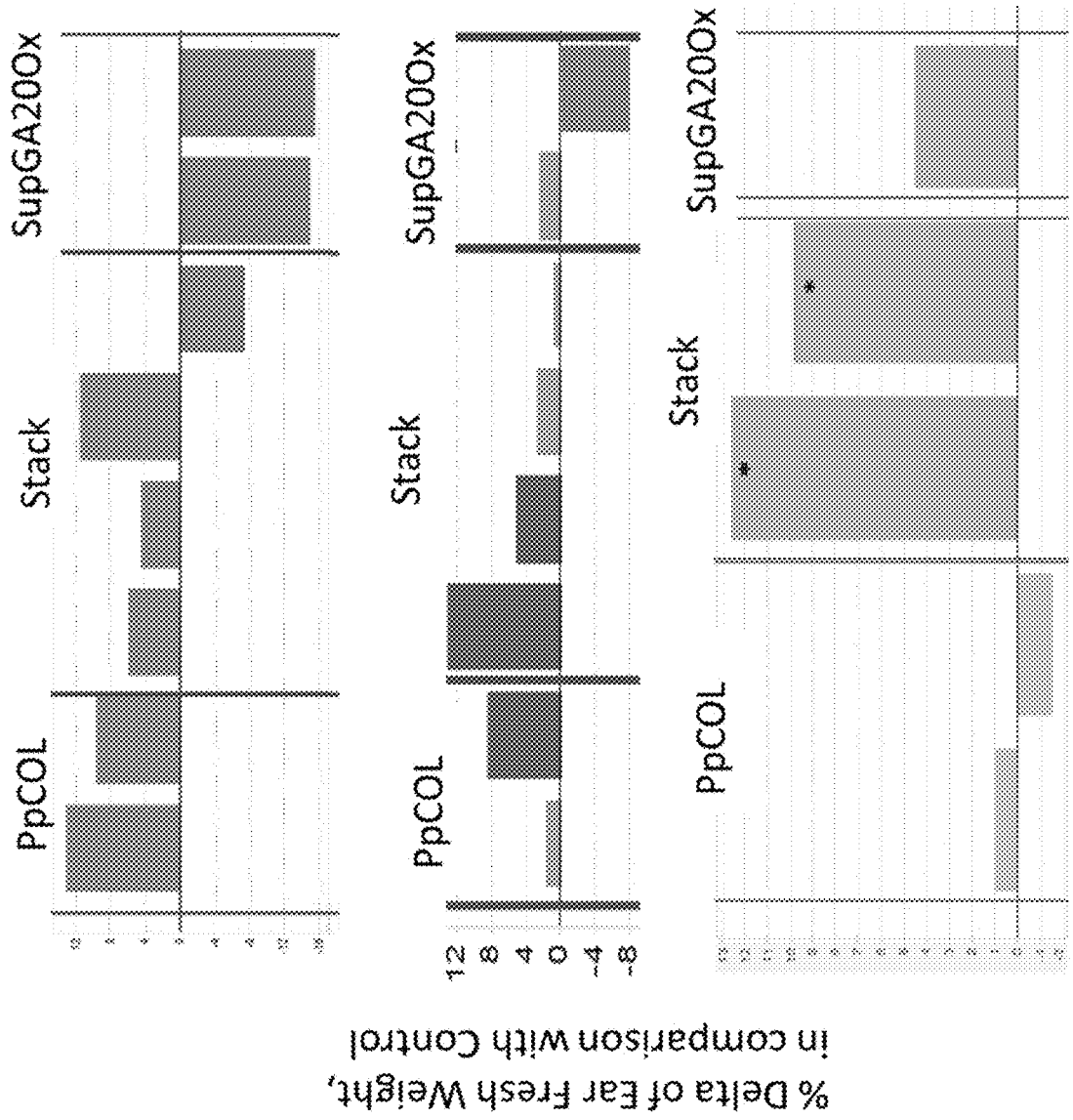
FIG. 4 shows ear fresh weight of GA20Ox_SUP/PpCOL stack plants in three consecutive growing seasons relative to control plants.

FIG. 4 provides the percent difference in ear fresh weight of PpCOL single, GA20Ox_SUP single, and GA20Ox_SUP/PpCOL stack plants relative to control plants over three consecutive growing seasons. Each bar in FIG. 4 is for a single event or a stacked combination of transformation events. Dark gray bars or those with an asterisk (*) are indicative of statistically significant positive or negative differences (p-value≤0.2), and light gray bars are indicative of numerically positive or negative, but not statistically significant, improvements or differences (increase or decrease).

Though the PpCOL single and GA20Ox_SUP single plants showed variation in ear fresh weight over three years, GA20Ox_SUP/PpCOL stack plants showed consistent and significant improvement of ear fresh weight over control plants, across years and event combinations. The increase in ear fresh weight with GA20Ox_SUP/PpCOL stack plants suggests that plants containing the GA20Ox_SUP/PpCOL stack combination could have improved and/or stabilized yield across growing seasons and environments.

Example 6. Increased Floret Numbers in the GA20Ox_SUP/PpCOL Stack Plants

Phenotypic analysis was conducted on R1 stage ears collected from GA20Ox_SUP single, PpCOL single, and GA20Ox_SUP/PpCOL stack plants, along with control plants. The number of florets is an early indicator of the number of potential corn kernels. Five plants and ears per genotype/event were used to sample the total number of unpollinated ear florets at R1 stage. To calculate total floret numbers, R1 ears were dissected from each plant, and for each ear, the number of longitudinal florets (rank number) was multiplied by the number of florets across the diameter of the ear (row number). A Student's-t test was then conducted to analyze and group the results.

Figure 5:
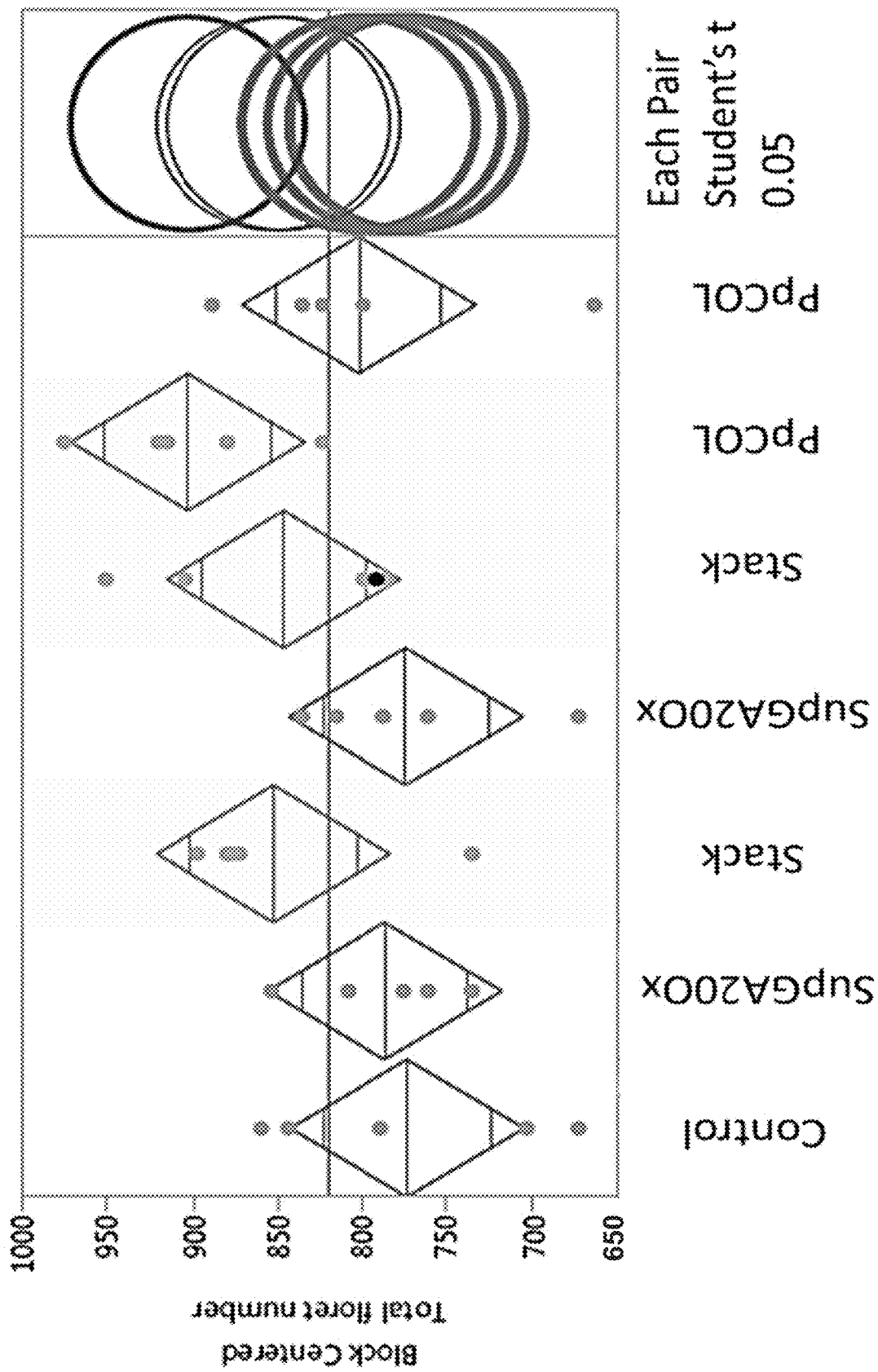
FIG. 5 shows the number of florets in GA20Ox_SUP/PpCOL stack plants relative to control plants.

As shown in FIG. 5, all GA20Ox_SUP/PpCOL stack plants (and one PpCOL single plant) showed a statistically significant increase in the number of florets per ear relative to control plants and/or GA20Ox_SUP single plants.

Example 7. Identification of CONSTANS (CO) and CONSTANS-Like (COL) Gene Homologs Sixty-eight CONSTANS (CO) and CONSTANS-like (COL) homologs were identified from *Arabidopsis*, rice, soybean and barley, and the CO/COL protein sequences were further searched in Genbank® to identify additional CO/COL homologs from various plant species using BlastP (e-value cutoff of 1e-10). The preliminary search results were then filtered to identify those having a full amino acid sequence with a starting methionine, and a CCT domain (HMMSEARCH vs. CCT Pfam, using gathering threshold cutoff) and one or two Zinc finger B-box domain(s) (HMMERSEARCH vs. zf-B_box Pfam, using gathering threshold cutoff). Compiled results of these searches include proteins having the following amino acid sequences: SEQ ID NOs: 176-397 (single B-box domain) and SEQ ID NOs: 398-452 (two B-box domains).

Figure 6:
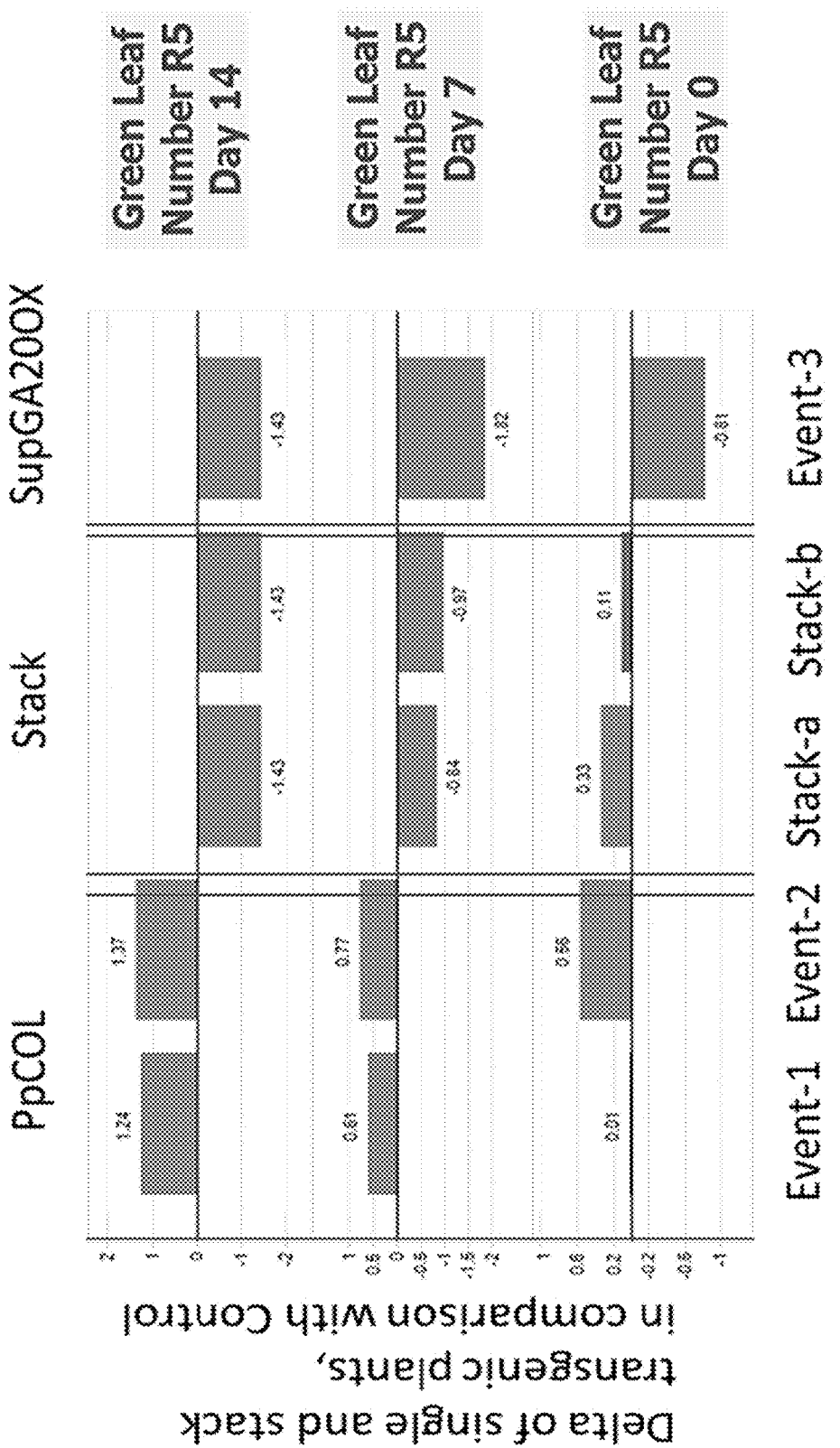
FIG. 6 shows the plot average of the number of green leaves from 0, 7, and 14 days after the onset of the R5 stage for GA20Ox_SUP/PpCOL stack plants relative to control plants.

Example 8. Green Leaf Number for GA20OX_SUP/PpCOL Stack Plants During Later Reproductive Stage The number of green leaves during reproductive stages can have an impact on corn yield. FIG. 6 shows the plot average of the number of green leaves at 0, 7, and 14 days after the onset of the R5 stage for GA20Ox_SUP single, PpCOL single, and GA20Ox_SUP/PpCOL stack plants. The data in FIG. 6 is presented as the difference (or delta) between the transgenic plants and control.

As shown in FIG. 6, the green leaf number of GA20Ox_SUP/PpCOL stack plants was similar to the number of green leaves on control plants during the R5 stage at day 0 and day 7, with a slight reduction in the number of green leaves on during the R5 stage at day 14 relative to control plants, and the number of green leaves on GA20Ox_SUP single plants was slightly less than control plants during the R5 stage of development.

Example 9. Flowering and Pollen Shedding in GA20OX_SUP/PpCOL Stack Plants

Variation in flowing time and differences in timing between pollen shed and silk emergence can impact corn yields.

As used herein, days to 50% pollen shedding (or days to pollen) measures the number of days between planting and the day when 50% of the plants reach the pollen shedding stage. Days to 50% visible silk (or days to silk) measures the number of days between planting and the day when 50% of the plants reach visible silking at the R1 stage. Anthesis-silking interval (ASI) measures the days between pollination and silking for 50% of the plants. A smaller ASI (i.e., closer to zero) tends to have a relatively positive effect on corn yield.

Figure 7:
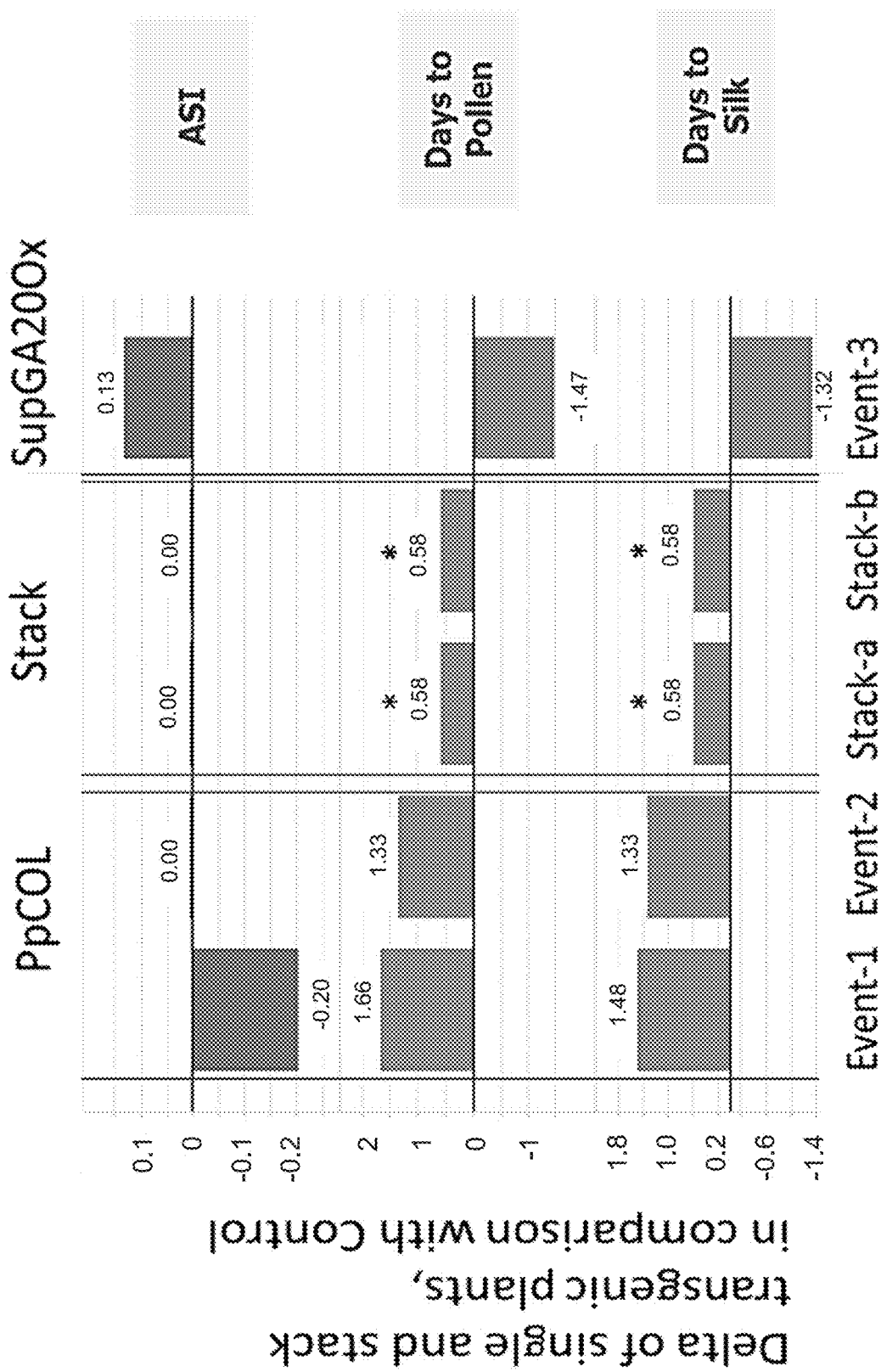
FIG. 7 shows days to 50% pollen shedding, days to 50% visible silk, and anthesis-silking interval (ASI) measurements for GA20Ox_SUP/PpCOL stack plants in one growing season relative to control plants.

The anthesis-silking interval (ASI), number of days to pollen shed, and number of days to silking of GA20Ox_SUP single plants (one event), PpCOL single plants (two events), and GA20Ox_SUP/PpCOL stack plants (two event combinations) were measured and compared to control plants. The results are shown in FIG. 7 as the difference (in days) in ASI, days to pollen, or days to silk, for each of the single and stack plants relative to control plants. The bars with an asterisk (*) are indicative of a statistically significant difference relative to the non-transgenic control plants (p-value≤0.2).

As shown in FIG. 7, the PpCOL single plants take more days to pollen and more days to silk than control plants, and the GA20Ox_SUP single plants take fewer days to pollen and silk relative to control plants (although the differences in both cases are relatively small). However, the timing for visible silking and pollen shed for GA20Ox_SUP/PpCOL stack plants was more similar or closer to that of control plants as compared to the GA20Ox_SUP single and PpCOL single plants, with a relatively neutral ASI value delta (relative to control plants) than the GA20Ox_SUP single plants.

Example 10. Enhanced Ear Traits in the GA20Ox_SUP/PpCOL Stack Plants

Ear traits including ear area, ear volume, ear diameter, ear length, kernels per ear, and single kernel weight were measured in a single growing season for GA20Ox_SUP single, PpCOL single, and GA20Ox_SUP/PpCOL stack plants, in addition to control plants.

Figure 8:
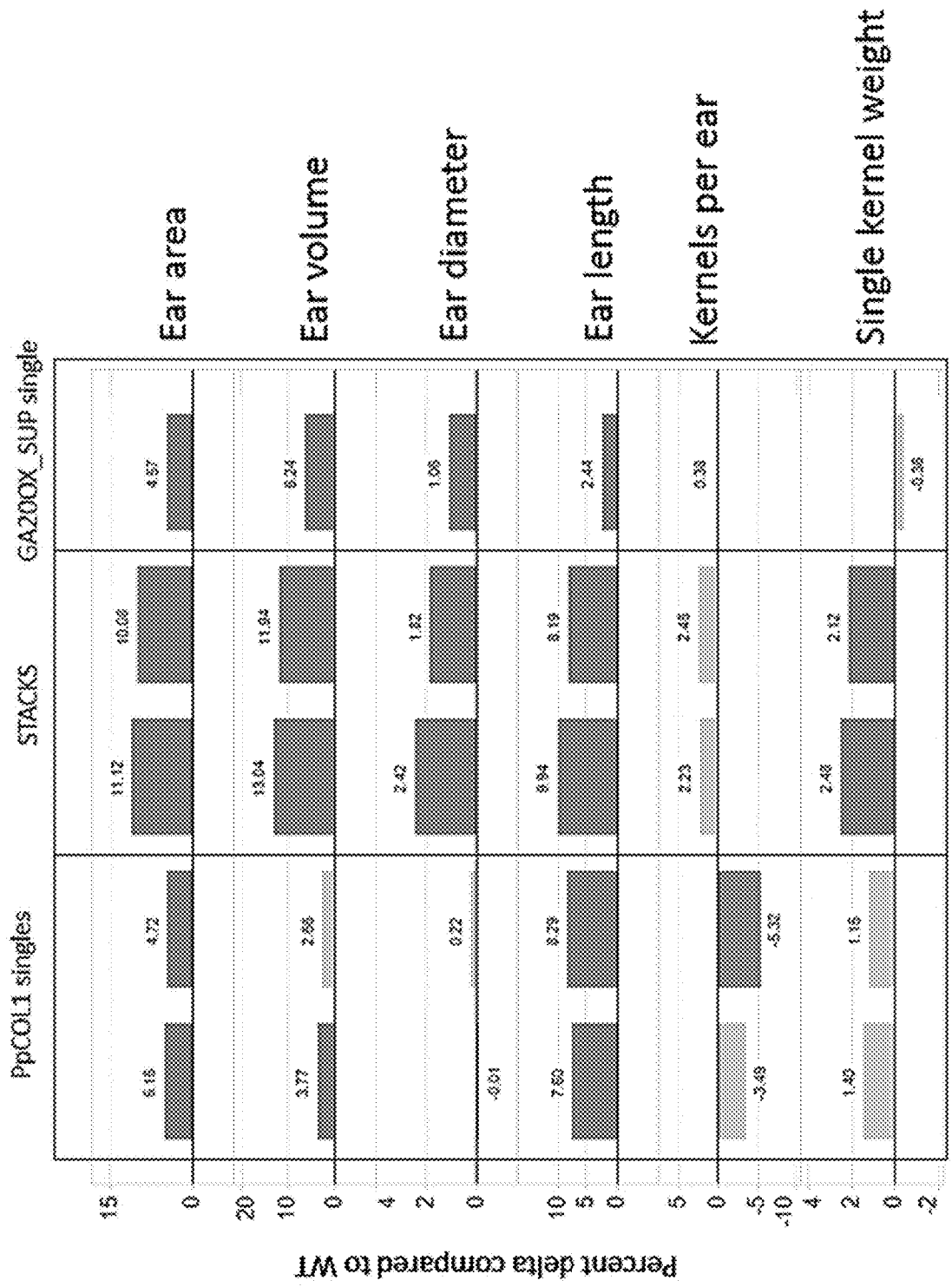
FIG. 8 shows ear traits of GA20Ox_SUP/PpCOL vector stack plants across two transformation events including ear area, ear volume, ear diameter, ear length, kernels per ear, and single kernel weight, relative to control plants.

FIG. 8 provides the ear trait results form this experiment as the difference (delta) of these traits for PpCOL single plants (two events), GA20OX_SUP single plants (one event), and GA20Ox_SUP/PpCOL breeding stack plants (two event combinations), relative to control plants (not containing the transgenes), with each bar indicating one transformation event (single) or event combination (stack). Dark gray bars in FIG. 8 are indicative of significantly positive or negative changes (p-value≤0.2), and light gray bars are indicative of numerically positive or negative changes, all compared to control plants not containing the transgenes.

As shown in FIG. 8, PpCOL single events demonstrated statistically significant improved or increased ear area, ear volume (one event), and ear length, with a numerically positive increase in single kernel weight, relative to control plants, and a potential negative effect on the number of kernels per ear, relative to control plants. The GA20Ox_SUP single plants showed a statistically significant increased ear area, ear volume, ear diameter, and ear length, relative to control plants. However, GA20Ox_SUP/PpCOL stack plants demonstrated a statistically significant increase in ear area, ear volume, ear diameter, ear length, and single kernel weight, relative to control plants. GA20Ox_SUP/PpCOL stack plants also showed a numerical increase in kernels per ear, relative to control plants. Moreover, the average increase in ear area, ear volume, ear diameter, ear length, kernels per ear, and single kernel weight of the GA20Ox_SUP/PpCOL stack plants relative to control plants, was greater than that of the PpCOL single or GA20Ox_SUP single plants.

These results demonstrate that GA20Ox_SUP/PpCOL stack plants have enhanced ear traits, such as increased ear area, ear volume, ear diameter, ear length, kernels per ear, and single kernel weight, compared to control plants, PpCOL single plants, and/or GA20Ox_SUP single plants.

Example 11. Increased Grain Yield Estimate in the GA20Ox_SUP/PpCOL Stack Plants

Grain yield estimate was measured for GA20Ox_SUP single, PpCOL single, and GA20Ox_SUP/PpCOL stack plants, in addition to control plants.

Figure 9:
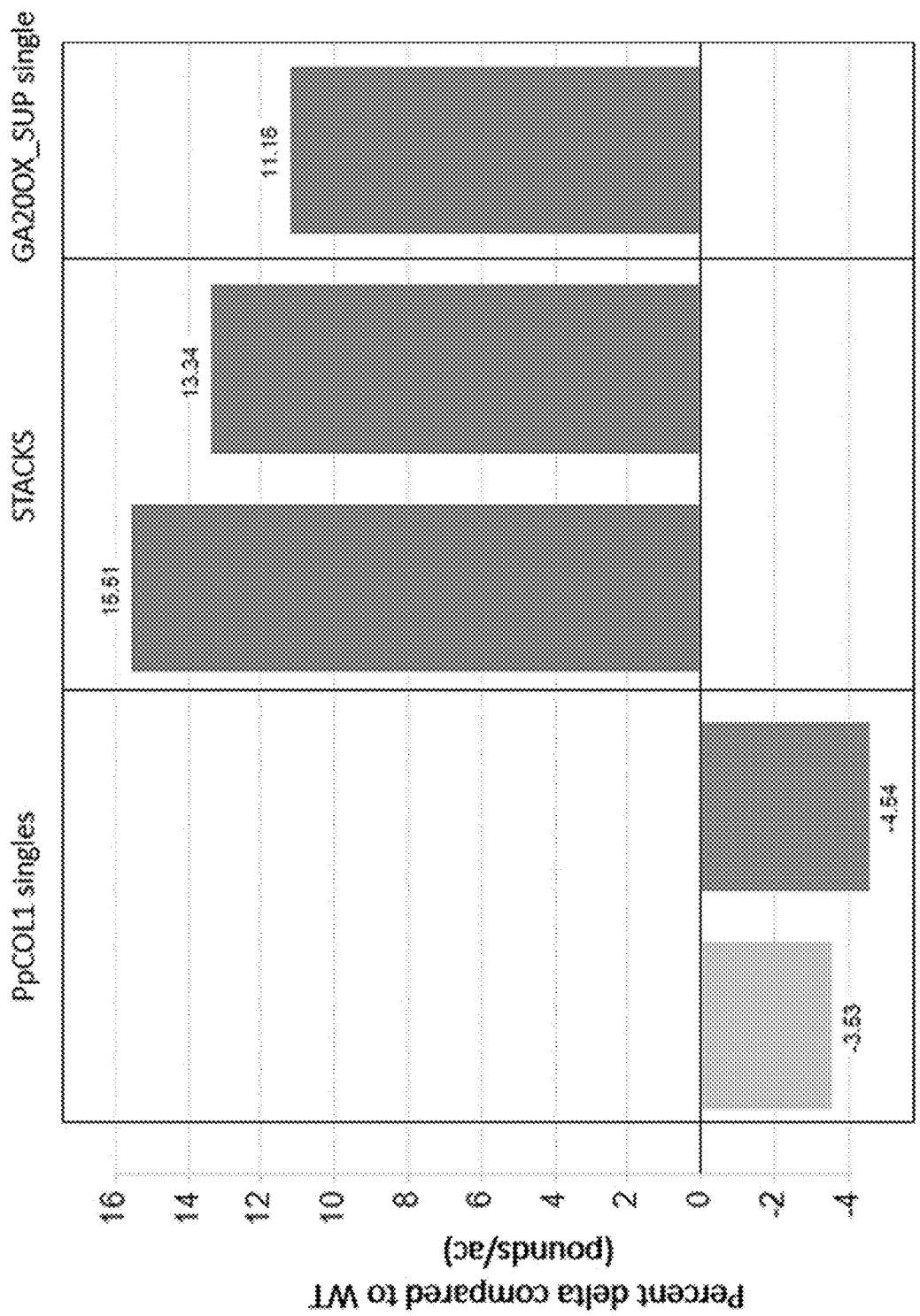
FIG. 9 shows the grain yield estimate of GA20Ox_SUP/PpCOL vector stack plants across two transformation events relative to control plants.

Grain yield estimate was measured (pounds/acre) for GA20OX_SUP single plants (one event), PpCOL single plants (two events), and GA20Ox_SUP/PpCOL stack plants (two event combinations) grown in a single growing season, with each bar indicating one transformation event or event combination. Results are shown in FIG. 9 as a percentage difference in grain yield estimate compared to wildtype control plants. Dark gray bars in FIG. 9 are indicative of statistically significant changes (p-value≤0.2), and light gray bars are indicative of numerically positive or negative changes, all compared to wildtype control plants.

As shown in FIG. 9, while PpCOL single plants for at least one event demonstrated a negative grain yield estimate in this experiment, relative to control plants, GA20Ox_SUP single plants showed an increased grain yield estimate, relative to control plants. GA20Ox_SUP/PpCOL stack plants demonstrated a statistically significant increase in grain yield estimate, relative to control plants, with an average increase that was greater than that of the PpCOL single or GA20Ox_SUP single plants.

These results indicate that GA20Ox_SUP/PpCOL stack plants have enhanced grain yield estimate, compared to control plants, PpCOL single plants, and/or GA20Ox_SUP single plants.

Example 12. Enhanced Ear Traits in the GA20Ox_SUP/PpCOL Stack Plants

Ear traits were measured with GA20Ox_SUP single, PpCOL single, and GA20Ox_SUP/PpCOL stack plants. Ear traits including ear area, ear volume, ear length, kernels per ear, and single kernel weight were measured in two breeding stack event combinations of the GA20Ox_SUP/PpCOL stack plants grown in a single growing season, with each bar representing one transformation event combination. Dark gray bars in FIG. 10 are indicative of statistically significant positive changes (p-value≤0.2), and light gray bars are indicative of numerically positive or negative changes, as compared to GA20Ox_SUP single or PpCOL single plants.

Figure 10:
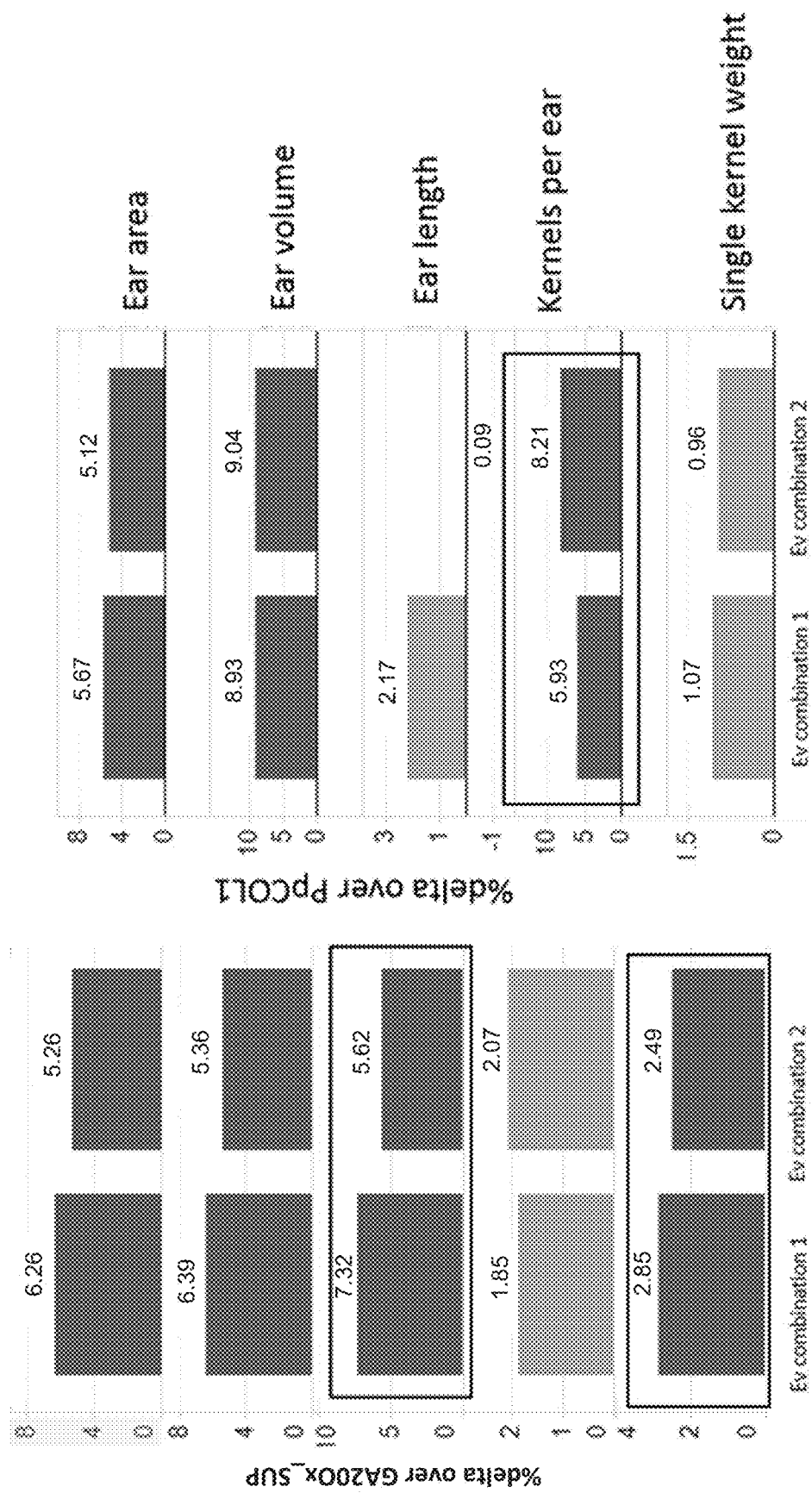
FIG. 10 shows ear traits of GA20Ox_SUP/PpCOL vector stack plants across two transformation events including ear area, ear volume, ear length, kernels per ear, and single kernel weight, relative to GA20Ox_SUP single or PpCOL single plants.

As shown in FIG. 10, GA20Ox_SUP/PpCOL stack plants demonstrated a statistically significant increase in ear area, ear volume, ear length, and single kernel weight, and a numerical increase in kernels per ear, relative to GA20Ox_SUP single plants. In addition, GA20Ox_SUP/PpCOL stack plants showed a statistically significant increase in ear area, ear volume, and kernels per ear, and a numerical increase in ear length and single kernel weight, relative to PpCOL single plants.

These results indicate that GA20Ox_SUP/PpCOL stack plants have enhanced ear traits, such as increased ear area, ear volume, ear length, kernels per ear, and single kernel weight, compared to PpCOL single plants and/or GA20Ox_SUP single plants.

Example 13. Generation of GA20Ox_SUP/PpCOL Vector Stack Plants Using a Single Vector Single constructs and vectors were created via molecular cloning having an expression cassette comprising a DNA sequence encoding a miRNA that targets the GA20 oxidase_3 and GA20 oxidase_5 genes in corn plants and another expression cassette comprising a DNA sequence encoding a PpCOL polypeptide. A first vector (Vector 1) was constructed comprising in order a gene sequence encoding a PpCOL polypeptide (SEQ ID NO: 169) and a miRNA-encoding DNA sequence (SEQ ID NO: 39) encoding a miRNA having a targeting sequence (SEQ ID NO: 40) for the GA20 oxidase_3 and GA20 oxidase_5 genes, wherein the two coding sequences are each operably linked to a promoter and a terminator sequence and are separated from each other by an intergenic sequence. A second vector (Vector 2) was constructed comprising in order a miRNA-encoding DNA sequence (SEQ ID NO: 39) encoding a miRNA having a targeting sequence (SEQ ID NO: 40) for the GA20 oxidase_3 and GA20 oxidase_5 genes, and a DNA sequence encoding a PpCOL polypeptide (SEQ ID NO: 169), wherein the two coding sequences are each operably linked to a promoter and a terminator sequence and are separated from each other by an intergenic sequence. The order of elements for each expression cassette is as provided above in Example 1.

Corn plants were transformed via *Agrobacterium*-mediated transformation with each of Vector 1 and Vector 2 to create transgenic corn plants. The transgenic corn plants containing a transformation event from Vector 1 or Vector 2 were then crossed as females to different male corn lines to create progeny plants comprising, from the female parent, the PpCOL transgene and the miRNA-encoding DNA sequence for GA20 oxidase suppression. The resulting stacked transgenic progeny plants are herein referred to as GA20Ox_SUP/PpCOL vector stack plants, as opposed to breeding or crossing stack plants where the transgenes are from different parents and are brought together in progeny plants by crossing the parents together. Thus, vector stacks will comprise a single event, whereas breeding or crossing stack plants will comprise a combination of two events in the case of a two-transgene stack. Vector 1 and Vector 2 differ in their intergenic regions and the arrangement order of the PpCOL-expression cassette and the GA20Ox3/5-miRNA cassette, although the cassettes themselves are the same.

Example 14. Increased Yield of the GA20Ox_SUP/PpCOL Vector Stack Plants Compared to Control Transgenic corn plants containing Vector 1 or Vector 2 were crossed as a female parent with two male tester corn lines ("Tester 1" and "Tester 2") to produce progeny GA20Ox_SUP/PpCOL vector stack plants. Four transformation events for each vector construct were tested for broad acre yield (BAY).

Figure 11A:
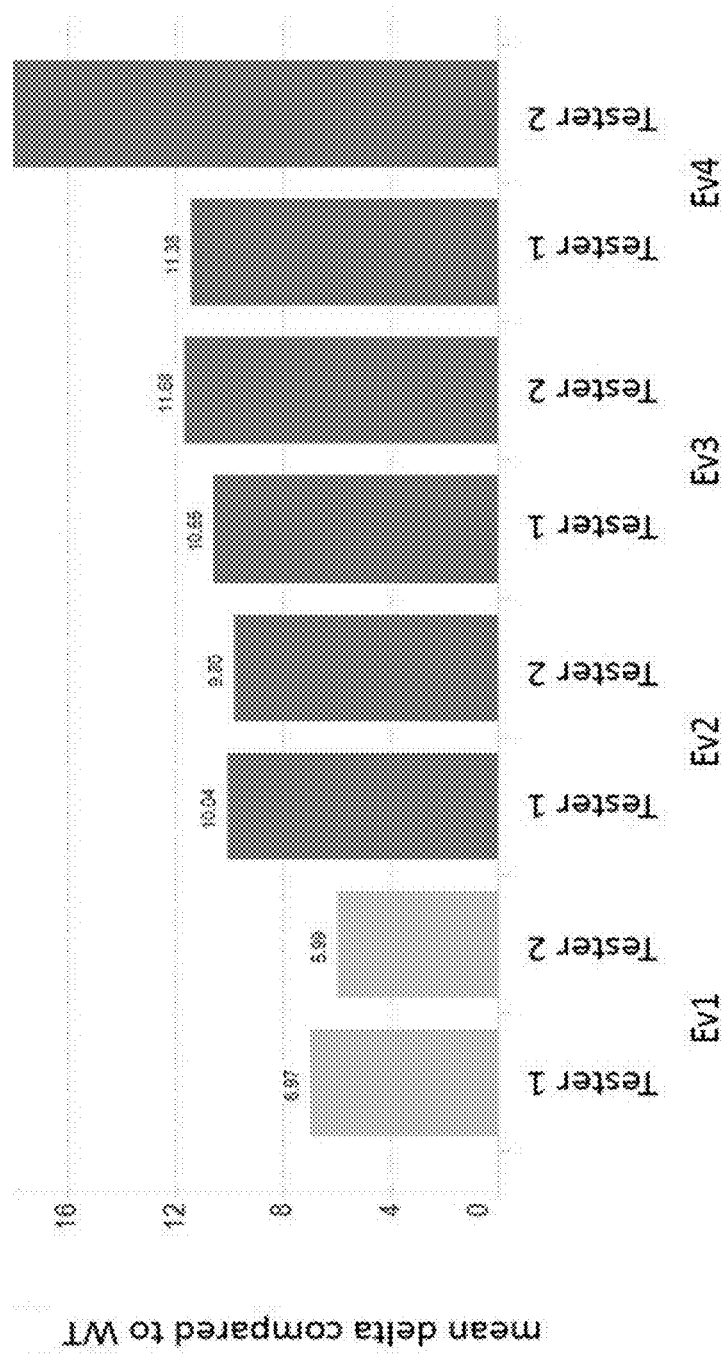
FIGS. 11A and 11B show the broad acreage yield of _GA20Ox_SUP/PpCOL vector stack plants for two different vectors, respectively, across four transformation events for each vector and two testers relative to control plants.
Figure 11B:
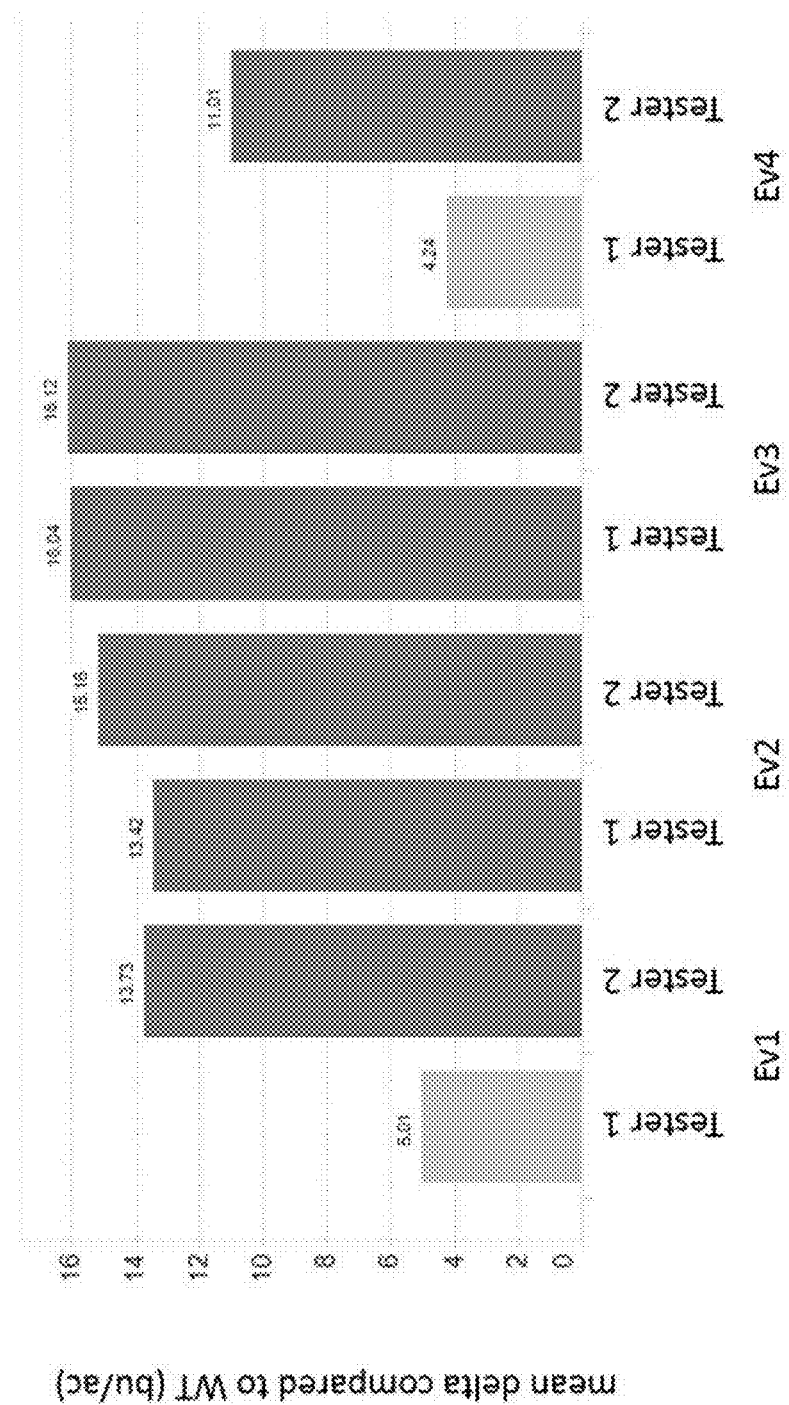

FIG. 11A shows BAY in one growing season across 15 locations from four events of GA20Ox_SUP/PpCOL vector stack plants containing a transformation event from Vector 1. FIG. 11B shows BAY in one growing season across 15 locations from four events of GA20Ox_SUP/PpCOL vector stack plants containing a transformation event from Vector 2. Results are shown as the mean difference in bushels/acre between the BAY of GA20Ox_SUP/PpCOL vector stack plants relative to wild-type control plants. Each bar in FIG. 11 represents a single vector stack transformation event crossed with either "Tester 1" or "Tester 2" male corn line. Dark gray bars in FIGS. 11A and 11B are indicative of statistically significant positive changes (p-value≤0.1), and light gray bars are indicative of numerically positive changes.

As shown in FIG. 11A, three out of four events of GA20Ox_SUP/PpCOL vector stack plants containing a transformation event from Vector 1 showed statistically significant increase in BAY relative to wildtype control plants, and one event of GA20Ox_SUP/PpCOL vector stack plants containing a transformation event from Vector 1 showed numerical increase in BAY relative to wildtype control plants. As shown in FIG. 11B, two out of four events of GA20Ox_SUP/PpCOL vector stack plants containing a transformation event from Vector 2 showed statistically significant increase in BAY relative to wildtype control plants across both testers, and the other two events of GA20Ox_SUP/PpCOL vector stack plants transformed with Vector 2 showed statistically significant increase in BAY for one of the testers and a numerical increase in BAY for the other tester.

Figure 12:
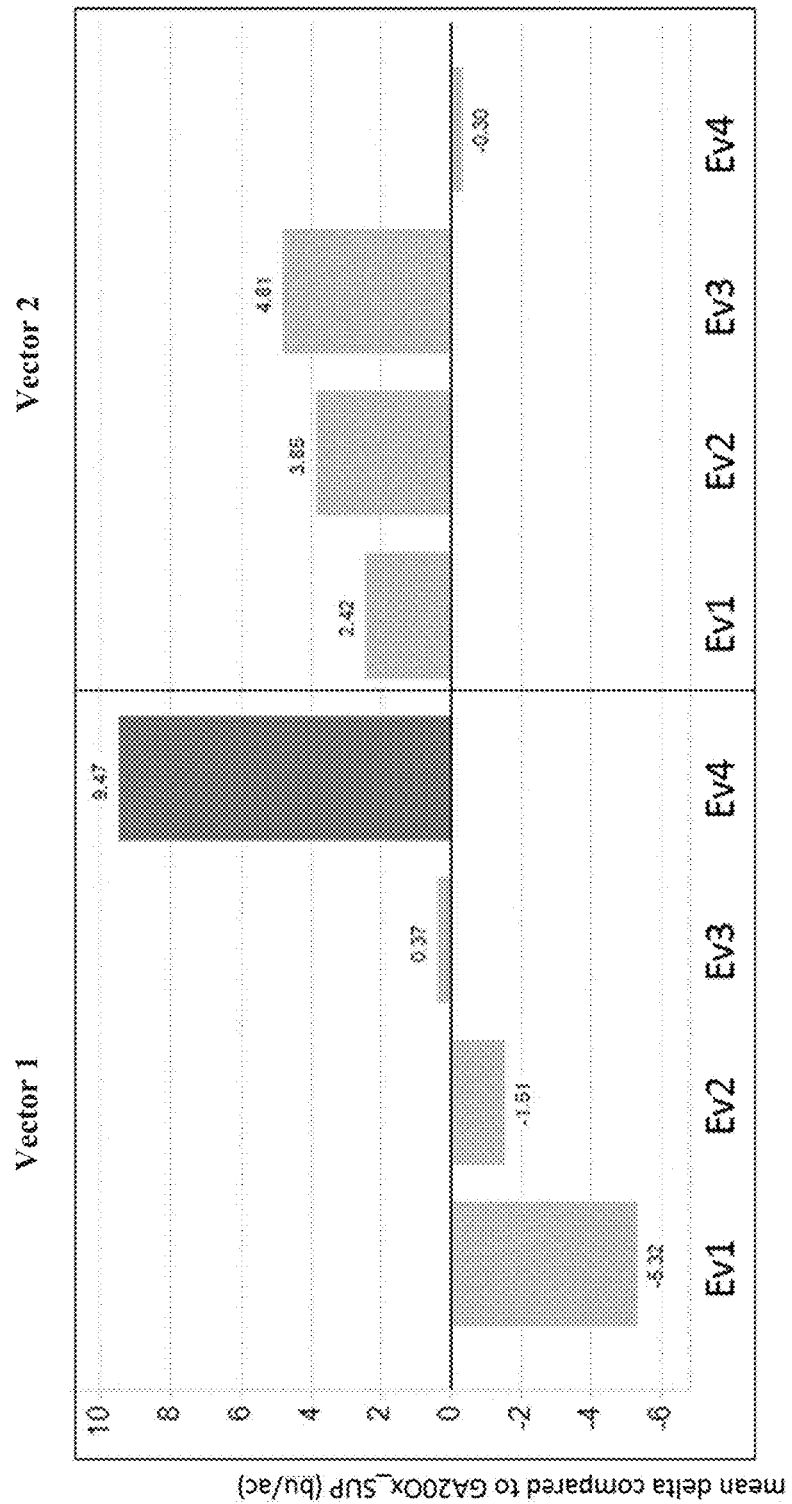
FIG. 12 shows the broad acreage yield of _GA20Ox_SUP/PpCOL vector stack plants for two different vectors across four transformation events relative to GA20Ox_SUP single plants.

Example 15. Increased Yield of the GA20Ox_SUP/PpCOL Vector Stack Plants Compared to the GA20Ox_SUP Single FIG. 12 shows BAY in one growing season across 15 locations for four events of GA20Ox_SUP/PpCOL vector stack plants containing Vector 1 or Vector 2. BAY results are shown as the mean difference in bushels/acre between GA20Ox_SUP/PpCOL vector stack plants and GA20Ox_SUP single plants. Each bar in FIG. 12 represents a single transformation event. Dark gray bars in FIG. 12 are indicative of statistically significant positive changes (p-value≤0.1), and light gray bars are indicative of numerically positive or negative changes.

As shown in FIG. 12, one out of four events of GA20Ox_SUP/PpCOL vector stack plants containing a transformation event from Vector 1 showed a statistically significant increase in BAY relative to GA20Ox_SUP single plants; and three out of four events of GA20Ox_SUP/PpCOL vector stack plants containing a transformation event from Vector 2 showed a numerical increase in BAY relative to GA20Ox_SUP single plants.

Figure 13:
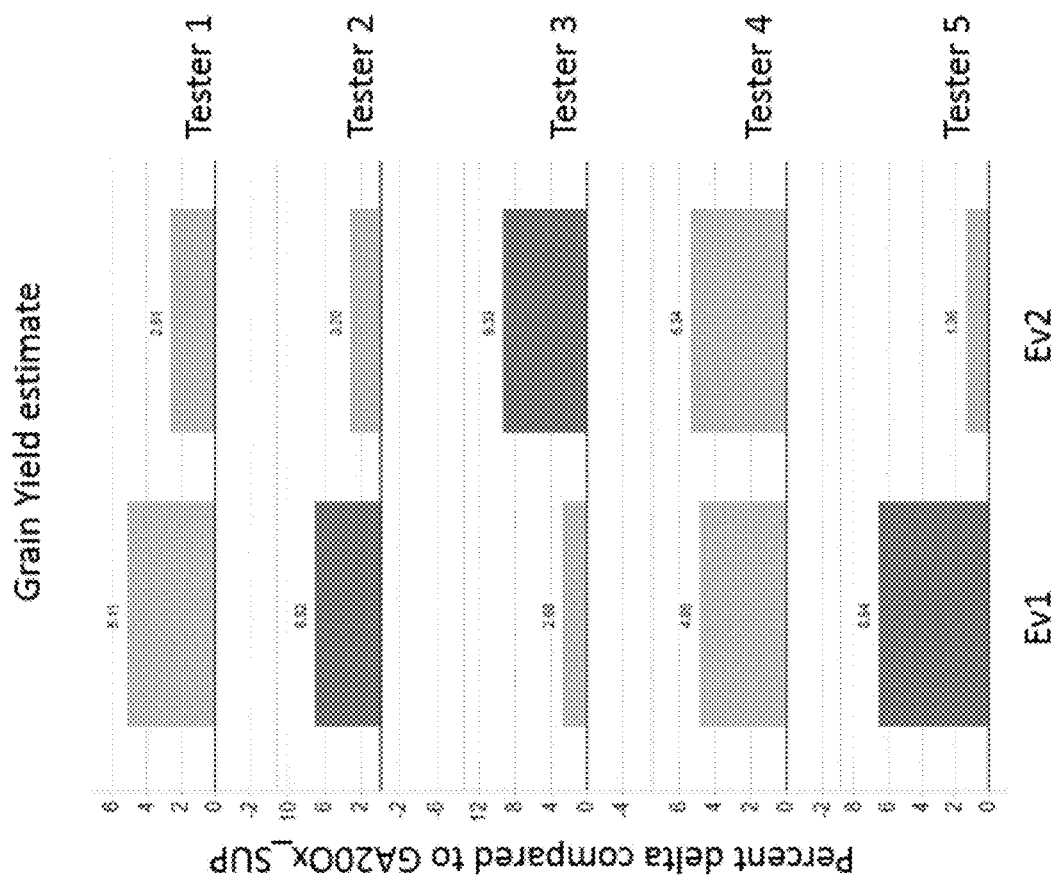
FIG. 13 shows the grain yield estimate of GA20Ox_SUP/PpCOL vector stack plants across two transformation events and five testers relative to GA20Ox_SUP single plants.

Example 16. Increased Grain Yield Estimate of the GA20Ox_SUP/PpCOL Vector Stack Plants Compared to the GA20Ox_SUP Single Female corn plants with one of two GA20Ox_SUP/PpCOL vector stack events made by transformation with Vector 2 were crossed with five different male tester corn lines ("Tester 1" to "Tester 5") to create transgenic GA20Ox_SUP/PpCOL vector stack progeny plants. FIG. 13 shows the measured grain yield estimate of GA20Ox_SUP/PpCOL vector stack plants from each of the two transformation events. Results are shown as the percentage difference between the grain yield estimate of the GA20Ox_SUP/PpCOL vector stack plants and that of GA20Ox_SUP single plants. Each bar in FIG. 13 is for a single transformation event. Dark gray bars in FIG. 13 are indicative of statistically significant positive changes (p-value≤0.2), and light gray bars are indicative of numerically positive changes.

As shown in FIG. 13, progeny of female corn plants comprising one event of the GA20Ox_SUP/PpCOL vector stack (Event 1) showed statistically significant increases in grain yield estimate relative to GA20Ox_SUP single plants when crossed to two out of five male testers, and numerical increases in grain yield estimate relative to GA20Ox_SUP single plants when crossed to the other three male tester lines.

As further shown in FIG. 13, progeny of female corn plants comprising another event of the GA20Ox_SUP/PpCOL vector stack (Event 2) showed a statistically significant increase in grain yield estimate relative to GA20Ox_SUP single plants when crossed to one of five male testers, and numerical increases in grain yield estimate relative to GA20Ox_SUP single plants when crossed to the other four male testers.

Figure 14:
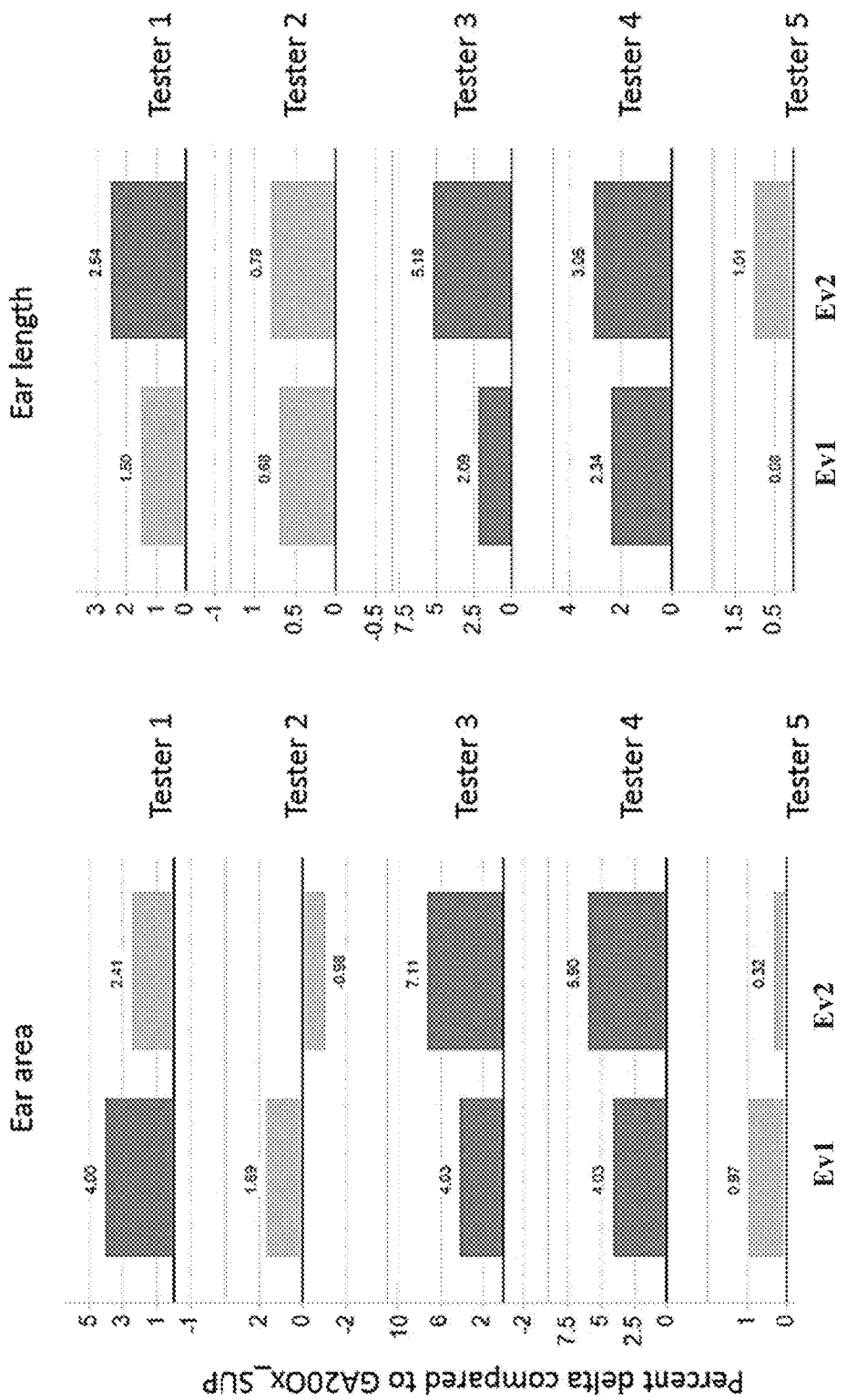
FIG. 14 shows ear area and ear length traits of GA20Ox_SUP/PpCOL vector stack plants across two transformation events and five testers relative to GA20Ox_SUP single plants.

Example 17. Enhanced Ear Area and Ear Length of the GA20Ox_SUP/PpCOL Vector Stack Plants Compared to the GA20Ox_SUP Single Female corn plants with one of two GA20Ox_SUP/PpCOL vector stack events made by transformation with Vector 2 were crossed with five different male tester corn lines ("Tester 1" to "Tester 5") to create transgenic GA20Ox_SUP/PpCOL vector stack progeny plants. FIG. 14 shows ear area and ear length traits of GA20Ox_SUP/PpCOL vector stack plants from each of two transformation events. Results are shown as the percentage difference between the ear area or ear length of the GA20Ox_SUP/PpCOL vector stack plants and that of GA20Ox_SUP single plants. Each bar in FIG. 14 is for a single transformation event. Dark gray bars in FIG. 14 are indicative of statistically significant positive changes (p-value≤0.2), and light gray bars are indicative of numerically positive or negative changes.

As shown in the left panel of FIG. 14, progeny of female corn plants comprising one of the GA20Ox_SUP/PpCOL vector stack events (Event 1) showed statistically significant increases in ear area relative to GA20Ox_SUP single plants when crossed to three out of five male tester lines, and progeny of female corn plants comprising Event 1 of the GA20Ox_SUP/PpCOL vector stack showed numerical increases in ear area relative to GA20Ox_SUP single plants when crossed to the other two male tester lines. In addition, progeny of female corn plants comprising the other GA20Ox_SUP/PpCOL vector stack event (Event 2) showed statistically significant increases in ear area relative to GA20Ox_SUP single plants when crossed to two out of five male tester lines; and progeny of female corn plants comprising Event 2 of the GA20Ox_SUP/PpCOL vector stack showed numerical increase or decrease in ear area relative to GA20Ox_SUP single plants when crossed to the other three male tester lines.

As further shown in the right panel FIG. 14, progeny of female corn plants comprising one of the GA20Ox_SUP/PpCOL vector stack events (Event 1) showed a statistically significant increase in ear length relative to GA20Ox_SUP single plants when crossed to one out of five male tester lines, and progeny of female corn plants comprising Event 1 of the GA20Ox_SUP/PpCOL vector stack showed numerical increases in ear length relative to GA20Ox_SUP single plants when crossed to the other three male tester lines. In addition, progeny of female corn plants comprising the other GA20Ox_SUP/PpCOL vector stack event (Event 2) showed statistically significant increases in ear length relative to GA20Ox_SUP single plants when crossed to three out of five male tester lines, and progeny of female corn plants comprising Event 2 of the GA20Ox_SUP/PpCOL vector stack showed numerical increases in ear length relative to GA20Ox_SUP single plants when crossed to the other two male tester lines.

Figure 15:
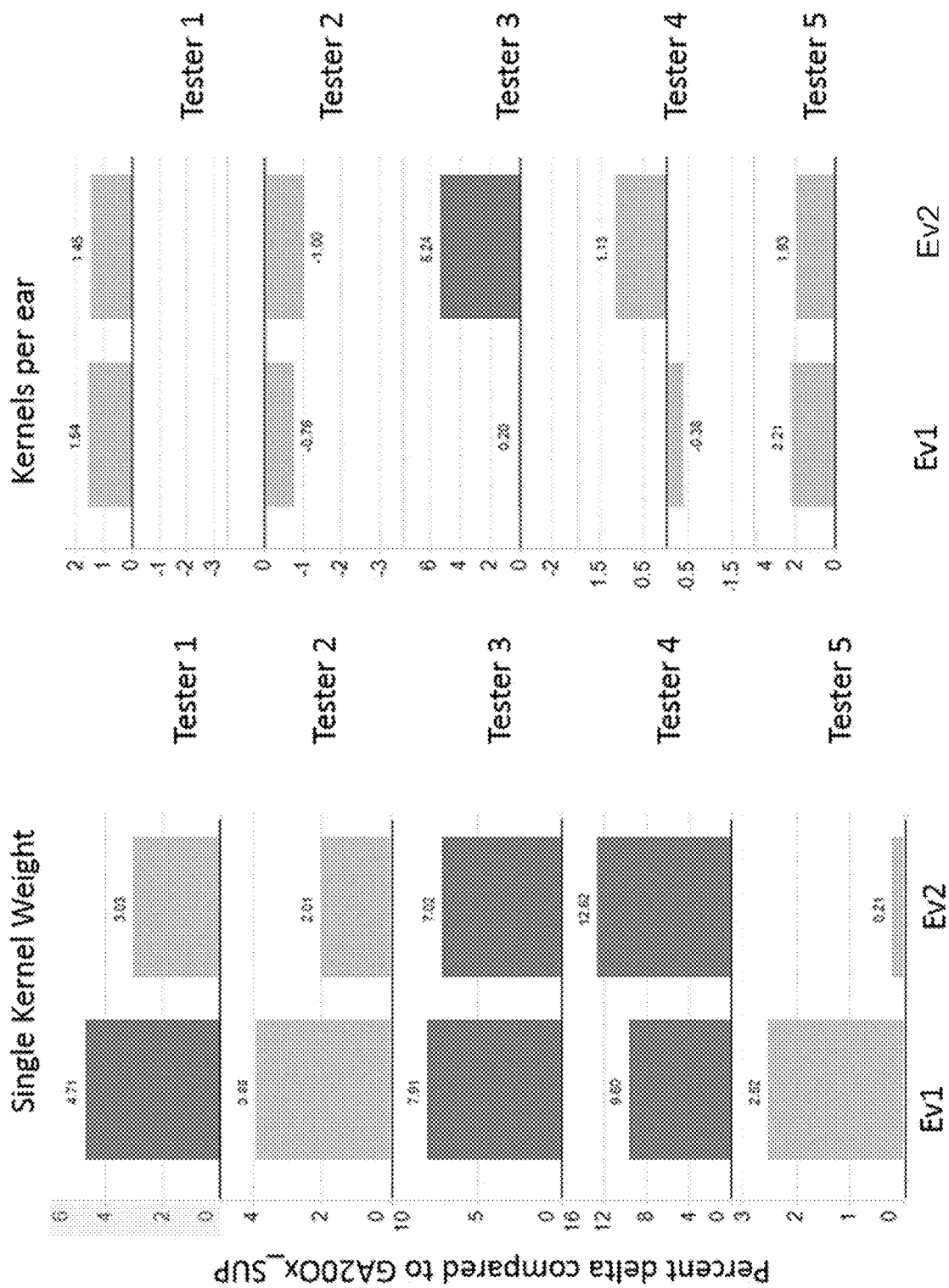
FIG. 15 shows single kernel weight and kernels per ear traits of GA20Ox_SUP/PpCOL vector stack plants across two transformation events and five testers relative to GA20Ox_SUP single plants.

Example 18. Enhanced Single Kernel Weight and Kernels Per Ear of the GA20Ox_SUP/PpCOL Vector Stack Plants Compared to GA20Ox_SUP Single Female corn plants with one of two GA20Ox_SUP/PpCOL vector stack events of corn plants made by transformation with Vector 2 were crossed with five different male tester corn lines ("Tester 1" to "Tester 5") to create transgenic GA20Ox_SUP/PpCOL vector stack progeny plants. FIG. 15 shows single kernel weight and kernels per ear of GA20Ox_SUP/PpCOL vector stack plants from each of two transformation events. Results are shown as the percentage difference between the single kernel weight or kernels per ear of the GA20Ox_SUP/PpCOL vector stack plants and that of GA20Ox_SUP single plants. Each bar in FIG. 15 is for a single transformation event. Dark gray bars in FIG. 15 are indicative of statistically significant positive changes (p-value≤0.2), and light gray bars are indicative of numerically positive or negative changes.

As shown in the left panel of FIG. 15, progeny of female corn plants comprising one of the GA20Ox_SUP/PpCOL vector stack events (Event 1) showed statistically significant increases in single kernel weight relative to GA20Ox_SUP single plants when crossed to three out of five male tester lines, and progeny of female corn plants comprising Event 1 of the GA20Ox_SUP/PpCOL vector stack showed numerical increases in single kernel weight relative to GA20Ox_SUP single plants when crossed to the other two male tester lines. In addition, progeny of female corn plants comprising the other GA20Ox_SUP/PpCOL vector stack event (Event 2) showed statistically significant increase in single kernel weight relative to GA20Ox_SUP single plants when crossed to two out of five male tester lines, and progeny of female corn plants comprising Event 2 of the GA20Ox_SUP/PpCOL vector stack plants from Event 2 showed numerical increases in single kernel weight relative to GA20Ox_SUP single plants when crossed to the other three male tester lines.

As further shown in the right panel FIG. 15, progeny of female corn plants comprising one of the GA20Ox_SUP/PpCOL vector stack events (Event 1) showed numerical increases in kernels per ear relative to GA20Ox_SUP single plants when crossed to two or three out of five male tester lines, although progeny of female corn plants comprising Event 1 of the GA20Ox_SUP/PpCOL vector stack showed numerical decreases in kernels per ear relative to GA20Ox_SUP single plants when crossed to two other male tester lines. In addition, progeny of female corn plants comprising the other GA20Ox_SUP/PpCOL vector stack event (Event 2) showed a statistically significant increase in kernels per ear relative to GA20Ox_SUP single plants when crossed to one out of five male tester lines, and progeny of female corn plants comprising Event 2 of GA20Ox_SUP/PpCOL vector stack showed numerical increases in kernels per ear relative to GA20Ox_SUP single plants when crossed to two other male tester lines, although progeny of female corn plants comprising Event 2 of GA20Ox_SUP/PpCOL vector stack showed a numerical decrease in kernels per ear relative to GA20Ox_SUP single plants when crossed to another male tester line.

Having described the present disclosure in detail, it will be apparent that modifications, variations, and equivalent aspects are possible without departing from the spirit and scope of the present disclosure as described herein and in the appended claims. Furthermore, it should be appreciated that all examples in the present disclosure are provided as non-limiting examples.

---

The invention claimed is:

1. A method for producing a transgenic corn plant, the method comprising:
    (I) introducing into a corn cell (i) a first recombinant expression cassette comprising a first heterologous plant-expressible promoter operably linked to a transcribable DNA sequence encoding a non-coding RNA for suppression of one or more gibberellic acid 20 (GA20) oxidase genes, wherein the non-coding RNA comprises a targeting sequence that is (a) at least 95% complementary to at least 19 consecutive nucleotides of a first mRNA molecule encoding a first endogenous GA20 oxidase protein that has at least 95% amino acid sequence identity to the amino acid sequence as set forth in SEQ ID NO: 9, and (b) at least 95% complementary to at least 19 consecutive nucleotides of a second mRNA molecule encoding a second endogenous GA20 oxidase protein that has at least 95% amino acid sequence identity to the amino acid sequence as set forth in SEQ ID NO: 15, and (ii) a second recombinant expression cassette comprising a DNA sequence encoding a CONSTANS-like (COL) polypeptide that has at least 95% amino acid sequence identity to the amino acid sequence as set forth in SEQ ID NO: 168; and
    (II) regenerating or developing a transgenic corn plant from the corn cell, wherein the transgenic corn plant comprises the first and second recombinant expression cassettes, and wherein expression cassettes expression of said non-coding RNA and said CONSTANS-like (COL) polypeptide in said transgenic corn plant results in a semi-dwarf phenotype, and an increase in one or more improved ear trait selected from the group consisting of ear area, ear volume, ear diameter, ear length, kernels per ear, single kernel weight, yield, grain yield estimate, broad acreage yield, and ear fresh weight as compared to a control wild-type corn plant grown under comparable conditions.

2. The method of claim 1, wherein the transcribable DNA sequence encoding said non-coding RNA comprises a nucleotide sequence that is at least 90% 100% identical or complementary to at least 15 consecutive nucleotides of SEQ ID NO: 39.

3. The method of claim 1, wherein the CONSTANS-like (COL) polypeptide comprises the amino acid sequence that is at least 90% identical to as set forth in SEQ ID NO: 168.

4. A method for producing a transgenic corn plant, the method comprising:
    (I) crossing a first transgenic corn plant with a second transgenic corn plant, wherein the first transgenic corn plant comprises a first recombinant expression cassette comprising a first heterologous plant-expressible promoter operably linked to a transcribable DNA sequence encoding a non-coding RNA for suppression of one or more gibberellic acid 20 (GA20) oxidase genes, wherein the non-coding RNA comprises a targeting sequence that is (a) at least 95% complementary to at least 19 consecutive nucleotides of a first mRNA molecule encoding a first endogenous GA20 oxidase protein that has at least 95% amino acid sequence identity to the amino acid sequence as set forth in SEQ ID NO: 9, and 2) (b) at least 95% complementary to at least 19 consecutive nucleotides of a second mRNA molecule encoding a second endogenous GA20 oxidase protein that has at least 95% amino acid sequence identity to the amino acid sequence as set forth in SEQ ID NO: 15, and wherein the expression of one or more endogenous GA20 oxidase genes is reduced in the first transgenic corn plant as compared to a control wild-type corn plant grown under comparable conditions, and wherein the second transgenic corn plant comprises a second recombinant expression cassette comprising a DNA sequence encoding a CONSTANS-like (COL) polypeptide that has at least 95% amino acid sequence identity to the amino acid sequence as set forth in SEQ ID NO: 168; and (II) producing a transgenic progeny corn plant comprising the first and second recombinant expression cassettes and that has the reduced expression of the one or more endogenous GA20 oxidase genes, and increased expression of said CONSTANS-like (COL) polypeptide as compared to a control wild-type corn plant grown under comparable conditions, and wherein expression of said non-coding RNA and said CONSTANS-like (COL) polypeptide in said transgenic progeny corn plant results in a semi-dwarf phenotype, and an increase in one or more improved ear trait selected from the group consisting of ear area, ear volume, ear diameter, ear length, kernels per ear, single kernel weight, yield, grain yield estimate, broad acreage yield, and ear fresh weight as compared to a control wild-type corn plant grown under comparable conditions.

5. The method of claim 4, wherein the first transgenic corn plant and the transgenic progeny corn plant comprise a transcribable DNA sequence encoding said non-coding RNA comprising a nucleotide sequence that is 100% identical or complementary to at least 15 consecutive nucleotides of SEQ ID NO: 39.

6. The method of claim 4, wherein the CONSTANS-like (COL) polypeptide comprises the amino acid sequence as set forth in SEQ ID NO: 168.

* * * * *